(12) United States Patent
Beckwith et al.

(10) Patent No.: US 10,647,701 B2
(45) Date of Patent: *May 12, 2020

(54) 3-(1-OXOISOINDOLIN-2-YL)PIPERIDINE-2,6-DIONE DERIVATIVES AND USES THEREOF

(71) Applicant: Novartis AG, Basel (CH)

(72) Inventors: Rohan Eric John Beckwith, Maynard, MA (US); Simone Bonazzi, Cambridge, MA (US); Artiom Cernijenko, Cambridge, MA (US); Ritesh Bhanudasji Tichkule, Cambridge, MA (US); Michael Scott Visser, Braintree, MA (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/532,118

(22) Filed: Aug. 5, 2019

(65) Prior Publication Data

US 2019/0359594 A1 Nov. 28, 2019

Related U.S. Application Data

(63) Continuation of application No. 16/108,713, filed on Aug. 22, 2018, now Pat. No. 10,414,755.

(60) Provisional application No. 62/549,225, filed on Aug. 23, 2017.

(51) Int. Cl.
| | |
|---|---|
| *C07D 401/14* | (2006.01) |
| *A61K 31/44* | (2006.01) |
| *C07D 401/04* | (2006.01) |
| *C07D 407/14* | (2006.01) |
| *C07D 409/14* | (2006.01) |
| *C07D 413/14* | (2006.01) |
| *C07D 417/14* | (2006.01) |
| *C07D 471/04* | (2006.01) |
| *C07D 487/04* | (2006.01) |
| *C07D 487/08* | (2006.01) |
| *C07D 495/04* | (2006.01) |
| *C07D 513/04* | (2006.01) |
| *A61P 35/00* | (2006.01) |

(52) U.S. Cl.
CPC ............ *C07D 401/14* (2013.01); *A61P 35/00* (2018.01); *C07D 401/04* (2013.01); *C07D 407/14* (2013.01); *C07D 409/14* (2013.01); *C07D 413/14* (2013.01); *C07D 417/14* (2013.01); *C07D 471/04* (2013.01); *C07D 487/04* (2013.01); *C07D 487/08* (2013.01); *C07D 495/04* (2013.01); *C07D 513/04* (2013.01)

(58) Field of Classification Search
CPC .............................. C07D 401/14; A61K 31/44
See application file for complete search history.

(56) References Cited

U.S. PATENT DOCUMENTS

| | | | |
|---|---|---|---|
| 7,612,096 B2 | 11/2009 | Zeldis et al. | |
| 8,394,832 B2 | 3/2013 | Xu et al. | |
| 9,212,177 B2 | 12/2015 | Kao et al. | |
| 9,295,664 B2 | 3/2016 | Adams et al. | |
| 9,598,669 B2 | 3/2017 | Edinger et al. | |
| 2004/0087558 A1 | 5/2004 | Zeldis et al. | |
| 2005/0130265 A1 | 6/2005 | Georgopoulos et al. | |
| 2005/0203142 A1 | 9/2005 | Zeldis et al. | |
| 2006/0073126 A1 | 4/2006 | Shiku et al. | |
| 2007/0128636 A1 | 6/2007 | Baker et al. | |
| 2007/0161696 A1 | 7/2007 | Zeldis et al. | |
| 2007/0269827 A1 | 11/2007 | Harley | |
| 2010/0291679 A1 | 11/2010 | Edinger et al. | |
| 2012/0149715 A1 | 6/2012 | Kao et al. | |
| 2013/0149339 A1 | 6/2013 | Honda et al. | |
| 2013/0157363 A1 | 6/2013 | Kim et al. | |
| 2013/0281304 A1 | 10/2013 | Feinberg et al. | |
| 2013/0325429 A1 | 12/2013 | Kao et al. | |
| 2014/0341921 A1 | 11/2014 | Honda et al. | |

(Continued)

FOREIGN PATENT DOCUMENTS

| | | |
|---|---|---|
| CN | 106932576 A | 7/2017 |
| EP | 2177615 A1 | 4/2010 |

(Continued)

OTHER PUBLICATIONS

Woo, Ken et al., "Identification of a thalidomide derivative that selectively targets tumorigenic liver progenitor cells and comparing its effect with lenalidomide and sorafenib", European Journal of medicinal Chemistry, 120:275-283. 2016.

Yeung, Sing Yee, et al., "Novel thalidomide analogues with potent NFkB and TNF expression inhibition", MedChemComm, 2(11):1073-1078. 2011.

Stewart, Scott G., et al., "New thalidomide analogues derived through Sonogashira or Suzuki reactions and their TNF expression inhibition profiles", Bioorganic & Medicinal Chemistry, 18(2):650-662. 2010.

(Continued)

*Primary Examiner* — Karen Cheng
(74) *Attorney, Agent, or Firm* — Judith D. Kuntz

(57) ABSTRACT

The present disclosure provides a compound of Formula (I'):

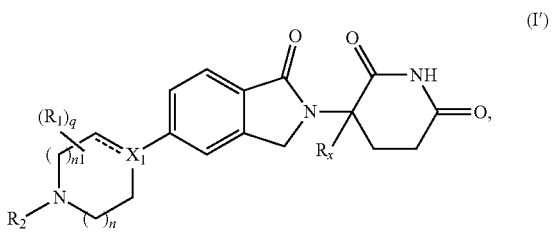

or a pharmaceutically acceptable salt, hydrate, solvate, prodrug, stereoisomer, or tautomer thereof, wherein $R_1$, $R_2$, $R_x$, $X_1$, n, n1, and q are as defined herein, and methods of making and using same.

16 Claims, 11 Drawing Sheets

(56) References Cited

U.S. PATENT DOCUMENTS

| | | |
|---|---|---|
| 2014/0342946 A1 | 11/2014 | Kuriakose et al. |
| 2015/0110733 A1 | 4/2015 | Tchelet et al. |
| 2015/0110761 A1 | 4/2015 | Tang et al. |
| 2015/0111771 A1 | 4/2015 | Lindstedt et al. |
| 2015/0266959 A1 | 9/2015 | Vignali et al. |
| 2015/0307846 A1 | 10/2015 | Chen et al. |
| 2016/0007893 A1 | 1/2016 | Roberts |
| 2016/0032317 A1 | 2/2016 | Rossi et al. |
| 2016/0356778 A1 | 12/2016 | Iha et al. |
| 2018/0009754 A1 | 1/2018 | Long et al. |
| 2018/0099940 A1 | 4/2018 | Crew et al. |
| 2018/0177750 A1 | 6/2018 | Crew et al. |
| 2018/0179183 A1 | 6/2018 | Crew et al. |
| 2019/0062309 A1 | 2/2019 | Beckwith et al. |

FOREIGN PATENT DOCUMENTS

| | | |
|---|---|---|
| EP | 2682750 A1 | 1/2014 |
| EP | 3050570 A1 | 8/2016 |
| EP | 3061758 A1 | 8/2016 |
| GB | 2456390 A | 7/2009 |
| JP | 2009092508 | 4/2009 |
| KR | 2007120709 | 12/2007 |
| KR | 2009071808 | 7/2009 |
| WO | 2002044372 A2 | 6/2002 |
| WO | 2003014315 A2 | 2/2003 |
| WO | 2005044178 A2 | 5/2005 |
| WO | 2006028964 A1 | 3/2006 |
| WO | 2006060507 A2 | 6/2006 |
| WO | 2006061216 A2 | 6/2006 |
| WO | 2007079185 A2 | 7/2007 |
| WO | 2009068621 A1 | 6/2009 |
| WO | 2009094592 A2 | 7/2009 |
| WO | 2009117122 A2 | 9/2009 |
| WO | 2009137095 A2 | 11/2009 |
| WO | 2011015037 A1 | 2/2011 |
| WO | 2011056505 A1 | 5/2011 |
| WO | 2011142827 A2 | 11/2011 |
| WO | 2012054509 A2 | 4/2012 |
| WO | 2012175613 A1 | 12/2012 |
| WO | 2013006474 A2 | 1/2013 |
| WO | 2013037118 A1 | 3/2013 |
| WO | 2014151764 A2 | 9/2014 |
| WO | 2014200952 A2 | 12/2014 |
| WO | 2015035367 A1 | 3/2015 |
| WO | 2015050875 A1 | 4/2015 |
| WO | 2015107196 A1 | 7/2015 |
| WO | 2015109212 A1 | 7/2015 |
| WO | 2015160845 A2 | 10/2015 |
| WO | 2016090273 A1 | 6/2016 |
| WO | 2016097059 A1 | 6/2016 |
| WO | 2016103269 A1 | 6/2016 |
| WO | 2016118638 A1 | 7/2016 |
| WO | 2016140974 A1 | 9/2016 |
| WO | 2016191178 A1 | 12/2016 |
| WO | 2016196580 A1 | 12/2016 |
| WO | 2016196912 A1 | 12/2016 |
| WO | 2016209806 A1 | 12/2016 |
| WO | 2017042337 A1 | 3/2017 |
| WO | 2017044979 A2 | 3/2017 |
| WO | 2017058881 A1 | 4/2017 |
| WO | 2017059062 A1 | 4/2017 |
| WO | 2017075451 A1 | 5/2017 |
| WO | 2017075465 A1 | 5/2017 |
| WO | 2017075478 A2 | 5/2017 |
| WO | 2017095525 A1 | 6/2017 |
| WO | 2017161001 A1 | 9/2017 |
| WO | 2017176958 A1 | 10/2017 |
| WO | 2017191274 A2 | 11/2017 |
| WO | 2017197051 A1 | 11/2017 |
| WO | 2017197056 A1 | 11/2017 |
| WO | 2018071606 A1 | 4/2018 |
| WO | 2018118598 A1 | 6/2018 |
| WO | 2018119357 A1 | 6/2018 |
| WO | 2018119448 A1 | 6/2018 |
| WO | 2018140809 A1 | 8/2018 |

OTHER PUBLICATIONS

Stewart, Scott G., et al., "Synthesis and TNF expression inhibitory properties of new thalidomide analogues derived via Heck cross coupling", Bioorganic & Medicinal Chemistry Letters, 17(2):5819-5824. 2007.
CAS Registry No. 2241326-47-4.
CAS Registry No. 2222115-39-9.
CAS Registry No. 1448326-82-6, entered Aug. 14, 2013.
CAS Registry No. 1384753-62-1, entered Jul. 27, 2012.
CAS Registry No. 1384753-63-2, entered Jul. 27, 2012.
CAS Registry No. 1384753-61-0, entered Jul. 27, 2012.
CAS Registry No. 1384753-60-9, entered Jul. 27, 2012.
CAS Registry No. 1384753-59-6, entered Jul. 27, 2012.
CAS Registry No. 1384753-58-5, entered Jul. 27, 2012.
CAS Registry No. 1384753-57-4, entered Jul. 27, 2012.
CAS Registry No. 1384753-56-3, entered Jul. 27, 2012.
CAS Registry No. 1384753-55-2, entered Jul. 27, 2012.
CAS Registry No. 1384753-54-1, entered Jul. 27, 2012.
CAS Registry No. 1384753-53-0, entered Jul. 27, 2012.
CAS Registry No. 1384753-52-9, entered Jul. 27, 2012.
CAS Registry No. 1384439-40-0, entered Jul. 26, 2012.
CAS Registry No. 1216805-57-0, entered Apr. 5, 2010.
CAS Registry No. 1216805-54-7, entered Apr. 5, 2010.
CAS Registry No. 1216805-53-6, entered Apr. 5, 2010.
CAS Registry No. 1216805-49-0, entered Apr. 5, 2010.
CAS Registry No. 1216805-28-5, entered Apr. 5, 2010.
CAS Registry No. 1216805-25-2, entered Apr. 5, 2010.
CAS Registry No. 1216805-51-4, entered Apr. 5, 2010.
CAS Registry No. 959150-76-6, entered Dec. 21, 2007.
Nakayama, et al., "Aiolos Overexpression in Systemic Lupus Erythematosus B Cell Subtypes and BAFF-Induced Memory B Cell Differentiation Are Reduced by CC-220 Modulation of Cereblon Activity," J. Immunol.,199(7), 2388-2407, (2017).
Hansen, et al., "Protein Degradation via CRL4CRBN Ubiquitin Ligase: Discovery and Structure-Activity Relationships of Novel Glutarimide Analogs That Promote Degradation of Aiolos and/or GSPT1," J. Med. Chem, 61 (2), pp. 492-503, (2018).
Kronke, et al., IKZF1 expression is a prognostic marker in newly diagnosed standard-risk multiple myeloma treated with lenalidomide and intensive chemotherapy: a study of the German Myeloma Study Group (DSMM), Leukemia vol. 31, pp. 1363-1367, (2017).
Harada, et. al, "Expansion of Th1-like Vgamma9Vdelta2T cells by new-generation IMiDs, lenalidomide and pomalidomide, in combination with zoledronic acid," Leukemia vol. 31, pp. 258-262, (2017).
Jones et. al., "Lenalidomide, Thalidomide, and Pomalidomide Reactivate the Epstein-Barr Virus Lytic Cycle through Phosphoinositide 3-Kinase Signaling and Ikaros Expression," Clin. Cancer Res., 22(19), 4901-4912, (2016).
CAS Registry No. 2154353-25-8, entered Dec. 8, 2017.
CAS Registry No. 2154353-21-4, entered Dec. 8, 2017.
CAS Registry No. 2154343-22-1, entered Dec. 8, 2017.
CAS Registry No. 2154342-61-5, entered Dec. 8, 2017.
CAS Registry No. 959150-73-3, entered Dec. 21, 2007.
PARNI006252 Matyskiela, et al., "A Cereblon Modulator (CC-220) with Improved Degradation of Ikaros and Aiolos", Journal of Medicinal Chemistry, 61(2):535-542. 2018.

3-(1-OXOISOINDOLIN-2-YL)PIPERIDINE-2,6-DIONE DERIVATIVES AND USES THEREOF

RELATED APPLICATIONS

This application is a continuation application of U.S. application Ser. No. 16/108,713, now allowed, filed on Aug. 22, 2018, which claims the benefit of and priority to U.S. Provisional application No. 62/549,225, filed Aug. 23, 2017, the entire contents of each of which are incorporated herein by reference in their entireties.

FIELD OF THE DISCLOSURE

The present disclosure relates to 3-(1-oxoisoindolin-2-yl) piperidine-2,6-dione compounds and compositions and their use for the treatment of IKAROS Family Zinc Finger 2 (IKZF2)-dependent diseases or disorders or where reduction of IKZF2 or IKZF4 protein levels can ameliorate a disease or disorder.

BACKGROUND OF THE DISCLOSURE

IKAROS Family Zinc Finger 2 (IKZF2) (also known as Helios) is one of the five members of the Ikaros family of transcription factors found in mammals. IKZF2 contains four zinc finger domains near the N-terminus which are involved in DNA binding and two zinc finger domains at the C-terminus which are involved in protein dimerization. IKZF2 is about 50% identical with Ikaros family members, Ikaros (IKZF1), Aiolos (IKZF3), and Eos (IKZF4) with highest homology in the zinc finger regions (80%+ identity). These four Ikaros family transcription factors bind to the same DNA consensus site and can heterodimerize with each other when co-expressed in cells. The fifth Ikaros family protein, Pegasus (IKZF5), is only 25% identical to IKZF2, binds a different DNA site than other Ikaros family members and does not readily heterodimerize with the other Ikaros family proteins. IKZF2, IKZF1 and IKZF3 are expressed mainly in hematopoietic cells while IKZF4 and IKZF5 are expressed in a wide variety of tissues. (John, L. B., et al., (2011), Mol. Immunol. 48:1272-1278; Perdomo, J., et al., (2000), J. Biol. Chem. 275:38347-38354.)

IKZF2 is believed to have an important role in the function and stability of regulatory T cells (Tregs). IKZF2 is highly expressed at the mRNA and protein level by regulatory T-cell populations. Knockdown of IKZF2 by siRNA has been shown to result in downregulation of FoxP3 and to impair the ability of isolated human CD4+CD25+ Tregs to block T-cell activation in vitro. Moreover, overexpression of IKZF2 in isolated murine Tregs has been shown to increase expression of Treg related markers such as CD103 and GITR and the IKZF2 overexpressing cells showed increased suppression of responder T-cells. IKZF2 has also been found to bind the promoter of FoxP3, the defining transcription factor of the regulatory T-cell lineage, and to affect FoxP3 expression.

Knockout of IKZF2 within FoxP3-expressing Tregs in mice has been shown to cause activated Tregs to lose their inhibitory properties, to express T-effector cytokines, and to take on T-effector functions. IKZF2 knockout mutant mice develop autoimmune disease by 6-8 months of age, with increased numbers of activated CD4 and CD8 T cells, follicular helper T cells and germinal center B cells. This observed effect is believed to be cell intrinsic, as Rag2−/− mice given bone marrow from IKZF2 knockout mice, but not bone marrow from IKZF2+/+ develop autoimmune disease. Direct evidence that IKZF2 affects regulatory T-cell function has been shown in the analysis of mice in which IKZF2 was deleted only in FoxP3 expressing cells (FoxP3-YFP-Cre Heliosfl/fl). The results showed that the mice also develop autoimmune disease with similar features as observed in the whole animal IKZF2 knockout. Moreover, pathway analysis of a CHIP-SEQ experiment has also suggested that IKZF2 is affecting expression of genes in the STAT5/IL-2Ra pathway in regulatory T-cells. This effect of IKZF2 loss was shown to be more apparent after an immune challenge (viral infection or injection with sheep's blood), and it was noted that after immune stimulation, the IKZF2 negative regulatory T cells began to take on features of effector T cells. (Getnet, D., et al., Mol. Immunol. (2010), 47:1595-1600; Bin Dhuban, K., et al., (2015), J. Immunol. 194:3687-96; Kim, H-J., et al., (2015), Science 350:334-339; Nakawaga, H., et al., (2016) PNAS, 113: 6248-6253)

Overexpression of Ikaros isoforms which lack the DNA binding regions have been shown to be associated with multiple human haematological malignancies. Recently, mutations in the IKZF2 gene, which lead to abnormal splicing variants, have been identified in adult T-cell leukemias and low hypodiploid acute lymphoblastic leukemia. It has been proposed that these isoforms, which are capable of dimerization, have a dominant negative effect on Ikaros family transcription factors which primes the development of lymphomas. IKZF2 knockout mutants that survive into adulthood do not develop lymphomas, supporting this hypothesis (Asanuma, S., et al., (2013), Cancer Sci. 104: 1097-1106; Zhang, Z., et al., (2007), Blood 109:2190-2197; Kataoka, D., et al., (2015), Nature Genetics 47:1304-1315.)

Currently, anti-CTLA4 antibodies are used in the clinic to target Tregs in tumors. However, targeting CTLA4 often causes systemic activation of T-effector cells, resulting in excessive toxicity and limiting therapeutic utility. Up to ¾ of patients treated with a combination of anti-PD1 and anti-CTLA4 have reported grade 3 or higher adverse events. Thus, a strong need exists to provide compounds that target Tregs in tumors without causing systemic activation of T-effector cells.

An IKZF2-specific degrader has the potential to focus the enhanced immune response to areas within or near tumors providing a potentially more tolerable and less toxic therapeutic agent for the treatment of cancer.

SUMMARY OF THE DISCLOSURE

The compounds of the disclosure have use as therapeutic agents, particularly for cancers and related diseases. In one aspect, the compounds of the disclosure have IKZF2 degrader activity, preferably having such activity at or below the 50 µM level, and more preferably having such activity at or below the 10 µM level. In another aspect, the compounds of the disclosure have degrader activity for IKZF2 that is selective over one or more of IKZF1, IKZF3, IKZF4, and/or IKZF5. In another aspect, the compounds of the disclosure have degrader activity for both IKZF2 and IKZF4. The compounds of the disclosure have usefulness in treating cancer and other diseases for which such degrader activity would be beneficial for the patient. For example, while not intending to be bound by any theory, the inventors believe that reducing levels of IKZF2 in Tregs in a tumor may allow the patient immune system to more effectively attack the disease. In summary, the present disclosure provides novel IKZF2 degraders useful for the treatment of cancer and other diseases.

A first aspect of the present disclosure relates to compounds of Formula (I')

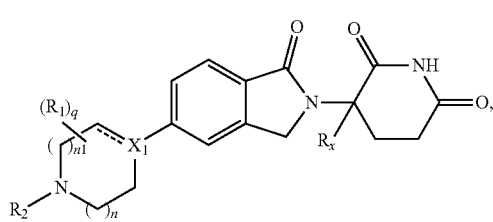

wherein:

$X_1$ is $CR_3$;

------- is optionally a double bond when $X_1$ is $CR_3$ and $R_3$ is absent;

each $R_1$ is independently $(C_1-C_6)$alkyl, $(C_1-C_6)$haloalkyl, $(C_1-C_6)$hydroxyalkyl, or halogen, or two $R_1$ together with the carbon atoms to which they are attached form a 5- or 6-membered heterocycloalkyl ring, or two $R_1$, when on adjacent atoms, together with the atoms to which they are attached form a $(C_6-C_{10})$aryl ring or a 5- or 6-membered heteroaryl ring comprising 1 to 3 heteroatoms selected from O, N, and S;

$R_2$ is H, $(C_1-C_6)$alkyl, —C(O)$(C_1-C_6)$alkyl, —C(O)$(CH_2)_{0-3}(C_6-C_{10})$aryl, —C(O)O$(CH_2)_{0-3}(C_6-C_{10})$aryl, $(C_6-C_{10})$aryl, 5- or 6-membered heteroaryl comprising 1 to 3 heteroatoms selected from O, N, and S, $(C_3-C_9)$cycloalkyl, or 5- to 7-membered heterocycloalkyl comprising 1 to 3 heteroatoms selected from O, N, and S, wherein the alkyl is optionally substituted with one or more $R_4$; and the aryl, heteroaryl, cycloalkyl, and heterocycloalkyl are optionally substituted with one or more $R_5$, or $R_1$ and $R_2$, when on adjacent atoms, together with the atoms to which they are attached form a 5- or 6-membered heterocycloalkyl ring;

$R_3$ is H or $R_3$ is absent when ------- is a double bond;

each $R_4$ is independently selected from —C(O)O$R_6$, —C(O)NR_6R_{6'}$, —NR_6C(O)R_{6'}$, halogen, —OH, —NH$_2$, CN, $(C_6-C_{10})$aryl, 5- or 6-membered heteroaryl comprising 1 to 4 heteroatoms selected from O, N, and S, $(C_3-C_8)$cycloalkyl, and 5- to 7-membered heterocycloalkyl ring comprising 1 to 3 heteroatoms selected from O, N, and S, wherein the aryl, heteroaryl, cycloalkyl, and heterocycloalkyl groups are optionally substituted with one or more $R_7$;

each $R_5$ is independently selected from $(C_1-C_6)$alkyl, $(C_2-C_6)$alkenyl, $(C_2-C_6)$alkynyl, $(C_1-C_6)$alkoxy, $(C_1-C_6)$haloalkyl, $(C_1-C_6)$haloalkoxy, $(C_1-C_6)$hydroxyalkyl, halogen, —OH, —NH$_2$, CN, $(C_3-C_7)$cycloalkyl, 5- to 7-membered heterocycloalkyl comprising 1 to 3 heteroatoms selected from O, N, and S, $(C_6-C_{10})$aryl, and 5- or 6-membered heteroaryl comprising 1 to 3 heteroatoms selected from O, N, and S, or two $R_5$, when on adjacent atoms, together with the atoms to which they are attached form a $(C_6-C_{10})$aryl ring or a 5- or 6-membered heteroaryl ring comprising 1 to 3 heteroatoms selected from O, N, and S, optionally substituted with one or more $R_{10}$, or two $R_5$, when on adjacent atoms, together with the atoms to which they are attached form a $(C_5-C_7)$cycloalkyl ring or a 5- to 7-membered heterocycloalkyl ring comprising 1 to 3 heteroatoms selected from O, N, and S optionally substituted with one or more $R_{10}$;

$R_6$ and $R_{6'}$ are each independently H, $(C_1-C_6)$alkyl, or $(C_6-C_{10})$aryl;

each $R_7$ is independently selected from $(C_1-C_6)$alkyl, $(C_2-C_6)$alkenyl, $(C_2-C_6)$alkynyl, $(C_1-C_6)$alkoxy, $(C_1-C_6)$haloalkyl, $(C_1-C_6)$haloalkoxy, —C(O)R$_8$, —(CH$_2$)$_{0-3}$C(O)OR$_8$, —C(O)NR$_8$R$_9$, —NR$_8$C(O)R$_9$, —NR$_8$C(O)OR$_9$, —S(O)NR$_8$R$_9$, —S(O)$_p$R$_{12}$, $(C_1-C_6)$hydroxyalkyl, halogen, —OH, —O(CH$_2$)$_{1-3}$CN, —NH$_2$, CN, —O(CH$_2$)$_{0-3}$$(C_6-C_{10})$aryl, adamantyl, —O(CH$_2$)$_{0-3}$-5- or 6-membered heteroaryl comprising 1 to 3 heteroatoms selected from O, N, and S, $(C_6-C_{10})$aryl, monocyclic or bicyclic 5- to 10-membered heteroaryl comprising 1 to 3 heteroatoms selected from O, N, and S, $(C_3-C_7)$cycloalkyl, and 5- to 7-membered heterocycloalkyl comprising 1 to 3 heteroatoms selected from O, N, and S, wherein the alkyl is optionally substituted with one or more $R_{11}$, and the aryl, heteroaryl, and heterocycloalkyl are optionally substituted with one or more substituents each independently selected from halogen, $(C_1-C_6)$alkyl, $(C_1-C_6)$haloalkyl, and $(C_1-C_6)$alkoxy, or two $R_7$ together with the carbon atom to which they are attached form a =(O), or two $R_7$, when on adjacent atoms, together with the atoms to which they are attached form a $(C_6-C_{10})$aryl ring or a 5- or 6-membered heteroaryl ring comprising 1 to 3 heteroatoms selected from O, N, and S, optionally substituted with one or more $R_{10}$, or two $R_7$ together with the atoms to which they are attached form a $(C_5-C_7)$ cycloalkyl ring or a 5- to 7-membered heterocycloalkyl ring comprising 1 to 3 heteroatoms selected from O, N, and S, optionally substituted with one or more $R_{10}$;

$R_8$ and $R_9$ are each independently H or $(C_1-C_6)$alkyl;

each $R_{10}$ is independently selected from $(C_1-C_6)$alkyl, $(C_1-C_6)$alkoxy, $(C_1-C_6)$haloalkyl, $(C_1-C_6)$haloalkoxy, $(C_1-C_6)$hydroxyalkyl, halogen, —OH, —NH$_2$, and CN, or two $R_{10}$ together with the carbon atom to which they are attached form a =(O);

each $R_{11}$ is independently selected from CN, $(C_1-C_6)$alkoxy, $(C_6-C_{10})$aryl, and 5- to 7-membered heterocycloalkyl comprising 1 to 3 heteroatoms selected from O, N, and S, wherein the aryl and heterocycloalkyl are optionally substituted with one or more substituents each independently selected from $(C_1-C_6)$alkyl, $(C_1-C_6)$alkoxy, $(C_1-C_6)$haloalkyl, $(C_1-C_6)$haloalkoxy, $(C_1-C_6)$hydroxyalkyl, halogen, —OH, —NH$_2$, and CN;

$R_{12}$ is $(C_1-C_6)$alkyl, $(C_1-C_6)$haloalkyl, $(C_6-C_{10})$aryl, or 5- to 7-membered heterocycloalkyl comprising 1 to 3 heteroatoms selected from O, N, and S;

$R_x$ is H or D;

p is 0, 1, or 2;

n is 0, 1, or 2;

n1 is 1 or 2, wherein n+n1≤3; and q is 0, 1, 2, 3, or 4;

or pharmaceutically acceptable salts, hydrates, solvates, prodrugs, stereoisomers, and tautomers thereof.

In one embodiment, the present disclosure relates to compounds of Formula (I') having the structure of Formula (I):

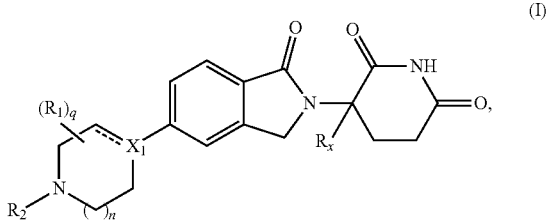

(I)

wherein:

X₁ is CR₃;

------- is optionally a double bond when X₁ is CR₃ and R₃ is absent;

each R₁ is independently (C₁-C₆)alkyl, (C₁-C₆)haloalkyl, (C₁-C₆)hydroxyalkyl, or halogen;

R₂ is H, (C₁-C₆)alkyl, (C₆-C₁₀)aryl, 5- or 6-membered heteroaryl comprising 1 to 3 heteroatoms selected from O, N, and S, (C₃-C₈)cycloalkyl, or 5- to 7-membered heterocycloalkyl comprising 1 to 3 heteroatoms selected from O, N, and S, wherein the alkyl is optionally substituted with one or more R₄; and the aryl, heteroaryl, cycloalkyl, and heterocycloalkyl are optionally substituted with one or more R₅;

R₃ is H or R₃ is absent when ------- is a double bond;

each R₄ is independently selected from —C(O)OR₆, —C(O)NR₆R₆', —NR₆C(O)R₆', (C₆-C₁₀)aryl, 5- or 6-membered heteroaryl comprising 1 to 3 heteroatoms selected from O, N, and S, (C₃-C₈)cycloalkyl, and 5- to 7-membered heterocycloalkyl comprising 1 to 3 heteroatoms selected from O, N, and S, wherein the aryl, heteroaryl, cycloalkyl, and heterocycloalkyl groups are optionally substituted with one or more R₇;

each R₅ is independently selected from (C₁-C₆)alkyl, (C₂-C₆)alkenyl, (C₂-C₆)alkynyl, (C₁-C₆)alkoxy, (C₁-C₆)haloalkyl, (C₁-C₆)haloalkoxy, (C₁-C₆)hydroxyalkyl, halogen, —OH, —NH₂, CN, (C₃-C₇)cycloalkyl, 5- to 7-membered heterocycloalkyl comprising 1 to 3 heteroatoms selected from O, N, and S, (C₆-C₁₀)aryl, and 5- or 6-membered heteroaryl comprising 1 to 3 heteroatoms selected from O, N, and S, or two R₅, when on adjacent atoms, together with the atoms to which they are attached form a (C₆-C₁₀)aryl ring or a 5- or 6-membered heteroaryl ring comprising 1 to 3 heteroatoms selected from O, N, and S, optionally substituted with one or more R₁₀, or two R₅, when on adjacent atoms, together with the atoms to which they are attached form a (C₅-C₇)cycloalkyl ring or a 5- to 7-membered heterocycloalkyl ring comprising 1 to 3 heteroatoms selected from O, N, and S optionally substituted with one or more R₁₀;

R₆ and R₆' are each independently H or (C₁-C₆)alkyl;

each R₇ is independently selected from (C₁-C₆)alkyl, (C₂-C₆)alkenyl, (C₂-C₆)alkynyl, (C₁-C₆)alkoxy, (C₁-C₆)haloalkyl, (C₁-C₆)haloalkoxy, —C(O)R₈, —C(O)OR₈, —C(O)NR₈R₉, —NR₈C(O)R₉, (C₁-C₆)hydroxyalkyl, halogen, —OH, —NH₂, CN, (C₆-C₁₀)aryl, 5- or 6-membered heteroaryl comprising 1 to 3 heteroatoms selected from O, N, and S, (C₃-C₇)cycloalkyl, and 5- to 7-membered heterocycloalkyl comprising 1 to 3 heteroatoms selected from O, N, and S, or two R₇, when on adjacent atoms, together with the atoms to which they are attached form a (C₆-C₁₀)aryl ring or a 5- or 6-membered heteroaryl ring comprising 1 to 3 heteroatoms selected from O, N, and S, optionally substituted with one or more R₁₀, or two R₇, when on adjacent atoms, together with the atoms to which they are attached form a (C₅-C₇)cycloalkyl ring or a 5- to 7-membered heterocycloalkyl ring comprising 1 to 3 heteroatoms selected from O, N, and S, optionally substituted with one or more R₁₀;

R₈ and R₉ are each independently H or (C₁-C₆)alkyl;

each R₁₀ is independently selected from (C₁-C₆)alkyl, (C₁-C₆)alkoxy, (C₁-C₆)haloalkyl, (C₁-C₆)haloalkoxy, (C₁-C₆)hydroxyalkyl, halogen, —OH, —NH₂, and CN;

R_x is H or D;

n is 1 or 2; and q is 0, 1, 2, 3, or 4, or pharmaceutically acceptable salts, hydrates, solvates, prodrugs, stereoisomers, and tautomers thereof.

In one aspect of the disclosure, the hydrogens in the compound of Formula (I') or Formula (I) are present in their normal isotopic abundances. In a preferred aspect of the disclosure, the hydrogens are isotopically enriched in deuterium (D), and in a particularly preferred aspect of the invention the hydrogen at position R_x is enriched in D, as discussed in more detail concerning isotopes and isotopic enrichment below.

Another aspect of the present disclosure relates to a pharmaceutical composition comprising a therapeutically effective amount of a compound of Formula (I') or Formula (I), or a pharmaceutically acceptable salt, hydrate, solvate, prodrug, stereoisomer, or tautomer thereof, and a pharmaceutically acceptable carrier or excipient. The pharmaceutical composition is useful in the treatment of IKZF2-dependent diseases or disorders. The pharmaceutical composition may further comprise at least one additional pharmaceutical agent.

In another aspect, the present disclosure relates to a pharmaceutical composition comprising a therapeutically effective amount of a compound of Formula (I') or Formula (I), or a pharmaceutically acceptable salt, hydrate, solvate, prodrug, stereoisomer, or tautomer thereof, and a pharmaceutically acceptable carrier or excipient for use in the treatment of an IKZF2-dependent disease or disorder by reducing IKZF2 protein levels wherein reduction of IKZF2 protein levels treats the IKZF2-dependent disease or disorder. The pharmaceutical composition is useful in the treatment of IKZF2-dependent diseases or disorders. The pharmaceutical composition may further comprise at least one additional pharmaceutical agent.

Another aspect of the present disclosure relates to a pharmaceutical composition comprising a therapeutically effective amount of a compound of Formula (I') or Formula (I), or a pharmaceutically acceptable salt, hydrate, solvate, prodrug, stereoisomer, or tautomer thereof, and a pharmaceutically acceptable carrier or excipient. The pharmaceutical composition is useful in the treatment of diseases or disorders affected by the reduction of IKZF2 protein levels. The pharmaceutical composition may further comprise at least one additional pharmaceutical agent.

In another aspect, the present disclosure relates to a pharmaceutical composition comprising a therapeutically effective amount of a compound of Formula (I') or Formula (I), or a pharmaceutically acceptable salt, hydrate, solvate, prodrug, stereoisomer, or tautomer thereof, and a pharmaceutically acceptable carrier or excipient for use in the treatment of a disease or disorder affected by the reduction of IKZF2 protein levels wherein reduction of IKZF2 protein levels treats the disease or disorder. The pharmaceutical composition may further comprise at least one additional pharmaceutical agent.

In another aspect, the present disclosure relates to a method of degrading IKZF2. The method comprises administering to the patient in need thereof a compound of Formula (I') or Formula (I), or a pharmaceutically acceptable salt, hydrate, solvate, prodrug, stereoisomer, or tautomer thereof.

Another aspect of the present disclosure relates to a method of modulating IKZF2 protein levels. The method comprises administering to the patient in need thereof a compound of Formula (I') or Formula (I), or a pharmaceutically acceptable salt, hydrate, solvate, prodrug, stereoisomer, or tautomer thereof.

In another aspect, the present disclosure relates to a method of reducing IKZF2 protein levels. The method comprises administering to the patient in need thereof a compound of Formula (I') or Formula (I), or a pharmaceutically acceptable salt, hydrate, solvate, prodrug, stereoisomer, or tautomer thereof.

In another aspect, the present disclosure relates to a method of decreasing IKZF2 protein levels. The method comprises administering to the patient in need thereof a compound of Formula (I') or Formula (I), or a pharmaceutically acceptable salt, hydrate, solvate, prodrug, stereoisomer, or tautomer thereof.

Another aspect of the present disclosure relates to a method of reducing the proliferation of a cell. The method comprises administering to the patient in need thereof a compound of Formula (I') or Formula (I), or a pharmaceutically acceptable salt, hydrate, solvate, prodrug, stereoisomer, or tautomer thereof and reducing IKZF2 protein levels.

In another aspect, the present disclosure relates to a method of reducing IKZF2 protein levels. The method comprises administering to the patient in need thereof a compound of Formula (I') or Formula (I), or a pharmaceutically acceptable salt, hydrate, solvate, prodrug, stereoisomer, or tautomer thereof.

In another aspect, the present disclosure relates to a method of treating cancer. The method comprises administering to the patient in need thereof a compound of Formula (I') or Formula (I), or a pharmaceutically acceptable salt, hydrate, solvate, prodrug, stereoisomer, or tautomer thereof. In one embodiment, the cancer is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiform, glioma, thyroid cancer, parathyroid tumor, nasopharyngeal cancer, tongue cancer, pancreatic cancer, esophageal cancer, cholangiocarcinoma, gastric cancer and soft tissue sarcomas selected from rhabdomyosarcoma (RMS), synovial sarcoma, osteosarcoma, rhabdoid cancers, and Ewing's sarcoma. In another embodiment, the cancer is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, and gastrointestinal stromal tumor (GIST). In yet another embodiment, the disease or disorder is selected from non-small cell lung cancer (NSCLC), melanoma, triple-negative breast cancer (TNBC), nasopharyngeal cancer (NPC), and microsatellite stable colorectal cancer (mssCRC). In another embodiment, the cancer is a cancer for which the immune response is deficient or an immunogenic cancer.

Another aspect of the present disclosure relates to a pharmaceutical composition comprising a therapeutically effective amount of a compound of Formula (I') or Formula (I), or a pharmaceutically acceptable salt, hydrate, solvate, prodrug, stereoisomer, or tautomer thereof, and a pharmaceutically acceptable carrier or excipient for use in the treatment of an IKZF2-dependent disease or disorder.

In another aspect, the present disclosure relates to the use of a pharmaceutical composition comprising a therapeutically effective amount of a compound of Formula (I') or Formula (I), or a pharmaceutically acceptable salt, hydrate, solvate, prodrug, stereoisomer, or tautomer thereof, and a pharmaceutically acceptable carrier or excipient in the manufacture of a medicament for treating of an IKZF2-dependent disease or disorder.

Another aspect of the present disclosure relates to a method for treating an IKZF2-dependent disease or disorder comprising the step of administering to a subject in need thereof a pharmaceutical composition comprising a therapeutically effective amount of a compound of Formula (I') or Formula (I), or a pharmaceutically acceptable salt, hydrate, solvate, prodrug, stereoisomer, or tautomer thereof, and a pharmaceutically acceptable carrier or excipient.

In another aspect, the present disclosure relates to a method for treating an IKZF2-dependent disease or disorder comprising the step of administering to a subject in need thereof a therapeutically effective amount of a compound of Formula (I') or Formula (I), or a pharmaceutically acceptable salt, hydrate, solvate, prodrug, stereoisomer, or tautomer thereof.

Another aspect of the present disclosure relates to a compound of Formula (I') or Formula (I), or a pharmaceutically acceptable salt, hydrate, solvate, prodrug, stereoisomer, or tautomer thereof, for use in the treatment of an IKZF2-dependent disease or disorder.

In another aspect, the present disclosure relates to the use of a compound of Formula (I') or Formula (I), or a pharmaceutically acceptable salt, hydrate, solvate, prodrug, stereoisomer, or tautomer thereof, in the manufacture of a medicament for treating an IKZF2-dependent disease or disorder.

Another aspect of the present disclosure relates to a method for treating a disease or disorder that is affected by the modulation of IKZF2 protein levels comprising the step of administering to a subject in need thereof a therapeutically effective amount of a compound of Formula (I') or Formula (I), or a pharmaceutically acceptable salt, hydrate, solvate, prodrug, stereoisomer, or tautomer thereof.

In another aspect, the present disclosure relates to a method for treating a disease or disorder that is affected by a decrease in IKZF2 protein levels comprising the step of administering to a subject in need thereof a therapeutically effective amount of a compound of Formula (I') or Formula (I), or a pharmaceutically acceptable salt, hydrate, solvate, prodrug, stereoisomer, or tautomer thereof.

Another aspect of the present disclosure relates to a method for treating a disease or disorder that is affected by the reduction of IKZF2 protein levels comprising the step of administering to a subject in need thereof a therapeutically effective amount of a compound of Formula (I') or Formula (I), or a pharmaceutically acceptable salt, hydrate, solvate, prodrug, stereoisomer, or tautomer thereof.

In another aspect, the present disclosure relates to a compound of Formula (I') or Formula (I), or a pharmaceutically acceptable salt, hydrate, solvate, prodrug, stereoisomer, or tautomer thereof, for use in the treatment of a disease or disorder that is affected by the modulation of IKZF2 protein levels.

Another aspect of the present disclosure relates to a compound of Formula (I') or Formula (I), or a pharmaceutically acceptable salt, hydrate, solvate, prodrug, stereoisomer, or tautomer thereof, for use in the treatment of a disease or disorder that is affected by the reduction of IKZF2 protein levels.

In another aspect, the present disclosure relates to a compound of Formula (I') or Formula (I), or a pharmaceutically acceptable salt, hydrate, solvate, prodrug, stereoisomer, or tautomer thereof, for use in the treatment of a disease or disorder that is affected by a decrease in IKZF2 protein levels.

In another aspect, the present disclosure relates to the use of a compound of Formula (I') or Formula (I), or a pharmaceutically acceptable salt, hydrate, solvate, prodrug, stereoisomer, or tautomer thereof, in the manufacture of a medicament for treating a disease or disorder that is affected by the modulation of IKZF2 protein levels.

Another aspect of the present disclosure relates to the use of a compound of Formula (I') or Formula (I), or a pharmaceutically acceptable salt, hydrate, solvate, prodrug, stereoisomer, or tautomer thereof, in the manufacture of a medicament for treating a disease or disorder that is affected by the reduction of IKZF2 protein levels.

Another aspect of the present disclosure relates to the use of a compound of Formula (I') or Formula (I), or a pharmaceutically acceptable salt, hydrate, solvate, prodrug, stereoisomer, or tautomer thereof, in the manufacture of a medicament for treating a disease or disorder that is affected by a decrease in IKZF2 protein levels.

In another aspect, the present disclosure relates to a method of treating cancer comprising the step of administering to a subject in need thereof a therapeutically effective amount of a compound of Formula (I') or Formula (I), or a pharmaceutically acceptable salt, hydrate, solvate, prodrug, stereoisomer, or tautomer thereof, wherein the cancer is a cancer for which the immune response is deficient or an immunogenic cancer.

Another aspect of the present disclosure relates to a compound of Formula (I') or Formula (I), or a pharmaceutically acceptable salt, hydrate, solvate, prodrug, stereoisomer, or tautomer thereof, for use in the manufacture of a medicament for treating a disease or disorder associated with the modulation of IKZF2 protein levels. In one embodiment, the disease or disorder is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiform, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma.

In another aspect, the present disclosure relates to the use of a compound of Formula (I') or Formula (I), or a pharmaceutically acceptable salt, hydrate, solvate, prodrug, stereoisomer, or tautomer thereof, in the treatment of a disease or disorder associated with the modulation of IKZF2 protein levels. In one embodiment, the disease or disorder is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiform, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma.

Another aspect of the present disclosure relates to a compound of Formula (I') or Formula (I), or a pharmaceutically acceptable salt, hydrate, solvate, prodrug, stereoisomer, or tautomer thereof, for use in the manufacture of a medicament for treating a disease or disorder associated with the modulation of IKZF2 protein levels. In one embodiment, the disease or disorder is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, and gastrointestinal stromal tumor (GIST). In another embodiment, the disease or disorder is selected from non-small cell lung cancer (NSCLC), melanoma, triple-negative breast cancer (TNBC), nasopharyngeal cancer (NPC), and microsatellite stable colorectal cancer (mssCRC).

In another aspect, the present disclosure relates to the use of a compound of Formula (I') or Formula (I), or a pharmaceutically acceptable salt, hydrate, solvate, prodrug, stereoisomer, or tautomer thereof, in the treatment of a disease or disorder associated with the modulation of IKZF2 protein levels. In one embodiment, the disease or disorder is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, and gastrointestinal stromal tumor (GIST). In another embodiment, the disease or disorder is selected from non-small cell lung cancer (NSCLC), melanoma, triple-negative breast cancer (TNBC), nasopharyngeal cancer (NPC), and microsatellite stable colorectal cancer (mssCRC).

Another aspect of the present disclosure relates to a compound of Formula (I') or Formula (I), or a pharmaceutically acceptable salt, hydrate, solvate, prodrug, stereoisomer, or tautomer thereof, for use in the manufacture of a medicament for treating a disease or disorder associated with the reduction of IKZF2 protein levels. In one embodiment, the disease or disorder is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiform, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma.

In another aspect, the present disclosure relates to the use of a compound of Formula (I') or Formula (I), or a pharmaceutically acceptable salt, hydrate, solvate, prodrug, stereoisomer, or tautomer thereof, in the treatment of a disease or disorder associated with the reduction of IKZF2 protein levels. In one embodiment, the disease or disorder is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiform, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma.

Another aspect of the present disclosure relates to a compound of Formula (I') or Formula (I), or a pharmaceutically acceptable salt, hydrate, solvate, prodrug, stereoisomer, or tautomer thereof, for use in the manufacture of a medicament for treating a disease or disorder associated with the reduction of IKZF2 protein levels. In one embodiment, the disease or disorder is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, and gastrointestinal stromal tumor (GIST). In another embodiment, the disease or disorder is selected from non-small cell lung cancer (NSCLC), melanoma, triple-negative breast cancer (TNBC), nasopharyngeal cancer (NPC), and microsatellite stable colorectal cancer (mssCRC).

In another aspect, the present disclosure relates to the use of a compound of Formula (I') or Formula (I), or a pharmaceutically acceptable salt, hydrate, solvate, prodrug, stereoisomer, or tautomer thereof, in the treatment of a disease or disorder associated with the reduction of IKZF2 protein levels. In one embodiment, the disease or disorder is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, and gastrointestinal stromal tumor (GIST). In another embodiment, the disease or disorder is selected from non-small cell lung cancer (NSCLC), melanoma, triple-negative breast cancer (TNBC), nasopharyngeal cancer (NPC), and microsatellite stable colorectal cancer (mssCRC).

Another aspect of the present disclosure relates to a compound of Formula (I') or Formula (I), or a pharmaceutically acceptable salt, hydrate, solvate, prodrug, stereoisomer, or tautomer thereof, for use in the manufacture of a medicament for treating a disease or disorder associated with a decrease in IKZF2 protein levels. In one embodiment, the disease or disorder is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiform, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma.

In another aspect, the present disclosure relates to the use of a compound of Formula (I') or Formula (I), or a pharmaceutically acceptable salt, hydrate, solvate, prodrug, stereoisomer, or tautomer thereof, in the treatment of a disease or disorder associated with a decrease in IKZF2 protein levels. In one embodiment, the disease or disorder is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiform, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma.

Another aspect of the present disclosure relates to a compound of Formula (I') or Formula (I), or a pharmaceutically acceptable salt, hydrate, solvate, prodrug, stereoisomer, or tautomer thereof, for use in the manufacture of a medicament for treating a disease or disorder associated with a decrease in IKZF2 protein levels. In one embodiment, the disease or disorder is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, and gastrointestinal stromal tumor (GIST). In another embodiment, the disease or disorder is selected from non-small cell lung cancer (NSCLC), melanoma, triple-negative breast cancer (TNBC), nasopharyngeal cancer (NPC), and microsatellite stable colorectal cancer (mssCRC).

In another aspect, the present disclosure relates to the use of a compound of Formula (I') or Formula (I), or a pharmaceutically acceptable salt, hydrate, solvate, prodrug, stereoisomer, or tautomer thereof, in the treatment of a disease or disorder associated with a decrease in IKZF2 protein levels. In one embodiment, the disease or disorder is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, and gastrointestinal stromal tumor (GIST). In another embodiment, the disease or disorder is selected from non-small cell lung cancer (NSCLC), melanoma, triple-negative breast cancer (TNBC), nasopharyngeal cancer (NPC), and microsatellite stable colorectal cancer (mssCRC).

Another aspect of the present disclosure relates to a method of treating cancer comprising the step of administering to a subject in need thereof a therapeutically effective amount of a compound of Formula (I') or Formula (I), or a pharmaceutically acceptable salt, hydrate, solvate, prodrug, stereoisomer, or tautomer thereof, wherein the cancer is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiforme, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma.

In another aspect, the present disclosure relates to a compound of Formula (I') or Formula (I), or a pharmaceutically acceptable salt, hydrate, solvate, prodrug, stereoisomer, or tautomer thereof, for use in the treatment of cancer, wherein the cancer is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiforme, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma.

Another aspect of the present disclosure relates to a method of treating cancer comprising the step of administering to a subject in need thereof a therapeutically effective amount of a compound of Formula (I') or Formula (I), or a pharmaceutically acceptable salt, hydrate, solvate, prodrug, stereoisomer, or tautomer thereof, wherein the cancer is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, and gastrointestinal stromal tumor (GIST). In another embodiment, the cancer is selected from non-small cell lung cancer (NSCLC), melanoma, triple-negative breast cancer (TNBC), nasopharyngeal cancer (NPC), and microsatellite stable colorectal cancer (mssCRC).

In another aspect, the present disclosure relates to a compound of Formula (I') or Formula (I), or a pharmaceutically acceptable salt, hydrate, solvate, prodrug, stereoisomer, or tautomer thereof, for use in the treatment of cancer, wherein the cancer is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, and gastrointestinal stromal tumor (GIST). In another embodiment, the cancer is selected from non-small cell lung cancer (NSCLC), melanoma, triple-negative breast cancer (TNBC), nasopharyngeal cancer (NPC), and microsatellite stable colorectal cancer (mssCRC).

Another aspect of the present disclosure relates to the use of a compound of Formula (I') or Formula (I), or a pharmaceutically acceptable salt, hydrate, solvate, prodrug, stereoisomer, or tautomer thereof, in the manufacture of a medicament for treating cancer, wherein the cancer is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiforme, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma.

In another aspect, the present disclosure relates to a method of treating a disease or disorder that is affected by the modulation of IKZF2 protein levels comprising the step of administering to a subject in need thereof a therapeutically effective amount of a compound of Formula (I') or Formula (I), or a pharmaceutically acceptable salt, hydrate, solvate, prodrug, stereoisomer, or tautomer thereof, wherein the disease or disorder is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiforme, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma.

Another aspect of the present disclosure relates to the use of a compound of Formula (I') or Formula (I), or a pharmaceutically acceptable salt, hydrate, solvate, prodrug, stereoisomer, or tautomer thereof, in the manufacture of a medicament for treating cancer, wherein the cancer is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, and gastrointestinal stromal tumor (GIST). In another embodiment, the cancer is selected from non-small cell lung cancer (NSCLC), melanoma, triple-negative breast cancer (TNBC), nasopharyngeal cancer (NPC), and microsatellite stable colorectal cancer (mssCRC).

In another aspect, the present disclosure relates to a method of treating a disease or disorder that is affected by the modulation of IKZF2 protein levels comprising the step of administering to a subject in need thereof a therapeutically effective amount of a compound of Formula (I') or Formula (I), or a pharmaceutically acceptable salt, hydrate, solvate, prodrug, stereoisomer, or tautomer thereof, wherein the disease or disorder is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, and gastrointestinal stromal tumor (GIST). In another embodiment, the disease or disorder is selected from non-small cell lung cancer (NSCLC), melanoma, triple-negative breast cancer (TNBC), nasopharyngeal cancer (NPC), and microsatellite stable colorectal cancer (mssCRC).

Another aspect of the present disclosure relates to a method of treating a disease or disorder that is affected by the reduction of IKZF2 protein levels comprising the step of administering to a subject in need thereof a therapeutically effective amount of a compound of Formula (I') or Formula (I), or a pharmaceutically acceptable salt, hydrate, solvate, prodrug, stereoisomer, or tautomer thereof, wherein the disease or disorder is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiforme, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma.

In another aspect, the present disclosure relates to a method of treating a disease or disorder that is affected by a decrease of IKZF2 protein levels comprising the step of administering to a subject in need thereof a therapeutically effective amount of a compound of Formula (I') or Formula (I), or a pharmaceutically acceptable salt, hydrate, solvate, prodrug, stereoisomer, or tautomer thereof, wherein the disease or disorder is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiforme, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma.

Another aspect of the present disclosure relates to a method of treating a disease or disorder that is affected by the reduction of IKZF2 protein levels comprising the step of administering to a subject in need thereof a therapeutically effective amount of a compound of Formula (I') or Formula (I), or a pharmaceutically acceptable salt, hydrate, solvate, prodrug, stereoisomer, or tautomer thereof, wherein the disease or disorder is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, and gastrointestinal stromal tumor (GIST). In another embodiment, the disease or disorder is selected from non-small cell lung cancer (NSCLC), melanoma, triple-negative breast cancer (TNBC), nasopharyngeal cancer (NPC), and microsatellite stable colorectal cancer (mssCRC).

In another aspect, the present disclosure relates to a method of treating a disease or disorder that is affected by a decrease of IKZF2 protein levels comprising the step of administering to a subject in need thereof a therapeutically effective amount of a compound of Formula (I') or Formula (I), or a pharmaceutically acceptable salt, hydrate, solvate, prodrug, stereoisomer, or tautomer thereof, wherein the disease or disorder is selected non-small cell lung cancer (NSCLC), melanoma, triple-negative breast cancer (TNBC), nasopharyngeal cancer (NPC), microsatellite stable colorectal cancer (mssCRC), thymoma, carcinoid, and gastrointestinal stromal tumor (GIST). In another embodiment, the disease or disorder is selected from non-small cell lung cancer (NSCLC), melanoma, triple-negative breast cancer (TNBC), nasopharyngeal cancer (NPC), and microsatellite stable colorectal cancer (mssCRC).

In another aspect, the present disclosure relates to a compound of Formula (I') or Formula (I), or a pharmaceutically acceptable salt, hydrate, solvate, prodrug, stereoisomer, or tautomer thereof, for use in the treatment of a disease or disorder that is affected by the modulation of IKZF2 protein levels wherein the disease or disorder is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiforme, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma.

In another aspect, the present disclosure relates to a compound of Formula (I') or Formula (I), or a pharmaceutically acceptable salt, hydrate, solvate, prodrug, stereoisomer, or tautomer thereof, for use in the treatment of a disease or disorder that is affected by the modulation of IKZF2 protein levels wherein the disease or disorder is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, and gastrointestinal stromal tumor (GIST). In another embodiment, the disease or disorder is selected from non-small cell lung cancer (NSCLC), melanoma, triple-negative breast cancer (TNBC), nasopharyngeal cancer (NPC), and microsatellite stable colorectal cancer (mssCRC).

Another aspect of the present disclosure relates to a compound of Formula (I') or Formula (I), or a pharmaceutically acceptable salt, hydrate, solvate, prodrug, stereoisomer, or tautomer thereof, for use in the treatment of a disease or disorder that is affected by the reduction of IKZF2 protein levels wherein the disease or disorder is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiforme, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma.

In another aspect, the present disclosure relates to a compound of Formula (I') or Formula (I), or a pharmaceutically acceptable salt, hydrate, solvate, prodrug, stereoisomer, or tautomer thereof, for use in the treatment of a disease or disorder that is affected by a decrease of IKZF2 protein levels wherein the disease or disorder is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiforme, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma.

In another aspect, the present disclosure relates to the use of a compound of Formula (I') or Formula (I), or a pharmaceutically acceptable salt, hydrate, solvate, prodrug, stereoisomer, or tautomer thereof, in the manufacture of a medicament for treating a disease or disorder that is affected by the modulation of IKZF2 levels, wherein the disease or disorder is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiforme, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma.

Another aspect of the present disclosure relates to the use of a compound of Formula (I') or Formula (I), or a pharmaceutically acceptable salt, hydrate, solvate, prodrug, stereoisomer, or tautomer thereof, in the manufacture of a medicament for treating a disease or disorder that is affected by the reduction of IKZF2 protein levels, wherein the disease or disorder is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiforme, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma.

Another aspect of the present disclosure relates to a compound of Formula (I') or Formula (I), or a pharmaceutically acceptable salt, hydrate, solvate, prodrug, stereoisomer, or tautomer thereof, for use in the treatment of a disease or disorder that is affected by the reduction of IKZF2 protein levels wherein the disease or disorder is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, and gastrointestinal stromal tumor (GIST). In another embodiment, the disease or disorder is selected from non-small cell lung cancer (NSCLC), melanoma, triple-negative breast cancer (TNBC), nasopharyngeal cancer (NPC), and microsatellite stable colorectal cancer (mssCRC).

In another aspect, the present disclosure relates to a compound of Formula (I') or Formula (I), or a pharmaceutically acceptable salt, hydrate, solvate, prodrug, stereoisomer, or tautomer thereof, for use in the treatment of a disease or disorder that is affected by a decrease of IKZF2 protein levels wherein the disease or disorder is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, and gastrointestinal stromal tumor (GIST). In another embodiment, the disease or disorder is selected from non-small cell lung cancer (NSCLC), melanoma, triple-negative breast cancer (TNBC), nasopharyngeal cancer (NPC), and microsatellite stable colorectal cancer (mssCRC).

In another aspect, the present disclosure relates to the use of a compound of Formula (I') or Formula (I), or a pharmaceutically acceptable salt, hydrate, solvate, prodrug, stereoisomer, or tautomer thereof, in the manufacture of a medicament for treating a disease or disorder that is affected by the modulation of IKZF2 levels, wherein the disease or disorder is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, and gastrointestinal stromal tumor (GIST). In another embodiment, the disease or disorder is selected from non-small cell lung cancer (NSCLC), melanoma, triple-negative breast cancer (TNBC), nasopharyngeal cancer (NPC), and microsatellite stable colorectal cancer (mssCRC).

Another aspect of the present disclosure relates to the use of a compound of Formula (I') or Formula (I), or a pharmaceutically acceptable salt, hydrate, solvate, prodrug, stereoisomer, or tautomer thereof, in the manufacture of a medicament for treating a disease or disorder that is affected by the reduction of IKZF2 protein levels, wherein the disease or disorder is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, and gastrointestinal stromal tumor (GIST). In another embodiment, the disease or disorder is selected from non-small cell lung cancer (NSCLC), melanoma, triple-negative breast cancer (TNBC), nasopharyngeal cancer (NPC), and microsatellite stable colorectal cancer (mssCRC).

In another aspect, the present disclosure relates to the use of a compound of Formula (I') or Formula (I), or a pharmaceutically acceptable salt, hydrate, solvate, prodrug, stereoisomer, or tautomer thereof, in the manufacture of a medicament for treating a disease or disorder that is affected by a decrease in IKZF2 protein levels, wherein the disease or disorder is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiforme, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma.

In another aspect, the present disclosure relates to the use of a compound of Formula (I') or Formula (I), or a pharmaceutically acceptable salt, hydrate, solvate, prodrug, stereoisomer, or tautomer thereof, in the manufacture of a medicament for treating a disease or disorder that is affected by a decrease in IKZF2 protein levels, wherein the disease or disorder is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, and gastrointestinal stromal tumor (GIST). In another embodiment, the disease or disorder is selected from non-small cell lung cancer (NSCLC), melanoma, triple-negative breast cancer (TNBC), nasopharyngeal cancer (NPC), and microsatellite stable colorectal cancer (mssCRC).

In another aspect, the present disclosure relates to a method of treating a disease or disorder that is affected by the modulation of IKZF2 protein levels comprising the step of administering to a subject in need thereof a therapeutically effective amount of a compound of Formula (I') or Formula (I), or a pharmaceutically acceptable salt, hydrate, solvate, prodrug, stereoisomer, or tautomer thereof, wherein the disease or disorder is a cancer for which the immune response is deficient or an immunogenic cancer.

Another aspect of the present disclosure relates to a method of treating a disease or disorder that is affected by the reduction of IKZF2 protein levels comprising the step of administering to a subject in need thereof a therapeutically effective amount of a compound of Formula (I') or Formula (I), or a pharmaceutically acceptable salt, hydrate, solvate, prodrug, stereoisomer, or tautomer thereof, wherein the disease or disorder is a cancer for which the immune response is deficient or an immunogenic cancer.

In another aspect, the present disclosure relates to a method of treating a disease or disorder that is affected by a decrease in IKZF2 protein levels comprising the step of administering to a subject in need thereof a therapeutically effective amount of a compound of Formula (I') or Formula (I), or a pharmaceutically acceptable salt, hydrate, solvate, prodrug, stereoisomer, or tautomer thereof, wherein the disease or disorder is a cancer for which the immune response is deficient or an immunogenic cancer.

In another aspect, the present disclosure relates to a compound of Formula (I') or Formula (I), or a pharmaceutically acceptable salt, hydrate, solvate, prodrug, stereoisomer, or tautomer thereof, for use in the treatment of a disease or disorder that is affected by the modulation of IKZF2 protein levels, wherein the disease or disorder is a cancer for which the immune response is deficient or an immunogenic cancer.

Another aspect of the present disclosure relates to a compound of Formula (I') or Formula (I), or a pharmaceutically acceptable salt, hydrate, solvate, prodrug, stereoisomer, or tautomer thereof, for use in the treatment of a disease or disorder that is affected by the reduction of IKZF2 protein levels, wherein the disease or disorder is a cancer for which the immune response is deficient or an immunogenic cancer.

In another aspect, the present disclosure relates to a compound of Formula (I') or Formula (I), or a pharmaceutically acceptable salt, hydrate, solvate, prodrug, stereoisomer, or tautomer thereof, for use in the treatment of a disease or disorder that is affected by a decrease in IKZF2 protein levels, wherein the disease or disorder is a cancer for which the immune response is deficient or an immunogenic cancer.

In another aspect, the present disclosure relates to the use of a compound of Formula (I') or Formula (I), or a pharmaceutically acceptable salt, hydrate, solvate, prodrug, stereoisomer, or tautomer thereof, in the manufacture of a medicament for treating a disease or disorder that is affected by the modulation of IKZF2 protein levels wherein the disease or disorder is a cancer for which the immune response is deficient or an immunogenic cancer.

Another aspect of the present disclosure relates to the use of a compound of Formula (I') or Formula (I), or a pharmaceutically acceptable salt, hydrate, solvate, prodrug, stereoisomer, or tautomer thereof, in the manufacture of a medicament for treating a disease or disorder that is affected by the reduction of IKZF2 protein levels wherein the disease or disorder is a cancer for which the immune response is deficient or an immunogenic cancer.

In another aspect, the present disclosure relates to the use of a compound of Formula (I') or Formula (I), or a pharmaceutically acceptable salt, hydrate, solvate, prodrug, stereoisomer, or tautomer thereof, in the manufacture of a medicament for treating a disease or disorder that is affected by a decrease in IKZF2 protein levels wherein the disease or disorder is a cancer for which the immune response is deficient or an immunogenic cancer.

In another aspect, the present disclosure relates to a method of treating cancer comprising the step of administering to a subject in need thereof a therapeutically effective amount of a compound of Formula (I') or Formula (I), or a pharmaceutically acceptable salt, hydrate, solvate, prodrug, stereoisomer, or tautomer thereof, wherein the cancer is a cancer for which the immune response is deficient or an immunogenic cancer.

Another aspect of the present disclosure relates to a compound of Formula (I') or Formula (I), or a pharmaceutically acceptable salt, hydrate, solvate, prodrug, stereoisomer, or tautomer thereof, for use in the treatment of a cancer for which the immune response is deficient or an immunogenic cancer.

In another aspect, the present disclosure relates to the use of a compound of Formula (I') or Formula (I), or a pharmaceutically acceptable salt, hydrate, solvate, prodrug, stereoisomer, or tautomer thereof, in the manufacture of a medicament for treating a cancer for which the immune response is deficient or an immunogenic cancer.

Another aspect of the present disclosure relates to a method of treating an IKZF2-dependent disease or disorder by modulating IKZF2 protein levels comprising the step of administering to a subject in need thereof a therapeutically effective amount of a compound of Formula (I') or Formula (I), or a pharmaceutically acceptable salt, hydrate, solvate, prodrug, stereoisomer, or tautomer thereof, wherein modulation of IKZF2 protein levels treats the IKZF2-dependent disease or disorder.

In another aspect, the present disclosure relates to a method of treating an IKZF2-dependent disease or disorder by reducing IKZF2 protein levels comprising the step of administering to a subject in need thereof a therapeutically effective amount of a compound of Formula (I') or Formula (I), or a pharmaceutically acceptable salt, hydrate, solvate, prodrug, stereoisomer, or tautomer thereof, wherein reduction of IKZF2 protein levels treats the IKZF2-dependent disease or disorder.

Another aspect of the present disclosure relates to a method of treating an IKZF2-dependent disease or disorder by decreasing IKZF2 protein levels comprising the step of administering to a subject in need thereof a therapeutically effective amount of a compound of Formula (I') or Formula (I), or a pharmaceutically acceptable salt, hydrate, solvate, prodrug, stereoisomer, or tautomer thereof, wherein the decrease in IKZF2 protein levels treats the IKZF2-dependent disease or disorder.

Another aspect of the present disclosure relates to a method of treating an IKZF2-dependent disease or disorder by modulating IKZF2 protein levels comprising the step of administering to a subject in need thereof a pharmaceutical composition comprising a therapeutically effective amount of a compound of Formula (I') or Formula (I), or a pharmaceutically acceptable salt, hydrate, solvate, prodrug, stereoisomer, or tautomer thereof, wherein modulation of IKZF2 protein levels treats the IKZF2-dependent disease or disorder.

In another aspect, the present disclosure relates to a method of treating an IKZF2-dependent disease or disorder by reducing IKZF2 protein levels comprising the step of administering to a subject in need thereof a pharmaceutical composition comprising a therapeutically effective amount of a compound of Formula (I') or Formula (I), or a pharmaceutically acceptable salt, hydrate, solvate, prodrug, stereoisomer, or tautomer thereof, wherein reduction of IKZF2 protein levels treats the IKZF2-dependent disease or disorder.

Another aspect of the present disclosure relates to a method of treating an IKZF2-dependent disease or disorder by decreasing IKZF2 protein levels comprising the step of administering to a subject in need thereof a pharmaceutical composition comprising a therapeutically effective amount of a compound of Formula (I') or Formula (I), or a pharmaceutically acceptable salt, hydrate, solvate, prodrug, stereoisomer, or tautomer thereof, wherein the decrease in IKZF2 protein levels treats the IKZF2-dependent disease or disorder.

In another aspect, the present disclosure relates to a pharmaceutical composition comprising a therapeutically effective amount of a compound of Formula (I') or Formula (I), or a pharmaceutically acceptable salt, hydrate, solvate, prodrug, stereoisomer, or tautomer thereof, for use in the treatment of an IKZF2-dependent disease or disorder by reducing IKZF2 protein levels wherein reduction of IKZF2 protein levels treats the IKZF2-dependent disease or disorder.

Another aspect of the present disclosure relates to a compound of Formula (I') or Formula (I), or a pharmaceutically acceptable salt, hydrate, solvate, prodrug, stereoisomer, or tautomer thereof, for use in the treatment of an IKZF2-dependent disease or disorder by reducing IKZF2 protein levels wherein reduction of IKZF2 protein levels treats the IKZF2-dependent disease or disorder.

In another aspect, the present disclosure relates to a pharmaceutical composition comprising a therapeutically effective amount of a compound of Formula (I') or Formula (I), or a pharmaceutically acceptable salt, hydrate, solvate, prodrug, stereoisomer, or tautomer thereof, for use in the treatment of an IKZF2-dependent disease or disorder by modulating IKZF2 protein levels wherein modulation of IKZF2 protein levels treats the IKZF2-dependent disease or disorder.

Another aspect of the present disclosure relates to a compound of Formula (I') or Formula (I), or a pharmaceutically acceptable salt, hydrate, solvate, prodrug, stereoisomer, or tautomer thereof, for use in the treatment of an IKZF2-dependent disease or disorder by modulating IKZF2 protein levels wherein modulation of IKZF2 protein levels treats the IKZF2-dependent disease or disorder.

In another aspect, the present disclosure relates to a pharmaceutical composition comprising a therapeutically effective amount of a compound of Formula (I') or Formula (I), or a pharmaceutically acceptable salt, hydrate, solvate, prodrug, stereoisomer, or tautomer thereof, for use in the treatment of an IKZF2-dependent disease or disorder by decreasing IKZF2 protein levels wherein the decrease in IKZF2 protein levels treats the IKZF2-dependent disease or disorder.

Another aspect of the present disclosure relates to a compound of Formula (I') or Formula (I), or a pharmaceutically acceptable salt, hydrate, solvate, prodrug, stereoisomer, or tautomer thereof, for use in the treatment of an IKZF2-dependent disease or disorder by decreasing IKZF2 protein levels wherein the decrease in IKZF2 protein levels treats the IKZF2-dependent disease or disorder.

In another aspect, the present disclosure relates to the use of a compound of Formula (I') or Formula (I), or a pharmaceutically acceptable salt, hydrate, solvate, prodrug, stereoisomer, or tautomer thereof, in the treatment of an IKZF2-dependent disease or disorder by reducing IKZF2 protein levels wherein reduction of IKZF2 protein levels treats the IKZF2-dependent disease or disorder.

Another aspect of the present disclosure relates to the use of a pharmaceutical composition comprising a therapeutically effective amount of a compound of Formula (I') or Formula (I), or a pharmaceutically acceptable salt, hydrate, solvate, prodrug, stereoisomer, or tautomer thereof, in the treatment of an IKZF2-dependent disease or disorder by reducing IKZF2 protein levels wherein reduction of IKZF2 protein levels treats the IKZF2-dependent disease or disorder.

In another aspect, the present disclosure relates to the use of a compound of Formula (I') or Formula (I), or a pharmaceutically acceptable salt, hydrate, solvate, prodrug, stereoisomer, or tautomer thereof, in the treatment of an IKZF2-dependent disease or disorder by modulating IKZF2 protein levels wherein modulation of IKZF2 protein levels treats the IKZF2-dependent disease or disorder.

Another aspect of the present disclosure relates to the use of a pharmaceutical composition comprising a therapeutically effective amount of a compound of Formula (I') or Formula (I), or a pharmaceutically acceptable salt, hydrate, solvate, prodrug, stereoisomer, or tautomer thereof, in the treatment of an IKZF2-dependent disease or disorder by modulating IKZF2 protein levels wherein modulation of IKZF2 protein levels treats the IKZF2-dependent disease or disorder.

In another aspect, the present disclosure relates to the use of a compound of Formula (I') or Formula (I), or a pharmaceutically acceptable salt, hydrate, solvate, prodrug, stereoisomer, or tautomer thereof, in the treatment of an IKZF2-dependent disease or disorder by decreasing IKZF2 protein levels wherein the decrease in IKZF2 protein levels treats the IKZF2-dependent disease or disorder.

Another aspect of the present disclosure relates to the use of a pharmaceutical composition comprising a therapeutically effective amount of a compound of Formula (I') or Formula (I), or a pharmaceutically acceptable salt, hydrate, solvate, prodrug, stereoisomer, or tautomer thereof, in the treatment of an IKZF2-dependent disease or disorder by decreasing IKZF2 protein levels wherein the decrease in IKZF2 protein levels treats the IKZF2-dependent disease or disorder.

Another aspect of the present disclosure relates to a method of treating a disease or disorder by reducing IKZF2 protein levels comprising the step of administering to a subject in need thereof a pharmaceutical composition comprising a therapeutically effective amount of a compound of Formula (I') or Formula (I), or a pharmaceutically acceptable salt, hydrate, solvate, prodrug, stereoisomer, or tautomer thereof, wherein reduction of IKZF2 protein levels treats the disease or disorder.

In another aspect, the present disclosure relates to a method of treating a disease or disorder by reducing IKZF2 protein levels comprising the step of administering to a subject in need thereof a compound of Formula (I') or Formula (I), or a pharmaceutically acceptable salt, hydrate, solvate, prodrug, stereoisomer, or tautomer thereof, wherein reduction of IKZF2 protein levels treats the disease or disorder.

Another aspect of the present disclosure relates to a method of treating a disease or disorder by modulating IKZF2 protein levels comprising the step of administering to a subject in need thereof a pharmaceutical composition comprising a therapeutically effective amount of a compound of Formula (I') or Formula (I), or a pharmaceutically acceptable salt, hydrate, solvate, prodrug, stereoisomer, or tautomer thereof, wherein modulation of IKZF2 protein levels treats the disease or disorder.

In another aspect, the present disclosure relates to a method of treating a disease or disorder by modulating IKZF2 protein levels comprising the step of administering to a subject in need thereof a compound of Formula (I') or Formula (I), or a pharmaceutically acceptable salt, hydrate, solvate, prodrug, stereoisomer, or tautomer thereof, wherein modulation of IKZF2 protein levels treats the disease or disorder.

Another aspect of the present disclosure relates to a method of treating a disease or disorder by decreasing IKZF2 protein levels comprising the step of administering to a subject in need thereof a pharmaceutical composition comprising a therapeutically effective amount of a compound of Formula (I') or Formula (I), or a pharmaceutically acceptable salt, hydrate, solvate, prodrug, stereoisomer, or tautomer thereof, wherein decreasing IKZF2 protein levels treats the disease or disorder.

In another aspect, the present disclosure relates to a method of treating a disease or disorder by decreasing IKZF2 protein levels comprising the step of administering to a subject in need thereof a compound of Formula (I') or Formula (I), or a pharmaceutically acceptable salt, hydrate, solvate, prodrug, stereoisomer, or tautomer thereof, wherein decreasing IKZF2 protein levels treats the disease or disorder.

Another aspect of the present disclosure relates to a compound of Formula (I') or Formula (I), or a pharmaceutically acceptable salt, hydrate, solvate, prodrug, stereoisomer, or tautomer thereof, for use in the treatment of an IKZF2-dependent disease or disorder by reducing IKZF2 protein levels wherein reduction of IKZF2 protein levels treats the IKZF2-dependent disease or disorder.

In another aspect, the present disclosure relates to a pharmaceutical composition comprising a therapeutically effective amount of a compound of Formula (I') or Formula (I), or a pharmaceutically acceptable salt, hydrate, solvate, prodrug, stereoisomer, or tautomer thereof, for use in the treatment of an IKZF2-dependent disease or disorder by reducing IKZF2 protein levels wherein reduction of IKZF2 protein levels treats the IKZF2-dependent disease or disorder.

Another aspect of the present disclosure relates to a pharmaceutical composition comprising a therapeutically effective amount of a compound of Formula (I') or Formula (I), or a pharmaceutically acceptable salt, hydrate, solvate, prodrug, stereoisomer, or tautomer thereof, for use in the treatment of an IKZF2-dependent disease or disorder by modulating IKZF2 protein levels wherein modulation of IKZF2 protein levels treats the IKZF2-dependent disease or disorder.

In another aspect, the present disclosure relates a compound of Formula (I') or Formula (I), or a pharmaceutically acceptable salt, hydrate, solvate, prodrug, stereoisomer, or tautomer thereof, for use in the treatment of an IKZF2-dependent disease or disorder by modulating IKZF2 protein levels wherein modulation of IKZF2 protein levels treats the IKZF2-dependent disease or disorder.

Another aspect of the present disclosure relates to a pharmaceutical composition comprising a therapeutically effective amount of a compound of Formula (I') or Formula (I), or a pharmaceutically acceptable salt, hydrate, solvate, prodrug, stereoisomer, or tautomer thereof, for use in the treatment of an IKZF2-dependent disease or disorder by decreasing IKZF2 protein levels wherein decreasing IKZF2 protein levels treats the IKZF2-dependent disease or disorder.

In another aspect, the present disclosure relates a compound of Formula (I') or Formula (I), or a pharmaceutically acceptable salt, hydrate, solvate, prodrug, stereoisomer, or tautomer thereof, for use in the treatment of an IKZF2-dependent disease or disorder by decreasing IKZF2 protein levels wherein decreasing IKZF2 protein levels treats the IKZF2-dependent disease or disorder.

Another aspect of the present disclosure relates to a compound of Formula (I') or Formula (I), or a pharmaceutically acceptable salt, hydrate, solvate, prodrug, stereoisomer, or tautomer thereof, for use in the treatment of a disease or disorder by reducing IKZF2 protein levels, wherein reduction of IKZF2 protein levels treats the disease or disorder.

In another aspect, the present disclosure relates to a pharmaceutical composition comprising a therapeutically effective amount of a compound of Formula (I') or Formula (I), or a pharmaceutically acceptable salt, hydrate, solvate, prodrug, stereoisomer, or tautomer thereof, for use in the treatment of a disease or disorder by reducing IKZF2 protein levels wherein reduction of IKZF2 protein levels treats the disease or disorder.

Another aspect of the present disclosure relates to a compound of Formula (I') or Formula (I), or a pharmaceutically acceptable salt, hydrate, solvate, prodrug, stereoisomer, or tautomer thereof, for use in the treatment of a disease or disorder by modulating IKZF2 protein levels, wherein modulation of IKZF2 protein levels treats the disease or disorder.

In another aspect, the present disclosure relates to a pharmaceutical composition comprising a therapeutically effective amount of a compound of Formula (I') or Formula (I), or a pharmaceutically acceptable salt, hydrate, solvate, prodrug, stereoisomer, or tautomer thereof, for use in the treatment of a disease or disorder by modulating IKZF2 protein levels wherein modulation of IKZF2 protein levels treats the disease or disorder.

Another aspect of the present disclosure relates to a compound of Formula (I') or Formula (I), or a pharmaceutically acceptable salt, hydrate, solvate, prodrug, stereoisomer, or tautomer thereof, for use in the treatment of a disease or disorder by decreasing IKZF2 protein levels, wherein decreasing IKZF2 protein levels treats the disease or disorder.

In another aspect, the present disclosure relates to a pharmaceutical composition comprising a therapeutically effective amount of a compound of Formula (I') or Formula (I), or a pharmaceutically acceptable salt, hydrate, solvate, prodrug, stereoisomer, or tautomer thereof, for use in the treatment of a disease or disorder by decreasing IKZF2 protein levels wherein decreasing IKZF2 protein levels treats the disease or disorder.

Another aspect of the present disclosure relates to the use of a compound of Formula (I') or Formula (I), or a pharmaceutically acceptable salt, hydrate, solvate, prodrug, stereoisomer, or tautomer thereof, in the manufacture of a medicament for treating a IKZF2-dependent disease or disorder by reducing IKZF2 protein levels, wherein reduction of IKZF2 protein levels treats the IKZF2-dependent disease or disorder.

In another aspect, the present disclosure relates to the use of a pharmaceutical composition comprising a therapeutically effective amount of a compound of Formula (I') or Formula (I), or a pharmaceutically acceptable salt, hydrate, solvate, prodrug, stereoisomer, or tautomer thereof, in the manufacture of a medicament for treating a IKZF2-dependent disease or disorder by reducing IKZF2 protein levels, wherein reduction of IKZF2 protein levels treats the IKZF2-dependent disease or disorder.

Another aspect of the present disclosure relates to the use of a compound of Formula (I') or Formula (I), or a pharmaceutically acceptable salt, hydrate, solvate, prodrug, stereoisomer, or tautomer thereof, in the manufacture of a medicament for treating a IKZF2-dependent disease or disorder by modulating IKZF2 protein levels, wherein modulation of IKZF2 protein levels treats the IKZF2-dependent disease or disorder.

In another aspect, the present disclosure relates to the use of a pharmaceutical composition comprising a therapeutically effective amount of a compound of Formula (I') or Formula (I), or a pharmaceutically acceptable salt, hydrate, solvate, prodrug, stereoisomer, or tautomer thereof, in the manufacture of a medicament for treating a IKZF2-dependent disease or disorder by modulating IKZF2 protein levels, wherein modulation of IKZF2 protein levels treats the IKZF2-dependent disease or disorder.

Another aspect of the present disclosure relates to the use of a compound of Formula (I') or Formula (I), or a pharmaceutically acceptable salt, hydrate, solvate, prodrug, stereoisomer, or tautomer thereof, in the manufacture of a medicament for treating a IKZF2-dependent disease or disorder by decreasing IKZF2 protein levels, wherein decreasing IKZF2 protein levels treats the IKZF2-dependent disease or disorder.

In another aspect, the present disclosure relates to the use of a pharmaceutical composition comprising a therapeutically effective amount of a compound of Formula (I') or Formula (I), or a pharmaceutically acceptable salt, hydrate, solvate, prodrug, stereoisomer, or tautomer thereof, in the manufacture of a medicament for treating a IKZF2-dependent disease or disorder by decreasing IKZF2 protein levels, wherein decreasing IKZF2 protein levels treats the IKZF2-dependent disease or disorder.

Another aspect of the present disclosure relates to the use of a compound of Formula (I') or Formula (I), or a pharmaceutically acceptable salt, hydrate, solvate, prodrug, stereoisomer, or tautomer thereof, in the manufacture of a medicament for treating a disease or disorder by reducing IKZF2 protein levels, wherein reduction of IKZF2 protein levels treats the disease or disorder.

In another aspect, the present disclosure relates to the use of a pharmaceutical composition comprising a therapeutically effective amount of a compound of Formula (I') or Formula (I), or a pharmaceutically acceptable salt, hydrate, solvate, prodrug, stereoisomer, or tautomer thereof, in the manufacture of a medicament for treating a disease or disorder by reducing IKZF2 protein levels, wherein reduction of IKZF2 protein levels treats the disease or disorder.

Another aspect of the present disclosure relates to the use of a compound of Formula (I') or Formula (I), or a pharmaceutically acceptable salt, hydrate, solvate, prodrug, stereoisomer, or tautomer thereof, in the manufacture of a medicament for treating a disease or disorder by modulating IKZF2 protein levels, wherein modulation of IKZF2 protein levels treats the disease or disorder.

In another aspect, the present disclosure relates to the use of a pharmaceutical composition comprising a therapeutically effective amount of a compound of Formula (I') or Formula (I), or a pharmaceutically acceptable salt, hydrate, solvate, prodrug, stereoisomer, or tautomer thereof, in the manufacture of a medicament for treating a disease or disorder by modulating IKZF2 protein levels, wherein modulation of IKZF2 protein levels treats the disease or disorder.

Another aspect of the present disclosure relates to the use of a compound of Formula (I') or Formula (I), or a pharmaceutically acceptable salt, hydrate, solvate, prodrug, stereoisomer, or tautomer thereof, in the manufacture of a medicament for treating a disease or disorder by decreasing IKZF2 protein levels, wherein decreasing IKZF2 protein levels treats the disease or disorder.

In another aspect, the present disclosure relates to the use of a pharmaceutical composition comprising a therapeutically effective amount of a compound of Formula (I') or Formula (I), or a pharmaceutically acceptable salt, hydrate, solvate, prodrug, stereoisomer, or tautomer thereof, in the manufacture of a medicament for treating a disease or disorder by decreasing IKZF2 protein levels, wherein decreasing IKZF2 protein levels treats the disease or disorder.

Another aspect of the present disclosure relates to a compound of Formula (I') or Formula (I), or a pharmaceutically acceptable salt, hydrate, solvate, prodrug, stereoisomer, or tautomer thereof, for use in the treatment of a disease or disorder by reducing IKZF2 protein levels wherein reduction of IKZF2 protein levels treats the disease or disorder.

In another aspect, the present disclosure relates to a compound of Formula (I') or Formula (I), or a pharmaceutically acceptable salt, hydrate, solvate, prodrug, stereoisomer, or tautomer thereof, for use in the treatment of a disease or disorder by modulating IKZF2 protein levels wherein modulation of IKZF2 protein levels treats the disease or disorder.

Another aspect of the present disclosure relates to a compound of Formula (I') or Formula (I), or a pharmaceutically acceptable salt, hydrate, solvate, prodrug, stereoisomer, or tautomer thereof, for use in the treatment of a disease or disorder by decreasing IKZF2 protein levels wherein decreasing IKZF2 protein levels treats the disease or disorder.

Another aspect of the present disclosure relates to the use of a compound of Formula (I') or Formula (I), or a pharmaceutically acceptable salt, hydrate, solvate, prodrug, stereoisomer, or tautomer thereof, in the treatment of a disease or disorder by reducing IKZF2 protein levels, wherein reduction of IKZF2 protein levels treats the disease or disorder.

In another aspect, the present disclosure relates to the use of a compound of Formula (I') or Formula (I), or a pharmaceutically acceptable salt, hydrate, solvate, prodrug, stereoisomer, or tautomer thereof, in the treatment of a disease or disorder by modulating IKZF2 protein levels, wherein modulation of IKZF2 protein levels treats the disease or disorder.

Another aspect of the present disclosure relates to the use of a compound of Formula (I') or Formula (I), or a pharmaceutically acceptable salt, hydrate, solvate, prodrug, stereoisomer, or tautomer thereof, in the treatment of a disease or disorder by decreasing IKZF2 protein levels, wherein decreasing of IKZF2 protein levels treats the disease or disorder.

In another aspect of the disclosure, the compounds according to the disclosure are formulated into pharmaceutical compositions comprising an effective amount, preferably a pharmaceutically effective amount, of a compound according to the disclosure or salt, hydrate, solvate, prodrug, stereoisomer, or tautomer thereof, and a pharmaceutically acceptable excipient or carrier.

Another aspect of the present disclosure relates to the use of a compound of Formula (I') or Formula (I), or a pharmaceutically acceptable salt, hydrate, solvate, prodrug, stereoisomer, or tautomer thereof, in the manufacture of a medicament for treating an IKZF2-dependent disease or disorder.

In another aspect, the present disclosure relates to a compound of Formula (I') or Formula (I), or a pharmaceutically acceptable salt, hydrate, solvate, prodrug, stereoisomer, or tautomer thereof, for use in the manufacture of a medicament for treating a disease associated with modulating IKZF2 protein levels.

Another aspect of the present disclosure relates to the use of a compound of Formula (I') or Formula (I), or a pharmaceutically acceptable salt, hydrate, solvate, prodrug, stereoisomer, or tautomer thereof, in the treatment of a disease associated with the modulation of IKZF2 protein levels.

In some embodiments of the methods disclosed herein, the administration of the compound of Formula (I') or Formula (I), or a pharmaceutically acceptable salt, hydrate, solvate, prodrug, stereoisomer, or tautomer thereof, is performed orally, parentally, subcutaneously, by injection, or by infusion.

The present disclosure provides degraders of IKZF2 that are therapeutic agents in the treatment of diseases such as cancer and metastasis, in the treatment of diseases affected by the modulation of IKZF2 protein levels, and in the treatment IKZF2-dependent diseases or disorders.

In one embodiment, the disease or disorder that can be treated by the compounds of the present disclosure is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, gastrointestinal stromal tumor (GIST), prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiform, glioma, thyroid cancer, parathyroid tumor, nasopharyngeal cancer, tongue cancer, pancreatic cancer, esophageal cancer, cholangiocarcinoma, gastric cancer, soft tissue sarcomas, rhabdomyosarcoma (RMS), synovial sarcoma, osteosarcoma, rhabdoid cancers, and Ewing's sarcoma. In another embodiment, the IKZF2-dependent disease or disorder is a cancer for which the immune response is deficient or an immunogenic cancer.

The present disclosure provides agents with novel mechanisms of action toward IKZF2 proteins in the treatment of various types of diseases including cancer and metastasis, in the treatment of diseases affected by the modulation of IKZF2 protein levels, and in the treatment IKZF2-dependent diseases or disorders. Ultimately the present disclosure provides the medical community with a novel pharmacological strategy for the treatment of diseases and disorders associated with IKZF2 proteins.

The present disclosure provides agents with novel mechanisms of action toward IKZF2 proteins in the treatment of various types of diseases including cancer and metastasis, in the treatment of diseases affected by the modulation of IKZF2 protein levels, and in the treatment IKZF2-dependent diseases or disorders. Ultimately the present disclosure provides the medical community with a novel pharmacological strategy for the treatment of diseases and disorders associated with IKZF2 proteins.

DETAILED DESCRIPTION OF THE DISCLOSURE

Figure 1:
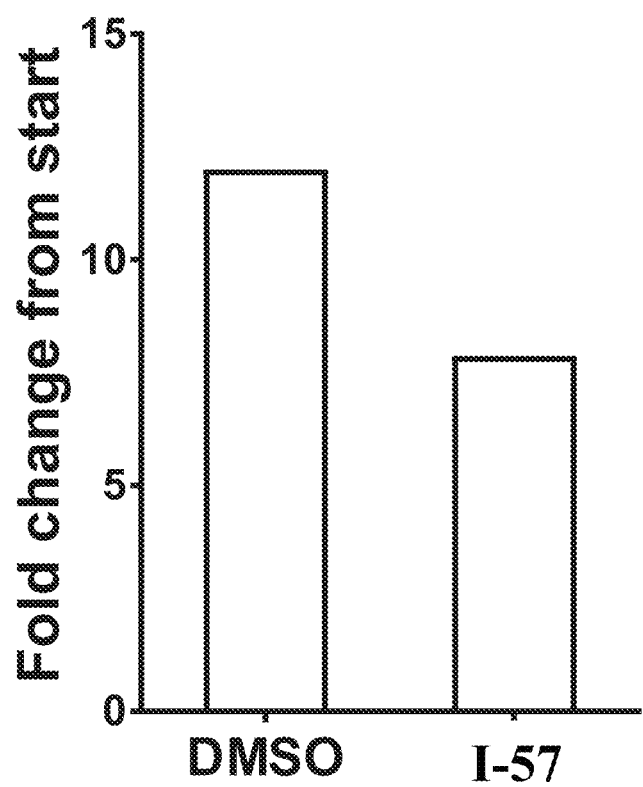
FIG. 1. is a bar graph showing the effects on cell expansion in purified primary human Treg cells when treated with DMSO (Control) or Compound I-57. The results in FIG. 1 show that the expansion of purified Treg cells is impaired when treated with Compound I-57 as compared to the control.

The present disclosure relates to compounds and compositions that are capable of modulating IKZF2 protein levels. The disclosure features methods of treating, preventing, or ameliorating a disease or disorder in which IKZF2 plays a role by administering to a patient in need thereof a therapeutically effective amount of a compound of Formula (I') or Formula (I), or a pharmaceutically acceptable salt, hydrate, solvate, prodrug, stereoisomer, or tautomer thereof. The methods of the present disclosure can be used in the treatment of a variety of IKZF2-dependent diseases and disorders by modulating IKZF2 protein levels. Modulation of IKZF2 protein levels through degradation provides a novel approach to the treatment, prevention, or amelioration of diseases including, but not limited to, cancer and metathesis, and other IKZF2-dependent diseases or disorders.

In one aspect, the compounds of the disclosure have use as therapeutic agents, particularly for cancers and related diseases. In one aspect, the compounds of the disclosure have IKZF2 degradation activity, preferably having such activity at or below the 50 μM level, and more preferably having such activity at or below the 10 μM level. In another aspect, the compounds of the disclosure have degrader activity for IKZF2 that is selective over one or more of IKZF1, IKZF3, IKZF4, and/or IKZF5. In another aspect, the compounds of the disclosure have degrader activity for both IKZF2 and IKZF4. The compounds of the disclosure have usefulness in treating cancer and other diseases for which such degradation activity would be beneficial for the patient. For example, while not intending to be bound by any theory, the inventors believe that reducing levels of IKZF2 in Tregs in a tumor may allow the patient immune system to more effectively attack the disease. In summary, the present disclosure provides novel IKZF2 degraders useful for the treatment of cancer and other diseases.

In a first aspect of the disclosure, the compounds of Formula (I') are described:

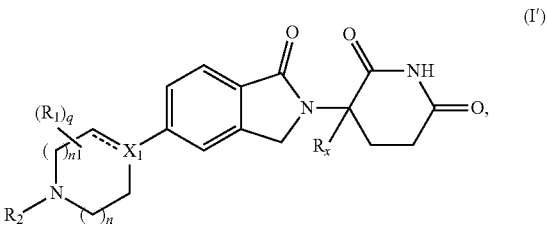

or pharmaceutically acceptable salts, hydrates, solvates, prodrugs, stereoisomers, and tautomers thereof, wherein $R_1$, $R_2$, $R_x$, $X_1$, n, n1, and q are as described herein above.

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

Definition of Terms and Conventions Used

Terms not specifically defined herein should be given the meanings that would be given to them by one of skill in the art in light of the disclosure and the context. As used in the specification and appended claims, however, unless specified to the contrary, the following terms have the meaning indicated and the following conventions are adhered to.

A. Chemical Nomenclature, Terms, and Conventions

In the groups, radicals, or moieties defined below, the number of carbon atoms is often specified preceding the group, for example, $(C_1-C_{10})$alkyl means an alkyl group or radical having 1 to 10 carbon atoms. In general, for groups comprising two or more subgroups, the last named group is the radical attachment point, for example, "alkylaryl" means a monovalent radical of the formula alkyl-aryl-, while "arylalkyl" means a monovalent radical of the formula aryl-alkyl-. Furthermore, the use of a term designating a monovalent radical where a divalent radical is appropriate shall be construed to designate the respective divalent radical and vice versa. Unless otherwise specified, conventional definitions of terms control and conventional stable atom valences are presumed and achieved in all formulas and groups. The articles "a" and "an" refer to one or more than one (e.g., to at least one) of the grammatical object of the article. By way of example, "an element" means one element or more than one element.

The term "and/or" means either "and" or "or" unless indicated otherwise.

The term "optionally substituted" means that a given chemical moiety (e.g., an alkyl group) can (but is not required to) be bonded other substituents (e.g., heteroatoms). For instance, an alkyl group that is optionally substituted can be a fully saturated alkyl chain (e.g., a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus, the term "optionally substituted" means that a given chemical moiety has the potential to contain other functional groups, but does not necessarily have any further functional groups. Suitable substituents used in the optional substitution of the described groups include, without limitation, halogen, oxo, —OH, —CN, —COOH, —CH$_2$CN, —O—(C$_1$-C$_6$)alkyl, (C$_1$-C$_6$)alkyl, (C$_1$-C$_6$)alkoxy, (C$_1$-C$_6$) haloalkyl, (C$_1$-C$_6$)haloalkoxy, —O—(C$_2$-C$_6$)alkenyl, —O—(C$_2$-C$_6$)alkynyl, (C$_2$-C$_6$)alkenyl, (C$_2$-C$_6$)alkynyl, —OH, —OP(O)(OH)$_2$, —OC(O)(C$_1$-C$_6$)alkyl, —C(O)(C$_1$-C$_6$)alkyl, —OC(O)O(C$_1$-C$_6$)alkyl, —NH$_2$, —NH((C$_1$-C$_6$) alkyl), —N((C$_1$-C$_6$)alkyl)$_2$, —NHC(O)(C$_1$-C$_6$)alkyl, —C(O)NH(C$_1$-C$_6$)alkyl, —S(O)$_2$(C$_1$-C$_6$)alkyl, —S(O)NH (C$_1$-C$_6$)alkyl, and S(O)N((C$_1$-C$_6$)alkyl)$_2$. The substituents can themselves be optionally substituted. "Optionally substituted" as used herein also refers to substituted or unsubstituted whose meaning is described below.

The term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

The term "unsubstituted" means that the specified group bears no substituents.

Unless otherwise specifically defined, "aryl" means a cyclic, aromatic hydrocarbon group having 1 to 3 aromatic rings, including monocyclic or bicyclic groups such as phenyl, biphenyl, or naphthyl. When containing two aromatic rings (bicyclic, etc.), the aromatic rings of the aryl group are optionally joined at a single point (e.g., biphenyl), or fused (e.g., naphthyl). The aryl group is optionally substituted by one or more substituents, e.g., 1 to 5 substituents, at any point of attachment. Exemplary substituents include, but are not limited to, —H, -halogen, —CN, —O—(C$_1$-C$_6$)alkyl, (C$_1$-C$_6$)alkyl, —O—(C$_2$-C$_6$)alkenyl, —O—(C$_2$-C$_6$)alkynyl, (C$_2$-C$_6$)alkenyl, (C$_2$-C$_6$)alkynyl, —OH, —OP(O)(OH)$_2$, —OC(O)(C$_1$-C$_6$)alkyl, —C(O)(C$_1$-C$_6$) alkyl, —OC(O)O(C$_1$-C$_6$) alkyl, NH$_2$, NH((C$_1$-C$_6$)alkyl), N((C$_1$-C$_6$)alkyl)$_2$, —S(O)$_2$—(C$_1$-C$_6$)alkyl, —S(O)NH(C$_1$-C$_6$)alkyl, and S(O)N((C$_1$-C$_6$)alkyl)$_2$. The substituents are themselves optionally substituted. Furthermore, when containing two fused rings, the aryl groups optionally have an unsaturated or partially saturated ring fused with a fully saturated ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Unless otherwise specifically defined, "heteroaryl" means a monovalent monocyclic aromatic radical of 5 to 24 ring atoms or a polycyclic aromatic radical, containing one or more ring heteroatoms selected from N, O, or S, the remaining ring atoms being C. Heteroaryl as herein defined also means a bicyclic heteroaromatic group wherein the heteroatom is selected from N, O, or S. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b] pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b] pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydropyrrolo[1,2-a]pyrimidinyl, 3,4-dihydro-2H-1$\Delta^2$-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, benzooxazolyl, benzoisoxazolyl, furo[2,3-b] pyridinyl, benzothiophenyl, 1,5-naphthyridinyl, furo[3,2-b] pyridine, [1,2,4]triazolo[1,5-a]pyridinyl, benzo[1,2,3] triazolyl, imidazo[1,2-a]pyrimidinyl, [1,2,4]triazolo[4,3-b]

pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo[1,5-b][1,2]oxazinyl, 4,5,6,7-tetrahydropyrazolo[1,5-a]pyridinyl, thiazolo[5,4d]thiazolyl, imidazo[2,1-b][1,3,4]thiadiazolyl, thieno[2,3-b]pyrrolyl, 3H-indolyl, and derivatives thereof. Furthermore, when containing two fused rings the aryl groups herein defined may have an unsaturated or partially saturated ring fused with a fully saturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuran, indolinyl, indolyl, and dihydrobenzoxanyl.

Halogen or "halo" mean fluorine, chlorine, bromine, or iodine.

"Alkyl" means a straight or branched chain saturated hydrocarbon containing I-12 carbon atoms. Examples of a $(C_1-C_6)$alkyl group include, but are not limited to, methyl, ethyl, propyl, butyl, pentyl, hexyl, isopropyl, isobutyl, sec-butyl, tert-butyl, isopentyl, neopentyl, and isohexyl.

"Alkoxy" means a straight or branched chain saturated hydrocarbon containing I-12 carbon atoms containing a terminal "O" in the chain, e.g., —O(alkyl). Examples of alkoxy groups include, without limitation, methoxy, ethoxy, propoxy, butoxy, t-butoxy, or pentoxy groups.

"Alkenyl" means a straight or branched chain unsaturated hydrocarbon containing 2-12 carbon atoms. The "alkenyl" group contains at least one double bond in the chain. The double bond of an alkenyl group can be unconjugated or conjugated to another unsaturated group. Examples of alkenyl groups include ethenyl, propenyl, n-butenyl, iso-butenyl, pentenyl, or hexenyl. An alkenyl group can be unsubstituted or substituted and may be straight or branched.

"Alkynyl" means a straight or branched chain unsaturated hydrocarbon containing 2-12 carbon atoms. The "alkynyl" group contains at least one triple bond in the chain. Examples of alkenyl groups include ethynyl, propargyl, n-butynyl, iso-butynyl, pentynyl, or hexynyl. An alkynyl group can be unsubstituted or substituted.

"Alkylene" or "alkylenyl" means a divalent alkyl radical. Any of the above mentioned monovalent alkyl groups may be an alkylene by abstraction of a second hydrogen atom from the alkyl. As herein defined, alkylene may also be a $(C_1-C_6)$alkylene. An alkylene may further be a $(C_1-C_4)$alkylene. Typical alkylene groups include, but are not limited to, —CH$_2$—, —CH(CH$_3$)—, —C(CH$_3$)$_2$—, —CH$_2$CH$_2$—, —CH$_2$CH(CH$_3$)—, —CH$_2$C(CH$_3$)$_2$—, —CH$_2$CH$_2$CH$_2$—, —CH$_2$CH$_2$CH$_2$CH—, and the like.

"Cycloalkyl" or "carbocyclyl" means a monocyclic or polycyclic saturated carbon ring containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl and derivatives thereof. A $(C_3-C_8)$cycloalkyl is a cycloalkyl group containing between 3 and 8 carbon atoms. A cycloalkyl group can be fused (e.g., decalin) or bridged (e.g., norbomane).

"Heterocyclyl" or "heterocycloalkyl" means a saturated or partially saturated monocyclic or polycyclic ring containing carbon and at least one heteroatom selected from oxygen, nitrogen, or sulfur (O, N, or S) and wherein there is not delocalized n electrons (aromaticity) shared among the ring carbon or heteroatoms. The heterocycloalkyl ring structure may be substituted by one or more substituents. The substituents can themselves be optionally substituted. Examples of heterocyclyl rings include, but are not limited to, oxetanyl, azetadinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, 1,4-dioxanyl, dihydrofuranyl, 1,3-dioxolanyl, imidazolidinyl, imidazolinyl, dithiolanyl, and homotropanyl.

"Hydroxyalkyl" means an alkyl group substituted with one or more —OH groups. Examples of hydroxyalkyl groups include HO—CH$_2$—, HO—CH$_2$CH$_2$—, and CH$_2$—CH(OH)—.

"Haloalkyl" means an alkyl group substituted with one or more halogens. Examples of haloalkyl groups include, but are not limited to, trifluoromethyl, difluoromethyl, pentafluoroethyl, trichloromethyl, etc.

"Haloalkoxy" means an alkoxy group substituted with one or more halogens. Examples of haloalkyl groups include, but are not limited to, trifluoromethoxy, difluoromethoxy, pentafluoroethoxy, trichloromethoxy, etc.

"Cyano" means a substituent having a carbon atom joined to a nitrogen atom by a triple bond, e.g., C≡N.

"Amino" means a substituent containing at least one nitrogen atom (e.g., NH$_2$).

"Alkylamino" means an amino or NH$_2$ group where one of the hydrogens is replaced with an alkyl group, e.g., —NH(alkyl). Examples of alkylamino groups include, but are not limited to, methylamino (e.g., —NH(CH$_3$)), ethylamino, propylamino, iso-propylamino, n-butylamino, sec-butylamino, tert-butylamino, etc.

"Dialkylamino" means an amino or NH$_2$ group where both of the hydrogens are replaced with alkyl groups, e.g., —N(alkyl)$_2$. The alkyl groups on the amino group are the same or different alkyl groups. Examples of dialkylamino groups include, but are not limited to, dimethylamino (e.g., —N(CH$_3$)$_2$), diethylamino, dipropylamino, diiso-propylamino, di-n-butylamino, di-sec-butylamino, di-tert-butylamino, methyl(ethyl)amino, methyl(butylamino), etc.

"Spirocycloalkyl" or "spirocyclyl" means carbogenic bicyclic ring systems with both rings connected through a single atom. The rings can be different in size and nature, or identical in size and nature. Examples include spiropentane, spriohexane, spiroheptane, spirooctane, spirononane, or spirodecane. One or both of the rings in a spirocycle can be fused to another ring carbocyclic, heterocyclic, aromatic, or heteroaromatic ring. A $(C_3-C_{12})$spirocycloalkyl is a spirocycle containing between 3 and 12 carbon atoms.

"Spiroheterocycloalkyl" or "spiroheterocyclyl" means a spirocycle wherein at least one of the rings is a heterocycle one or more of the carbon atoms can be substituted with a heteroatom (e.g., one or more of the carbon atoms can be substituted with a heteroatom in at least one of the rings). One or both of the rings in a spiroheterocycle can be fused to another ring carbocyclic, heterocyclic, aromatic, or heteroaromatic ring.

"Pomalidomide" or 4-amino-2-(2,6-dioxopiperidin-3-yl)isoindoline-1,3-dione has the following structure:

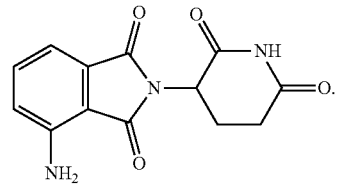

B. Salt, Prodrug, Derivative, and Solvate Terms and Conventions

"Prodrug" or "prodrug derivative" mean a covalently-bonded derivative or carrier of the parent compound or active drug substance which undergoes at least some biotransformation prior to exhibiting its pharmacological effect(s). In general, such prodrugs have metabolically cleavable groups and are rapidly transformed in vivo to yield the parent compound, for example, by hydrolysis in blood, and generally include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; Bioreversible Carriers in Drug Design, E. B. Roche (ed.), Elsevier, 1987, each of which is incorporated herein by reference in their entireties.

"Pharmaceutically acceptable prodrug" as used herein means a prodrug of a compound of the disclosure which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

"Salt" means an ionic form of the parent compound or the product of the reaction between the parent compound with a suitable acid or base to make the acid salt or base salt of the parent compound. Salts of the compounds of the present disclosure can be synthesized from the parent compounds which contain a basic or acidic moiety by conventional chemical methods. Generally, the salts are prepared by reacting the free base or acid parent compound with stoichiometric amounts or with an excess of the desired salt-forming inorganic or organic acid or base in a suitable solvent or various combinations of solvents.

"Pharmaceutically acceptable salt" means a salt of a compound of the disclosure which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. As the compounds of the present disclosure are useful in both free base and salt form, in practice, the use of the salt form amounts to use of the base form. Lists of suitable salts are found in, e.g., S. M. Birge et al., J. Pharm. Sci., 1977, 66, pp. 1-19, which is hereby incorporated by reference in its entirety.

"Pharmaceutically-acceptable acid addition salt" means those salts which retain the biological effectiveness and properties of the free bases and which are not biologically or otherwise undesirable, formed with inorganic acids such as hydrochloric acid, hydrobromic acid, hydroiodic acid, sulfuric acid, sulfamic acid, nitric acid, phosphoric acid, and the like, and organic acids such as acetic acid, trichloroacetic acid, trifluoroacetic acid, adipic acid, alginic acid, ascorbic acid, aspartic acid, benzenesulfonic acid, benzoic acid, 2-acetoxybenzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, heptanoic acid, hexanoic acid, formic acid, fumaric acid, 2-hydroxyethanesulfonic acid (isethionic acid), lactic acid, maleic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, picric acid, pivalic acid, propionic acid, pyruvic acid, pyruvic acid, salicylic acid, stearic acid, succinic acid, sulfanilic acid, tartaric acid, p-toluenesulfonic acid, undecanoic acid, and the like.

"Pharmaceutically-acceptable base addition salt" means those salts which retain the biological effectiveness and properties of the free acids and which are not biologically or otherwise undesirable, formed with inorganic bases such as ammonia or hydroxide, carbonate, or bicarbonate of ammonium or a metal cation such as sodium, potassium, lithium, calcium, magnesium, iron, zinc, copper, manganese, aluminum, and the like. Particularly preferred are the ammonium, potassium, sodium, calcium, and magnesium salts. Salts derived from pharmaceutically-acceptable organic nontoxic bases include salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins, and the like. Particularly preferred organic nontoxic bases are isopropylamine, diethylamine, ethanolamine, trimethylamine, dicyclohexylamine, choline, and caffeine.

"Solvate" means a complex of variable stoichiometry formed by a solute, for example, a compound of Formula (I') or Formula (I)) and solvent, for example, water, ethanol, or acetic acid. This physical association may involve varying degrees of ionic and covalent bonding, including hydrogen bonding. In certain instances, the solvate will be capable of isolation, for example, when one or more solvent molecules are incorporated in the crystal lattice of the crystalline solid. In general, such solvents selected for the purpose of the disclosure do not interfere with the biological activity of the solute. Solvates encompasses both solution-phase and isolatable solvates. Representative solvates include hydrates, ethanolates, methanolates, and the like.

"Hydrate" means a solvate wherein the solvent molecule(s) is/are water.

The compounds of the present disclosure as discussed below include the free base or acid thereof, their salts, solvates, and prodrugs and may include oxidized sulfur atoms or quaternized nitrogen atoms in their structure, although not explicitly stated or shown, particularly the pharmaceutically acceptable forms thereof. Such forms, particularly the pharmaceutically acceptable forms, are intended to be embraced by the appended claims.

C. Isomer Terms and Conventions

"Isomers" means compounds having the same number and kind of atoms, and hence the same molecular weight, but differing with respect to the arrangement or configuration of the atoms in space. The term includes stereoisomers and geometric isomers.

"Stereoisomer" or "optical isomer" mean a stable isomer that has at least one chiral atom or restricted rotation giving rise to perpendicular dissymmetric planes (e.g., certain biphenyls, allenes, and spiro compounds) and can rotate plane-polarized light. Because asymmetric centers and other chemical structure exist in the compounds of the disclosure which may give rise to stereoisomerism, the disclosure contemplates stereoisomers and mixtures thereof. The compounds of the disclosure and their salts include asymmetric carbon atoms and may therefore exist as single stereoisomers, racemates, and as mixtures of enantiomers and diastereomers. Typically, such compounds will be prepared as a racemic mixture. If desired, however, such compounds can be prepared or isolated as pure stereoisomers, i.e., as individual enantiomers or diastereomers, or as stereoisomer-enriched mixtures. As discussed in more detail below, individual stereoisomers of compounds are prepared by synthesis from optically active starting materials containing the desired chiral centers or by preparation of mixtures of enantiomeric products followed by separation or resolution, such as conversion to a mixture of diastereomers followed by separation or recrystallization, chromatographic techniques, use of chiral resolving agents, or direct separation of the enantiomers on chiral chromatographic columns. Starting compounds of particular stereochemistry are either commercially available or are made by the methods described below and resolved by techniques well-known in the art.

"Enantiomers" means a pair of stereoisomers that are non-superimposable mirror images of each other.

"Diastereoisomers" or "diastereomers" mean optical isomers which are not mirror images of each other.

"Racemic mixture" or "racemate" mean a mixture containing equal parts of individual enantiomers.

"Non-racemic mixture" means a mixture containing unequal parts of individual enantiomers.

"Geometrical isomer" means a stable isomer which results from restricted freedom of rotation about double bonds (e.g., cis-2-butene and trans-2-butene) or in a cyclic structure (e.g., cis-1,3-dichlorocyclobutane and trans-1,3-dichlorocyclobutane). Because carbon-carbon double (olefinic) bonds, C=N double bonds, cyclic structures, and the like may be present in the compounds of the disclosure, the disclosure contemplates each of the various stable geometric isomers and mixtures thereof resulting from the arrangement of substituents around these double bonds and in these cyclic structures. The substituents and the isomers are designated using the cis/trans convention or using the E or Z system, wherein the term "E" means higher order substituents on opposite sides of the double bond, and the term "Z" means higher order substituents on the same side of the double bond. A thorough discussion of E and Z isomerism is provided in J. March, Advanced Organic Chemistry: Reactions, Mechanisms, and Structure, 4th ed., John Wiley & Sons, 1992, which is hereby incorporated by reference in its entirety. Several of the following examples represent single E isomers, single Z isomers, and mixtures of E/Z isomers. Determination of the E and Z isomers can be done by analytical methods such as x-ray crystallography, $^1$H NMR, and $^{13}$C NMR.

Some of the compounds of the disclosure can exist in more than one tautomeric form. As mentioned above, the compounds of the disclosure include all such tautomers.

It is well-known in the art that the biological and pharmacological activity of a compound is sensitive to the stereochemistry of the compound. Thus, for example, enantiomers often exhibit strikingly different biological activity including differences in pharmacokinetic properties, including metabolism, protein binding, and the like, and pharmacological properties, including the type of activity displayed, the degree of activity, toxicity, and the like. Thus, one skilled in the art will appreciate that one enantiomer may be more active or may exhibit beneficial effects when enriched relative to the other enantiomer or when separated from the other enantiomer. Additionally, one skilled in the art would know how to separate, enrich, or selectively prepare the enantiomers of the compounds of the disclosure from this disclosure and the knowledge of the prior art.

Thus, although the racemic form of drug may be used, it is often less effective than administering an equal amount of enantiomerically pure drug; indeed, in some cases, one enantiomer may be pharmacologically inactive and would merely serve as a simple diluent. For example, although ibuprofen had been previously administered as a racemate, it has been shown that only the S-isomer of ibuprofen is effective as an anti-inflammatory agent (in the case of ibuprofen, however, although the R-isomer is inactive, it is converted in vivo to the S-isomer, thus, the rapidity of action of the racemic form of the drug is less than that of the pure S-isomer). Furthermore, the pharmacological activities of enantiomers may have distinct biological activity. For example, S-penicillamine is a therapeutic agent for chronic arthritis, while R-penicillamine is toxic. Indeed, some purified enantiomers have advantages over the racemates, as it has been reported that purified individual isomers have faster transdermal penetration rates compared to the racemic mixture. See U.S. Pat. Nos. 5,114,946 and 4,818,541.

Thus, if one enantiomer is pharmacologically more active, less toxic, or has a preferred disposition in the body than the other enantiomer, it would be therapeutically more beneficial to administer that enantiomer preferentially. In this way, the patient undergoing treatment would be exposed to a lower total dose of the drug and to a lower dose of an enantiomer that is possibly toxic or an inhibitor of the other enantiomer.

Preparation of pure enantiomers or mixtures of desired enantiomeric excess (ee) or enantiomeric purity are accomplished by one or more of the many methods of (a) separation or resolution of enantiomers, or (b) enantioselective synthesis known to those of skill in the art, or a combination thereof. These resolution methods generally rely on chiral recognition and include, for example, chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in Chiral Separation Techniques: A Practical Approach (2nd Ed.), G. Subramanian (ed.), Wiley-VCH, 2000; T. E. Beesley and R. P. W. Scott, Chiral Chromatography, John Wiley & Sons, 1999; and Satinder Ahuja, Chiral Separations by Chromatography, Am. Chem. Soc., 2000. Furthermore, there are equally well-known methods for the quantitation of enantiomeric excess or purity, for example, GC, HPLC, CE, or NMR, and assignment of absolute configuration and conformation, for example, CD ORD, X-ray crystallography, or NMR.

In general, all tautomeric forms and isomeric forms and mixtures, whether individual geometric isomers or stereoisomers or racemic or non-racemic mixtures, of a chemical structure or compound is intended, unless the specific stereochemistry or isomeric form is specifically indicated in the compound name or structure.

D. Pharmaceutical Administration and Treatment Terms and Conventions

A "patient" or "subject" is a mammal, e.g., a human, mouse, rat, guinea pig, dog, cat, horse, cow, pig, or nonhuman primate, such as a monkey, chimpanzee, baboon or, rhesus. In certain embodiments, the subject is a primate. In yet other embodiments, the subject is a human.

An "effective amount" or "therapeutically effective amount" when used in connection with a compound means an amount of a compound of the present disclosure that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The terms "pharmaceutically effective amount" or "therapeutically effective amount" means an amount of a compound according to the disclosure which, when administered to a patient in need thereof, is sufficient to effect treatment for disease-states, conditions, or disorders for which the compounds have utility. Such an amount would be sufficient to elicit the biological or medical response of a tissue, system, or patient that is sought by a researcher or clinician. The amount of a compound of according to the disclosure which constitutes a therapeutically effective amount will vary depending on such factors as the compound and its biological activity, the composition used for administration, the time of administration, the route of administration, the rate of excretion of the compound, the duration of treatment, the type of disease-state or disorder being treated and its severity, drugs used in combination with or coincidentally with the compounds of the disclosure, and the age, body weight, general health, sex, and diet of the patient. Such a therapeutically effective amount can be determined routinely by one of ordinary skill in the art having regard to their own knowledge, the prior art, and this disclosure.

As used herein, the term "pharmaceutical composition" refers to a compound of the disclosure, or a pharmaceutically acceptable salt, hydrate, solvate, prodrug, stereoisomer, or tautomer thereof, together with at least one pharmaceutically acceptable carrier, in a form suitable for oral or parenteral administration.

"Carrier" encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

A subject is "in need of" a treatment if such subject would benefit biologically, medically, or in quality of life from such treatment (preferably, a human).

As used herein, the term "inhibit", "inhibition", or "inhibiting" refers to the reduction or suppression of a given condition, symptom, or disorder, or disease, or a significant decrease in the baseline activity of a biological activity or process.

As used herein, the term "treat", "treating", or "treatment" of any disease or disorder refers to alleviating or ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient.

As used herein, the term "prevent", "preventing", or "prevention" of any disease or disorder refers to the prophylactic treatment of the disease or disorder; or delaying the onset or progression of the disease or disorder.

"Pharmaceutically acceptable" means that the substance or composition must be compatible chemically and/or toxicologically, with the other ingredients comprising a formulation, and/or the mammal being treated therewith.

"Disorder" means, and is used interchangeably with, the terms disease, condition, or illness, unless otherwise indicated.

"Administer", "administering", or "administration" means to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

"Prodrug" means a compound which is convertible in vivo by metabolic means (e.g., by hydrolysis) to a disclosed compound.

"Compounds of the present disclosure", "Compounds of Formula (I')", "compounds of the disclosure", and equivalent expressions (unless specifically identified otherwise) refer to compounds of Formulae (I'), (I), (Ia), (Ib), (Ic), and (Id) as herein described including the tautomers, the prodrugs, salts particularly the pharmaceutically acceptable salts, and the solvates and hydrates thereof, where the context so permits thereof, as well as all stereoisomers (including diastereoisomers and enantiomers), rotamers, tautomers, and isotopically labelled compounds (including deuterium substitutions), as well as inherently formed moieties (e.g., polymorphs, solvates and/or hydrates). For purposes of this disclosure, solvates and hydrates are generally considered compositions. In general and preferably, the compounds of the disclosure and the formulas designating the compounds of the disclosure are understood to only include the stable compounds thereof and exclude unstable compounds, even if an unstable compound might be considered to be literally embraced by the compound formula. Similarly, reference to intermediates, whether or not they themselves are claimed, is meant to embrace their salts and solvates, where the context so permits. For the sake of clarity, particular instances when the context so permits are sometimes indicated in the text, but these instances are purely illustrative and it is not intended to exclude other instances when the context so permits.

"Stable compound" or "stable structure" means a compound that is sufficiently robust to survive isolation to a useful degree of purity from a reaction mixture, and formulation into an efficacious therapeutic or diagnostic agent. For example, a compound which would have a "dangling valency" or is a carbanion is not a compound contemplated by the disclosure.

In a specific embodiment, the term "about" or "approximately" means within 20%, preferably within 10%, and more preferably within 5% of a given value or range.

The yield of each of the reactions described herein is expressed as a percentage of the theoretical yield. "Cancer" means any cancer caused by the proliferation of malignant neoplastic cells, such as tumors, neoplasms, carcinomas, sarcomas, leukemias, lymphomas, and the like. For example, cancers include, but are not limited to, mesothelioma, leukemias, and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute nonlymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, and nasopharyngeal), esophageal cancer, genitourinary cancers (e.g., prostate, bladder, renal, uterine, ovarian, testicular), lung cancer (e.g., small-cell and non-small cell), breast cancer, pancreatic cancer, melanoma, and other skin cancers, stomach cancer, brain tumors, tumors related to Gorlin's syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the compounds described herein may be useful in preventing, treating, and studying are, for example, colon carcinoma, familiary adenomatous polyposis carcinoma, and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing's sarcoma, and plasmocytoma.

"IKZF2-dependent disease or disorder" means any disease or disorder which is directly or indirectly affected by the modulation of IKZF2 protein levels.

"IKZF4-dependent disease or disorder" means any disease or disorder which is directly or indirectly affected by the modulation of IKZF4 protein levels.

D. Specific Embodiments and Methods for Testing Compounds of Formula (I')

The present disclosure relates to compounds or pharmaceutically acceptable salts, hydrates, solvates, prodrugs, stereoisomers, or tautomers thereof, capable of modulating IKZF2 protein levels, which are useful for the treatment of diseases and disorders associated with modulation of IKZF2 protein levels. The disclosure further relates to compounds, or pharmaceutically acceptable salts, hydrates, solvates, prodrugs, stereoisomers, or tautomers thereof, which are useful for reducing or decreasing IKZF2 protein levels.

In one embodiment, the compounds of Formula (I') have the structure of Formula (I):

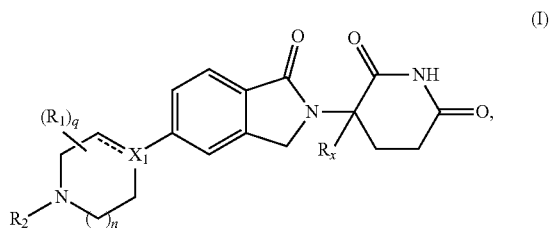

or pharmaceutically acceptable salts, hydrates, solvates, prodrugs, stereoisomers, and tautomers thereof.

In one embodiment, the compounds of Formula (I') or Formula (I) have the structure of Formula (Ia):

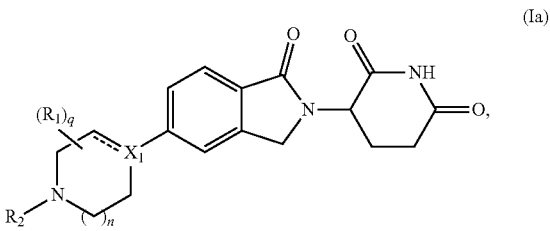

or pharmaceutically acceptable salts, hydrates, solvates, prodrugs, stereoisomers, and tautomers thereof.

In one embodiment, the compounds of Formula (I') or Formula (I) have the structure of Formula (Ib):

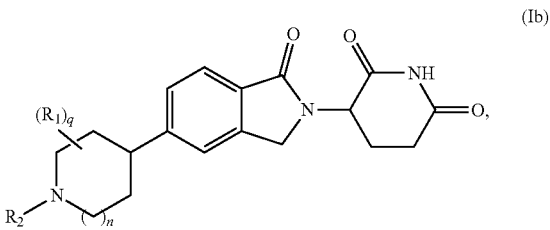

or pharmaceutically acceptable salts, hydrates, solvates, prodrugs, stereoisomers, and tautomers thereof.

In another embodiment, the compounds of Formula (I') or Formula (I) have the structure of Formula (Ic):

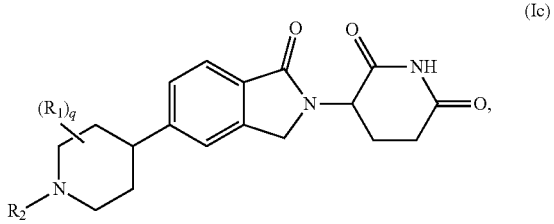

(Ic)

or pharmaceutically acceptable salts, hydrates, solvates, prodrugs, stereoisomers, and tautomers thereof.

In another embodiment, the compounds of Formula (I') or Formula (I) have the structure of Formula (Id):

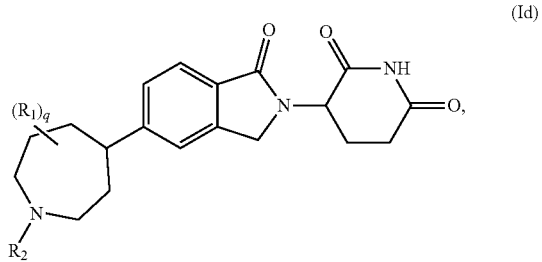

(Id)

or pharmaceutically acceptable salts, hydrates, solvates, prodrugs, stereoisomers, and tautomers thereof.

In some embodiments of the formulae above (i.e., Formula (I'), Formula (I), Formula (Ia), Formula (Ib), Formula (Ic), and/or Formula (Id)), $R_2$ is $(C_1-C_6)$alkyl, —C(O)($C_1$-$C_6$)alkyl, —C(O)(CH$_2$)$_{0-3}$($C_6$-$C_{10}$)aryl, —C(O)O(CH$_2$)$_{0-3}$($C_6$-$C_{10}$)aryl, ($C_6$-$C_{10}$)aryl, 5- or 6-membered heteroaryl comprising 1 to 3 heteroatoms selected from O, N, and S, ($C_3$-$C_8$)cycloalkyl, or 5- to 7-membered heterocycloalkyl comprising 1 to 3 heteroatoms selected from O, N, and S, wherein the alkyl is optionally substituted with one to four $R_4$; and the aryl, heteroaryl, cycloalkyl, and heterocycloalkyl are optionally substituted with one to four $R_5$; or $R_1$ and $R_2$, when on adjacent atoms, together with the atoms to which they are attached form a 5- or 6-membered heterocycloalkyl ring;

each $R_4$ is independently selected from —C(O)OR$_6$, —C(O)NR$_6$R$_{6'}$, —NR$_6$C(O)R$_{6'}$, halogen, —OH, —NH$_2$, CN, ($C_6$-$C_{10}$)aryl, 5- or 6-membered heteroaryl comprising 1 to 4 heteroatoms selected from O, N, and S, ($C_3$-$C_8$)cycloalkyl, and 5- to 7-membered heterocycloalkyl ring comprising 1 to 3 heteroatoms selected from O, N, and S, wherein the aryl, heteroaryl, cycloalkyl, and heterocycloalkyl groups are optionally substituted with one to four $R_7$;

each $R_5$ is independently selected from ($C_1$-$C_6$)alkyl, ($C_2$-$C_6$)alkenyl, ($C_2$-$C_6$)alkynyl, ($C_1$-$C_6$)alkoxy, ($C_1$-$C_6$)haloalkyl, ($C_1$-$C_6$)haloalkoxy, ($C_1$-$C_6$)hydroxyalkyl, halogen, —OH, —NH$_2$, CN, ($C_3$-$C_7$)cycloalkyl, 5- to 7-membered heterocycloalkyl comprising 1 to 3 heteroatoms selected from O, N, and S, ($C_6$-$C_{10}$)aryl, and 5- or 6-membered heteroaryl comprising 1 to 3 heteroatoms selected from O, N, and S, or two $R_5$, when on adjacent atoms, together with the atoms to which they are attached form a ($C_6$-$C_{10}$)aryl ring or a 5- or 6-membered heteroaryl ring comprising 1 to 3 heteroatoms selected from O, N, and S, optionally substituted with one to four $R_{10}$, or two $R_5$, when on adjacent atoms, together with the atoms to which they are attached form a ($C_5$-$C_7$)cycloalkyl ring or a 5- to 7-membered heterocycloalkyl ring comprising 1 to 3 heteroatoms selected from O, N, and S optionally substituted with one to four $R_{10}$;

each $R_7$ is independently selected from ($C_1$-$C_6$)alkyl, ($C_2$-$C_6$)alkenyl, ($C_2$-$C_6$)alkynyl, ($C_1$-$C_6$)alkoxy, ($C_1$-$C_6$)haloalkyl, ($C_1$-$C_6$)haloalkoxy, —C(O)R$_8$, —(CH$_2$)$_{0-3}$C(O)OR$_8$, —C(O)NR$_8$R$_9$, —NR$_8$C(O)R$_9$, —NR$_8$C(O)OR$_9$, —S(O)NR$_8$R$_9$, —S(O)$_p$R$_{12}$, ($C_1$-$C_6$)hydroxyalkyl, halogen, —OH, —O(CH$_2$)$_{1-3}$CN, —NH$_2$, CN, —O(CH$_2$)$_{0-3}$($C_6$-$C_{10}$)aryl, adamantyl, —O(CH$_2$)$_{0-3}$-5- or 6-membered heteroaryl comprising 1 to 3 heteroatoms selected from O, N, and S, ($C_6$-$C_{10}$)aryl, monocyclic or bicyclic 5- to 10-membered heteroaryl comprising 1 to 3 heteroatoms selected from O, N, and S, ($C_3$-$C_7$)cycloalkyl, and 5- to 7-membered heterocycloalkyl comprising 1 to 3 heteroatoms selected from O, N, and S, wherein the alkyl is optionally substituted with one to four $R_{11}$, and the aryl, heteroaryl, and heterocycloalkyl are optionally substituted with one to four substituents each independently selected from halogen, ($C_1$-$C_6$)alkyl, ($C_1$-$C_6$)haloalkyl, and ($C_1$-$C_6$)alkoxy, or two $R_7$ together with the carbon atom to which they are attached form a =(O), or two $R_7$, when on adjacent atoms, together with the atoms to which they are attached form a ($C_6$-$C_{10}$)aryl ring or a 5- or 6-membered heteroaryl ring comprising 1 to 3 heteroatoms selected from O, N, and S, optionally substituted with one to four $R_{10}$, or two $R_7$ together with the atoms to which they are attached form a ($C_5$-$C_7$) cycloalkyl ring or a 5- to 7-membered heterocycloalkyl ring comprising 1 to 3 heteroatoms selected from O, N, and S, optionally substituted with one to four $R_{10}$; and each $R_{11}$ is independently selected from CN, ($C_1$-$C_6$) alkoxy, ($C_6$-$C_{10}$)aryl, 5- to 7-membered heterocycloalkyl comprising 1 to 3 heteroatoms selected from O, N, and S, wherein the aryl and heterocycloalkyl are optionally substituted with one to four substituents each independently selected from ($C_1$-$C_6$)alkyl, ($C_1$-$C_6$)alkoxy, ($C_1$-$C_6$)haloalkyl, ($C_1$-$C_6$)haloalkoxy, ($C_1$-$C_6$)hydroxyalkyl, halogen, —OH, —NH$_2$, and CN.

In some embodiments of the formulae above, $R_2$ is ($C_1$-$C_6$)alkyl, ($C_6$-$C_{10}$)aryl, 5- or 6-membered heteroaryl comprising 1 to 3 heteroatoms selected from O, N, and S, ($C_3$-$C_8$)cycloalkyl, or 5- to 7-membered heterocycloalkyl comprising 1 to 3 heteroatoms selected from O, N, and S, wherein the alkyl is optionally substituted with one to four $R_4$; and the aryl, heteroaryl, cycloalkyl, and heterocycloalkyl are optionally substituted with one to four $R_5$;

each $R_4$ is independently selected from —C(O)OR$_6$, —C(O)NR$_6$R$_{6'}$, —NR$_6$C(O)R$_{6'}$, ($C_6$-$C_{10}$)aryl, 5- or 6-membered heteroaryl comprising 1 to 3 heteroatoms selected from O, N, and S, ($C_3$-$C_8$)cycloalkyl, and 5- to 7-membered heterocycloalkyl comprising 1 to 3 heteroatoms selected from O, N, and S, wherein the aryl, heteroaryl, cycloalkyl, and heterocycloalkyl groups are optionally substituted with one to four $R_7$;

each $R_5$ is independently selected from ($C_1$-$C_6$)alkyl, ($C_2$-$C_6$)alkenyl, ($C_2$-$C_6$)alkynyl, ($C_1$-$C_6$)alkoxy, ($C_1$-$C_6$)haloalkyl, ($C_1$-$C_6$)haloalkoxy, ($C_1$-$C_6$)hydroxyalkyl, halogen, —OH, —NH$_2$, CN, ($C_3$-$C_7$)cycloalkyl, 5- to 7-membered heterocycloalkyl comprising 1 to 3 heteroatoms selected from O, N, and S, ($C_6$-$C_{10}$)aryl, and 5- or 6-membered heteroaryl comprising 1 to 3 heteroatoms selected from O, N, and S, or two $R_5$, when on adjacent atoms, together with the atoms to which they are attached form a $(C_6-C_{10})$aryl ring or a 5- or 6-membered heteroaryl ring comprising 1 to 3 heteroatoms selected from O, N, and S, optionally substituted with one to four $R_{10}$, or two $R_5$, when on adjacent atoms, together with the atoms to which they are attached form a $(C_5-C_7)$cycloalkyl ring or a 5- to 7-membered heterocycloalkyl ring comprising 1 to 3 heteroatoms selected from O, N, and S optionally substituted with one to four $R_{10}$; and each $R_7$ is independently selected from $(C_1-C_6)$alkyl, $(C_2-C_6)$alkenyl, $(C_2-C_6)$alkynyl, $(C_1-C_6)$alkoxy, $(C_1-C_6)$haloalkyl, $(C_1-C_6)$haloalkoxy, —C(O)$R_8$, —C(O)O$R_8$, —C(O)N$R_8R_9$, —N$R_8$C(O)$R_9$, $(C_1-C_6)$hydroxyalkyl, halogen, —OH, —NH$_2$, CN, $(C_6-C_{10})$aryl, 5- or 6-membered heteroaryl comprising 1 to 3 heteroatoms selected from O, N, and S, $(C_3-C_7)$cycloalkyl, and 5- to 7-membered heterocycloalkyl comprising 1 to 3 heteroatoms selected from O, N, and S, or two $R_7$, when on adjacent atoms, together with the atoms to which they are attached form a $(C_6-C_{10})$aryl ring or a 5- or 6-membered heteroaryl ring comprising 1 to 3 heteroatoms selected from O, N, and S, optionally substituted with one to four $R_{10}$, or two $R_7$, when on adjacent atoms, together with the atoms to which they are attached form a $(C_5-C_7)$cycloalkyl ring or a 5- to 7-membered heterocycloalkyl ring comprising 1 to 3 heteroatoms selected from O, N, and S, optionally substituted with one to four $R_{10}$.

In some embodiments of the formulae above, $X_1$ is $CR_3$. In another embodiment, $X_1$ is CH.

In some embodiments of the formulae above, $X_1$ is $CR_3$, $R_3$ is absent, and ----- is a double bond. In another embodiment, $X_1$ is $CR_3$ and ----- is a single bond In some embodiments of the formulae above, $R_x$ is H. In another embodiment, $R_x$ is D.

In some embodiments of the formulae above, each $R_1$ is independently $(C_1-C_4)$alkyl, $(C_1-C_4)$haloalkyl, $(C_1-C_4)$hydroxyalkyl, or halogen. In another embodiment, each $R_1$ is independently $(C_1-C_4)$alkyl, $(C_1-C_4)$haloalkyl, or $(C_1-C_4)$hydroxyalkyl. In yet another embodiment, each $R_1$ is independently $(C_1-C_4)$alkyl, $(C_1-C_4)$hydroxyalkyl, or halogen. In another embodiment, each $R_1$ is independently $(C_1-C_4)$alkyl, $(C_1-C_4)$haloalkyl, or halogen. In yet another embodiment, each $R_1$ is independently $(C_1-C_4)$alkyl or $(C_1-C_4)$haloalkyl. In another embodiment, each $R_1$ is independently $(C_1-C_4)$alkyl or $(C_1-C_4)$hydroxyalkyl. In yet another embodiment, each $R_1$ is independently $(C_1-C_4)$alkyl or halogen. In another embodiment, each $R_1$ is independently $(C_1-C_3)$alkyl. In yet another embodiment, each $R_1$ is independently methyl, ethyl, or n-propyl, isopropyl. In another embodiment, each $R_1$ is independently methyl or ethyl. In another embodiment, each $R_1$ is independently methyl.

In some embodiments of the formulae above, two $R_1$ together with the carbon atoms to which they are attached form a 5-membered heterocycloalkyl ring. In another embodiment, two $R_1$ together with the carbon atoms to which they are attached form a 6-membered heterocycloalkyl ring.

In some embodiments of the formulae above, two $R_1$, when on adjacent atoms, together with the atoms to which they are attached form a phenyl ring or a 5- or 6-membered heteroaryl ring comprising 1 to 3 heteroatoms selected from O, N, and S. In another embodiment, two $R_1$, when on adjacent atoms, together with the atoms to which they are attached form a $(C_6-C_{10})$aryl ring. In another embodiment, two $R_1$, when on adjacent atoms, together with the atoms to which they are attached form a phenyl ring. In yet another embodiment, two $R_1$, when on adjacent atoms, together with the atoms to which they are attached form a 5- or 6-membered heteroaryl ring comprising 1 to 3 heteroatoms selected from O, N, and S. In another embodiment, two $R_1$, when on adjacent atoms, together with the atoms to which they are attached form a 5-membered heteroaryl ring comprising 1 to 3 heteroatoms selected from O, N, and S. In yet another embodiment, two $R_1$, when on adjacent atoms, together with the atoms to which they are attached form a 6-membered heteroaryl ring comprising 1 to 3 heteroatoms selected from O, N, and S.

In some embodiments of the formulae above, $R_2$ is H, $(C_1-C_6)$alkyl, —C(O)$(C_1-C_6)$alkyl, —C(O)$(CH_2)_{0-3}(C_6-C_{10})$aryl, —C(O)O$(C_6-C_{10})$aryl, $(C_6-C_{10})$aryl, 5- or 6-membered heteroaryl comprising 1 to 3 heteroatoms selected from O, N, and S, $(C_3-C_8)$cycloalkyl, or 5- to 7-membered heterocycloalkyl comprising 1 to 3 heteroatoms selected from O, N, and S, wherein the alkyl is optionally substituted with one to four $R_4$; and the aryl, heteroaryl, cycloalkyl, and heterocycloalkyl are optionally substituted with one to four $R_5$. In another embodiment, $R_2$ is H, $(C_1-C_6)$alkyl, —C(O)$(C_1-C_6)$alkyl, —C(O)$(CH_2)_{0-3}(C_6-C_{10})$aryl, $(C_6-C_{10})$aryl, 5- or 6-membered heteroaryl comprising 1 to 3 heteroatoms selected from O, N, and S, $(C_3-C_9)$cycloalkyl, or 5- to 7-membered heterocycloalkyl comprising 1 to 3 heteroatoms selected from O, N, and S, wherein the alkyl is optionally substituted with one to four $R_4$; and the aryl, heteroaryl, cycloalkyl, and heterocycloalkyl are optionally substituted with one to four $R_5$.

In another embodiment, $R_2$ is $(C_1-C_6)$alkyl, —C(O)$(C_1-C_6)$alkyl, —C(O)$(CH_2)_{0-3}(C_6-C_{10})$aryl, —C(O)O$(CH_2)_{0-3}(C_6-C_{10})$aryl, $(C_6-C_{10})$aryl, 5- or 6-membered heteroaryl comprising 1 to 3 heteroatoms selected from O, N, and S, $(C_3-C_8)$cycloalkyl, or 5- to 7-membered heterocycloalkyl comprising 1 to 3 heteroatoms selected from O, N, and S, wherein the alkyl is optionally substituted with one to four $R_4$; and the aryl, heteroaryl, cycloalkyl, and heterocycloalkyl are optionally substituted with one to four $R_5$. In yet another embodiment, $R_2$ is $(C_1-C_6)$alkyl, —C(O)$(C_1-C_6)$alkyl, —C(O)$(CH_2)_{0-3}(C_6-C_{10})$aryl, —C(O)O$(CH_2)_{0-3}(C_6-C_{10})$aryl, $(C_6-C_{10})$aryl, or 5- or 6-membered heteroaryl comprising 1 to 3 heteroatoms selected from O, N, and S, $(C_3-C_8)$cycloalkyl, or 5- to 7-membered heterocycloalkyl comprising 1 to 3 heteroatoms selected from O, N, and S, wherein the alkyl is optionally substituted with one to four $R_4$; and the aryl and heteroaryl are optionally substituted with one to four $R_5$. In another embodiment, $R_2$ is $(C_1-C_6)$alkyl, —C(O)$(C_1-C_6)$alkyl, —C(O)$(CH_2)_{0-3}(C_6-C_{10})$aryl, or —C(O)O$(CH_2)_{0-3}(C_6-C_{10})$aryl, wherein the alkyl is optionally substituted with one to four $R_4$.

In another embodiment, $R_2$ is H, $(C_1-C_4)$alkyl, $(C_6-C_{10})$aryl, 5- or 6-membered heteroaryl comprising 1 to 3 heteroatoms selected from O, N, and S, $(C_3-C_8)$cycloalkyl, or 5- to 7-membered heterocycloalkyl comprising 1 to 3 heteroatoms selected from O, N, and S, wherein the alkyl is optionally substituted with one to three $R_4$; and wherein the aryl, heteroaryl, cycloalkyl, and heterocycloalkyl are optionally substituted with one to three $R_5$.

In another embodiment, $R_2$ is H, $(C_1-C_6)$alkyl, $(C_6-C_{10})$aryl, 5- or 6-membered heteroaryl comprising 1 to 3 heteroatoms selected from O, N, and S, $(C_3-C_8)$cycloalkyl, or 5- to 7-membered heterocycloalkyl comprising 1 to 3 heteroatoms selected from O, N, and S, wherein the alkyl is optionally substituted with one to three $R_4$; and wherein the aryl, heteroaryl, cycloalkyl, and heterocycloalkyl are optionally substituted with one to three $R_5$. In another embodiment, $R_2$ is H or $(C_1-C_6)$alkyl optionally substituted with one to four $R_4$. In yet another embodiment, $R_2$ is H or $(C_1-C_6)$ alkyl substituted with one to three $R_4$. In another embodiment, $R_2$ is $(C_1-C_6)$alkyl, $(C_6-C_{10})$aryl, 5- or 6-membered heteroaryl comprising 1 to 3 heteroatoms selected from O, N, and S, $(C_3-C_8)$cycloalkyl, or 5- to 7-membered heterocycloalkyl comprising 1 to 3 heteroatoms selected from O, N, and S, wherein the alkyl is substituted with one to four $R_4$; and wherein the aryl, heteroaryl, cycloalkyl, and heterocycloalkyl are optionally substituted with one to four $R_5$. In yet another embodiment, $R_2$ is $(C_1-C_6)$alkyl, $(C_6-C_{10})$ aryl, 5- or 6-membered heteroaryl comprising 1 to 3 heteroatoms selected from O, N, and S, $(C_3-C_8)$cycloalkyl, or 5- to 7-membered heterocycloalkyl comprising 1 to 3 heteroatoms selected from O, N, and S, wherein the alkyl is substituted with one to three $R_4$; and wherein the aryl, heteroaryl, cycloalkyl, and heterocycloalkyl are optionally substituted with one to three $R_5$.

In another embodiment, $R_2$ is $(C_1-C_6)$alkyl optionally substituted with one to three $R_4$. In yet another embodiment, $R_2$ is $(C_1-C_6)$alkyl substituted with one to three $R_4$. In yet another embodiment, $R_2$ is $(C_6-C_{10})$aryl, 5- or 6-membered heteroaryl comprising 1 to 3 heteroatoms selected from O, N, and S, $(C_3-C_9)$cycloalkyl, or 5- to 7-membered heterocycloalkyl comprising 1 to 3 heteroatoms selected from O, N, and S, wherein the aryl, heteroaryl, cycloalkyl, and heterocycloalkyl are optionally substituted with one to three $R_5$. In another embodiment, $R_2$ is $(C_6-C_{10})$aryl, $(C_3-C_8)$ cycloalkyl, or 5- to 7-membered heterocycloalkyl comprising 1 to 3 heteroatoms selected from O, N, and S, wherein the aryl, cycloalkyl, and heterocycloalkyl are optionally substituted with one to three $R_5$. In yet another embodiment, $R_2$ is phenyl, $(C_3-C_8)$cycloalkyl, or 5- to 7-membered heterocycloalkyl comprising 1 to 3 heteroatoms selected from O, N, and S, wherein the phenyl, cycloalkyl, and heterocycloalkyl are optionally substituted with one to three $R_5$. In another embodiment, $R_2$ is $(C_1-C_3)$alkyl optionally substituted with one to three $R_4$. In yet another embodiment, $R_2$ is $(C_1-C_3)$alkyl substituted with one to three $R_4$.

In another embodiment, $R_2$ is $(C_3-C_8)$cycloalkyl or 5- to 7-membered heterocycloalkyl comprising 1 to 3 heteroatoms selected from O, N, and S, wherein the cycloalkyl and heterocycloalkyl are optionally substituted with one to three $R_5$. In yet another embodiment, $R_2$ is $(C_6-C_{10})$aryl or 5- or 6-membered heteroaryl comprising 1 to 3 heteroatoms selected from O, N, and S, wherein the aryl and heteroaryl are optionally substituted with one to three $R_5$. In another embodiment, $R_2$ is $(C_6-C_{10})$aryl optionally substituted with one to three $R_5$. In yet another embodiment, $R_2$ is 5- or 6-membered heteroaryl comprising 1 to 3 heteroatoms selected from O, N, and S, optionally substituted with one to three $R_5$. In another embodiment, $R_2$ is $(C_3-C_8)$cycloalkyl optionally substituted with one to three $R_5$. In yet another embodiment, $R_2$ is 5- to 7-membered heterocycloalkyl comprising 1 to 3 heteroatoms selected from O, N, and S, optionally substituted with one to three $R_5$.

In some embodiments of the formulae above, R and $R_2$, when on adjacent atoms, together with the atoms to which they are attached form a 5-membered heterocycloalkyl ring. In another embodiment, R and $R_2$, when on adjacent atoms, together with the atoms to which they are attached form a 6-membered heterocycloalkyl ring.

In some embodiments of the formulae above, $R_3$ is H. In another embodiment, $R_3$ is absent when ===== is a double bond.

In some embodiments of the formulae above, each $R_4$ is independently selected from —C(O)OR$_6$, —C(O)NR$_6$R$_{6'}$, —NR$_6$C(O)R$_{6'}$, halogen, —OH, —NH$_2$, CN, $(C_6-C_{10})$aryl, 5- or 6-membered heteroaryl comprising 1 to 4 heteroatoms selected from O, N, and S, $(C_3-C_8)$cycloalkyl, and 5- to 7-membered heterocycloalkyl ring comprising 1 to 3 heteroatoms selected from O, N, and S, wherein the aryl, heteroaryl, cycloalkyl, and heterocycloalkyl groups are optionally substituted with one to four $R_7$. In another embodiment, each $R_4$ is independently selected from —C(O)OR$_6$, —C(O)NR$_6$R$_{6'}$, —NR$_6$C(O)R$_{6'}$, halogen, —OH, —NH$_2$, or CN. In another embodiment, each $R_4$ is independently selected from —C(O)OR$_6$, —C(O)NR$_6$R$_{6'}$, —NR$_6$C(O)R$_{6'}$, halogen, or —OH. In another embodiment, each $R_4$ is independently selected from halogen, —OH, $(C_6-C_{10})$aryl, 5- or 6-membered heteroaryl comprising 1 to 4 heteroatoms selected from O, N, and S, $(C_3-C_9)$cycloalkyl, and 5- to 7-membered heterocycloalkyl ring comprising 1 to 3 heteroatoms selected from O, N, and S, wherein the aryl, heteroaryl, cycloalkyl, and heterocycloalkyl groups are optionally substituted with one to four $R_7$. In another embodiment, each $R_4$ is independently selected from halogen, —OH, $(C_6-C_{10})$aryl, 5- or 6-membered heteroaryl comprising 1 to 3 heteroatoms selected from O, N, and S, $(C_3-C_9)$cycloalkyl, and 5- to 7-membered heterocycloalkyl ring comprising 1 to 3 heteroatoms selected from O, N, and S, wherein the aryl, heteroaryl, cycloalkyl, and heterocycloalkyl groups are optionally substituted with one to four $R_7$.

In another embodiment, each $R_4$ is independently selected from —C(O)OR$_6$, —C(O)NR$_6$R$_{6'}$, and —NR$_6$C(O)R$_{6'}$. In another embodiment, each $R_4$ is independently selected from —C(O)OR$_6$, $(C_6-C_{10})$aryl, 5- or 6-membered heteroaryl comprising 1 to 3 heteroatoms selected from O, N, and S, $(C_3-C_8)$cycloalkyl, and 5- to 7-membered heterocycloalkyl comprising 1 to 3 heteroatoms selected from O, N, and S, wherein the aryl, heteroaryl, cycloalkyl, and heterocycloalkyl groups are optionally substituted with one to four $R_7$. In yet another embodiment, each $R_4$ is independently selected from $(C_6-C_{10})$aryl, 5- or 6-membered heteroaryl comprising 1 to 3 heteroatoms selected from O, N, and S, $(C_3-C_8)$cycloalkyl, and 5- to 7-membered heterocycloalkyl comprising 1 to 3 heteroatoms selected from O, N, and S, wherein the aryl, heteroaryl, cycloalkyl, and heterocycloalkyl groups are optionally substituted with one to four $R_7$. In another embodiment, each $R_4$ is independently selected from $(C_6-C_{10})$aryl, 5- or 6-membered heteroaryl comprising 1 to 3 heteroatoms selected from O, N, and S, $(C_3-C_8)$cycloalkyl, and 5- to 7-membered heterocycloalkyl comprising 1 to 3 heteroatoms selected from O, N, and S, wherein the aryl, heteroaryl, cycloalkyl, and heterocycloalkyl groups are optionally substituted with one to three $R_7$.

In another embodiment, each $R_4$ is independently selected from $(C_6-C_{10})$aryl and 5- or 6-membered heteroaryl comprising 1 to 3 heteroatoms selected from O, N, and S, wherein the aryl and heteroaryl are optionally substituted with one to three $R_7$. In yet another embodiment, each $R_4$ is independently selected from $(C_6-C_{10})$aryl and 5- or 6-membered heteroaryl comprising 1 to 3 heteroatoms selected from O, N, and S, wherein the aryl and heteroaryl are substituted with one to three $R_7$.

In another embodiment, each $R_4$ is independently selected from $(C_3-C_8)$cycloalkyl and 5- to 7-membered heterocycloalkyl comprising 1 to 3 heteroatoms selected from O, N, and S, wherein the cycloalkyl and heterocycloalkyl groups are optionally substituted with one to three $R_7$. In another embodiment, each $R_4$ is independently selected from $(C_3-C_8)$cycloalkyl and 5- to 7-membered heterocycloalkyl comprising 1 to 3 heteroatoms selected from O, N, and S, wherein the cycloalkyl and heterocycloalkyl groups are substituted with one to three $R_7$.

In another embodiment, each $R_4$ is independently ($C_6$-$C_{10}$)aryl optionally substituted with one to three $R_7$. In yet another embodiment, each $R_4$ is independently 5- or 6-membered heteroaryl comprising 1 to 3 heteroatoms selected from O, N, and S, optionally substituted with one to three $R_7$.

In another embodiment, each $R_4$ is ($C_3$-$C_8$)cycloalkyl optionally substituted with one to three $R_7$. In another embodiment, each $R_4$ is independently 5- to 7-membered heterocycloalkyl comprising 1 to 3 heteroatoms selected from O, N, and S, optionally substituted with one to three $R_7$.

In some embodiments of the formulae above, each $R_5$ is independently selected from ($C_1$-$C_6$)alkyl, ($C_2$-$C_6$)alkenyl, ($C_2$-$C_6$)alkynyl, ($C_1$-$C_6$)alkoxy, ($C_1$-$C_6$)haloalkyl, ($C_1$-$C_6$)haloalkoxy, ($C_1$-$C_6$)hydroxyalkyl, halogen, —OH, —NH$_2$, CN, ($C_3$-$C_7$)cycloalkyl, 5- to 7-membered heterocycloalkyl comprising 1 to 3 heteroatoms selected from O, N, and S, ($C_6$-$C_{10}$)aryl, and 5- or 6-membered heteroaryl comprising 1 to 3 heteroatoms selected from O, N, and S. In another embodiment, each $R_5$ is independently selected from ($C_1$-$C_6$)alkyl, ($C_2$-$C_6$)alkenyl, ($C_2$-$C_6$)alkynyl, ($C_1$-$C_6$)alkoxy, ($C_1$-$C_6$)haloalkyl, ($C_1$-$C_6$)haloalkoxy, ($C_1$-$C_6$)hydroxyalkyl, halogen, —OH, —NH$_2$, and CN. In yet another embodiment, each $R_5$ is independently selected from ($C_3$-$C_7$)cycloalkyl, 5- to 7-membered heterocycloalkyl comprising 1 to 3 heteroatoms selected from O, N, and S, ($C_6$-$C_{10}$)aryl, and 5- or 6-membered heteroaryl comprising 1 to 3 heteroatoms selected from O, N, and S.

In another embodiment, each $R_5$ is independently selected from ($C_1$-$C_6$)alkyl, ($C_1$-$C_6$)alkoxy, ($C_1$-$C_6$)haloalkyl, ($C_1$-$C_6$)haloalkoxy, ($C_1$-$C_6$)hydroxyalkyl, halogen, —OH, —NH$_2$, CN, ($C_3$-$C_7$)cycloalkyl, 5- to 7-membered heterocycloalkyl comprising 1 to 3 heteroatoms selected from O, N, and S, ($C_6$-$C_{10}$)aryl, and 5- or 6-membered heteroaryl comprising 1 to 3 heteroatoms selected from O, N, and S.

In another embodiment, each $R_5$ is independently selected from ($C_1$-$C_6$)alkyl, ($C_1$-$C_6$)alkoxy, ($C_1$-$C_6$)haloalkyl, and ($C_1$-$C_6$)haloalkoxy. In yet another embodiment, each $R_5$ is independently selected from ($C_1$-$C_6$)hydroxyalkyl, halogen, —OH, —NH$_2$, and CN. In another embodiment, each $R_5$ is independently selected from ($C_1$-$C_6$)alkyl, ($C_1$-$C_6$)alkoxy, ($C_1$-$C_6$)haloalkyl, ($C_1$-$C_6$)haloalkoxy, ($C_1$-$C_6$)hydroxyalkyl, halogen, —OH, and CN.

In some embodiments of the formulae above, two $R_5$, when on adjacent atoms, together with the atoms to which they are attached form a ($C_6$-$C_{10}$)aryl ring or a 5- or 6-membered heteroaryl ring comprising 1 to 3 heteroatoms selected from O, N, and S, optionally substituted with one to four $R_{10}$, or two $R_5$, when on adjacent atoms, together with the atoms to which they are attached form a ($C_5$-$C_7$)cycloalkyl ring or a 5- to 7-membered heterocycloalkyl ring comprising 1 to 3 heteroatoms selected from O, N, and S optionally substituted with one to four $R_{10}$. In another embodiment, two $R_5$, when on adjacent atoms, together with the atoms to which they are attached form a ($C_6$-$C_{10}$)aryl ring or a 5- or 6-membered heteroaryl ring comprising 1 to 3 heteroatoms selected from O, N, and S, optionally substituted with one to three $R_{10}$, or two $R_5$, when on adjacent atoms, together with the atoms to which they are attached form a ($C_5$-$C_7$)cycloalkyl ring or a 5- to 7-membered heterocycloalkyl ring comprising 1 to 3 heteroatoms selected from O, N, and S optionally substituted with one three $R_{10}$.

In another embodiment, two $R_5$, when on adjacent atoms, together with the atoms to which they are attached form a ($C_6$-$C_{10}$)aryl ring or a 5- or 6-membered heteroaryl ring comprising 1 to 3 heteroatoms selected from O, N, and S, optionally substituted with one to three $R_{10}$. In yet another embodiment, two $R_5$, when on adjacent atoms, together with the atoms to which they are attached form a ($C_5$-$C_7$)cycloalkyl ring or a 5- to 7-membered heterocycloalkyl ring comprising 1 to 3 heteroatoms selected from O, N, and S optionally substituted with one three $R_{10}$.

In another embodiment, two $R_5$, when on adjacent atoms, together with the atoms to which they are attached form a ($C_6$-$C_{10}$)aryl ring optionally substituted with one to three $R_{10}$. In yet another embodiment, two $R_5$, when on adjacent atoms, together with the atoms to which they are attached form a 5- or 6-membered heteroaryl ring comprising 1 to 3 heteroatoms selected from O, N, and S, optionally substituted with one to three $R_{10}$.

In another embodiment, two $R_5$, when on adjacent atoms, together with the atoms to which they are attached form a ($C_5$-$C_7$)cycloalkyl ring optionally substituted with one three $R_{10}$. In yet another embodiment, two $R_5$, when on adjacent atoms, together with the atoms to which they are attached form a 5- to 7-membered heterocycloalkyl ring comprising 1 to 3 heteroatoms selected from O, N, and S optionally substituted with one three $R_{10}$.

In some embodiments of the formulae above, $R_6$ is H or ($C_1$-$C_3$)alkyl. In another embodiment, $R_6$ is H or ($C_6$-$C_{10}$)aryl. In yet another embodiment, $R_6$ is ($C_1$-$C_3$)alkyl or ($C_6$-$C_{10}$)aryl. In another embodiment, $R_6$ is H, methyl, ethyl, n-propyl, or isopropyl. In another embodiment, $R_6$ is H, methyl or ethyl. In yet another embodiment, $R_6$ is H or methyl. In another embodiment, $R_6$ is H.

In some embodiments of the formulae above, $R_{6'}$ is H or ($C_1$-$C_3$)alkyl. In another embodiment, $R_{6'}$ is H or ($C_6$-$C_{10}$)aryl. In yet another embodiment, $R_{6'}$ is ($C_1$-$C_3$)alkyl or ($C_6$-$C_{10}$)aryl. In another embodiment, $R_{6'}$ is H, methyl, ethyl, n-propyl, or isopropyl. In another embodiment, $R_{6'}$ is H, methyl or ethyl. In yet another embodiment, $R_{6'}$ is H or methyl. In another embodiment, $R_{6'}$ is H.

In some embodiments of the formulae above, each $R_7$ is independently selected from ($C_1$-$C_6$)alkyl, ($C_2$-$C_6$)alkenyl, ($C_2$-$C_6$)alkynyl, ($C_1$-$C_6$)alkoxy, ($C_1$-$C_6$)haloalkyl, ($C_1$-$C_6$)haloalkoxy, —C(O)$R_8$, —(CH$_2$)$_{0-3}$C(O)OR$_8$, —C(O)NR$_8$R$_9$, —NR$_8$C(O)R$_9$, —NR$_8$C(O)OR$_9$, —S(O)NR$_8$R$_9$, —S(O)$_p$R$_{12}$, ($C_1$-$C_6$)hydroxyalkyl, halogen, —OH, —O(CH$_2$)$_{1-3}$CN, —NH$_2$, CN, —O(CH$_2$)$_{0-3}$($C_6$-$C_{10}$)aryl, adamantyl, —O(CH$_2$)$_{0-3}$-5- or 6-membered heteroaryl comprising 1 to 3 heteroatoms selected from O, N, and S, ($C_6$-$C_{10}$)aryl, monocyclic or bicyclic 5- to 10-membered heteroaryl comprising 1 to 3 heteroatoms selected from O, N, and S, ($C_3$-$C_7$)cycloalkyl, and 5- to 7-membered heterocycloalkyl comprising 1 to 3 heteroatoms selected from O, N, and S, wherein the alkyl is optionally substituted with one to four $R_{11}$, and the aryl, heteroaryl, and heterocycloalkyl are optionally substituted with one to four substituent each independently selected from halogen, ($C_1$-$C_6$)alkyl, ($C_1$-$C_6$)haloalkyl, and ($C_1$-$C_6$)alkoxy. In another embodiment, each $R_7$ is independently selected from ($C_1$-$C_6$)alkyl, ($C_2$-$C_6$)alkenyl, ($C_2$-$C_6$)alkynyl, ($C_1$-$C_6$)alkoxy, ($C_1$-$C_6$)haloalkyl, ($C_1$-$C_6$)haloalkoxy, —C(O)$R_8$, —(CH$_2$)$_{0-3}$C(O)OR$_8$, —C(O)NR$_8$R$_9$, —NR$_8$C(O)R$_9$, —NR$_8$C(O)OR$_9$, —S(O)$_p$NR$_8$R$_9$, —S(O)$_p$R$_{12}$, ($C_1$-$C_6$)hydroxyalkyl, halogen, —OH, —O(CH$_2$)$_{1-3}$CN, —NH$_2$, CN, —O(CH$_2$)$_{0-3}$($C_6$-$C_{10}$)aryl, —O(CH$_2$)$_{0-3}$-5- or 6-membered heteroaryl comprising 1 to 3 heteroatoms selected from O, N, and S, ($C_6$-$C_{10}$)aryl, monocyclic or bicyclic 5- to 10-membered heteroaryl comprising 1 to 3 heteroatoms selected from O, N, and S, ($C_3$-$C_7$)cycloalkyl, and 5- to 7-membered heterocycloalkyl comprising 1 to 3 heteroatoms selected from O, N, and S, wherein the alkyl is optionally substituted with one to four $R_{11}$, and the aryl, heteroaryl, and heterocycloalkyl are optionally substituted with one to four substituent each independently selected from halogen, ($C_1$-$C_6$)alkyl, ($C_1$-$C_6$)haloalkyl, and ($C_1$-$C_6$)alkoxy.

In another embodiment, each $R_7$ is independently selected from ($C_1$-$C_6$)alkyl, ($C_1$-$C_6$)alkoxy, ($C_1$-$C_6$)haloalkyl, ($C_1$-$C_6$)haloalkoxy, —C(O)$R_8$, —(CH$_2$)$_{0-3}$C(O)O$R_8$, —C(O)N$R_8R_9$, —N$R_8$C(O)$R_9$, —N$R_8$C(O)O$R_9$, —S(O)$_p$N$R_8R_9$, —S(O)$_p R_{12}$, ($C_1$-$C_6$)hydroxyalkyl, halogen, —OH, —O(CH$_2$)$_{1-3}$CN, —NH$_2$, CN, —O(CH$_2$)$_{0-3}$($C_6$-$C_{10}$)aryl, —O(CH$_2$)$_{0-3}$-5- or 6-membered heteroaryl comprising 1 to 3 heteroatoms selected from O, N, and S, ($C_6$-$C_{10}$)aryl, monocyclic or bicyclic 5- to 10-membered heteroaryl comprising 1 to 3 heteroatoms selected from O, N, and S, ($C_3$-$C_7$)cycloalkyl, and 5- to 7-membered heterocycloalkyl comprising 1 to 3 heteroatoms selected from O, N, and S, wherein the alkyl is optionally substituted with one to four $R_1$, and the aryl, heteroaryl, and heterocycloalkyl are optionally substituted with one to four substituent each independently selected from halogen, ($C_1$-$C_6$)alkyl, ($C_1$-$C_6$)haloalkyl, and ($C_1$-$C_6$)alkoxy.

In another embodiment, each $R_7$ is independently selected from —(CH$_2$)$_{0-3}$C(O)O$R_8$, —N$R_8$C(O)O$R_9$, —S(O)N$R_8R_9$, —S(O)$_p R_{12}$, ($C_1$-$C_6$)hydroxyalkyl, halogen, —OH, —O(CH$_2$)$_{1-3}$CN, —NH$_2$, CN, —O(CH$_2$)$_{0-3}$($C_6$-$C_{10}$)aryl, —O(CH$_2$)$_{0-3}$-5- or 6-membered heteroaryl comprising 1 to 3 heteroatoms selected from O, N, and S, bicyclic 9- or 10-membered heteroaryl comprising 1 to 3 heteroatoms selected from O, N, and S, wherein the aryl and heteroaryl and heterocycloalkyl are optionally substituted with one or more substituent each independently selected from halogen, ($C_1$-$C_6$)alkyl, ($C_1$-$C_6$)haloalkyl, and ($C_1$-$C_6$)alkoxy.

In another embodiment, each $R_7$ is independently selected from ($C_1$-$C_6$)alkyl, ($C_2$-$C_6$)alkenyl, ($C_2$-$C_6$)alkynyl, ($C_1$-$C_6$)alkoxy, ($C_1$-$C_6$)haloalkyl, ($C_1$-$C_6$)haloalkoxy, —C(O)$R_8$, —C(O)O$R_8$, —C(O)N$R_8R_9$, —N$R_8$C(O)$R_9$, ($C_1$-$C_6$)hydroxyalkyl, halogen, —OH, —NH$_2$, CN, ($C_6$-$C_{10}$)aryl, 5- or 6-membered heteroaryl comprising 1 to 3 heteroatoms selected from O, N, and S, ($C_3$-$C_7$)cycloalkyl, and 5- to 7-membered heterocycloalkyl comprising 1 to 3 heteroatoms selected from O, N, and S. In another embodiment, each $R_7$ is independently selected from ($C_1$-$C_6$)alkyl, ($C_2$-$C_6$)alkenyl, ($C_2$-$C_6$)alkynyl, ($C_1$-$C_6$)alkoxy, ($C_1$-$C_6$)haloalkyl, ($C_1$-$C_6$)haloalkoxy, —C(O)$R_8$, —C(O)O$R_8$, —C(O)N$R_8R_9$, —N$R_8$C(O)$R_9$, ($C_1$-$C_6$)hydroxyalkyl, halogen, —OH, —NH$_2$, and CN.

In another embodiment, each $R_7$ is independently selected from ($C_1$-$C_6$)alkyl, ($C_1$-$C_6$)alkoxy, ($C_1$-$C_6$)haloalkyl, ($C_1$-$C_6$)haloalkoxy, —C(O)$R_8$, —C(O)O$R_8$, —C(O)N$R_8R_9$, —N$R_8$C(O)$R_9$, ($C_1$-$C_6$)hydroxyalkyl, halogen, —OH, —NH$_2$, and CN. In yet another embodiment, each $R_7$ is independently selected from ($C_1$-$C_6$)alkyl, ($C_1$-$C_6$)alkoxy, ($C_1$-$C_6$)haloalkyl, ($C_1$-$C_6$)haloalkoxy. In another embodiment, each $R_7$ is independently selected from —C(O)$R_8$, —C(O)O$R_8$, —C(O)N$R_8R_9$, —N$R_8$C(O)$R_9$, ($C_1$-$C_6$)hydroxyalkyl, halogen, —OH, —NH$_2$, and CN. In another embodiment, each $R_7$ is independently selected from ($C_6$-$C_{10}$)aryl, 5- or 6-membered heteroaryl comprising 1 to 3 heteroatoms selected from O, N, and S, ($C_3$-$C_7$)cycloalkyl, and 5- to 7-membered heterocycloalkyl comprising 1 to 3 heteroatoms selected from O, N, and S.

In another embodiment, each $R_7$ is independently selected from ($C_1$-$C_6$)alkyl, ($C_1$-$C_6$)alkoxy, ($C_1$-$C_6$)haloalkyl, ($C_1$-$C_6$)haloalkoxy, —C(O)$R_8$, —C(O)O$R_8$, —C(O)N$R_8R_9$, —N$R_8$C(O)$R_9$, ($C_1$-$C_6$)hydroxyalkyl, halogen, —OH, —NH$_2$, CN, ($C_6$-$C_{10}$)aryl, 5- or 6-membered heteroaryl comprising 1 to 3 heteroatoms selected from O, N, and S, ($C_3$-$C_7$)cycloalkyl, and 5- to 7-membered heterocycloalkyl comprising 1 to 3 heteroatoms selected from O, N, and S. In yet another embodiment, each $R_7$ is independently selected from ($C_1$-$C_6$)alkyl, ($C_1$-$C_6$)alkoxy, halogen, —OH, CN, and ($C_6$-$C_{10}$)aryl.

In some embodiments of the formulae above, two $R_7$, when on adjacent atoms, together with the atoms to which they are attached form a ($C_6$-$C_{10}$)aryl ring or a 5- or 6-membered heteroaryl ring comprising 1 to 3 heteroatoms selected from O, N, and S, optionally substituted with one or more $R_{10}$. In another embodiment, two $R_7$, when on adjacent atoms, together with the atoms to which they are attached form a ($C_6$-$C_{10}$)aryl ring optionally substituted with one or more $R_{10}$. In another embodiment, two $R_7$, when on adjacent atoms, together with the atoms to which they are attached form a 5- or 6-membered heteroaryl ring comprising 1 to 3 heteroatoms selected from O, N, and S, optionally substituted with one or more $R_{10}$. In another embodiment, two $R_7$ together with the atoms to which they are attached form a ($C_5$-$C_7$) cycloalkyl ring optionally substituted with one or more $R_{10}$. In another embodiment, two $R_7$ together with the atoms to which they are attached form a 5- to 7-membered heterocycloalkyl ring comprising 1 to 3 heteroatoms selected from O, N, and S, optionally substituted with one or more $R_{10}$.

In another embodiment, two $R_7$, when on adjacent atoms, together with the atoms to which they are attached form a ($C_6$-$C_{10}$)aryl ring or a 5- or 6-membered heteroaryl ring comprising 1 to 3 heteroatoms selected from O, N, and S, optionally substituted with one to four $R_{10}$, or two $R_7$, when on adjacent atoms, together with the atoms to which they are attached form a ($C_5$-$C_7$)cycloalkyl ring or a 5- to 7-membered heterocycloalkyl ring comprising 1 to 3 heteroatoms selected from O, N, and S, optionally substituted with one to four $R_{10}$.

In another embodiment, two $R_7$, when on adjacent atoms, together with the atoms to which they are attached form a ($C_5$-$C_7$)cycloalkyl ring or a 5- to 7-membered heterocycloalkyl ring comprising 1 to 3 heteroatoms selected from O, N, and S, optionally substituted with one to four $R_{10}$. In another embodiment, two $R_7$, when on adjacent atoms, together with the atoms to which they are attached form a ($C_5$-$C_7$)cycloalkyl ring optionally substituted with one to four $R_{10}$. In another embodiment, two $R_7$, when on adjacent atoms, together with the atoms to which they are attached form a 5- to 7-membered heterocycloalkyl ring comprising 1 to 3 heteroatoms selected from O, N, and S, optionally substituted with one to four $R_{10}$.

In some embodiments of the formulae above, $R_8$ is H or ($C_1$-$C_3$)alkyl. In another embodiment, $R_8$ is H, methyl, ethyl, n-propyl, or isopropyl. In another embodiment, $R_5$ is H, methyl or ethyl. In yet another embodiment, $R_5$ is H or methyl. In another embodiment, $R_5$ is H In some embodiments of the formulae above, $R_9$ is H or ($C_1$-$C_3$)alkyl. In another embodiment, $R_9$ is H, methyl, ethyl, n-propyl, or isopropyl. In another embodiment, $R_9$ is H, methyl or ethyl. In yet another embodiment, $R_9$ is H or methyl. In another embodiment, $R_9$ is H.

In some embodiments of the formulae above, each $R_{10}$ is independently selected from ($C_1$-$C_6$)alkyl, ($C_1$-$C_6$)alkoxy, ($C_1$-$C_6$)haloalkyl, ($C_1$-$C_6$)haloalkoxy, ($C_1$-$C_6$)hydroxyalkyl, and halogen. In another embodiment, each $R_{10}$ is independently selected from —OH, —NH$_2$, and CN. In yet another embodiment, each $R_{10}$ is independently selected from $(C_1$-$C_6)$alkyl, $(C_1$-$C_6)$alkoxy, $(C_1$-$C_6)$haloalkyl, $(C_1$-$C_6)$haloalkoxy, and halogen. In another embodiment, each $R_{10}$ is independently selected from $(C_1$-$C_6)$alkyl, $(C_1$-$C_6)$haloalkyl, and halogen. In yet another embodiment, each $R_{10}$ is independently selected from $(C_1$-$C_6)$alkyl and halogen.

In some embodiments of the formulae above, two $R_{10}$ together with the carbon atom to which they are attached form a =(O).

In some embodiments of the formulae above, each $R_1$ is independently selected from CN, $(C_1$-$C_6)$alkoxy, $(C_6$-$C_{10})$aryl, and 5- to 7-membered heterocycloalkyl comprising 1 to 3 heteroatoms selected from O, N, and S, wherein the aryl and heterocycloalkyl are optionally substituted with one to four substituents each independently selected from $(C_1$-$C_6)$alkyl, $(C_1$-$C_6)$alkoxy, $(C_1$-$C_6)$haloalkyl, $(C_1$-$C_6)$haloalkoxy, $(C_1$-$C_6)$hydroxyalkyl, halogen, —OH, —NH$_2$, and CN. In another embodiment, each $R_{11}$ is independently selected from CN, $(C_1$-$C_6)$alkoxy, $(C_6$-$C_{10})$aryl, and 5- to 7-membered heterocycloalkyl comprising 1 to 3 heteroatoms selected from O, N, and S, wherein the aryl and heterocycloalkyl are optionally substituted with one to three substituents each independently selected from $(C_1$-$C_6)$alkyl, $(C_1$-$C_6)$alkoxy, $(C_1$-$C_6)$haloalkyl, $(C_1$-$C_6)$haloalkoxy, $(C_1$-$C_6)$hydroxyalkyl, halogen, —OH, —NH$_2$, and CN. In yet another embodiment, each $R_1$ is independently selected from CN, $(C_1$-$C_6)$alkoxy, and $(C_6$-$C_{10})$aryl, wherein the aryl is optionally substituted with one to three substituents each independently selected from $(C_1$-$C_6)$alkyl, $(C_1$-$C_6)$alkoxy, $(C_1$-$C_6)$haloalkyl, $(C_1$-$C_6)$haloalkoxy, $(C_1$-$C_6)$hydroxyalkyl, halogen, —OH, —NH$_2$, and CN.

In another embodiment, each $R_1$ is independently selected from CN, $(C_1$-$C_6)$alkoxy, and 5- to 7-membered heterocycloalkyl comprising 1 to 3 heteroatoms selected from O, N, and S, wherein the heterocycloalkyl is optionally substituted with one to four substituents each independently selected from $(C_1$-$C_6)$alkyl, $(C_1$-$C_6)$alkoxy, $(C_1$-$C_6)$haloalkyl, $(C_1$-$C_6)$haloalkoxy, $(C_1$-$C_6)$hydroxyalkyl, halogen, —OH, —NH$_2$, and CN. In another embodiment, each $R_1$ is independently selected from CN and $(C_1$-$C_6)$alkoxy. In yet another embodiment, each $R_1$ is independently selected from $(C_6$-$C_{10})$aryl and 5- to 7-membered heterocycloalkyl comprising 1 to 3 heteroatoms selected from O, N, and S, wherein the aryl and heterocycloalkyl are optionally substituted with one to four substituents each independently selected from $(C_1$-$C_6)$alkyl, $(C_1$-$C_6)$alkoxy, $(C_1$-$C_6)$haloalkyl, $(C_1$-$C_6)$haloalkoxy, $(C_1$-$C_6)$hydroxyalkyl, halogen, —OH, —NH$_2$, and CN.

In some embodiments of the formulae above, $R_{12}$ is $(C_1$-$C_6)$alkyl, $(C_1$-$C_6)$haloalkyl, $(C_6$-$C_{10})$aryl, or 5- or 6-membered heterocycloalkyl comprising 1 to 3 heteroatoms selected from O, N, and S. In another embodiment, $R_{12}$ is $(C_1$-$C_6)$alkyl, $(C_1$-$C_6)$haloalkyl, phenyl, or 5- or 6-membered heterocycloalkyl comprising 1 to 3 heteroatoms selected from O, N, and S. In another embodiment, $R_{12}$ is $(C_1$-$C_4)$alkyl, $(C_1$-$C_4)$haloalkyl, phenyl, or 5- or 6-membered heterocycloalkyl comprising 1 to 3 heteroatoms selected from O, N, and S.

In some embodiments of the formulae above, p is 0 or 1. In another embodiment, p is 1 or 2. In yet another embodiment, p is 0 or 2. In another embodiment, p is 0. In yet another embodiment, p is 1. In another embodiment, p is 2.

In some embodiments of the formulae above, n is 0 or 1. In another embodiment, n is 1 or 2. In yet another embodiment, n is 0 or 2. In another embodiment, n is 0. In yet another embodiment, n is 1. In another embodiment, n is 2.

In some embodiments of the formulae above, n+n1≤3.

In some embodiments of the formulae above, n1 is 1. In another embodiment, n1 is 2.

In some embodiments of the formulae above, n is 0 and n1 is 1. In another embodiment, n is 1 and n1 is 2. In another embodiment, n is 2 and n1 is 1. In another embodiment, n is 1 and n1 is 1.

In some embodiments of the formulae above, q is 0, 1, 2, or 3. In another embodiment, q is 1, 2, 3, or 4. In yet another embodiment, q is 0, 1, or 2. In another embodiment, q is 1, 2, or 3. In yet another embodiment, q is 2, 3, or 4. In another embodiment, q is 0 or 1. In yet another embodiment, q is 1 or 2. In another embodiment, q is 2 or 3. In yet another embodiment, q is 3 or 4. In another embodiment, q is 0. In yet another embodiment, q is 1. In another embodiment, q is 2. In yet another embodiment, q is 3. In another embodiment, q is 4.

In some embodiments of the formulae above, $X_1$ is CH and n is 1. In another embodiment, $X_1$ is CH, n is 1, and q is 0.

In some embodiments of the formulae above, $X_1$ is CH, n is 1, and q is 0 or 1. In another embodiment, $X_1$ is CH, n is 1, q is 0 or 1, and $R_1$ is $(C_1$-$C_6)$alkyl. In another embodiment, $X_1$ is CH, n is 1, q is 0 or 1, $R_1$ is $(C_1$-$C_6)$alkyl, and $R_2$ is $(C_1$-$C_6)$alkyl optionally substituted with one to three $R_4$. In another embodiment, $X_1$ is CH, n is 1, q is 0 or 1, $R_1$ is $(C_1$-$C_6)$alkyl, and $R_2$ is $(C_1$-$C_6)$alkyl substituted with one to three $R_4$.

In another embodiment, $X_1$ is CH, n is 1, q is 0, and $R_2$ is $(C_1$-$C_6)$alkyl optionally substituted with one to three $R_4$. In another embodiment, $X_1$ is CH, n is 1, q is 0, and $R_2$ is $(C_1$-$C_6)$alkyl substituted with one to three $R_4$.

In some embodiments of the formulae above, $X_1$ is CH, n is 1, q is 0 or 1, $R_1$ is $(C_1$-$C_6)$alkyl, $R_2$ is $(C_1$-$C_6)$alkyl optionally substituted with one to three $R_4$, and each $R_4$ is independently selected from —C(O)OR$_6$, $(C_6$-$C_{10})$aryl, 5- or 6-membered heteroaryl comprising 1 to 3 heteroatoms selected from O, N, and S, $(C_3$-$C_8)$cycloalkyl, and 5- to 7-membered heterocycloalkyl comprising 1 to 3 heteroatoms selected from O, N, and S, wherein the aryl, heteroaryl, cycloalkyl, and heterocycloalkyl groups are optionally substituted with one to three $R_7$.

In some embodiments of the formulae above, $X_1$ is CH, n is 1, q is 0 or 1, $R_1$ is $(C_1$-$C_6)$alkyl, $R_2$ is $(C_1$-$C_6)$alkyl substituted with one to three $R_4$, and each $R_4$ is independently selected from —C(O)OR$_6$, $(C_6$-$C_{10})$aryl, 5- or 6-membered heteroaryl comprising 1 to 3 heteroatoms selected from O, N, and S, $(C_3$-$C_9)$cycloalkyl, and 5- to 7-membered heterocycloalkyl comprising 1 to 3 heteroatoms selected from O, N, and S, wherein the aryl, heteroaryl, cycloalkyl, and heterocycloalkyl groups are optionally substituted with one to three $R_7$.

In some embodiments of the formulae above, $X_1$ is CH, n is 1, q is 0 or 1, $R_1$ is $(C_1$-$C_6)$alkyl, $R_2$ is $(C_1$-$C_6)$alkyl optionally substituted with one to three $R_4$, and each $R_4$ is independently selected from $(C_6$-$C_{10})$aryl, 5- or 6-membered heteroaryl comprising 1 to 3 heteroatoms selected from O, N, and S, $(C_3$-$C_9)$cycloalkyl, and 5- to 7-membered heterocycloalkyl comprising 1 to 3 heteroatoms selected from O, N, and S, wherein the aryl, heteroaryl, cycloalkyl, and heterocycloalkyl groups are optionally substituted with one to three $R_7$.

In some embodiments of the formulae above, $X_1$ is CH, n is 1, q is 0 or 1, $R_1$ is $(C_1$-$C_6)$alkyl, $R_2$ is $(C_1$-$C_6)$alkyl substituted with one to three $R_4$, and each $R_4$ is independently selected from $(C_6$-$C_{10})$aryl, 5- or 6-membered heteroaryl comprising 1 to 3 heteroatoms selected from O, N, and S, $(C_3$-$C_8)$cycloalkyl, and 5- to 7-membered heterocycloalkyl comprising 1 to 3 heteroatoms selected from O, N, and S, wherein the aryl, heteroaryl, cycloalkyl, and heterocycloalkyl groups are optionally substituted with one to three $R_7$.

In some embodiments of the formulae above, $X_1$ is CH, n is 1, q is 0, and $R_2$ is $(C_6-C_{00})$aryl, $(C_3-C_9)$cycloalkyl, or 5- to 7-membered heterocycloalkyl comprising 1 to 3 heteroatoms selected from O, N, and S, wherein the aryl, cycloalkyl, and heterocycloalkyl are optionally substituted with one to three $R_5$. In yet another embodiment, $X_1$ is CH, n is 1, q is 0, and $R_2$ is $(C_6-C_{10})$aryl, $(C_3-C_8)$cycloalkyl, or 5- to 7-membered heterocycloalkyl comprising 1 to 3 heteroatoms selected from O, N, and S.

In some embodiments of the formulae above, $X_1$ is CH, n is 1, q is 0, and $R_2$ is $(C_6-C_{10})$aryl optionally substituted with one to three $R_5$. In another embodiment, $X_1$ is CH, n is 1, q is 0, and $R_2$ is 5- or 6-membered heteroaryl comprising 1 to 3 heteroatoms selected from O, N, and S optionally substituted with one to three $R_5$. In yet another embodiment, $X_1$ is CH, n is 1, q is 0, and $R_2$ is $(C_3-C_8)$cycloalkyl optionally substituted with one to three $R_5$. In another embodiment, $X_1$ is CH, n is 1, q is 0, and $R_2$ is 5- to 7-membered heterocycloalkyl comprising 1 to 3 heteroatoms selected from O, N, and S, optionally substituted with one to three $R_5$.

In some embodiments of the formulae above, $X_1$ is CH, n is 1, q is 0 or 1, $R_1$ is $(C_1-C_6)$alkyl, and $R_2$ is $(C_6-C_{10})$aryl, $(C_3-C_8)$cycloalkyl, or 5- to 7-membered heterocycloalkyl comprising 1 to 3 heteroatoms selected from O, N, and S, wherein the aryl, cycloalkyl, and heterocycloalkyl are optionally substituted with one to three $R_5$. In yet another embodiment, $X_1$ is CH, n is 1, q is 0 or 1, $R_1$ is $(C_1-C_6)$alkyl, and $R_2$ is $(C_6-C_{10})$aryl, $(C_3-C_8)$cycloalkyl, or 5- to 7-membered heterocycloalkyl comprising 1 to 3 heteroatoms selected from O, N, and S.

In some embodiments of the formulae above, $X_1$ is CH, n is 1, q is 0 or 1, $R_1$ is $(C_1-C_6)$alkyl, and $R_2$ is $(C_6-C_{10})$aryl optionally substituted with one to three $R_5$. In another embodiment, $X_1$ is CH, n is 1, q is 0, and $R_2$ is 5- or 6-membered heteroaryl comprising 1 to 3 heteroatoms selected from O, N, and S optionally substituted with one to three $R_5$. In yet another embodiment, $X_1$ is CH, n is 1, q is 0 or 1, $R_1$ is $(C_1-C_6)$alkyl, and $R_2$ is $(C_3-C_8)$cycloalkyl optionally substituted with one to three $R_5$. In another embodiment, $X_1$ is CH, n is 1, q is 0 or 1, $R_1$ is $(C_1-C_6)$alkyl, and $R_2$ is 5- to 7-membered heterocycloalkyl comprising 1 to 3 heteroatoms selected from O, N, and S, optionally substituted with one to three $R_5$.

In some embodiments of the formulae above, $X_1$ is CH, n is 1, q is 0, and $R_2$ is $(C_1-C_6)$alkyl optionally substituted with one to three $R_4$. In another embodiment $X_1$ is CH, n is 1, q is 0, and $R_2$ is $(C_1-C_6)$alkyl substituted with one to three $R_4$.

In some embodiments of the formulae above, $X_1$ is CH, n is 1, q is 0, $R_2$ is $(C_1-C_6)$alkyl optionally substituted with one to three $R_4$, and each $R_4$ is independently selected from —C(O)OR$_6$, $(C_6-C_{10})$aryl, 5- or 6-membered heteroaryl comprising 1 to 3 heteroatoms selected from O, N, and S, $(C_3-C_8)$cycloalkyl, and 5- to 7-membered heterocycloalkyl comprising 1 to 3 heteroatoms selected from O, N, and S, wherein the aryl, heteroaryl, cycloalkyl, and heterocycloalkyl groups are optionally substituted with one to three $R_7$.

In some embodiments of the formulae above, $X_1$ is CH, n is 1, q is 0, $R_2$ is $(C_1-C_6)$alkyl substituted with one to three $R_4$, and each $R_4$ is independently selected from —C(O)OR$_6$, $(C_6-C_{10})$aryl, 5- or 6-membered heteroaryl comprising 1 to 3 heteroatoms selected from O, N, and S, $(C_3-C_8)$cycloalkyl, and 5- to 7-membered heterocycloalkyl comprising 1 to 3 heteroatoms selected from O, N, and S, wherein the aryl, heteroaryl, cycloalkyl, and heterocycloalkyl groups are optionally substituted with one to three $R_7$.

In some embodiments of the formulae above, $X_1$ is CH, n is 1, q is 0, $R_2$ is $(C_1-C_6)$alkyl optionally substituted with one to three $R_4$, and each $R_4$ is independently selected from halogen, —OH, $(C_6-C_{10})$aryl, 5- or 6-membered heteroaryl comprising 1 to 3 heteroatoms selected from O, N, and S, $(C_3-C_8)$cycloalkyl, and 5- to 7-membered heterocycloalkyl comprising 1 to 3 heteroatoms selected from O, N, and S, wherein the aryl, heteroaryl, cycloalkyl, and heterocycloalkyl groups are optionally substituted with one to three $R_7$.

In some embodiments of the formulae above, $X_1$ is CH, n is 1, q is 0, $R_2$ is $(C_1-C_6)$alkyl substituted with one to three $R_4$, and each $R_4$ is independently selected from halogen, —OH, $(C_6-C_{10})$aryl, 5- or 6-membered heteroaryl comprising 1 to 3 heteroatoms selected from O, N, and S, $(C_3-C_8)$cycloalkyl, and 5- to 7-membered heterocycloalkyl comprising 1 to 3 heteroatoms selected from O, N, and S, wherein the aryl, heteroaryl, cycloalkyl, and heterocycloalkyl groups are optionally substituted with one to three $R_7$.

In some embodiments of the formulae above, $X_1$ is CH, n is 1, n1 is 1, q is 0, $R_2$ is $(C_1-C_6)$alkyl optionally substituted with one to three $R_4$, and each $R_4$ is independently selected from halogen, —OH, $(C_6-C_{10})$aryl, 5- or 6-membered heteroaryl comprising 1 to 3 heteroatoms selected from O, N, and S, $(C_3-C_9)$cycloalkyl, and 5- to 7-membered heterocycloalkyl comprising 1 to 3 heteroatoms selected from O, N, and S, wherein the aryl, heteroaryl, cycloalkyl, and heterocycloalkyl groups are optionally substituted with one to three $R_7$.

In some embodiments of the formulae above, $X_1$ is CH, n is 1, n1 is 1, q is 0, $R_2$ is $(C_1-C_6)$alkyl substituted with one to three $R_4$, and each $R_4$ is independently selected from halogen, —OH, $(C_6-C_{10})$aryl, 5- or 6-membered heteroaryl comprising 1 to 3 heteroatoms selected from O, N, and S, $(C_3-C_8)$cycloalkyl, and 5- to 7-membered heterocycloalkyl comprising 1 to 3 heteroatoms selected from O, N, and S, wherein the aryl, heteroaryl, cycloalkyl, and heterocycloalkyl groups are optionally substituted with one to three $R_7$.

In some embodiments of the formulae above, $X_1$ is CH, n is 1, q is 0, $R_2$ is $(C_1-C_6)$alkyl optionally substituted with one to three $R_4$, and each $R_4$ is independently selected from $(C_6-C_{10})$aryl, 5- or 6-membered heteroaryl comprising 1 to 3 heteroatoms selected from O, N, and S, $(C_3-C_8)$cycloalkyl, and 5- to 7-membered heterocycloalkyl comprising 1 to 3 heteroatoms selected from O, N, and S, wherein the aryl, heteroaryl, cycloalkyl, and heterocycloalkyl groups are optionally substituted with one to three $R_7$.

In some embodiments of the formulae above, $X_1$ is CH, n is 1, q is 0, $R_2$ is $(C_1-C_6)$alkyl substituted with one to three $R_4$, and each $R_4$ is independently selected from $(C_6-C_{10})$aryl, 5- or 6-membered heteroaryl comprising 1 to 3 heteroatoms selected from O, N, and S, $(C_3-C_8)$cycloalkyl, and 5- to 7-membered heterocycloalkyl comprising 1 to 3 heteroatoms selected from O, N, and S, wherein the aryl, heteroaryl, cycloalkyl, and heterocycloalkyl groups are optionally substituted with one to three $R_7$.

In some embodiments of the formulae above, $X_1$ is CH, n is 1, q is 0, $R_2$ is $(C_1-C_6)$alkyl optionally substituted with one to three $R_4$, and each $R_4$ is independently selected from halogen, —OH, phenyl, 5- or 6-membered heteroaryl comprising 1 to 3 heteroatoms selected from O, N, and S, $(C_3-C_8)$cycloalkyl, and 5- to 7-membered heterocycloalkyl comprising 1 to 3 heteroatoms selected from O, N, and S, wherein the aryl, heteroaryl, cycloalkyl, and heterocycloalkyl groups are optionally substituted with one to three $R_7$.

In some embodiments of the formulae above, $X_1$ is CH, n is 1, q is 0, $R_2$ is $(C_1-C_6)$alkyl substituted with one to three $R_4$, and each $R_4$ is independently selected from halogen, —OH, phenyl, 5- or 6-membered heteroaryl comprising 1 to 3 heteroatoms selected from O, N, and S, $(C_3-C_8)$cycloalkyl, and 5- to 7-membered heterocycloalkyl comprising 1 to 3 heteroatoms selected from O, N, and S, wherein the aryl, heteroaryl, cycloalkyl, and heterocycloalkyl groups are optionally substituted with one to three $R_7$.

In some embodiments of the formulae above, $X_1$ is CH, n is 1, n1 is 1, q is 0, $R_2$ is $(C_1-C_6)$alkyl optionally substituted with one to three $R_4$, and each $R_4$ is independently selected from halogen, —OH, phenyl, 5- or 6-membered heteroaryl comprising 1 to 3 heteroatoms selected from O, N, and S, $(C_3-C_9)$cycloalkyl, and 5- to 7-membered heterocycloalkyl comprising 1 to 3 heteroatoms selected from O, N, and S, wherein the aryl, heteroaryl, cycloalkyl, and heterocycloalkyl groups are optionally substituted with one to three $R_7$.

In some embodiments of the formulae above, $X_1$ is CH, n is 1, n1 is 1, q is 0, $R_2$ is $(C_1-C_6)$alkyl substituted with one to three $R_4$, and each $R_4$ is independently selected from halogen, —OH, phenyl, 5- or 6-membered heteroaryl comprising 1 to 3 heteroatoms selected from O, N, and S, $(C_3-C_8)$cycloalkyl, and 5- to 7-membered heterocycloalkyl comprising 1 to 3 heteroatoms selected from O, N, and S, wherein the aryl, heteroaryl, cycloalkyl, and heterocycloalkyl groups are optionally substituted with one to three $R_7$.

In some embodiments of the formulae above, $X_1$ is CH, n is 1, q is 0, $R_2$ is $(C_1-C_6)$alkyl optionally substituted with one to three $R_4$, and each $R_4$ is independently selected from phenyl, 5- or 6-membered heteroaryl comprising 1 to 3 heteroatoms selected from O, N, and S, $(C_3-C_8)$cycloalkyl, and 5- to 7-membered heterocycloalkyl comprising 1 to 3 heteroatoms selected from O, N, and S, wherein the aryl, heteroaryl, cycloalkyl, and heterocycloalkyl groups are optionally substituted with one to three $R_7$.

In some embodiments of the formulae above, $X_1$ is CH, n is 1, q is 0, $R_2$ is $(C_1-C_6)$alkyl substituted with one to three $R_4$, and each $R_4$ is independently selected from phenyl, 5- or 6-membered heteroaryl comprising 1 to 3 heteroatoms selected from O, N, and S, $(C_3-C_8)$cycloalkyl, and 5- to 7-membered heterocycloalkyl comprising 1 to 3 heteroatoms selected from O, N, and S, wherein the aryl, heteroaryl, cycloalkyl, and heterocycloalkyl groups are optionally substituted with one to three $R_7$.

In some embodiments of the formulae above, $X_1$ is CH, n is 1, n1 is 1, q is 0, $R_2$ is $(C_1-C_6)$alkyl optionally substituted with one to three $R_4$, and each $R_4$ is independently selected from phenyl, 5- or 6-membered heteroaryl comprising 1 to 3 heteroatoms selected from O, N, and S, $(C_3-C_8)$cycloalkyl, and 5- to 7-membered heterocycloalkyl comprising 1 to 3 heteroatoms selected from O, N, and S, wherein the aryl, heteroaryl, cycloalkyl, and heterocycloalkyl groups are optionally substituted with one to three $R_7$.

In some embodiments of the formulae above, $X_1$ is CH, n is 1, n1 is 1, q is 0, $R_2$ is $(C_1-C_6)$alkyl substituted with one to three $R_4$, and each $R_4$ is independently selected from phenyl, 5- or 6-membered heteroaryl comprising 1 to 3 heteroatoms selected from O, N, and S, $(C_3-C_8)$cycloalkyl, and 5- to 7-membered heterocycloalkyl comprising 1 to 3 heteroatoms selected from O, N, and S, wherein the aryl and heteroaryl groups are optionally substituted with one to three $R_7$.

In some embodiments of the formulae above, $X_1$ is CH, n is 1, q is 0, $R_2$ is $(C_1-C_6)$alkyl optionally substituted with one to three $R_4$, and each $R_4$ is independently selected from phenyl and 5- or 6-membered heteroaryl comprising 1 to 3 heteroatoms selected from O, N, and S, wherein the aryl and heteroaryl groups are optionally substituted with one to three $R_7$.

In some embodiments of the formulae above, $X_1$ is CH, n is 1, q is 0, $R_2$ is $(C_1-C_6)$alkyl substituted with one to three $R_4$, and each $R_4$ is independently selected from phenyl and 5- or 6-membered heteroaryl comprising 1 to 3 heteroatoms selected from O, N, and S, $(C_3-C_8)$cycloalkyl, and 5- to 7-membered heterocycloalkyl comprising 1 to 3 heteroatoms selected from O, N, and S, wherein the aryl and heteroaryl groups are optionally substituted with one to three $R_7$.

In some embodiments of the formulae above, $X_1$ is CH, n is 1, n1 is 1, q is 0, $R_2$ is $(C_1-C_6)$alkyl optionally substituted with one to three $R_4$, and each $R_4$ is independently selected from phenyl and 5- or 6-membered heteroaryl comprising 1 to 3 heteroatoms selected from O, N, and S, wherein the aryl and heteroaryl groups are optionally substituted with one to three $R_7$.

In some embodiments of the formulae above, $X_1$ is CH, n is 1, n1 is 1, q is 0, $R_2$ is $(C_1-C_6)$alkyl substituted with one to three $R_4$, and each $R_4$ is independently selected from phenyl and 5- or 6-membered heteroaryl comprising 1 to 3 heteroatoms selected from O, N, and S, $(C_3-C_8)$cycloalkyl, and 5- to 7-membered heterocycloalkyl comprising 1 to 3 heteroatoms selected from O, N, and S, wherein the aryl and heteroaryl groups are optionally substituted with one to three $R_7$.

In some embodiments of the formulae above, $X_1$ is CH, n is 1, q is 0, $R_2$ is $(C_1-C_6)$alkyl optionally substituted with one to three $R_4$, and each $R_4$ is phenyl optionally substituted with one to three $R_7$.

In some embodiments of the formulae above, $X_1$ is CH, n is 1, q is 0, $R_2$ is $(C_1-C_6)$alkyl substituted with one to three $R_4$, and each $R_4$ is phenyl optionally substituted with one to three $R_7$.

In some embodiments of the formulae above, $X_1$ is CH, n is 1, n1 is 1, q is 0, $R_2$ is $(C_1-C_6)$alkyl optionally substituted with one to three $R_4$, and each $R_4$ is phenyl optionally substituted with one to three $R_7$.

In some embodiments of the formulae above, $X_1$ is CH, n is 1, n1 is 1, q is 0, $R_2$ is $(C_1-C_6)$alkyl substituted with one to three $R_4$, and each $R_4$ is phenyl optionally substituted with one to three $R_7$.

In some embodiments of the formulae above, $X_1$ is CH and n is 2. In another embodiment, $X_1$ is CH, n is 2, and q is 0. In yet another embodiment, $X_1$ is CH, n is 2, and q is 0 or 1. In another embodiment, $X_1$ is CH, n is 2, q is 0 or 1, and $R_1$ is $(C_1-C_6)$alkyl.

In some embodiments of the formulae above, $X_1$ is CH, n is 2, q is 0 or 1, $R_1$ is $(C_1-C_6)$alkyl, and $R_2$ is $(C_1-C_6)$alkyl optionally substituted with one to three $R_4$. In another embodiment, $X_1$ is CH, n is 2, q is 0 or 1, $R_1$ is $(C_1-C_6)$alkyl, and $R_2$ is $(C_1-C_6)$alkyl substituted with one to three $R_4$.

In some embodiments of the formulae above, $X_1$ is CH, n is 2, q is 0, and $R_2$ is $(C_1-C_6)$alkyl optionally substituted with one to three $R_4$. In another embodiment, $X_1$ is CH, n is 2, q is 0, and $R_2$ is $(C_1-C_6)$alkyl substituted with one to three $R_4$.

In some embodiments of the formulae above, $X_1$ is CH, n is 2, q is 0 or 1, $R_1$ is $(C_1-C_6)$alkyl, $R_2$ is $(C_1-C_6)$alkyl optionally substituted with one to three $R_4$, and each $R_4$ is independently selected from —C(O)OR$_6$, (C$_6$-C$_{10}$)aryl, 5- or 6-membered heteroaryl comprising 1 to 3 heteroatoms selected from O, N, and S, (C$_3$-C$_8$)cycloalkyl, and 5- to 7-membered heterocycloalkyl comprising 1 to 3 heteroatoms selected from O, N, and S, wherein the aryl, heteroaryl, cycloalkyl, and heterocycloalkyl groups are optionally substituted with one to three R$_7$.

In some embodiments of the formulae above, X$_1$ is CH, n is 2, q is 0 or 1, R$_1$ is (C$_1$-C$_6$)alkyl, R$_2$ is (C$_1$-C$_6$)alkyl substituted with one to three R$_4$, and each R$_4$ is independently selected from —C(O)OR$_6$, (C$_6$-C$_{10}$)aryl, 5- or 6-membered heteroaryl comprising 1 to 3 heteroatoms selected from O, N, and S, (C$_3$-C$_9$)cycloalkyl, and 5- to 7-membered heterocycloalkyl comprising 1 to 3 heteroatoms selected from O, N, and S, wherein the aryl, heteroaryl, cycloalkyl, and heterocycloalkyl groups are optionally substituted with one to three R$_7$.

In some embodiments of the formulae above, X$_1$ is CH, n is 2, q is 0 or 1, R$_1$ is (C$_1$-C$_6$)alkyl, R$_2$ is (C$_1$-C$_6$)alkyl optionally substituted with one to three R$_4$, and each R$_4$ is independently selected from (C$_6$-C$_{10}$)aryl, 5- or 6-membered heteroaryl comprising 1 to 3 heteroatoms selected from O, N, and S, (C$_3$-C$_9$)cycloalkyl, and 5- to 7-membered heterocycloalkyl comprising 1 to 3 heteroatoms selected from O, N, and S, wherein the aryl, heteroaryl, cycloalkyl, and heterocycloalkyl groups are optionally substituted with one to three R$_7$.

In some embodiments of the formulae above, X$_1$ is CH, n is 2, q is 0 or 1, R$_1$ is (C$_1$-C$_6$)alkyl, R$_2$ is (C$_1$-C$_6$)alkyl substituted with one to three R$_4$, and each R$_4$ is independently selected from (C$_6$-C$_{10}$)aryl, 5- or 6-membered heteroaryl comprising 1 to 3 heteroatoms selected from O, N, and S, (C$_3$-C$_8$)cycloalkyl, and 5- to 7-membered heterocycloalkyl comprising 1 to 3 heteroatoms selected from O, N, and S, wherein the aryl, heteroaryl, cycloalkyl, and heterocycloalkyl groups are optionally substituted with one to three R$_7$.

In some embodiments of the formulae above, X$_1$ is CH, n is 2, q is 0, and R$_2$ is (C$_6$-C$_{10}$)aryl, (C$_3$-C$_9$)cycloalkyl, or 5- to 7-membered heterocycloalkyl comprising 1 to 3 heteroatoms selected from O, N, and S, wherein the aryl, cycloalkyl, and heterocycloalkyl are optionally substituted with one to three R$_5$. In yet another embodiment, X$_1$ is CH, n is 2, q is 0, and R$_2$ is (C$_6$-C$_{10}$)aryl, (C$_3$-C$_8$)cycloalkyl, or 5- to 7-membered heterocycloalkyl comprising 1 to 3 heteroatoms selected from O, N, and S.

In some embodiments of the formulae above, X$_1$ is CH, n is 2, q is 0, and R$_2$ is (C$_6$-C$_{10}$)aryl optionally substituted with one to three R$_5$. In another embodiment, X$_1$ is CH, n is 2, q is 0, and R$_2$ is 5- or 6-membered heteroaryl comprising 1 to 3 heteroatoms selected from O, N, and S optionally substituted with one to three R$_5$. In yet another embodiment, X$_1$ is CH, n is 2, q is 0, and R$_2$ is (C$_3$-C$_8$)cycloalkyl optionally substituted with one to three R$_5$. In another embodiment, X$_1$ is CH, n is 2, q is 0, and R$_2$ is 5- to 7-membered heterocycloalkyl comprising 1 to 3 heteroatoms selected from O, N, and S, optionally substituted with one to three R$_5$.

In some embodiments of the formulae above, X$_1$ is CH, n is 2, q is 0 or 1, R$_1$ is (C$_1$-C$_6$)alkyl, and R$_2$ is (C$_6$-C$_{10}$)aryl, (C$_3$-C$_8$)cycloalkyl, or 5- to 7-membered heterocycloalkyl comprising 1 to 3 heteroatoms selected from O, N, and S, wherein the aryl, cycloalkyl, and heterocycloalkyl are optionally substituted with one to three R$_5$. In yet another embodiment, X$_1$ is CH, n is 2, q is 0 or 1, R$_1$ is (C$_1$-C$_6$)alkyl, and R$_2$ is (C$_6$-C$_{10}$)aryl, (C$_3$-C$_8$)cycloalkyl, or 5- to 7-membered heterocycloalkyl comprising 1 to 3 heteroatoms selected from O, N, and S.

In some embodiments of the formulae above, X$_1$ is CH, n is 2, q is 0 or 1, R$_1$ is (C$_1$-C$_6$)alkyl, and R$_2$ is (C$_6$-C$_{10}$)aryl optionally substituted with one to three R$_5$. In another embodiment, X$_1$ is CH, n is 2, q is 0, and R$_2$ is 5- or 6-membered heteroaryl comprising 1 to 3 heteroatoms selected from O, N, and S optionally substituted with one to three R$_5$. In yet another embodiment, X$_1$ is CH, n is 2, q is 0 or 1, R$_1$ is (C$_1$-C$_6$)alkyl, and R$_2$ is (C$_3$-C$_8$)cycloalkyl optionally substituted with one to three R$_5$. In another embodiment, X$_1$ is CH, n is 2, q is 0 or 1, R$_1$ is (C$_1$-C$_6$)alkyl, and R$_2$ is 5- to 7-membered heterocycloalkyl comprising 1 to 3 heteroatoms selected from O, N, and S, optionally substituted with one to three R$_5$.

In some embodiments of the formulae above,

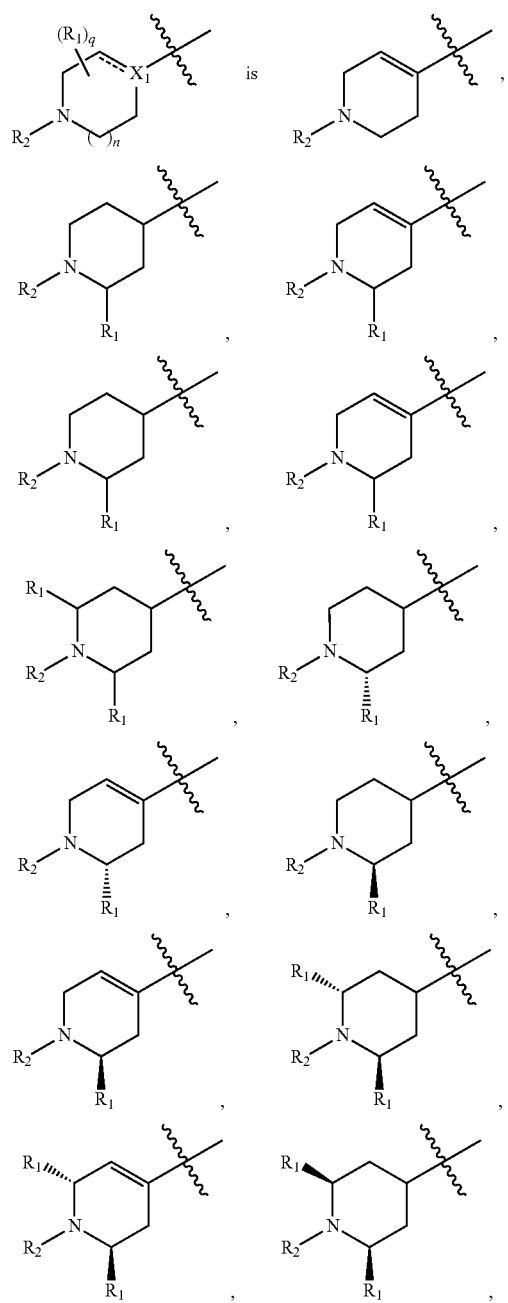

-continued
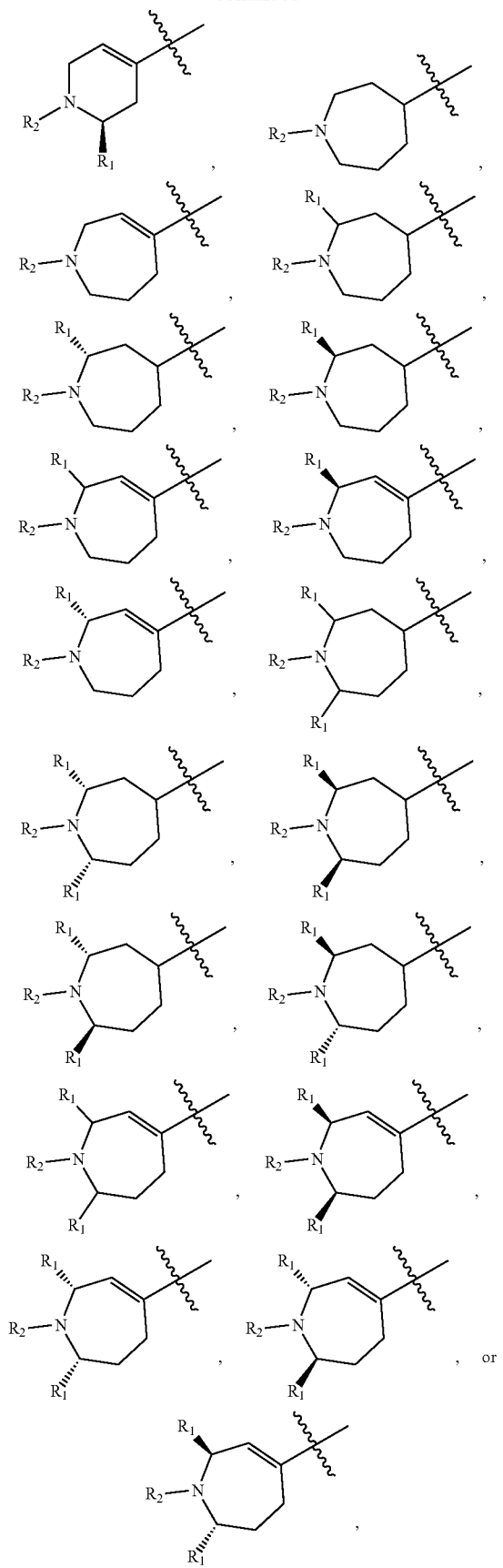
In some embodiments of the formulae above,
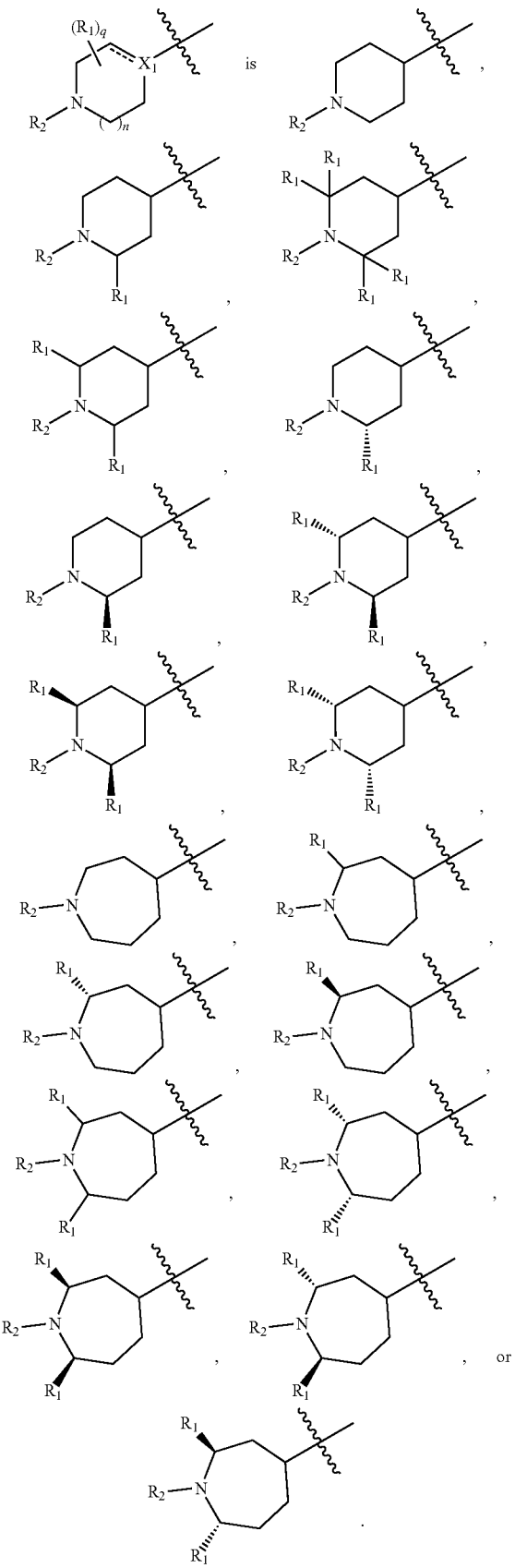

In some embodiments of the formulae above,
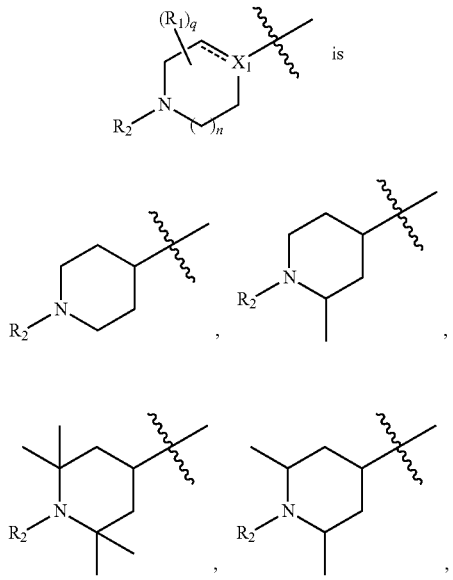
is
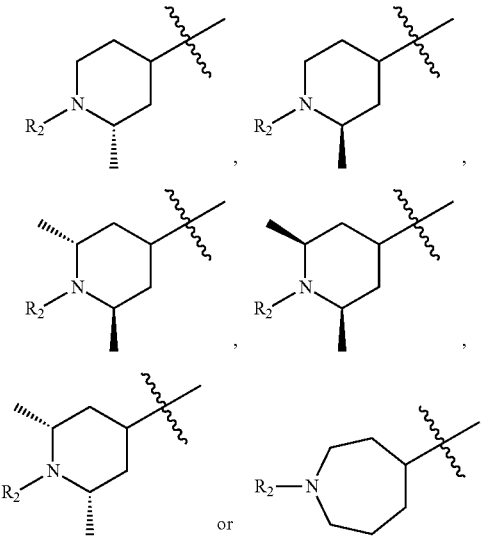
Non-limiting illustrative compounds of the disclosure include:
| Cmpd No. | Structure | Compound Name |
|---|---|---|
| I-1 | 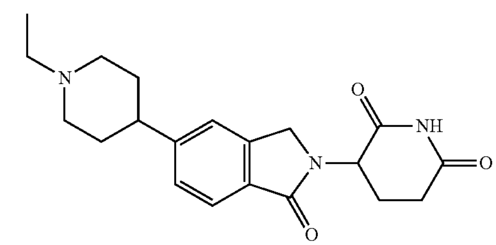 [SMILES: CCN1CCC(c2ccc3c(c2)CN(C2CCC(=O)NC2=O)C3=O)CC1] | 3-(5-(1-ethylpiperidin-4-yl)-1-oxoisoindolin-2-yl)piperidine-2,6-dione |
| I-2 | 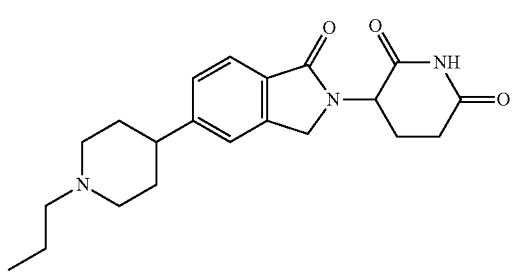 [SMILES: CCCN1CCC(c2ccc3c(c2)CN(C2CCC(=O)NC2=O)C3=O)CC1] | 3-(1-oxo-5-(1-propylpiperidin-4-yl)isoindolin-2-yl)piperidine-2,6-dione |
| I-3 | 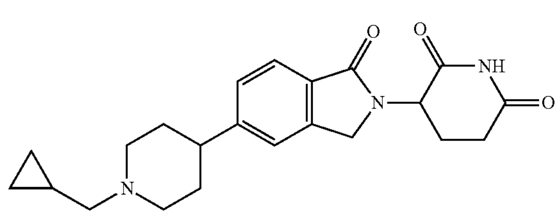 [SMILES: O=C1CCC(N2Cc3cc(C4CCN(CC5CC5)CC4)ccc3C2=O)C(=O)N1] | 3-(5-(1-(cyclopropylmethyl)piperidin-4-yl)-1-oxoisoindolin-2-yl)piperidine-2,6-dione |

-continued

| Cmpd No. | Structure | Compound Name |
|---|---|---|
| I-4 | 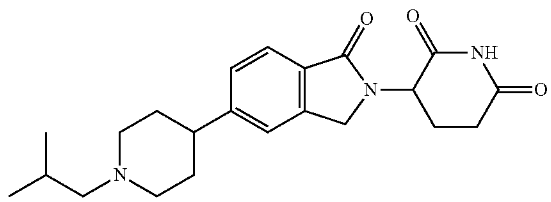 [SMILES: CC(C)CN1CCC(c2ccc3c(c2)CN(C2CCC(=O)NC2=O)C3=O)CC1] | 3-(5-(1-isobutylpiperidin-4-yl)-1-oxoisoindolin-2-yl)piperidine-2,6-dione |
| I-5 | 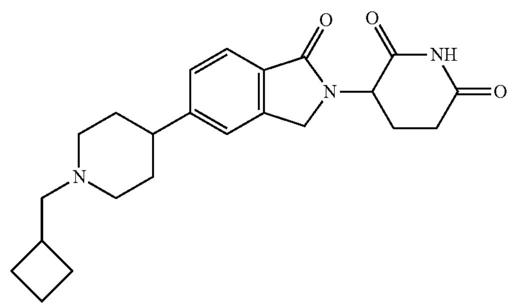 [SMILES: O=C1CCC(N2Cc3cc(C4CCN(CC5CCC5)CC4)ccc3C2=O)C(=O)N1] | 3-(5-(1-(cyclobutylmethyl)piperidin-4-yl)-1-oxoisoindolin-2-yl)piperidine-2,6-dione |
| I-6 | 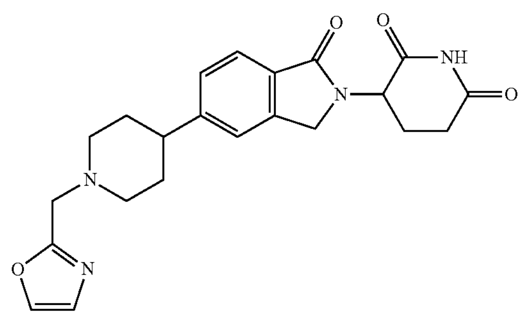 [SMILES: O=C1CCC(N2Cc3cc(C4CCN(Cc5ncco5)CC4)ccc3C2=O)C(=O)N1] | 3-(5-(1-oxazol-2-ylmethyl)piperidin-4-yl)-1-oxoisoindol-2-yl)piperidine-2,6-dione |
| I-7 | 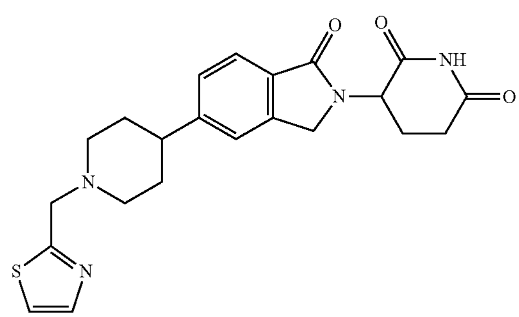 [SMILES: O=C1CCC(N2Cc3cc(C4CCN(Cc5nccs5)CC4)ccc3C2=O)C(=O)N1] | 3-(1-oxo-5-(1-(thiazol-2-ylmethyl)piperidin-4-yl)isoindolin-2-yl)piperidine-2,6-dione |
| I-8 | 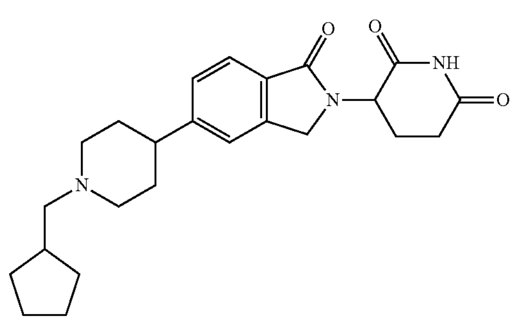 [SMILES: O=C1CCC(N2Cc3cc(C4CCN(CC5CCCC5)CC4)ccc3C2=O)C(=O)N1] | 3-(5-(1-(cyclopentylmethyl)piperidin-4-yl)-1-oxoisoindolin-2-yl)piperidine-2,6-dione |

-continued

| Cmpd No. | Structure | Compound Name |
| --- | --- | --- |
| I-9 | 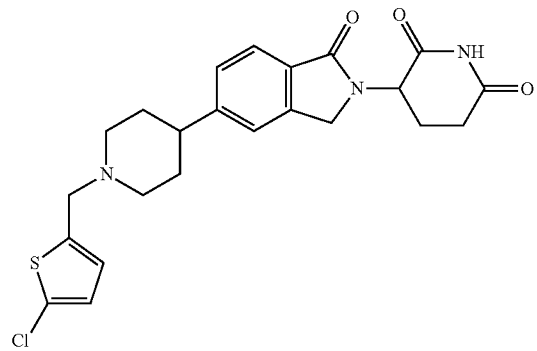 [SMILES: O=C1CCC(N2Cc3cc(C4CCN(Cc5ccc(Cl)s5)CC4)ccc3C2=O)C(=O)N1] | 3-(5-(1-((5-chlorothiophen-2-yl)methyl)piperidin-4-yl)-1-oxoisoindolin-2-yl)piperidine-2,6-dione |
| I-10 | 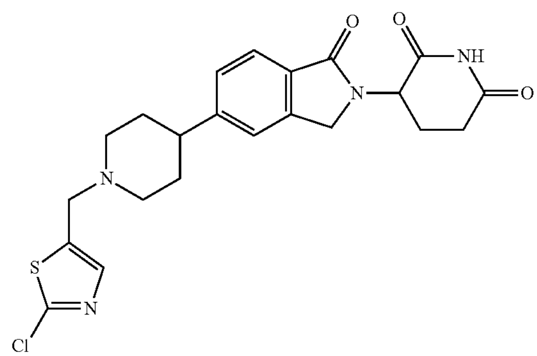 [SMILES: O=C1CCC(N2Cc3cc(C4CCN(Cc5cnc(Cl)s5)CC4)ccc3C2=O)C(=O)N1] | 3-(5-(1-((2-chlorothiazol-5-yl)methyl)piperidin-4-yl)-1-oxoisoindolin-2-yl)piperidine-2,6-dione |
| I-11 | 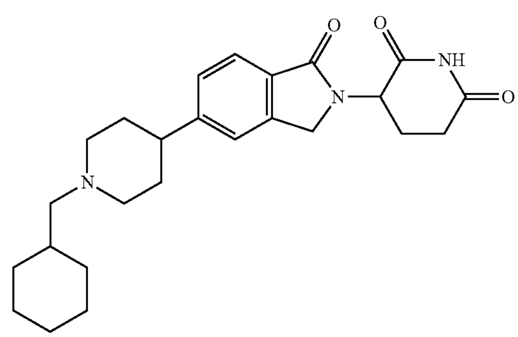 [SMILES: O=C1CCC(N2Cc3cc(C4CCN(CC5CCCCC5)CC4)ccc3C2=O)C(=O)N1] | 3-(5-(1-(cyclohexylmethyl)piperidin-4-yl)-1-oxoisoindolin-2-yl)piperidine-2,6-dione |
| I-12 | 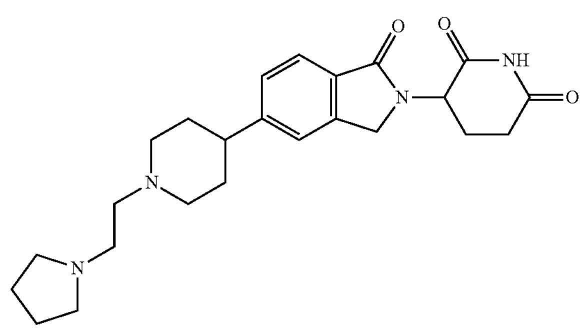 [SMILES: O=C1CCC(N2Cc3cc(C4CCN(CCN5CCCC5)CC4)ccc3C2=O)C(=O)N1] | 3-(1-oxo-5-(1-(2-(pyrrolidin-1-yl)ethyl)piperidin-4-yl)isoindolin-2-yl)piperidine-2,6-dione |

-continued

| Cmpd No. | Structure | Compound Name |
|---|---|---|
| I-13 | 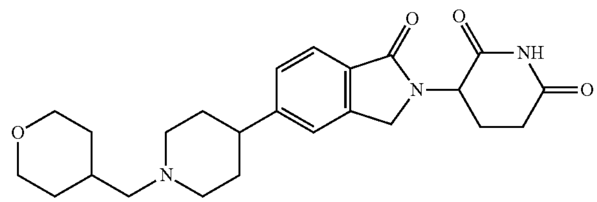 [SMILES: O=C1CCC(N2Cc3cc(C4CCN(CC5CCOCC5)CC4)ccc3C2=O)C(=O)N1] | 3-(1-oxo-5-(1-((tetrahydro-2H-pyran-4-yl)methyl)piperidin-4-yl)isoindolin-2-yl)piperidine-2,6-dione |
| I-14 | 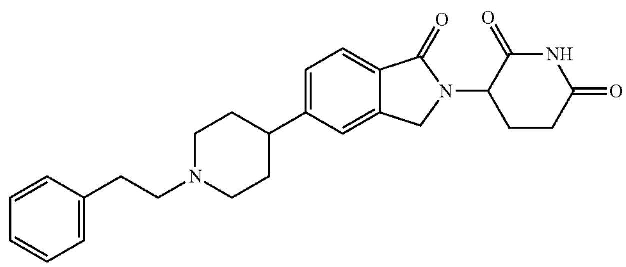 [SMILES: O=C1CCC(N2Cc3cc(C4CCN(CCc5ccccc5)CC4)ccc3C2=O)C(=O)N1] | 3-(1-oxo-5-(1-phenethylpiperidin-4-yl)isoindolin-2-yl)piperidine-2,6-dione |
| I-15 | 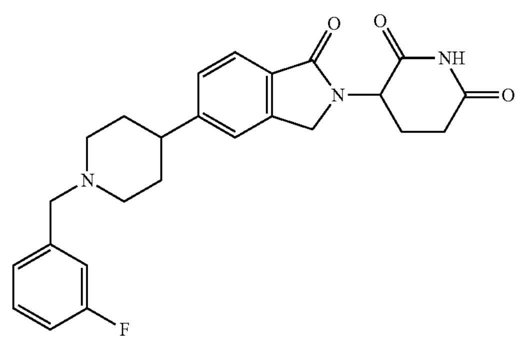 [SMILES: O=C1CCC(N2Cc3cc(C4CCN(Cc5cccc(F)c5)CC4)ccc3C2=O)C(=O)N1] | 3-(5-(1-(3-fluorobenzyl)piperidin-4-yl)-1-oxoisoindolin-2-yl)piperidine-2,6-dione |
| I-16 | 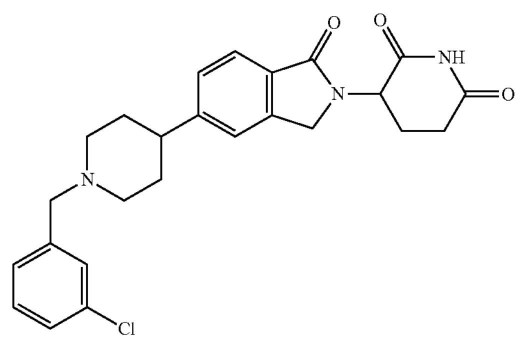 [SMILES: O=C1CCC(N2Cc3cc(C4CCN(Cc5cccc(Cl)c5)CC4)ccc3C2=O)C(=O)N1] | 3-(5-(1-(3-chlorobenzyl)piperidin-4-yl)-1-oxoisoindolin-2-yl)piperidine-2,6-dione |
| I-17 | 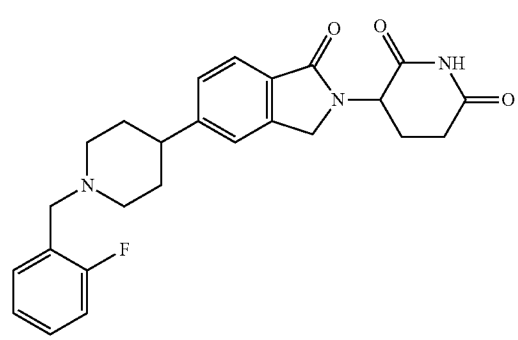 [SMILES: O=C1CCC(N2Cc3cc(C4CCN(Cc5ccccc5F)CC4)ccc3C2=O)C(=O)N1] | 3-(5-(1-(2-fluorobenzyl)piperidin-4-yl)-1-oxoisoindolin-2-yl)piperidine-2,6-dione |

| Cmpd No. | Structure | Compound Name |
|---|---|---|
| I-18 | 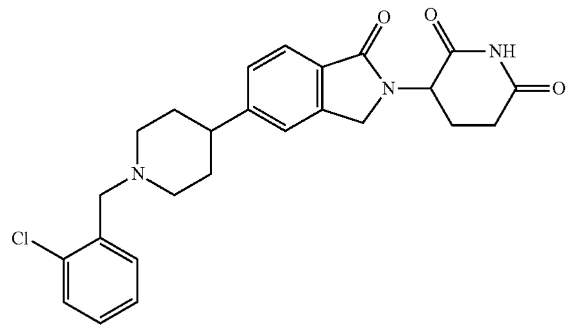 [SMILES: O=C1CCC(N2Cc3cc(C4CCN(Cc5ccccc5Cl)CC4)ccc3C2=O)C(=O)N1] | 3-(5-(1-(2-chlorobenzyl)piperidin-4-yl)-1-oxoisoindolin-2-yl)piperidine-2,6-dione |
| I-19 | 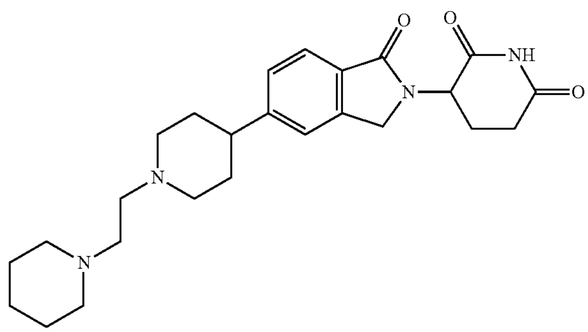 [SMILES: O=C1CCC(N2Cc3cc(C4CCN(CCN5CCCCC5)CC4)ccc3C2=O)C(=O)N1] | 3-(1-oxo-5-(1-(2-(piperidin-1-yl)ethyl)piperidin-4-yl)isoindolin-2-yl)piperidine-2,6-dione |
| I-20 | 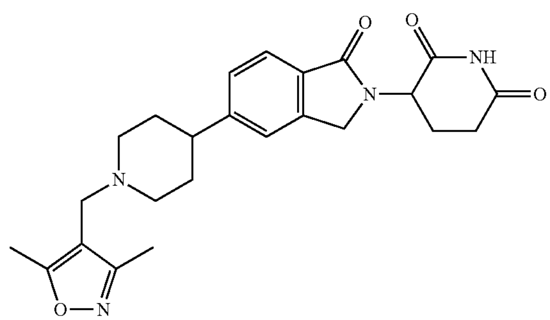 [SMILES: Cc1noc(C)c1CN1CCC(c2ccc3c(c2)CN(C2CCC(=O)NC2=O)C3=O)CC1] | 3-(5-(1-((3,5-dimethylisoxazol-4-yl)methyl)piperidin-4-yl)-1-oxoisoindolin-2-yl)piperidine-2,6-dione |
| I-21 | 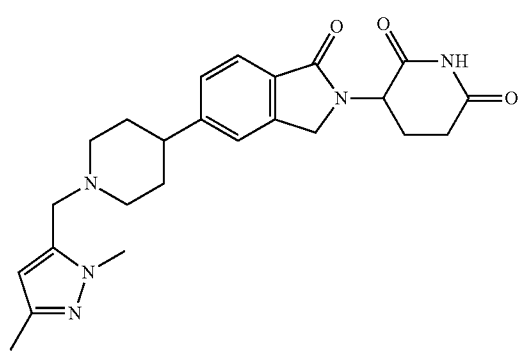 [SMILES: Cc1cc(CN2CCC(c3ccc4c(c3)CN(C3CCC(=O)NC3=O)C4=O)CC2)n(C)n1] | 3-(5-(1-((1,3-dimethyl-1H-pyrazol-5-yl)methyl)piperidin-4-yl)-1-oxoisoindolin-2-yl)piperidine-2,6-dione |

| Cmpd No. | Structure | Compound Name |
|---|---|---|
| I-22 | 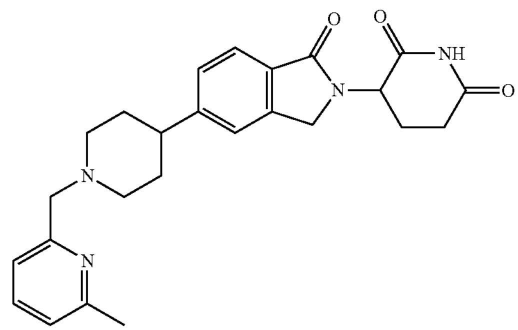 [SMILES: Cc1cccc(CN2CCC(c3ccc4c(c3)CN(C3CCC(=O)NC3=O)C4=O)CC2)n1] | 3-(5-(1-((6-methylpyridin-2-yl)methyl)piperidin-4-yl)-1-oxoisoindolin-2-yl)piperidine-2,6-dione |
| I-23 | 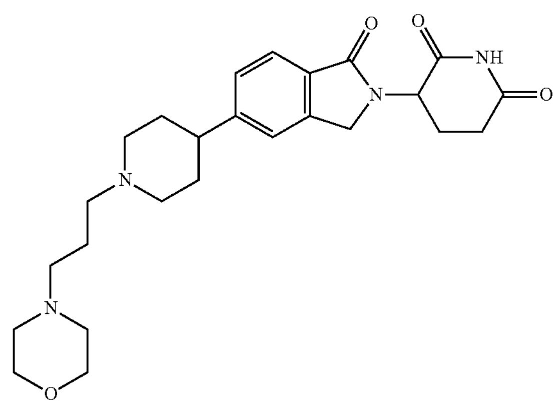 [SMILES: O=C1CCC(N2Cc3cc(C4CCN(CCCN5CCOCC5)CC4)ccc3C2=O)C(=O)N1] | 3-(5-(1-(3-morpholinopropyl)piperidin-4-yl)-1-oxoisoindolin-2-yl)piperidine-2,6-dione |
| I-24 | 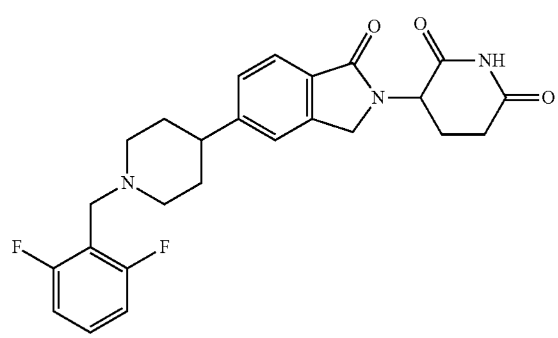 [SMILES: O=C1CCC(N2Cc3cc(C4CCN(Cc5c(F)cccc5F)CC4)ccc3C2=O)C(=O)N1] | 3-(5-(1-(2,6-difluorobenzyl)piperidin-4-yl)-1-oxoisoindolin-2-yl)piperidine-2,6-dione |
| I-25 | 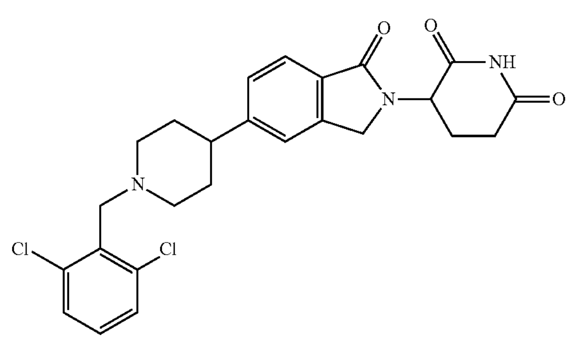 [SMILES: O=C1CCC(N2Cc3cc(C4CCN(Cc5c(Cl)cccc5Cl)CC4)ccc3C2=O)C(=O)N1] | 3-(5-(1-(2,6-dichlorobenzyl)piperidin-4-yl)-1-oxoisoindolin-2-yl)piperidine-2,6-dione |

-continued

| Cmpd No. | Structure | Compound Name |
|---|---|---|
| I-26 | 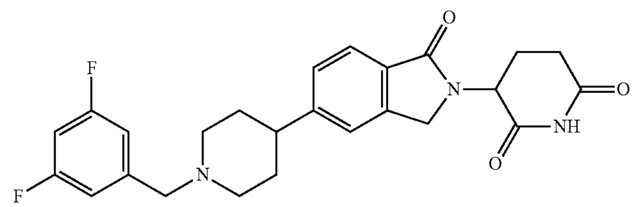 [SMILES: O=C1CCC(N2Cc3cc(C4CCN(Cc5cc(F)cc(F)c5)CC4)ccc3C2=O)C(=O)N1] | 3-(5-(1-(3,5-difluorobenzyl)piperidin-4-yl)-1-oxoisoindolin-2-yl)piperidine-2,6-dione |
| I-27 | 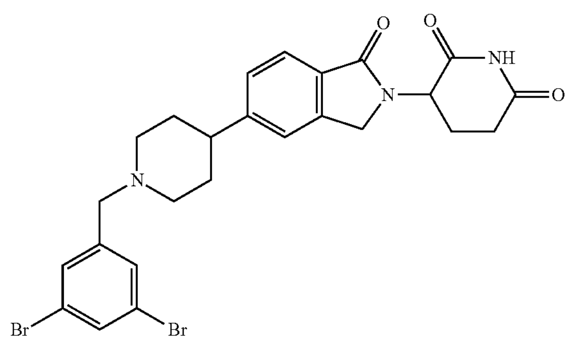 | 3-(5-(1-(3,5-dibromobenzyl)piperidin-4-yl)-1-oxoisoindolin-2-yl)piperidine-2,6-dione |
| I-28 | 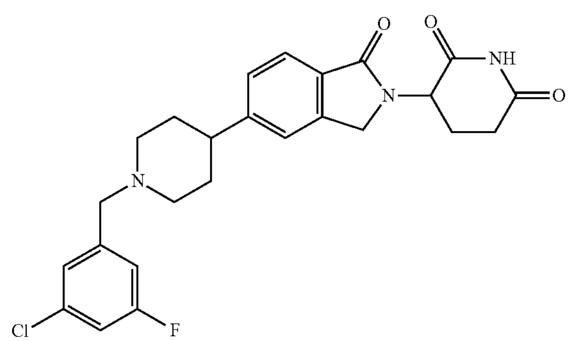 [SMILES: O=C1CCC(N2Cc3cc(C4CCN(Cc5cc(F)cc(Cl)c5)CC4)ccc3C2=O)C(=O)N1] | 3-(5-(1-(3-chloro-5-fluorobenzyl)piperidin-4-yl)-1-oxoisoindolin-2-yl)piperidine-2,6-dione |
| I-29 | 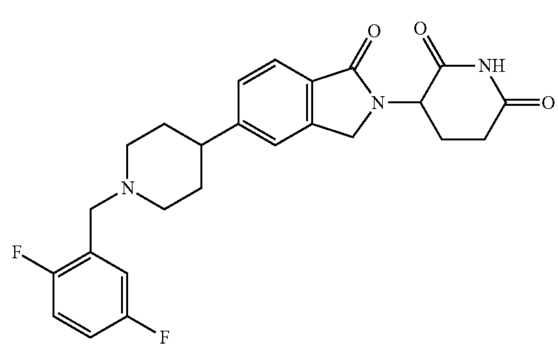 [SMILES: O=C1CCC(N2Cc3cc(C4CCN(Cc5cc(F)ccc5F)CC4)ccc3C2=O)C(=O)N1] | 3-(5-(1-(2,5-difluorobenzyl)piperidin-4-yl)-1-oxoisoindolin-2-yl)piperidine-2,6-dione |

-continued

| Cmpd No. | Structure | Compound Name |
|---|---|---|
| I-30 | 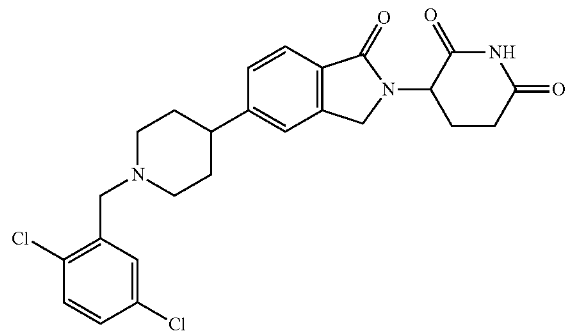 [SMILES: O=C1CCC(N2Cc3cc(C4CCN(Cc5cc(Cl)ccc5Cl)CC4)ccc3C2=O)C(=O)N1] | 3-(5-(1-(2,5-dichlorobenzyl)piperidin-4-yl)-1-oxoisoindolin-2-yl)piperidine-2,6-dione |
| I-31 | 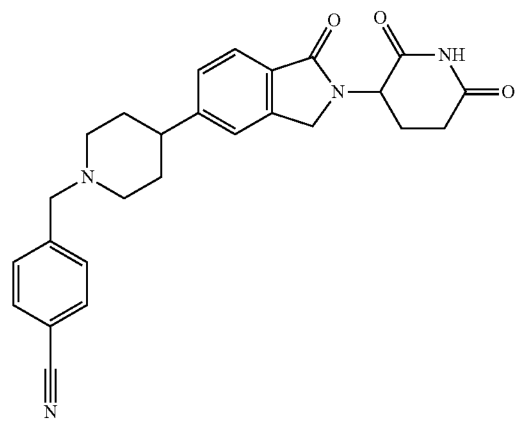 [SMILES: N#Cc1ccc(CN2CCC(c3ccc4c(c3)CN(C3CCC(=O)NC3=O)C4=O)CC2)cc1] | 4-((4-(2-(2,6-dioxopiperidin-3-yl)-1-oxoisoindolin-5-yl)piperidin-1-yl)methyl)benzonitrile (or 3-(5-(1-(4-nitrilebenzyl)piperidin-4-yl)-1-oxoisoindolin-2-yl)piperidine-2,6-dione) |
| I-32 | 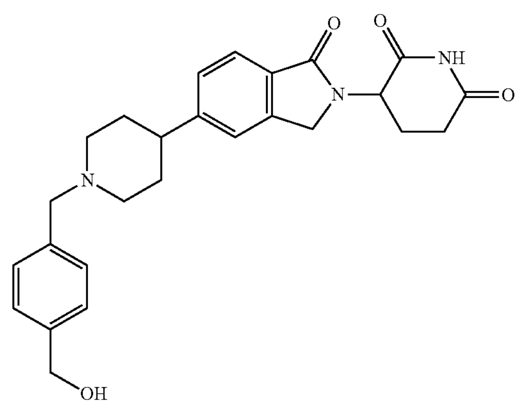 [SMILES: O=C1CCC(N2Cc3cc(C4CCN(Cc5ccc(CO)cc5)CC4)ccc3C2=O)C(=O)N1] | 3-(5-(1-(4-(hydroxymethyl)benzyl)piperidin-4-yl)-1-oxoisoindolin-2-yl)piperidine-2,6-dione |
| I-33 | 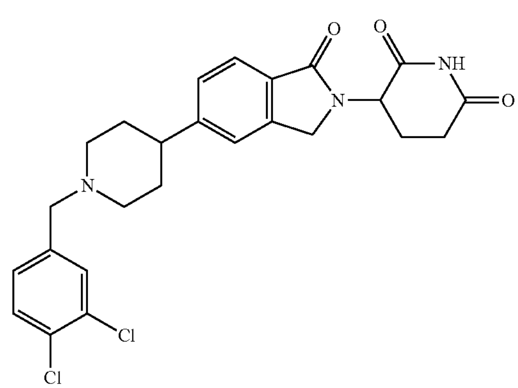 | 3-(5-(1-(3,4-dichlorobenzyl)piperidin-4-yl)-1-oxoisoindolin-2-yl)piperidine-2,6-dione |

-continued
| Cmpd No. | Structure | Compound Name |
|---|---|---|
| I-34 | 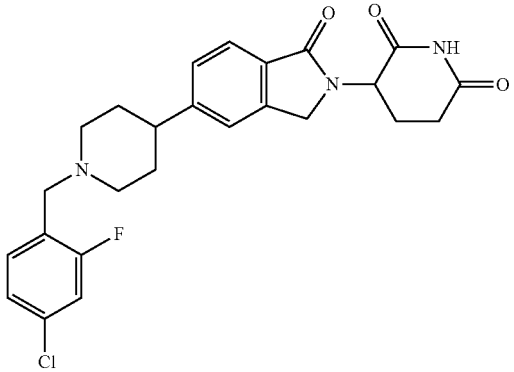 | 3-(5-(1-(4-chloro-2-fluorobenzyl)piperidin-4-yl)-1-oxoisoindolin-2-yl)piperidine-2,6-dione |
| I-35 | 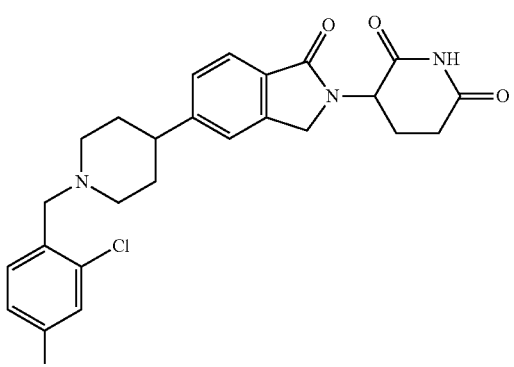 | 3-(5-(1-(2-chloro-4-fluorobenzyl)piperidin-4-yl)-1-oxoisoindolin-2-yl)piperidine-2,6-dione |
| I-36 | 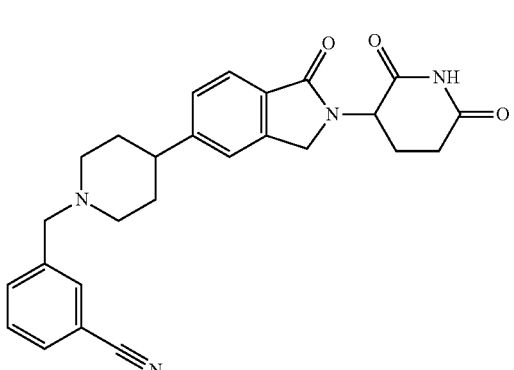 | 3-((4-(2-(2,6-dioxopiperidin-3-yl)-1-oxoisoindolin-5-yl)piperidin-1-yl)methyl)benzonitrile |
| I-37 | 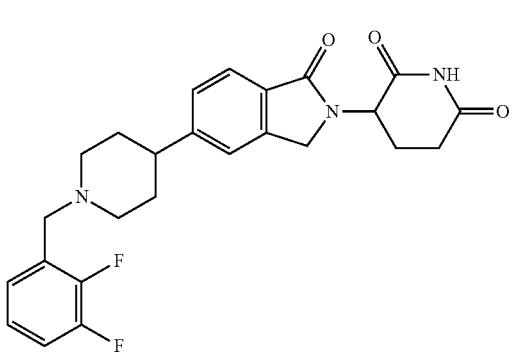 [SMILES: O=C1CCC(N2Cc3cc(C4CCN(Cc5cccc(F)c5F)CC4)ccc3C2=O)C(=O)N1] | 3-(5-(1-(2,3-difluorobenzyl)piperidin-4-yl)-1-oxoisoindolin-2-yl)piperidine-2,6-dione |

-continued

| Cmpd No. | Structure | Compound Name |
|---|---|---|
| I-38 | 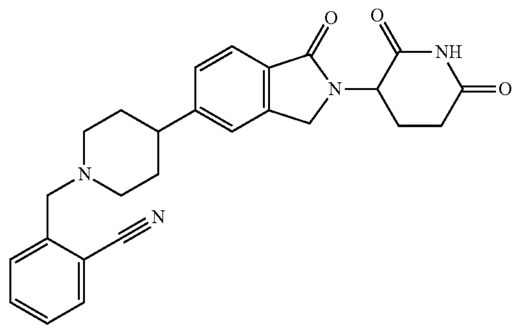 [SMILES: N#Cc1ccccc1CN1CCC(c2ccc3c(c2)CN(C2CCC(=O)NC2=O)C3=O)CC1] | 2-((4-(2-(2,6-dioxopiperidin-3-yl)-1-oxoisoindolin-5-yl)piperidin-1-yl)methyl)benzonitrile |
| I-39 | 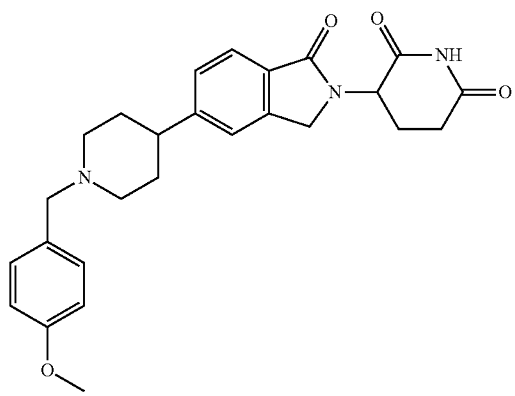 | 3-(5-(1-(4-methoxybenzyl)piperidin-4-yl)-1-oxoisoindolin-2-yl)piperidine-2,6-dione |
| I-40 | 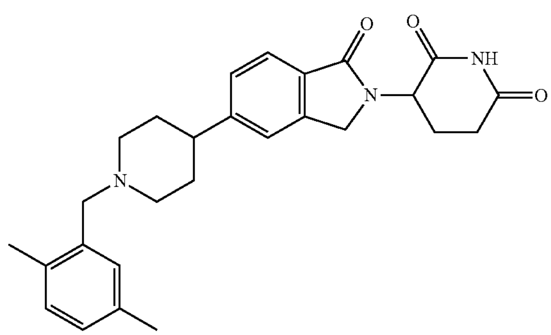 [SMILES: Cc1ccc(C)c(CN2CCC(c3ccc4c(c3)CN(C3CCC(=O)NC3=O)C4=O)CC2)c1] | 3-(5-(1-(2,5-dimethylbenzyl)piperidin-4-yl)-1-oxoisoindolin-2-yl)piperidine-2,6-dione |
| I-41 | 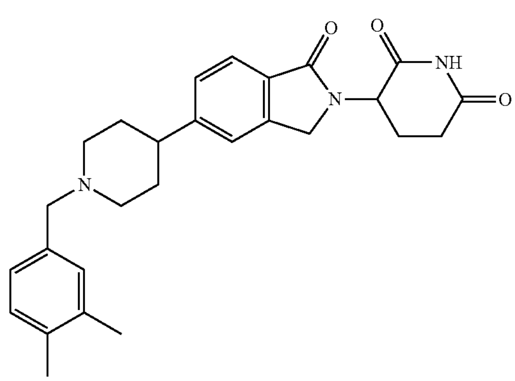 [SMILES: Cc1ccc(CN2CCC(c3ccc4c(c3)CN(C3CCC(=O)NC3=O)C4=O)CC2)cc1C] | 3-(5-(1-(3,4-dimethylbenzyl)piperidin-4-yl)-1-oxoisoindolin-2-yl)piperidine-2,6-dione |

-continued

| Cmpd No. | Structure | Compound Name |
|---|---|---|
| I-42 | 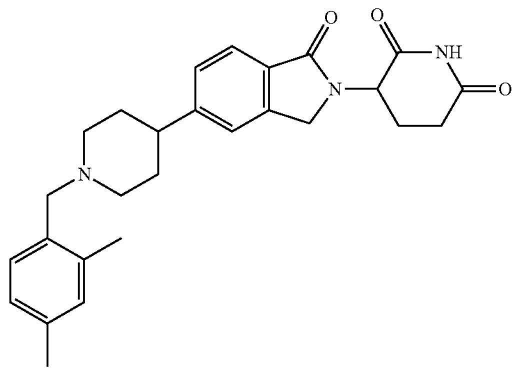 [SMILES: Cc1ccc(CN2CCC(c3ccc4c(c3)CN(C3CCC(=O)NC3=O)C4=O)CC2)c(C)c1] | 3-(5-(1-(2,4-dimethylbenzyl)piperidin-4-yl)-1-oxoisoindolin-2-yl)piperidine-2,6-dione |
| I-43 | 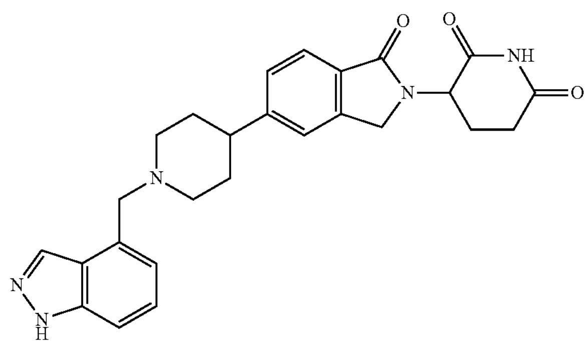 [SMILES: O=C1CCC(N2Cc3cc(C4CCN(Cc5cccc6[nH]ncc56)CC4)ccc3C2=O)C(=O)N1] | 3-(5-(1-((1H-indazol-4-yl)methyl)piperidin-4-yl)-1-oxoisoindolin-2-yl)piperidine-2,6-dione |
| I-44 | 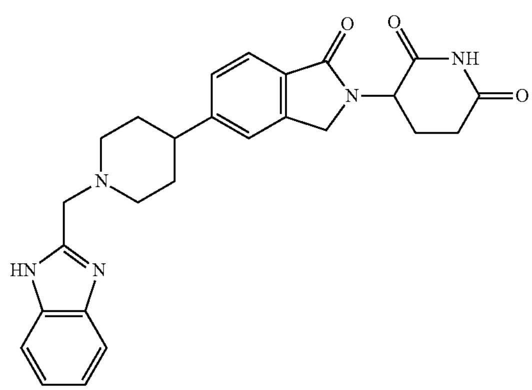 [SMILES: O=C1CCC(N2Cc3cc(C4CCN(Cc5nc6ccccc6[nH]5)CC4)ccc3C2=O)C(=O)N1] | 3-(5-(1-((1H-benzo[d]imidazol-2-yl)methyl)piperidin-4-yl)-1-oxoisoindolin-2-yl)piperidine-2,6-dione |
| I-45 | 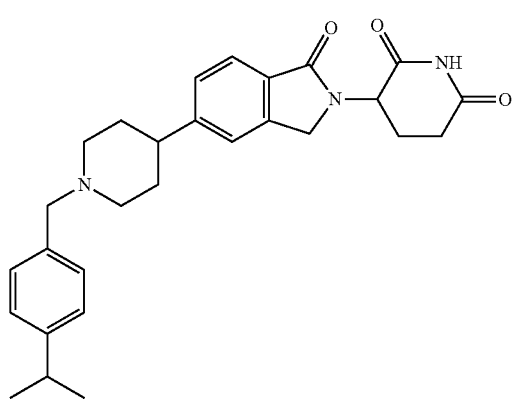 [SMILES: CC(C)c1ccc(CN2CCC(c3ccc4c(c3)CN(C3CCC(=O)NC3=O)C4=O)CC2)cc1] | 3-(5-(1-(4-isopropylbenzyl)piperidin-4-yl)-1-oxoisoindolin-2-yl)piperidine-2,6-dione |

| Cmpd No. | Structure | Compound Name |
|---|---|---|
| I-46 | 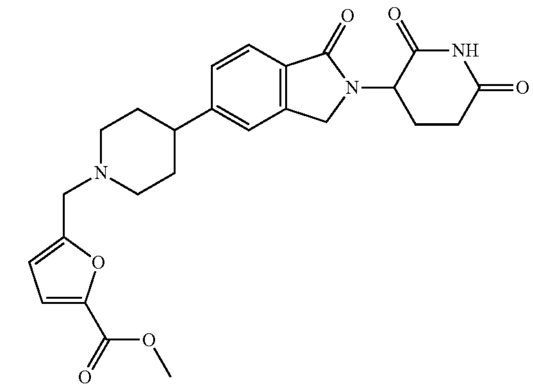 [SMILES: COC(=O)c1ccc(CN2CCC(c3ccc4c(c3)CN(C3CCC(=O)NC3=O)C4=O)CC2)o1] | methyl 5-((4-(2-(2,6-dioxopiperidin-3-yl)-1-oxoisoindolin-5-yl)piperidin-1-yl)methyl)furan-2-carboxylate |
| I-47 | 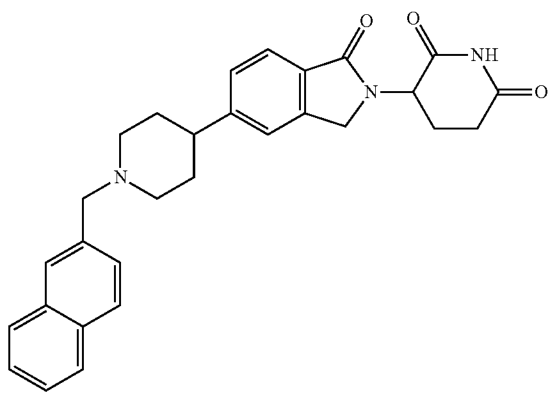 [SMILES: O=C1CCC(N2Cc3cc(C4CCN(Cc5ccc6ccccc6c5)CC4)ccc3C2=O)C(=O)N1] | 3-(5-(1-(naphthalen-2-ylmethyl)piperidin-4-yl)-1-oxoisoindolin-2-yl)piperidine-2,6-dione |
| I-48 | 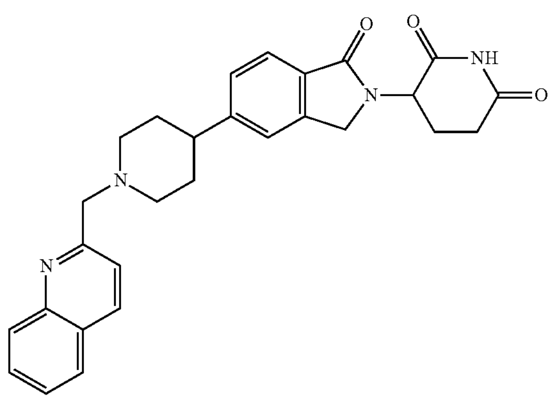 [SMILES: O=C1CCC(N2Cc3cc(C4CCN(Cc5ccc6ccccc6n5)CC4)ccc3C2=O)C(=O)N1] | 3-(1-oxo-5-(1-(quinolin-2-ylmethyl)piperidin-4-yl)isoindolin-2-yl)piperidine-2,6-dione |
| I-49 | 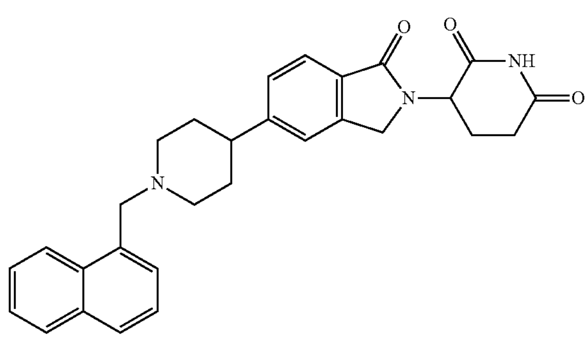 [SMILES: O=C1CCC(N2Cc3cc(C4CCN(Cc5cccc6ccccc56)CC4)ccc3C2=O)C(=O)N1] | 3-(5-(1-(naphthalen-1-ylmethyl)piperidin-4-yl)-1-oxoisoindolin-2-yl)piperidine-2,6-dione |

| Cmpd No. | Structure | Compound Name |
|---|---|---|
| I-50 | 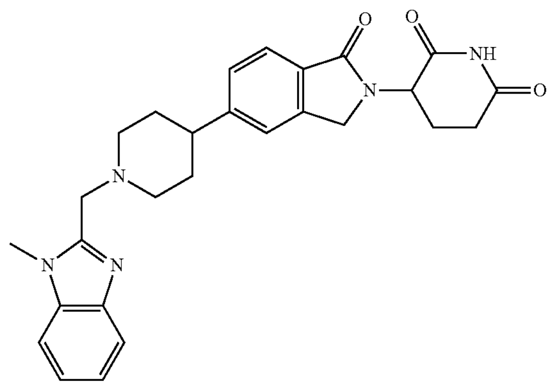 [SMILES: Cn1c(CN2CCC(c3ccc4c(c3)CN(C3CCC(=O)NC3=O)C4=O)CC2)nc2ccccc21] | 3-(5-(1-((1-methyl-1H-benzo[d]imidazol-2-yl)methyl)piperidin-4-yl)-1-oxoisoindolin-2-yl)piperidine-2,6-dione |
| I-51 | 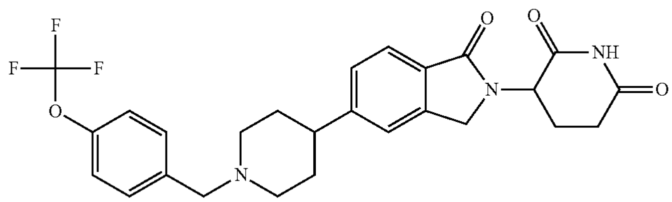 [SMILES: O=C1CCC(N2Cc3cc(C4CCN(Cc5ccc(OC(F)(F)F)cc5)CC4)ccc3C2=O)C(=O)N1] | 3-(1-oxo-5-(1-(4-(trifluoromethoxy)benzyl)piperidin-4-yl)isoindolin-2-yl)piperidine-2,6-dione |
| I-52 | 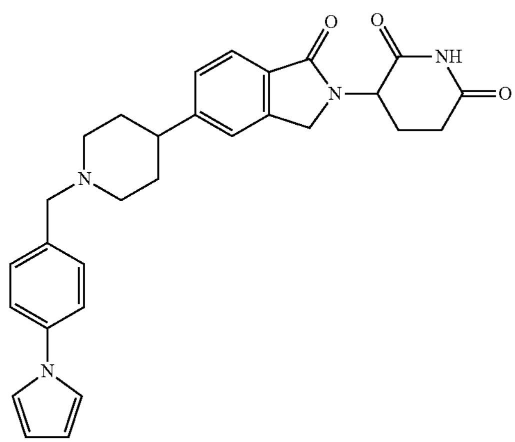 [SMILES: O=C1CCC(N2Cc3cc(C4CCN(Cc5ccc(-n6cccc6)cc5)CC4)ccc3C2=O)C(=O)N1] | 3-(5-(1-(4-(1H-pyrrol-1-yl)benzyl)piperidin-4-yl)-1-oxoisoindolin-2-yl)piperidine-2,6-dione |
| I-53 | 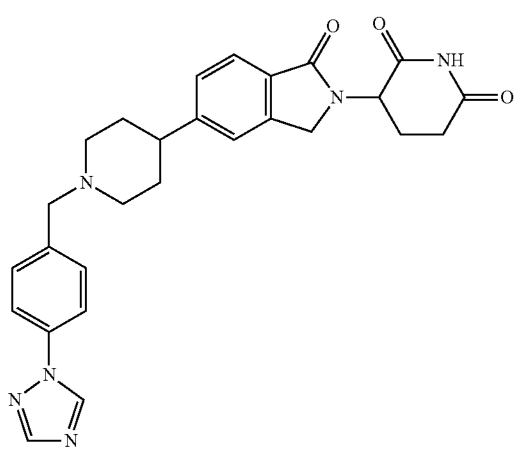 [SMILES: O=C1CCC(N2Cc3cc(C4CCN(Cc5ccc(-n6cncn6)cc5)CC4)ccc3C2=O)C(=O)N1] | 3-(5-(1-(4-(1H-1,2,4-triazol-1-yl)benzyl)piperidin-4-yl)-1-oxoisoindolin-2-yl)piperidine-2,6-dione |

| Cmpd No. | Structure | Compound Name |
|---|---|---|
| I-54 | 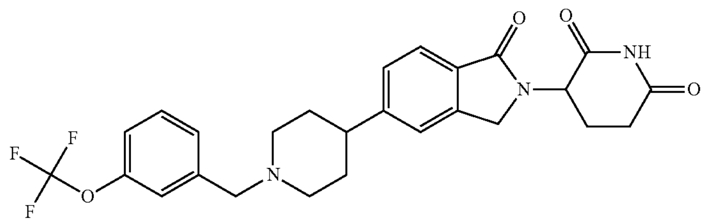 [SMILES: O=C1CCC(N2Cc3cc(C4CCN(Cc5cccc(OC(F)(F)F)c5)CC4)ccc3C2=O)C(=O)N1] | 3-(1-oxo-5-(1-(3-(trifluoromethoxy)benzyl)piperidin-4-yl)isoindolin-2-yl)piperidine-2,6-dione |
| I-55 | 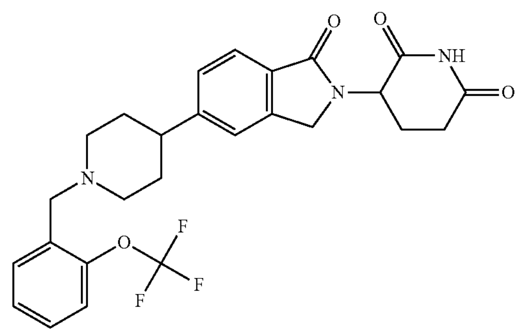 [SMILES: O=C1CCC(N2Cc3cc(C4CCN(Cc5ccccc5OC(F)(F)F)CC4)ccc3C2=O)C(=O)N1] | 3-(1-oxo-5-(1-(2-(trifluoromethoxy)benzyl)piperidin-4-yl)isoindolin-2-yl)piperidine-2,6-dione |
| I-56 | 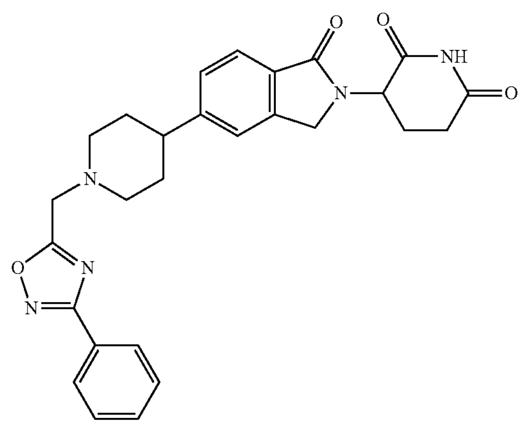 [SMILES: O=C1CCC(N2Cc3cc(C4CCN(Cc5nc(-c6ccccc6)no5)CC4)ccc3C2=O)C(=O)N1] | 3-(1-oxo-5-(1-((3-phenyl-1,2,4-oxadiazol-5-yl)methyl)piperidin-4-yl)isoindolin-2-yl)piperidine-2,6-dione |
| I-57 | 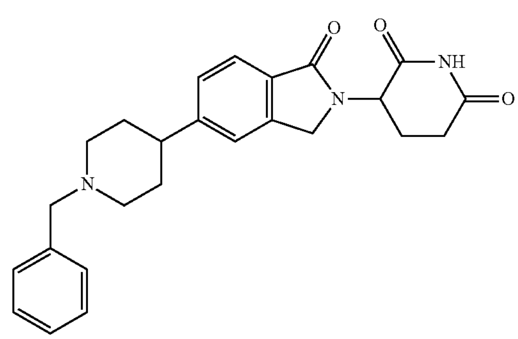 [SMILES: O=C1CCC(N2Cc3cc(C4CCN(Cc5ccccc5)CC4)ccc3C2=O)C(=O)N1] | 3-(5-(1-benzylpiperidin-4-yl)-1-oxoisoindolin-2-yl)piperidine-2,6-dione |
| I-58 | 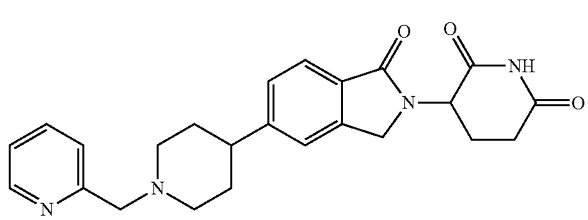 [SMILES: O=C1CCC(N2Cc3cc(C4CCN(Cc5ccccn5)CC4)ccc3C2=O)C(=O)N1] | 3-(1-oxo-5-(1-(pyridin-2-ylmethyl)piperidin-4-yl)isoindolin-2-yl)piperidine-2,6-dione |

| Cmpd No. | Structure | Compound Name |
|---|---|---|
| I-59 | 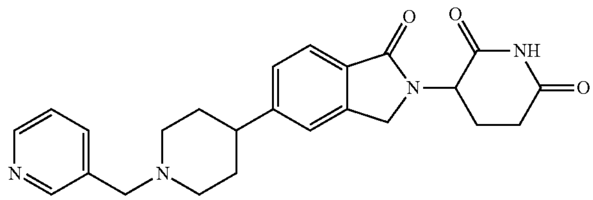 [SMILES: O=C1CCC(N2Cc3cc(C4CCN(Cc5cccnc5)CC4)ccc3C2=O)C(=O)N1] | 3-(1-oxo-5-(1-(pyridin-3-ylmethyl)piperidin-4-yl)isoindolin-2-yl)piperidine-2,6-dione |
| I-60 | 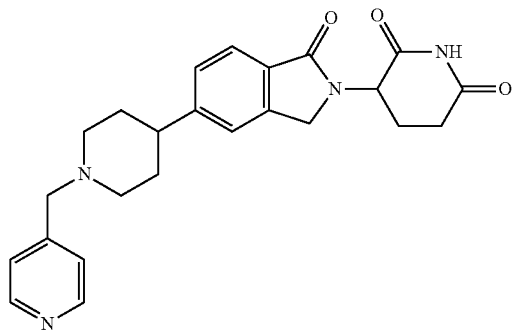 [SMILES: O=C1CCC(N2Cc3cc(C4CCN(Cc5ccncc5)CC4)ccc3C2=O)C(=O)N1] | 3-(1-oxo-5-(1-(pyridin-4-ylmethyl)piperidin-4-yl)isoindolin-2-yl)piperidine-2,6-dione |
| I-61 | 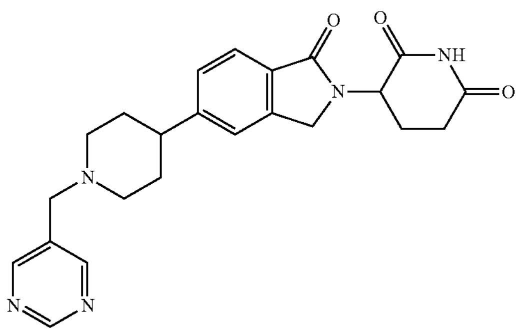 [SMILES: O=C1CCC(N2Cc3cc(C4CCN(Cc5cncnc5)CC4)ccc3C2=O)C(=O)N1] | 3-(1-oxo-5-(1-(pyrimidin-5-ylmethyl)piperidin-4-yl)isoindolin-2-yl)piperidine-2,6-dione |
| I-62 | 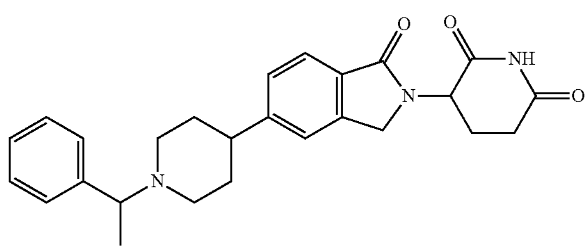 [SMILES: CC(c1ccccc1)N1CCC(c2ccc3c(c2)CN(C2CCC(=O)NC2=O)C3=O)CC1] | 3-(1-oxo-5-(1-(1-phenylethyl)piperidin-4-yl)isoindolin-2-yl)piperidine-2,6-dione |
| I-63 | 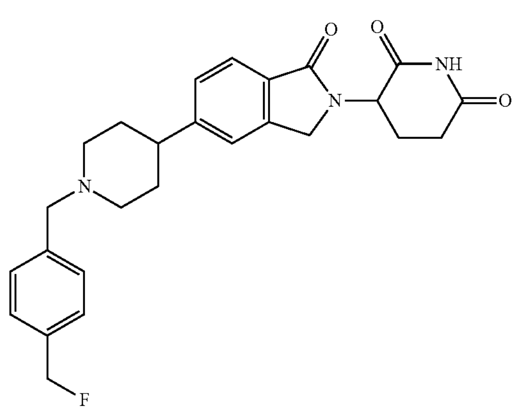 [SMILES: O=C1CCC(N2Cc3cc(C4CCN(Cc5ccc(CF)cc5)CC4)ccc3C2=O)C(=O)N1] | 3-(5-(1-(4-(fluoromethyl)benzyl)piperidin-4-yl)-1-oxoisoindolin-2-yl)piperidine-2,6-dione |

| Cmpd No. | Structure | Compound Name |
|---|---|---|
| I-64 | 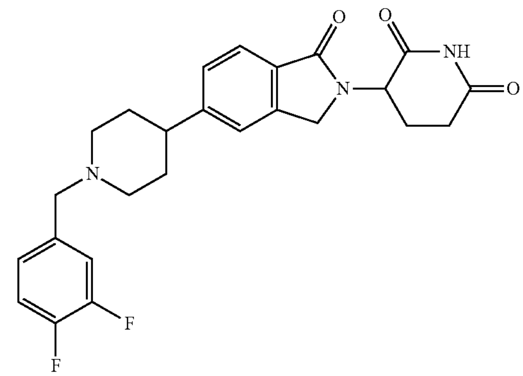 [SMILES: O=C1CCC(N2Cc3cc(C4CCN(Cc5ccc(F)c(F)c5)CC4)ccc3C2=O)C(=O)N1] | 3-(5-(1-(3,4-difluorobenzyl)piperidin-4-yl)-1-oxoisoindolin-2-yl)piperidine-2,6-dione |
| I-65 | 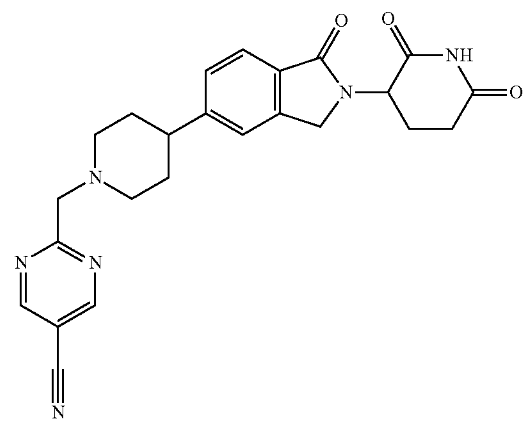 [SMILES: N#Cc1cnc(CN2CCC(c3ccc4c(c3)CN(C3CCC(=O)NC3=O)C4=O)CC2)nc1] | 2-((4-(2-(2,6-dioxopiperidin-3-yl)-1-oxoisoindolin-5-yl)piperidin-1-yl)methyl)pyrimidine-5-carbonitrile |
| I-66 | 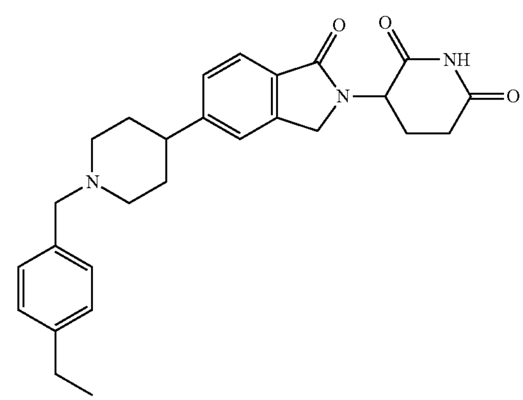 [SMILES: CCc1ccc(CN2CCC(c3ccc4c(c3)CN(C3CCC(=O)NC3=O)C4=O)CC2)cc1] | 3-(5-(1-(4-ethylbenzyl)piperidin-4-yl)-1-oxoisoindolin-2-yl)piperidine-2,6-dione |
| I-67 | 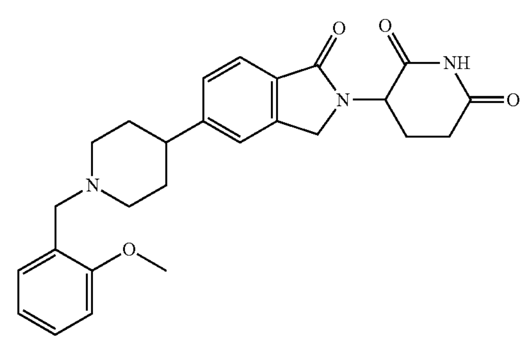 [SMILES: COc1ccccc1CN1CCC(c2ccc3c(c2)CN(C2CCC(=O)NC2=O)C3=O)CC1] | 3-(5-(1-(2-methoxybenzyl)piperidin-4-yl)-1-oxoisoindolin-2-yl)piperidine-2,6-dione |

-continued

| Cmpd No. | Structure | Compound Name |
|---|---|---|
| I-68 | 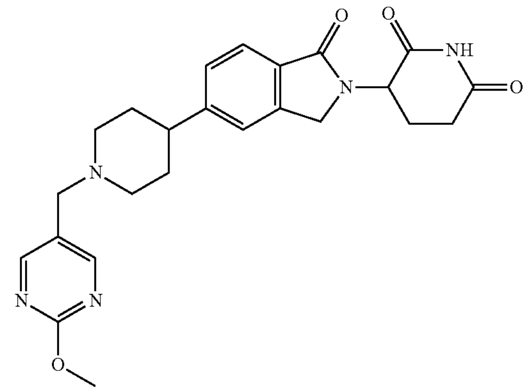 [SMILES: COc1ncc(CN2CCC(c3ccc4c(c3)CN(C3CCC(=O)NC3=O)C4=O)CC2)cn1] | 3-(5-(1-((2-methoxypyrimidin-5-yl)methyl)piperidin-4-yl)-1-oxoisoindolin-2-yl)piperidine-2,6-dione |
| I-69 | 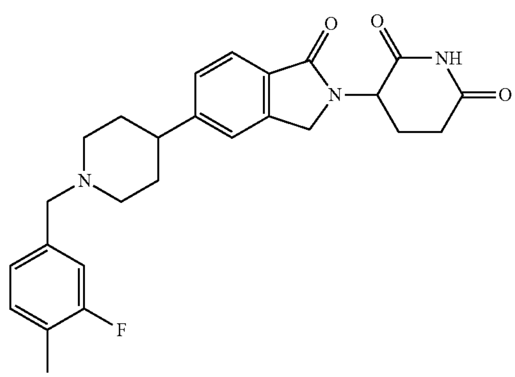 [SMILES: Cc1ccc(CN2CCC(c3ccc4c(c3)CN(C3CCC(=O)NC3=O)C4=O)CC2)cc1F] | 3-(5-(1-(3-fluoro-4-methylbenzyl)piperidin-4-yl)-1-oxoisoindolin-2-yl)piperidine-2,6-dione |
| I-70 | 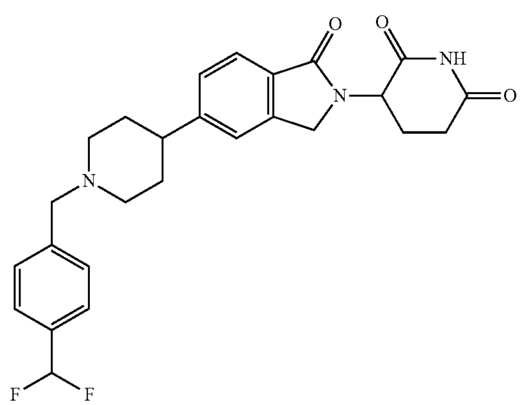 | 3-(5-(1-(4-(difluoromethyl)benzyl)piperidin-4-yl)-1-oxoisoindolin-2-yl)piperidine-2,6-dione |
| I-71 | 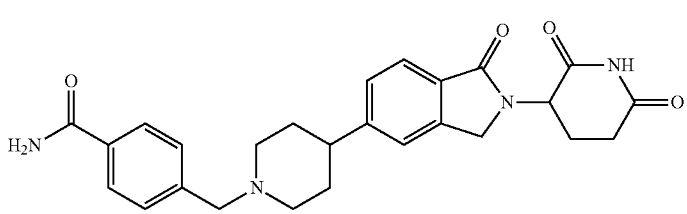 [SMILES: NC(=O)c1ccc(CN2CCC(c3ccc4c(c3)CN(C3CCC(=O)NC3=O)C4=O)CC2)cc1] | 4-((4-(2-(2,6-dioxopiperidin-3-yl)-1-oxoisoindolin-5-yl)piperidin-1-yl)methyl)benzamide |

-continued

| Cmpd No. | Structure | Compound Name |
|---|---|---|
| I-72 | 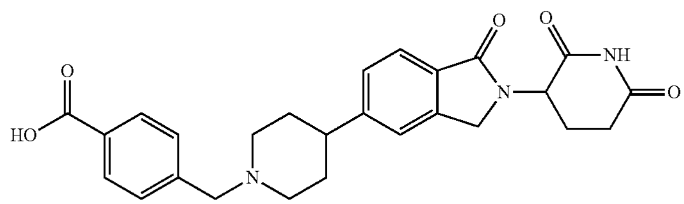 [SMILES: O=C1CCC(N2Cc3cc(C4CCN(Cc5ccc(C(=O)O)cc5)CC4)ccc3C2=O)C(=O)N1] | 4-((4-(2-(2,6-dioxopiperidin-3-yl)-1-oxoisoindolin-5-yl)piperidin-1-yl)methyl)benzoic acid |
| I-73 | 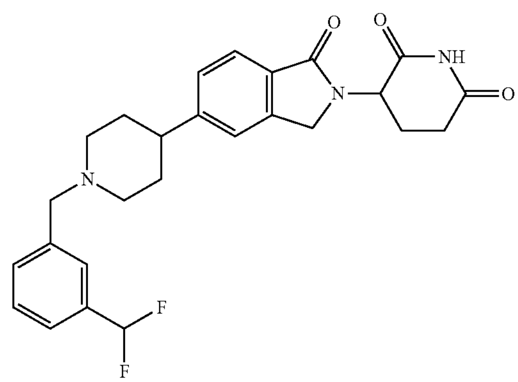 [SMILES: O=C1CCC(N2Cc3cc(C4CCN(Cc5cccc(C(F)F)c5)CC4)ccc3C2=O)C(=O)N1] | 3-(5-(1-(3-(difluoromethyl)benzyl)piperidin-4-yl)-1-oxoisoindolin-2-yl)piperidine-2,6-dione |
| I-74 | 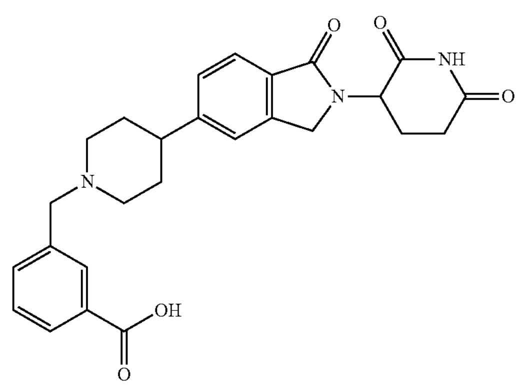 [SMILES: O=C1CCC(N2Cc3cc(C4CCN(Cc5cccc(C(=O)O)c5)CC4)ccc3C2=O)C(=O)N1] | 3-((4-(2-(2,6-dioxopiperidin-3-yl)-1-oxoisoindolin-5-yl)piperidin-1-yl)methyl)benzoic acid |
| I-75 | 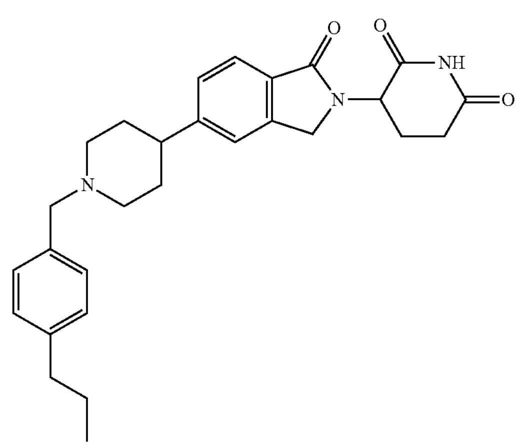 [SMILES: CCCc1ccc(CN2CCC(c3ccc4c(c3)CN(C3CCC(=O)NC3=O)C4=O)CC2)cc1] | 3-(1-oxo-5-(1-(4-propylbenzyl)piperidin-4-yl)isoindolin-2-yl)piperidine-2,6-dione |

| Cmpd No. | Structure | Compound Name |
|---|---|---|
| I-76 | 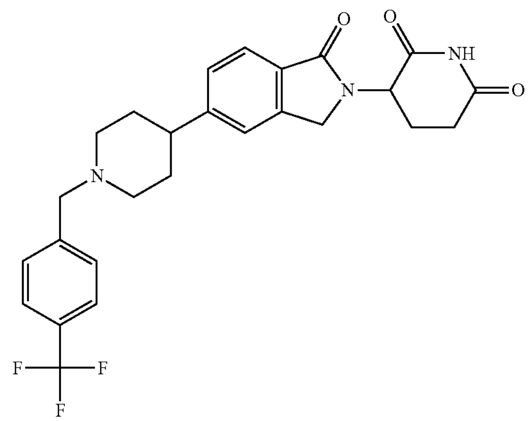 [SMILES: O=C1CCC(N2Cc3cc(C4CCN(Cc5ccc(C(F)(F)F)cc5)CC4)ccc3C2=O)C(=O)N1] | 3-(1-oxo-5-(1-(4-(trifluoromethyl)benzyl)piperidin-4-yl)isoindolin-2-yl)piperidine-2,6-dione |
| I-77 | 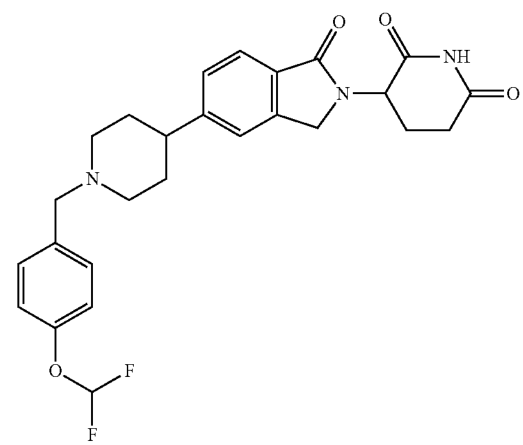 [SMILES: O=C1CCC(N2Cc3cc(C4CCN(Cc5ccc(OC(F)F)cc5)CC4)ccc3C2=O)C(=O)N1] | 3-(5-(1-(4-(difluoromethoxy)benzyl)piperidin-4-yl)-1-oxoisoindolin-2-yl)piperidine-2,6-dione |
| I-78 | 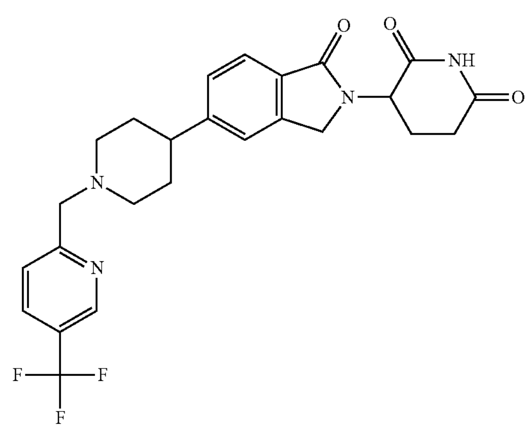 [SMILES: O=C1CCC(N2Cc3cc(C4CCN(Cc5ccc(C(F)(F)F)cn5)CC4)ccc3C2=O)C(=O)N1] | 3-(1-oxo-5-(1-((5-(trifluoromethyl)pyridin-2-yl)methyl)piperidin-4-yl)isoindolin-2-yl)piperidine-2,6-dione |

| Cmpd No. | Structure | Compound Name |
| --- | --- | --- |
| I-79 | 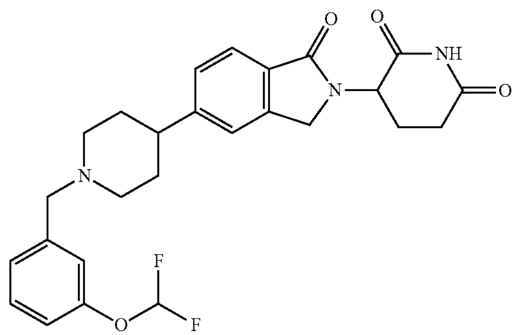 | 3-(5-(1-(3-(difluoromethoxy)benzyl)piperidin-4-yl)-1-oxoisoindolin-2-yl)piperidine-2,6-dione |
| I-80 | 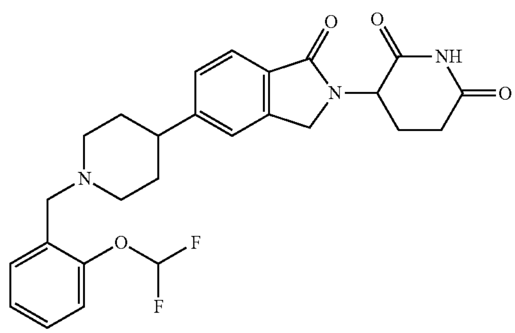 [SMILES: O=C1CCC(N2Cc3cc(C4CCN(Cc5ccccc5OC(F)F)CC4)ccc3C2=O)C(=O)N1] | 3-(5-(1-(2-(difluoromethoxy)benzyl)piperidin-4-yl)-1-oxoisoindolin-2-yl)piperidine-2,6-dione |
| I-81 | 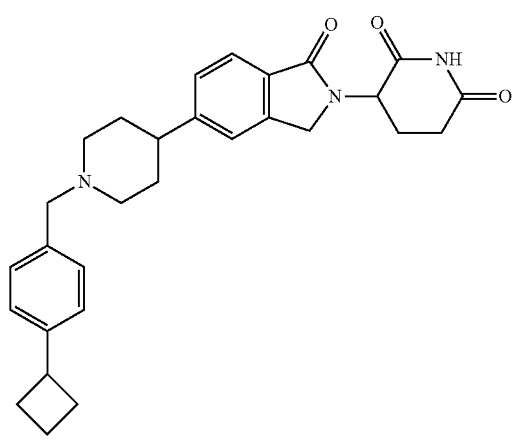 [SMILES: O=C1CCC(N2Cc3cc(C4CCN(Cc5ccc(C6CCC6)cc5)CC4)ccc3C2=O)C(=O)N1] | 3-(5-(1-(4-cyclobutylbenzyl)piperidin-4-yl)-1-oxoisoindolin-2-yl)piperidine-2,6-dione |
| I-82 | 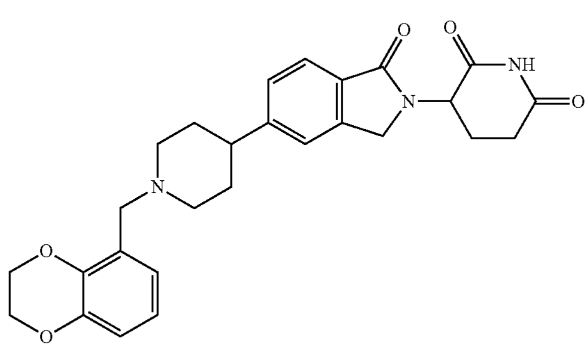 [SMILES: O=C1CCC(N2Cc3cc(C4CCN(Cc5cccc6c5OCCO6)CC4)ccc3C2=O)C(=O)N1] | 3-(5-(1-((2,3-dihydrobenzo[b][1,4]dioxin-5-yl)methyl)piperidin-4-yl)-1-oxoisoindolin-2-yl)piperidine-2,6-dione |

| Cmpd No. | Structure | Compound Name |
|---|---|---|
| I-83 | 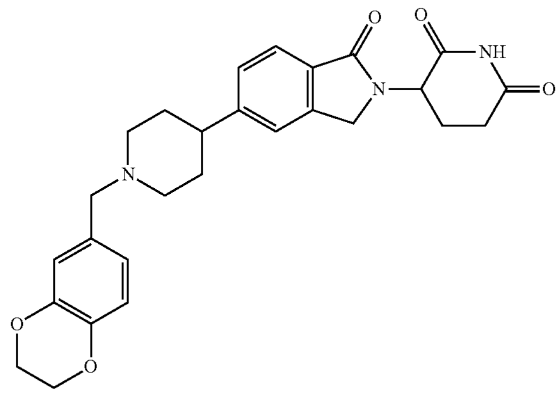 [SMILES: O=C1CCC(N2Cc3cc(C4CCN(Cc5ccc6c(c5)OCCO6)CC4)ccc3C2=O)C(=O)N1] | 3-(5-(1-((2,3-dihydrobenzo[b][1,4]dioxin-6-yl)methyl)piperidin-4-yl)-1-oxoisoindolin-2-yl)piperidine-2,6-dione |
| I-84 | 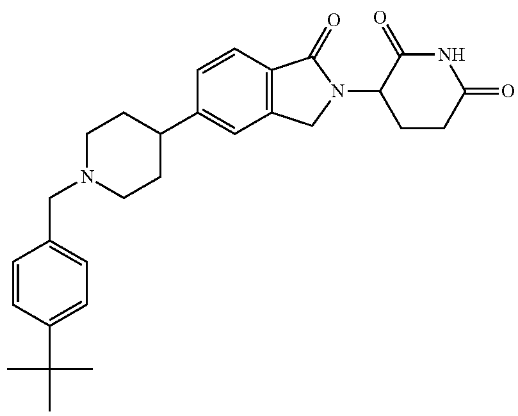 [SMILES: CC(C)(C)c1ccc(CN2CCC(c3ccc4c(c3)CN(C3CCC(=O)NC3=O)C4=O)CC2)cc1] | 3-(5-(1-(4-(tert-butyl)benzyl)piperidin-4-yl)-1-oxoisoindolin-2-yl)piperidine-2,6-dione |
| I-85 | 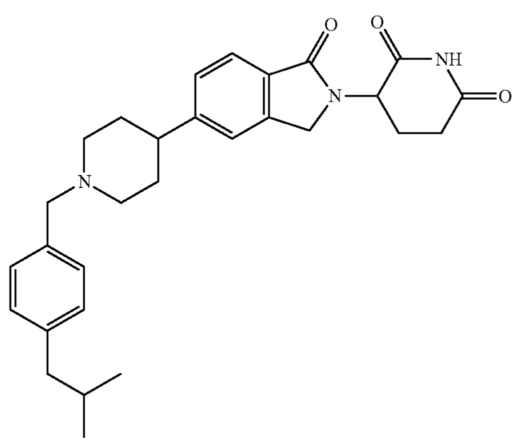 [SMILES: CC(C)Cc1ccc(CN2CCC(c3ccc4c(c3)CN(C3CCC(=O)NC3=O)C4=O)CC2)cc1] | 3-(5-(1-(4-isobutylbenzyl)piperidin-4-yl)-1-oxoisoindolin-2-yl)piperidine-2,6-dione |
| I-86 | 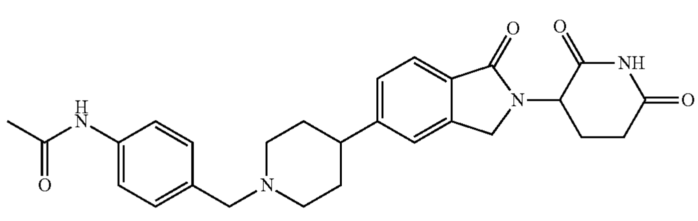 [SMILES: CC(=O)Nc1ccc(CN2CCC(c3ccc4c(c3)CN(C3CCC(=O)NC3=O)C4=O)CC2)cc1] | N-(4-((4-(2-(2,6-dioxopiperidin-3-yl)-1-oxoisoindolin-5-yl)piperidin-1-yl)methyl)phenyl)acetamide |

-continued

| Cmpd No. | Structure | Compound Name |
|---|---|---|
| I-87 | 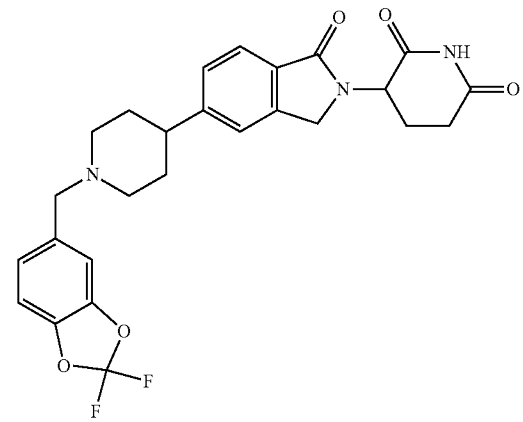 [SMILES: O=C1CCC(N2Cc3cc(C4CCN(Cc5ccc6c(c5)OC(F)(F)O6)CC4)ccc3C2=O)C(=O)N1] | 3-(5-(1-((2,2-difluorobenzo[d][1,3]dioxol-5-yl)methyl)piperidin-4-yl)-1-oxoisoindolin-2-yl)piperidine-2,6-dione |
| I-88 | 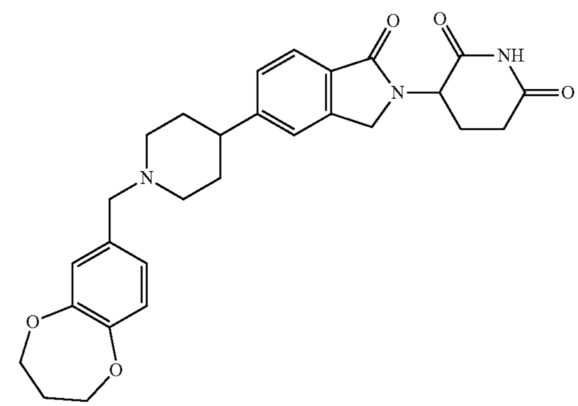 [SMILES: O=C1CCC(N2Cc3cc(C4CCN(Cc5ccc6c(c5)OCCCO6)CC4)ccc3C2=O)C(=O)N1] | 3-(5-(1-((3,4-dihydro-2H-benzo[b][1,4]dioxepin-7-yl)methyl)piperidin-4-yl)-1-oxoisoindolin-2-yl)piperidine-2,6-dione |
| I-89 | 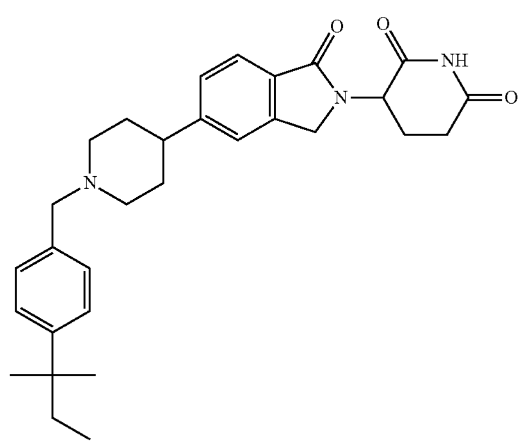 [SMILES: CCC(C)(C)c1ccc(CN2CCC(c3ccc4c(c3)CN(C3CCC(=O)NC3=O)C4=O)CC2)cc1] | 3-(1-oxo-5-(1-(4-(tert-pentyl)benzyl)piperidin-4-yl)isoindolin-2-yl)piperidine-2,6-dione |

-continued

| Cmpd No. | Structure | Compound Name |
|---|---|---|
| I-90 | 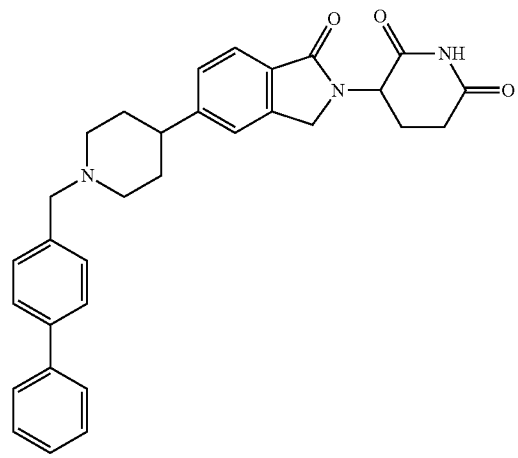 [SMILES: O=C1CCC(N2Cc3cc(C4CCN(Cc5ccc(-c6ccccc6)cc5)CC4)ccc3C2=O)C(=O)N1] | 3-(5-(1-([1,1'-biphenyl]-4-ylmethyl)piperidin-4-yl)-1-oxoisoindolin-2-yl)piperidine-2,6-dione |
| I-91 | 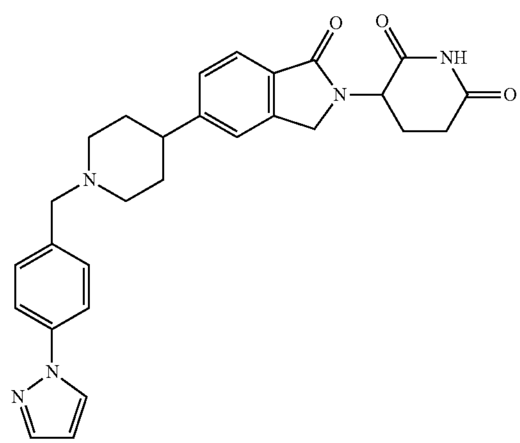 [SMILES: O=C1CCC(N2Cc3cc(C4CCN(Cc5ccc(-n6cccn6)cc5)CC4)ccc3C2=O)C(=O)N1] | 3-(5-(1-(4-(1H-pyrazol-1-yl)benzyl)piperidin-4-yl)-1-oxoisoindolin-2-yl)piperidine-2,6-dione |
| I-92 | 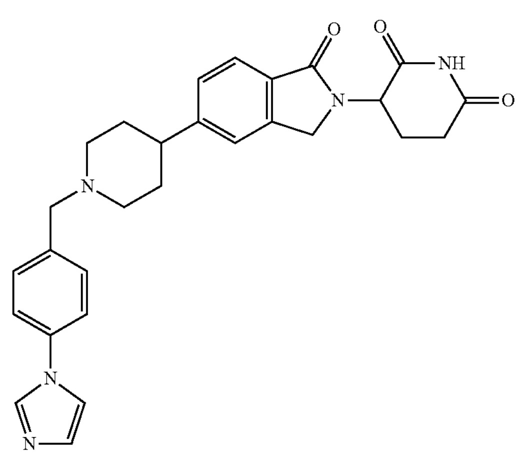 [SMILES: O=C1CCC(N2Cc3cc(C4CCN(Cc5ccc(-n6ccnc6)cc5)CC4)ccc3C2=O)C(=O)N1] | 3-(5-(1-(4-(1H-imidazol-1-yl)benzyl)piperidin-4-yl)-1-oxoisoindolin-2-yl)piperidine-2,6-dione |

-continued

| Cmpd No. | Structure | Compound Name |
|---|---|---|
| I-93 | 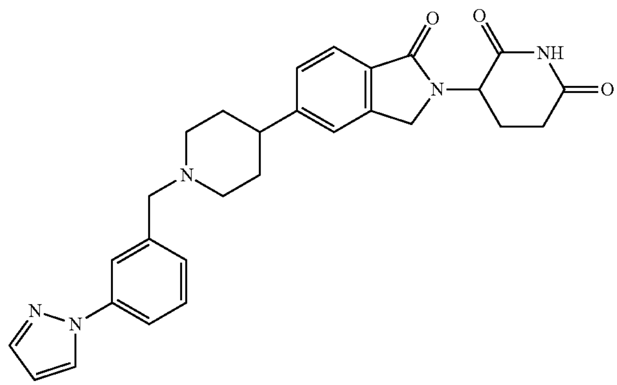 [SMILES: O=C1CCC(N2Cc3cc(C4CCN(Cc5cccc(-n6cccn6)c5)CC4)ccc3C2=O)C(=O)N1] | 3-(5-(1-(3-(1H-pyrazol-1-yl)benzyl)piperidin-4-yl)-1-oxoisoindolin-2-yl)piperidine-2,6-dione |
| I-94 | 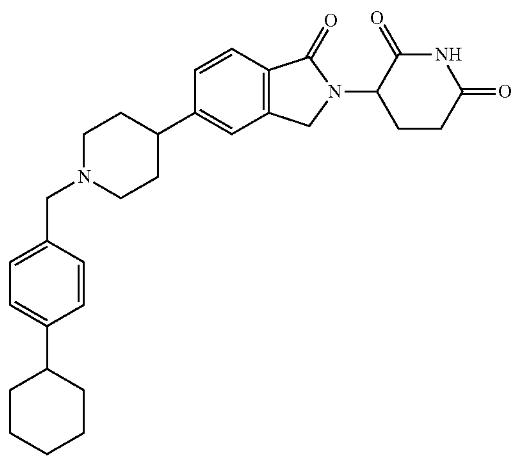 [SMILES: O=C1CCC(N2Cc3cc(C4CCN(Cc5ccc(C6CCCCC6)cc5)CC4)ccc3C2=O)C(=O)N1] | 3-(5-(1-(4-cyclohexylbenzyl)piperidin-4-yl)-1-oxousoindolin-2-yl)piperidine-2,6-dione |
| I-95 | 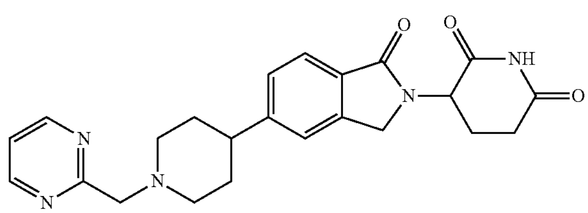 [SMILES: O=C1CCC(N2Cc3cc(C4CCN(Cc5ncccn5)CC4)ccc3C2=O)C(=O)N1] | 3-(1-oxo-5-(1-(pyrimidin-2-yl)methyl)piperidin-4-yl)isoindolin-2-yl)piperidine-2,6-dione |
| I-96 | 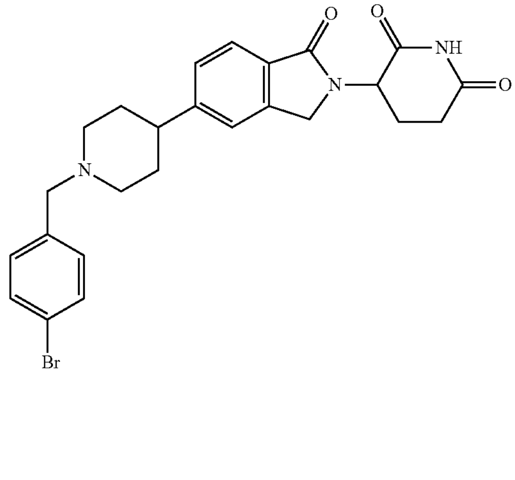 [SMILES: O=C1CCC(N2Cc3cc(C4CCN(Cc5ccc(Br)cc5)CC4)ccc3C2=O)C(=O)N1] | 3-(5-(1-(4-bromobenzyl)piperidin-4-yl)-1-oxoisoindolin-2-yl)piperidine-2,6-dione |

-continued

| Cmpd No. | Structure | Compound Name |
|---|---|---|
| I-97 | 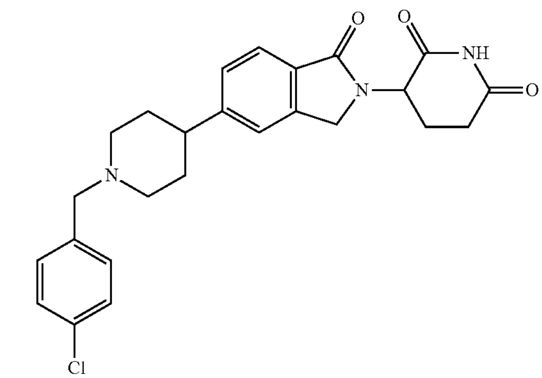 [SMILES: O=C1CCC(N2Cc3cc(C4CCN(Cc5ccc(Cl)cc5)CC4)ccc3C2=O)C(=O)N1] | 3-(5-(1-(4-chlorobenzyl)piperidin-4-yl)-1-oxoisoindolin-2-yl)piperidine-2,6-dione |
| I-98 | 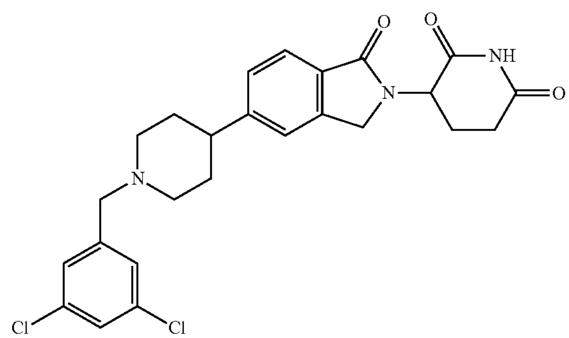 [SMILES: O=C1CCC(N2Cc3cc(C4CCN(Cc5cc(Cl)cc(Cl)c5)CC4)ccc3C2=O)C(=O)N1] | 3-(5-(1-(3,5-dichlorobenzyl)piperidin-4-yl)-1-oxoisoindolin-2-yl)piperidine-2,6-dione |
| I-99 | 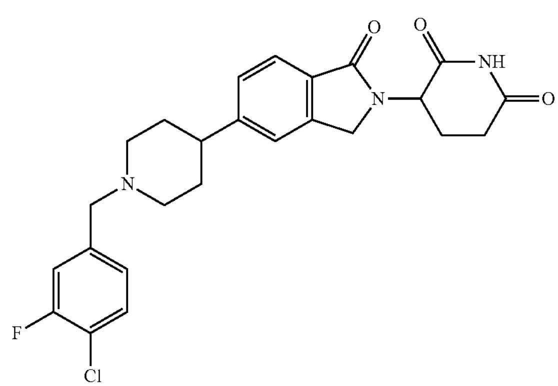 [SMILES: O=C1CCC(N2Cc3cc(C4CCN(Cc5ccc(Cl)c(F)c5)CC4)ccc3C2=O)C(=O)N1] | 3-(5-(1-(4-chloro-3-fluorobenzyl)piperidin-4-yl)-1-oxoisoindolin-2-yl)piperidine-2,6-dione |
| I-100 | 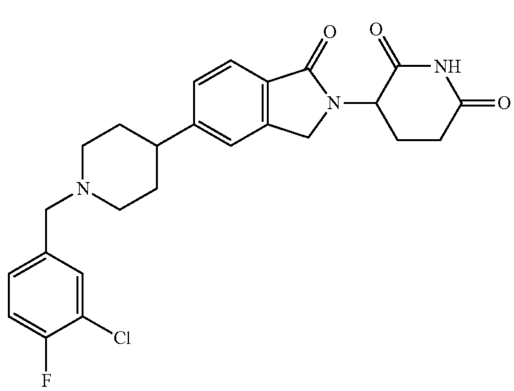 [SMILES: O=C1CCC(N2Cc3cc(C4CCN(Cc5ccc(F)c(Cl)c5)CC4)ccc3C2=O)C(=O)N1] | 3-(5-(1-(3-chloro-4-fluorobenzyl)piperidin-4-yl)-1-oxoisoindolin-2-yl)piperidine-2,6-dione |

| Cmpd No. | Structure | Compound Name |
|---|---|---|
| I-101 | 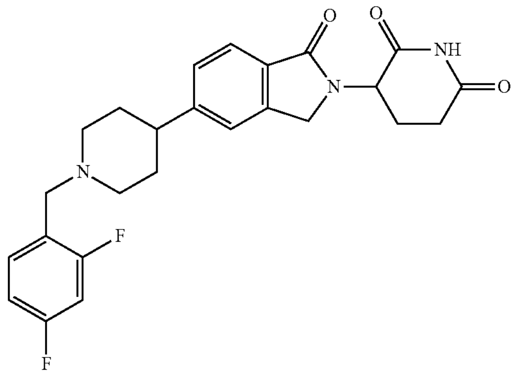 [SMILES: O=C1CCC(N2Cc3cc(C4CCN(Cc5ccc(F)cc5F)CC4)ccc3C2=O)C(=O)N1] | 3-(5-(1-(2,4-difluorobenzyl)piperidin-4-yl)-1-oxoisoindolin-2-yl)piperidine-2,6-dione |
| I-102 | 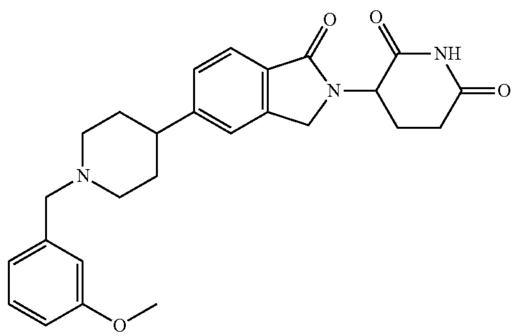 [SMILES: COc1cccc(CN2CCC(c3ccc4c(c3)CN(C3CCC(=O)NC3=O)C4=O)CC2)c1] | 3-(5-(1-(3-methoxybenzyl)piperidin-4-yl)-1-oxoisoindolin-2-yl)piperidine-2,6-dione |
| I-103 | 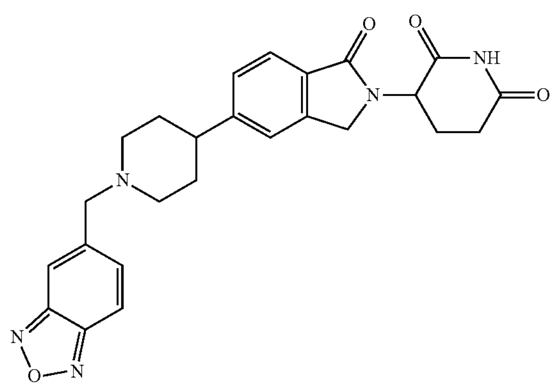 [SMILES: O=C1CCC(N2Cc3cc(C4CCN(Cc5ccc6nonc6c5)CC4)ccc3C2=O)C(=O)N1] | 3-(5-(1-(benzo[c][1,2,5]oxadiazol-5-ylmethyl)piperidin-4-yl)-1-oxoisoindolin-2-yl)piperidine-2,6-dione |
| I-104 | 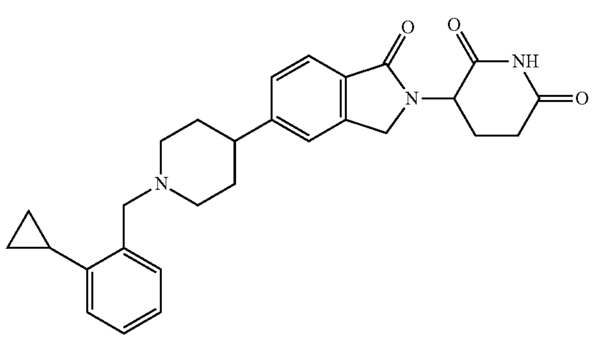 [SMILES: O=C1CCC(N2Cc3cc(C4CCN(Cc5ccccc5C5CC5)CC4)ccc3C2=O)C(=O)N1] | 3-(5-(1-(2-cyclopropylbenzyl)piperidin-4-yl)-1-oxoisoindolin-2-yl)piperidine-2,6-dione |

-continued

| Cmpd No. | Structure | Compound Name |
|---|---|---|
| I-105 | 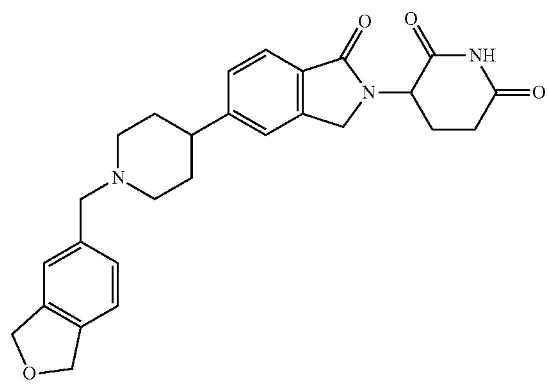 [SMILES: O=C1CCC(N2Cc3cc(C4CCN(Cc5ccc6c(c5)COC6)CC4)ccc3C2=O)C(=O)N1] | 3-(5-(1-((1,3-dihydroisobenzofuran-5-yl)methyl)piperidin-4-yl)-1-oxoisoindolin-2-yl)piperidine-2,6-dione |
| I-106 | 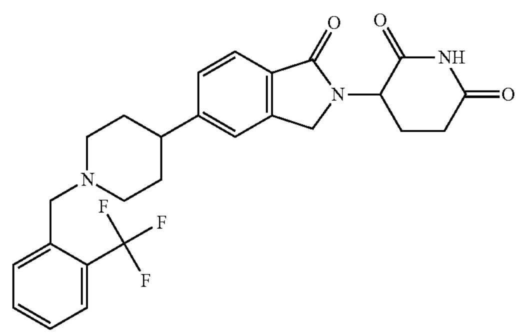 [SMILES: O=C1CCC(N2Cc3cc(C4CCN(Cc5ccccc5C(F)(F)F)CC4)ccc3C2=O)C(=O)N1] | 3-(1-oxo-5-(1-(2-(trifluoromethyl)benzyl)piperidin-4-yl)isoindolin-2-yl)piperidine-2,6-dione |
| I-107 | 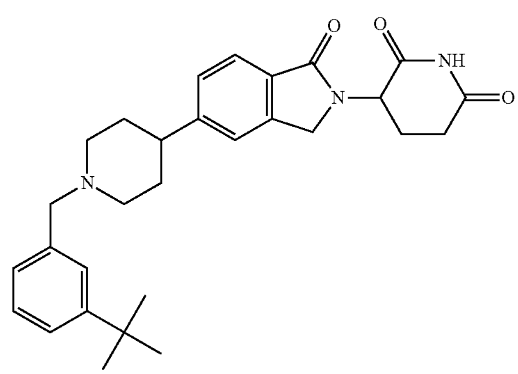 [SMILES: CC(C)(C)c1cccc(CN2CCC(c3ccc4c(c3)CN(C3CCC(=O)NC3=O)C4=O)CC2)c1] | 3-(5-(1-(3-(tert-butyl)benzyl)piperidin-4-yl)-1-oxoisoindolin-2-yl)piperidine-2,6-dione |
| I-108 | 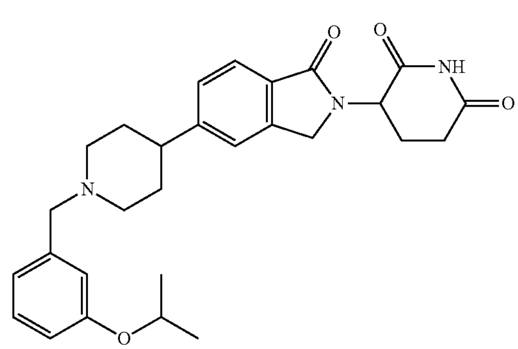 [SMILES: CC(C)Oc1cccc(CN2CCC(c3ccc4c(c3)CN(C3CCC(=O)NC3=O)C4=O)CC2)c1] | 3-(5-(1-(3-isopropoxybenzyl)piperidin-4-yl)-1-oxoisoindolin-2-yl)piperidine-2,6-dione |

-continued

| Cmpd No. | Structure | Compound Name |
|---|---|---|
| I-109 | 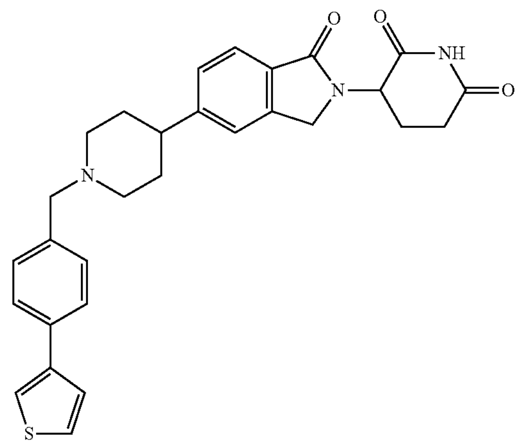 [SMILES: O=C1CCC(N2Cc3cc(C4CCN(Cc5ccc(-c6ccsc6)cc5)CC4)ccc3C2=O)C(=O)N1] | 3-(1-oxo-5-(1-(4-(thiophen-3-yl)benzyl)piperidin-4-yl)isoindolin-2-yl)piperidine-2,6-dione |
| I-110 | 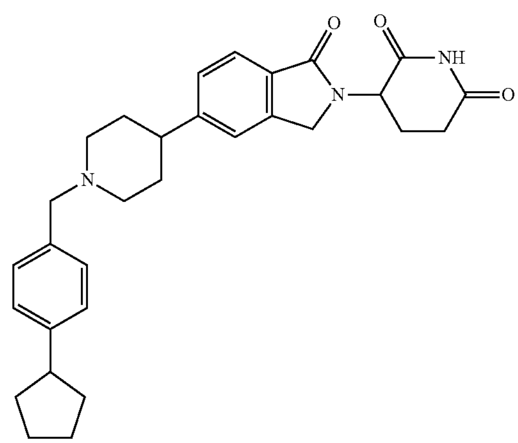 [SMILES: O=C1CCC(N2Cc3cc(C4CCN(Cc5ccc(C6CCCC6)cc5)CC4)ccc3C2=O)C(=O)N1] | 3-(5-(1-(4-cyclopentylbenzyl)piperidin-4-yl)-1-oxoisoindolin-2-yl)piperidine-2,6-dione |
| I-111 | 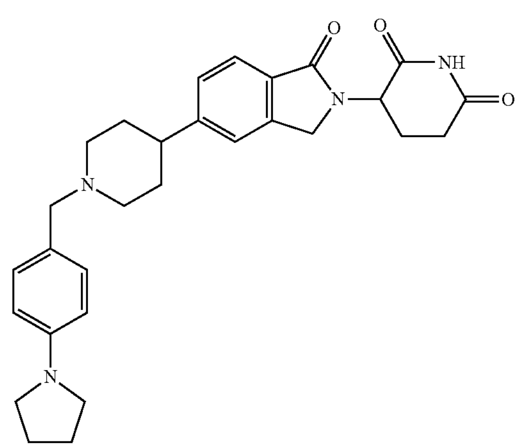 [SMILES: O=C1CCC(N2Cc3cc(C4CCN(Cc5ccc(N6CCCC6)cc5)CC4)ccc3C2=O)C(=O)N1] | 3-(1-oxo-5-(1-(4-(pyrrolidin-1-yl)benzyl)piperidin-4-yl)isoindolin-2-yl)piperidine-2,6-dione |

-continued

| Cmpd No. | Structure | Compound Name |
| --- | --- | --- |
| I-112 | 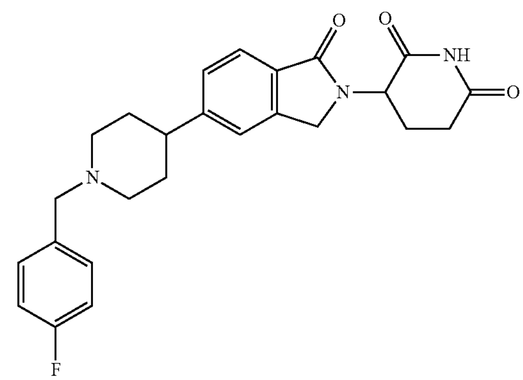 [SMILES: O=C1CCC(N2Cc3cc(C4CCN(Cc5ccc(F)cc5)CC4)ccc3C2=O)C(=O)N1] | 3-(5-(1-(4-fluorobenzyl)piperidin-4-yl)-1-oxoisoindolin-2-yl)piperidine-2,6-dione |
| I-113 | 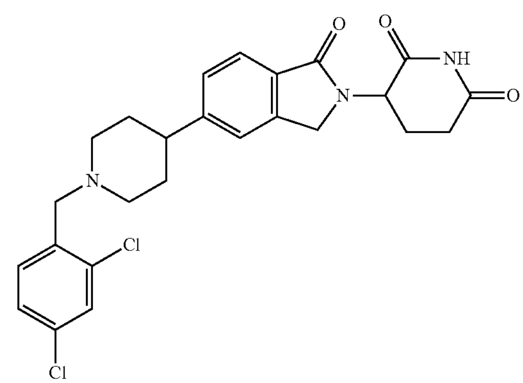 [SMILES: O=C1CCC(N2Cc3cc(C4CCN(Cc5ccc(Cl)cc5Cl)CC4)ccc3C2=O)C(=O)N1] | 3-(5-(1-(2,4-dichlorobenzyl)piperidin-4-yl)-1-oxoisoindolin-2-yl)piperidine-2,6-dione |
| I-114 | 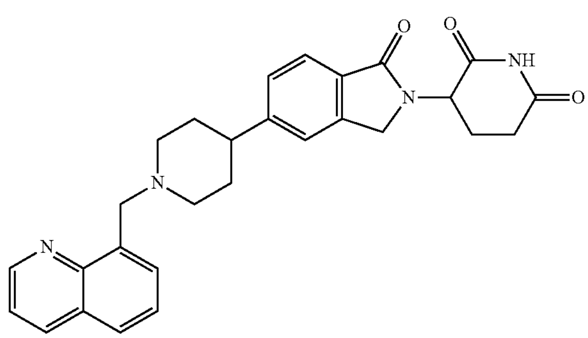 | 3-(1-oxo-5-(1-(quinolin-8-ylmethyl)piperidin-4-yl)isoindolin-2-yl)piperidine-2,6-dione |
| I-115 | 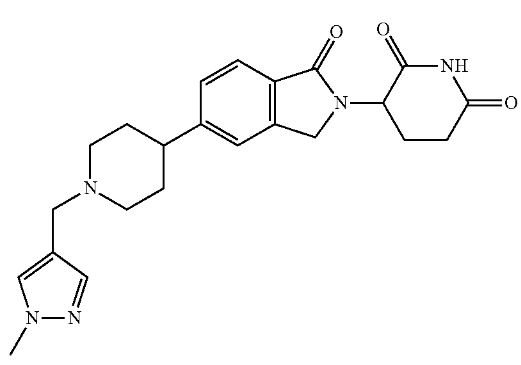 [SMILES: Cn1cc(CN2CCC(c3ccc4c(c3)CN(C3CCC(=O)NC3=O)C4=O)CC2)cn1] | 3-(5-(1-((1-methyl-1H-pyrazol-4-yl)methyl)piperidin-4-yl)-1-oxoisoindolin-2-yl)piperidine-2,6-dione |

-continued

| Cmpd No. | Structure | Compound Name |
|---|---|---|
| I-116 | 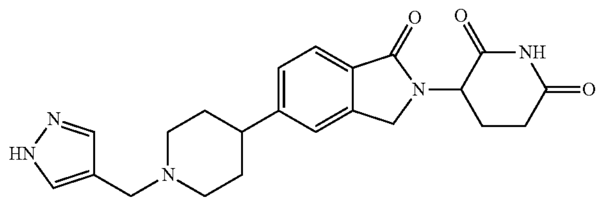 [SMILES: O=C1CCC(N2Cc3cc(C4CCN(Cc5cn[nH]c5)CC4)ccc3C2=O)C(=O)N1] | 3-(5-(1-((1H-pyrazol-4-yl)methyl)piperidin-4-yl)-1-oxoisoindolin-2-yl)piperidine-2,6-dione |
| I-117 | 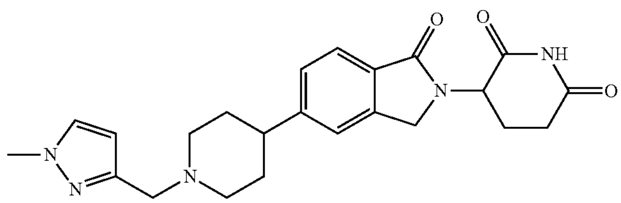 [SMILES: Cn1ccc(CN2CCC(c3ccc4c(c3)CN(C3CCC(=O)NC3=O)C4=O)CC2)n1] | 3-(5-(1-((1-methyl-1H-pyrazol-3-yl)methyl)piperidin-4-yl)-1-oxoisoindolin-2-yl)piperidine-2,6-dione |
| I-118 | 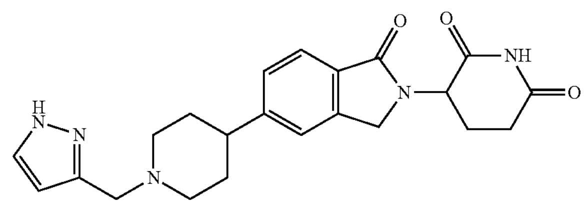 [SMILES: O=C1CCC(N2Cc3cc(C4CCN(Cc5cc[nH]n5)CC4)ccc3C2=O)C(=O)N1] | 3-(5-(1-((1H-pyrazol-3-yl)methyl)piperidin-4-yl)-1-oxoisoindolin-2-yl)piperidine-2,6-dione |
| I-119 | 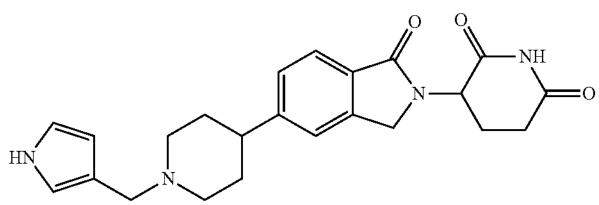 [SMILES: O=C1CCC(N2Cc3cc(C4CCN(Cc5cc[nH]c5)CC4)ccc3C2=O)C(=O)N1] | 3-(5-(1-((1H-pyrrol-3-yl)methyl)piperidin-4-yl)-1-oxoisoindolin-2-yl)piperidine-2,6-dione |
| I-120 | 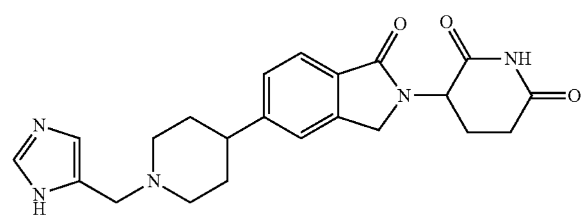 [SMILES: O=C1CCC(N2Cc3cc(C4CCN(Cc5cnc[nH]5)CC4)ccc3C2=O)C(=O)N1] | 3-(5-(1-((1H-imidazol-5-yl)methyl)piperidin-4-yl)-1-oxoisoindolin-2-yl)piperidine-2,6-dione |
| I-121 | 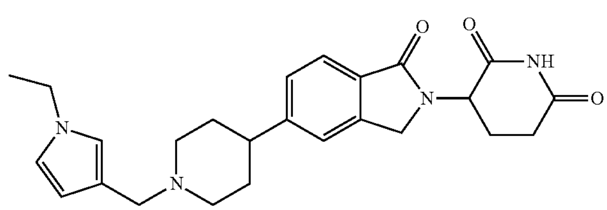 [SMILES: CCn1ccc(CN2CCC(c3ccc4c(c3)CN(C3CCC(=O)NC3=O)C4=O)CC2)c1] | 3-(5-(1-((1-ethyl-1H-pyrazol-3-yl)methyl)piperidin-4-yl)-1-oxoisoindolin-2-yl)piperidine-2,6-dione |
| I-122 | 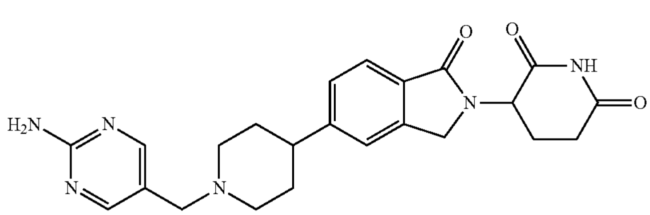 [SMILES: Nc1ncc(CN2CCC(c3ccc4c(c3)CN(C3CCC(=O)NC3=O)C4=O)CC2)cn1] | 3-(5-(1-((2-aminopyrimidin-5-yl)methyl)piperidin-4-yl)-1-oxoisoindolin-2-yl)piperidine-2,6-dione |

-continued

| Cmpd No. | Structure | Compound Name |
|---|---|---|
| I-123 | 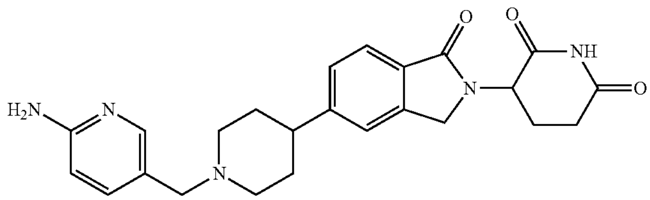 [SMILES: Nc1ccc(CN2CCC(c3ccc4c(c3)CN(C3CCC(=O)NC3=O)C4=O)CC2)cn1] | 3-(5-(1-((6-aminopyridin-3-yl)methyl)piperidin-4-yl)-1-oxoisoindolin-2-yl)piperidine-2,6-dione |
| I-124 | 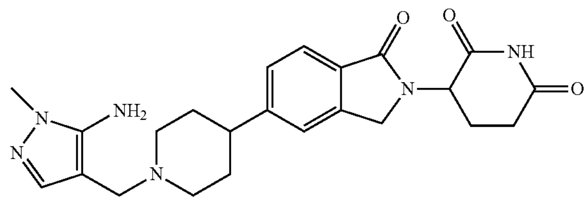 [SMILES: Cn1ncc(CN2CCC(c3ccc4c(c3)CN(C3CCC(=O)NC3=O)C4=O)CC2)c1N] | 3-(5-(1-((5-amino-1-methyl-1H-pyrazol-4-yl)methyl)piperidin-4-yl)-1-oxoisoindolin-2-yl)piperidine-2,6-dione |
| I-125 | 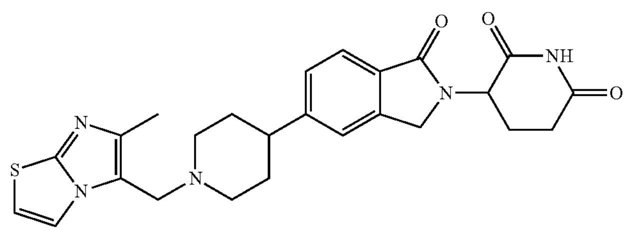 [SMILES: Cc1nc2sccn2c1CN1CCC(c2ccc3c(c2)CN(C2CCC(=O)NC2=O)C3=O)CC1] | 3-(5-(1-((6-methylimidazo[2,1-b]thiazol-5-yl)methyl)piperidin-4-yl)-1-oxoisoindolin-2-yl)piperidine-2,6-dione |
| I-126 | 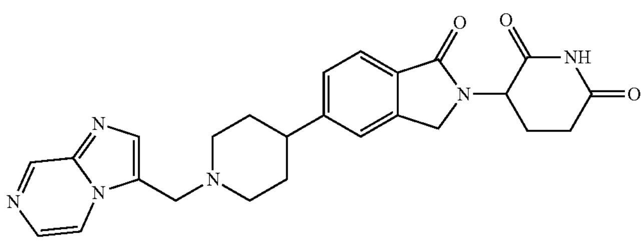 [SMILES: O=C1CCC(N2Cc3cc(C4CCN(Cc5cnc6cnccn56)CC4)ccc3C2=O)C(=O)N1] | 3-(5-(1-(imidazo[1,2-a]pyrazin-3-ylmethyl)piperidin-4-yl)-1-oxoisoindolin-2-yl)piperidine-2,6-dione |
| I-127 | 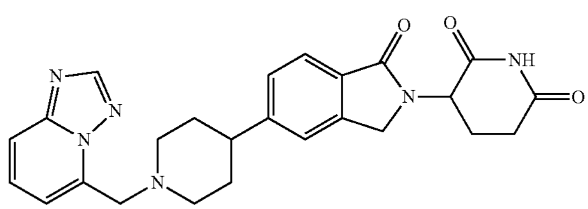 [SMILES: O=C1CCC(N2Cc3cc(C4CCN(Cc5cccc6ncnn56)CC4)ccc3C2=O)C(=O)N1] | 3-(5-(1-([1,2,4]triazolo[1,5-a]pyridin-5-ylmethyl)piperidin-4-yl)-1-oxoisoindolin-2-yl)piperidine-2,6-dione |
| I-128 | 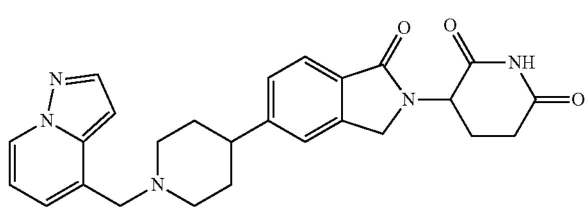 [SMILES: O=C1CCC(N2Cc3cc(C4CCN(Cc5cccn6nccc56)CC4)ccc3C2=O)C(=O)N1] | 3-(1-oxo-5-(1-(pyrazolo[1,5-a]pyridin-4-ylmethyl)piperidin-4-yl)isoindolin-2-yl)piperidine-2,6-dione |
| I-129 | 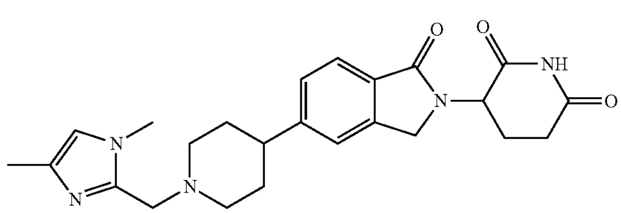 [SMILES: Cc1cn(C)c(CN2CCC(c3ccc4c(c3)CN(C3CCC(=O)NC3=O)C4=O)CC2)n1] | 3-(5-(1-((1,4-dimethyl-1H-imidazol-2-yl)methyl)piperidin-4-yl)-1-oxoisoindolin-2-yl)piperidine-2,6-dione |

| Cmpd No. | Structure | Compound Name |
| --- | --- | --- |
| I-130 | 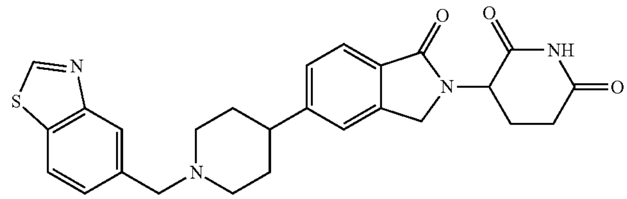 [SMILES: O=C1CCC(N2Cc3cc(C4CCN(Cc5ccc6scnc6c5)CC4)ccc3C2=O)C(=O)N1] | 3-(5-(1-(benzo[d]thiazol-5-ylmethyl)piperidin-4-yl)-1-oxoisoindolin-2-yl)piperidine-2,6-dione |
| I-131 | 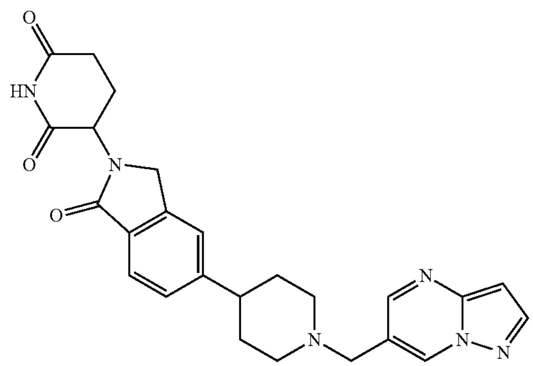 [SMILES: O=C1CCC(N2Cc3cc(C4CCN(Cc5cnc6ccnn6c5)CC4)ccc3C2=O)C(=O)N1] | 3-(1-oxo-5-(1-(pyrazolo[1,5-a]pyrimidin-6-ylmethyl)piperidin-4-yl)isoindolin-2-yl)piperidine-2,6-dione |
| I-132 | 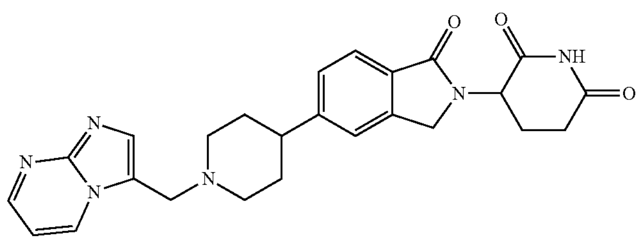 [SMILES: O=C1CCC(N2Cc3cc(C4CCN(Cc5cnc6ncccn56)CC4)ccc3C2=O)C(=O)N1] | 3-(5-(1-(imidazo[1,2-a]pyrimidin-3-ylmethyl)piperidin-4-yl)-1-oxoisoindolin-2-yl)piperidine-2,6-dione |
| I-133 | 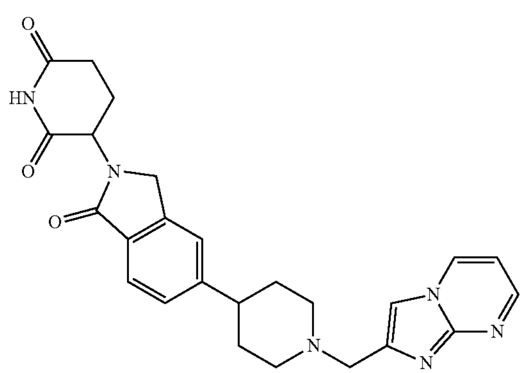 [SMILES: O=C1CCC(N2Cc3cc(C4CCN(Cc5cn6cccnc6n5)CC4)ccc3C2=O)C(=O)N1] | 3-(5-(1-(imidazo[1,2-a]pyrimidin-2-ylmethyl)piperidin-4-yl)-1-oxoisoindolin-2-yl)piperidine-2,6-dione |
| I-134 | 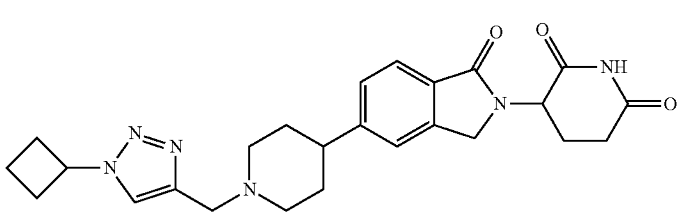 [SMILES: O=C1CCC(N2Cc3cc(C4CCN(Cc5cn(C6CCC6)nn5)CC4)ccc3C2=O)C(=O)N1] | 3-(5-(1-((1-cyclobutyl-1H-1,2,3-triazol-4-yl)methyl)piperidin-4-yl)-1-oxoisoindolin-2-yl)piperidine-2,6-dione |

-continued

| Cmpd No. | Structure | Compound Name |
|---|---|---|
| I-135 | 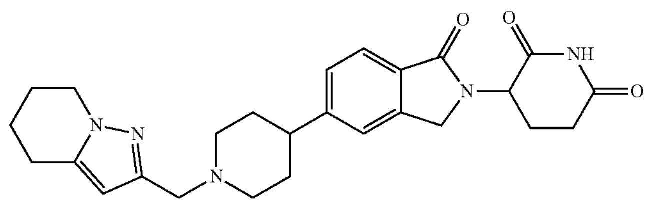 [SMILES: O=C1CCC(N2Cc3cc(C4CCN(Cc5cc6n(n5)CCCC6)CC4)ccc3C2=O)C(=O)N1] | 3-(1-oxo-5-(1-((4,5,6,7-tetrahydropyrazolo[1,5-a]pyridin-2-yl)methyl)piperidin-4-yl)isoindolin-2-yl)piperidine-2,6-dione |
| I-136 | 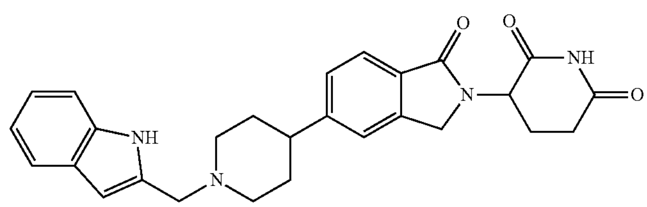 [SMILES: O=C1CCC(N2Cc3cc(C4CCN(Cc5cc6ccccc6[nH]5)CC4)ccc3C2=O)C(=O)N1] | 3-(5-(1-((1H-indol-2-yl)methyl)piperidin-4-yl)-1-oxoisoindolin-2-yl)piperidine-2,6-dione |
| I-137 | 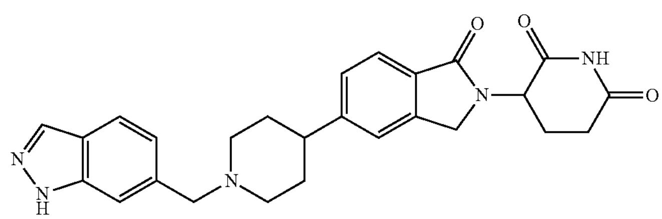 [SMILES: O=C1CCC(N2Cc3cc(C4CCN(Cc5ccc6cn[nH]c6c5)CC4)ccc3C2=O)C(=O)N1] | 3-(5-(1-((1H-indazol-6-yl)methyl)piperidin-4-yl)-1-oxoisoindolin-2-yl)piperidine-2,6-dione |
| I-138 | 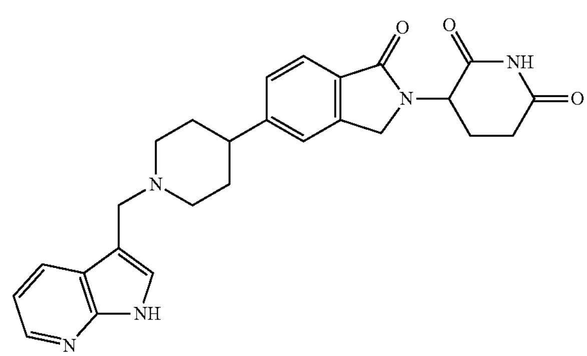 [SMILES: O=C1CCC(N2Cc3cc(C4CCN(Cc5c[nH]c6ncccc56)CC4)ccc3C2=O)C(=O)N1] | 3-(5-(1-((1H-pyrrolo[2,3-b]pyridin-3-yl)methyl)piperidin-4-yl)-1-oxoisoindolin-2-yl)piperidine-2,6-dione |
| I-139 | 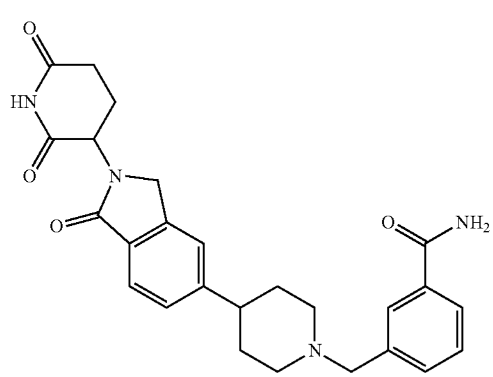 [SMILES: NC(=O)c1cccc(CN2CCC(c3ccc4c(c3)CN(C3CCC(=O)NC3=O)C4=O)CC2)c1] | 3-((4-(2-(2,6-dioxopiperidin-3-yl)-1-oxoisoindolin-5-yl)piperidin-1-yl)methyl)benzamide |

-continued

| Cmpd No. | Structure | Compound Name |
|---|---|---|
| I-140 | 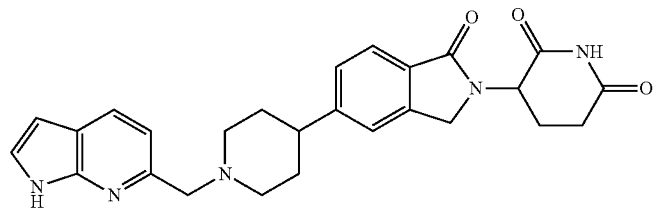 [SMILES: O=C1CCC(N2Cc3cc(C4CCN(Cc5ccc6cc[nH]c6n5)CC4)ccc3C2=O)C(=O)N1] | 3-(5-(1-((1H-pyrrolo[2,3-b]pyridin-6-yl)methyl)piperidin-4-yl)-1-oxoisoindolin-2-yl)piperidine-2,6-dione |
| I-141 | 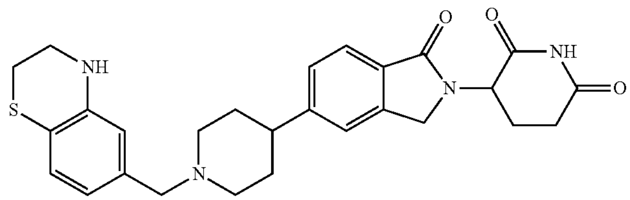 [SMILES: O=C1CCC(N2Cc3cc(C4CCN(Cc5ccc6c(c5)NCCS6)CC4)ccc3C2=O)C(=O)N1] | 3-(5-(1-((3,4-dihydro-2H-benzo[b][1,4]thiazin-6-yl)methyl)piperidin-4-yl)-1-oxoisoindolin-2-yl)piperidine-2,6-dione |
| I-142 | 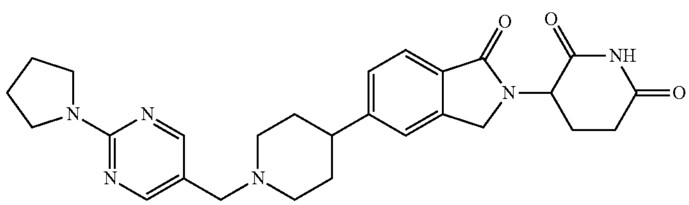 [SMILES: O=C1CCC(N2Cc3cc(C4CCN(Cc5cnc(N6CCCC6)nc5)CC4)ccc3C2=O)C(=O)N1] | 3-(1-oxo-5-(1-((2-(pyrrolidin-1-yl)pyrimidin-5-yl)methyl)piperidin-4-yl)isoindolin-2-yl)piperidine-2,6-dione |
| I-143 | 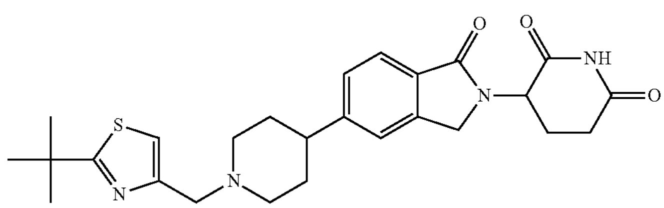 [SMILES: CC(C)(C)c1nc(CN2CCC(c3ccc4c(c3)CN(C3CCC(=O)NC3=O)C4=O)CC2)cs1] | 3-(5-(1-((2-(tert-butyl)thiazol-4-yl)methyl)piperidin-4-yl)-1-oxoisoindolin-2-yl)piperidine-2,6-dione |
| I-144 | 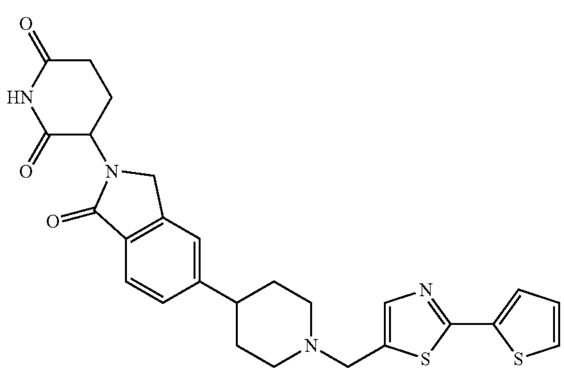 [SMILES: O=C1CCC(N2Cc3cc(C4CCN(Cc5cnc(-c6cccs6)s5)CC4)ccc3C2=O)C(=O)N1] | 3-(1-oxo-5-(1-((2-(thiophen-2-yl)thiazol-5-yl)methyl)piperidin-4-yl)isoindolin-2-yl)piperidine-2,6-dione |

-continued

| Cmpd No. | Structure | Compound Name |
|---|---|---|
| I-145 | 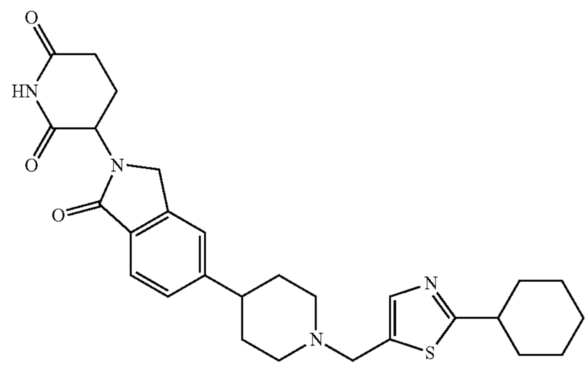 [SMILES: O=C1CCC(N2Cc3cc(C4CCN(Cc5cnc(C6CCCCC6)s5)CC4)ccc3C2=O)C(=O)N1] | 3-(5-(1-((2-cyclohexylthiazol-5-yl)methyl)piperidin-4-yl)-1-oxoisoindolin-2-yl)piperidine-2,6-dione |
| I-146 | 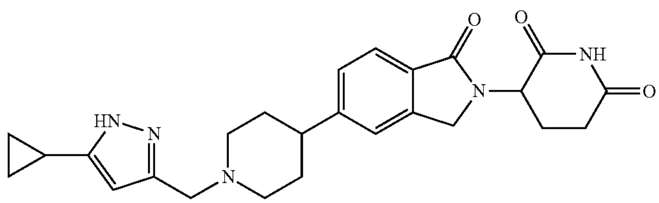 [SMILES: O=C1CCC(N2Cc3cc(C4CCN(Cc5cc(C6CC6)[nH]n5)CC4)ccc3C2=O)C(=O)N1] | 3-(5-(1-((5-cyclopropyl-1H-pyrazol-3-yl)methyl)piperidin-4-yl)-1-oxoisoindolin-2-yl)piperidine-2,6-dione |
| I-147 | 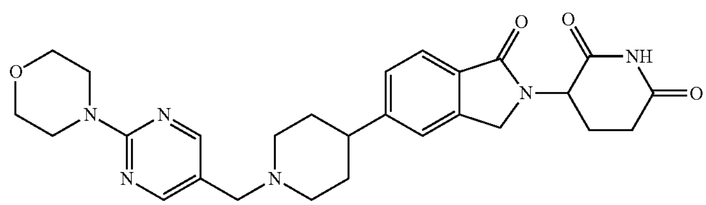 [SMILES: O=C1CCC(N2Cc3cc(C4CCN(Cc5cnc(N6CCOCC6)nc5)CC4)ccc3C2=O)C(=O)N1] | 3-(5-(1-((2-morpholinopyrimidin-5-yl)methyl)piperidin-4-yl)-1-oxoisoindolin-2-yl)piperidine-2,6-dione |
| I-148 | 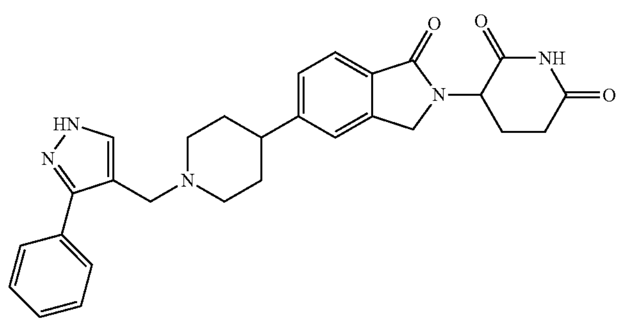 [SMILES: O=C1CCC(N2Cc3cc(C4CCN(Cc5c[nH]nc5-c5ccccc5)CC4)ccc3C2=O)C(=O)N1] | 3-(1-oxo-5-(1-((3-phenyl-1H-pyrazol-4-yl)methyl)piperidin-4-yl)isoindolin-2-yl)piperidine-2,6-dione |
| I-149 | 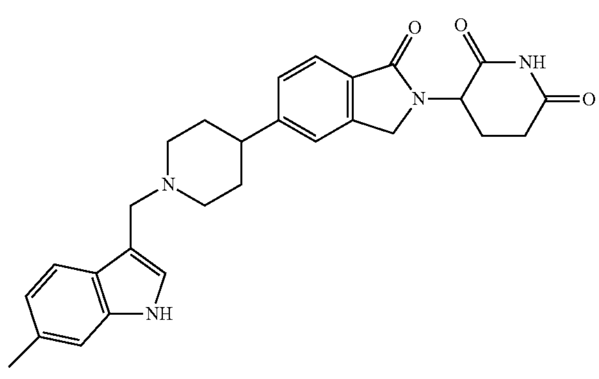 [SMILES: Cc1ccc2c(CN3CCC(c4ccc5c(c4)CN(C4CCC(=O)NC4=O)C5=O)CC3)c[nH]c2c1] | 3-(5-(1-((6-methyl-1H-indol-3-yl)methyl)piperidin-4-yl)-1-oxoisoindolin-2-yl)piperidine-2,6-dione |

| Cmpd No. | Structure | Compound Name |
|---|---|---|
| I-150 | 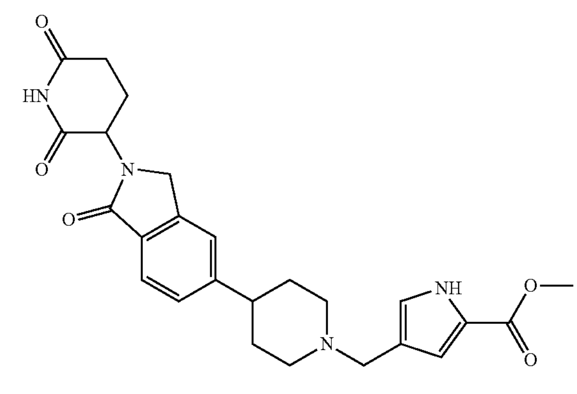 [SMILES: COC(=O)c1cc(CN2CCC(c3ccc4c(c3)CN(C3CCC(=O)NC3=O)C4=O)CC2)c[nH]1] | methyl 4-((4-(2-(2,6-dioxopiperidin-3-yl)-1-oxoisoindolin-5-yl)piperidin-1-yl)methyl)-1H-pyrrole-2-carboxylate |
| I-151 | 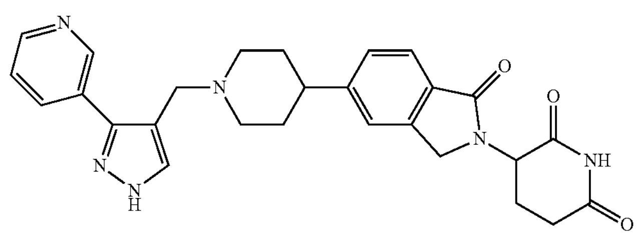 [SMILES: O=C1CCC(N2Cc3cc(C4CCN(Cc5c[nH]nc5-c5cccnc5)CC4)ccc3C2=O)C(=O)N1] | 3-(1-oxo-5-(1-((3-(pyridin-3-yl)-1H-pyrazol-4-yl)methyl)piperidin-4-yl)isoindolin-2-yl)piperidine-2,6-dione |
| I-152 | 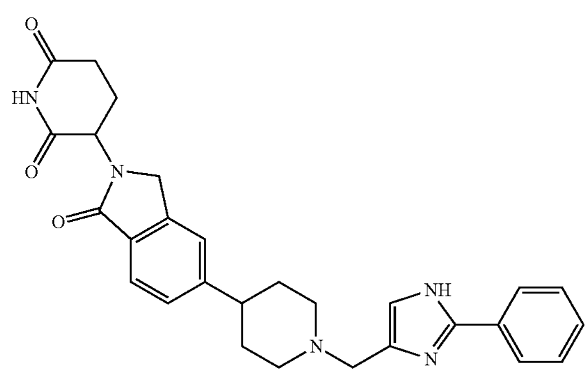 [SMILES: O=C1CCC(N2Cc3cc(C4CCN(Cc5c[nH]c(-c6ccccc6)n5)CC4)ccc3C2=O)C(=O)N1] | 3-(1-oxo-5-(1-((2-phenyl-1H-imidazol-4-yl)methyl)piperidin-4-yl)isoindolin-2-yl)piperidine-2,6-dione |
| I-153 | 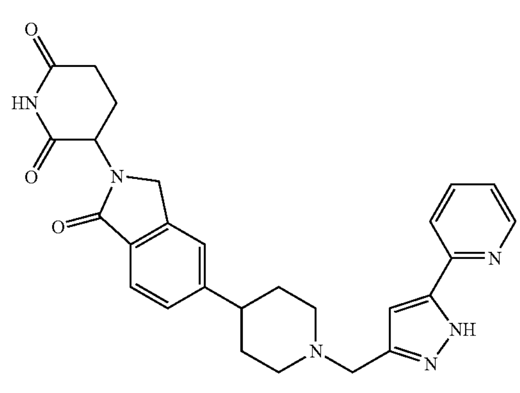 [SMILES: O=C1CCC(N2Cc3cc(C4CCN(Cc5cc(-c6ccccn6)[nH]n5)CC4)ccc3C2=O)C(=O)N1] | 3-(1-oxo-5-(1-((5-(pyridin-2-yl)-1H-pyrazol-3-yl)methyl)piperidin-4-yl)isoindolin-2-yl)piperidine-2,6-dione |

-continued

| Cmpd No. | Structure | Compound Name |
|---|---|---|
| I-154 | 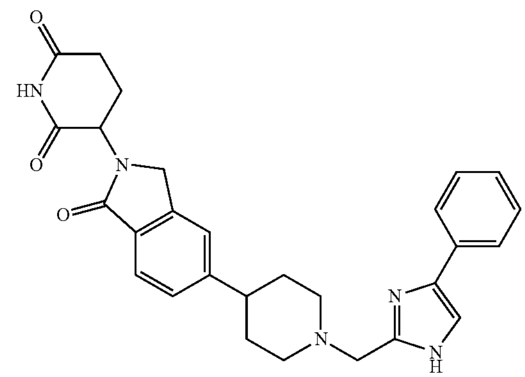 [SMILES: O=C1CCC(N2Cc3cc(C4CCN(Cc5nc(-c6ccccc6)c[nH]5)CC4)ccc3C2=O)C(=O)N1] | 3-(1-oxo-5-(1-((4-phenyl-1H-imidazol-2-yl)methyl)piperidin-4-yl)isoindolin-2-yl)piperidine-2,6-dione |
| I-155 | 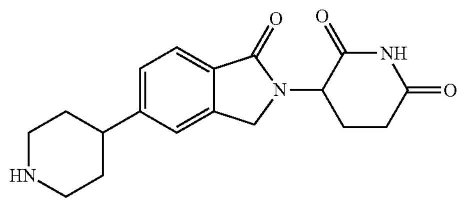 [SMILES: O=C1CCC(N2Cc3cc(C4CCNCC4)ccc3C2=O)C(=O)N1] | 3-(1-oxo-5-(piperidin-4-yl)isoindolin-2-yl)piperidine-2,6-dione |
| I-156 | 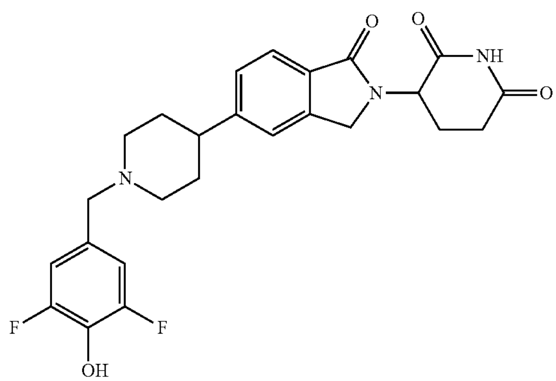 [SMILES: O=C1CCC(N2Cc3cc(C4CCN(Cc5cc(F)c(O)c(F)c5)CC4)ccc3C2=O)C(=O)N1] | 3-(5-(1-(3,5-difluoro-4-hydroxybenzyl)piperidin-4-yl)-1-oxoisoindolin-2-yl)piperidine-2,6-dione |
| I-157 | 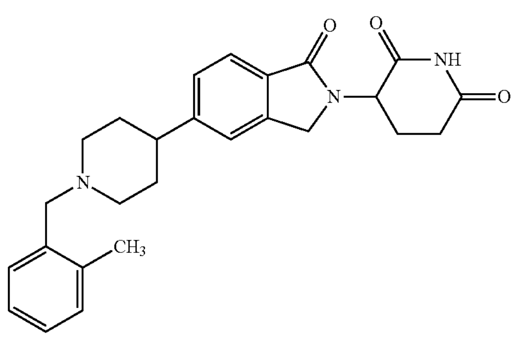 [SMILES: Cc1ccccc1CN1CCC(c2ccc3c(c2)CN(C2CCC(=O)NC2=O)C3=O)CC1] | 3-(5-(1-(2-methylbenzyl)piperidin-4-yl)-1-oxoisoindolin-2-yl)piperidine-2,6-dione |

| Cmpd No. | Structure | Compound Name |
|---|---|---|
| I-158 | 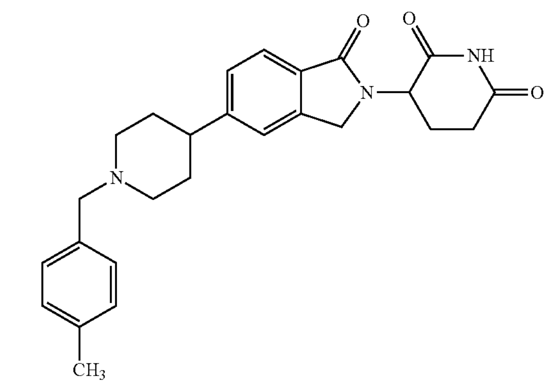 [SMILES: Cc1ccc(CN2CCC(c3ccc4c(c3)CN(C3CCC(=O)NC3=O)C4=O)CC2)cc1] | 3-(5-(1-(4-methylbenzyl)piperidin-4-yl)-1-oxoisoindolin-2-yl)piperidine-2,6-dione |
| I-159 | 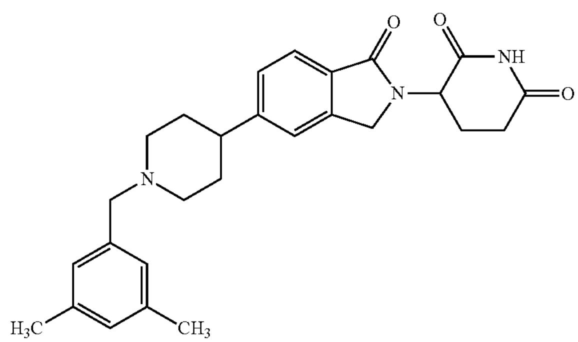 [SMILES: Cc1cc(C)cc(CN2CCC(c3ccc4c(c3)CN(C3CCC(=O)NC3=O)C4=O)CC2)c1] | 3-(5-(1-(3,5-dimethylbenzyl)piperidin-4-yl)-1-oxoisoindolin-2-yl)piperidine-2,6-dione |
| I-160 | 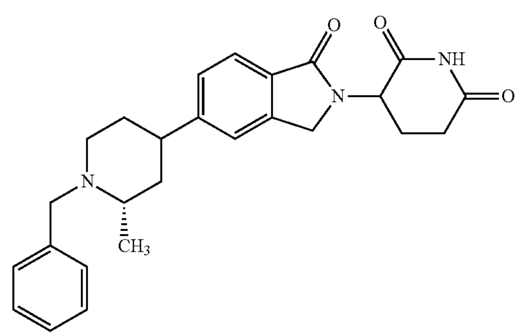 [SMILES: C[C@H]1CC(c2ccc3c(c2)CN(C2CCC(=O)NC2=O)C3=O)CCN1Cc1ccccc1] | 3-(5-((2S)-1-benzyl-2-methylpiperidin-4-yl)-1-oxoisoindolin-2-yl)piperidine-2,6-dione |
| I-161 | 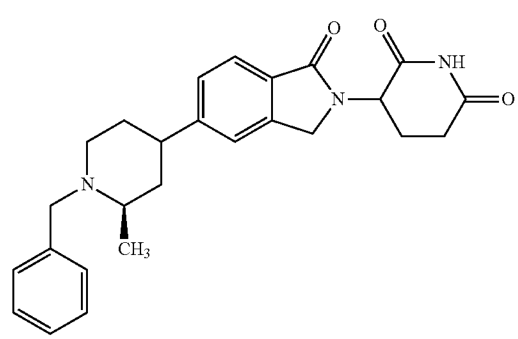 [SMILES: C[C@@H]1CC(c2ccc3c(c2)CN(C2CCC(=O)NC2=O)C3=O)CCN1Cc1ccccc1] | 3-(5-((2R)-1-benzyl-2-methylpiperidin-4-yl)-1-oxoisoindolin-2-yl)piperidine-2,6-dione |

| Cmpd No. | Structure | Compound Name |
|---|---|---|
| I-162 | 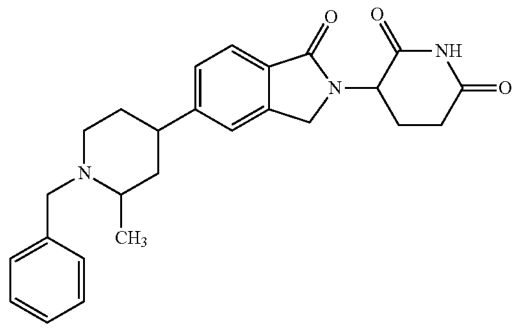 [SMILES: CC1CC(c2ccc3c(c2)CN(C2CCC(=O)NC2=O)C3=O)CCN1Cc1ccccc1] | 3-(5-(1-benzyl-2-methylpiperidin-4-yl)-1-oxoisoindolin-2-yl)piperidine-2,6-dione |
| I-163 | 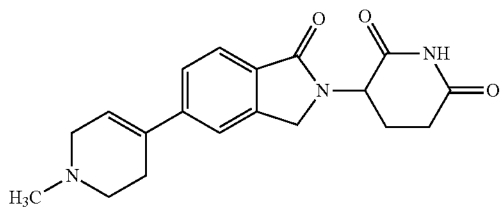 [SMILES: CN1CC=C(c2ccc3c(c2)CN(C2CCC(=O)NC2=O)C3=O)CC1] | 3-(5-(1-methyl-1,2,3,6-tetrahydropyridin-4-yl)-1-oxoisoindolin-2-yl)piperidine-2,6-dione |
| I-164 | 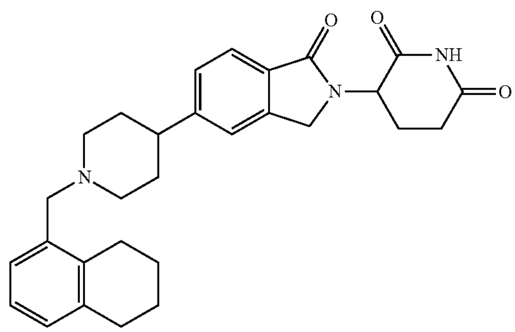 [SMILES: O=C1CCC(N2Cc3cc(C4CCN(Cc5cccc6c5CCCC6)CC4)ccc3C2=O)C(=O)N1] | 3-(1-oxo-5-(1-((5,6,7,8-tetrahydronaphthalen-1-yl)methyl)piperidin-4-yl)isoindolin-2-yl)piperidine-2,6-dione |
| I-165 | 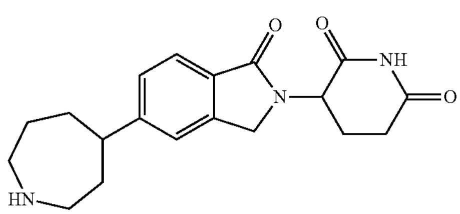 [SMILES: O=C1CCC(N2Cc3cc(C4CCCNCC4)ccc3C2=O)C(=O)N1] | 3-(5-(azepan-4-yl)-1-oxoisoindolin-2-yl)piperidine-2,6-dione |
| I-166 | 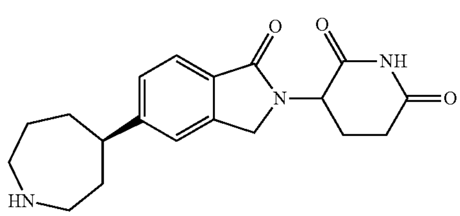 [SMILES: O=C1CCC(N2Cc3cc([C@@H]4CCCNCC4)ccc3C2=O)C(=O)N1] | 3-(5-((R)-azepan-4-yl)-1-oxoisoindolin-2-yl)piperidine-2,6-dione |
| I-167 | 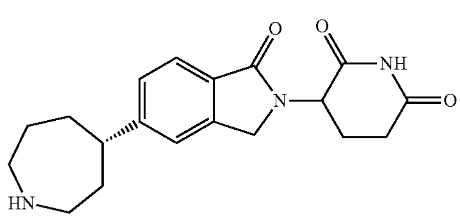 [SMILES: O=C1CCC(N2Cc3cc([C@H]4CCCNCC4)ccc3C2=O)C(=O)N1] | 3-(5-((S)-azepan-4-yl)-1-oxoisoindolin-2-yl)piperidine-2,6-dione |

| Cmpd No. | Structure | Compound Name |
|---|---|---|
| I-168 | 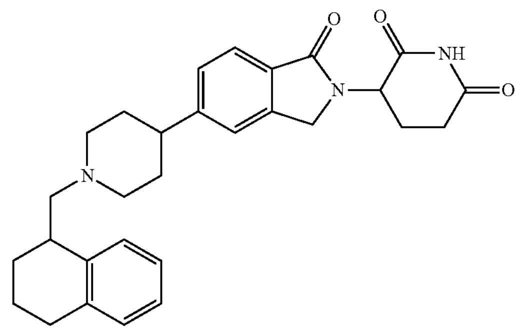 [SMILES: O=C1CCC(N2Cc3cc(C4CCN(CC5CCCc6ccccc65)CC4)ccc3C2=O)C(=O)N1] | 3-(1-oxo-5-(1-((1,2,3,4-tetrahydronaphthalen-1-yl)methyl)piperidin-4-yl)isoindolin-2-yl)piperidine-2,6-dione |
| I-169 | 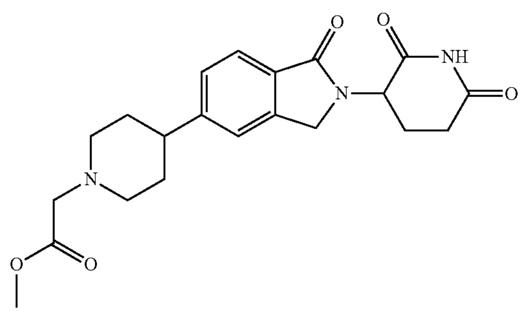 [SMILES: COC(=O)CN1CCC(c2ccc3c(c2)CN(C2CCC(=O)NC2=O)C3=O)CC1] | methyl 2-(4-(2-(2,6-dioxopiperidin-3-yl)-1-oxoisoindolin-5-yl)piperidin-1-yl)acetate |
| I-170 | 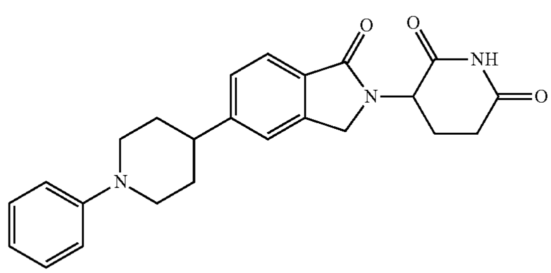 [SMILES: O=C1CCC(N2Cc3cc(C4CCN(c5ccccc5)CC4)ccc3C2=O)C(=O)N1] | 3-(1-oxo-5-(1-phenylpiperidin-4-yl)isoindolin-2-yl)piperidine-2,6-dione |
| I-171 | 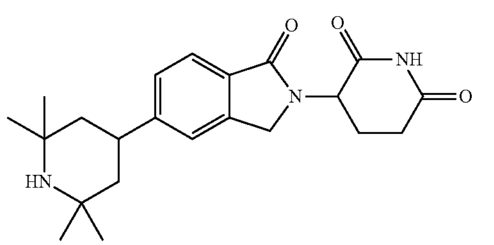 [SMILES: CC1(C)CC(c2ccc3c(c2)CN(C2CCC(=O)NC2=O)C3=O)CC(C)(C)N1] | 3-(1-oxo-5-(2,2,6,6-tetramethylpiperidin-4-yl)isoindolin-2-yl)piperidine-2,6-dione |
| I-172 | 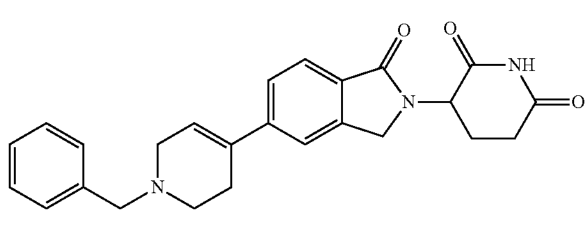 [SMILES: O=C1CCC(N2Cc3cc(C4=CCN(Cc5ccccc5)CC4)ccc3C2=O)C(=O)N1] | 3-(5-(1-benzyl-1,2,3,6-tetrahydropyridin-4-yl)-1-oxoisoindolin-2-yl)piperidine-2,6-dione |

| Cmpd No. | Structure | Compound Name |
| --- | --- | --- |
| I-173 | 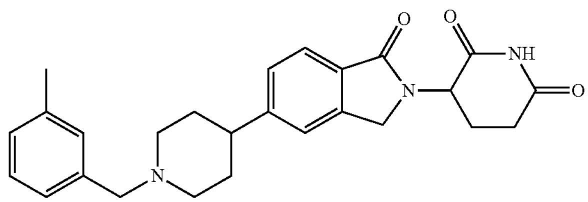 [SMILES: Cc1cccc(CN2CCC(c3ccc4c(c3)CN(C3CCC(=O)NC3=O)C4=O)CC2)c1] | 3-(5-(1-(3-methylbenzyl)piperidin-4-yl)-1-oxoisoindolin-2-yl)piperidine-2,6-dione |
| I-174 | 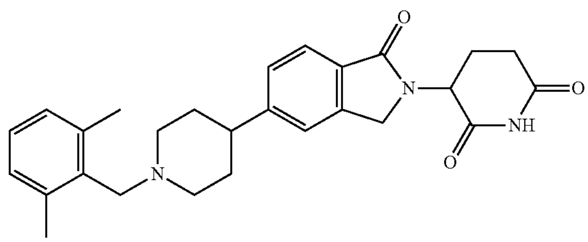 [SMILES: Cc1cccc(C)c1CN1CCC(c2ccc3c(c2)CN(C2CCC(=O)NC2=O)C3=O)CC1] | 3-(5-(1-(2,6-dimethylbenzyl)piperidin-4-yl)-1-oxoisoindolin-2-yl)piperidine-2,6-dione |
| I-175 | 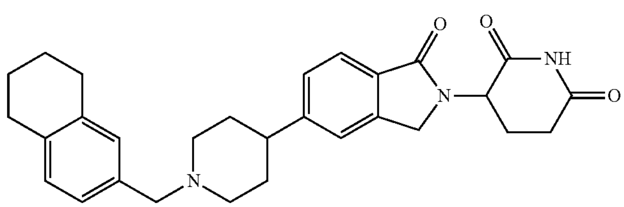 [SMILES: O=C1CCC(N2Cc3cc(C4CCN(Cc5ccc6c(c5)CCCC6)CC4)ccc3C2=O)C(=O)N1] | 3-(1-oxo-5-(1-((5,6,7,8-tetrahydronaphthalen-2-yl)methyl)piperidin-4-yl)isoindolin-2-yl)piperidine-2,6-dione |
| I-176 | 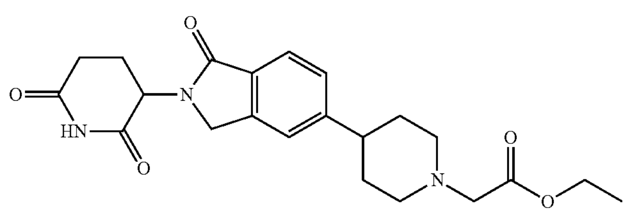 [SMILES: CCOC(=O)CN1CCC(c2ccc3c(c2)CN(C2CCC(=O)NC2=O)C3=O)CC1] | ethyl 2-(4-(2-(2,6-dioxopiperidin-3-yl)-1-oxoisoindolin-5-yl)piperidin-1-yl)acetate |
| I-177 | 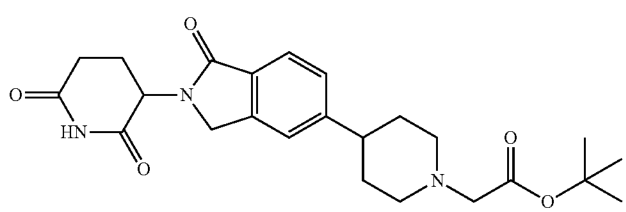 [SMILES: CC(C)(C)OC(=O)CN1CCC(c2ccc3c(c2)CN(C2CCC(=O)NC2=O)C3=O)CC1] | tert-butyl 2-(4-(2-(2,6-dioxopiperidin-3-yl)-1-oxoisoindolin-5-yl)piperidin-1-yl)acetate |
| I-178 | 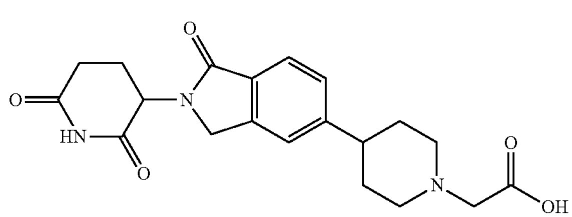 [SMILES: O=C(O)CN1CCC(c2ccc3c(c2)CN(C2CCC(=O)NC2=O)C3=O)CC1] | 2-(4-(2-(2,6-dioxopiperidin-3-yl)-1-oxoisoindolin-5-yl)piperidin-1-yl)acetic acid |

-continued

| Cmpd No. | Structure | Compound Name |
|---|---|---|
| I-179 | 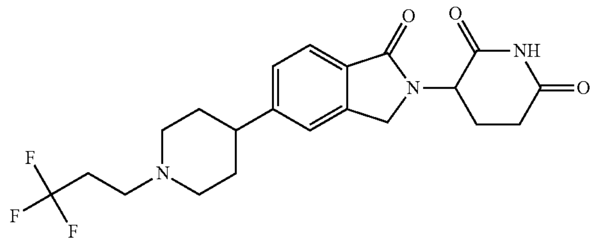 [SMILES: O=C1CCC(N2Cc3cc(C4CCN(CCC(F)(F)F)CC4)ccc3C2=O)C(=O)N1] | 3-(1-oxo-5-(1-(3,3,3-trifluoropropyl)piperidin-4-yl)isoindolin-2-yl)piperidine-2,6-dione |
| I-180 | 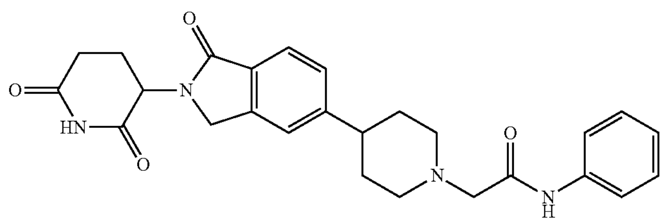 [SMILES: O=C1CCC(N2Cc3cc(C4CCN(CC(=O)Nc5ccccc5)CC4)ccc3C2=O)C(=O)N1] | 2-(4-(2-(2,6-dioxopiperidin-3-yl)-1-oxoisoindolin-5-yl)piperidin-1-yl)-N-phenylacetamide |
| I-181 | 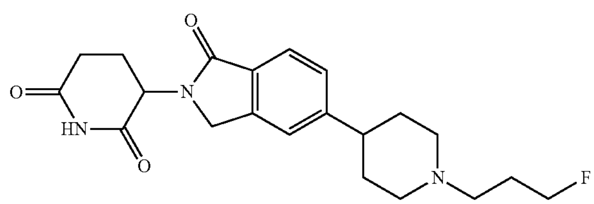 [SMILES: O=C1CCC(N2Cc3cc(C4CCN(CCCF)CC4)ccc3C2=O)C(=O)N1] | 3-(5-(1-(3-fluoropropyl)piperidin-4-yl)-1-oxoisoindolin-2-yl)piperidine-2,6-dione |
| I-182 | 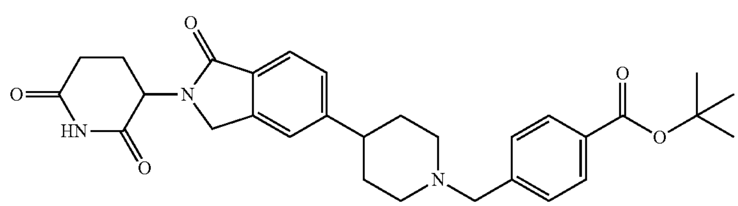 [SMILES: CC(C)(C)OC(=O)c1ccc(CN2CCC(c3ccc4c(c3)CN(C3CCC(=O)NC3=O)C4=O)CC2)cc1] | tert-butyl 4-((4-(2-(2,6-dioxopiperidin-3-yl)-1-oxoisoindolin-5-yl)piperidine-1-yl)methyl)benzoate |
| I-183 | 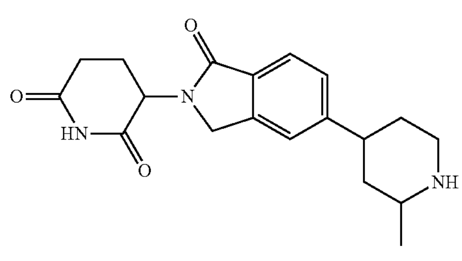 [SMILES: CC1CC(c2ccc3c(c2)CN(C2CCC(=O)NC2=O)C3=O)CCN1] | 3-(5-(2-methylpiperidin-4-yl)-1-oxoisoindolin-2-yl)piperidine-2,6-dione |
| I-184 | 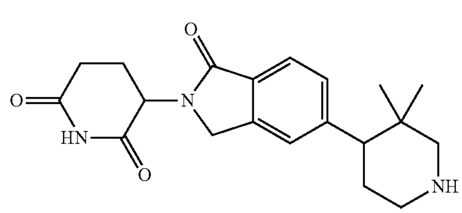 [SMILES: CC1(C)CNCCC1c1ccc2c(c1)CN(C1CCC(=O)NC1=O)C2=O] | 3-(5-(3,3-dimethylpiperiidn-4-yl)-1-oxoisoindolin-2-yl)piperidine-2,6-dione |

-continued

| Cmpd No. | Structure | Compound Name |
|---|---|---|
| I-185 | 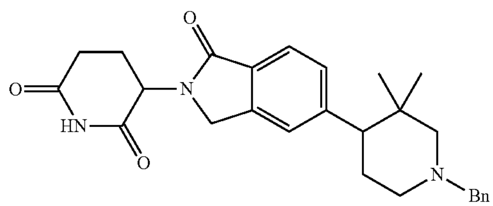 [SMILES: CC1(C)CN(Cc2ccccc2)CCC1c1ccc2c(c1)CN(C1CCC(=O)NC1=O)C2=O] | 3-(5-(1-benzyl-3,3-dimethylpiperidin-4-yl)-1-oxoisoindolin-2-yl)piperidine-2,6-dione |
| I-186 | 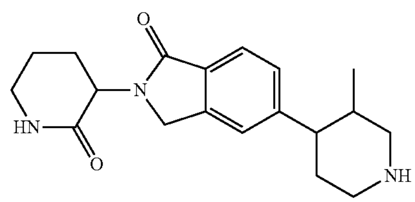 [SMILES: CC1CNCCC1c1ccc2c(c1)CN(C1CCCNC1=O)C2=O] | 5-(3-methylpiperidin-4-yl)-2-(2-oxopiperidin-3-yl)isoindolin-1-one |
| I-187 | 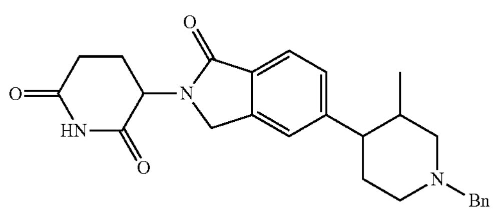 [SMILES: CC1CN(Cc2ccccc2)CCC1c1ccc2c(c1)CN(C1CCC(=O)NC1=O)C2=O] | 3-(5-(1-benzyl-3-methylpiperidin-4-yl)-1-oxoisoindolin-2-yl)piperidine-2,6-dione |
| I-188 | 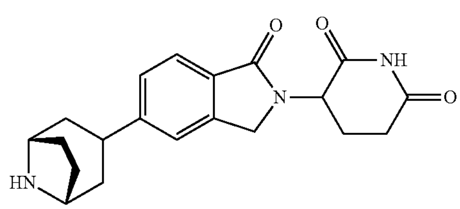 | 3-(5-(8-azabicyclo[3.2.1]octan-3-yl)-1-oxoisoindolin-2-yl)piperidine-2,6-dione |
| I-189 | 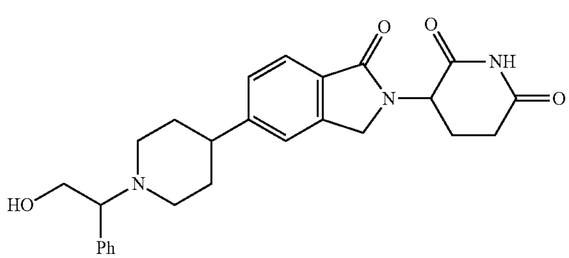 [SMILES: O=C1CCC(N2Cc3cc(C4CCN(C(CO)c5ccccc5)CC4)ccc3C2=O)C(=O)N1] | 3-(5-(1-(2-hydroxy-1-phenylethyl)piperidin-4-yl)-1-oxoisoindolin-2-yl)piperidine-2,6-dione |
| I-190 | 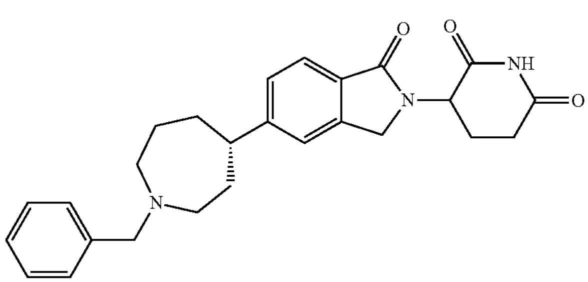 [SMILES: O=C1CCC(N2Cc3cc([C@H]4CCCN(Cc5ccccc5)CC4)ccc3C2=O)C(=O)N1] | 3-(5-((S)-1-benzylazepan-4-yl)-1-oxoisoindolin-2-yl)piperidine-2,6-dione |

| Cmpd No. | Structure | Compound Name |
|---|---|---|
| I-191 | 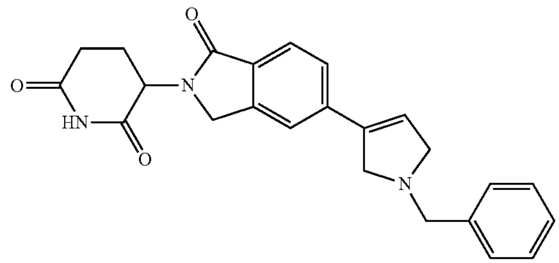 [SMILES: O=C1CCC(N2Cc3cc(C4=CCN(Cc5ccccc5)C4)ccc3C2=O)C(=O)N1] | 3-(5-(1-benzyl-2,5-dihydro-1H-pyrrol-3-yl)-1-oxoisoindolin-2-yl)piperidine-2,6-dione |
| I-192 | 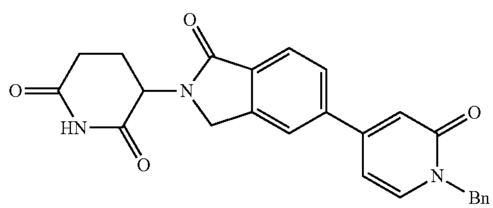 [SMILES: O=C1CCC(N2Cc3cc(-c4ccn(Cc5ccccc5)c(=O)c4)ccc3C2=O)C(=O)N1] | 3-(5-(1-benzyl-2-oxo-1,2-dihydropyridin-4-yl)-1-oxoisoindolin-2-yl)piperidine-2,6-dione |
| I-193 | 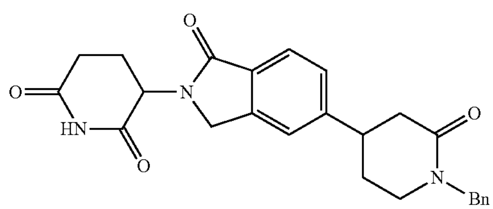 [SMILES: O=C1CCC(N2Cc3cc(C4CCN(Cc5ccccc5)C(=O)C4)ccc3C2=O)C(=O)N1] | 3-(5-(1-benzyl-2-oxopiperidin-4-yl)-1-oxoisoindolin-2-yl)piperidine-2,6-dione |
| I-194 | 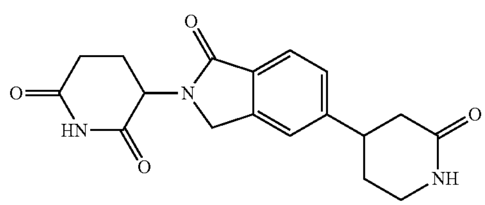 [SMILES: O=C1CC(c2ccc3c(c2)CN(C2CCC(=O)NC2=O)C3=O)CCN1] | 3-(1-oxo-5-(2-oxopiperidin-4-yl)isoindolin-2-yl)piperidine-2,6-dione |
| I-195 | 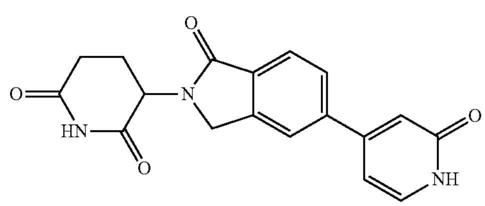 [SMILES: O=C1CCC(N2Cc3cc(-c4cc[nH]c(=O)c4)ccc3C2=O)C(=O)N1] | 3-(1-oxo-5-(2-oxo-1,2-dihydropyrridin-4-yl)isoindolin-2-yl)piperidine-2,6-dione |
| I-196 | 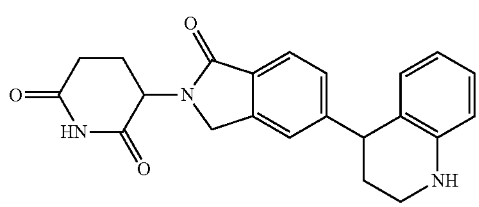 [SMILES: O=C1CCC(N2Cc3cc(C4CCNc5ccccc54)ccc3C2=O)C(=O)N1] | 3-(1-oxo-5-(1,2,3,4-tetrahydroquinolin-4-yl)isoindolin-2-yl)piperidine-2,6-dione |
| I-197 | 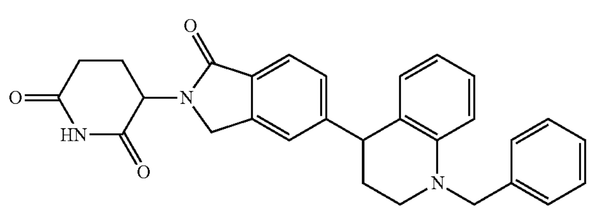 [SMILES: O=C1CCC(N2Cc3cc(C4CCN(Cc5ccccc5)c5ccccc54)ccc3C2=O)C(=O)N1] | 3-(5-(1-benzyl-1,2,3,4-tetrahydroquinolin-4-yl)-1-oxoisoindolin-2-yl)piperidine-2,6-dione |

| Cmpd No. | Structure | Compound Name |
| --- | --- | --- |
| I-198 | 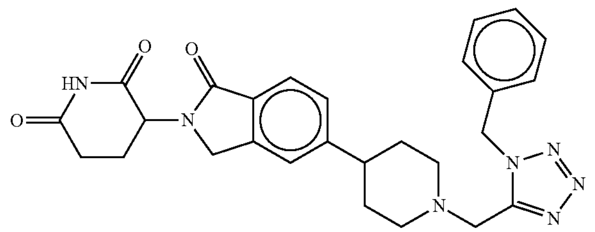 | 3-(5-(1-((1-benzyl-1H-tetrazol-5-yl)methyl)piperidin-4-yl)-1-oxoisoindolin-2-yl)piperidine-2,6-dione |
| I-199 | 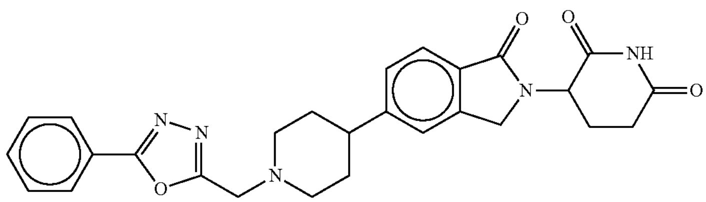 | 3-(1-oxo-5-(1-((5-phenyl-1,3,4-oxadiazol-2-yl)methyl)piperidin-4-yl)isoindolin-2-yl)piperidine-2,6-dione |
| I-200 | 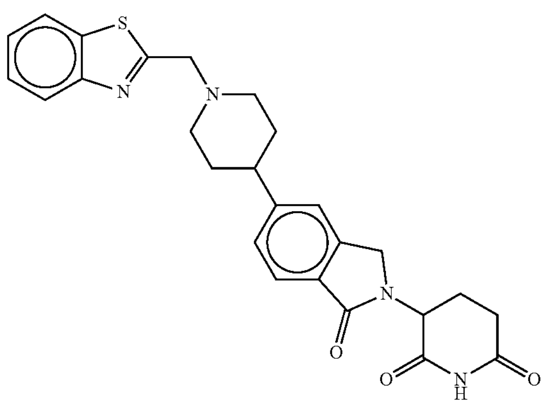 | 3-(5-(1-(benzo[d]thiazol-2-ylmethyl)piperidin-4-yl)-1-oxoisoindolin-2-yl)piperidine-2,6-dione |
| I-201 | 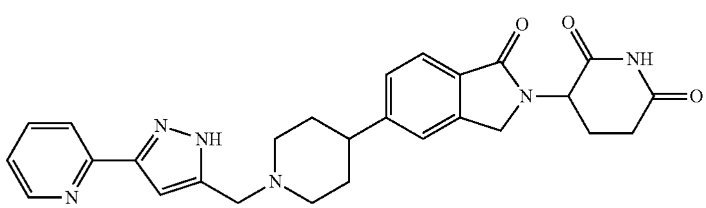 [SMILES: O=C1CCC(N2Cc3cc(C4CCN(Cc5cc(-c6ccccn6)n[nH]5)CC4)ccc3C2=O)C(=O)N1] | 3-(1-oxo-5-(1-((3-(pyridin-2-yl)-1H-pyrazol-5-yl)methyl)piperidin-4-yl)isoindolin-2-yl)piperidine-2,6-dione |
| I-202 | 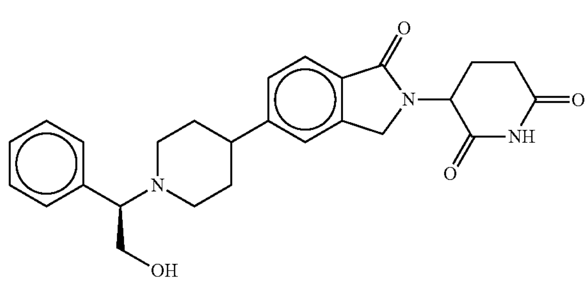 | 3-(5-(1-((R)-2-hydroxy-1-phenylethyl)piperidin-4-yl)-1-oxoisoindolin-2-yl)piperidine-2,6-dione |

-continued

| Cmpd No. | Structure | Compound Name |
|---|---|---|
| I-203 | 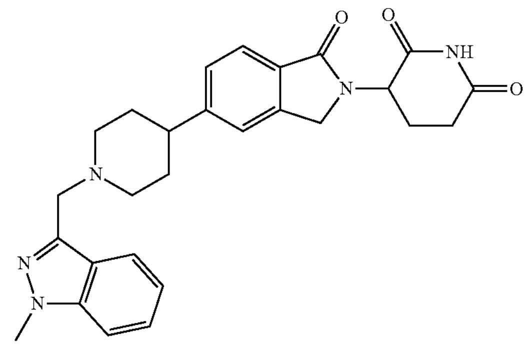 [SMILES: Cn1nc(CN2CCC(c3ccc4c(c3)CN(C3CCC(=O)NC3=O)C4=O)CC2)c2ccccc21] | 3-(5-(1-((1-methyl-1H-indazol-3-yl)methyl)piperidin-4-yl)-1-oxoisoindolin-2-yl)piperidine-2,6-dione |
| I-204 | 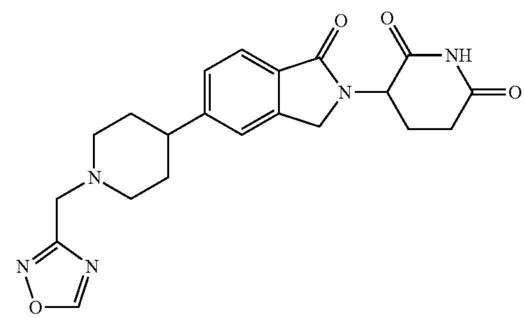 [SMILES: O=C1CCC(N2Cc3cc(C4CCN(Cc5ncon5)CC4)ccc3C2=O)C(=O)N1] | 3-(5-(1-((1,2,4-oxadiazol-3-yl)methyl)piperidin-4-yl)-1-oxoisoindolin-2-yl)piperidine-2,6-dione |
| I-205 | 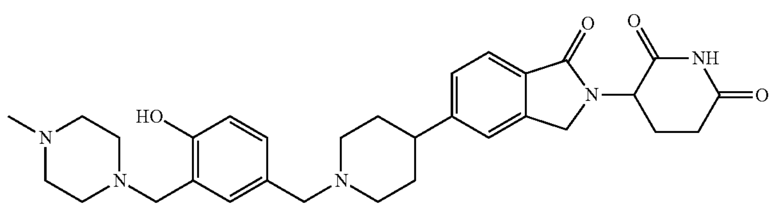 [SMILES: CN1CCN(Cc2cc(CN3CCC(c4ccc5c(c4)CN(C4CCC(=O)NC4=O)C5=O)CC3)ccc2O)CC1] | 3-(5-(1-(4-hydroxy-3-((4-methylpiperazin-1-yl)methyl)benzyl)piperidin-4-yl)-1-oxoisoindolin-2-yl)piperidine-2,6-dione |
| I-206 | 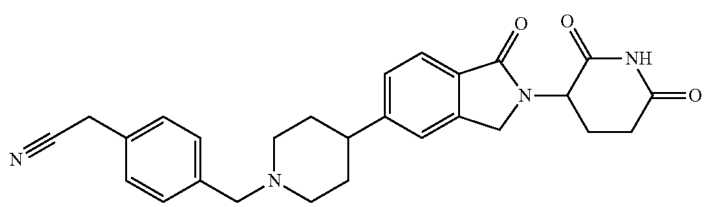 [SMILES: N#CCc1ccc(CN2CCC(c3ccc4c(c3)CN(C3CCC(=O)NC3=O)C4=O)CC2)cc1] | 2-(4-((4-(2-(2,6-dioxopiperidin-3-yl)-1-oxoisoindolin-5-yl)piperidin-1-yl)methyl)phenyl)acetonitrile |
| I-207 | 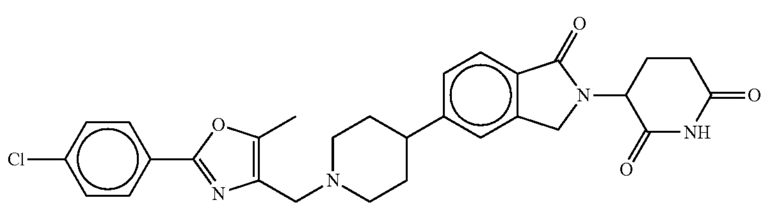 | 3-(5-(1-((2-(4-chlorophenyl)-5-methyloxazol-4-yl)methyl)piperidin-4-yl)-1-oxoisoindolin-2-yl)piperidine-2,6-dione |
| I-208 | 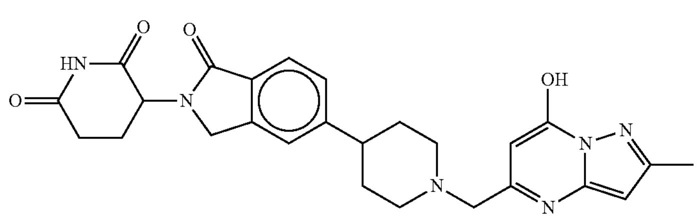 | 3-(5-(1-((7-hydroxy-2-methylpyrazolo[1,5-a]pyrimidin-5-yl)methyl)piperidin-4-yl)-1-oxoisoindolin-2-yl)piperidine-2,6-dione |

-continued

| Cmpd No. | Structure | Compound Name |
| --- | --- | --- |
| I-209 | 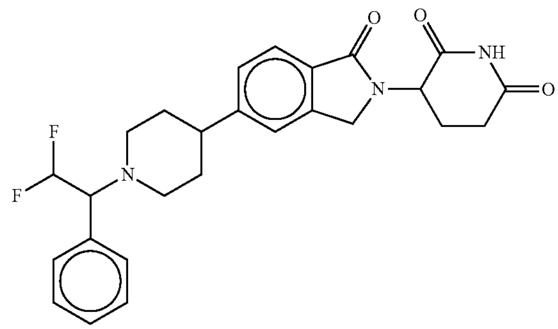 | 3-(5-(1-(2,2-difluoro-1-phenylethyl)piperidin-4-yl)-1-oxoisoindolin-2-yl)piperidine-2,6-dione |
| I-210 | 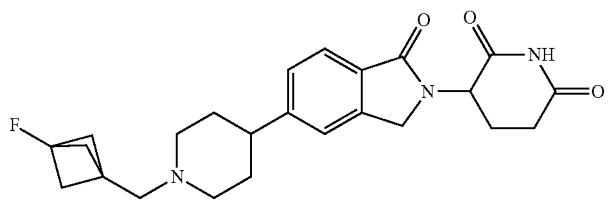 [SMILES: O=C1CCC(N2Cc3cc(C4CCN(CC56CC(F)(C5)C6)CC4)ccc3C2=O)C(=O)N1] | 3-(5-(1-((3-fluorobicyclo[1.1.1]pentan-1-yl)methyl)piperidin-4-yl)-1-oxoisoindolin-2-yl)piperidine-2,6-dione |
| I-211 | 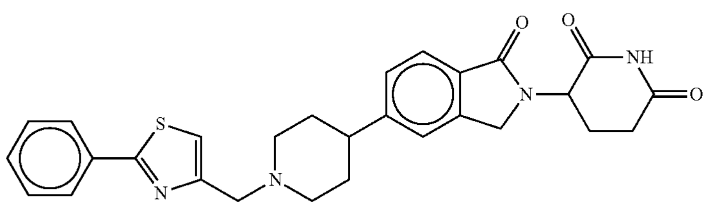 | 3-(1-oxo-5-(1-((2-phenylthiazol-4-yl)methyl)piperidin-4-yl)isoindolin-2-yl)piperidine-2,6-dione |
| I-212 | 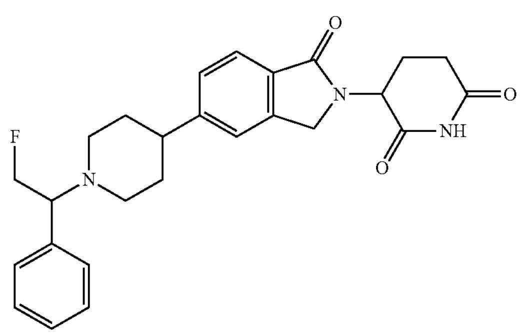 [SMILES: O=C1CCC(N2Cc3cc(C4CCN(C(CF)c5ccccc5)CC4)ccc3C2=O)C(=O)N1] | 3-(5-(1-(2-fluoro-1-phenylethyl)piperidin-4-yl)-1-oxoisoindolin-2-yl)piperidine-2,6-dione |
| I-213 | 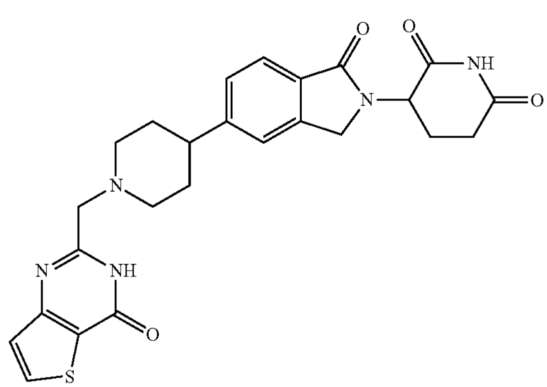 [SMILES: O=C1CCC(N2Cc3cc(C4CCN(Cc5nc6ccsc6c(=O)[nH]5)CC4)ccc3C2=O)C(=O)N1] | 3-(1-oxo-5-(1-((4-oxo-3,4-dihydrothieno[3,2-d]pyrimidin-2-yl)methyl)piperidin-4-yl)isoindolin-2-yl)piperidine-2,6-dione |

| Cmpd No. | Structure | Compound Name |
| --- | --- | --- |
| I-214 | 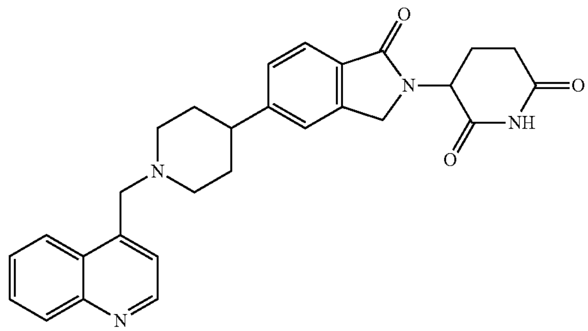 [SMILES: O=C1CCC(N2Cc3cc(C4CCN(Cc5ccnc6ccccc56)CC4)ccc3C2=O)C(=O)N1] | 3-(1-oxo-5-(1-(quinolin-4-ylmethyl)piperidin-4-yl)isoindolin-2-yl)piperidine-2,6-dione |
| I-215 | 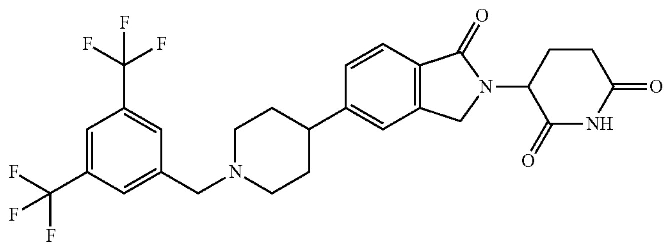 [SMILES: O=C1CCC(N2Cc3cc(C4CCN(Cc5cc(C(F)(F)F)cc(C(F)(F)F)c5)CC4)ccc3C2=O)C(=O)N1] | 3-(5-(1-(3,5-bis(trifluoromethyl)benzyl)piperidin-4-yl)-1-oxoisoindolin-2-yl)piperidine-2,6-dione |
| I-216 | 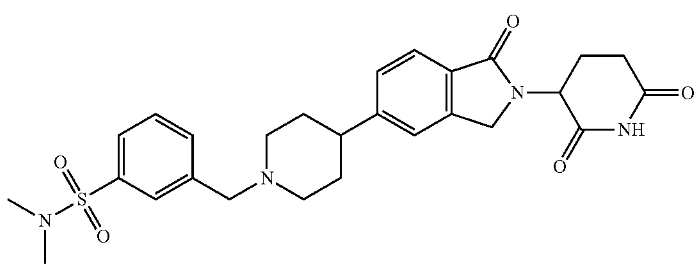 [SMILES: CN(C)S(=O)(=O)c1cccc(CN2CCC(c3ccc4c(c3)CN(C3CCC(=O)NC3=O)C4=O)CC2)c1] | 3-((4-(2-(2,6-dioxopiperidin-3-yl)-1-oxoisoindolin-5-yl)piperidin-1-yl)methyl)-N,N-dimethylbenzenesulfonamide |
| I-217 | 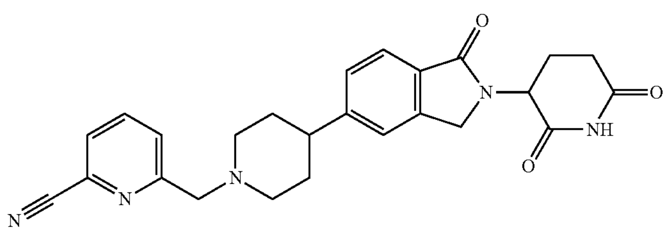 [SMILES: N#Cc1cccc(CN2CCC(c3ccc4c(c3)CN(C3CCC(=O)NC3=O)C4=O)CC2)n1] | 6-((4-(2-(2,6-dioxopiperidin-3-yl)-1-oxoisoindolin-5-yl)piperidin-1-yl)methyl)picolinonitrile |
| I-218 | 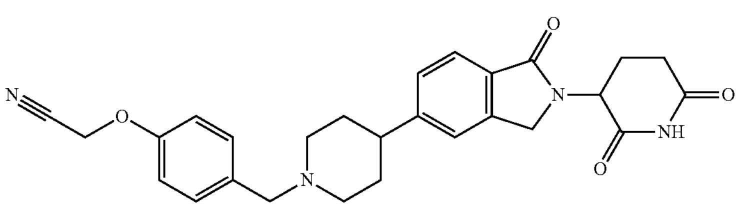 [SMILES: N#CCOc1ccc(CN2CCC(c3ccc4c(c3)CN(C3CCC(=O)NC3=O)C4=O)CC2)cc1] | 2-(4-((4-(2-(2,6-dioxopiperidin-3-yl)-1-oxoisoindolin-5-yl)piperidin-1-yl)methyl)phenoxy)acetonitrile |
| I-219 | 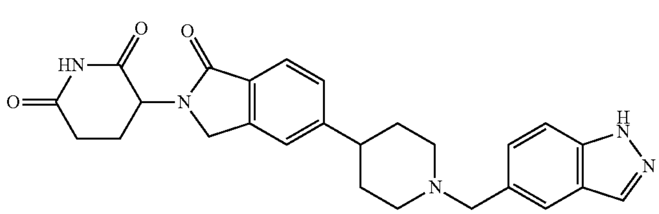 [SMILES: O=C1CCC(N2Cc3cc(C4CCN(Cc5ccc6[nH]ncc6c5)CC4)ccc3C2=O)C(=O)N1] | 3-(5-(1-((1H-indazol-5-yl)methyl)piperidin-4-yl)-1-oxoisoindolin-2-yl)piperidine-2,6-dione |

-continued

| Cmpd No. | Structure | Compound Name |
|---|---|---|
| I-220 | 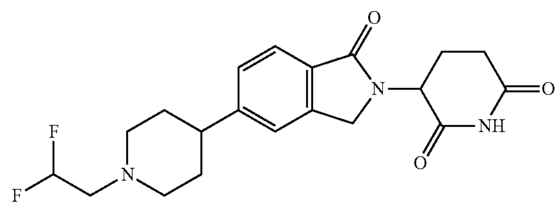 [SMILES: O=C1CCC(N2Cc3cc(C4CCN(CC(F)F)CC4)ccc3C2=O)C(=O)N1] | 3-(5-(1-(2,2-difluoroethyl)piperidin-4-yl)-1-oxoisoindolin-2-yl)piperidine-2,6-dione |
| I-221 | 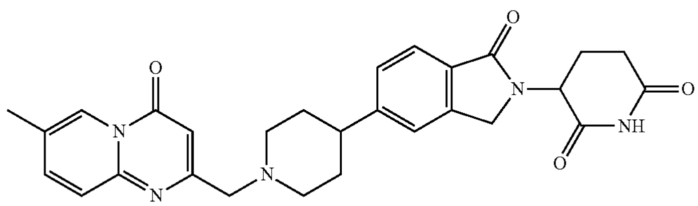 [SMILES: Cc1ccc2nc(CN3CCC(c4ccc5c(c4)CN(C4CCC(=O)NC4=O)C5=O)CC3)cc(=O)n2c1] | 3-(5-(1-((7-methyl-4-oxo-4H-pyrido[1,2-a]pyrimidin-2-yl)methyl)piperidin-4-yl)-1-oxoisoindolin-2-yl)piperidine-2,6-dione |
| I-222 | 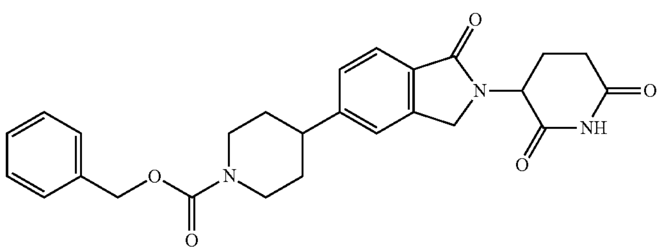 [SMILES: O=C1CCC(N2Cc3cc(C4CCN(C(=O)OCc5ccccc5)CC4)ccc3C2=O)C(=O)N1] | benzyl 4-(2-(2,6-dioxopiperidin-3-yl)-1-oxoisoindolin-5-yl)piperidine-1-carboxylate |
| I-223 | 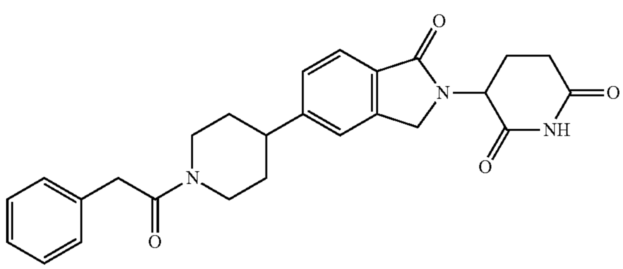 [SMILES: O=C1CCC(N2Cc3cc(C4CCN(C(=O)Cc5ccccc5)CC4)ccc3C2=O)C(=O)N1] | 3-(1-oxo-5-(1-(2-phenylacetyl)piperidin-4-yl)isoindolin-2-yl)piperidine-2,6-dione |
| I-224 | 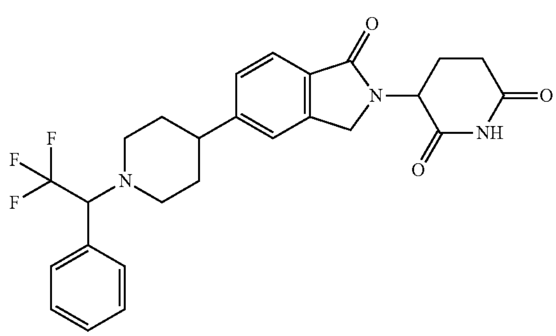 [SMILES: O=C1CCC(N2Cc3cc(C4CCN(C(c5ccccc5)C(F)(F)F)CC4)ccc3C2=O)C(=O)N1] | 3-(1-oxo-5-(1-(2,2,2-trifluoro-1-phenylethyl)piperidin-4-yl)isoindolin-2-yl)piperidine-2,6-dione |

-continued

| Cmpd No. | Structure | Compound Name |
|---|---|---|
| I-225 | 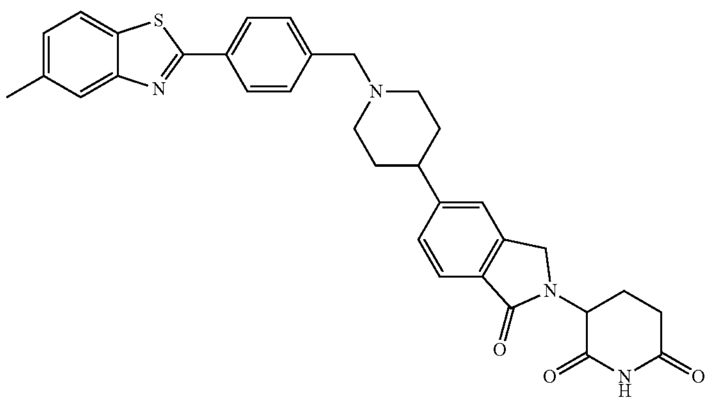 [SMILES: Cc1ccc2sc(-c3ccc(CN4CCC(c5ccc6c(c5)CN(C5CCC(=O)NC5=O)C6=O)CC4)cc3)nc2c1] | 3-(5-(1-(4-(5-methylbenzo[d]thiazol-2-yl)benzyl)piperidin-4-yl)-1-oxoisoindolin-2-yl)piperidine-2,6-dione |
| I-226 | 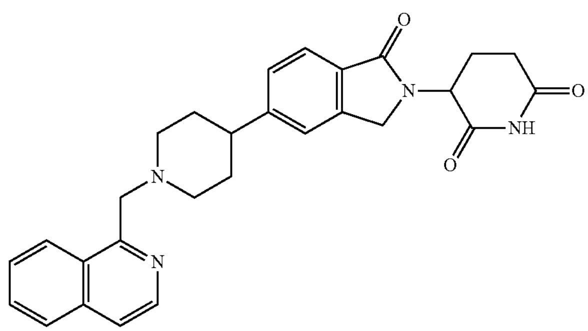 [SMILES: O=C1CCC(N2Cc3cc(C4CCN(Cc5nccc6ccccc56)CC4)ccc3C2=O)C(=O)N1] | 3-(5-(1-(isoquinolin-1-ylmethyl)piperidin-4-yl)-1-oxoisoindolin-2-yl)piperidine-2,6-dione |
| I-227 | 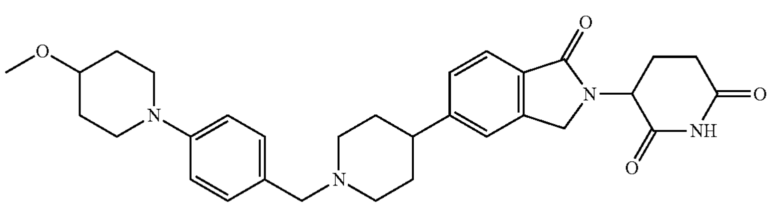 [SMILES: COC1CCN(c2ccc(CN3CCC(c4ccc5c(c4)CN(C4CCC(=O)NC4=O)C5=O)CC3)cc2)CC1] | 3-(5-(1-(4-(4-methoxypiperidin-1-yl)benzyl)piperidin-4-yl)-1-oxoisoindolin-2-yl)piperidine-2,6-dione |
| I-228 | 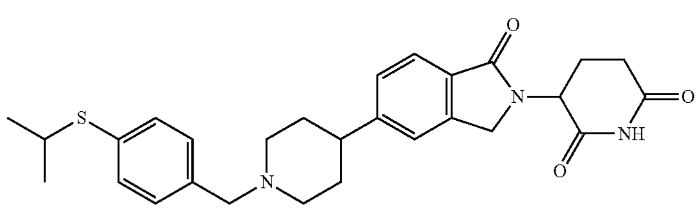 [SMILES: CC(C)Sc1ccc(CN2CCC(c3ccc4c(c3)CN(C3CCC(=O)NC3=O)C4=O)CC2)cc1] | 3-(5-(1-(4-(isopropylthio)benzyl)piperidn-4-yl)-1-oxoisoindolin-2-yl)piperidine-2,6-dione |
| I-229 | 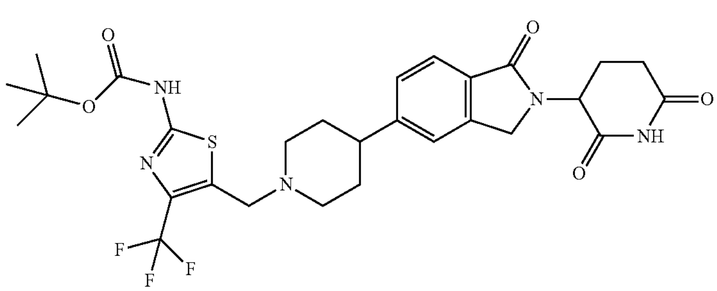 [SMILES: CC(C)(C)OC(=O)Nc1nc(C(F)(F)F)c(CN2CCC(c3ccc4c(c3)CN(C3CCC(=O)NC3=O)C4=O)CC2)s1] | tert-butyl (5-((4-(2-(2,6-dioxopiperidin-3-yl)-1-oxoisoindolin-5-yl)piperidin-1-yl)methyl)-4-(trifluoromethyl)thiazol-2-yl)carbamate |

-continued

| Cmpd No. | Structure | Compound Name |
|---|---|---|
| I-230 | 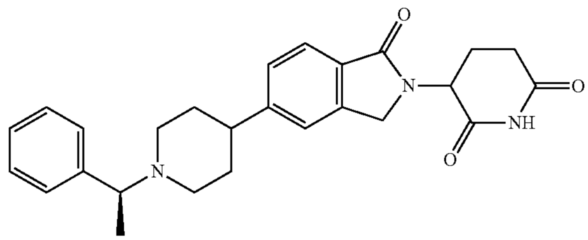 [SMILES: C[C@@H](c1ccccc1)N1CCC(c2ccc3c(c2)CN(C2CCC(=O)NC2=O)C3=O)CC1] | 3-(1-oxo-5-(1-((S)-1-phenylethyl)piperidin-4-yl)isoindolin-2-yl)piperidine-2,6-dione |
| I-231 | 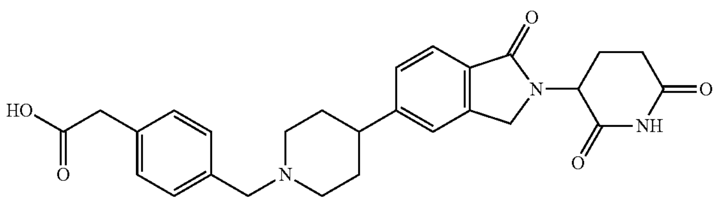 [SMILES: O=C(O)Cc1ccc(CN2CCC(c3ccc4c(c3)CN(C3CCC(=O)NC3=O)C4=O)CC2)cc1] | 2-(4-((4-(2-(2,6-dioxopiperidin-3-yl)-1-oxoisoindolin-5-yl)piperidin-1-yl)methyl)phenyl)acetic acid |
| I-232 | 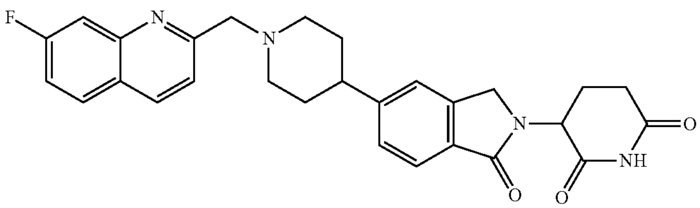 [SMILES: O=C1CCC(N2Cc3cc(C4CCN(Cc5ccc6ccc(F)cc6n5)CC4)ccc3C2=O)C(=O)N1] | 3-(5-(1-((7-fluoroquinolin-2-yl)methyl)piperidin-4-yl)-1-oxoisoindolin-2-yl)piperidine-2,6-dione |
| I-233 | 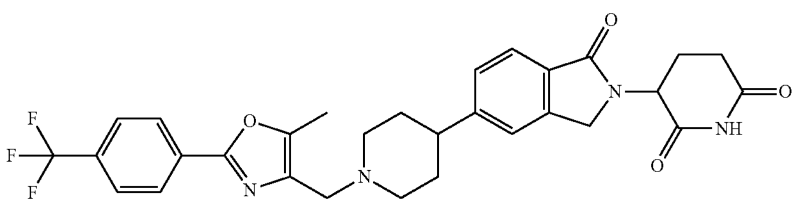 [SMILES: Cc1oc(-c2ccc(C(F)(F)F)cc2)nc1CN1CCC(c2ccc3c(c2)CN(C2CCC(=O)NC2=O)C3=O)CC1] | 3-(5-(1-((5-methyl-2-(4-(trifluoromethyl)phenyl)oxazol-4-yl)methyl)piperidin-4-yl)-1-oxoisoindolin-2-yl)piperidine-2,6-dione |
| I-234 | 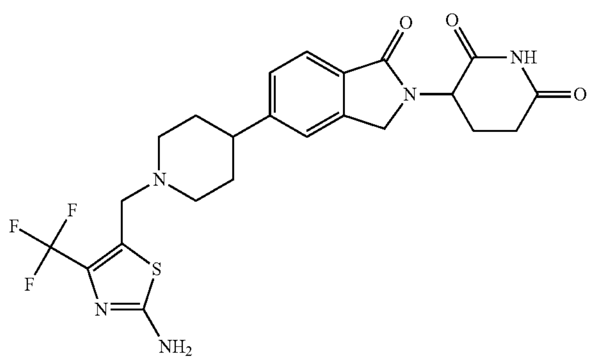 [SMILES: Nc1nc(C(F)(F)F)c(CN2CCC(c3ccc4c(c3)CN(C3CCC(=O)NC3=O)C4=O)CC2)s1] | 3-(5-(1-((2-amino-4-(trifluoromethyl)thiazol-5-yl)methyl)piperidin-4-yl)-1-oxoisoindolin-2-yl)piperidine-2,6-dione |
| I-235 | 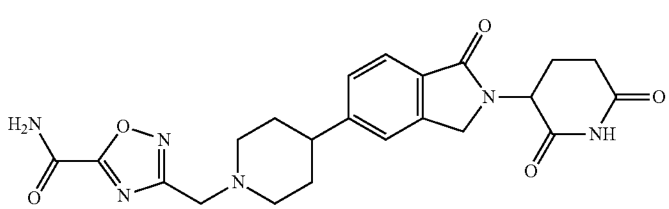 [SMILES: NC(=O)c1nc(CN2CCC(c3ccc4c(c3)CN(C3CCC(=O)NC3=O)C4=O)CC2)no1] | 3-((4-(2-(2,6-dioxopiperidin-3-yl)-1-oxoisoindolin-5-yl)piperidin-1-yl)methyl)-1,2,4-oxadiazole-5-carboxamide |

-continued

| Cmpd No. | Structure | Compound Name |
|---|---|---|
| I-236 | 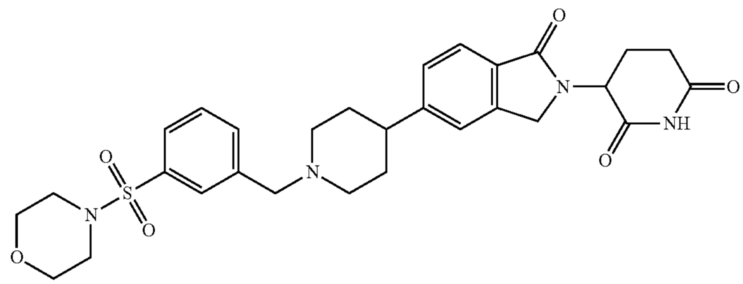 [SMILES: O=C1CCC(N2Cc3cc(C4CCN(Cc5cccc(S(=O)(=O)N6CCOCC6)c5)CC4)ccc3C2=O)C(=O)N1] | 3-(5-(1-(3-(morpholinosulfonyl)benzyl)piperidin-4-yl)-1-oxoisoindolin-2-yl)piperidine-2,6-dione |
| I-237 | 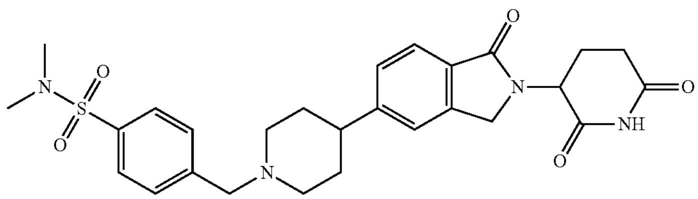 [SMILES: CN(C)S(=O)(=O)c1ccc(CN2CCC(c3ccc4c(c3)CN(C3CCC(=O)NC3=O)C4=O)CC2)cc1] | 4-((4-(2-(2,6-dioxopiperidin-3-yl)-1-oxoisoindolin-5-yl)piperidin-1-yl)methyl)-N,N-dimethylbenzenesulfonamide |
| I-238 | 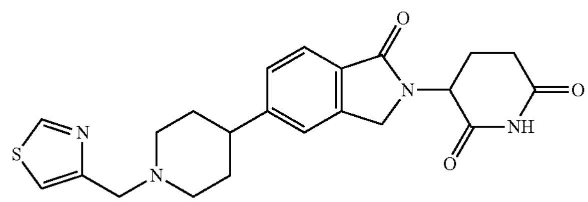 [SMILES: O=C1CCC(N2Cc3cc(C4CCN(Cc5cscn5)CC4)ccc3C2=O)C(=O)N1] | 3-(1-oxo-5-(1-(thiazol-4-ylmethyl)piperidin-4-yl)isoindolin-2-yl)piperidine-2,6-dione |
| I-239 | 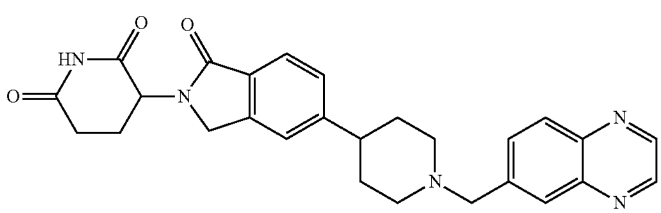 [SMILES: O=C1CCC(N2Cc3cc(C4CCN(Cc5ccc6nccnc6c5)CC4)ccc3C2=O)C(=O)N1] | 3-(1-oxo-5-(1-(quinoxalin-6-ylmethyl)piperidin-4-yl)isoindolin-2-yl)piperidine-2,6-dione |
| I-240 | 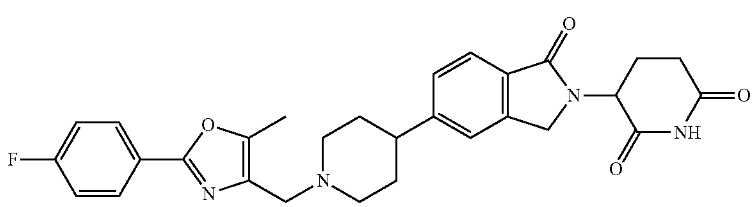 [SMILES: Cc1oc(-c2ccc(F)cc2)nc1CN1CCC(c2ccc3c(c2)CN(C2CCC(=O)NC2=O)C3=O)CC1] | 3-(5-(1-((2-(4-fluorophenyl)-5-methyloxazol-4-yl)methyl)piperidin-4-yl)-1-oxoisoindolin-2-yl)piperidine-2,6-dione |
| I-241 | 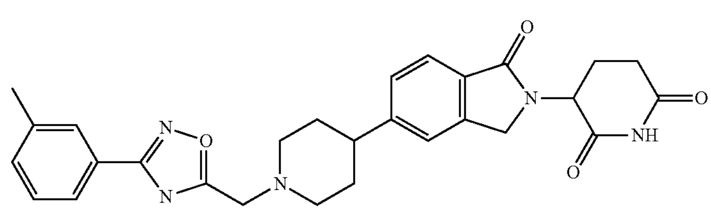 | 3-(1-oxo-5-(1-((3-(m-tolyl)-1,2,4-oxadiazol-5-yl)methyl)piperidin-4-yl)isoindolin-2-yl)piperidine-2,6-dione |

| Cmpd No. | Structure | Compound Name |
|---|---|---|
| I-242 | 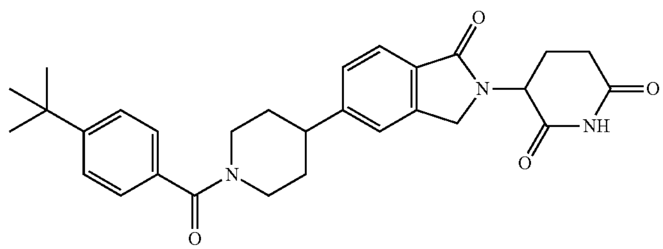 [SMILES: CC(C)(C)c1ccc(C(=O)N2CCC(c3ccc4c(c3)CN(C3CCC(=O)NC3=O)C4=O)CC2)cc1] | 3-(5-(1-(4-(tert-butyl)benzoyl)piperidin-4-yl)-1-oxoisoindolin-2-yl)piperidine-2,6-dione |
| I-243 | 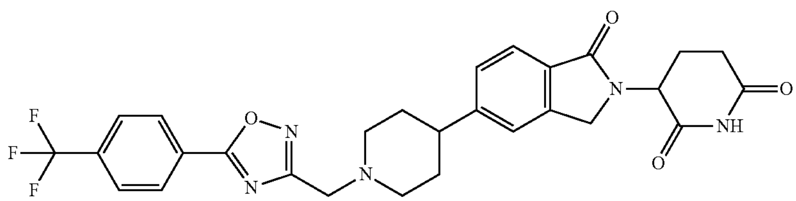 [SMILES: O=C1CCC(N2Cc3cc(C4CCN(Cc5noc(-c6ccc(C(F)(F)F)cc6)n5)CC4)ccc3C2=O)C(=O)N1] | 3-(1-oxo-5-(1-((5-(4-(trifluoromethyl)phenyl)-1,2,4-oxadiaozl-3-yl)methyl)piperidin-4-yl)isoindolin-2-yl)piperidine-2,6-dione |
| I-244 | 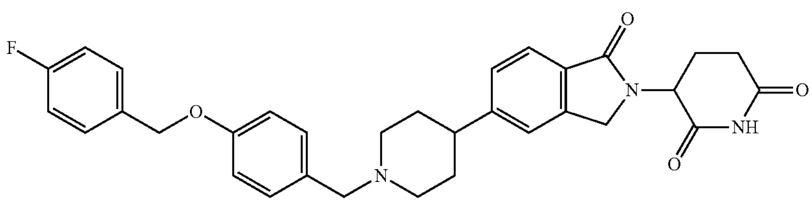 [SMILES: O=C1CCC(N2Cc3cc(C4CCN(Cc5ccc(OCc6ccc(F)cc6)cc5)CC4)ccc3C2=O)C(=O)N1] | 3-(5-(1-(4-((4-fluorobenzyl)oxy)benzyl)piperidin-4-yl)-1-oxoisoindolin-2-yl)piperidine-2,6-dione |
| I-245 | 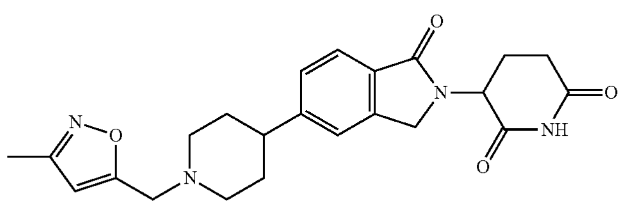 [SMILES: Cc1cc(CN2CCC(c3ccc4c(c3)CN(C3CCC(=O)NC3=O)C4=O)CC2)on1] | 3-(5-(1-((3-methylisoxazol-5-yl)methyl)piperidin-4-yl)-1-oxoisoindolin-2-yl)piperidine-2,6-dione |
| I-246 | 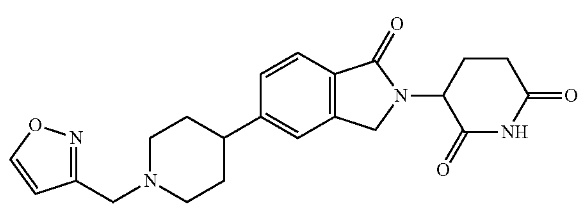 [SMILES: O=C1CCC(N2Cc3cc(C4CCN(Cc5ccon5)CC4)ccc3C2=O)C(=O)N1] | 3-(5-(1-(isoxazol-3-ylmethyl)piperidin-4-yl)-1-oxoisoindolin-2-yl)piperidine-2,6-dione |
| I-247 | 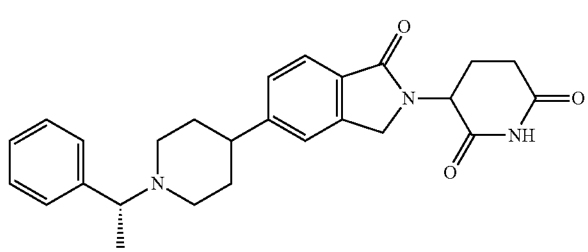 [SMILES: C[C@H](c1ccccc1)N1CCC(c2ccc3c(c2)CN(C2CCC(=O)NC2=O)C3=O)CC1] | 3-(1-oxo-5-(1-((R)-1-phenylethyl)piperidin-4-yl)isoindolin-2-yl)piperidine-2,6-dione |

-continued

| Cmpd No. | Structure | Compound Name |
| --- | --- | --- |
| I-248 | 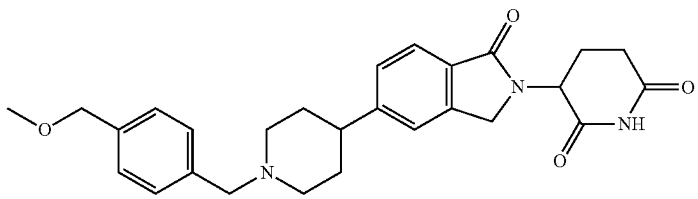 [SMILES: COCc1ccc(CN2CCC(c3ccc4c(c3)CN(C3CCC(=O)NC3=O)C4=O)CC2)cc1] | 3-(5-(1-(4-(methoxymethyl)benzyl)piperidin-4-yl)-1-oxoisoindolin-2-yl)piperidine-2,6-dione |
| I-249 | 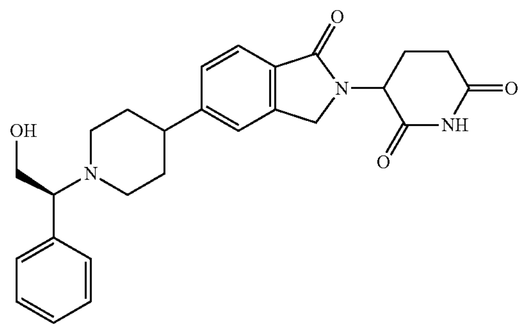 [SMILES: O=C1CCC(N2Cc3cc(C4CCN([C@H](CO)c5ccccc5)CC4)ccc3C2=O)C(=O)N1] | 3-(5-(1-((S)-2-hydroxy-1-phenylethyl)piperidin-4-yl)-1-oxoisoindolin-2-yl)piperidine-2,6-dione |
| I-250 | 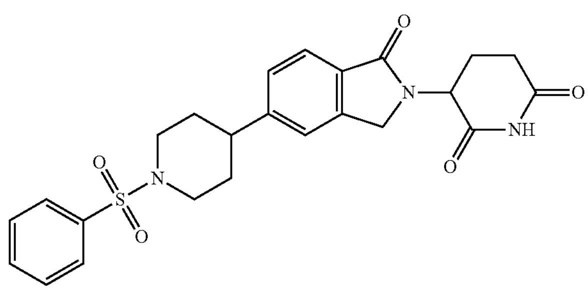 [SMILES: O=C1CCC(N2Cc3cc(C4CCN(S(=O)(=O)c5ccccc5)CC4)ccc3C2=O)C(=O)N1] | 3-(1-oxo-5-(1-(phenylsulfonyl)piperidin-4-yl)isoindolin-2-yl)piperidine-2,6-dione |
| I-251 | 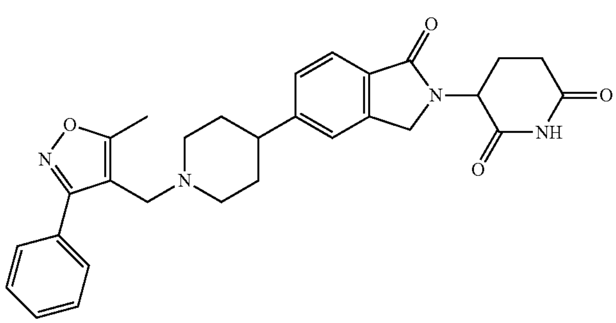 [SMILES: Cc1onc(-c2ccccc2)c1CN1CCC(c2ccc3c(c2)CN(C2CCC(=O)NC2=O)C3=O)CC1] | 3-(5-(1-((5-methyl-3-phenylisoxazol-4-yl)methyl)piperidin-4-yl)-1-oxoisoindolin-2-yl)piperidine-2,6-dione |
| I-252 | 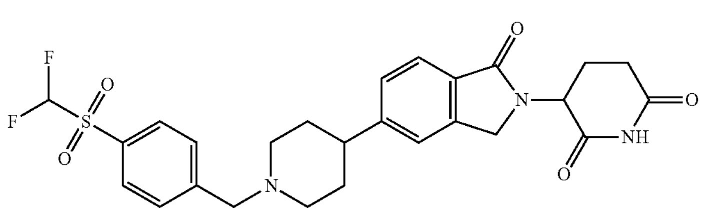 [SMILES: O=C1CCC(N2Cc3cc(C4CCN(Cc5ccc(S(=O)(=O)C(F)F)cc5)CC4)ccc3C2=O)C(=O)N1] | 3-(5-(1-(4-((difluoromethyl)sulfonyl)benzyl)piperidin-4-yl)-1-oxoisoindolin-2-yl)piperidine-2,6-dione |

| Cmpd No. | Structure | Compound Name |
|---|---|---|
| I-253 | 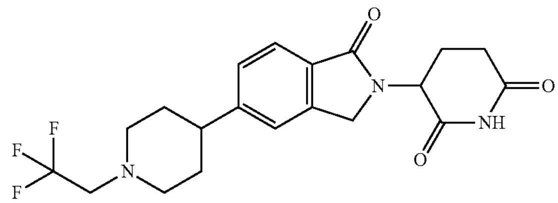 [SMILES: O=C1CCC(N2Cc3cc(C4CCN(CC(F)(F)F)CC4)ccc3C2=O)C(=O)N1] | 3-(1-oxo-5-(1-(2,2,2-trifluoroethyl)piperidin-4-yl)isoindolin-2-yl)piperidine-2,6-dione |
| I-254 | 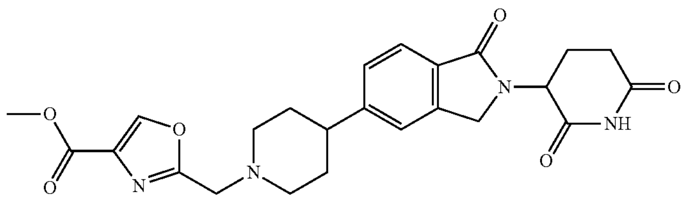 [SMILES: COC(=O)c1coc(CN2CCC(c3ccc4c(c3)CN(C3CCC(=O)NC3=O)C4=O)CC2)n1] | methyl 2-((4-(2-(2,6-dioxopiperidin-3-yl)-1-oxoisoindolin-5-yl)piperidin-1-yl)methyl)oxazole-4-carboxylate |
| I-255 | 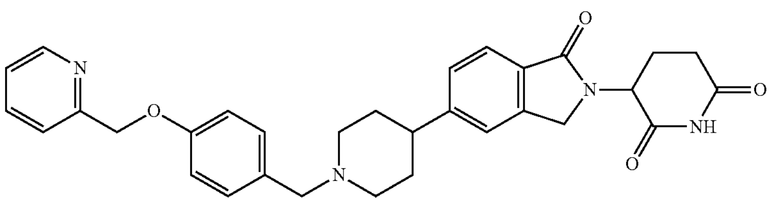 [SMILES: O=C1CCC(N2Cc3cc(C4CCN(Cc5ccc(OCc6ccccn6)cc5)CC4)ccc3C2=O)C(=O)N1] | 3-(1-oxo-5-(1-(4-(pyridin-2-ylmethoxy)benzyl)piperidin-4-yl)isoindolin-2-yl)piperidine-2,6-dione |
| I-256 | 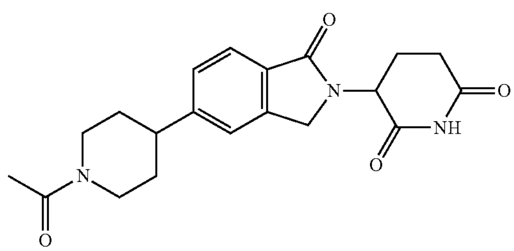 | 3-(5-(1-acetylpiperidin-4-yl)-1-oxoisoindolin-2-yl)piperidine-2,6-dione |
| I-257 | 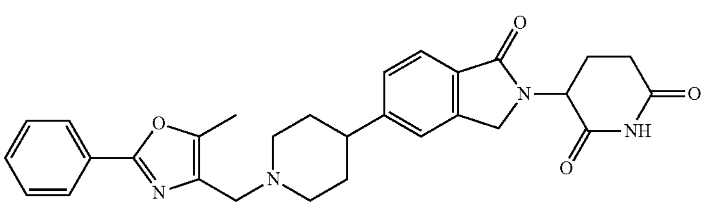 [SMILES: Cc1oc(-c2ccccc2)nc1CN1CCC(c2ccc3c(c2)CN(C2CCC(=O)NC2=O)C3=O)CC1] | 3-(5-(1-((5-methyl-2-phenyloxazol-4-yl)methyl)piperidin-4-yl)-1-oxoisoindolin-2-yl)piperidine-2,6-dione |
| I-258 | 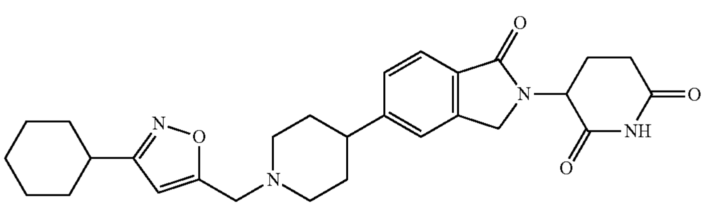 [SMILES: O=C1CCC(N2Cc3cc(C4CCN(Cc5cc(C6CCCCC6)no5)CC4)ccc3C2=O)C(=O)N1] | 3-(5-(1-((3-cyclohexylisoxazol-5-yl)methyl)piperidin-4-yl)-1-oxoisoindolin-2-yl)piperidine-2,6-dione |
| I-259 | 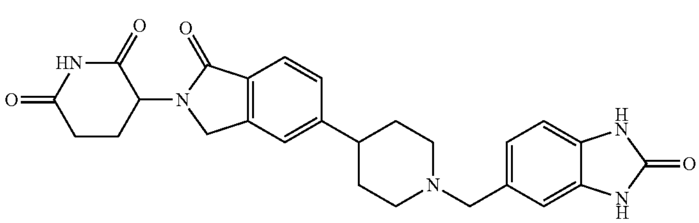 [SMILES: O=C1CCC(N2Cc3cc(C4CCN(Cc5ccc6[nH]c(=O)[nH]c6c5)CC4)ccc3C2=O)C(=O)N1] | 3-(1-oxo-5-(1-((2-oxo-2,3-dihydro-1H-benzo[d]imidazol-5-yl)methyl)piperidin-4-yl)isoindolin-2-yl)piperidine-2,6-dione |

-continued

| Cmpd No. | Structure | Compound Name |
|---|---|---|
| I-260 | 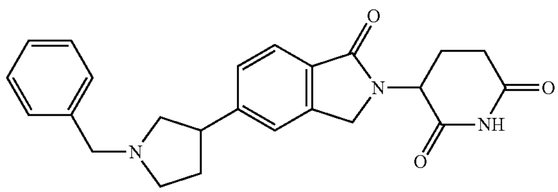 [SMILES: O=C1CCC(N2Cc3cc(C4CCN(Cc5ccccc5)C4)ccc3C2=O)C(=O)N1] | 3-(5-(1-benzylpyrrolidin-3-yl)-1-oxoisoindolin-2-yl)piperidine-2,6-dione |
| I-261 | 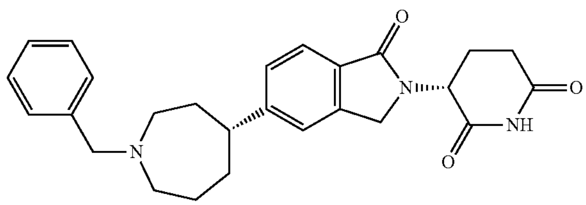 | (R)-3-(5-((R)-1-benzylazepan-4-yl)-1-oxoisoindolin-2-yl)piperidine-2,6-dione |
| I-262 | 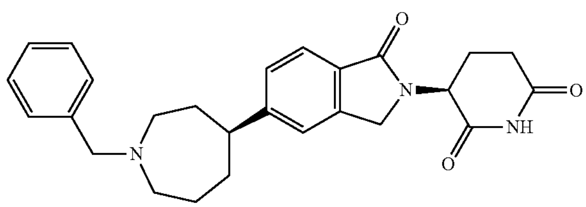 [SMILES: O=C1CC[C@H](N2Cc3cc([C@H]4CCCN(Cc5ccccc5)CC4)ccc3C2=O)C(=O)N1] | (S)-3-(5-((S)-1-benzylazepan-4-yl)-1-oxoisoindolin-2-yl)piperidine-2,6-dione |
| I-263 | 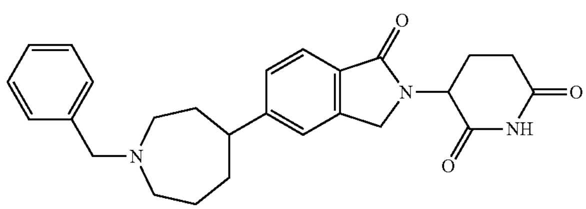 [SMILES: O=C1CCC(N2Cc3cc(C4CCCN(Cc5ccccc5)CC4)ccc3C2=O)C(=O)N1] | 3-(5-(1-benzylazepan-4-yl)-1-oxoisoindolin-2-yl)piperidine-2,6-dione |
| I-264 | 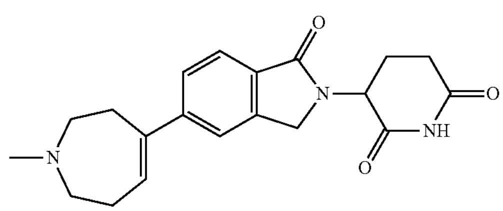 [SMILES: CN1CCC=C(c2ccc3c(c2)CN(C2CCC(=O)NC2=O)C3=O)CC1] | 3-(5-(1-methyl-2,3,6,7-tetrahydro-1H-azepin-4-yl)-1-oxoisoindolin-2-yl)piperidine-2,6-dione |
| I-265 | 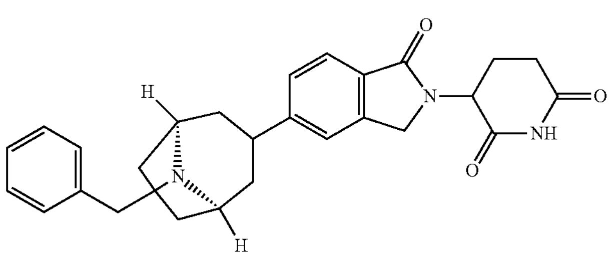 | 3-(5-(8-benzyl-8-azabicyclo[3.2.1]octan-3-yl)-1-oxoisoindolin-2-yl)piperidine-2,6-dione |
| I-266 | 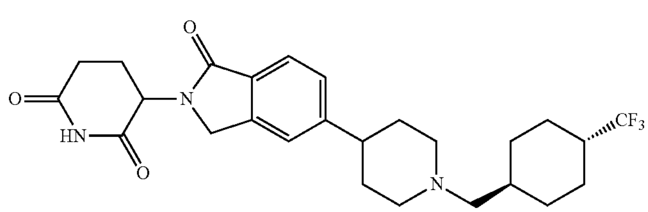 [SMILES: O=C1CCC(N2Cc3cc(C4CCN(C[C@H]5CC[C@H](C(F)(F)F)CC5)CC4)ccc3C2=O)C(=O)N1] | trans-3-(1-oxo-5-(1-((4-(trifluoromethyl)cyclohexyl)methyl)piperidin-4-yl)isoindolin-2-yl)piperidine-2,6-dione |

-continued

| Cmpd No. | Structure | Compound Name |
| --- | --- | --- |
| I-267 | 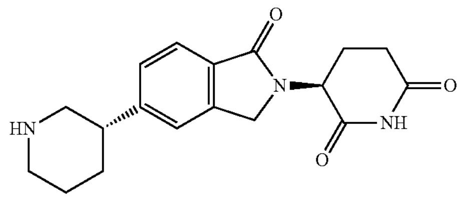 [SMILES: O=C1CC[C@H](N2Cc3cc([C@@H]4CCCNC4)ccc3C2=O)C(=O)N1] | (S)-3-(1-oxo-5-((S)-piperidin-3-yl)isoindolin-2-yl)piperidine-2,6-dione |
| I-268 | 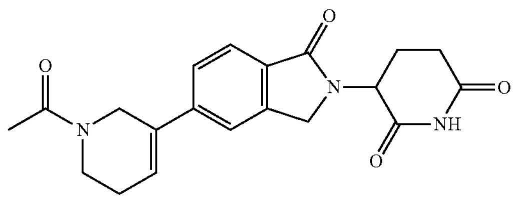 [SMILES: CC(=O)N1CCC=C(c2ccc3c(c2)CN(C2CCC(=O)NC2=O)C3=O)C1] | 3-(5-(1-acetyl-1,2,5,6-tetrahydropyridin-3-yl)-1-oxoisoindolin-2-yl)piperidine-2,6-dione |
| I-269 | 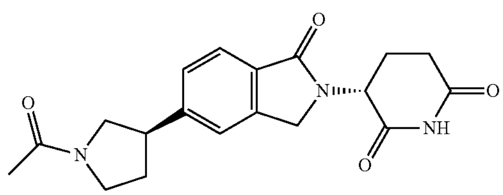 [SMILES: CC(=O)N1CC[C@H](c2ccc3c(c2)CN([C@@H]2CCC(=O)NC2=O)C3=O)C1] | (R)-3-(5-((R)-1-acetylpyrrolidin-3-yl)-1-oxoisoindolin-2-yl)piperidine-2,6-dione |
| I-270 | 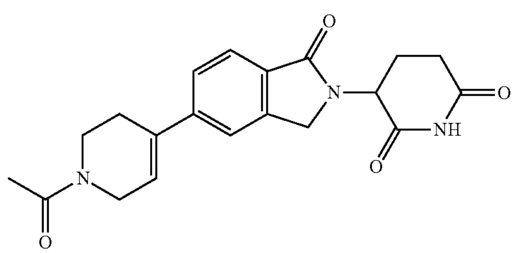 [SMILES: CC(=O)N1CC=C(c2ccc3c(c2)CN(C2CCC(=O)NC2=O)C3=O)CC1] | 3-(5-(1-acetyl-1,2,3,6-tetrahydropyridin-4-yl)-1-oxoisoindolin-2-yl)piperidine-2,6-dione |
| I-271 | 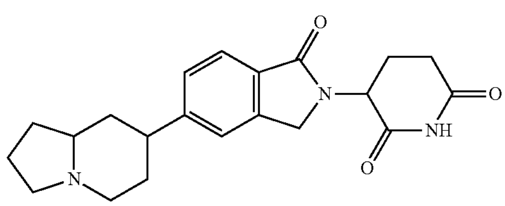 [SMILES: O=C1CCC(N2Cc3cc(C4CCN5CCCC5C4)ccc3C2=O)C(=O)N1] | 3-(5-(octahydroindolizin-7-yl)-1-oxoisoindolin-2-yl)piperidine-2,6-dione |
| I-272 | 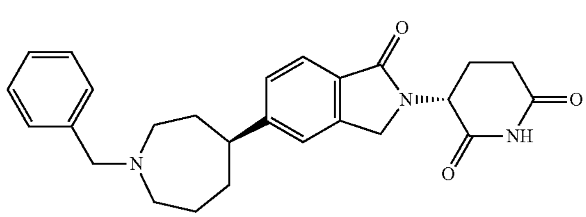 [SMILES: O=C1CC[C@@H](N2Cc3cc([C@H]4CCCN(Cc5ccccc5)CC4)ccc3C2=O)C(=O)N1] | (R)-3-(5-((S)-1-benzylazepan-4-yl)-1-oxoisoindolin-2-yl)piperidine-2,6-dione |

| Cmpd No. | Structure | Compound Name |
|---|---|---|
| I-273 | 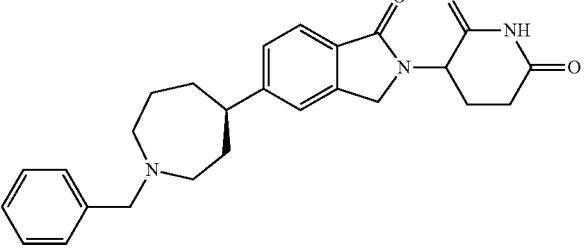 | 3-(5-((R)-1-benzylazepan-4-yl)-1-oxoisoindolin-2-yl)piperidine-2,6-dione |
| I-274 | 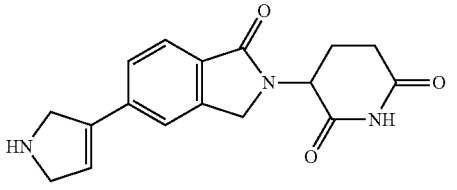 [SMILES: O=C1CCC(N2Cc3cc(C4=CCNC4)ccc3C2=O)C(=O)N1] | 3-(5-(2,5-dihydro-1H-pyrrol-3-yl)-1-oxoisoindolin-2-yl)piperidine-2,6-dione |
| I-275 | 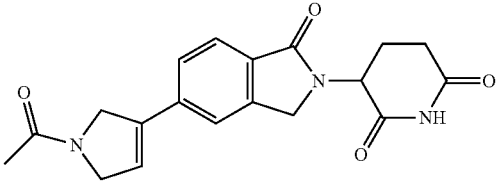 [SMILES: CC(=O)N1CC=C(c2ccc3c(c2)CN(C2CCC(=O)NC2=O)C3=O)C1] | 3-(5-(1-acetyl-2,5-dihydro-1H-pyrrol-3-yl)-1-oxoisoindolin-2-yl)piperidine-2,6-dione |
| I-276 | 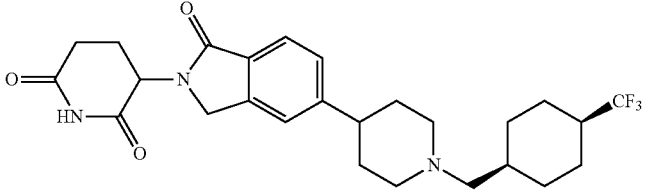 [SMILES: O=C1CCC(N2Cc3cc(C4CCN(C[C@H]5CC[C@@H](C(F)(F)F)CC5)CC4)ccc3C2=O)C(=O)N1] | cis-3-(1-oxo-5-(1-((4-(trifluoromethyl)cyclohexyl)methyl)piperidin-4-yl)isoindolin-2-yl)piperidine-2,6-dione |
| I-277 | 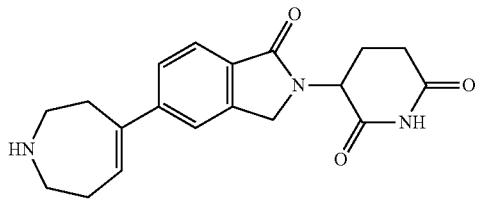 [SMILES: O=C1CCC(N2Cc3cc(C4=CCCNCC4)ccc3C2=O)C(=O)N1] | 3-(1-oxo-5-(2,3,6,7-tetrahydro-1H-azepin-4-yl)isoindolin-2-yl)piperidine-2,6-dione |
| I-278 | 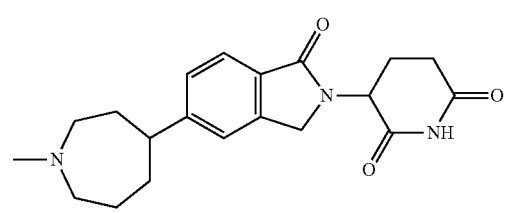 [SMILES: CN1CCCC(c2ccc3c(c2)CN(C2CCC(=O)NC2=O)C3=O)CC1] | 3-(5-(1-methylazepan-4-yl)-1-oxoisoindolin-2-yl)piperidine-2,6-dione |
| I-279 | 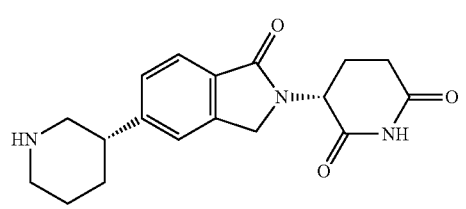 [SMILES: O=C1CC[C@@H](N2Cc3cc([C@@H]4CCCNC4)ccc3C2=O)C(=O)N1] | (R)-3-(1-oxo-5-((S)-piperidin-3-yl)isoindolin-2-yl)piperidine-2,6-dione |

-continued

| Cmpd No. | Structure | Compound Name |
|---|---|---|
| I-280 | 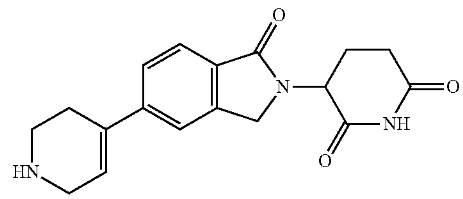 [SMILES: O=C1CCC(N2Cc3cc(C4=CCNCC4)ccc3C2=O)C(=O)N1] | 3-(1-oxo-5-(1,2,3,6-tetrahydropyridin-4-yl)isoindolin-2-yl)piperidine-2,6-dione |
| I-281 | 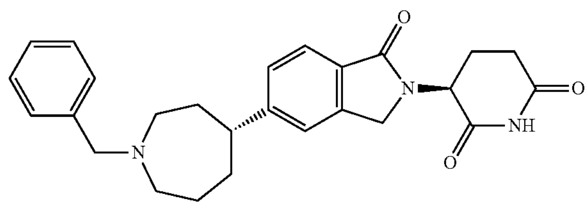 [SMILES: O=C1CC[C@H](N2Cc3cc([C@@H]4CCCN(Cc5ccccc5)CC4)ccc3C2=O)C(=O)N1] | (S)-3-(5-((R)-1-benzylazepan-4-yl)-1-oxoisoindolin-2-yl)piperidine-2,6-dione |
| I-282 | 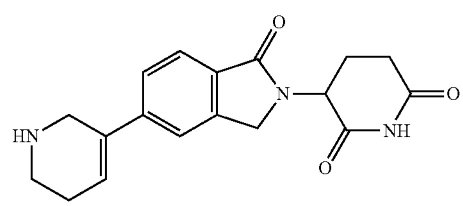 [SMILES: O=C1CCC(N2Cc3cc(C4=CCCNC4)ccc3C2=O)C(=O)N1] | 3-(1-oxo-5-(1,2,5,6-tetrahydropyridin-3-yl)isoindolin-2-yl)piperidine-2,6-dione |
| I-283 | 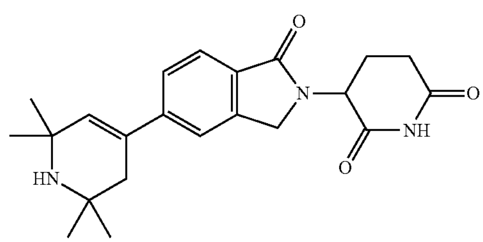 [SMILES: CC1(C)C=C(c2ccc3c(c2)CN(C2CCC(=O)NC2=O)C3=O)CC(C)(C)N1] | 3-(1-oxo-5-(2,2,6,6-tetramethyl-1,2,3,6-tetrahydropyridin-4-yl)isoindolin-2-yl)piperidine-2,6-dione |
| I-284 | 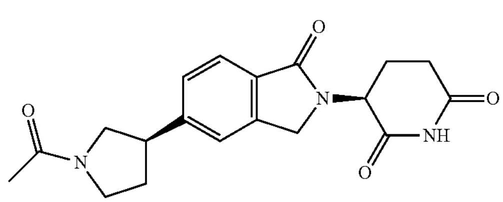 [SMILES: CC(=O)N1CC[C@H](c2ccc3c(c2)CN([C@H]2CCC(=O)NC2=O)C3=O)C1] | (S)-3-(5-((R)-1-acetylpyrrolidin-3-yl)-1-oxoisoindolin-2-yl)piperidine-2,6-dione |
| I-285 | 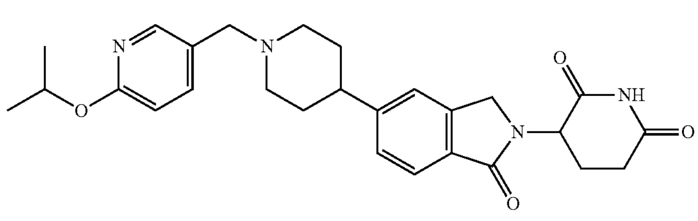 [SMILES: CC(C)Oc1ccc(CN2CCC(c3ccc4c(c3)CN(C3CCC(=O)NC3=O)C4=O)CC2)cn1] | 3-(5-(1-((6-isopropoxypyridin-3-yl)methyl)piperidin-4-yl)-1-oxoisoindolin-2-yl)piperidine-2,6-dione |

| Cmpd No. | Structure | Compound Name |
|---|---|---|
| I-286 | 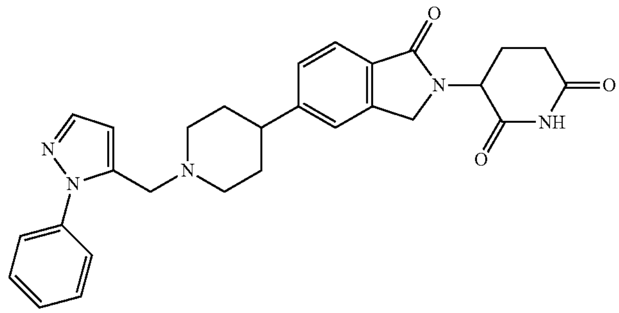 [SMILES: O=C1CCC(N2Cc3cc(C4CCN(Cc5ccnn5-c5ccccc5)CC4)ccc3C2=O)C(=O)N1] | 3-(1-oxo-5-(1-((1-phenyl-1H-pyrazol-5-yl)methyl)piperidin-4-yl)isoindolin-2-yl)piperidine-2,6-dione |
| I-287 | 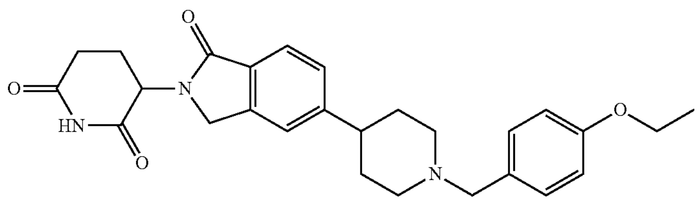 [SMILES: CCOc1ccc(CN2CCC(c3ccc4c(c3)CN(C3CCC(=O)NC3=O)C4=O)CC2)cc1] | 3-(5-(1-(4-ethoxybenzyl)piperidin-4-yl)-1-oxoisoindolin-2-yl)piperidine-2,6-dione |
| I-288 | 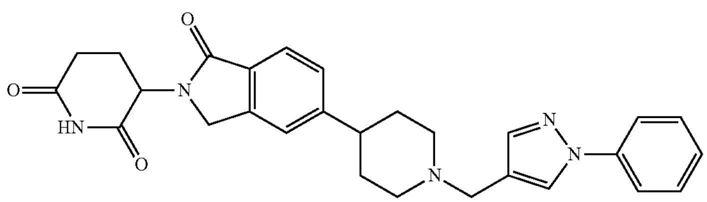 [SMILES: O=C1CCC(N2Cc3cc(C4CCN(Cc5cnn(-c6ccccc6)c5)CC4)ccc3C2=O)C(=O)N1] | 3-(1-oxo-5-(1-((1-phenyl-1H-pyrazol-4-yl)methyl)piperidin-4-yl)isoindolin-2-yl)piperidine-2,6-dione |
| I-289 | 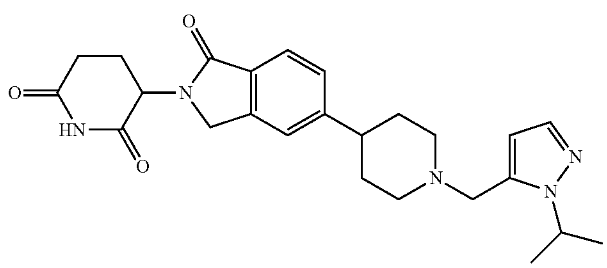 [SMILES: CC(C)n1nccc1CN1CCC(c2ccc3c(c2)CN(C2CCC(=O)NC2=O)C3=O)CC1] | 3-(5-(1-((1-isopropyl-1H-pyrazol-5-yl)methyl)piperidin-4-yl)-1-oxoisoindolin-2-yl)piperidine-2,6-dione |
| I-290 | 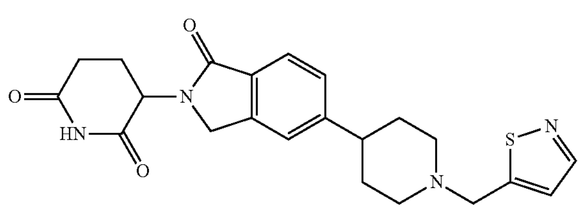 [SMILES: O=C1CCC(N2Cc3cc(C4CCN(Cc5ccns5)CC4)ccc3C2=O)C(=O)N1] | 3-(5-(1-(isothiazol-5-ylmethyl)piperidin-4-yl)-1-oxoisoindolin-2-yl)piperidine-2,6-dione |
| I-291 | 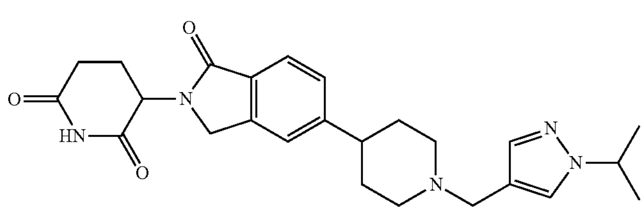 [SMILES: CC(C)n1cc(CN2CCC(c3ccc4c(c3)CN(C3CCC(=O)NC3=O)C4=O)CC2)cn1] | 3-(5-(1-((1-isopropyl-1H-pyrazol-4-yl)methyl)piperidin-4-yl)-1-oxoisoindolin-2-yl)piperidine-2,6-dione |

| Cmpd No. | Structure | Compound Name |
|---|---|---|
| I-292 | 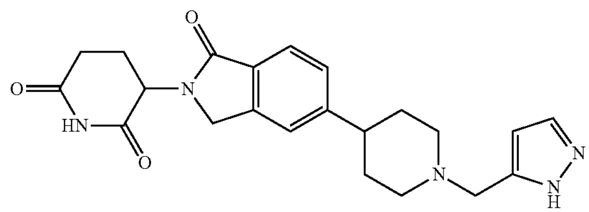 [SMILES: O=C1CCC(N2Cc3cc(C4CCN(Cc5ccn[nH]5)CC4)ccc3C2=O)C(=O)N1] | 3-(5-(1-((1H-pyrazol-5-yl)methyl)piperidin-4-yl)-1-oxoisoindolin-2-yl)piperidine-2,6-dione |
| I-293 | 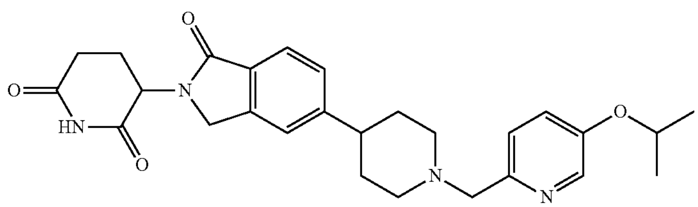 [SMILES: CC(C)Oc1ccc(CN2CCC(c3ccc4c(c3)CN(C3CCC(=O)NC3=O)C4=O)CC2)nc1] | 3-(5-(1-((5-isopropoxypyridin-2-yl)methyl)piperidin-4-yl)-1-oxoisoindolin-2-yl)piperidine-2,6-dione |
| I-294 | 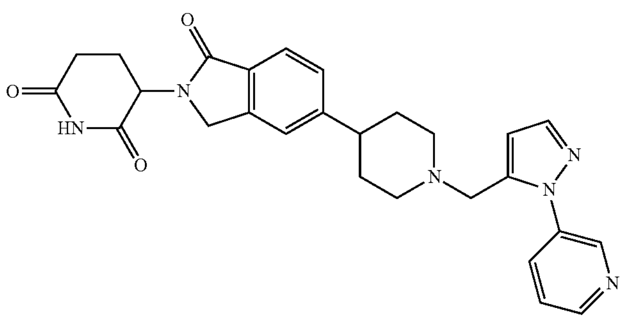 [SMILES: O=C1CCC(N2Cc3cc(C4CCN(Cc5ccnn5-c5cccnc5)CC4)ccc3C2=O)C(=O)N1] | 3-(1-oxo-5-(1-((1-(pyridin-3-yl)-1H-pyrazol-5-yl)methyl)piperidin-4-yl)isoindolin-2-yl)piperidine-2,6-dione |
| I-295 | 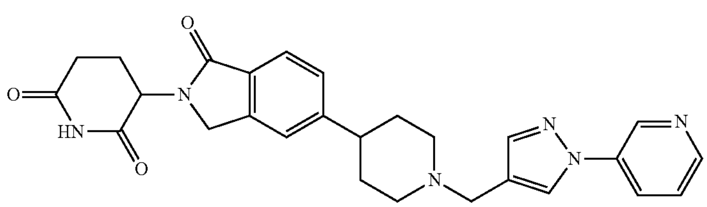 [SMILES: O=C1CCC(N2Cc3cc(C4CCN(Cc5cnn(-c6cccnc6)c5)CC4)ccc3C2=O)C(=O)N1] | 3-(1-oxo-5-(1-((1-(pyridin-3-yl)-1H-pyrazol-4-y)methyl)piperidin-4-yl)isoindolin-2-yl)piperidine-2,6-dione |
| I-296 | 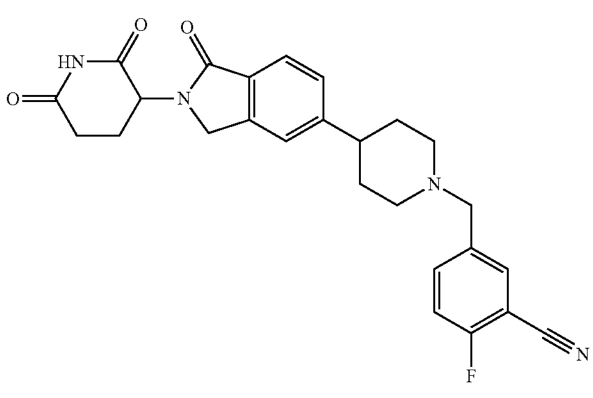 [SMILES: N#Cc1cc(CN2CCC(c3ccc4c(c3)CN(C3CCC(=O)NC3=O)C4=O)CC2)ccc1F] | 5-((4-(2-(2,6-dioxopiperidin-3-yl)-1-oxoisoindolin-5-yl)piperidin-1-yl)methyl)-2-fluorobenzonitrile |

-continued

| Cmpd No. | Structure | Compound Name |
|---|---|---|
| I-297 | 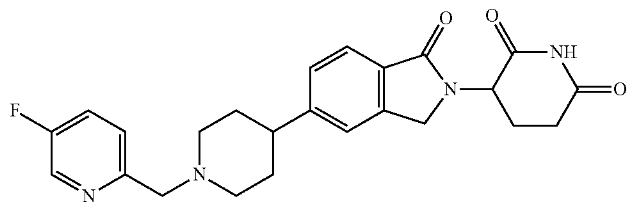 [SMILES: O=C1CCC(N2Cc3cc(C4CCN(Cc5ccc(F)cn5)CC4)ccc3C2=O)C(=O)N1] | 3-(5-(1-((5-fluoropyridin-2-yl)methyl)piperidin-4-yl)-1-oxoisoindolin-2-yl)piperidine-2,6-dione |
| I-298 | 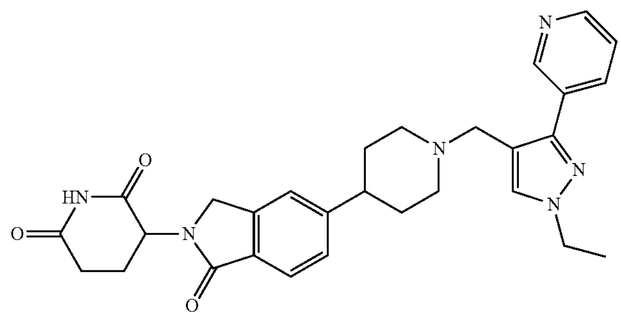 [SMILES: CCn1cc(CN2CCC(c3ccc4c(c3)CN(C3CCC(=O)NC3=O)C4=O)CC2)c(-c2cccnc2)n1] | 3-(5-(1-((1-ethyl-3-(pyridin-3-yl)-1H-pyrazol-4-yl)methyl)piperidin-4-yl)-1-oxoisoindolin-2-yl)piperidine-2,6-dione |
| I-299 | 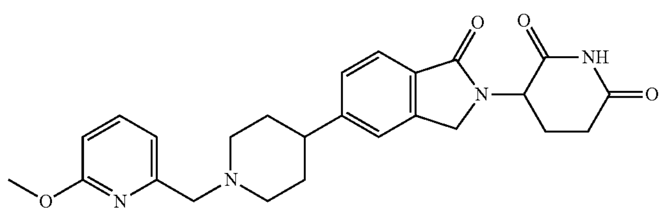 [SMILES: COc1cccc(CN2CCC(c3ccc4c(c3)CN(C3CCC(=O)NC3=O)C4=O)CC2)n1] | 3-(5-(1-((6-methoxypyridin-2-yl)methyl)piperidin-4-yl)-1-oxoisoindolin-2-yl)piperidine-2,6-dione |
| I-300 | 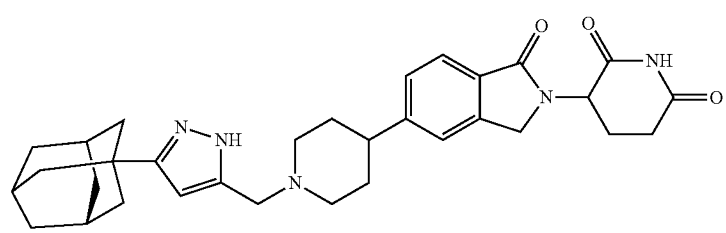 | 3-(5-(1-((3-((3S,5S)-adamantan-1-yl)-1H-pyrazol-5-yl)methyl)piperidin-4-yl)-1-oxoisoindolin-2-yl)piperidine-2,6-dione |
| I-301 | 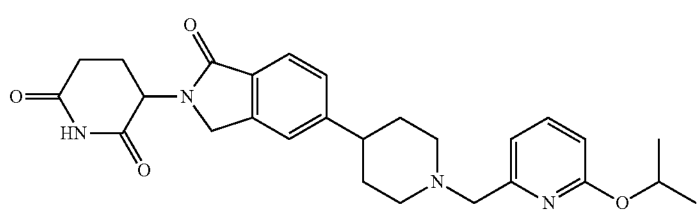 [SMILES: CC(C)Oc1cccc(CN2CCC(c3ccc4c(c3)CN(C3CCC(=O)NC3=O)C4=O)CC2)n1] | 3-(5-(1-((6-isopropoxypyridin-2-yl)methyl)piperidin-4-yl)-1-oxoisoindolin-2-yl)piperidine-2,6-dione |
| I-302 | 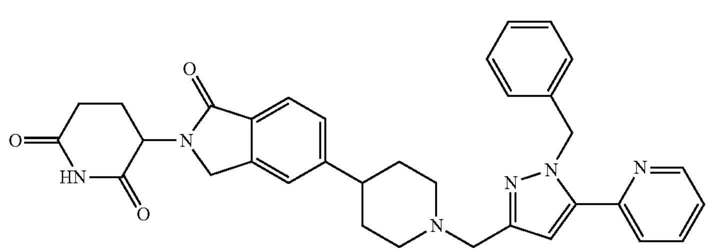 [SMILES: O=C1CCC(N2Cc3cc(C4CCN(Cc5cc(-c6ccccn6)n(Cc6ccccc6)n5)CC4)ccc3C2=O)C(=O)N1] | 3-(5-(1-((1-benzyl-5-(pyridin-2-yl)-1H-pyrazol-3-yl)methyl)piperidin-4-yl)-1-oxoisoindolin-2-yl)piperidine-2,6-dione |

| Cmpd No. | Structure | Compound Name |
|---|---|---|
| I-303 | 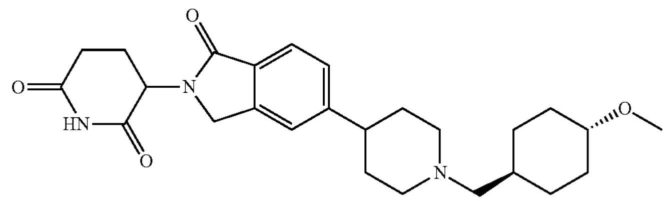 [SMILES: CO[C@H]1CC[C@H](CN2CCC(c3ccc4c(c3)CN(C3CCC(=O)NC3=O)C4=O)CC2)CC1] | trans-3-(5-(1-((4-methoxycyclohexyl)methyl)piperidin-4-yl)-1-oxoisoindolin-2-yl)piperidine-2,6-dione |

In another embodiment of the disclosure, the compounds of the present disclosure are enantiomers. In some embodiments the compounds are the (S)-enantiomer. In other embodiments the compounds are the (R)-enantiomer. In yet other embodiments, the compounds of the present disclosure may be (+) or (−) enantiomers.

It should be understood that all isomeric forms are included within the present disclosure, including mixtures thereof. If the compound contains a double bond, the substituent may be in the E or Z configuration. If the compound contains a disubstituted cycloalkyl, the cycloalkyl substituent may have a cis- or trans configuration. All tautomeric forms are also intended to be included.

Compounds of the disclosure, and pharmaceutically acceptable salts, hydrates, solvates, stereoisomers, and prodrugs thereof may exist in their tautomeric form (for example, as an amide or imino ether). All such tautomeric forms are contemplated herein as part of the present disclosure.

The compounds of the disclosure may contain asymmetric or chiral centers and, therefore, exist in different stereoisomeric forms. It is intended that all stereoisomeric forms of the compounds of the disclosure as well as mixtures thereof, including racemic mixtures, form part of the present disclosure. In addition, the present disclosure embraces all geometric and positional isomers. For example, if a compound of the disclosure incorporates a double bond or a fused ring, both the cis- and trans-forms, as well as mixtures, are embraced within the scope of the disclosure. Each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the disclosure may be atropisomers (e.g., substituted biaryls) and are considered as part of this disclosure. Enantiomers can also be separated by use of a chiral HPLC column.

It is also possible that the compounds of the disclosure may exist in different tautomeric forms, and all such forms are embraced within the scope of the disclosure and chemical structures and names. Also, for example, all keto-enol and imine-enamine forms of the compounds are included in the disclosure.

All stereoisomers (for example, geometric isomers, optical isomers, and the like) of the present compounds (including those of the salts, solvates, esters, and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this disclosure, as are positional isomers (such as, for example, 4-pyridyl and 3-pyridyl). (For example, if a compound of Formula (I') or Formula (I) incorporates a double bond or a fused ring, both the cis- and trans-forms, as well as mixtures, are embraced within the scope of the disclosure. Also, for example, all keto-enol and imine-enamine forms of the compounds are included in the disclosure.) Individual stereoisomers of the compounds of the disclosure may, for example, be substantially free of other isomers, or is admixed, for example, as racemates or with all other, or other selected, stereoisomers.

The chiral centers of the compounds of the disclosure can have the S or R configuration as defined by the IUPAC 1974 Recommendations. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

The use of the terms "salt", "solvate", "ester," "prodrug", and the like, is intended to equally apply to the salt, solvate, ester, and prodrug of enantiomers, stereoisomers, rotamers, tautomers, positional isomers, racemates, or prodrugs of the inventive compounds.

The compounds of the disclosure may form salts which are also within the scope of this disclosure. Reference to a compound of the Formula herein is generally understood to include reference to salts thereof, unless otherwise indicated.

The compounds and intermediates may be isolated and used as the compound per se. Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number.

Examples of isotopes that can be incorporated into compounds of the disclosure include isotopes of hydrogen, carbon, nitrogen, oxygen, phosphorous, fluorine, and, such as $^{2}$H, $^{3}$H, $^{11}$C, $^{13}$C, $^{14}$C, $^{15}$N, $^{18}$F, $^{31}$P, $^{32}$P, respectively. The disclosure includes various isotopically labeled compounds as defined herein, for example those into which radioactive isotopes, such as $^{3}$H, $^{13}$C, and $^{14}$C, are present. Such isotopically labelled compounds are useful in metabolic studies (with $^{14}$C), reaction kinetic studies (with, for example $^{2}$H or $^{3}$H), detection or imaging techniques, such as positron emission tomography (PET) or single-photon emission computed tomography (SPECT) including drug or substrate tissue distribution assays, or in radioactive treatment of patients. In particular, an $^{18}$F, $^{11}$C or labeled compound may be particularly desirable for PET or SPECT studies.

Further, substitution with heavier isotopes, particularly deuterium (i.e., $^{2}$H or D) may afford certain therapeutic advantages resulting from greater metabolic stability, for example, increased in vivo half-life, reduced dosage requirements, reduced CYP450 inhibition (competitive or time dependent) or an improvement in therapeutic index. For example, substitution with deuterium may modulate undesirable side effects of the undeuterated compound, such as competitive CYP450 inhibition, time dependent CYP450 inactivation, etc. It is understood that deuterium in this context is regarded as a substituent in compounds of the present disclosure. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this disclosure is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds of the present disclosure can generally be prepared by conventional techniques known to those skilled in the art or by carrying out the procedures disclosed in the schemes or in the examples and preparations described below using an appropriate isotopically-labeled reagent in place of the non-isotopically labeled reagent.

Pharmaceutically acceptable solvates in accordance with the disclosure include those wherein the solvent of crystallization may be isotopically substituted, e.g., $D_2O$, $d_6$-acetone, $d_6$-DMSO.

The present disclosure relates to compounds which are modulators of IKZF2 protein levels. In one embodiment, the compounds of the present disclosure decrease IKZF2 protein levels. In yet one embodiment, the compounds of the present disclosure reduce IKZF2 protein levels. In another embodiment, the compounds of the present disclosure are degraders of IKZF2.

The present disclosure relates to compounds which are modulators of IKZF2 and IKZF4 protein levels. In one embodiment, the compounds of the present disclosure decrease IKZF2 and IKZF4 protein levels. In yet one embodiment, the compounds of the present disclosure reduce IKZF2 and IKZF4 protein levels. In another embodiment, the compounds of the present disclosure are degraders of IKZF2.

In some embodiments, the compounds of the disclosure are selective over other proteins. As used herein "selective modulator", "selective degrader", or "selective compound" means, for example, a compound of the disclosure, that effectively modulates, decreases, or reduces the levels of a specific protein or degrades a specific protein to a greater extent than any other protein. A "selective modulator", "selective degrader", or "selective compound" can be identified, for example, by comparing the ability of a compound to modulate, decrease, or reduce the levels of or to degrade a specific protein to its ability to modulate, decrease, or reduce the levels of or to degrade other proteins. In some embodiments, the selectivity can be identified by measuring the $EC_{50}$ or $IC_{50}$ of the compounds.

In some embodiments, the compounds of the present application are selective IKZF2 modulators. As used herein "selective IKZF2 modulator", "selective IKZF2 degrader", or "selective IKZF2 compound" refers to a compound of the application, for example, that effectively modulates, decrease, or reduces the levels of IKZF2 protein or degrades IKZF2 protein to a greater extent than any other protein, particularly any protein (transcription factor) from the Ikaros protein family (e.g., IKZF1, IKZF3, IKZF4, and IKZF5).

A "selective IKZF2 modulator", "selective IKZF2 degrader", or "selective IKZF2 compound" can be identified, for example, by comparing the ability of a compound to modulate IKZF2 protein levels to its ability to modulate levels of other members of the Ikaros protein family or other proteins. For example, a substance may be assayed for its ability to modulate IKZF2 protein levels, as well as IKZF1, IKZF3, IKZF4, IKZF5, and other proteins. In some embodiments, the selectivity can be identified by measuring the $EC_{50}$ of the compounds. In some embodiments, a selective IKZF2 degrader is identified by comparing the ability of a compound to degrade IKZF2 to its ability to degrade other members of the Ikaros protein family or other proteins.

In certain embodiments, the compounds of the application are IKZF2 degraders that exhibit at least 2-fold, 3-fold, 5-fold, 10-fold, 25-fold, 50-fold or 100-fold selectivity for the degradation of IKZF2 over other proteins (e.g., IKZF1, IKZF3, IKZF4, and IKZF5). In various embodiments, the compounds of the application exhibit up to 1000-fold selectivity for the degradation of IKZF2 over other proteins.

In certain embodiments, the compounds of the application exhibit at least 2-fold, 3-fold, 5-fold, 10-fold, 25-fold, 50-fold or 100-fold selectivity for the degradation of IKZF2 over the other members of the Ikaros protein family (e.g., IKZF1, IKZF3, IKZF4, and IKZF5). In various embodiments, the compounds of the application exhibit up to 1000-fold selectivity for the degradation of IKZF2 over the other members of the Ikaros protein family (e.g., IKZF1, IKZF3, IKZF4, and IKZF5).

In certain embodiments, the compounds of the application exhibit at least 2-fold, 3-fold, 5-fold, 10-fold, 25-fold, 50-fold or 100-fold selectivity for the degradation of IKZF2 over IKZF1. In various embodiments, the compounds of the application exhibit up to 1000-fold selectivity for the degradation of IKZF2 over IKZF1.

In certain embodiments, the compounds of the application exhibit at least 2-fold, 3-fold, 5-fold, 10-fold, 25-fold, 50-fold or 100-fold selectivity for the degradation of IKZF2 over IKZF3. In various embodiments, the compounds of the application exhibit up to 1000-fold selectivity for the degradation of IKZF2 over IKZF3.

In certain embodiments, the compounds of the application exhibit at least 2-fold, 3-fold, 5-fold, 10-fold, 25-fold, 50-fold or 100-fold selectivity for the degradation of IKZF2 over IKZF4. In various embodiments, the compounds of the application exhibit up to 1000-fold selectivity for the degradation of IKZF2 over IKZF4.

In certain embodiments, the compounds of the application exhibit at least 2-fold, 3-fold, 5-fold, 10-fold, 25-fold, 50-fold or 100-fold selectivity for the degradation of IKZF2 over IKZF5. In various embodiments, the compounds of the application exhibit up to 1000-fold selectivity for the degradation of IKZF2 over IKZF5.

In certain embodiments, the compounds of the application exhibit at least 2-fold, 3-fold, 5-fold, 10-fold, 25-fold, 50-fold or 100-fold selectivity for the degradation of IKZF2 and IKZF4 over the other members of the Ikaros protein family (e.g., IKZF1, IKZF3, and IKZF5). In various embodiments, the compounds of the application exhibit up to 1000-fold selectivity for the degradation of IKZF2 and IKZF4 over the other members of the Ikaros protein family (e.g., IKZF1, IKZF3, and IKZF5).

In certain embodiments, the compounds of the application exhibit at least 2-fold, 3-fold, 5-fold, 10-fold, 25-fold, 50-fold or 100-fold selectivity for the degradation of IKZF2 and IKZF4 over IKZF1. In various embodiments, the compounds of the application exhibit up to 1000-fold selectivity for the degradation of IKZF2 and IKZF4 over IKZF1.

In certain embodiments, the compounds of the application exhibit at least 2-fold, 3-fold, 5-fold, 10-fold, 25-fold, 50-fold or 100-fold selectivity for the degradation of IKZF2 and IKZF4 over IKZF3. In various embodiments, the compounds of the application exhibit up to 1000-fold selectivity for the degradation of IKZF2 and IKZF4 over IKZF3.

In certain embodiments, the compounds of the application exhibit at least 2-fold, 3-fold, 5-fold, 10-fold, 25-fold, 50-fold or 100-fold selectivity for the degradation of IKZF2 and IKZF4 over IKZF5. In various embodiments, the compounds of the application exhibit up to 1000-fold selectivity for the degradation of IKZF2 and IKZF4 over IKZF5.

In some embodiments, the degradation of IKZF2 is measured by $EC_{50}$.

Potency of can be determined by $EC_{50}$ value. A compound with a lower $EC_{50}$ value, as determined under substantially similar degradation conditions, is a more potent degrader relative to a compound with a higher $EC_{50}$ value. In some embodiments, the substantially similar conditions comprise determining degradation of protein levels in cells expressing the specific protein, or a fragment of any thereof.

The disclosure is directed to compounds as described herein and pharmaceutically acceptable salts, hydrates, solvates, prodrugs, stereoisomers, or tautomers thereof, and pharmaceutical compositions comprising one or more compounds as described herein, or pharmaceutically acceptable salts, hydrates, solvates, prodrugs, stereoisomers, or tautomers thereof.

E. Methods of Synthesizing Compounds of Formula (I')

The compounds of the present disclosure may be made by a variety of methods, including standard chemistry. Suitable synthetic routes are depicted in the Schemes given below.

The compounds of the present disclosure may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of Compounds of Formula (I').

Those skilled in the art will recognize if a stereocenter exists in the compounds of the present disclosure. Accordingly, the present disclosure includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

Preparation of Compounds

The compounds of the present disclosure can be prepared in a number of ways well known to those skilled in the art of organic synthesis. By way of example, compounds of the present disclosure can be synthesized using the methods described below, together with synthetic methods known in the art of synthetic organic chemistry, or variations thereon as appreciated by those skilled in the art. Preferred methods include but are not limited to those methods described below.

Compounds of the present disclosure can be synthesized by following the steps outlined in General Schemes I, II, III, IV, and V which comprise different sequences of assembling intermediates I-a to I-p. Starting materials are either commercially available or made by known procedures in the reported literature or as illustrated.

General Scheme I

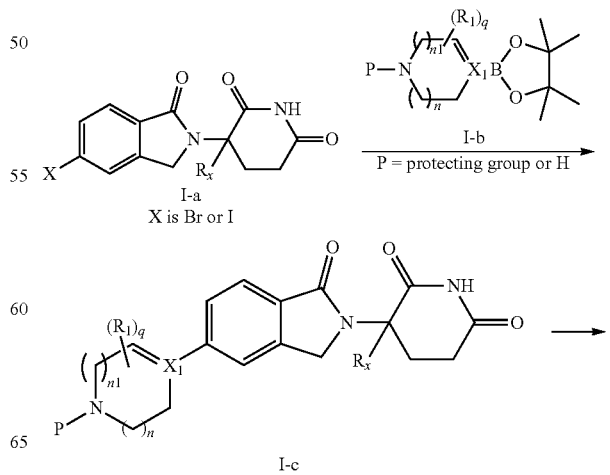

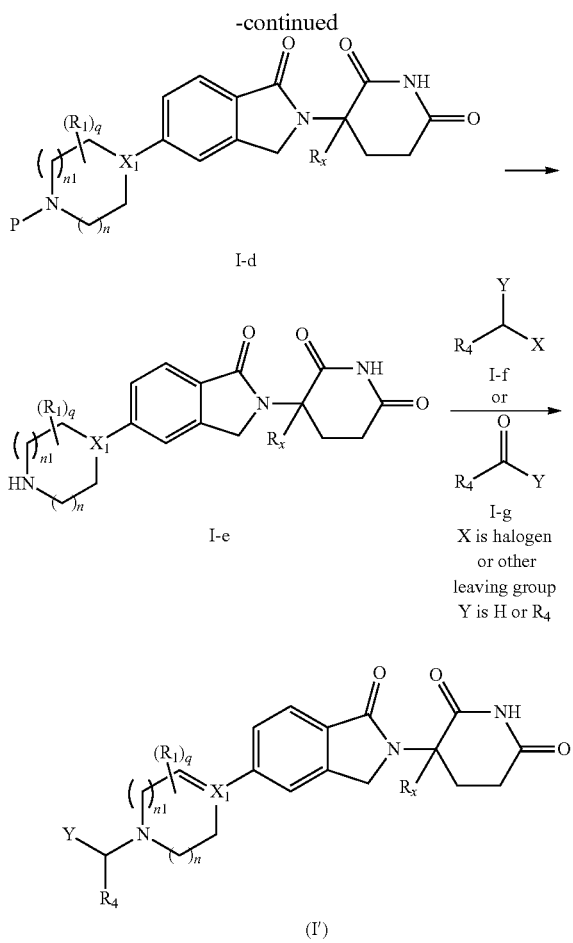

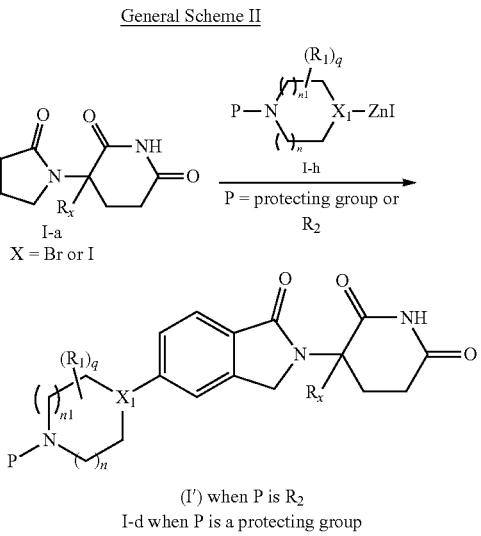

General Scheme II wherein $X_1$ is $CR_3$, and $R_1$, $R_2$, $R_3$, $R_x$, n, n1, and q are as defined in Formula (I').

The general way of preparing Compounds of Formula (I') (wherein $X_1$ is CH and P is $R_2$) and intermediate I-d (wherein $X_1$ is CH and P is a protecting group) by using intermediate I-h, is outlined in General Scheme II. Coupling of I-a with zincate I-h using a catalyst (e.g., XphosPd G2) in a solvent (e.g. THF) at elevated temperature yields Compounds of Formula (I') or intermediate I-d. When P is an amine protecting group (e.g., tert-butyloxycarbonyl (Boc)) intermediate 1-d is deprotected using a strong acid such as trifluoroacetic acid (TFA) or hydrochloric acid (HCl) in a solvent (e.g., tetrahydrofuran (THF), 1,2-dichloroethane or dichloromethane (DCM)) optionally at elevated temperature to provide I-e which can be further functionalized as described in General Scheme I. When P is the desired substituent then the product equates to a compound of Formula (I').

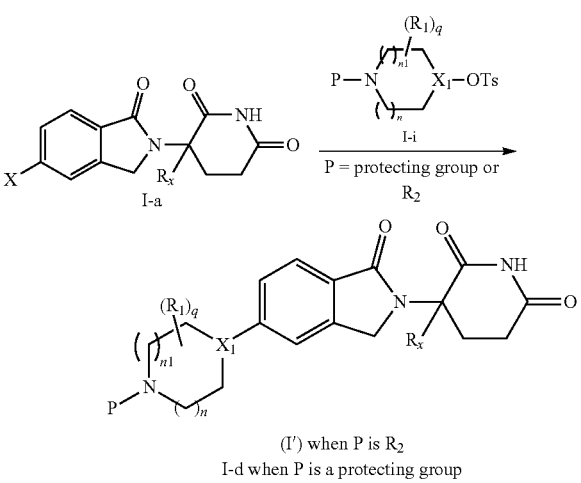

General Scheme III wherein $X_1$ is $CR_3$, and $R_1$, $R_2$, $R_3$, $R_x$, n, n1, and q are as defined in Formula (I').

wherein $X_1$ is $CR_3$, and $R_1$, $R_2$, $R_3$, $R_x$, n, n1, and q are as defined in Formula (I').

The general way of preparing Compounds of Formula (I') wherein $X_1$ is CH and $R_2$ is a substituted alkyl (optionally substituted with one or more $R_4$) by using intermediates I-a, I-b, I-c, I-d, I-e, I-f, and I-g is outlined in General Scheme I. Coupling of I-a with boronic ester I-b using a catalyst (e.g., Pd(dppf)Cl$_2$.DCM), and a base (e.g., cesium carbonate (Cs$_2$CO$_3$)), in a solvent (e.g., N,N-dimethylformamide (DMF)) at elevated temperature yields 1-c. Hydrogenation of I-d in the presence of a suitable catalyst (e.g., Pd/C or PtO$_2$) in a solvent (e.g., DMF) and under an atmosphere of hydrogen gas provides I-d. When P is an amine protecting group (e.g., tert-butyloxycarbonyl (Boc)) intermediate I-d is deprotected using a strong acid such as trifluoroacetic acid (TFA) or hydrochloric acid (HCl) in a solvent (e.g., tetrahydrofuran (THF), 1,2-dichloroethane, dioxane or dichloromethane (DCM)) optionally at elevated temperature to provide I-e. Reductive amination of I-e with aldehyde or ketone I-g provides a compound of Formula (I') where $X_1$ is CH and $R_2$ is a substituted alkyl. Alternatively, Compounds of Formula (I') where $X_1$ is CH and $R_2$ is a substituted alkyl can be obtained by alkylation of I-e with an alkyl halide (I-f) in the presence of a base (e.g., NEt$_3$, Cs$_2$CO$_3$, etc.), in a solvent (e.g., DCM, DMF, etc.), and optionally at elevated temperature.

The general way of preparing Compounds of Formula (I') (wherein $X_1$ is CH and P is $R_2$) and intermediate I-d (wherein $X_1$ is CH and P is a protecting group) by using intermediate I-i, is outlined in General Scheme III. Coupling of I-a with tosylate I-i using a catalyst (e.g. $NiBr_2$.DME with 4,4-di-tert-butyl-2,2'-dipyridyl (di-t-Bu-bipy), and manganese powder (Mn)), with potassium iodide (KI), and a base (e.g., 4-ethyl-pyridine) in a solvent (e.g., N,N-dimethylacetamide (DMA)) at elevated temperature yields Compounds of Formula (I') or intermediate I-d.

General Scheme IV

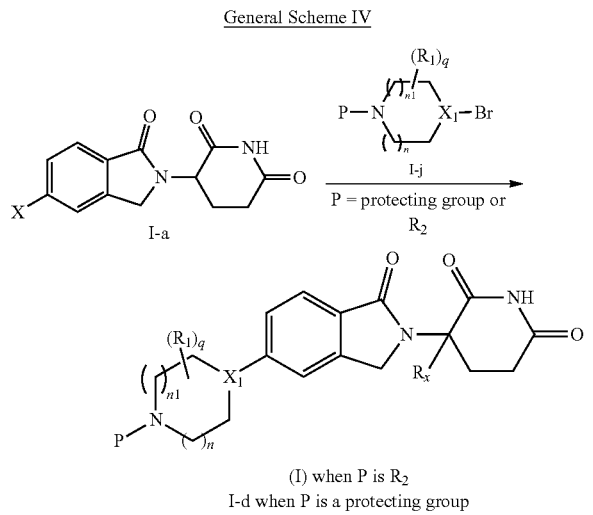

(I) when P is $R_2$
I-d when P is a protecting group wherein $X_1$ is $CR_3$, and $R_1$, $R_2$, $R_3$, $R_x$, n, n1, and q are as defined in Formula (I').

The general way of preparing Compounds of Formula (I') (wherein $X_1$ is CH and P is $R_2$) and intermediate I-d (wherein $X_1$ is CH and P is a protecting group) by using intermediates I-j, is outlined in General Scheme IV. Coupling of I-a with bromide I-j using a catalyst (e.g. $NiI_2$ with 4,4-di-tert-butyl-2,2'-dipyridyl (di-t-Bu-bipy), magnesium chloride and manganese powder (Mn)), with a base (e.g., 4-ethyl-pyridine), in a solvent (e.g., N,N-dimethylacetamide (DMA)) at elevated temperature yields Compounds of Formula (I') or intermediate I-d.

General Scheme IV

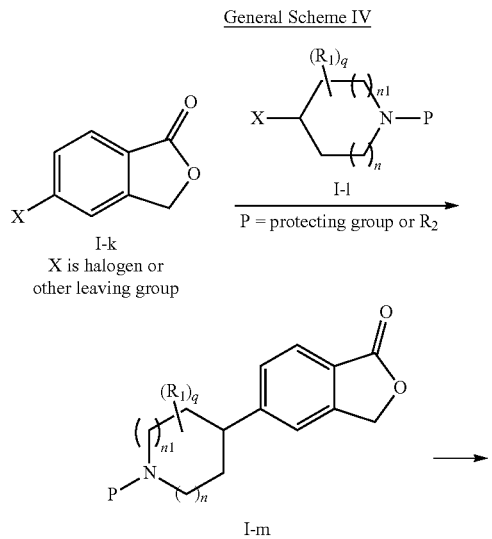

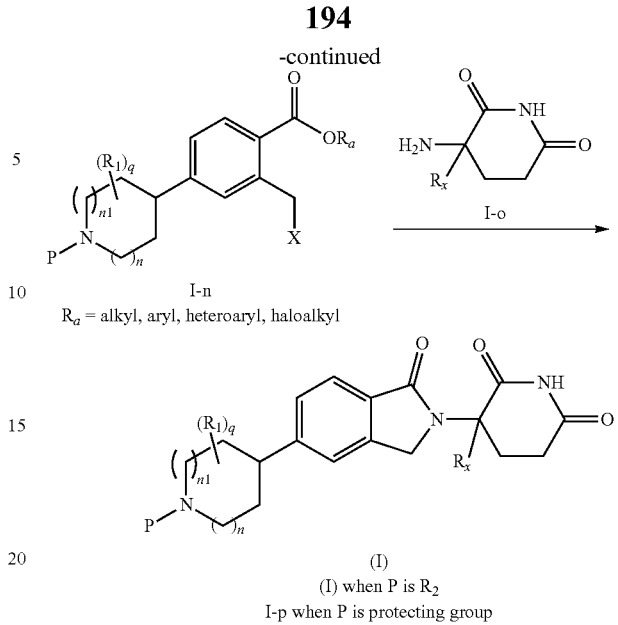

$R_a$ = alkyl, aryl, heteroaryl, haloalkyl (I)
(I) when P is $R_2$
I-p when P is protecting group wherein $R_1$, $R_2$, R, q, n, and n1 are as defined in Formula (I').

The general way of preparing Compounds of Formula (I') wherein $X_1$ is CH and ══════ is a single bond and intermediate I-p using intermediates I-k, I-l, I-m, I-n, and I-o is outlined in General Scheme V. Coupling of I-k with I-l using a catalyst (e.g., $NiBr_2$.DME with 4,4-di-tert-butyl-2,2'-dipyridyl (di-t-Bu-bipy) or 2-amidinopyridine), manganese powder (Mn), and potassium iodide (KI), in a solvent (e.g. N,N-dimethylacetamide (DMA)) optionally at elevated temperature yields intermediate I-m. Intermediate I-m can then be converted to the corresponding haloester I-n using thionyl chloride ($SOCl_2$) in a solvent (e.g. EtOH) and optionally at elevated temperature. Cyclization with 3-aminopiperidine-2,6-dione I-o or its HCl or $CF_3CO_2H$ salt using a base (e.g., i-$Pr_2NEt$) in a solvent (e.g. DMF) and optionally at elevated temperature provides compounds of Formula (I') or intermediate I-p.

A mixture of enantiomers, diastereomers, and cis/trans isomers resulting from the process described above can be separated into their single components by chiral salt technique, chromatography using normal phase, reverse phase or chiral column, depending on the nature of the separation.

Any resulting racemates of compounds of the present disclosure or of intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present disclosure into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid, or camphor-10-sulfonic acid. Racemic compounds of the present disclosure or racemic intermediates can also be resolved by chiral chromatography, e.g., high pressure liquid chromatography (HPLC) using a chiral adsorbent.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

It should be understood that in the description and formula shown above, the various groups $R_1$, $R_2$, $R_3$, $R_x$, n, n1, and q and other variables are as defined above, except where otherwise indicated. Furthermore, for synthetic purposes, the compounds of General Schemes I, II, III, IV, and V are merely representative with elected radicals to illustrate the general synthetic methodology of the Compounds of Formula (I') as defined herein.

F. Methods of Using Compounds of Formula (I')

Another aspect of the disclosure relates to a method of treating, preventing, inhibiting, or eliminating a disease or disorder in a patient associated with modulation of IKZF2 protein levels. The method comprises administering to a patient in need of a treatment for diseases or disorders associated with modulation of IKZF2 protein levels an effective amount of a Compound of Formula (I') or Formula (I), or a pharmaceutically acceptable salt, hydrate, solvate, prodrug, stereoisomer, or tautomer thereof or a composition comprising a Compound of Formula (I') or Formula (I), or a pharmaceutically acceptable salt, hydrate, solvate, prodrug, stereoisomer, or tautomer thereof.

In another aspect, the disclosure relates to a method of treating, preventing, inhibiting, or eliminating a disease or disorder that is affected by the modulation of IKZF2 protein levels. The method comprises administering to a patient in need of a treatment for diseases or disorders affected by the modulation of IKZF2 protein levels an effective amount of a Compound of Formula (I') or Formula (I), or a pharmaceutically acceptable salt, hydrate, solvate, prodrug, stereoisomer, or tautomer thereof or a composition comprising a Compound of Formula (I') or Formula (I), or a pharmaceutically acceptable salt, hydrate, solvate, prodrug, stereoisomer, or tautomer thereof.

In another aspect, the disclosure relates to a method of treating, preventing, inhibiting, or eliminating a disease or disorder that is affected by the reduction of IKZF2 protein levels. The method comprises administering to a patient in need of a treatment for diseases or disorders affected by the reduction of IKZF2 protein levels an effective amount of a Compound of Formula (I') or Formula (I), or a pharmaceutically acceptable salt, hydrate, solvate, prodrug, stereoisomer, or tautomer thereof or a composition comprising a Compound of Formula (I') or Formula (I), or a pharmaceutically acceptable salt, hydrate, solvate, prodrug, stereoisomer, or tautomer thereof.

Another aspect of the disclosure relates to a method of treating, preventing, inhibiting, or eliminating a disease or disorder that is affected by a decrease in IKZF2 protein levels. The method comprises administering to a patient in need of a treatment for diseases or disorders affected by the reduction or decrease of IKZF2 protein levels an effective amount of a Compound of Formula (I') or Formula (I), or a pharmaceutically acceptable salt, hydrate, solvate, prodrug, stereoisomer, or tautomer thereof or a composition comprising a Compound of Formula (I') or Formula (I), or a pharmaceutically acceptable salt, hydrate, solvate, prodrug, stereoisomer, or tautomer thereof.

In another aspect, the disclosure relates to the use of a Compound of Formula (I') or Formula (I), or a pharmaceutically acceptable salt, hydrate, solvate, prodrug, stereoisomer, or tautomer thereof, or a composition comprising a Compound of Formula (I') or Formula (I), or a pharmaceutically acceptable salt, hydrate, solvate, prodrug, stereoisomer, or tautomer thereof, in the manufacture of a medicament for the treatment, prevention, inhibition or elimination of a disease or disorder that is affected by the modulation of IKZF2 protein levels.

In another aspect, the disclosure relates to the use of a Compound of Formula (I') or Formula (I), or a pharmaceutically acceptable salt, hydrate, solvate, prodrug, stereoisomer, or tautomer thereof, or a composition comprising a Compound of Formula (I') or Formula (I), or a pharmaceutically acceptable salt, hydrate, solvate, prodrug, stereoisomer, or tautomer thereof, in the manufacture of a medicament for the treatment, prevention, inhibition or elimination of a disease or disorder that is affected by the reduction of or a decrease in IKZF2 protein levels.

Another aspect of the disclosure relates to a Compound of Formula (I') or Formula (I), or a pharmaceutically acceptable salt, hydrate, solvate, prodrug, stereoisomer, or tautomer thereof or a composition comprising a Compound of Formula (I') or Formula (I), or a pharmaceutically acceptable salt, hydrate, solvate, prodrug, stereoisomer, or tautomer thereof, for use in the manufacture of a medicament for treating, preventing, inhibiting, or eliminating a disease or disorder that is affected by the modulation of IKZF2 protein levels.

Another aspect of the disclosure relates to a Compound of Formula (I') or Formula (I), or a pharmaceutically acceptable salt, hydrate, solvate, prodrug, stereoisomer, or tautomer thereof or a composition comprising a Compound of Formula (I') or Formula (I), or a pharmaceutically acceptable salt, hydrate, solvate, prodrug, stereoisomer, or tautomer thereof, for use in the manufacture of a medicament for treating, preventing, inhibiting, or eliminating a disease or disorder that is affected by the reduction of or a decrease in IKZF2 protein levels.

In another aspect, the present disclosure is directed to a method of modulating IKZF2 protein levels. The method involves administering to a patient in need thereof an effective amount of a Compound of Formula (I') or Formula (I), or a pharmaceutically acceptable salt, hydrate, solvate, prodrug, stereoisomer, or tautomer thereof or a composition comprising a Compound of Formula (I') or Formula (I), or a pharmaceutically acceptable salt, hydrate, solvate, prodrug, stereoisomer, or tautomer thereof. In some embodiments, IKZF2 protein levels are modulated through degradation of the IKZF2 protein. In other embodiments, IKZF2 protein levels are modulated through degradation of the IKZF2 protein mediated by an E3 ligase.

Another aspect of the present disclosure relates to a method of treating, preventing, inhibiting, or eliminating a disease or disorder in a patient associated with the reduction of or decrease in IKZF2 protein levels, the method comprising administering to a patient in need thereof an effective amount of a Compound of Formula (I') or Formula (I), or a pharmaceutically acceptable salt, hydrate, solvate, prodrug, stereoisomer, or tautomer thereof or a composition comprising a Compound of Formula (I') or Formula (I), or a pharmaceutically acceptable salt, hydrate, solvate, prodrug, stereoisomer, or tautomer thereof.

The present disclosure also relates to the use of a degrader of IKZF2 for the preparation of a medicament used in the treatment, prevention, inhibition or elimination of a IKZF2-dependent disease or disorder, wherein the medicament comprises a Compound of Formula (I') or Formula (I), or a pharmaceutically acceptable salt, hydrate, solvate, prodrug, stereoisomer, or tautomer thereof or a composition comprising a Compound of Formula (I') or Formula (I), or a pharmaceutically acceptable salt, hydrate, solvate, prodrug, stereoisomer, or tautomer thereof.

In another aspect, the present disclosure relates to a method for treating, preventing, inhibiting, or eliminating a IKZF2-dependent disease or disorder, wherein the medicament comprises a Compound of Formula (I') or Formula (I), or a pharmaceutically acceptable salt, hydrate, solvate, prodrug, stereoisomer, or tautomer thereof or a composition comprising a Compound of Formula (I') or Formula (I), or a pharmaceutically acceptable salt, hydrate, solvate, prodrug, stereoisomer, or tautomer thereof.

In another aspect, the present disclosure relates to a method for the manufacture of a medicament for treating, preventing, inhibiting, or eliminating a IKZF2-dependent disease or disorder mediated, wherein the medicament comprises a Compound of Formula (I') or Formula (I), or a pharmaceutically acceptable salt, hydrate, solvate, prodrug, stereoisomer, or tautomer thereof or a composition comprising a Compound of Formula (I') or Formula (I), or a pharmaceutically acceptable salt, hydrate, solvate, prodrug, stereoisomer, or tautomer thereof.

Another aspect of the present disclosure relates to a Compound of Formula (I') or Formula (I), or a pharmaceutically acceptable salt, hydrate, solvate, prodrug, stereoisomer, or tautomer thereof, or a composition comprising a Compound of Formula (I') or Formula (I), or a pharmaceutically acceptable salt, hydrate, solvate, prodrug, stereoisomer, or tautomer thereof, for use in the manufacture of a medicament for treating a disease or disorder associated with the modulation of IKZF2 protein levels. In some embodiments, IKZF2 levels are modulated through degradation of the IKZF2 protein. In some embodiments, IKZF2 protein levels are modulated through degradation of the IKZF2 protein mediated by an E3 ligase.

Another aspect of the present disclosure relates to a Compound of Formula (I') or Formula (I), or a pharmaceutically acceptable salt, hydrate, solvate, prodrug, stereoisomer, or tautomer thereof, or a composition comprising a Compound of Formula (I') or Formula (I), or a pharmaceutically acceptable salt, hydrate, solvate, prodrug, stereoisomer, or tautomer thereof, for use in treating a disease associated with the modulation of IKZF2 protein levels. In some embodiments, IKZF2 levels are modulated through degradation of the IKZF2 protein. In some embodiments, IKZF2 protein levels are modulated through degradation of the IKZF2 protein mediated by an E3 ligase.

In another aspect, the present disclosure relates to the use of a Compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, in the treatment of a disease associated with the modulation of IKZF2 protein levels. In some embodiments, IKZF2 protein levels are modulated through degradation of the IKZF2 protein. In some embodiments, IKZF2 protein levels are modulated through degradation of the IKZF2 protein mediated by an E3 ligase.

Another aspect of the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for treating a disease or disorder associated with the reduction of IKZF2 protein levels. In some embodiments, IKZF2 levels are reduced through degradation of the IKZF2 protein. In some embodiments, IKZF2 levels are reduced through degradation of the IKZF2 protein mediated by an E3 ligase.

Another aspect of the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in treating a disease associated with the reduction of IKZF2 protein levels. In some embodiments, IKZF2 levels are reduced through degradation of the IKZF2 protein. In some embodiments, IKZF2 levels are reduced through degradation of the IKZF2 protein mediated by an E3 ligase.

In another aspect, the present disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, in the treatment of a disease associated with the reduction of IKZF2 protein levels. In some embodiments, IKZF2 protein levels are reduced through degradation of the IKZF2 protein. In some embodiments, IKZF2 levels are reduced through degradation of the IKZF2 protein mediated by an E3 ligase.

Another aspect of the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for treating a disease or disorder associated with a decrease in IKZF2 protein levels. In some embodiments, IKZF2 levels are decreased through degradation of the IKZF2 protein. In some embodiments, IKZF2 protein levels are decreased through degradation of the IKZF2 protein mediated by an E3 ligase.

Another aspect of the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in treating a disease associated with a decrease in IKZF2 protein levels. In some embodiments, IKZF2 levels are decreased through degradation of the IKZF2 protein. In some embodiments, IKZF2 protein levels are decreased through degradation of the IKZF2 protein mediated by an E3 ligase.

In another aspect, the present disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, in the treatment of a disease associated with a decrease in IKZF2 protein levels. In some embodiments, IKZF2 protein levels are reduced through degradation of the IKZF2 protein. In some embodiments, IKZF2 protein levels are decreased through degradation of the IKZF2 protein mediated by an E3 ligase.

In another aspect, the present disclosure relates to a method of inhibiting IKZF2 activity through degradation of IKZF2. In some embodiments, IKZF2 and IKZF4 protein degradation is mediated by an E3 ligase.

Another aspect of the disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for inhibiting IKZF2 activity through degradation of IKZF2. In some embodiments, IKZF2 protein degradation is mediated by an E3 ligase.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the inhibition of IKZF2 activity through degradation of IKZF2. In some embodiments, IKZF2 protein degradation is mediated by an E3 ligase.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for inhibiting IKZF2 activity through degradation of IKZF2. In some embodiments, IKZF2 protein degradation is mediated by an E3 ligase.

In another aspect, the present disclosure relates to a method of inhibiting IKZF2 and IKZF4 activity through degradation of IKZF2 and IKZF4. In some embodiments, IKZF2 and IKZF4 protein degradation is mediated by an E3 ligase.

Another aspect of the disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for inhibiting IKZF2 and IKZF4 activity through degradation of IKZF2 and IKZF4. In some embodiments, IKZF2 and IKZF4 protein degradation is mediated by an E3 ligase.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the inhibition of IKZF2 and IKZF4 activity through degradation of IKZF2 and IKZF4. In some embodiments, IKZF2 and IKZF4 protein degradation is mediated by an E3 ligase.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for inhibiting IKZF2 and IKZF4 activity through degradation of IKZF2 and IKZF4. In some embodiments, IKZF2 and IKZF4 protein degradation is mediated by an E3 ligase.

Another aspect of the disclosure relates to a method of treating, preventing, inhibiting, or eliminating a disease or disorder associated with modulation of IKZF2 and IKZF4 protein levels. The method comprises administering to a patient in need of a treatment for diseases or disorders associated with modulation of IKZF2 and IKZF4 protein levels an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

In another aspect, the present disclosure is directed to a method of modulating IKZF2 and IKZF4 protein levels. The method involves administering to a patient in need thereof an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof. In some embodiments, IKZF2 and IKZF4 protein levels are modulated through degradation of the IKZF2 and IKZF4 proteins. In other embodiments, IKZF2 and IKZF4 protein levels are modulated through degradation of the IKZF2 and IKZF4 proteins mediated by an E3 ligase.

Another aspect of the disclosure relates to a method of treating, preventing, inhibiting, or eliminating a disease or disorder associated with modulation of, reduction of, or a decrease in IKZF4 protein levels. The method comprises administering to a patient in need of a treatment for diseases or disorders associated with modulation of, reduction of, or decrease in IKZF4 protein levels an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof. In some embodiments, IKZF4 protein levels are modulated, reduced, or decreased through degradation of the IKZF4 proteins. In some embodiments, IKZF4 protein levels are modulated, reduced, or decreased through degradation of the IKZF4 protein mediated by an E3 ligase.

In another aspect, the present disclosure is directed to a method of modulating, reducing or decreasing IKZF4 protein levels. The method involves administering to a patient in need thereof an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof. In some embodiments, IKZF4 protein levels are modulated, reduced, or decreased through degradation of the IKZF4 proteins. In other embodiments, IKZF4 protein levels are modulated, reduced, or decreased through degradation of the IKZF4 protein mediated by an E3 ligase.

Another aspect of the disclosure relates to the use of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof, for treating, preventing, inhibiting, or eliminating a disease or disorder associated with modulation of, reduction of, or a decrease in IKZF4 protein levels. In some embodiments, IKZF4 protein levels are modulated, reduced, or decreased through degradation of the IKZF4 proteins. In some embodiments, IKZF4 protein levels are modulated, reduced, or decreased through degradation of the IKZF4 protein mediated by an E3 ligase.

Another aspect of the disclosure relates to a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof, for use in treating, preventing, inhibiting, or eliminating a disease or disorder associated with modulation of, reduction of, or a decrease in IKZF4 protein levels. In some embodiments, IKZF4 protein levels are modulated, reduced, or decreased through degradation of the IKZF4 proteins. In some embodiments, IKZF4 protein levels are modulated, reduced, or decreased through degradation of the IKZF4 protein mediated by an E3 ligase.

In another aspect, the present disclosure is directed to a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof, for use in the manufacture of a medicament for treating, preventing, inhibiting, or eliminating a disease or disorder associated with modulation of, reduction of, or a decrease in IKZF4 protein levels. In some embodiments, IKZF4 protein levels are modulated, reduced, or decreased through degradation of the IKZF4 proteins. In some embodiments, IKZF4 protein levels are modulated, reduced, or decreased through degradation of the IKZF4 protein mediated by an E3 ligase.

Another aspect of the disclosure relates to a method of treating, preventing, inhibiting, or eliminating a disease or disorder associated with the reduction of IKZF2 and IKZF4 protein levels. The method comprises administering to a patient in need of a treatment for diseases or disorders associated with reduction of IKZF2 and IKZF4 protein levels an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

In another aspect, the present disclosure is directed to a method of reducing IKZF2 and IKZF4 protein levels. The method involves administering to a patient in need thereof an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof. In some embodiments, IKZF2 and IKZF4 protein levels are reduced through degradation of the IKZF2 and IKZF4 proteins. In other embodiments, IKZF2 and IKZF4 protein levels are reduced through degradation of the IKZF2 and IKZF4 proteins mediated by an E3 ligase.

Another aspect of the disclosure relates to a method of treating, preventing, inhibiting, or eliminating a disease or disorder associated with a decrease in IKZF2 and IKZF4 protein levels. The method comprises administering to a patient in need of a treatment for diseases or disorders associated with a decrease of IKZF2 and IKZF4 protein levels an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

In another aspect, the present disclosure is directed to a method of decreasing IKZF2 and IKZF4 protein levels. The method involves administering to a patient in need thereof an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof. In some embodiments, IKZF2 and IKZF4 protein levels are decreased through degradation of the IKZF2 and IKZF4 proteins. In some embodiments, IKZF2 and IKZF4 protein levels are decreased through degradation of the IKZF2 and IKZF4 proteins mediated by an E3 ligase.

Another aspect of the present disclosure relates to a method of treating, preventing, inhibiting, or eliminating a disease or disorder in a patient associated with the modulation of IKZF2 and IKZF4 protein levels, the method comprising administering to a patient in need thereof an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof. In one embodiment, the disease or disorder is selected from the group consisting of cancer and metastasis.

In another aspect, the present disclosure relates to a method of treating, preventing, inhibiting, or eliminating a disease or disorder in a patient associated with the reduction of IKZF2 and IKZF4 protein levels, the method comprising administering to a patient in need thereof an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof. In one embodiment, the disease or disorder is selected from the group consisting of cancer and metastasis.

Another aspect of the present disclosure relates to a method of treating, preventing, inhibiting, or eliminating a disease or disorder in a patient associated with a decrease in IKZF2 and IKZF4 protein levels, the method comprising administering to a patient in need thereof an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof. In one embodiment, the disease or disorder is selected from the group consisting of cancer and metastasis.

The present disclosure also relates to the use of a modulator of IKZF2 and IKZF4 protein levels for the preparation of a medicament used in the treatment, prevention, inhibition or elimination of a IKZF2 and IKZF4-dependent disease or disorder, wherein the medicament comprises a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof. In another aspect, the present disclosure relates to a method for the manufacture of a medicament for treating, preventing, inhibiting, or eliminating a IKZF2 and IKZF4-dependent disease or disorder, wherein the medicament comprises a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

Another aspect of the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for treating a disease associated with the modulation of IKZF2 and IKZF4 protein levels. In some embodiments, IKZF2 and IKZF4 protein levels are modulated through degradation of the IKZF2 and IKZF4 proteins. In other embodiments, IKZF2 and IKZF4 protein levels are modulated through degradation of the IKZF2 and IKZF4 proteins mediated by an E3 ligase.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in treating a disease associated with the modulation of IKZF2 and IKZF4 protein levels. In some embodiments, IKZF2 and IKZF4 protein levels are modulated through degradation of the IKZF2 and IKZF4 proteins. In other embodiments, IKZF2 and IKZF4 protein levels are modulated through degradation of the IKZF2 and IKZF4 proteins mediated by an E3 ligase.

Another aspect of the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for treating a disease associated with the reduction of IKZF2 and IKZF4 protein levels. In some embodiments, IKZF2 and IKZF4 protein levels are reduced through degradation of the IKZF2 and IKZF4 proteins. In other embodiments, IKZF2 and IKZF4 protein levels are reduced through degradation of the IKZF2 and IKZF4 proteins mediated by an E3 ligase.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in treating a disease associated with the reduction of IKZF2 and IKZF4 protein levels. In some embodiments, IKZF2 and IKZF4 are reduced through degradation of the IKZF2 and IKZF4 proteins. In other embodiments, IKZF2 and IKZF4 protein levels are reduced through degradation of the IKZF2 and IKZF4 proteins mediated by an E3 ligase.

Another aspect of the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for treating a disease associated with a decrease in IKZF2 and IKZF4 protein levels. In some embodiments, IKZF2 and IKZF4 protein levels are decreased through degradation of the IKZF2 and IKZF4 proteins. In some embodiments, IKZF2 and IKZF4 protein levels are decreased through degradation of the IKZF2 and IKZF4 proteins mediated by an E3 ligase.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in treating a disease associated with a decrease in IKZF2 and IKZF4 protein levels. In some embodiments, IKZF2 and IKZF4 are decreased through degradation of the IKZF2 and IKZF4 proteins. In some embodiments, IKZF2 and IKZF4 protein levels are decreased through degradation of the IKZF2 and IKZF4 proteins mediated by an E3 ligase.

In another aspect, the present disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, in the treatment of a disease associated with the modulation of IKZF2 and IKZF4 protein levels. In some embodiments, IKZF2 and IKZF4 protein levels are modulated through degradation of the IKZF2 and IKZF4 proteins. In other embodiments, IKZF2 and IKZF4 protein levels are modulated through degradation of the IKZF2 and IKZF4 proteins mediated by an E3 ligase.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the treatment of an IKZF2-dependent disease or disorder by reducing or decreasing IKZF2 protein levels, wherein reduction or decrease of IKZF2 protein levels treats the IKZF2-dependent disease or disorder.

In another aspect, the present disclosure the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, in the treatment of an IKZF2-dependent disease or disorder by reducing or decreasing IKZF2 protein levels wherein reduction of or decrease in IKZF2 protein levels treats the IKZF2-dependent disease or disorder.

In another aspect, the present disclosure the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, in the manufacture of a medicament for treating an IKZF2-dependent disease or disorder by reducing or decreasing IKZF2 protein levels wherein reduction of or decrease in IKZF2 protein levels treats the IKZF2-dependent disease or disorder.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the treatment of an IKZF2 and IKZF4-dependent disease or disorder by reducing or decreasing IKZF2 and IKZF4 protein levels wherein the reduction of or decrease in IKZF2 and IKZF4 protein levels treats the IKZF2 and IKZF4-dependent disease or disorder.

In another aspect, the present disclosure the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, in the treatment of an IKZF2 and IKZF4-dependent disease or disorder by reducing or decreasing IKZF2 and IKZF4 protein levels wherein the reduction of or decrease in IKZF2 and IKZF4 protein levels treats the IKZF2 and IKZF4-dependent disease or disorder.

In another aspect, the present disclosure the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, in the manufacture of a medicament for treating an IKZF2 and IKZF4-dependent disease or disorder by reducing or decreasing IKZF2 and IKZF4 protein levels wherein the reduction of or decrease in IKZF2 and IKZF4 protein levels treats the IKZF2 and IKZF4-dependent disease or disorder.

Another aspect of the disclosure relates to a method of treating cancer. The method comprises administering to a patient in need thereof an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

In another aspect, the present disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, in the treatment of treating cancer.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for treating cancer.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the treatment of cancer.

Another aspect of the disclosure relates to a method of treating an IKZF2-dependent cancer. The method comprises administering to a patient in need thereof an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

In another aspect, the present disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, in the treatment of treating an IKZF2-dependent cancer.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for treating an IKZF2-dependent cancer.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the treatment of an IKZF2-dependent cancer.

Another aspect of the disclosure relates to a method of treating an IKZF2-dependent and IKZF4-dependent cancer. The method comprises administering to a patient in need thereof an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

In another aspect, the present disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, in the treatment of treating an IKZF2-dependent and IKZF4-dependent cancer.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for treating an IKZF2-dependent and IKZF4-dependent cancer.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the treatment of an IKZF2-dependent and IKZF4-dependent cancer.

Another aspect of the disclosure relates to a method of treating a cancer affected by the modulation of, the reduction of, or a decrease in IKZF2 protein levels. The method comprises administering to a patient in need thereof an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

In another aspect, the present disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, in the treatment of treating a cancer affected by the modulation of, the reduction of, or a decrease in IKZF2 protein levels Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for treating a cancer affected by the modulation of, the reduction of, or a decrease in IKZF2 protein levels.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the treatment of a cancer affected by the modulation of, the reduction of, or a decrease in IKZF2 protein levels.

Another aspect of the disclosure relates to a method of treating a cancer affected by the modulation of, the reduction of, or a decrease in IKZF2 and IKZF4 protein levels. The method comprises administering to a patient in need thereof an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

In another aspect, the present disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, in the treatment of treating a cancer affected by the modulation of, the reduction of, or a decrease in IKZF2 and IKZF4 protein levels.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for treating a cancer affected by the modulation of, the reduction of, or a decrease in IKZF2 and IKZF4 protein levels.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the treatment of a cancer affected by the modulation of, the reduction of, or a decrease in IKZF2 and IKZF4 protein levels.

Another aspect of the disclosure relates to a method of degrading IKZF2. The method comprises administering to a patient in need thereof an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof. In some embodiments, IKZF2 protein degradation is mediated by an E3 ligase.

In another aspect, the present disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for degrading IKZF2. In some embodiments, IKZF2 protein degradation is mediated by an E3 ligase.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the degradation IKZF2. In some embodiments, IKZF2 protein degradation is mediated by an E3 ligase.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for degrading IKZF2. In some embodiments, IKZF2 protein degradation is mediated by an E3 ligase.

In another aspect, the present disclosure relates to a method of modulating IKZF2 protein levels through degradation of IKZF2. In some embodiments, IKZF2 protein degradation is mediated by an E3 ligase.

Another aspect of the disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for modulating IKZF2 protein levels through degradation of IKZF2. In some embodiments, IKZF2 protein degradation is mediated by an E3 ligase.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the modulation IKZF2 protein levels through degradation of IKZF2. In some embodiments, IKZF2 protein degradation is mediated by an E3 ligase.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for modulating IKZF2 protein levels through degradation of IKZF2. In some embodiments, IKZF2 protein degradation is mediated by an E3 ligase.

Another aspect of the disclosure relates to a method of treating an IKZF2-dependent disease or disorder in a patient in need thereof by modulating IKZF2 protein levels through the degradation of IKZF2. In some embodiments, IKZF2 protein degradation is mediated by an E3 ligase.

In another aspect, the present disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for treating an IKZF2-dependent disease or disorder in a patient in need thereof by modulating IKZF2 protein levels through the degradation of IKZF2. In some embodiments, IKZF2 protein degradation is mediated by an E3 ligase.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in treating an IKZF2-dependent disease or disorder in a patient in need thereof, by modulating IKZF2 protein levels through the degradation of IKZF2. In some embodiments, IKZF2 protein degradation is mediated by an E3 ligase.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for treating an IKZF2-dependent disease or disorder in a patient in need thereof by modulating IKZF2 protein levels through the degradation of IKZF2. In some embodiments, IKZF2 protein degradation is mediated by an E3 ligase.

In another aspect, the present disclosure relates to a method of degrading IKZF2. The method comprises administering to a patient in need thereof an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof. In some embodiments, IKZF2 protein degradation is mediated by an E3 ligase.

Another aspect of the disclosure relates to the use of a compound of Formula (I') or Formula (I), or a pharmaceutically acceptable salt, hydrate, solvate, prodrug, stereoisomer, or tautomer thereof, for degrading IKZF2. In some embodiments, IKZF2 protein degradation is mediated by an E3 ligase.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in degrading IKZF2. In some embodiments, IKZF2 protein degradation is mediated by an E3 ligase.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for degrading IKZF2. In some embodiments, IKZF2 protein degradation is mediated by an E3 ligase.

Another aspect of the disclosure relates to a method of reducing the proliferation of a cell, the method comprising contacting the cell with a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, that reduces IKZF2 protein levels. In some embodiments, IKZF2 protein levels are reduced through degradation of the IKZF2 protein. In some embodiments, IKZF2 protein levels are reduced through degradation of the IKZF2 protein mediated by an E3 ligase.

In another aspect, the present disclosure relates to the use a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for reducing the proliferation of a cell by reducing IKZF2 protein levels. In some embodiments, IKZF2 protein levels are reduced through degradation of the IKZF2 protein. In some embodiments, IKZF2 protein levels are reduced through degradation of the IKZF2 protein mediated by an E3 ligase.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in reducing the proliferation of a cell by IKZF 2 protein levels. In some embodiments, IKZF2 protein levels are reduced through degradation of the IKZF2 protein. In some embodiments, IKZF2 protein levels are reduced through degradation of the IKZF2 protein mediated by an E3 ligase.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for reducing the proliferation of a cell by reducing IKZF2 protein levels. In some embodiments, IKZF2 protein levels are reduced through degradation of the IKZF2 protein. In some embodiments, IKZF2 protein levels are reduced through degradation of the IKZF2 protein mediated by an E3 ligase.

In another aspect, the disclosure relates to a method of treating, preventing, inhibiting, or eliminating a disease or disorder that is affected by the modulation of IKZF2 and IKZF4 protein levels. The method comprises administering to a patient in need of a treatment for diseases or disorders affected by the modulation of IKZF2 and IKZF4 protein levels an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

Another aspect of the disclosure relates to a method of treating, preventing, inhibiting, or eliminating a disease or disorder that is affected by the reduction of or a decrease in IKZF2 and IKZF4 protein levels. The method comprises administering to a patient in need of a treatment for diseases or disorders affected by the reduction or decrease of IKZF2 and IKZF4 protein levels an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

In another aspect, the disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, in the manufacture of a medicament for the treatment, prevention, inhibition or elimination of a disease or disorder that is affected by the modulation of IKZF2 and IKZF4 protein levels.

Another aspect of the disclosure relates to a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof, for use in the manufacture of a medicament for treating, preventing, inhibiting, or eliminating a disease or disorder that is affected by the modulation of IKZF2 and IKZF4 protein levels.

In another aspect, the disclosure relates to the use a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, in the manufacture of a medicament for the treatment, prevention, inhibition or elimination of a disease or disorder that is affected by the reduction of or a decrease in IKZF2 and IKZF4 protein levels.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for treating, preventing, inhibiting, or eliminating a disease or disorder that is affected by the reduction of or a decrease in IKZF2 and IKZF4 protein levels.

Another aspect of the disclosure relates to a method of degrading IKZF2 and IKZF4. The method comprises administering to a patient in need thereof an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof. In some embodiments, IKZF2 and IKZF4 protein degradation is mediated by an E3 ligase.

In another aspect, the present disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for degrading IKZF2 and IKZF4. In some embodiments, IKZF2 and IKZF4 protein degradation is mediated by an E3 ligase.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the degradation IKZF2 and IKZF4. In some embodiments, IKZF2 and IKZF4 protein degradation is mediated by an E3 ligase.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for degrading IKZF2 and IKZF4. In some embodiments, IKZF2 and IKZF4 protein degradation is mediated by an E3 ligase.

In another aspect, the present disclosure relates to a method of modulating IKZF2 and IKZF4 protein levels through degradation of IKZF2 and IKZF4. In some embodiments, IKZF2 and IKZF4 protein degradation is mediated by an E3 ligase.

Another aspect of the disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for modulating IKZF2 and IKZF4 protein levels through degradation of IKZF2 and IKZF4. In some embodiments, IKZF2 and IKZF4 protein degradation is mediated by an E3 ligase.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the modulation of IKZF2 and IKZF4 protein levels through degradation of IKZF2 and IKZF4. In some embodiments, IKZF2 and IKZF4 protein degradation is mediated by an E3 ligase.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for modulating IKZF2 and IKZF4 protein levels through degradation of IKZF2 and IKZF4. In some embodiments, IKZF2 and IKZF4 protein degradation is mediated by an E3 ligase.

Another aspect of the disclosure relates to a method of treating an IKZF2-dependent and IKZF4-dependent disease or disorder in a patient in need thereof by modulating IKZF2 and IKZF4 protein levels through the degradation of IKZF2 and IKZF4. In some embodiments, IKZF2 and IKZF4 protein degradation is mediated by an E3 ligase.

In another aspect, the present disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for treating an IKZF2-dependent and IKZF4-dependent disease or disorder in a patient in need thereof by modulating IKZF2 and IKZF4 protein levels through the degradation of IKZF2 and IKZF4. In some embodiments, IKZF2 and IKZF4 protein degradation is mediated by an E3 ligase.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in treating an IKZF2-dependent and IKZF4-dependent disease or disorder in a patient in need thereof by modulating IKZF2 and IKZF4 protein levels through the degradation of IKZF2 and IKZF4. In some embodiments, IKZF2 and IKZF4 protein degradation is mediated by an E3 ligase.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for treating an IKZF2-dependent or IKZF4-dependent disease or disorder in a patient in need thereof by modulating IKZF2 and IKZF4 protein levels through the degradation of IKZF2 and IKZF4. In some embodiments, IKZF2 and IKZF4 protein degradation is mediated by an E3 ligase.

In another aspect, the present disclosure relates to a method of degrading IKZF2 and IKZF4. The method comprises administering to a patient in need thereof an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof. In some embodiments, IKZF2 and IKZF4 protein degradation is mediated by an E3 ligase.

Another aspect of the disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for degrading IKZF2 and IKZF4. In some embodiments, IKZF2 and IKZF4 protein degradation is mediated by an E3 ligase.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in degrading IKZF2 and IKZF4. In some embodiments, IKZF2 and IKZF4 protein degradation is mediated by an E3 ligase.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for degrading IKZF2 and IKZF4. In some embodiments, IKZF2 and IKZF4 protein degradation is mediated by an E3 ligase.

Another aspect of the disclosure relates to a method of reducing the proliferation of a cell, the method comprising contacting the cell with a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, and reducing IKZF2 and IKZF4 protein levels. In some embodiments, IKZF2 and IKZF4 protein levels are reduced through degradation of the IKZF2 and IKZF4 proteins. In other embodiments, IKZF2 and IKZF4 protein levels are reduced through degradation of the IKZF2 and IKZF4 proteins mediated by an E3 ligase.

In another aspect, the present disclosure relates to the use a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for reducing the proliferation of a cell by reducing IKZF2 and IKZF4 protein levels. In some embodiments, IKZF2 and IKZF4 protein levels are reduced through degradation of the IKZF2 and IKZF4 proteins. In other embodiments, IKZF2 and IKZF4 protein levels are reduced through degradation of the IKZF2 and IKZF4 proteins mediated by an E3 ligase.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in reducing the proliferation of a cell by reducing IKZF2 and IKZF4 protein levels. In some embodiments, IKZF2 and IKZF4 protein levels are reduced through degradation of the IKZF2 and IKZF4 proteins. In other embodiments, IKZF2 and IKZF4 protein levels are reduced through degradation of the IKZF2 and IKZF4 proteins mediated by an E3 ligase.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for reducing the proliferation of a cell by reducing IKZF2 and IKZF4 protein levels. In some embodiments, IKZF2 and IKZF4 protein levels are reduced through degradation of the IKZF2 and IKZF4 proteins. In other embodiments, IKZF2 and IKZF4 protein levels are reduced through degradation of the IKZF2 and IKZF4 proteins mediated by an E3 ligase.

In another aspect, the present disclosure relates to a method for treating an IKZF2-dependent disease or disorder. The method comprises the step of administering to a subject in need thereof a therapeutically effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the treatment of an IKZF2-dependent disease or disorder.

In another aspect, the present disclosure relates to the use of a compound of Formula (I') or Formula (I), or a pharmaceutically acceptable salt, hydrate, solvate, prodrug, stereoisomer, or tautomer thereof, in the manufacture of a medicament for treating an IKZF2-dependent disease or disorder.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for treating an IKZF2-dependent disease or disorder.

In another aspect, the present disclosure relates to a method for treating an IKZF2-dependent and IKZF4-dependent disease or disorder. The method comprises the step of administering to a subject in need thereof a therapeutically effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the treatment of an IKZF2-dependent and IKZF4-dependent disease or disorder.

In another aspect, the present disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, in the manufacture of a medicament for treating an IKZF2-dependent and IKZF4-dependent disease or disorder.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for treating an IKZF2-dependent and IKZF4-dependent disease or disorder.

In another aspect, the present disclosure relates to a method of reducing IKZF2 protein levels. The method comprises administering to the patient in need thereof a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

Another aspect of the present disclosure relates to a method of reducing IKZF2 and IKZF4 protein levels. The method comprises administering to the patient in need thereof a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

In another aspect, the present disclosure relates to a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof for use in the reduction of IKZF2 protein levels.

Another aspect of the present disclosure relates to a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof for use in the reduction of IKZF2 and IKZF4 protein levels.

In another aspect, the present disclosure relates to the use of a compound of Formula (I') or Formula (I), or a pharmaceutically acceptable salt, hydrate, solvate, prodrug, stereoisomer, or tautomer thereof or a composition, in the manufacture of a medicament for reducing IKZF2 protein levels.

Another aspect of the present disclosure relates to the use of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof, in the manufacture of a medicament for reducing IKZF2 and IKZF4 protein levels.

In another aspect, the present disclosure relates to a method of reducing IKZF2 protein levels, wherein reduction of IKZF2 protein levels treats or ameliorates the disease or disorder. The method comprises administering to the patient in need thereof a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

Another aspect of the present disclosure relates to a method of reducing IKZF2 and IKZF4 protein levels, wherein reduction of IKZF2 and IKZF4 protein levels treats or ameliorates the disease or disorder. The method comprises administering to the patient in need thereof a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

In another aspect, the present disclosure relates to a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof for use in the reduction of IKZF2 protein levels, wherein reduction of IKZF2 protein levels treats or ameliorates the disease or disorder.

Another aspect of the present disclosure relates to a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof for use in the reduction of IKZF2 and IKZF4 protein levels, wherein reduction of IKZF2 and IKZF4 protein levels treats or ameliorates the disease or disorder.

In another aspect, the present disclosure relates to the use of a compound of Formula (I') or Formula (I), or a pharmaceutically acceptable salt, hydrate, solvate, prodrug, stereoisomer, or tautomer thereof or a composition, in the manufacture of a medicament for reducing IKZF2 protein levels, wherein reduction of IKZF2 protein levels treats or ameliorates the disease or disorder.

Another aspect of the present disclosure relates to the use of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof, in the manufacture of a medicament for reducing IKZF2 and IKZF4 protein levels, wherein reduction of IKZF2 and IKZF4 protein levels treats or ameliorates the disease or disorder.

In another aspect, the present disclosure relates to a method of treating a disease or disorder by reducing IKZF2 protein levels, wherein reduction of IKZF2 protein levels treats or ameliorates the disease or disorder. The method comprises administering to the patient in need thereof a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

Another aspect of the present disclosure relates to a method of treating a disease or disorder by reducing IKZF2 and IKZF4 protein levels, wherein reduction of IKZF2 and IKZF4 protein levels treats or ameliorates the disease or disorder. The method comprises administering to the patient in need thereof a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

In another aspect, the present disclosure relates to a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof for use in the treatment of a disease or disorder by reducing IKZF2 protein levels, wherein reduction of IKZF2 protein levels treats or ameliorates the disease or disorder.

Another aspect of the present disclosure relates to a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof for use in the treatment of a disease or disorder by reducing IKZF2 and IKZF4 protein levels, wherein reduction of IKZF2 and IKZF4 protein levels treats or ameliorates the disease or disorder.

In another aspect, the present disclosure relates to the use of a compound of Formula (I') or Formula (I), or a pharmaceutically acceptable salt, hydrate, solvate, prodrug, stereoisomer, or tautomer thereof or a composition, in the manufacture of a medicament for treating a disease or disorder by reducing IKZF2 protein levels, wherein reduction of IKZF2 protein levels treats or ameliorates the disease or disorder.

Another aspect of the present disclosure relates to the use of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof, in the manufacture of a medicament for treating a disease or disorder by reducing IKZF2 and IKZF4 protein levels, wherein reduction of IKZF2 and IKZF4 protein levels treats or ameliorates the disease or disorder.

The compounds of the present disclosure present disclosure can be used for the treatment, of cancers including, but not limited to, liposarcoma, neuroblastoma, glioblastoma, bladder cancer, adrenocortical cancer, multiple myeloma, colorectal cancer, non-small cell lung cancer (NSCLC), triple-negative breast cancer (TNBC), nasopharyngeal cancer (NPC), microsatellite stable colorectal cancer (mss-CRC), thymoma, carcinoid, gastrointestinal stromal tumor (GIST), Human Papilloma Virus-associated cervical, oropharyngeal, penis, anal, thyroid, or vaginal cancer or Epstein-Barr Virus-associated nasopharyngeal carcinoma, gastric cancer, rectal cancer, thyroid cancer, Hodgkin lymphoma or diffuse large B-cell lymphoma. The cancer is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiform, glioma, thyroid cancer, parathyroid tumor, nasopharyngeal cancer, tongue cancer, pancreatic cancer, esophageal cancer, cholangiocarcinoma, gastric cancer, soft tissue sarcomas, rhabdomyosarcoma (RMS), synovial sarcoma, osteosarcoma, rhabdoid cancers, cancer for which the immune response is deficient, an immunogenic cancer, and Ewing's sarcoma.

In some embodiments of the methods above, the IKZF2-dependent disease or disorder is a disease or disorder including, but not limited to, liposarcoma, neuroblastoma, glioblastoma, bladder cancer, adrenocortical cancer, multiple myeloma, colorectal cancer, non-small cell lung cancer, Human Papilloma Virus-associated cervical, oropharyngeal, penis, anal, thyroid, or vaginal cancer or Epstein-Barr Virus-associated nasopharyngeal carcinoma, gastric cancer, rectal cancer, thyroid cancer, Hodgkin lymphoma or diffuse large B-cell lymphoma. The cancer is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiform, glioma, thyroid cancer, parathyroid tumor, nasopharyngeal cancer, tongue cancer, pancreatic cancer, esophageal cancer, cholangiocarcinoma, gastric cancer, soft tissue sarcomas, rhabdomyosarcoma (RMS), synovial sarcoma, osteosarcoma, rhabdoid cancers, cancer for which the immune response is deficient, an immunogenic cancer, and Ewing's sarcoma. In one embodiment, the IKZF2-dependent disease or disorder is a disease or disorder is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, and gastrointestinal stromal tumor (GIST). In another embodiment, the IKZF2-dependent disease or disorder is a disease or disorder is selected from non-small cell lung cancer (NSCLC), melanoma, triple-negative breast cancer (TNBC), nasopharyngeal cancer (NPC), and microsatellite stable colorectal cancer (mssCRC).

In some embodiments of the methods above, the disease or disorder affected by the modulation, reduction or decrease of IKZF2 and/or IKZF4 protein levels is a disease or disorder including, but not limited to, liposarcoma, neuroblastoma, glioblastoma, bladder cancer, adrenocortical cancer, multiple myeloma, colorectal cancer, non-small cell lung cancer, Human Papilloma Virus-associated cervical, oropharyngeal, penis, anal, thyroid, or vaginal cancer or Epstein-Barr Virus-associated nasopharyngeal carcinoma, gastric cancer, rectal cancer, thyroid cancer, Hodgkin lymphoma or diffuse large B-cell lymphoma. The cancer is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiform, glioma, thyroid cancer, parathyroid tumor, nasopharyngeal cancer, tongue cancer, pancreatic cancer, esophageal cancer, cholangiocarcinoma, gastric cancer, soft tissue sarcomas, rhabdomyosarcoma (RMS), synovial sarcoma, osteosarcoma, rhabdoid cancers, cancer for which the immune response is deficient, an immunogenic cancer, and Ewing's sarcoma. In one embodiment, the disease or disorder affected by the modulation, reduction or decrease of IKZF2 and/or IKZF4 protein levels is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, and gastrointestinal stromal tumor (GIST). In another embodiment, the disease or disorder affected by the modulation, reduction or decrease of IKZF2 and/or IKZF4 protein levels is a disease or disorder is selected from non-small cell lung cancer (NSCLC), melanoma, triple-negative breast cancer (TNBC), nasopharyngeal cancer (NPC), and microsatellite stable colorectal cancer (mssCRC).

In some embodiments of the methods above, the IKZF2-dependent cancer and IKZF2-dependent and IKZF4-dependent cancer is a cancer selected from liposarcoma, neuroblastoma, glioblastoma, bladder cancer, adrenocortical cancer, multiple myeloma, colorectal cancer, non-small cell lung cancer, Human Papilloma Virus-associated cervical, oropharyngeal, penis, anal, thyroid, or vaginal cancer or Epstein-Barr Virus-associated nasopharyngeal carcinoma, gastric cancer, rectal cancer, thyroid cancer, Hodgkin lymphoma or diffuse large B-cell lymphoma. The cancer is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiform, glioma, thyroid cancer, parathyroid tumor, nasopharyngeal cancer, tongue cancer, pancreatic cancer, esophageal cancer, cholangiocarcinoma, gastric cancer, soft tissue sarcomas, rhabdomyosarcoma (RMS), synovial sarcoma, osteosarcoma, rhabdoid cancers, cancer for which the immune response is deficient, an immunogenic cancer, and Ewing's sarcoma. In one embodiment, the IKZF2-dependent cancer and IKZF2-dependent and IKZF4-dependent cancer is a cancer selected from non-small cell lung cancer (NSCLC), melanoma, triple-negative breast cancer (TNBC), nasopharyngeal cancer (NPC), microsatellite stable colorectal cancer (mssCRC), thymoma, carcinoid, and gastrointestinal stromal tumor (GIST). In another embodiment, the IKZF2-dependent cancer and IKZF2-dependent and IKZF4-dependent cancer is a cancer selected from non-small cell lung cancer (NSCLC), melanoma, triple-negative breast cancer (TNBC), nasopharyngeal cancer (NPC), and microsatellite stable colorectal cancer (mssCRC).

In some embodiments of the methods above, IKZF2 protein levels are modulated by degradation of IKZF2. In some embodiments of the methods above, IKZF2 protein levels are reduced by degradation of IKZF2. In some embodiments of the methods above, IKZF2 protein levels are decreased by degradation of IKZF2.

In some embodiments of the methods above, IKZF2 and IKZF4 protein levels are modulated by degradation of IKZF2 and IKZF4. In some embodiments of the methods above, IKZF2 and IKZF4 protein levels are reduced by degradation of IKZF2 and IKZF4. In some embodiments of the methods above, IKZF2 protein levels are decreased by degradation of IKZF2 and IKZF4.

One therapeutic use of the compounds or compositions of the present disclosure, which modulate IKZF2 and/or IKZF4 protein levels by degradation of IKZF2 and/or IKZF4, is to provide treatment to patients or subjects suffering from cancer and metastasis.

The disclosed compounds of the disclosure can be administered in effective amounts to treat or prevent a disorder and/or prevent the development thereof in subjects.

Compounds of the application can be administered in therapeutically effective amounts in a combinational therapy with one or more therapeutic agents (pharmaceutical combinations) or modalities, e.g., non-drug therapies. For example, synergistic effects can occur with other antiproliferative, anti-cancer, immunomodulatory or anti-inflammatory substances. Where the compounds of the application are administered in conjunction with other therapies, dosages of the co-administered compounds will of course vary depending on the type of co-drug employed, on the specific drug employed, on the condition being treated and so forth.

Combination therapy includes the administration of the subject compounds in further combination with other biologically active ingredients (such as, but not limited to, a second and different antineoplastic agent or a second agent that targets Helios or another cancer target) and non-drug therapies (such as, but not limited to, surgery or radiation treatment). For instance, the compounds of the application can be used in combination with other pharmaceutically active compounds, preferably compounds that are able to enhance the effect of the compounds of the application. The compounds of the application can be administered simultaneously (as a single preparation or separate preparation) or sequentially to the other drug therapy or treatment modality. In general, a combination therapy envisions administration of two or more drugs during a single cycle or course of therapy.

G. Administration, Pharmaceutical Compositions, and Dosing of Compounds of Formula (I')

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising a compound of the disclosure and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride, and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes, and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles, and multilamellar vesicles. Liposomes can be formed from a variety of phospholipids, containing cholesterol, stearylamine or phosphatidylcholines.

In some embodiments, a film of lipid components is hydrated with an aqueous solution of drug to a form lipid layer encapsulating the drug, as described in U.S. Pat. No. 5,262,564 which is hereby incorporated by reference in its entirety.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates, and cross-linked or amphipathic block copolymers of hydrogels. In one embodiment, disclosed compounds are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the disclosure is directed to pharmaceutical compositions comprising a compound of Formula (I') and a pharmaceutically acceptable carrier. The pharmaceutical acceptable carrier may further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

In one embodiment, the disclosure provides a kit comprising two or more separate pharmaceutical compositions, at least one of which contains a compound of the present disclosure. In one embodiment, the kit comprises means for separately retaining said compositions, such as a container, divided bottle, or divided foil packet. An example of such a kit is a blister pack, as typically used for the packaging of tablets, capsules and the like.

The kit of the disclosure may be used for administering different dosage forms, for example, oral and parenteral, for administering the separate compositions at different dosage intervals, or for titrating the separate compositions against one another. To assist compliance, the kit of the disclosure typically comprises directions for administration.

The dosage regimen utilizing the disclosed compound is selected in accordance with a variety of factors including type, species, age, weight, sex, and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Compounds of the present disclosure may be prepared by methods known in the art of organic synthesis. In all of the methods it is understood that protecting groups for sensitive or reactive groups may be employed where necessary in accordance with general principles of chemistry. Protecting groups are manipulated according to standard methods of organic synthesis (T. W. Green and P. G. M. Wuts (1999) Protective Groups in Organic Synthesis, 3rd edition, John Wiley & Sons). These groups are removed at a convenient stage of the compound synthesis using methods that are readily apparent to those skilled in the art.

Analytical Methods, Materials, and Instrumentation

Unless otherwise noted, reagents and solvents were used as received from commercial suppliers.

Proton nuclear magnetic resonance (NMR) spectra were obtained on either Bruker Avance spectrometer or Varian Oxford 400 MHz spectrometer unless otherwise noted. Spectra are given in ppm (δ) and coupling constants, J, are reported in Hertz. Tetramethylsilane (TMS) was used as an internal standard. Chemical shifts are reported in ppm relative to dimethyl sulfoxide (δ 2.50), methanol (δ 3.31), chloroform (δ 7.26) or other solvent as indicated in NMR spectral data. A small amount of the dry sample (2-5 mg) is dissolved in an appropriate deuterated solvent (1 mL). The chemical names were generated using ChemBioDraw Ultra v12 from CambridgeSoft.

Mass spectra (ESI-MS) were collected using a Waters System (Acquity UPLC and a Micromass ZQ mass spectrometer) or Agilent-1260 Infinity (6120 Quadrupole); all masses reported are the m/z of the protonated parent ions unless recorded otherwise. The sample was dissolved in a suitable solvent such as MeCN, DMSO, or MeOH and was injected directly into the column using an automated sample handler. The analysis is performed on Waters Acquity UPLC system (Column: Waters Acquity UPLC BEH C18 1.7 μm, 2.1×30 mm; Flow rate: 1 mL/min; 55° C. (column temperature); Solvent A: 0.05% formic acid in water, Solvent B: 0.04% formic acid in MeOH; gradient 95% Solvent A from 0 to 0.10 min; 95% Solvent A to 20% Solvent A from 0.10 to 0.50 min; 20% Solvent A to 5% Solvent A from 0.50 to 0.60 min; hold at 5% Solvent A from 0.6 min to 0.8 min; 5% Solvent A to 95% Solvent A from 0.80 to 0.90 min; and hold 95% Solvent A from 0.90 to 1.15 min.

Abbreviations used in the following examples and elsewhere herein are:

AIBN azobisisobutyronitrile
Bn benzyl
br broad
Bu$_4$NI tetrabutylammonium iodide
d doublet
dd doublet of doublets
ddd doublet of doublet of doublets
ddq doublet of doublet of quartets
ddt doublet of doublet of triplets
dq doublet of quartets
dt doublet of triplets
dtd doublet of triplet of doublets
CCl$_4$ carbon tetrachloride
Cs$_2$CO$_3$ cesium carbonate
Cu(OAc)$_2$ copper (II) acetate
DCM dichloromethane
di-tBu-bipy 4,4'-di-tert-butyl-2,2'-dipyridyl
DIBAL-H Diisobutylaluminium hydride
DMA N,N-dimethylacetamide
DMAP 4-dimethylaminopyridine
DME 1,2-Dimethoxyethane
DMF N,N-dimethylformamide
DMP Dess-Martin periodinane or 1,1,1-Tris(acetyloxy)-1,1-dihydro-1,2-benziodoxol-3-(1H)-one
DMSO dimethylsulfoxide
EC$_{50}$ half maximal effective concentration
Et$_2$O diethyl ether
EtOAc ethyl acetate
4-Et-Py 4-ethylpyridine
HATU 1-[Bis(dimethylamino)methylene]-1H-1,2,3-triazolo[4,5-b]pyridinium 3-oxid hexafluorophosphate
HCl hydrogen chloride
hept heptet
HPLC high performance liquid chromatography
h or hr hour
HRMS high resolution mass spectrometry
g gram
IC$_{50}$ half maximal inhibitory concentration
K$_2$CO$_3$ potassium carbonate
KI potassium iodide
K$_3$PO$_4$ tripotassium phosphate
KOAc potassium acetate
LiAlH$_4$ Lithium aluminum hydride
LCMS liquid chromatography mass spectrometry
LiHMDS Lithium bis(trimethylsilyl)amide
m multiplet MeCN acetonitrile
MeOH methanol
mg milligram
MgCl$_2$ magnesium chloride
MHz megahertz
min minutes
mL milliliter
mmol millimole
M molar
MS mass spectrometry
NaBH(OAc)$_3$ sodium triacetoxyborohydride
NaHCO$_3$ sodium bicarbonate
Na$_2$SO$_4$ sodium sulfate
NBS N-bromosuccinimide
NEt$_3$ triethylamine
NH$_4$OAc ammonium acetate
NH$_4$OH ammonium hydroxide
NiBr$_2$(DME) nickel (II) bromide ethylene glycol dimethyl ether complex
NiBr$_2$(glyme) nickel (II) bromide ethylene glycol dimethyl ether complex
NiI$_2$ nickel (II) iodide
NMR Nuclear magnetic resonance
PCC Pyridinium chlorochromate
PdCl$_2$(dppf)$_2$ [1,1'-Bis(diphenylphosphino)ferrocene]palladium(II) dichloride
PdCl$_2$(dppf)*DCM [1,1'-Bis(diphenylphosphino)ferrocene]dichloropalladium(II), complex with dichloromethane\Pd(Ph$_3$P)$_4$ tetrakis(triphenylphosphine)palladium(0)
PtO$_2$ platinum (IV) oxide
q quartet
qd quartet of doublets
quint quintet
quintd quintet of doublets
rt room temperature
Rt retention time
s singlet
SFC supercritical fluid chromatography
t triplet
TEA triethylamine
td triplet of doublets
tdd triplet of doublet of doublets
THF tetrahydrofuran
Ti(Oi-Pr)$_4$ titanium isopropoxide
TfOH triflic acid
Ts tosyl
TsCl 4-toluenesulfonyl chloride
tt triplet of triplets
ttd triplet of triplet of doublets
TLC thin-layer chromatography
UPLC ultra-Performance Liquid Chromatography
Xphos Pd G2 chloro(2-dicyclohexylphosphino-2',4',6'-triisopropyl-1,1'-biphenyl)[2-(2'-amino-1,1'-biphenyl)]palladium(II)
μW microwave Example 1: 3-(1-oxo-5-(piperidin-4-yl)isoindolin-2-yl)piperidine-2,6-dione (I-155)

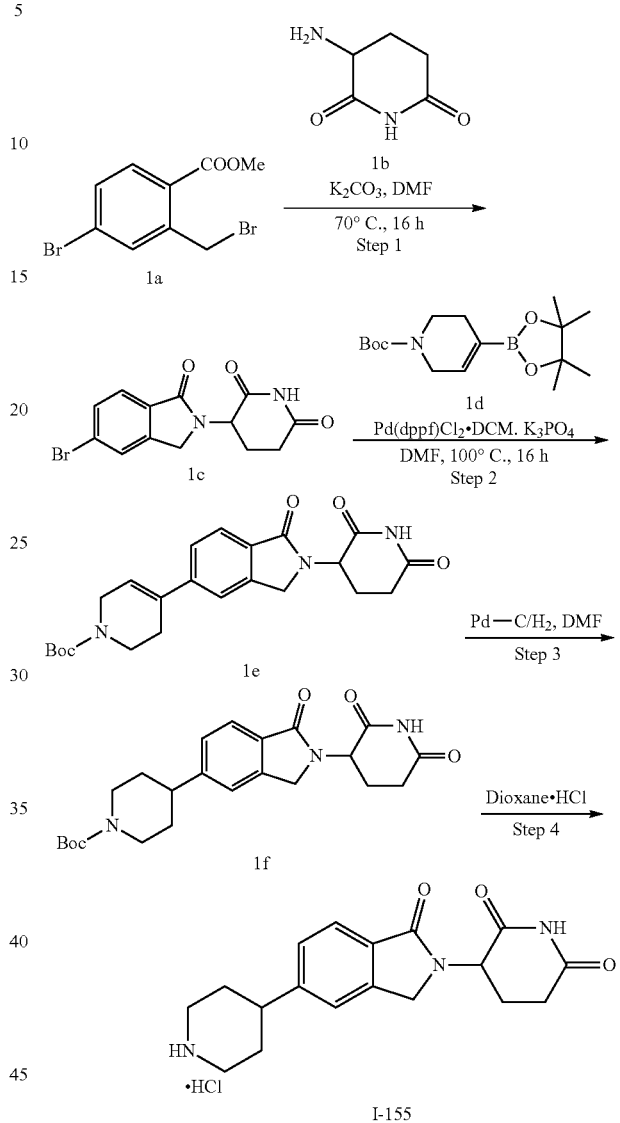

Intermediate 1a was prepared as reported in U.S. Patent Application US 2009/0142297.

To a stirred solution of methyl 4-bromo-2-(bromomethyl)benzoate (1a, 15 g, 48.7 mmol) in DMF (150 mL) was added 3-aminopiperidine-2,6-dione-HCl (1b, 6.9 g, 53.6 mmol) and K$_2$CO$_3$ (20.2 g, 146.1 mmol). The resulting mixture was heated at 70° C. for 16 h after which time the reaction mixture was cooled to rt and then concentrated to dryness. To the resulting residue, water was added and the mixture stirred at rt for 30 min. The resultant solid was filtered and washed with ether and ethyl acetate. The solid was dried under vacuum filtration to afford 1c (10.6 g, 32.9 mmol, 67% yield). MS [M+H]$^+$=323.0. $^1$H NMR (400 MHz, DMSO-d$_6$) δ 10.99 (s, 1H), 7.91-7.88 (m, 1H), 7.72 (dd, J=8.1, 1.6 Hz, 1H), 7.67 (d, J=8.0 Hz, 1H), 5.11 (dd, J=13.3, 5.1 Hz, 1H), 4.47 (d, J=17.7 Hz, 1H), 4.34 (d, J=17.7 Hz, 1H), 2.98-2.83 (m, 1H), 2.65-2.55 (m, 1H), 2.45-2.29 (m, 1H), 2.01 (dtd, J=12.7, 5.3, 2.3 Hz, 1H).

Step 2. tert-Butyl-4-(2-(2,6-dioxopiperidin-3-yl)-1-oxoisoindolin-5-yl)-3,6-dihydropyridine-1(2H)-carboxylate (1e)

A solution of 1c (1.8 g, 5.6 mmol) in DMF (10 mL) in a sealed tube was purged with argon for 5 min prior to addition of 3,6-dihydro-2H-pyridine-1-tert-butoxycarbonyl-4-boronic acid pinacol ester (1d, 2.2 g, 7.2 mmol), K₃PO₄ (1.42 g, 6.7 mmol) and Pd(dppf)Cl₂.DCM (227 mg, 0.28 mmol). The reaction mixture was again purged with argon for 5 min and then heated at 90° C. for 16 h. After this time the reaction mixture was cooled to rt and then concentrated under reduced pressure. Water was added to the residue which was then extracted with EtOAc. The organic layer was washed with brine, dried over Na₂SO₄, filtered, and then concentrated under a reduced pressure. The crude compound was purified by silica gel chromatography, eluting with 70-80% of EtOAc in hexanes, to afford 1e as a light brown solid (1.0 g, 2.4 mmol, 42% yield). MS [M+H]+=426.3.

Step 3. tert-Butyl 4-(2-(2,6-dioxopiperidin-3-yl)-1-oxoisoindolin-5-yl)piperidine-1-carboxylate (1f)

To a stirred solution of 1e (1.0 g, 2.35 mmol) in DMF (20 mL) was added 10% Pd/C (150 mg) and the mixture was stirred under a hydrogen atmosphere (balloon) at rt for 6 h. The reaction mixture was then filtered through a bed of Celite® R filter aid. The filtrate was concentrated under reduced pressure affording 1f as an off-white solid (0.85 g, 1.97 mmol, 84% yield). MS [M-tBu]+=372.3. ¹H NMR (400 MHz, CDCl₃) δ 8.40 (s, 1H), 7.81 (d, J=7.9 Hz, 1H), 7.32 (d, J=8.0 Hz, 1H), 7.29 (s, 1H), 5.22 (dd, J=13.3, 5.1 Hz, 1H), 4.46 (d, J=16.0 Hz, 1H), 4.31 (d, J=16.1 Hz, 1H), 4.27 (d, J=16.2 Hz, 2H), 2.97-2.67 (m, 5H), 2.41-2.26 (m, 1H), 2.23-2.13 (m, 1H), 1.83 (d, J=12.6 Hz, 2H), 1.71-1.55 (m, 2H), 1.48 (s, 9H).

Step 4. 3-(1-oxo-5-(piperidin-4-yl)isoindolin-2-yl)piperidine-2,6-dione hydrochloride (I-155)

To a stirred solution of 1f (0.85 g, 2.0 mmol) in dioxane (10 mL) was added 4N HCl in dioxane (5.0 mL). The reaction mixture was then stirred at rt for 2 h. The reaction mass was concentrated under reduced pressure to afford the HCl salt of desired compound I-155 as an off-white solid (0.65 g, 1.8 mmol, 90% yield, hydrochloride salt). MS [M+H]+=328.3. ¹H NMR (400 MHz, DMSO-d6): δ 10.99 (s, 1H), 9.28 (s, 1H), 7.70 (d, J=7.8 Hz, 1H), 7.46 (s, 1H), 7.39 (d, J=8.0 Hz, 1H), 5.74 (s, 1H), 5.11 (dd, J=13.3, 5.2 Hz, 1H), 4.46 (d, J=17.3 Hz, 1H), 4.32 (d, J=17.3 Hz, 1H), 3.36 (d, J=11.5 Hz, 2H), 3.10-2.86 (m, 4H), 2.61 (d, J=14.8 Hz, 1H), 2.39 (qd, J=13.2, 4.3 Hz, 1H), 2.14-1.79 (m, 5H).

Conversion of 1c to 1f was also achieved in a single step via Negishi coupling using the following procedure:

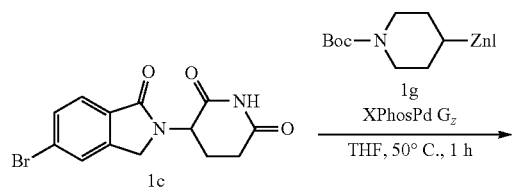

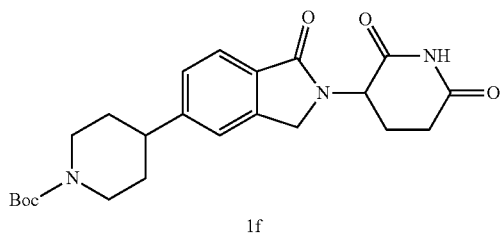

1-(tert-butoxycarbonyl)piperidin-4-yl)zinc(II) iodide (1 g) was prepared as reported in Corley, E. G., et al., *J. Org. Chem.* 2004, 69, 5120.

A mixture of 1c (41 mg, 0.125 mmol) and XPhos Pd cycle G2 (15 mg, 0.019 mmol) in THF (1.5 mL) was purged with nitrogen prior to addition of (1-(tert-butoxycarbonyl)piperidin-4-yl)zinc(II) iodide (1 g, 0.142 mg, 0.376 mmol) in THF (0.7 mL). The resulting mixture was heated to 50° C. for 1 h after which time the reaction was cooled to rt, quenched with brine, and extracted with EtOAc. The organic layer was passed through a phase separator and concentrated. The crude material was purified by silica gel chromatography (eluting with 0-100% EtOAc in heptane) to afford 1f as a white solid (30 mg, 0.070 mmol, 56% yield).

Alternatively, Conversion of 1c to 1f was Also Achieved in a Single Step Via the Following Reductive Cross-Coupling Procedure:

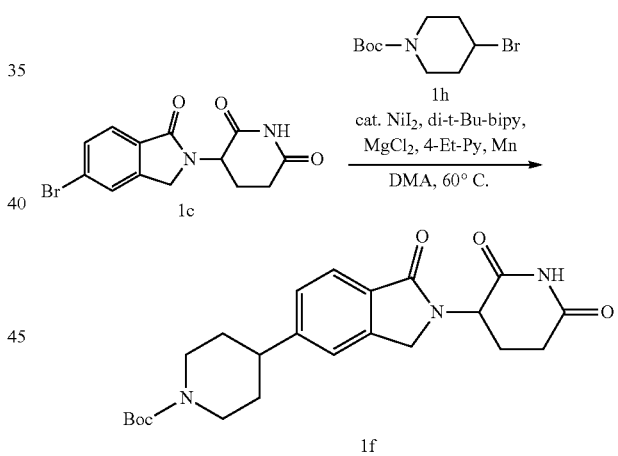

To a mixture of 1c (934 mg, 2.89 mmol), tert-butyl 4-bromopiperidine-1-carboxylate (1 h, 1530 mg, 5.80 mmol), NiI₂ (90 mg, 0.289 mmol), di-t-Bu-bipy (78 mg, 0.289 mol), MgCl₂ (275 mg, 2.89 mmol), and manganese powder (317 mg, 5.78 mmol) in DMA (5 mL) was added 4-ethylpyridine (0.33 mL, 2.89 mmol) and the reaction mixture was stirred vigorously for 18 h at 60° C. The reaction mixture was filtered through a short pad of Celite® filter aid and eluted with EtOAc. The obtained solution was then concentrated by azeotroping with heptane. The crude product was purified via chromatography on silica gel eluting with MeOH in DCM to afford 1f (285 mg, 0.653 mmol, 23% yield) as a white solid.

Conversion of 1c to 1f was Also Achieved in a Single Step Via an Alternative Reductive Cross-Coupling Procedure:

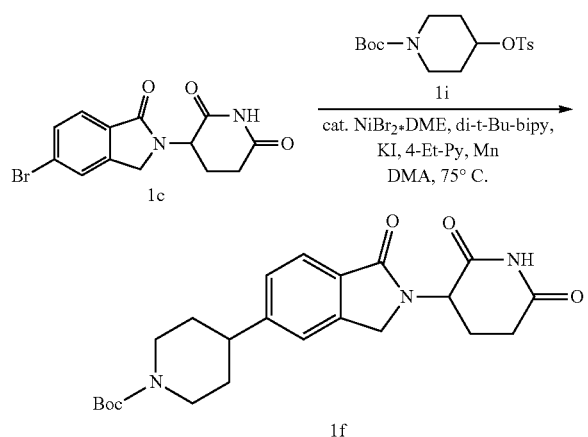

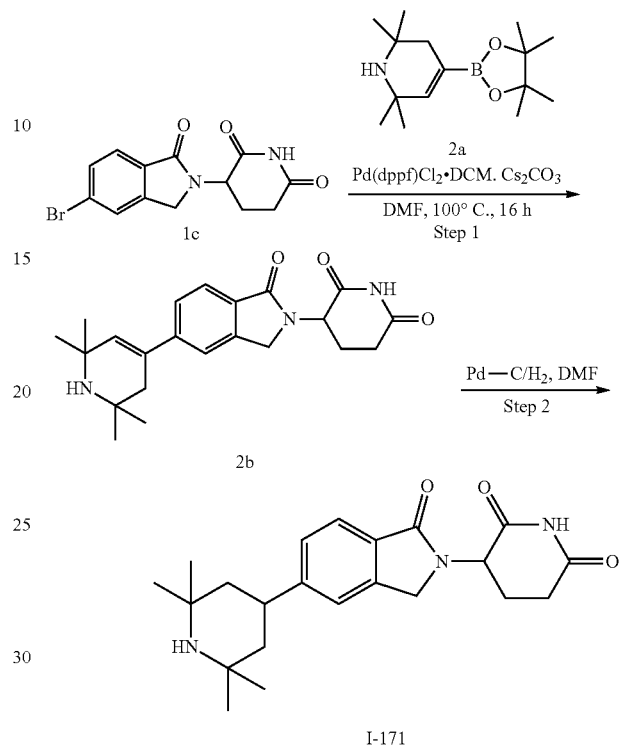

Example 2: 3-(1-oxo-5-(2,2,6,6-tetramethylpiperidin-4-yl)isoindolin-2-yl)piperidine-2,6-dione (I-171)

Step 1: 3-(1-oxo-5-(2,2,6,6-tetramethyl-1,2,3,6-tetrahydropyridin-4-yl)isoindolin-2-yl)piperidine-2,6-dione (2b)

A stirred solution of 1c (150 mg, 0.46 mmol) in DMF (5 mL) in a sealed tube was purged with argon for 5 min prior to the addition of 2,2,6,6-tetramethyl-4-(4,4,5,5-tetramethyl-1,3,2-dioxaborolan-2-yl)piperidine (2a, 185 mg, 0.69 mmol), $Cs_2CO_3$ (300 mg, 0.92 mmol), and Pd(dppf) $Cl_2$.DCM (19 mg, 0.02 mmol) and the resulting mixture was again purged with argon for 5 min. The reaction mixture was then heated at 90° C. for 5 h after which time the reaction mixture was cooled to rt, water was added, and was extracted with EtOAc. The organic layer was washed with brine, dried over $Na_2SO_4$, filtered, and then concentrated under reduced pressure. The crude material was purified by silica gel chromatography (eluting with 15% MeOH/DCM) to afford 2b as a brown solid (35 mg, 0.092 mmol, 20% yield). MS $[M+H]^+$=382.3.

To crude 1c (84% pure, 34 mg, 0.088 mmol), tert-butyl 4-(tosyloxy)piperidine-1-carboxylate (1i, 38 mg, 0.11 mmol), $NiBr_2$.DME (2.7 mg, 8.8 μmol), di-t-Bu-bipy (2.4 mg, 8.8 μmol), KI (15 mg, 0.09 mmol) and manganese powder (10 mg, 0.18 mmol) in DMA (0.50 mL) was added 4-ethylpyridine (10 μL, 0.088 mmol) and the reaction mixture was stirred vigorously at 75° C. for 5 h. The reaction mixture was filtered through a short pad of Celite® filter aid and eluted with MeCN. The obtained solution was concentrated by azeotroping with heptane. The crude product was purified via chromatography on silica gel eluting with MeOH in DCM to afford 1f (21.7 mg, 0.051 mmol, 57% yield) as a white solid.

In a Similar Fashion, Intermediate 1f could be Obtained from Intermediate 29d, (the Route for Synthesis of 29d is Outlined in Example 29):

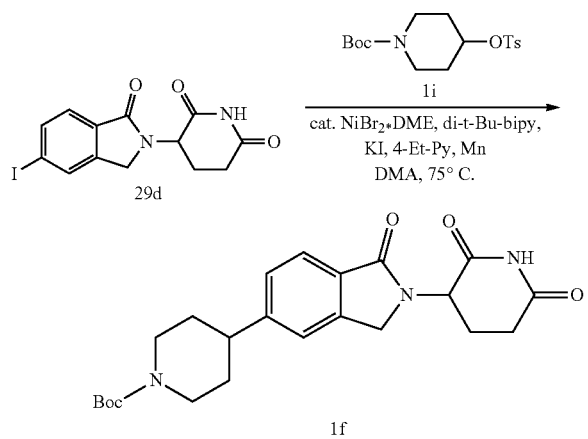

To 29d (48 mg, 0.13 mmol), tert-butyl 4-(tosyloxy)piperidine-1-carboxylate (1i, 55 mg, 0.16 mmol), $NiBr_2$.DME (4.0 mg, 0.013 mmol), di-t-Bu-bipy (3.5 mg, 0.013 mmol), KI (22 mg, 0.13 mmol) and manganese powder (14 mg, 0.26 mmol) in DMA (0.67 mL) was added 4-ethylpyridine (0.015 mL, 0.14 mmol) and the reaction mixture was stirred vigorously at 80° C. for 5 h. The reaction mixture was filtered through a short pad of Celite® filter aid and eluted with MeCN. The obtained solution was concentrated by azeotroping with heptane. The crude product was purified via chromatography on silica gel eluting with MeOH in DCM to afford 1f (33.3 mg, 0.078 mmol, 60% yield) as a white solid.

Step 2. 3-(1-oxo-5-(2,2,6,6-tetramethylpiperidin-4-yl)isoindolin-2-yl)piperidine-2,6-dione (I-171)

To a stirred solution of 3-(1-oxo-5-(2,2,6,6-tetramethyl-1,2,3,6-tetrahydropyridin-4-yl)isoindolin-2-yl)piperidine-2,6-dione (2b, 25 mg, 0.07 mmol) in DMF (2 mL) was added Pd/C (5 mg). The resulting mixture was stirred under a hydrogen atmosphere (balloon) at rt for 5 h. The reaction mixture was then filtered through a Celite® filter aid pad and the filtrate was concentrated to dryness. The crude material was purified by reverse phase HPLC (MeCN/$H_2O$ with 0.05% formic acid). The fractions containing the desired product were collected and concentrated to dryness affording I-171 as an off-white solid (11 mg, 0.03 mmol, 44% yield). MS [M+H]⁺=384.4. $^1$H NMR (600 MHz, DMSO-d6): δ 11.0 (s, 1H), 8.33-8.32 (m, 1H), 7.68 (d, J=8.0 Hz, 1H), 7.5 (s, 1H), 7.43 (d, J=8.4 Hz, 1H), 5.12 (dd, J=13.2, 4.8 Hz, 1H), 4.36 (d, J=17.4 Hz, 1H), 4.31 (d, J=17.4 Hz, 1H), 2.95-2.90 (m, 1H), 2.43-2.39 (m, 2H), 2.00-1.99 (m, 2H), 1.54-1.50 (m, 2H), 1.52-1.50 (m, 2H), 1.26 (s, 6H), 1.23 (s, 6H).

Example 3: Diastereomers of 3-(5-(1-benzylazepan-4-yl)-1-oxoisoindolin-2-yl)piperidine-2,6-dione (I-190) and (I-273)

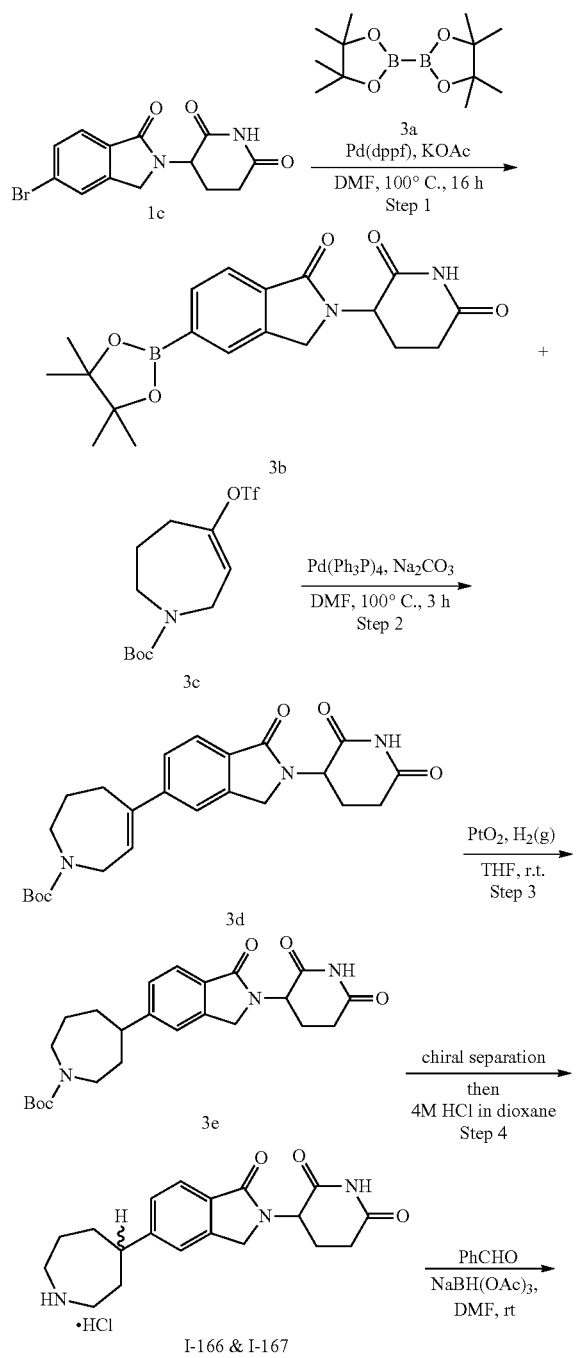

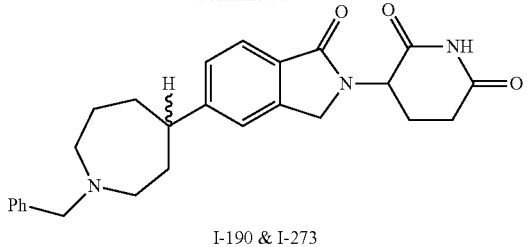

I-190 & I-273

Step 1: 3-(1-oxo-5-(4,4,5,5-tetramethyl-1,3,2-dioxaborolan-2-yl)isoindolin-2-yl)piperidine-2,6-dione (3b)

To a stirred solution of Ic (3.0 g, 9.28 mmol) in DMF (20 mL) in a sealed tube was added bis(pinacolato)diboron (3a, 2.6 g, 10.2 mmol), KOAc (2.37 g, 27.9 mmol), and PdCl₂(dppf)₂ (0.22 g, 0.28 mmol). The reaction mixture was purged with argon for 5 min, sealed, and then heated at 100° C. for 16 h. Water was added to the reaction mixture and stirred at rt for 15 min. The solid was precipitated, filtered, and dried under vacuum to afford 3b as brown solid (2.3 g, 6.2 mmol, 66% yield). MS [M+H]⁺=371.0.

Step 2: tert-butyl 5-(2-(2,6-dioxopiperidin-3-yl)-1-oxoisoindolin-5-yl)-2,3,4,7-tetrahydro-1H-azepine-1-carboxylate (3d)

tert-Butyl 5-(((trifluoromethyl)sulfonyl)oxy)-2,3,4,7-tetrahydro-1H-azepine-1-carboxylate 3c was prepared as reported in PCT Application Publication No. 2007/111904.

To a stirred solution of 3b (1.0 g, 2.70 mmol) in DMF (10.0 mL) in a sealed tube was added tert-butyl 5-(((trifluoromethyl)sulfonyl)oxy)-2,3,4,7-tetrahydro-1H-azepine-1-carboxylate (3c, 1.19 g, 3.24 mmol), Pd(PPh₃)₄(0.16 g, 0.13 mmol), and Na₂CO₃ (0.85 g, 8.10 mmol). The mixture was purged with argon for 5 min and then sealed and heated at 100° C. for 3 h. After this time, the reaction was cooled and water added prior to extraction with EtOAc. The organic layer was dried over Na₂SO₄, filtered, concentrated under reduced pressure, and purified by silica gel chromatography (eluting with 60-70% EtOAc/hexanes) to afford 3d as a brown solid (350 mg, 0.796 mmol, 29% yield). MS [M+H]⁺=440.0.

Step 3: tert-butyl 4-(2-(2,6-dioxopiperidin-3-yl)-1-oxoisoindolin-5-yl)azepane-1-carboxylate (3e)

To a stirred solution of 3d (0.35 g, 0.80 mmol) in THF (10 mL) was added PtO₂ (100 mg). The mixture was stirred under hydrogen balloon for 5 h. The reaction mixture was then filtered on a bed of Celite® filter aid and then concentrated under reduced pressure. The resulting residue was purified by silica gel chromatography (eluting with 40-50% EtOAc/hexane) to afford 3e as a white solid consisting of a mixture of diastereomers (0.31 g, 0.70 mmol, 88% yield). MS [M+H]⁺=442.0.

Step 4a: Chiral Separation of tert-butyl 4-(2-(2,6-dioxopiperidin-3-yl)-1-oxoisoindolin-5-yl)azepane-1-carboxylate (3e)

Chiral separation of 3e (350 mg) was performed using a Kinetex (150 mm×21 mm), 5.0 g column, with eluent consisting of mobile phase A=0.05% TFA in water; mobile phase B=acetonitrile and a flow rate of 20 mL/min at 25° C. with 20-70% mobile phase B: mobile phase A over 20 min. Under these conditions two compounds were isolated 3e (peak 1) Rt=11.64 min and 3e (peak 2) Rt=17.41 min). The fractions corresponding to peak 1 and peak 2 were collected and concentrated under reduced pressure then neutralized with aqueous saturated NaHCO$_3$ solution prior to extraction with DCM. The organic layers were combined, dried over Na$_2$SO$_4$, filtered, and concentrated to dryness affording peak 1 (50 mg) and peak 2 (45 mg) as white solids. MS [M+H]$^+$=442.0.

Step 4b: 3-(5-(azepan-4-yl)-1-oxoisoindolin-2-yl)piperidine-2,6-dione (I-166 & I-167)

To a stirred solution of 3e (peak 1) (50 mg, 0.113 mmol) in dioxane (2.0 mL) at 0° C. was added 4M HCl in dioxane (0.5 mL). The reaction was then allowed to stir and warm up to rt over 2 h. The reaction mixture was then concentrated under reduced pressure to afford diastereomer A as a white solid (40 mg, 0.106 mmol, 94%, hydrochloride salt). MS [M+H]$^+$=342.3. $^1$H NMR (CD$_3$OD, 300 MHz): δ 7.74 (d, J=8.1 Hz, 1H), 7.49 (1H, s), 7.43 (d, J=8.4 Hz, 1H), 5.14 (dd, J=13.5, 5.1 Hz, 1H), 4.48-4.46 (m, 2H), 3.74-3.71 (m, 1H), 3.68-3.63 (m, 2H), 3.59-3.55 (m, 1H), 3.44-3.37 (m, 2H), 3.02 (m, 1H), 2.90-2.78 (m, 2H), 2.51-2.47 (m, 1H), 2.16-2.08 (m, 5H), 2.00-1.80 (m, 2H).

To a stirred solution of 3e (peak 2) (40 mg, 0.091 mmol) in dioxane (2.0 mL) at 0° C. was added 4M HCl in dioxane (0.5 mL). The reaction was then allowed to stir and warm up to rt over 2 h. The reaction mixture was then concentrated under reduced pressure to afford diastereomer B as a white solid (30 mg, 0.079 mmol, 87% yield, hydrochloride salt). MS [M+H]$^+$=342.4. $^1$H NMR (CD$_3$OD, 300 MHz): δ 7.74 (d, J=7.5 Hz, 1H), 7.49 (s, 1H), 7.42 (d, J=7.8 Hz, 1H), 5.15 (dd, J=13.5, 5.1 Hz, 1H), 4.47-4.45 (d, 2H), 3.74-3.71 (m, 1H), 3.67-3.62 (m, 3H), 3.58-3.55 (m, 1H), 3.43-3.38 (m, 2H), 3.02 (m, 1H), 2.90-2.78 (m, 2H), 2.51-2.48 (m, 1H), 2.17-2.08 (m, 5H), 2.09-1.87 (m, 1H).

Step 5. Diastereomers of 3-(5-(1-benzylazepan-4-yl)-1-oxoisoindolin-2-yl)piperidine-2,6-dione (I-190 and I-273)

Compound I-190 was prepared from I-166 (80 mg, 0.21 mmol) and benzaldehyde (27 mg, 0.25 mmol) via reductive amination as described for Example 8. After complete consumption of starting materials, the crude reaction mixture was concentrated under reduced pressure and sat. aq. NaHCO$_3$ was added. The resulting mixture was extracted with DCM and the organic layer was dried over Na$_2$SO$_4$, filtered, and concentrated to dryness. The resulting solid was washed with ether (5 mL) and EtOAc (0.1 mL) affording I-190 as an off-white solid (55 mg, 0.13 mmol, 60% yield). Absolute stereochemistry is not known and was arbitrarily assigned. MS [M+H]+=439.1. $^1$H NMR (CD$_3$OD, 600 MHz): δ 7.69 (d, J=5.2 Hz, 1H), 7.44 (s, 1H), 7.39-7.36 (m, 3H), 7.32-7.30 (m, 2H), 7.26-7.24 (m, 1H), 5.12 (dd, J=8.8, 3.2 Hz, 1H), 4.47 (d, J=11.6 Hz, 1H), 4.41 (d, J=11.2 Hz, 1H), 3.71 (2H, s), 2.98-2.97 (m, 1H), 2.92-2.86 (m, 2H), 2.80-2.74 (m, 4H), 2.47-2.45 (m, 1H), 2.16-2.14 (m, 1H), 1.94-1.84 (m, 1H), 1.80 (m, 1H).

Compound I-273 was prepared from I-167 (80 mg, 0.21 mmol) and benzaldehyde (27 mg, 0.25 mmol) in a similar manner as describe above for I-190. I-273 was isolated as an off-white solid (55 mg, 0.13 mmol, 60% yield). Absolute stereochemistry is not known and was arbitrarily assigned. MS [M+H]$^+$=439.1. $^1$H NMR (DMSO-d$_6$, 400 MHz): δ 11.0 (1H, s), 7.62 (d, J=5.2 Hz, 1H), 7.46 (s, 1H), 7.38-7.32 (m, 5H), 7.24-7.23 (m, 1H), 5.09 (dd, J=8.8, 3.6 Hz, 1H), 4.31 (d, J=11.6 Hz, 1H), 4.28 (d, J=11.6 Hz, 1H), 3.65 (d, J=9.1 Hz, 1H), 3.63 (d, J=9.2 Hz, 1H), 2.96-2.88 (m, 2H), 2.76-2.69 (m, 1H), 2.67-2.62 (m, 3H), 2.61-2.50 (m, 2H), 2.46-2.36 (m, 3H), 1.99 (m, 2H), 1.82 (m, 2H).

Example 4: 3-(5-(1-methyl-1,2,3,6-tetrahydropyridin-4-yl)-1-oxoisoindolin-2-yl)piperidine-2,6-dione (I-163)

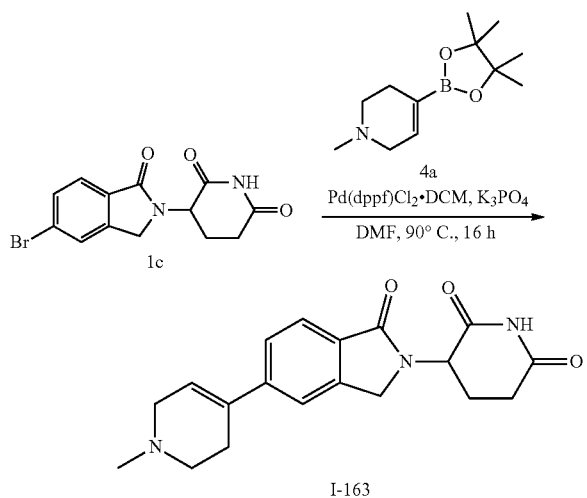

A stirred solution of 1c (50 mg, 0.22 mmol) in DMF (3.0 mL) in a sealed tube was purged with argon for 5 min prior to the addition of 1-methyl-4-(4,4,5,5-tetramethyl-1,3,2-dioxaborolan-2-yl)-1,2,3,6-tetrahydropyridine (4a, 55 mg, 0.24 mmol), K$_3$PO$_4$ (94 mg, 0.44 mmol), and Pd(dppf)Cl$_2$.DCM (9 mg, 0.011 mmol). The resulting mixture was then purged with argon for 5 min and then heated to 90° C. for 16 h. The reaction mixture was cooled to rt and then concentrated under reduced pressure. The crude material was purified by preparative TLC eluting with 10% MeOH/DCM to afford I-163 as an off white solid (9.0 mg, 0.03 mmol, 12% yield). MS [M+H]$^+$=340.3. $^1$H NMR (DMSO-d$_6$, 400 MHz): δ 7.68 (d, J=8.0 Hz, 1H), 7.63 (s, 1H), 7.58 (d, J=9.2 Hz, 1H), 6.28 (brs, 1H), 5.00 (dd, J=13.2 Hz, 5.2 Hz, 1H), 4.45 (d, J=17.6 Hz, 1H), 4.31 (d, J=17.6 Hz, 1H), 3.07 (brs, 2H), 2.68-2.60 (m, 4H), 2.35-2.32 (m, 2H), 2.27 (s, 3H) 2.06-1.99 (m, 1H).

Example 5: methyl 2-(4-(2-(2,6-dioxopiperidin-3-yl)-1-oxoisoindolin-5-yl)piperidin-1-yl)acetate (I-169)

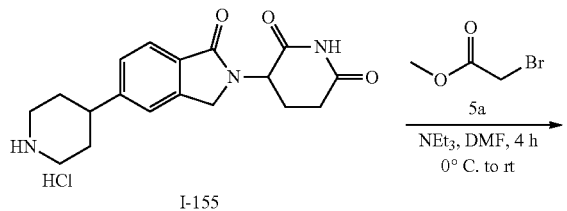

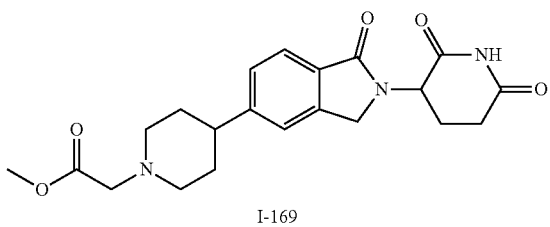

I-169

To a stirred solution of I-155 (100 mg, 0.27 mmol) in DMF (2 mL) was added NEt₃ (0.095 mL, 0.69 mmol) at 0° C. and the resulting solution was stirred for 10 min. Methyl 2-bromoacetate (5a, 50 mg, 0.33 mmol) was then added and the resulting mixture was allowed to stir at rt for 4 h. The reaction was quenched with water and extracted with EtOAc (2×10 mL) and the combined organic layers were washed with brine, dried over Na$_2$SO$_4$, and concentrated under reduced pressure to afford I-169 as a white solid (39 mg, 0.097 mmol, 36% yield). MS [M+H]$^+$=400.3. $^1$H NMR (400 MHz, DMSO-d$_6$): δ 10.99 (s, 1H), 7.64 (d, J=8.1 Hz, 1H), 7.50 (s, 1H), 7.41 (d, J=8.0 Hz, 1H), 5.10 (dd, J=13.6, 5.2 Hz, 1H), 4.42 (d, J=17.2 Hz, 1H), 4.28 (d, J=17.2 Hz, 1H), 3.62 (s, 3H), 3.27 (s, 2H) 2.95-2.87 (m, 3H), 2.67-2.57 (m, 2H), 2.49-2.36 (m, 1H), 2.33-2.27 (m, 2H), 2.00-1.97 (m, 1H), 1.74-1.68 (m, 4H).

Example 6: 3-(1-oxo-5-(1-phenylpiperidin-4-yl)isoindolin-2-yl)piperidine-2,6-dione (I-170)

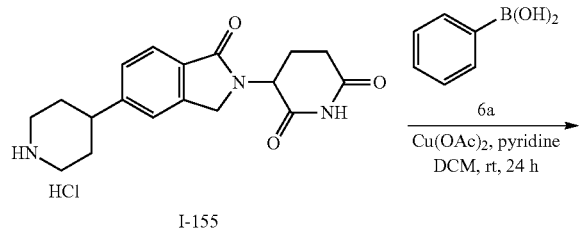

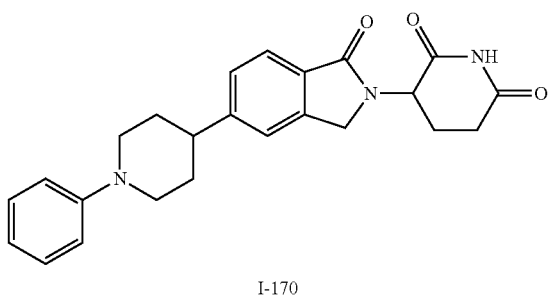

I-170

To 3-(1-oxo-5-(piperidin-4-yl)isoindolin-2-yl)piperidine-2,6-dione I-155 (50 mg, 0.14 mmol) in DCM (0.5 mL) at rt was added pyridine (0.63 mL, 0.46 mmol). After stirring for 10 min, phenyl boronic acid (6a, 22 mg, 0.18 mmol) and copper acetate (13 mg, 0.076 mmol) were added and the reaction mixture was stirred at rt for 24 h. Water was added and the resulting mixture was extracted with EtOAc. The organic layer was washed with brine, dried over Na$_2$SO$_4$, filtered, and concentrated under reduced pressure. The resulting residue was purified by reverse phase HPLC (MeCN/H$_2$O). The fractions containing the desired product were concentrated to dryness affording the title compound I-170 as an off-white solid (3 mg, 5% yield). MS [M+H]$^+$=404.5. $^1$H NMR (CDCl$_3$, 600 MHz): δ 7.90 (s, 1H), 7.83 (d, J=7.8 Hz, 1H), 7.39 (d, J=8.4 Hz, 1H), 7.36 (s, 1H), 7.30-7.25 (m, 2H), 7.00 (d, J=7.8 Hz, 2H), 6.88-6.86 (m, 1H), 5.25-5.20 (m, 1H), 4.48 (d, J=15.6 Hz, 1H), 4.33 (d, J=15.6 Hz, 1H), 3.84-3.82 (m, 2H), 2.93-2.91 (m, 1H), 2.86-2.75 (m, 4H), 2.40-2.35 (m, 1H), 2.25-2.18 (m, 1H), 1.96-1.92 (m, 4H).

Example 7: 3-(5-(1-(cyclohexylmethyl)piperidin-4-yl)-1-oxoisoindolin-2-yl)piperidine-2,6-dione (I-11)

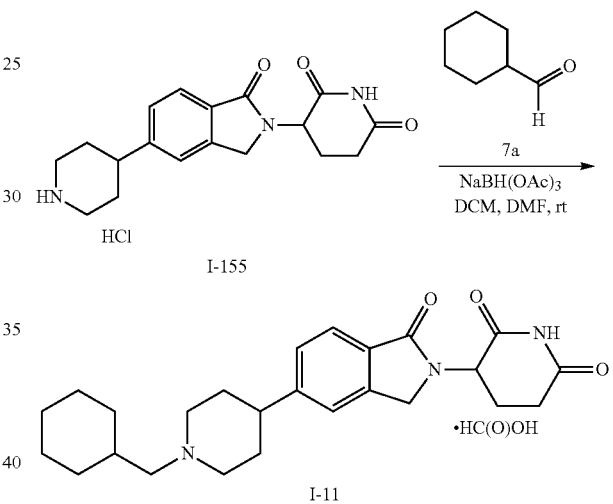

I-11

To a stirred solution of I-155 (20 mg, 0.055 mmol) and cyclohexanecarbaldehyde 7a (0.02 mL, 0.17 mmol) in DCM (0.6 mL) and DMF (0.6 mL) was added sodium triacetoxyborohydride (35 mg, 0.17 mmol) in one portion and the reaction mixture was stirred vigorously overnight at rt. The reaction mixture was concentrated under reduced pressure and the crude product diluted with aqueous formic acid (0.1 M in H$_2$O) and MeCN. The resulting solution was directly purified by reverse phase HPLC (MeCN/H$_2$O with 0.1% formic acid). The pure fractions containing the desired product were combined and concentrated to afford the formate salt of I-11 (15.3 mg, 0.033 mmol, 59% yield, formate salt) as a white solid. MS [M+H]$^+$=424.6. $^1$H NMR (400 MHz, DMSO-d$_6$): δ 10.98 (s, 1H), 8.23 (s, 1H), 7.64 (d, J=7.9 Hz, 1H), 7.49 (s, 1H), 7.39 (d, J=7.8 Hz, 1H), 5.10 (dd, J=13.3, 5.1 Hz, 1H), 4.42 (d, J=17.2 Hz, 1H), 4.28 (d, J=17.1 Hz, 1H), 3.00-2.82 (m, 3H), 2.69-2.54 (m, 2H), 2.39 (qd, J=13.4, 4.6 Hz, 1H), 2.12 (d, J=7.2 Hz, 2H), 2.04-1.91 (m, 3H), 1.83-1.57 (m, 9H), 1.55-1.43 (m, 1H), 1.30-1.06 (m, 3H), 0.84 (q, J=13.2 Hz, 2H). $^{13}$C NMR (100 MHz, DMSO-d$_6$): δ 172.91, 171.11, 168.04, 150.71, 142.47, 129.74, 126.92, 122.92, 121.71, 65.18, 54.21, 51.53, 47.10, 42.35, 34.62, 33.12, 31.37, 31.23, 26.42, 25.60, 22.52.

Example 8: 3-(5-(1-benzylpiperidin-4-yl)-1-ox-oisoindolin-2-yl)piperidine-2,6-dione (I-57)

Method 1

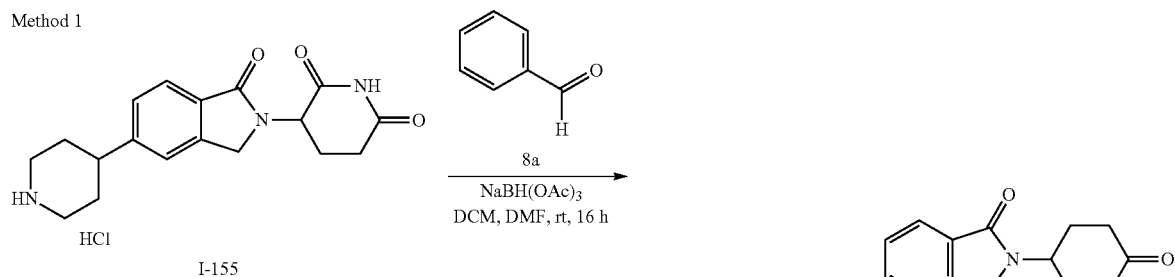

Method 2

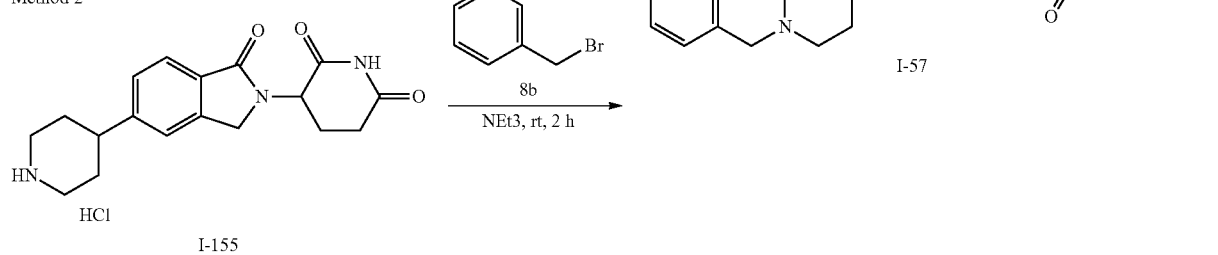

Example 8 was prepared by two different methods:

Method 1—Via a Reductive Amination Procedure:

To a stirred solution of I-155 (450 mg, 1.2 mmol) in a mixture of DMF (5 mL), DCM (5 mL), and benzaldehyde (157 mg, 1.5 mmol) was added NaBH(OAc)$_3$ (0.78 g, 3.7 mmol) in a single portion. The reaction mixture was stirred at rt for 16 h. The reaction mass was then concentrated under reduced pressure, neutralized with NaHCO$_3$ solution, and extracted in DCM. The organic layer was then dried over Na$_2$SO$_4$, filtered, and concentrated under reduced pressure affording a light brown solid. The solid was then purified by column chromatography, eluting with 0-10% NEt$_3$/EtOAc, affording I-57 as a white solid (210 mg, 0.50 mmol, 42% yield). MS [M+H]$^+$=418.2. $^1$H NMR (400 MHz, DMSO-d6): δ 10.98 (s, 1H), 7.64 (d, J=7.9 Hz, 1H), 7.50 (s, 1H), 7.40 (d, J=7.9 Hz, 1H), 7.33 (d, J=4.4 Hz, 4H), 7.29-7.23 (m, 1H), 5.10 (dd, J=13.3, 5.1 Hz, 1H), 4.42 (d, J=17.2 Hz, 1H), 4.28 (d, J=17.2 Hz, 1H), 3.51 (s, 2H), 2.99-2.84 (m, 3H), 2.71-2.56 (m, 2H), 2.46-2.31 (m, 1H), 2.16-1.94 (m, 3H), 1.84-1.64 (m, 4H).

Method 2—Via an Alkylation Reaction:

To a stirred solution of I-155 (80 mg, 0.22 mmol) in DMF (0.8 mL) was added NEt$_3$ (0.09 mL, 0.62 mmol) and the resulting mixture was stirred for 15 min. Benzyl bromide (0.03 mL, 0.27 mmol) was then added and the reaction mixture was stirred at rt for 2 h. The reaction mixture was then concentrated to dryness and the resulting residue was washed with Et$_2$O then decanted. The remaining residue was dried under high vacuum to afford I-57 as an off-white solid (50 mg, 0.12 mmol, 54% yield).

Preparation of I-57 was also achieved in a single step from intermediate 29d using the following procedure, (preparation of 29d is outlined in Example 29):

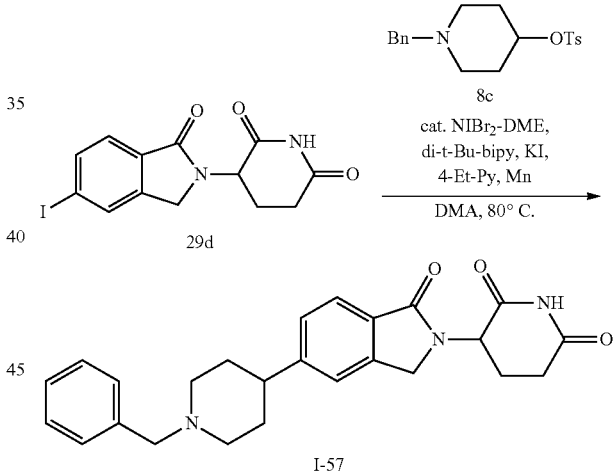

To a mixture of 29d (50 mg, 0.135 μmmol), tert-butyl 1-benzylpiperidin-4-yl 4-methylbenzenesulfonate (8c, 65 mg, 0.19 mmol), NiBr$_2$.DME (4.2 mg, 0.014 mmol), di-t-Bu-bipy (3.6 mg, 0.014 mmol), KI (22.4 mg, 0.135 mmol), and manganese powder (15 mg, 0.27 mmol) in DMA (0.67 mL) was added 4-ethylpyridine (15 μL, 0.14 mmol) and the reaction mixture was stirred vigorously at 80° C. for 4.5 h. The reaction mixture was then filtered through a short pad of Celite® filter aid and eluted with DCM. The obtained solution was concentrated by azeotroping with heptane. The crude product was purified via chromatography on silica gel eluting with NEt$_3$ (0-10%) in EtOAc to afford I-57 (24.5 mg, 0.059 mmol, 43.4% yield) as a white solid.

The following compounds in Table 1 were prepared from intermediate I-155 and corresponding aldehyde according to a reductive amination procedure described in Example 8 (Method 1):

TABLE 1

| Cmpd No. | Compound Name | MS [M + 1] |
|---|---|---|
| I-119 | 3-(5-(1-((1H-pyrrol-3-yl)methyl)piperidin-4-yl)-1-oxoisoindolin-2-yl)piperidine-2,6-dione | 407.2 |
| I-127 | 3-(5-(1-([1,2,4]triazolo[1,5-a]pyridin-5-ylmethyl)piperidin-4-yl)-1-oxoisoindolin-2-yl)piperidine-2,6-dione | 459.2 |
| I-137 | 3-(5-(1-((1H-indazol-6-yl)methyl)piperidin-4-yl)-1-oxoisoindolin-2-yl)piperidine-2,6-dione | 458.2 |
| I-154 | 3-(1-oxo-5-(1-((4-phenyl-1H-imidazol-2-yl)methyl)piperidin-4-yl)isoindolin-2-yl)piperidine-2,6-dione | 484.2 |
| I-132 | 3-(5-(1-(imidazo[1,2-a]pyrimidin-3-ylmethyl)piperidin-4-yl)-1-oxoisoindolin-2-yl)piperidine-2,6-dione | 459.2 |
| I-141 | 3-(5-(1-((3,4-dihydro-2H-benzo[b][1,4]thiazin-6-yl)methyl)piperidin-4-yl)-1-oxoisoindolin-2-yl)piperidine-2,6-dione | 491.2 |
| I-136 | 3-(5-(1-((1H-indol-2-yl)methyl)piperidin-4-yl)-1-oxoisoindolin-2-yl)piperidine-2,6-dione | 457.2 |
| I-116 | 3-(5-(1-((1H-pyrazol-4-yl)methyl)piperidin-4-yl)-1-oxoisoindolin-2-yl)piperidine-2,6-dione | 408.2 |
| I-139 | 3-((4-(2-(2,6-dioxopiperidin-3-yl)-1-oxoisoindolin-5-yl)piperidin-1-yl)methyl)benzamide | 461.2 |
| I-126 | 3-(5-(1-(imidazo[1,2-a]pyrazin-3-ylmethyl)piperidin-4-yl)-1-oxoisoindolin-2-yl)piperidine-2,6-dione | 459.2 |
| I-131 | 3-(1-oxo-5-(1-(pyrazolo[1,5-a]pyrimidin-6-ylmethyl)piperidin-4-yl)isoindolin-2-yl)piperidine-2,6-dione | 459.2 |
| I-259 | 3-(1-oxo-5-(1-((2-oxo-2,3-dihydro-1H-benzo[d]imidazol-5-yl)methyl)piperidin-4-yl)isoindolin-2-yl)piperidine-2,6-dione | 474.2 |
| I-115 | 3-(5-(1-((1-methyl-1H-pyrazol-4-yl)methyl)piperidin-4-yl)-1-oxoisoindolin-2-yl)piperidine-2,6-dione | 422.2 |
| I-121 | 3-(5-(1-((1-ethyl-1H-pyrazol-3-yl)methyl)piperidin-4-yl)-1-oxoisoindolin-2-yl)piperidine-2,6-dione | 436.2 |
| I-152 | 3-(1-oxo-5-(1-((2-phenyl-1H-imidazol-4-yl)methyl)piperidin-4-yl)isoindolin-2-yl)piperidine-2,6-dione | 484.2 |
| I-129 | 3-(5-(1-((1,4-dimethyl-1H-imidazol-2-yl)methyl)piperidin-4-yl)-1-oxoisoindolin-2-yl)piperidine-2,6-dione | 436.2 |
| I-143 | 3-(5-(1-((2-(tert-butyl)thiazol-4-yl)methyl)piperidin-4-yl)-1-oxoisoindolin-2-yl)piperidine-2,6-dione | 481.2 |
| I-125 | 3-(5-(1-((6-methylimidazo[2,1-b]thiazol-5-yl)methyl)piperidin-4-yl)-1-oxoisoindolin-2-yl)piperidine-2,6-dione | 478.2 |
| I-151 | 3-(1-oxo-5-(1-((3-(pyridin-3-yl)-1H-pyrazol-4-yl)methyl)piperidin-4-yl)isoindolin-2-yl)piperidine-2,6-dione | 485.2 |
| I-147 | 3-(5-(1-((2-morpholinopyrimidin-5-yl)methyl)piperidin-4-yl)-1-oxoisoindolin-2-yl)piperidine-2,6-dione | 505.3 |
| I-86 | N-(4-((4-(2-(2,6-dioxopiperidin-3-yl)-1-oxoisoindolin-5-yl)piperidin-1-yl)methyl)phenyl)acetamide | 475.2 |
| I-148 | 3-(1-oxo-5-(1-((3-phenyl-1H-pyrazol-4-yl)methyl)piperidin-4-yl)isoindolin-2-yl)piperidine-2,6-dione | 484.2 |
| I-149 | 3-(5-(1-((6-methyl-1H-indol-3-yl)methyl)piperidin-4-yl)-1-oxoisoindolin-2-yl)piperidine-2,6-dione | 471.2 |
| I-120 | 3-(5-(1-((1H-imidazol-5-yl)methyl)piperidin-4-yl)-1-oxoisoindolin-2-yl)piperidine-2,6-dione | 408.2 |
| I-146 | 3-(5-(1-((5-cyclopropyl-1H-pyrazol-3-yl)methyl)piperidin-4-yl)-1-oxoisoindolin-2-yl)piperidine-2,6-dione | 448.2 |
| I-135 | 3-(1-oxo-5-(1-((4,5,6,7-tetrahydropyrazolo[1,5-a]pyridin-2-yl)methyl)piperidin-4-yl)isoindolin-2-yl)piperidine-2,6-dione | 462.2 |
| I-140 | 3-(5-(1-((1H-pyrrolo[2,3-b]pyridin-6-yl)methyl)piperidin-4-yl)-1-oxoisoindolin-2-yl)piperidine-2,6-dione | 458.2 |
| I-122 | 3-(5-(1-((2-aminopyrimidin-5-yl)methyl)piperidin-4-yl)-1-oxoisoindolin-2-yl)piperidine-2,6-dione | 435.2 |
| I-130 | 3-(5-(1-(benzo[d]thiazol-5-ylmethyl)piperidin-4-yl)-1-oxoisoindolin-2-yl)piperidine-2,6-dione | 475.2 |
| I-124 | 3-(5-(1-((5-amino-1-methyl-1H-pyrazol-4-yl)methyl)piperidin-4-yl)-1-oxoisoindolin-2-yl)piperidine-2,6-dione | 437.2 |
| I-123 | 3-(5-(1-((6-aminopyridin-3-yl)methyl)piperidin-4-yl)-1-oxoisoindolin-2-yl)piperidine-2,6-dione | 434.2 |
| I-142 | 3-(1-oxo-5-(1-((2-(pyrrolidin-1-yl)pyrimidin-5-yl)methyl)piperidin-4-yl)isoindolin-2-yl)piperidine-2,6-dione | 489.3 |
| I-117 | 3-(5-(1-((1-methyl-1H-pyrazol-3-yl)methyl)piperidin-4-yl)-1-oxoisoindolin-2-yl)piperidine-2,6-dione | 422.2 |
| I-201 | 3-(1-oxo-5-(1-((3-(pyridin-2-yl)-1H-pyrazol-5-yl)methyl)piperidin-4-yl)isoindolin-2-yl)piperidine-2,6-dione | 485.2 |
| I-145 | 3-(5-(1-((2-cyclohexylthiazol-5-yl)methyl)piperidin-4-yl)-1-oxoisoindolin-2-yl)piperidine-2,6-dione | 507.2 |
| I-300 | 3-(5-(1-((3-((3S,5S)-adamantan-1-yl)-1H-pyrazol-5-yl)methyl)piperidin-4-yl)-1-oxoisoindolin-2-yl)piperidine-2,6-dione | 542.3 |
| I-134 | 3-(5-(1-((1-cyclobutyl-1H-1,2,3-triazol-4-yl)methyl)piperidin-4-yl)-1-oxoisoindolin-2-yl)piperidine-2,6-dione | 463.2 |
| I-128 | 3-(1-oxo-5-(1-(pyrazolo[1,5-a]pyridin-4-ylmethyl)piperidin-4-yl)isoindolin-2-yl)piperidine-2,6-dione | 458.2 |

TABLE 1-continued

| Cmpd No. | Compound Name | MS [M + 1] |
|---|---|---|
| I-205 | 3-(5-(1-(4-hydroxy-3-((4-methylpiperazin-1-yl)methyl)benzyl)piperidin-4-yl)-1-oxoisoindolin-2-yl)piperidine-2,6-dione | 546.3 |
| I-59 | 3-(1-oxo-5-(1-(pyridin-3-ylmethyl)piperidin-4-yl)isoindolin-2-yl)piperidine-2,6-dione | 419.2 |
| I-60 | 3-(1-oxo-5-(1-(pyridin-4-ylmethyl)piperidin-4-yl)isoindolin-2-yl)piperidine-2,6-dione | 419.2 |
| I-58 | 3-(1-oxo-5-(1-(pyridin-2-ylmethyl)piperidin-4-yl)isoindolin-2-yl)piperidine-2,6-dione | 419.2 |

The following compounds in Table 2 were prepared from intermediate I-155 and corresponding halide according to an alkylation procedure described in Example 8 (Method 2):

TABLE 2

| Cmpd No. | Compound Name | MS [M + 1] |
|---|---|---|
| I-204 | 3-(5-(1-((1,2,4-oxadiazol-3-yl)methyl)piperidin-4-yl)-1-oxoisoindolin-2-yl)piperidine-2,6-dione | 410.2 |
| I-243 | 3-(1-oxo-5-(1-((5-(4-(trifluoromethyl)phenyl)-1,2,4-oxadiazol-3-yl)methyl)piperidin-4-yl)isoindolin-2-yl)piperidine-2,6-dione | 554.2 |
| I-199 | 3-(1-oxo-5-(1-((5-phenyl-1,3,4-oxadiazol-2-yl)methyl)piperidin-4-yl)isoindolin-2-yl)piperidine-2,6-dione | 486.2 |
| I-211 | 3-(1-oxo-5-(1-((2-phenylthiazol-4-yl)methyl)piperidin-4-yl)isoindolin-2-yl)piperidine-2,6-dione | 501.2 |
| I-10 | 3-(5-(1-((2-chlorothiazol-5-yl)methyl)piperidin-4-yl)-1-oxoisoindolin-2-yl)piperidine-2,6-dione | 459.1 |
| I-238 | 3-(1-oxo-5-(1-(thiazol-4-ylmethyl)piperidin-4-yl)isoindolin-2-yl)piperidine-2,6-dione | 425.2 |
| I-221 | 3-(5-(1-((7-methyl-4-oxo-4H-pyrido[1,2-a]pyrimidin-2-yl)methyl)piperidin-4-yl)-1-oxoisoindolin-2-yl)piperidine-2,6-dione | 500.2 |
| I-213 | 3-(1-oxo-5-(1-((4-oxo-3,4-dihydrothieno[3,2-d]pyrimidin-2-yl)methyl)piperidin-4-yl)isoindolin-2-yl)piperidine-2,6-dione | 492.2 |
| I-254 | methyl 2-((4-(2-(2,6-dioxopiperidin-3-yl)-1-oxoisoindolin-5-yl)piperidin-1-yl)methyl)oxazole-4-carboxylate | 467.2 |
| I-246 | 3-(5-(1-(isoxazol-3-ylmethyl)piperidin-4-yl)-1-oxoisoindolin-2-yl)piperidine-2,6-dione | 409.2 |
| I-245 | 3-(5-(1-((3-methylisoxazol-5-yl)methyl)piperidin-4-yl)-1-oxoisoindolin-2-yl)piperidine-2,6-dione | 423.2 |
| I-258 | 3-(5-(1-((3-cyclohexylisoxazol-5-yl)methyl)piperidin-4-yl)-1-oxoisoindolin-2-yl)piperidine-2,6-dione | 491.3 |
| I-203 | 3-(5-(1-((1-methyl-1H-indazol-3-yl)methyl)piperidin-4-yl)-1-oxoisoindolin-2-yl)piperidine-2,6-dione | 472.2 |
| I-198 | 3-(5-(1-((l-benzyl-1H-tetrazol-5-yl)methyl)piperidin-4-yl)-1-oxoisoindolin-2-yl)piperidine-2,6-dione | 500.2 |
| I-217 | 6-((4-(2-(2,6-dioxopiperidin-3-yl)-1-oxoisoindolin-5-yl)piperidin-1-yl)methyl)picolinonitrile | 444.2 |
| I-219 | 3-(5-(1-((1H-indazol-5-yl)methyl)piperidin-4-yl)-1-oxoisoindolin-2-yl)piperidine-2,6-dione | 458.2 |
| I-214 | 3-(1-oxo-5-(1-(quinolin-4-ylmethyl)piperidin-4-yl)isoindolin-2-yl)piperidine-2,6-dione | 469.2 |
| I-235 | 3-((4-(2-(2,6-dioxopiperidin-3-yl)-1-oxoisoindolin-5-yl)piperidin-1-yl)methyl)-1,2,4-oxadiazole-5-carboxamide | 453.2 |
| I-200 | 3-(5-(1-(benzo[d]thiazol-2-ylmethyl)piperidin-4-yl)-1-oxoisoindolin-2-yl)piperidine-2,6-dione | 475.2 |
| I-239 | 3-(1-oxo-5-(1-(quinoxalin-6-ylmethyl)piperidin-4-yl)isoindolin-2-yl)piperidine-2,6-dione | 470.2 |
| I-241 | 3-(1-oxo-5-(1-((3-(m-tolyl)-1,2,4-oxadiazol-5-yl)methyl)piperidin-4-yl)isoindolin-2-yl)piperidine-2,6-dione | 500.2 |
| I-43 | 3-(5-(1-((1H-indazol-4-yl)methyl)piperidin-4-yl)-1-oxoisoindolin-2-yl)piperidine-2,6-dione | 458.2 |
| I-232 | 3-(5-(1-((7-fluoroquinolin-2-yl)methyl)piperidin-4-yl)-1-oxoisoindolin-2-yl)piperidine-2,6-dione | 487.2 |
| I-207 | 3-(5-(1-((2-(4-chlorophenyl)-5-methyloxazol-4-yl)methyl)piperidin-4-yl)-1-oxoisoindolin-2-yl)piperidine-2,6-dione | 533.2 |
| I-251 | 3-(5-(1-((5-methyl-3-phenylisoxazol-4-yl)methyl)piperidin-4-yl)-1-oxoisoindolin-2-yl)piperidine-2,6-dione | 499.2 |
| I-226 | 3-(5-(1-(isoquinolin-1-ylmethyl)piperidin-4-yl)-1-oxoisoindolin-2-yl)piperidine-2,6-dione | 469.2 |
| I-257 | 3-(5-(1-((5-methyl-2-phenyloxazol-4-yl)methyl)piperidin-4-yl)-1-oxoisoindolin-2-yl)piperidine-2,6-dione | 499.2 |
| I-56 | 3-(1-oxo-5-(1-((3-phenyl-1,2,4-oxadiazol-5-yl)methyl)piperidin-4-yl)isoindolin-2-yl)piperidine-2,6-dione | 486.2 |

TABLE 2-continued

| Cmpd No. | Compound Name | MS [M + 1] |
|---|---|---|
| I-208 | 3-(5-(1-((7-hydroxy-2-methylpyrazolo[1,5-a]pyrimidin-5-yl)methyl)piperidin-4-yl)-1-oxoisoindolin-2-yl)piperidine-2,6-dione | 489.2 |
| I-229 | tert-butyl (5-((4-(2-(2,6-dioxopiperidin-3-yl)-1-oxoisoindolin-5-yl)piperidin-1-yl)methyl)-4-(trifluoromethyl)thiazol-2-yl)carbamate | 608.2 |
| I-240 | 3-(5-(1-((2-(4-fluorophenyl)-5-methyloxazol-4-yl)methyl)piperidin-4-yl)-1-oxoisoindolin-2-yl)piperidine-2,6-dione | 517.2 |
| I-233 | 3-(5-(1-((5-methyl-2-(4-(trifluoromethyl)phenyl)oxazol-4-yl)methyl)piperidin-4-yl)-1-oxoisoindolin-2-yl)piperidine-2,6-dione | 567.2 |
| I-88 | 3-(5-(1-((3,4-dihydro-2H-benzo[b][1,4]dioxepin-7-yl)methyl)piperidin-4-yl)-1-oxoisoindolin-2-yl)piperidine-2,6-dione | 490.2 |
| I-64 | 3-(5-(1-(3,4-difluorobenzyl)piperidin-4-yl)-1-oxoisoindolin-2-yl)piperidine-2,6-dione | 454.2 |
| I-225 | 3-(5-(1-(4-(5-methylbenzo[d]thiazol-2-yl)benzyl)piperidin-4-yl)-1-oxoisoindolin-2-yl)piperidine-2,6-dione | 565.2 |
| I-38 | 2-((4-(2-(2,6-dioxopiperidin-3-yl)-1-oxoisoindolin-5-yl)piperidin-1-yl)methyl)benzonitrile | 443.2 |
| I-255 | 3-(1-oxo-5-(1-(4-(pyridin-2-ylmethoxy)benzyl)piperidin-4-yl)isoindolin-2-yl)piperidine-2,6-dione | 525.3 |
| I-75 | 3-(1-oxo-5-(1-(4-propylbenzyl)piperidin-4-yl)isoindolin-2-yl)piperidine-2,6-dione | 460.3 |
| I-244 | 3-(5-(1-(4-((4-fluorobenzyl)oxy)benzyl)piperidin-4-yl)-1-oxoisoindolin-2-yl)piperidine-2,6-dione | 542.2 |
| I-74 | 3-((4-(2-(2,6-dioxopiperidin-3-yl)-1-oxoisoindolin-5-yl)piperidin-1-yl)methyl)benzoic acid | 462.2 |
| I-248 | 3-(5-(1-(4-(methoxymethyl)benzyl)piperidin-4-yl)-1-oxoisoindolin-2-yl)piperidine-2,6-dione | 462.2 |
| I-79 | 3-(5-(1-(3-(difluoromethoxy)benzyl)piperidin-4-yl)-1-oxoisoindolin-2-yl)piperidine-2,6-dione | 484.2 |
| I-77 | 3-(5-(1-(4-(difluoromethoxy)benzyl)piperidin-4-yl)-1-oxoisoindolin-2-yl)piperidine-2,6-dione | 484.2 |
| I-32 | 3-(5-(1-(4-(hydroxymethyl)benzyl)piperidin-4-yl)-1-oxoisoindolin-2-yl)piperidine-2,6-dione | 448.2 |
| I-216 | 3-((4-(2-(2,6-dioxopiperidin-3-yl)-1-oxoisoindolin-5-yl)piperidin-1-yl)methyl)-N,N-dimethylbenzenesulfonamide | 525.2 |
| I-76 | 3-(1-oxo-5-(1-(4-(trifluoromethyl)benzyl)piperidin-4-yl)isoindolin-2-yl)piperidine-2,6-dione | 486.2 |
| I-29 | 3-(5-(1-(2,5-difluorobenzyl)piperidin-4-yl)-1-oxoisoindolin-2-yl)piperidine-2,6-dione | 454.2 |
| I-91 | 3-(5-(1-(4-(1H-pyrazol-1-yl)benzyl)piperidin-4-yl)-1-oxoisoindolin-2-yl)piperidine-2,6-dione | 484.2 |
| I-36 | 3-((4-(2-(2,6-dioxopiperidin-3-yl)-1-oxoisoindolin-5-yl)piperidin-1-yl)methyl)benzonitrile | 443.2 |
| I-70 | 3-(5-(1-(4-(difluoromethyl)benzyl)piperidin-4-yl)-1-oxoisoindolin-2-yl)piperidine-2,6-dione | 468.2 |
| I-236 | 3-(5-(1-(3-(morpholinosulfonyl)benzyl)piperidin-4-yl)-1-oxoisoindolin-2-yl)piperidine-2,6-dione | 567.2 |
| I-95 | 3-(1-oxo-5-(1-(pyrimidin-2-ylmethyl)piperidin-4-yl)isoindolin-2-yl)piperidine-2,6-dione | 420.2 |
| I-110 | 3-(5-(1-(4-cyclopentylbenzyl)piperidin-4-yl)-1-oxoisoindolin-2-yl)piperidine-2,6-dione | 486.3 |
| I-65 | 2-((4-(2-(2,6-dioxopiperidin-3-yl)-1-oxoisoindolin-5-yl)piperidin-1-yl)methyl)pyrimidine-5-carbonitrile | 445.2 |
| I-67 | 3-(5-(1-(2-methoxybenzyl)piperidin-4-yl)-1-oxoisoindolin-2-yl)piperidine-2,6-dione | 448.2 |
| I-83 | 3-(5-(1-((2,3-dihydrobenzo[b][1,4]dioxin-6-yl)methyl)piperidin-4-yl)-1-oxoisoindolin-2-yl)piperidine-2,6-dione | 476.2 |
| I-252 | 3-(5-(1-(4-((difluoromethyl)sulfonyl)benzyl)piperidin-4-yl)-1-oxoisoindolin-2-yl)piperidine-2,6-dione | 532.2 |
| I-87 | 3-(5-(1-((2,2-difluorobenzo[d][1,3]dioxol-5-yl)methyl)piperidin-4-yl)-1-oxoisoindolin-2-yl)piperidine-2,6-dione | 498.2 |
| I-69 | 3-(5-(1-(3-fluoro-4-methylbenzyl)piperidin-4-yl)-1-oxoisoindolin-2-yl)piperidine-2,6-dione | 450.2 |
| I-68 | 3-(5-(1-((2-methoxypyrimidin-5-yl)methyl)piperidin-4-yl)-1-oxoisoindolin-2-yl)piperidine-2,6-dione | 450.2 |
| I-107 | 3-(5-(1-(3-(tert-butyl)benzyl)piperidin-4-yl)-1-oxoisoindolin-2-yl)piperidine-2,6-dione | 474.3 |
| I-108 | 3-(5-(1-(3-isopropoxybenzyl)piperidin-4-yl)-1-oxoisoindolin-2-yl)piperidine-2,6-dione | 476.3 |
| I-78 | 3-(1-oxo-5-(1-((5-(trifluoromethyl)pyridin-2-yl)methyl)piperidin-4-yl)isoindolin-2-yl)piperidine-2,6-dione | 487.2 |
| I-89 | 3-(1-oxo-5-(1-(4-(tert-pentyl)benzyl)piperidin-4-yl)isoindolin-2-yl)piperidine-2,6-dione | 488.3 |
| I-82 | 3-(5-(1-((2,3-dihydrobenzo[b][1,4]dioxin-5-yl)methyl)piperidin-4-yl)-1-oxoisoindolin-2-yl)piperidine-2,6-dione | 476.2 |
| I-93 | 3-(5-(1-(3-(1H-pyrazol-1-yl)benzyl)piperidin-4-yl)-1-oxoisoindolin-2-yl)piperidine-2,6-dione | 484.2 |

TABLE 2-continued

| Cmpd No. | Compound Name | MS [M + 1] |
|---|---|---|
| I-206 | 2-(4-((4-(2-(2,6-dioxopiperidin-3-yl)-1-oxoisoindolin-5-yl)piperidin-1-yl)methyl)phenyl)acetonitrile | 457.2 |
| I-113 | 3-(5-(1-(2,4-dichlorobenzyl)piperidin-4-yl)-1-oxoisoindolin-2-yl)piperidine-2,6-dione | 486.1 |
| I-106 | 3-(1-oxo-5-(1-(2-(trifluoromethyl)benzyl)piperidin-4-yl)isoindolin-2-yl)piperidine-2,6-dione | 486.2 |
| I-81 | 3-(5-(1-(4-cyclobutylbenzyl)piperidin-4-yl)-1-oxoisoindolin-2-yl)piperidine-2,6-dione | 472.3 |
| I-218 | 2-(4-((4-(2-(2,6-dioxopiperidin-3-yl)-1-oxoisoindolin-5-yl)piperidin-1-yl)methyl)phenoxy)acetonitrile | 473.2 |
| I-104 | 3-(5-(1-(2-cyclopropylbenzyl)piperidin-4-yl)-1-oxoisoindolin-2-yl)piperidine-2,6-dione | 458.2 |
| I-101 | 3-(5-(1-(2,4-difluorobenzyl)piperidin-4-yl)-1-oxoisoindolin-2-yl)piperidine-2,6-dione | 454.2 |
| I-42 | 3-(5-(1-(2,4-dimethylbenzyl)piperidin-4-yl)-1-oxoisoindolin-2-yl)piperidine-2,6-dione | 446.2 |
| I-227 | 3-(5-(1-(4-(4-methoxypiperidin-1-yl)benzyl)piperidin-4-yl)-1-oxoisoindolin-2-yl)piperidine-2,6-dione | 531.3 |
| I-228 | 3-(5-(1-(4-(isopropylthio)benzyl)piperidin-4-yl)-1-oxoisoindolin-2-yl)piperidine-2,6-dione | 492.2 |
| I-24 | 3-(5-(1-(2,6-difluorobenzyl)piperidin-4-yl)-1-oxoisoindolin-2-yl)piperidine-2,6-dione | 454.2 |
| I-231 | 2-(4-((4-(2-(2,6-dioxopiperidin-3-yl)-1-oxoisoindolin-5-yl)piperidin-1-yl)methyl)phenyl)acetic acid | 476.2 |
| I-73 | 3-(5-(1-(3-(difluoromethyl)benzyl)piperidin-4-yl)-1-oxoisoindolin-2-yl)piperidine-2,6-dione | 468.2 |
| I-237 | 4-((4-(2-(2,6-dioxopiperidin-3-yl)-1-oxoisoindolin-5-yl)piperidin-1-yl)methyl)-N,N-dimethylbenzenesulfonamide | 525.2 |
| I-63 | 3-(5-(1-(4-(fluoromethyl)benzyl)piperidin-4-yl)-1-oxoisoindolin-2-yl)piperidine-2,6-dione | 450.2 |
| I-114 | 3-(1-oxo-5-(1-(quinolin-8-ylmethyl)piperidin-4-yl)isoindolin-2-yl)piperidine-2,6-dione | 469.2 |
| I-80 | 3-(5-(1-(2-(difluoromethoxy)benzyl)piperidin-4-yl)-1-oxoisoindolin-2-yl)piperidine-2,6-dione | 484.2 |
| I-234 | 3-(5-(1-((2-amino-4-(trifluoromethyl)thiazol-5-yl)methyl)piperidin-4-yl)-1-oxoisoindolin-2-yl)piperidine-2,6-dione | 508.2 |

Example 9: 3-(5-(1-benzyl-1,2,3,6-tetrahydropyridin-4-yl)-1-oxoisoindolin-2-yl)piperidine-2,6-dione (I-172)

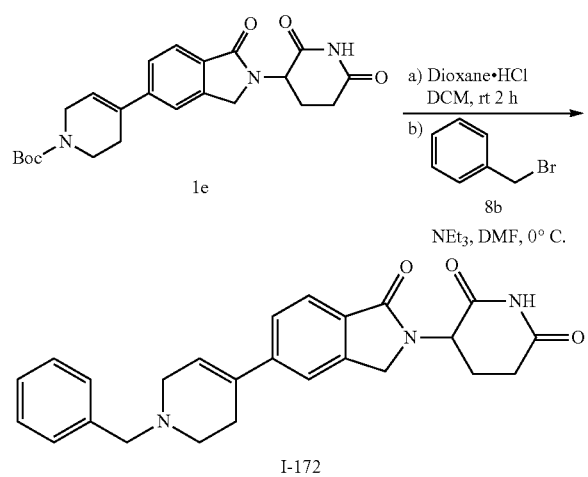

A solution of 4N HCl in dioxane (2.0 mL) was added to 1e (300 mg, 0.71 mmol) in DCM (2.0 mL) at rt and the resulting mixture was stirred at rt for 2 h. The reaction mixture was then concentrated to dryness and the resulting residue was washed with ether, decanted, and then dried under high vacuum. The crude material was dissolved in DMF (3.0 mL) and then NEt₃ (0.46 mL, 2.48 mmol) was added. The mixture was cooled in an ice bath for 10 min prior to the dropwise addition of benzyl bromide (8b, 0.08 mL, 0.663 mmol). The resulting reaction mixture was then stirred at 0° C. for 1 h. The reaction mixture was then diluted with water and extracted with ethyl acetate. The organic layer was washed with brine, dried over Na$_2$SO$_4$, filtered, and concentrated to dryness. The crude material was purified by reverse phase HPLC (MeCN/H$_2$O). The fractions with the desired product were collected and concentrated to dryness affording I-172 as an off-white solid (30 mg, 0.071 mmol, 10% yield). MS [M+H]$^+$=416.4. $^1$H NMR (400 MHz, DMSO-d$_6$): δ 10.99 (s, 1H), 7.77-7.69 (m, 2H), 7.66-7.57 (m, 3H), 7.51 (d, J=3.0 Hz, 3H), 6.32 (s, 1H), 5.12 (dd, J=13.3, 5.1 Hz, 1H), 4.54-4.40 (m, 3H), 4.34 (d, J=17.5 Hz, 1H), 3.83 (s, 2H), 3.65 (brs, 1H), 2.99-2.80 (m, 3H), 2.70-2.55 (m, 2H), 2.11-1.92 (m, 1H).

Example 10: 3-(5-(1-(4-fluorobenzyl)piperidin-4-yl)-1-oxoisoindolin-2-yl)piperidine-2,6-dione HC(O)OH (I-112)

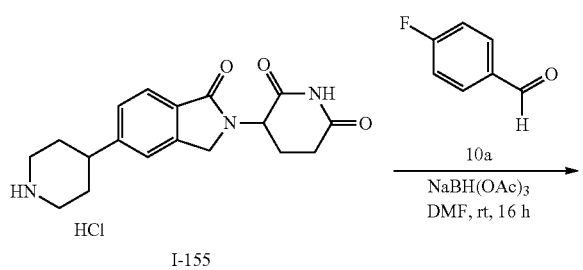

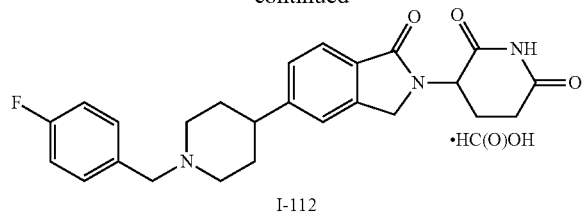

I-112

To a solution of I-155 (60 mg, 0.17 mmol) and 4-fluorobenzaldehyde (10a, 0.05 mL, 0.5 mmol) in DMF (2 mL) was added sodium triacetoxyborohydride (105 mg, 0.495 mmol) in one portion and the resulting mixture was stirred vigorously at rt overnight. The reaction mixture was then concentrated under reduced pressure. The crude product was diluted with aqueous formic acid (0.1 M in $H_2O$) and MeCN. The resulting solution was directly purified by reverse phase HPLC (MeCN/$H_2O$ with 0.1% formic acid). The pure fractions containing the desired product were combined, concentrated, and the product lyophilized to afford the formate salt of I-112 (41.0 mg, 0.094 mmol, 57% yield, formate salt) as a white solid. MS $[M+H]^+$=436.4. $^1$H NMR (400 MHz, $D_2O$): δ 8.45 (s, 1H), 7.80 (d, J=8.0 Hz, 1H), 7.60-7.43 (m, 4H), 7.26 (t, J 8.7 Hz, 2H), 5.17 (dd, J=13.3, 5.3 Hz, 1H), 4.60 (d, J=17.4 Hz, 1H), 4.51 (d, J=17.6 Hz, 1H), 4.36 (s, 2H), 3.66 (d, J=12.3 Hz, 2H), 3.20 (t, J=12.6 Hz, 2H), 3.07 (t, J=12.5 Hz, 1H), 3.02-2.83 (m, 2H), 2.55 (qd, J=12.9, 5.3 Hz, 1H), 2.35-2.24 (m, 1H), 2.19 (d, J=14.2 Hz, 2H), 2.05-1.85 (m, 2H). $^{13}$C NMR (100 MHz, DMSO-$d_6$) δ 172.91, 171.10, 168.04, 161.22 (d, J=242 Hz), 150.63, 142.47, 134.70 (d, J=3.0 Hz), 130.62 (d, J=8.1 Hz), 129.76, 126.93, 122.92, 121.73, 114.85 (d, J=20.8 Hz), 61.44, 53.40, 51.53, 47.10, 42.17, 33.05, 31.23, 22.52.

Example 11: 3-(5-(1-(4-chlorobenzyl)piperidin-4-yl)-1-oxoisoindolin-2-yl)piperidine-2,6-dione (I-97)

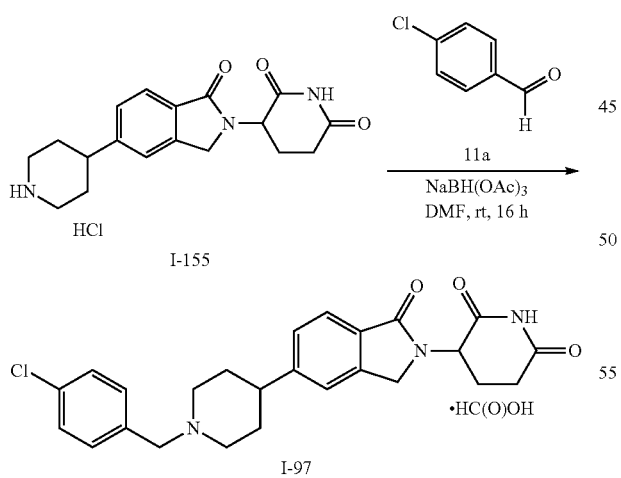

Compound I-97 was prepared from I-155 (70 mg, 0.19 mmol) and 4-chlorobenzaldehyde (11a, 81 mg, 0.58 mmol) via reductive amination as described for Example 8. Upon completion of the reaction, the crude reaction mixture was concentrated to dryness. The resulting material was triturated with $Et_2O$ then decanted. The remaining residue was then purified by reverse phase HPLC (MeCN/$H_2O$ with 0.1% formic acid). Concentration of the solvent afforded the formate salt of I-97 as an off-white solid (18 mg, 0.036 mmol, 19% yield, formate salt). MS $[M+H]^+$=452.4. $^1$H NMR (CDCl$_3$, 400 MHz): δ 7.90 (s, 1H), 7.79 (d, J=8.0 Hz, 1H), 7.35-7.29 (m, 6H), 5.23-5.19 (dd, J=13.2 Hz, 5.2 Hz, 1H), 4.45 (d, J=14 Hz, 1H), 4.3 (d, J=16 Hz, 1H), 3.50 (s, 2H), 3.00-2.82 (m, 4H), 2.65-2.55 (m, 2H), 2.36-2.32 (m, 1H), 2.21-2.19 (m, 1H), 2.09-2.08 (m, 2H), 1.82-1.80 (m, 3H).

Example 12: 3-(5-(1-(4-methylbenzyl)piperidin-4-yl)-1-oxoisoindolin-2-yl)piperidine-2,6-dione (I-158)

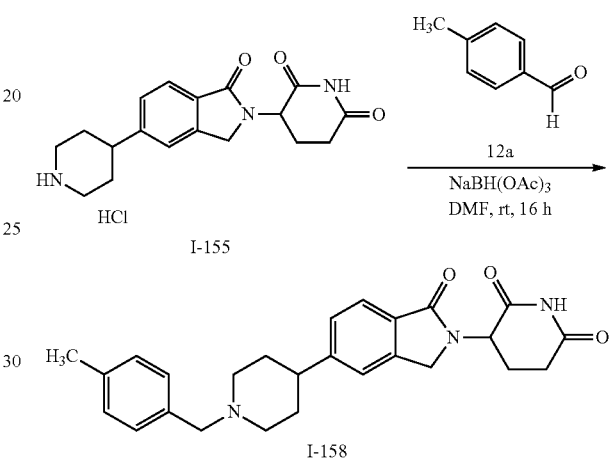

Compound I-158 was prepared from I-155 (50 mg, 0.14 mmol) and 4-methylbenzaldehyde (12a, 20 mg, 0.16 mmol) via reductive amination as described for Example 8. After workup, the crude material was purified by silica gel chromatography eluting with 5% MeOH in DCM affording I-158 as an off-white solid (25.3 mg, 0.059 mmol, 42% yield). MS $[M+H]^+$=432.5. $^1$H NMR (DMSO-$d_6$, 400 MHz): δ 11.0 (s, 1H), 7.69 (d, J=8.0 Hz, 1H), 7.50 (d, J=8.0 Hz, 2H), 7.45 (s, 1H), 7.38-7.36 (d, J=8.0 Hz, 1H), 7.28 (d, J=8.0 Hz, 2H), 5.11 (dd, J=13.6, 5.2 Hz, 1H), 4.48 (d, J=18.4 Hz, 1H), 4.32-4.28 (m, 3H), 3.43-3.40 (m, 2H), 3.03-2.86 (m, 4H), 2.73-2.57 (m, 2H), 2.42-2.34 (m, 4H), 2.11-1.96 (m, 4H).

Example 13: 3-(5-(1-(3-methylbenzyl)piperidin-4-yl)-1-oxoisoindolin-2-yl)piperidine-2,6-dione (I-173)

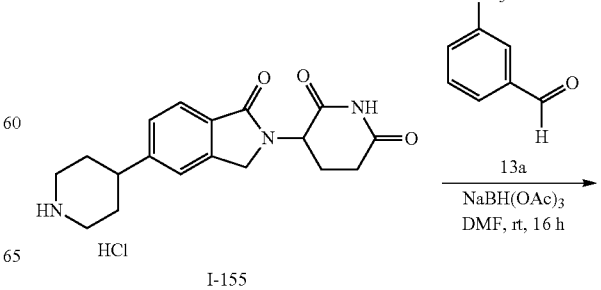

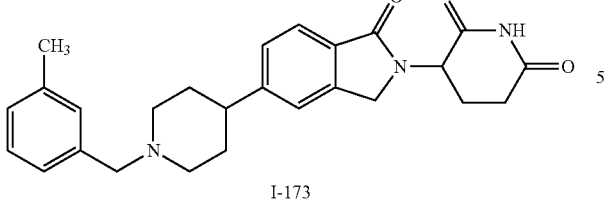

I-173

Compound I-173 was prepared from I-155 (50 mg, 0.14 mmol) and 3-methylbenzaldehyde (13a, 20 mg, 0.16 mmol) via reductive amination as described for Example 8. After workup, the crude material was purified by reverse phase HPLC (MeCN/H$_2$O with 0.05 formic acid). The fractions were collected and concentrated to dryness affording the formate salt of I-173 as an off-white solid (18.5 mg, 0.039 mmol, 27% yield, formate salt). MS [M+H]$^+$=432.6. $^1$H NMR (DMSO-d$_6$, 600 MHz): δ 10.98 (s, 1H), 8.14 (s, 1H), 7.64 (d, J=7.9 Hz, 1H), 7.50 (s, 1H), 7.40 (d, J=7.9 Hz, 1H), 7.23 (t, J=7.5 Hz, 1H), 7.18-7.11 (m, 2H), 7.08 (d, J=7.4 Hz, 1H), 5.10 (dd, J=13.3, 5.1 Hz, 1H), 4.42 (d, J=17.2 Hz, 1H), 4.28 (d, J=17.2 Hz, 1H), 3.54 (s, 2H), 3.03-2.85 (m, 3H), 2.73-2.56 (m, 2H), 2.39 (dd, J=13.0, 4.5 Hz, 1H), 2.31 (s, 3H), 2.15 (t, J=10.7 Hz, 2H), 1.99 (dd, J=9.0, 3.7 Hz, 1H), 1.83-1.67 (m, 4H).

Example 14: 3-(5-(1-(2-methylbenzyl)piperidin-4-yl)-1-oxoisoindolin-2-yl)piperidine-2,6-dione (I-157)

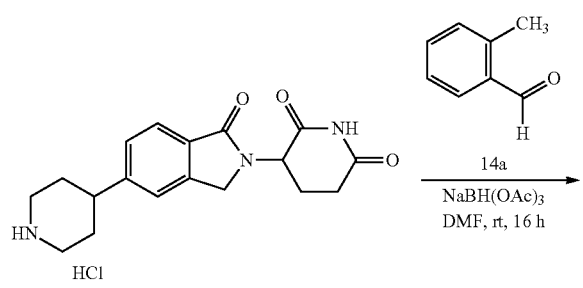

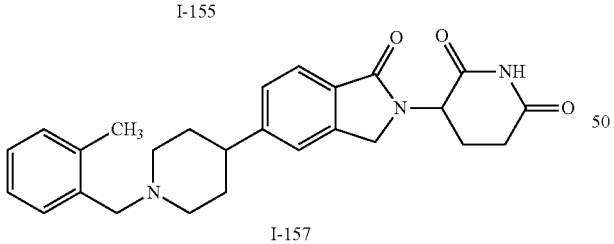

I-157

Compound I-157 was prepared from I-155 (50 mg, 0.14 mmol) and 2-methylbenzaldehyde (14a, 20 mg, 0.16 mmol) via reductive amination as described for Example 8. After workup, the crude material was purified by silica gel chromatography eluting with 5% MeOH in DCM affording I-157 as a light brown solid (23.3 mg, 0.054 mmol, 39% yield). MS [M+H]$^+$=432.5. $^1$H NMR (400 MHz, DMSO-d6) δ 10.98 (s, 1H), 7.77-7.15 (m, 7H), 5.11 (d, J=13.5 Hz, 1H), 4.54-4.19 (m, 3H), 3.58-3.38 (m, 2H), 3.34 (s, 2H), 3.27-3.13 (m, 1H), 3.08-2.82 (m, 2H), 2.74-2.55 (m, 2H), 2.48-2.28 (m, 4H), 2.19-1.92 (m, 4H).

Example 15: 3-(5-(1-(2,6-dimethylbenzyl)piperidin-4-yl)-1-oxoisoindolin-2-yl)piperidine-2,6-dione (I-174)

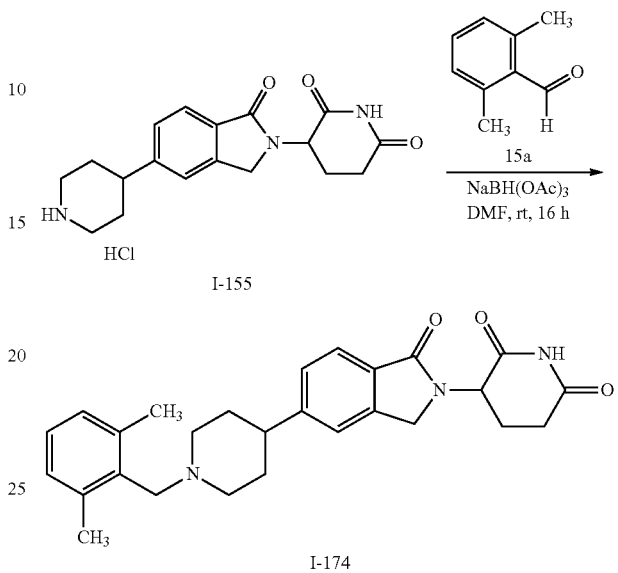

I-174

Compound I-174 was prepared from I-155 (70 mg, 0.19 mmol) and 2,6-dimethylbenzaldehyde (15a, 77 mg, 0.57 mmol) via reductive amination as described for Example 8. After workup, the crude material was triturated with Et$_2$O, EtOAc, and then heptane. The resultant solid was dried under high vacuum affording I-174 as a grey solid (17 mg, 0.038 mmol, 20% yield). MS [M+H]+=446.1. $^1$H NMR (DMSO-d$_6$, 400 MHz): δ 10.98 (s, 1H), 7.62 (d, J=8.0 Hz, 1H), 7.47 (s, 1H), 7.37 (d, J=8.0 Hz, 1H), 7.05-6.96 (m, 3H), 5.09 (dd, J=13.2, 5.2 Hz, 1H), 4.40 (d, J=16.8 Hz, 1H), 4.26 (d, J=17.2 Hz, 1H), 3.47 (s, 2H), 2.93-2.84 (m, 3H), 2.66-2.60 (m, 1H), 2.40-2.36 (m, 7H), 2.20-2.14 (m, 2H), 1.98-1.95 (m, 1H), 1.76-1.73 (m, 2H), 1.63-1.58 (m, 2H).

Example 16: 3-(5-(1-(3,5-dimethylbenzyl)piperidin-4-yl)-1-oxoisoindolin-2-yl)piperidine-2,6-dione (I-159)

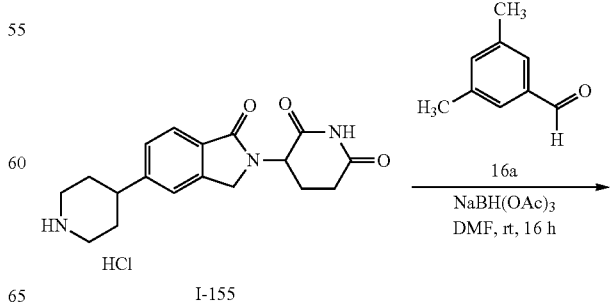

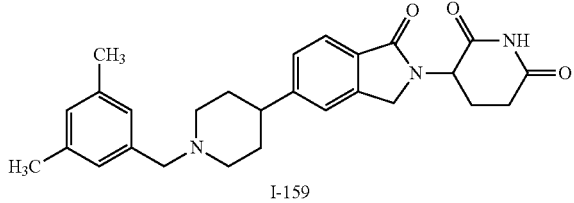

I-159

Compound I-159 was prepared from I-155 (90 mg, 0.25 mmol) and 3,5-dimethylbenzaldehyde (16a, 110 mg, 0.82 mmol) via reductive amination as described for Example 8. After the reaction was complete, the crude reaction mixture was concentrated to dryness. The resulting material was triturated with Et$_2$O and then decanted. The remaining residue was dried under high vacuum affording I-159 as a brown solid (70 mg, 0.16 mmol, 64% yield). MS [M+H]$^+$=446.1. $^1$H NMR (DMSO-d$_6$, 400 MHz): δ 10.99 (s, 1H), 7.63 (d, J=8.0 Hz, 1H), 7.50 (s, 1H), 7.40 (d, J=8.0 Hz, 1H), 6.91 (s, 2H), 6.87-6.86 (m, 1H), 5.09 (dd, J=13.2 Hz, 4.8 Hz, 1H), 4.41 (d, J=17.2 Hz, 1H), 4.27 (d, J=16 Hz, 1H), 3.41 (s, 2H), 2.93-2.88 (m, 3H), 2.67-2.60 (m, 1H), 2.41-2.37 (m, 1H), 2.26-2.23 (s, 6H), 2.05-1.98 (m, 4H), 1.74-1.67 (m, 4H).

Example 17: 3-(5-(1-(4-methoxybenzyl)piperidin-4-yl)-1-oxoisoindolin-2-yl)piperidine-2,6-dione (I-39)

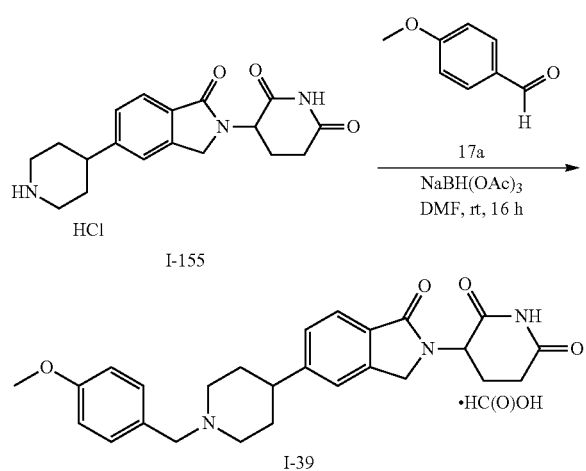

I-39

Compound I-39 was prepared from I-155 (90 mg, 0.25 mmol) and p-anisaldehyde (17a, 40 mg, 0.30 mmol) via reductive amination as described for Example 8. After the reaction was complete, the crude reaction mixture was concentrated to dryness. The resulting material was triturated with Et$_2$O then decanted. The remaining residue was then purified by reverse phase HPLC (MeCN/H$_2$O with 0.1% formic acid). Removal of the solvent afforded the formate salt of I-39 as a yellow oil (40 mg, 0.081 mmol, 32% yield, formate salt). MS [M+H]$^+$=448.4. $^1$H NMR (DMSO-d$_6$, 400 MHz): δ 10.98 (s, 1H), 8.14 (s, 1H), 7.63 (d, J=8.0 Hz, 1H), 7.48 (s, 1H), 7.39 (d, J=8.0 Hz, 1H), 7.24 (d, J=8.3 Hz, 2H), 6.89 (d, J=8.8 Hz, 2H), 5.11 (dd, J=13.3 Hz, 5.2 Hz, 1H), 4.41 (d, J=17.2 Hz, 1H), 4.27 (d, J=17.2 Hz, 1H), 3.73 (s, 3H), 3.47 (s, 2H), 2.95-2.87 (m, 3H), 2.67-2.61 (m, 2H), 2.40-2.32 (m, 1H), 2.10-2.05 (m, 2H), 1.99-1.97 (m, 1H), 1.78-1.60 (m, 4H).

Example 18: 3-(5-(1-(4-nitrilebenzyl)piperidin-4-yl)-1-oxoisoindolin-2-yl)piperidine-2,6-dione (I-31)

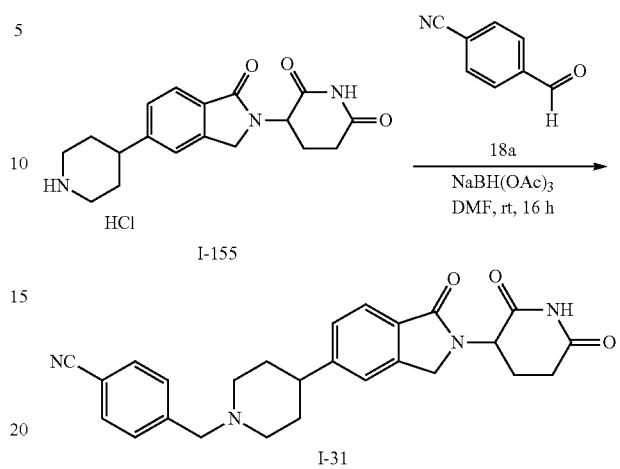

I-31

Compound I-31 was prepared from I-155 (90 mg, 0.25 mmol) and 4-formylbenzonitrile (18a, 97 mg, 0.74 mmol) via reductive amination as described for Example 8. After the reaction was complete, the crude reaction mixture was concentrated to dryness. The resulting material was triturated with Et$_2$O and then decanted. The remaining residue was dried under high vacuum affording I-31 as a grey solid (42 mg, 0.10 mmol, 38% yield). MS [M+H]$^+$=443.1. $^1$H NMR (DMSO-d$_6$, 300 MHz): δ 10.99 (1H, s), 7.81 (d, J=8.4 Hz, 2H), 7.64 (d, J=7.6 Hz, 1H), 7.55 (d, J=8.4 Hz, 2H), 7.50 (1H, s), 7.41 (d, J=8.0 Hz, 1H), 5.09 (dd, J=13.6, 5.2 Hz, 1H), 4.42 (d, J=16.8 Hz, 1H), 4.29 (d, J=17.2 Hz, 1H), 3.60 (s, 2H), 2.94-2.88 (m, 2H), 2.66-2.52 (m, 2H), 2.40-2.32 (m, 2H), 2.13-2.08 (m, 2H), 1.99-1.96 (m, 1H), 1.78-1.70 (m, 4H).

Example 19: 3-(5-(1-(4-ethylbenzyl)piperidin-4-yl)-1-oxoisoindolin-2-yl)piperidine-2,6-dione (I-66)

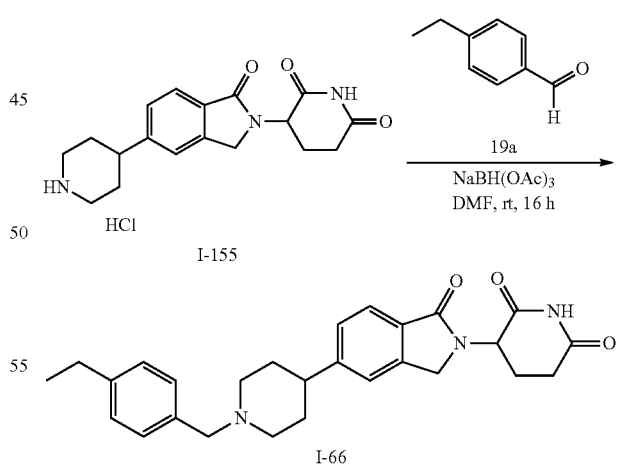

I-66

Compound I-66 was prepared from I-155 (25 mg, 0.07 mmol) and 4-ethyl benzaldehyde (19a, 11 mg, 0.08 mmol) via reductive amination as described for Example 8. After workup, the crude material was purified by silica gel chromatography eluting with 5% MeOH in DCM affording I-66 as an off-white solid (11 mg, 0.025 mol, 35% yield). MS [M+H]$^+$=446.5. $^1$H NMR (400 MHz, DMSO-d6) δ 10.97 (s, 1H), 7.63 (d, J=7.9 Hz, 1H), 7.49 (s, 1H), 7.40 (d, J=7.7 Hz, 1H), 7.23 (d, J=8.0 Hz, 2H), 7.16 (d, J=7.9 Hz, 2H), 5.10 (dd, J=13.3, 5.1 Hz, 1H), 4.42 (d, J=17.2 Hz, 1H), 4.28 (d, J=17.2 Hz, 1H), 3.46 (s, 2H), 2.98-2.85 (m, 3H), 2.68-2.55 (m, 4H), 2.45-2.32 (m, 1H), 2.11-1.94 (m, 3H), 1.81-1.64 (m, 4H), 1.18 (t, J=7.6 Hz, 3H).

Example 20: 3-(5-(1-(4-isopropylbenzyl)piperidin-4-yl)-1-oxoisoindolin-2-yl)piperidine-2,6-dione (I-45)

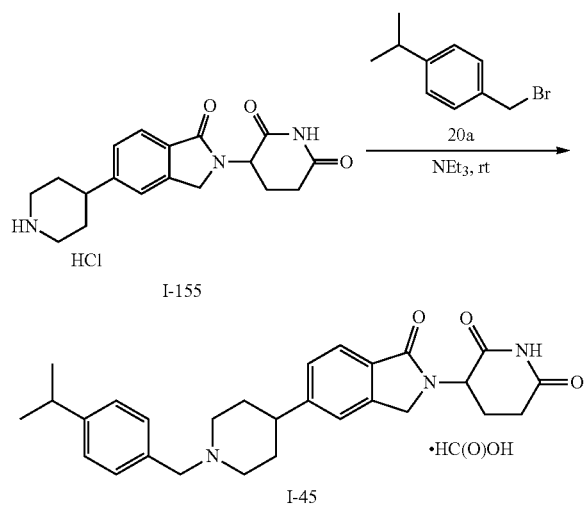

Compound I-45 was prepared from I-155 (100 mg, 0.27 mmol), 1-(bromomethyl)-4-isopropylbenzene (20a, 58 mg, 0.27 mmol) and NEt₃ (0.077 mL, 0.55 mmol) similar to the alkylation procedure described in method 2 of Example 8. Upon work up the crude material was purified by reverse phase HPLC (MeCN/H₂O with 0.05% formic acid). The fractions with the desired product were concentrated to dryness to afford the formate salt of I-45 as an off-white solid (18 mg, 0.036 mmol, 13% yield, formate salt). MS [M+H]⁺=460.5. ¹H NMR (400 MHz, DMSO-d₆): δ 10.97 (s, 1H), 7.63 (d, J=7.9 Hz, 1H), 7.49 (s, 1H), 7.40 (d, J=6.8 Hz, 1H), 7.24 (d, J=8.2 Hz, 2H), 7.19 (d, J=8.2 Hz, 2H), 5.10 (dd, J=13.3, 5.1 Hz, 1H), 4.42 (d, J=17.2 Hz, 1H), 4.28 (d, J=17.2 Hz, 1H), 3.47 (s, 2H), 2.98-2.80 (m, 4H), 2.72-2.57 (m, 2H), 2.43-2.30 (m, 1H), 2.10-1.93 (m, 3H), 1.80-1.64 (m, 4H), 1.20 (d, J=6.9 Hz, 6H).

Example 21: 3-(5-(1-(4-(tert-butyl)benzyl)piperidin-4-yl)-1-oxoisoindolin-2-yl)piperidine-2,6-dione

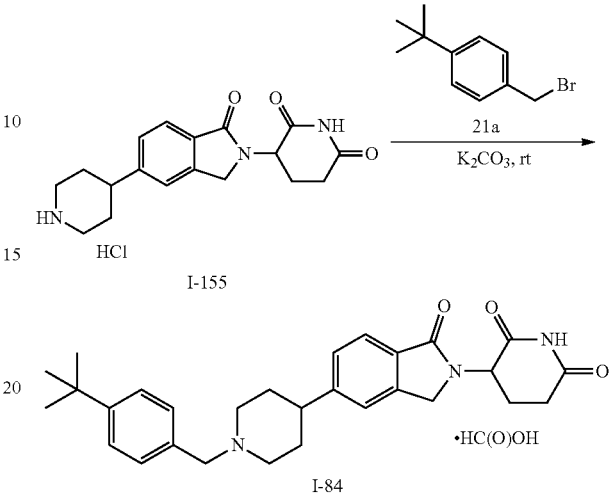

Compound I-84 was prepared from I-155 (70 mg, 0.19 mmol) and 1-(bromomethyl)-4-(tert-butyl)benzene (21a, 43 mg, 0.19 mmol) and K₂CO₃ (79 mg, 0.58 mmol) similar to the alkylation procedure described in method 2 of Example 8. The crude material, after trituration with Et₂O, was purified by reverse phase HPLC (MeCN/H₂O with 0.1% formic acid. The fractions containing the desired product were concentrated to dryness to afford the formate salt of I-84 as an off-white solid (25 mg, 0.048 mmol, 25% yield, formate salt). MS [M+H]⁺=474.4. ¹H NMR (400 MHz, DMSO-d6) δ 10.98 (s, 1H), 8.18 (s, 1H), 7.64 (d, J=7.8 Hz, 1H), 7.49 (s, 1H), 7.40 (d, J=7.9 Hz, 1H), 7.35 (d, J=8.3 Hz, 2H), 7.25 (d, J=8.2 Hz, 2H), 5.10 (dd, J=13.3, 5.1 Hz, 1H), 4.42 (d, J=17.3 Hz, 1H), 4.28 (d, J=17.2 Hz, 1H), 3.50 (s, 2H), 2.99-2.84 (m, 3H), 2.72-2.60 (m, 1H), 2.46-2.30 (m, 2H), 2.09 (t, J=10.8 Hz, 2H), 2.03-1.93 (m, 1H), 1.82-1.65 (m, 4H), 1.28 (s, 9H).

Example 22: 3-(5-(1-([1,1'-biphenyl]-4-ylmethyl)piperidin-4-yl)-1-oxoisoindolin-2-yl)piperidine-2,6-dione (I-90)

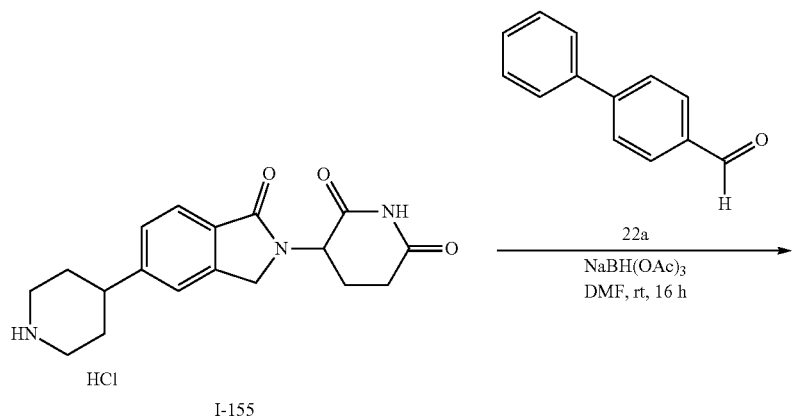

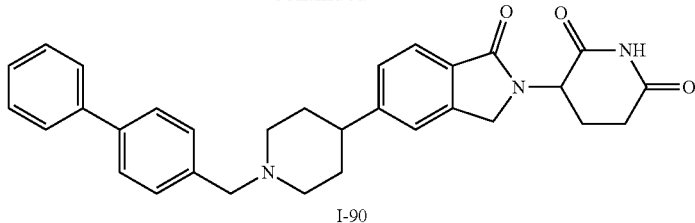

I-90

Compound I-90 was prepared from I-155 (90 mg, 0.25 mmol) and [1,1'-biphenyl]-4-carbaldehyde (22a, 135 mg, 0.74 mmol) via reductive amination as described for Example 8. After workup, the crude material was triturated with EtOAc and then filtered. The solid was dried under high vacuum affording I-90 as an off-white solid (45 mg, 0.09 mmol, 37% yield). MS [M+H]$^+$=494.1. $^1$H NMR (DMSO-d$_6$, 400 MHz): δ 11.0 (s, 1H), 7.67-7.61 (m, 4H), 7.51-7.35 (m, 6H), 5.08 (dd, J=13.2, 5.2 Hz, 1H), 4.41 (d, J=17.2 Hz, 1H), 4.28 (d, J=17.2 Hz, 1H), 3.55 (s, 2H), 2.98-2.85 (m, 3H), 2.66-2.56 (m, 2H), 2.39-2.32 (m, 2H), 2.10 (m, 2H), 1.95 (m, 2H), 1.77-1.73 (m, 4H).

Example 23: 3-(5-(1-(3,5-difluoro-4-hydroxybenzyl)piperidin-4-yl)-1-oxoisoindolin-2-yl)piperidine-2,6-dione (I-156)

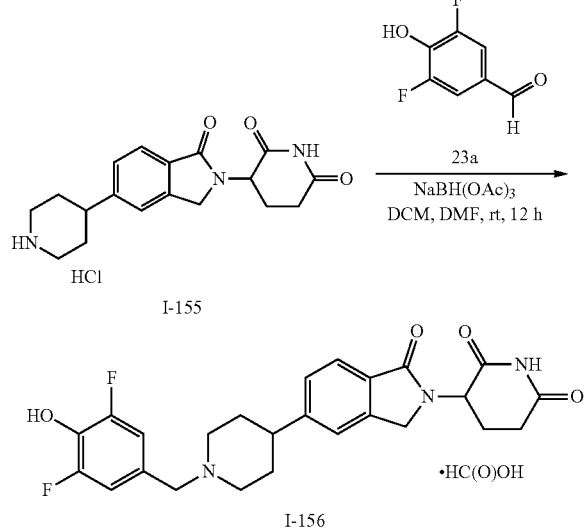

To compound I-155 (15 mg, 0.041 mmol) and 3,5-difluoro-4-hydroxybenzaldehyde (23a, 20 mg, 0.13 mmol) in DCM (0.6 mL) and DMF (0.6 mL) was added sodium triacetoxyborohydride (26 mg, 0.12 mmol) in one portion and the resulting mixture was stirred vigorously for 12 h at rt. The reaction mixture was then concentrated under reduced pressure and the crude product was diluted with aqueous formic acid (0.1 M in H$_2$O) and MeCN. The resulting solution was directly purified by reverse phase HPLC (MeCN/H$_2$O with 0.1% formic acid). The pure fractions were combined and concentrated to dryness to afford the formate salt of I-156 (12.1 mg, 0.023 mmol, 57% yield, formate salt) as a white solid. MS [M+H]$^+$=470.3. $^1$H NMR (400 MHz, acetonitrile-d$_3$) δ 8.82 (s, 1H), 8.18 (s, 1H), 7.66 (s, 1H), 7.45 (d, J=1.3 Hz, 1H), 7.39 (dd, J=7.9, 1.4 Hz, 1H), 7.10-6.86 (m, 2H), 5.06 (dd, J=13.4, 5.2 Hz, 1H), 4.38 (d, J=16.7 Hz, 1H), 4.30 (d, J=16.8 Hz, 1H), 3.49 (s, 2H), 2.99 (d, J=11.5 Hz, 2H), 2.82 (ddd, J=17.7, 13.3, 5.3 Hz, 1H), 2.77-2.62 (m, 2H), 2.41 (qd, J=13.2, 4.8 Hz, 1H), 2.22-2.07 (m, 3H), 1.86-1.73 (m, 4H).

Example 24: 3-(5-(1-((1H-pyrazol-3-yl)methyl)piperidin-4-yl)-1-oxoisoindolin-2-yl)piperidine-2,6-dione (I-118)

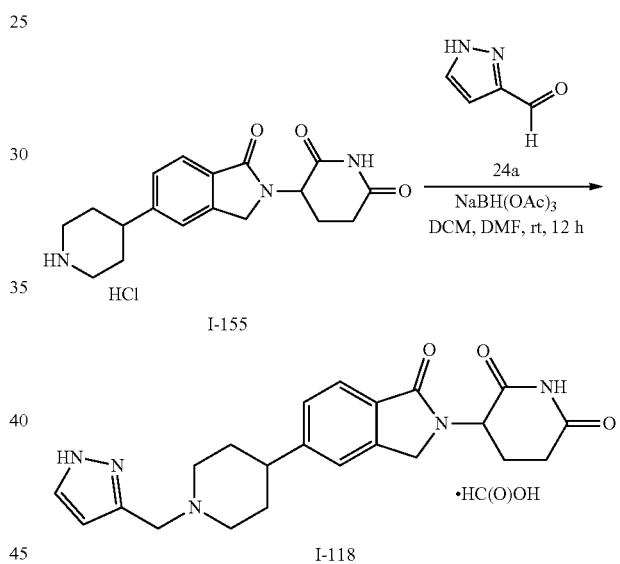

To I-155 (15 mg, 0.041 mmol) and 1H-pyrazole-3-carbaldehyde (24a, 12 mg, 0.12 mmol) in DCM (0.6 mL) and DMF (0.6 mL) was added sodium triacetoxyborohydride (26 mg, 0.12 mmol) in one portion and the resulting mixture was stirred vigorously for 12 h at rt. The reaction mixture was concentrated under reduced pressure and the crude product was diluted with aqueous formic acid (0.1 M in H$_2$O) and MeCN. The resulting solution was directly purified by reverse phase HPLC (MeCN/H$_2$O with 0.1% formic acid). The pure fractions containing the desired product were combined and concentrated to dryness to afford the formate salt of I-118 (9.7 mg, 0.021 mmol, 52% yield, formate salt) as a white solid. MS [M+H]$^+$=408.1. $^1$H NMR (400 MHz, D$_2$O): δ 8.44 (s, 1H), 7.82 (d, J=2.4 Hz, 1H), 7.77-7.71 (m, 1H), 7.52 (s, 1H), 7.45 (dd, J=8.0, 1.5 Hz, 1H), 6.59 (d, J=2.4 Hz, 1H), 5.13 (dd, J=13.3, 5.2 Hz, 1H), 4.56 (d, J=17.6 Hz, 1H), 4.47 (d, J=17.6 Hz, 1H), 4.40 (s, 2H), 3.64 (d, J=12.3 Hz, 2H), 3.19 (t, J=12.6 Hz, 2H), 3.08-2.81 (m, 3H), 2.51 (qd, J=12.9, 5.4 Hz, 1H), 2.24 (dtd, J=13.0, 5.2, 2.7 Hz, 1H), 2.14 (d, J=14.3 Hz, 2H), 2.05-1.89 (m, 2H).

Example 25: 3-(1-oxo-5-(1-((5,6,7,8-tetrahydronaphthalen-1-yl)methyl)piperidin-4-yl)isoindolin-2-yl)piperidine-2,6-dione (I-164)

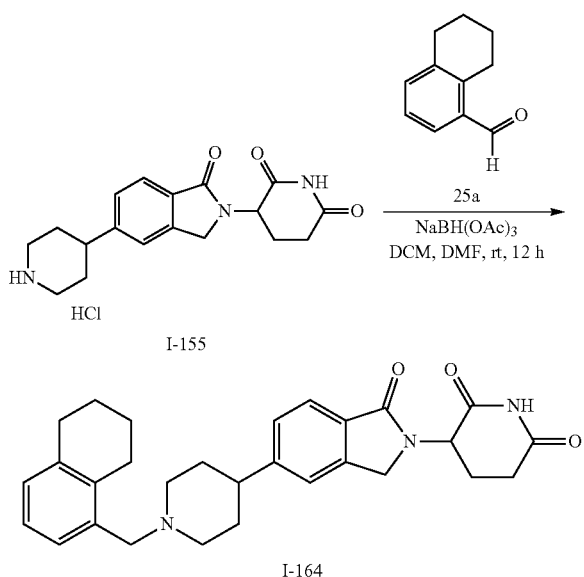

Compound I-164 was prepared from I-155 (60 mg, 0.16 mmol) and 5,6,7,8-tetrahydronaphthalene-1-carbaldehyde (25a, 78 mg, 0.48 mmol) via reductive amination as described for Example 8. After reaction was complete, the crude reaction mixture was concentrated to dryness. The resulting material was triturated with Et$_2$O then decanted. The remaining residue was then purified by reverse phase HPLC (MeCN/H$_2$O with 0.02% NH$_4$OH) and the desired fractions concentrated to dryness to afford I-164 as brown solid (6 mg, 0.012 mmol, 8% yield). MS [M+H]$^+$=472.4. $^1$H NMR (CDCl$_3$, 600 MHz): δ 7.92 (brs, 1H), 7.81-7.80 (d, J=6 Hz, 1H), 7.37-7.33 (m, 2H), 7.16-7.12 (m, 1H), 7.10-7.04 (m, 1H), 7.03-7.01 (m, 1H), 5.26-5.20 (m, 1H) 4.46 (d, J=15.6 Hz, 1H), 4.30-4.33 (d, J=16.2 Hz, 1H), 3.44 (s, 2H), 3.02 (m, 2H), 2.91 (d, 1H), 2.80-2.83 (m, 6H), 2.22 (m, 1H), 2.10 (m, 2H), 1.82-1.80 (m, 9H).

Example 26: 3-(1-oxo-5-(1-((1,2,3,4-tetrahydronaphthalen-1-yl)methyl)piperidin-4-yl)isoindolin-2-yl)piperidine-2,6-dione (I-168)

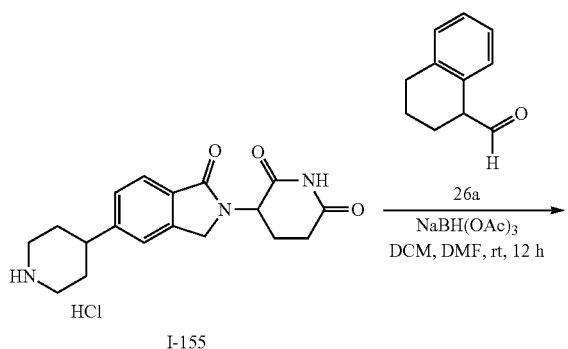

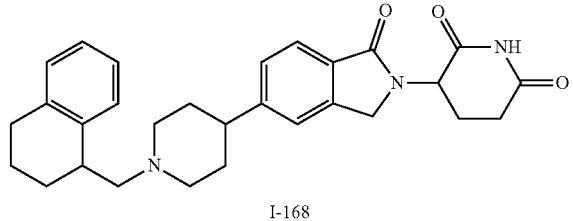

Compound I I-168 was prepared from I-155 (60 mg, 0.16 mmol) and 1,2,3,4-tetrahydronaphthalene-1-carbaldehyde (26a, 78 mg, 0.48 mmol) via reductive amination as described for Example 8. Upon completion of the reaction, the crude reaction mixture was concentrated to dryness. The resulting material was triturated with Et$_2$O then decanted. The remaining residue was then purified by reverse phase HPLC (MeCN/H$_2$O) and the desired fractions were concentrated to dryness to afford I-168 as a brown solid (10 mg, 0.02 mmol, 14% yield). MS [M+H]$^+$=472.4. $^1$H NMR (CDCl$_3$, 300 MHz): δ 7.92 (s, 1H), 7.82 (d, J=7.5 Hz, 1H), 7.39-7.36 (m, 2H), 7.26-7.23 (s, 1H), 7.13-7.06 (m, 3H), 5.23 (dd, J=12.9, 5.1 Hz, 1H), 4.48 (d, J=15.9 Hz, 1H), 4.32 (d, J=15.6 Hz, 1H), 3.23-3.19 (m, 1H), 3.00-2.77 (m, 7H), 2.63-2.54 (m, 3H), 2.39-2.35 (m, 1H), 2.24-2.17 (m, 2H), 1.98-2.08 (m, 3H), 1.26-1.86 (m, 4H).

Example 27: 3-(1-oxo-5-(1-((5,6,7,8-tetrahydronaphthalen-2-yl)methyl)piperidin-4-yl)isoindolin-2-yl)piperidine-2,6-dione (I-175)

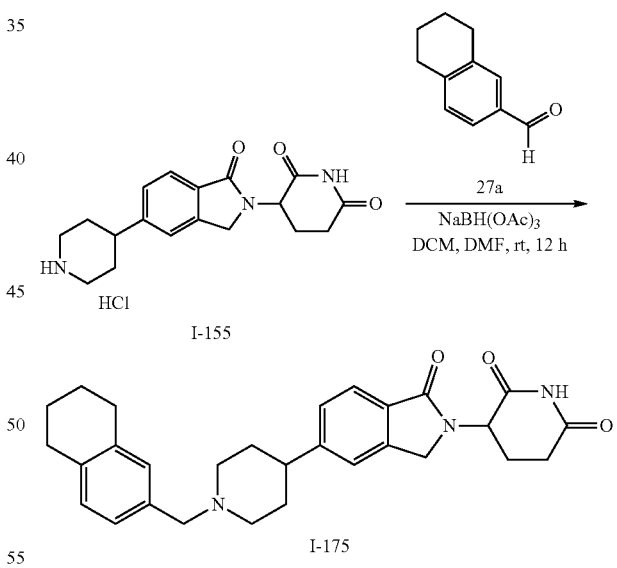

Compound I-175 was prepared from I-155 (100 mg, 0.27 mmol) and 5,6,7,8-tetrahydronaphthalene-2-carbaldehyde (27a, 49 mg, 0.30 mmol) via reductive amination as described for Example 8. Upon completion of the reaction, the crude reaction mixture was concentrated to dryness. The resulting material was triturated with Et$_2$O then decanted. The remaining residue was then purified by reverse phase HPLC (MeCN/H$_2$O with 0.02% NH$_4$OH). Concentration to dryness of the desired fractions afforded I-175 as an off-white solid (18 mg, 0.038 mmol, 14% yield). MS [M+H]$^+$=472.4. $^1$H NMR (400 MHz, DMSO-d6): δ 10.97 (s, 1H), 8.16 (s, 1H), 7.63 (d, J=7.9 Hz, 1H), 7.49 (s, 1H), 7.39 (d, J=8.0 Hz, 1H), 7.03-6.96 (m, 3H), 5.10 (dd, J=13.3, 5.1 Hz, 1H), 4.41 (d, J=17.2 Hz, 1H), 4.28 (d, J=17.3 Hz, 1H), 3.43 (s, 2H), 2.97-2.88 (m, 3H), 2.76-2.59 (m, 6H), 2.45-2.30 (m, 1H), 2.12-1.92 (m, 3H), 1.77-1.69 (m, 7H).

Example 28: Preparation of Intermediate 29f: (2S)-tert-butyl 2-methyl-4-(tosyloxy)piperidine-1-carboxylate (29f)

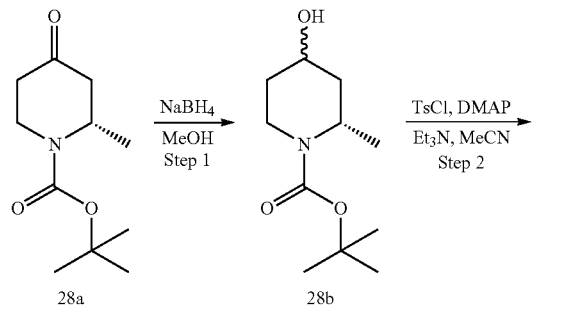

Step 1. tert-butyl (2S)-4-hydroxy-2-methylpiperidine-1-carboxylate

To (S)-tert-butyl 2-methyl-4-oxopiperidine-1-carboxylate (28a, 1.0 g, 4.7 mmol) in MeOH (5 mL) was added NaBH$_4$ (213 mg, 5.63 mmol) portionwise, and the reaction mixture was stirred overnight at rt. The reaction mixture was then quenched with brine and extracted with DCM. The combined organic phases were concentrated to afford 28b (957 mg, 4.45 mmol, 95% yield, 1:0.6 mixture of diastereomers). The compound was sufficiently pure to use in the next step without further purification. $^1$H NMR of major diastereomer (400 MHz, CDCl$_3$): δ 4.28 (quintd, J=6.8, 2.3 Hz, 1H), 4.17 (quint, J=3.4 Hz, 1H), 3.82 (ddd, J=13.5, 4.9, 2.8 Hz, 1H), 3.25 (ddd, J=13.5, 11.8, 4.0 Hz, 1H), 1.85-1.79 (m, 1H), 1.69-1.64 (m, 2H), 1.55-1.51 (m, 1H), 1.46 (s, 9H), 1.32 (d, J=7.1 Hz, 3H), 1.40-1.26 (m, 1H). $^1$H NMR of minor diastereomer (400 MHz, CDCl$_3$) δ 4.55-4.44 (m, 1H), 4.04 (d, J=14.2 Hz, 1H), 3.95 (tt, J=11.3, 4.4 Hz, 1H), 2.87 (td, J=13.5, 2.8 Hz, 1H), 1.93 (ddq, J=12.3, 5.0, 2.6 Hz, 1H), 1.88-1.84 (m, 1H), 1.77-1.70 (m, 1H), 1.62 (dt, J=3.8, 2.0 Hz, 1H), 1.51 (s, 1H), 1.45 (s, 9H), 1.14 (d, J=7.0 Hz, 3H).

Step 2. (2S)-tert-butyl 2-methyl-4-(tosyloxy)piperidine-1-carboxylate (29f)

To 28b (500 mg, 2.28 mmol), TEA (0.65 mL, 4.64 mmol) and DMAP (57 mg, 0.46 mmol) in MeCN (4 mL) was added TsCl (531 mg, 2.79 mmol) in one portion and the resulting mixture was stirred for 48 h at rt. After this time the reaction mixture was quenched with saturated aqueous NaHCO$_3$ and extracted with DCM (3×). The combined organic phases were dried over Na$_2$SO$_4$ and concentrated under reduced pressure. The crude product was then purified via chromatography on silica gel eluting with 0 to 40% EtOAc in heptane to afford 29f (597 mg, 1.62 mmol, 70% yield, 1:0.7 mixture of diastereoisomers) as a slightly yellow solid. MS [M−56+H]$^+$=314.2 and [M+Na]$^+$=392.3. $^1$H NMR of a 1:0.7 mixture of diastereoisomers (400 MHz, CDCl$_3$): δ 7.87-7.72 (m, 3.4H), 7.42-7.30 (m, 3.4H), 4.84 (quint, J=3.1 Hz, 1H), 4.75 (hept, 0.7H), 4.51-4.42 (m, 0.7H), 4.36-4.23 (m, 1H), 4.01 (d, J=14.2 Hz, 1H), 3.90-3.78 (m, 1H), 3.11 (td, J=13.5, 2.8 Hz, 1H), 2.83 (td, J=13.6, 2.8 Hz, 0.7H), 2.45 (s, 5.1H), 1.91 (ddt, J=12.0, 4.6, 2.5 Hz, 1H), 1.85-1.69 (m, 4.5H), 1.66-1.60 (m, 1H), 1.55-1.50 (m, 0.6H), 1.43 (s, 9H), 1.43 (s, 6H), 1.23 (d, J=7.1 Hz, 3H), 1.08 (d, J=7.1 Hz, 2H).

Example 29: 3-(5-((2S)-1-benzyl-2-methylpiperidin-4-yl)-1-oxoisoindolin-2-yl)piperidine-2,6-dione HC(O)OH salt (I-160)

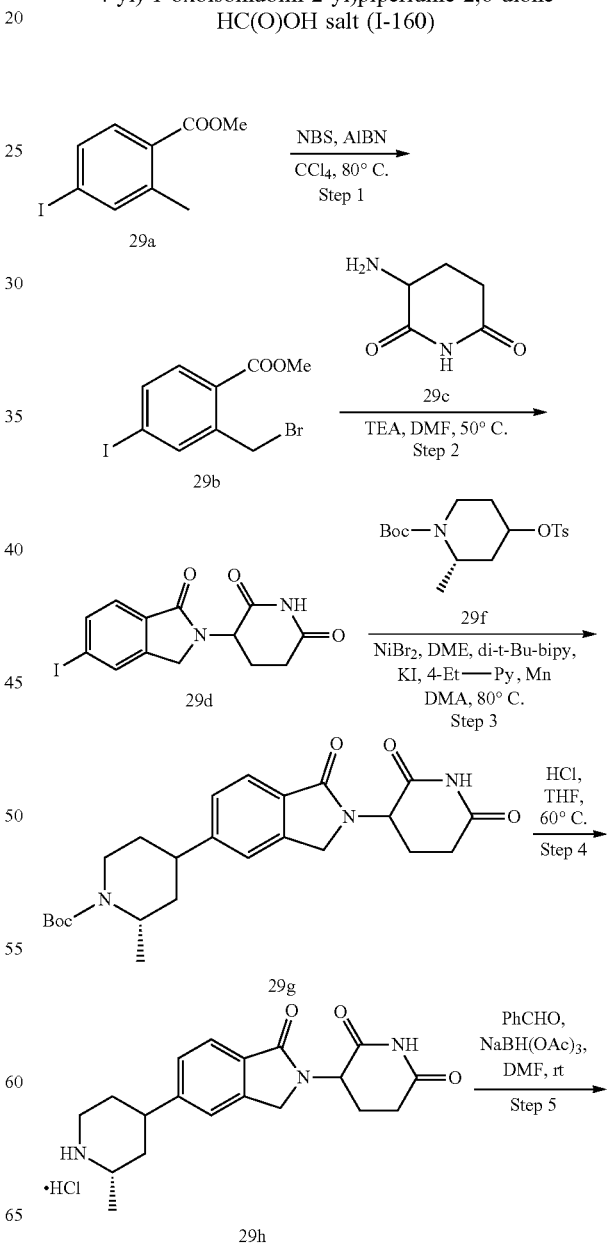

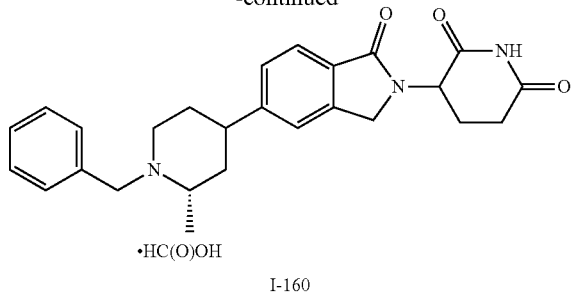

I-160

Step 1. 3-(5-iodo-1-oxoisoindolin-2-yl)piperidine-2,6-dione (29b)

To methyl 4-iodo-2-methylbenzoate (29a, 170 g, 615.78 mmol) in MeCN (1 L) was added AIBN (10.1 g, 61.51 mmol), and NBS (131.56 g, 739.18 mmol). The resulting solution was stirred overnight at 80° C. The reaction mixture was cooled to rt and the solids were filtered out. The resulting mixture was concentrated under vacuum and was applied onto a silica gel column with ethyl acetate/petroleum ether (0-10%). The collected fractions were concentrated under vacuum to afford 29b (50 g, 140.9 mmol, 23% yield) as a white solid. $^1$H NMR (300 MHz, DMSO-$d_6$) δ 8.04-8.01 (m, 1H), 7.88-7.81 (m, 1H), 7.67-7.59 (m, 1H), 4.96 (s, 2H), 3.87 (s, 3H).

Step 2. 3-(5-iodo-1-oxoisoindolin-2-yl)piperidine-2,6-dione (29d)

To 29b (50 g, 140.86 mmol) was added 3-aminopiperidine-2,6-dione TFA salt (29c, 34.18 g, 141.15 mmol), DMF (500 mL), and TEA (42.4 g, 419.01 mmol). The resulting solution was stirred for 48 h at 60° C. The reaction mixture was then cooled to rt and quenched by the addition of 500 mL of water/ice. The pH value of the solution was adjusted to 5 with HCl (1 M). The resulting solids were collected by filtration, washed with EtOAc, and dried to afford 29d (13 g, 35.1 mmol, 25% yield) as a gray solid. [M+H]$^+$=371.0. $^1$H NMR (300 MHz, DMSO-$d_6$) δ 11.00 (s, 1H), 8.06 (s, 1H), 7.90 (d, J=7.8 Hz, 1H), 7.52 (d, J=7.8 Hz, 1H), 5.14-5.08 (m, 1H), 4.47-4.28 (m, 2H), 2.97-2.85 (m, 1H), 2.73-2.01 (m, 2H), 1.98-1.20 (m, 1H).

Step 3. tert-Butyl-(2S)-4-(2-(2,6-dioxopiperidin-3-yl)-1-oxoisoindolin-5-yl)-2-methylpiperidine-1-carboxylate (29 g)

To 29d (20 mg, 0.054 mmol), 29f (24 mg, 0.065 mmol), NiBr$_2$·DME (1.7 mg, 5.4 μmol), di-t-Bu-bipy (1.5 mg, 5.4 μmol), KI (9 mg, 0.05 mmol), and manganese powder (6 mg, 0.1 mmol) under a nitrogen atmosphere was added DMA (0.27 mL) followed by 4-ethylpyridine (6.2 μL, 0.054 mmol) and the reaction mixture was stirred vigorously at 80° C. overnight. The reaction mixture was then diluted with MeCN and filtered through a short pad of Celite® filter aid eluting with MeCN. The obtained solution was concentrated by azeotroping with heptane. The crude product was purified by reverse phase HPLC (MeCN/H$_2$O with 0.1% formic acid). The pure fractions were combined, concentrated to dryness to afford 29 g (11 mg, 0.026 mmol, 47% yield) as a white solid. MS [M−56+H]$^+$=386.4 and [M+H]$^+$=442.5. $^1$H NMR (400 MHz, CDCl$_3$) δ 8.27 (s, 1H), 7.81 (d, J=7.9 Hz, 1H), 7.33 (d, J=8.1 Hz, 1H), 7.30 (s, 1H), 5.33-5.09 (m, 1H), 4.69-4.47 (m, 1H), 4.46 (d, J=15.8 Hz, 1H), 4.31 (d, J=15.9 Hz, 1H), 4.23-3.94 (m, 1H), 3.12-2.73 (m, 4H), 2.34 (dq, J=14.6, 9.6 Hz, 1H), 2.20 (s, 1H), 1.84 (td, J=13.4, 5.3 Hz, 2H), 1.70 (d, J=13.8 Hz, 1H), 1.48 (s, 9H), 1.38 (s, 1H), 1.24 (d, J=6.9 Hz, 3H)

Step 4. 3-(5-((2S)-1-benzyl-2-methylpiperidin-4-yl)-1-oxoisoindolin-2-yl)piperidine-2,6-dione (29 h)

To 29 g (11 mg, 0.025 mmol) in THF (1 mL) was added 4 M HCl in dioxane (0.7 mL, 2.8 mmol) and the reaction mixture was stirred for 2 h at 60° C. Formation of a white precipitate was observed. The reaction mixture was then diluted with Et$_2$O and filtered. The precipitate was washed with Et$_2$O and then dried to afford the hydrochloride salt of 29 h (9 mg, 0.024 mmol, 97% yield, hydrochloride salt) as a white solid. MS [M+H]$^+$=342.2. The compound was used in the next step without further purification.

Step 5. 3-(5-((2S)-1-benzyl-2-methylpiperidin-4-yl)-1-oxoisoindolin-2-yl)piperidine-2,6-dione HC(O)OH salt (I-160)

To 29 h (9 mg, 0.024 mmol) and benzaldehyde (8 μL, 0.08 mmol) in DMF (1 mL) was added sodium triacetoxyborohydride (15 mg, 0.071 mmol) in one portion and the reaction mixture was stirred vigorously at rt overnight. The reaction mixture was then stirred for an additional 8 h at 60° C. The resulting mixture was concentrated under reduced pressure and the crude product was diluted with aqueous formic acid (0.1 M in H$_2$O) and MeCN. The resulting solution was directly purified by reverse phase HPLC (MeCN/H$_2$O with 0.1% formic acid). The two fractions obtained were concentrated to dryness separately. The first fraction afforded a diastereomeric mixture containing I-160 (1.9 mg, 4.0 μmol, 17% yield, 10:1 mixture of diastereoisomers, formate salt) as a white solid. The second fraction afforded I-160 (1.2 mg, 2.5 μmol, 10% yield, single diastereomer, formate salt) as a white solid. Overall yield: 27% yield. MS [M+H]$^+$=432.3. Major diastereomer $^1$H NMR (400 MHz, acetonitrile-$d_3$): δ 8.72 (s, 1H), 8.04 (s, 1H), 7.58 (d, J=7.9 Hz, 1H), 7.43-7.37 (m, 3H), 7.33 (dd, J=7.9, 1.4 Hz, 1H), 7.27 (t, J=7.3 Hz, 2H), 7.23-7.17 (m, 1H), 4.97 (dd, J=13.4, 5.2 Hz, 1H), 4.30 (d, J=16.7 Hz, 1H), 4.22 (d, J=16.7 Hz, 1H), 3.77-3.65 (m, 2H), 3.29-3.17 (m, 1H), 3.06-2.94 (m, 1H), 2.78-2.59 (m, 4H), 2.06-2.00 (m, 3H), 1.75-1.61 (m, 3H), 1.14 (d, J=6.8 Hz, 3H). $^1$H NMR of minor diastereomer was not obtained due to insufficient material.

Example 30: 3-(5-(1-isobutylpiperidin-4-yl)-1-oxoisoindolin-2-yl) piperidine-2,6-dione (I-4)

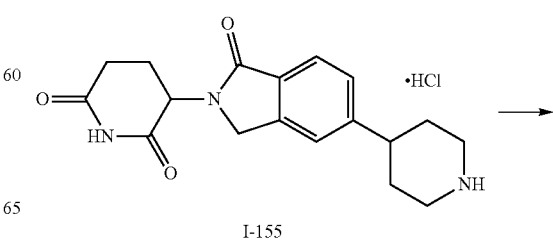

I-155

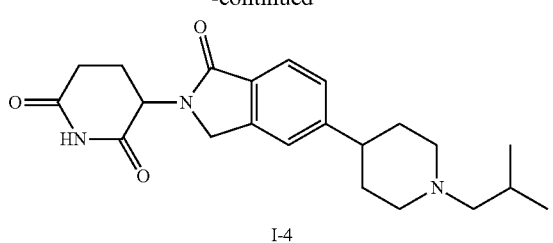

I-4

To a stirred solution of I-155 (100 mg, 0.30 mmol) and Et₃N (0.21 mL, 1.52 mmol) in DMF (2 mL) was added isobutyl bromide (0.06 mL, 0.60 mmol) and the resulting mixture was stirred at 80° C. for 16 h. The reaction mixture was then cooled to rt and quenched with ice-cold water. The resulting solid was filtered, washed with water, and dried under reduced pressure to afford I-4 as off-white solid (45 mg, 0.11 mmol, 38% yield). MS [M+H]⁺=384.1. 1H NMR (400 MHz, DMSO-d₆): δ 10.96 (s, 1H), 7.63 (d, J=8.0 Hz, 1H), 7.50 (s, 1H), 7.39 (d, J=8.0 Hz, 1H), 5.09 (dd, J=13.2, 5.2 Hz, 1H), 4.40 (d, J=17.2 Hz, 1H), 4.27 (d, J=17.2 Hz, 1H), 2.94-2.86 (m, 3H), 2.67-2.57 (m, 2H), 2.45-2.32 (m, 2H), 2.06 (d, J=7.2 Hz, 2H), 1.99-1.96 (m, 3H), 1.94-1.67 (m, 4H), 0.87 (d, J=6.8 Hz, 6H).

Example 31: 3-(5-(1-(cyclobutylmethyl)piperidin-4-yl)-1-oxoisoindolin-2-yl)piperidine-2,6-dione (I-5)

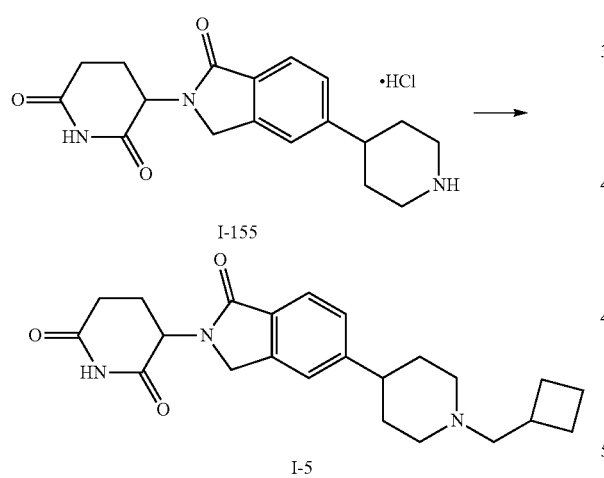

I-155

I-5

To a stirred solution of I-155 (75 mg, 0.23 mmol) and Et₃N (0.16 mL, 1.14 mmol) in DMF (2 mL) was added (bromomethyl)cyclobutane (0.05 mL, 0.46 mmol) and the resulting mixture was stirred at 80° C. for 16 h. The reaction mixture was then cooled to rt and quenched with ice-cold water. The resulting solid was filtered, washed with water, and dried under reduced pressure to afford I-5 as off-white solid (20 mg, 0.05 mmol, 22% yield). MS [M+H]⁺=396.1. ¹H NMR (400 MHz, DMSO-d₆): δ 10.96 (s, 1H), 7.63 (d, J=8.0 Hz, 1H), 7.48 (s, 1H), 7.39 (d, J=8.0 Hz, 1H), 5.10 (dd, J=13.2, 4.8 Hz, 1H) 4.42 (d, J=17.2 Hz, 1H), 4.28 (d, J=17.2 Hz, 1H), 2.94-2.86 (m, 3H), 2.65-2.55 (m, 2H), 2.43-2.32 (m, 1H), 2.35 (d, J=7.2 Hz, 2H), 2.04-1.96 (m, 5H), 1.86-1.62 (m, 7H).

Example 32: 3-(5-(1-(cyclopropylmethyl)piperidin-4-yl)-1-oxoisoindolin-2-yl)piperidine-2,6-dione (I-3)

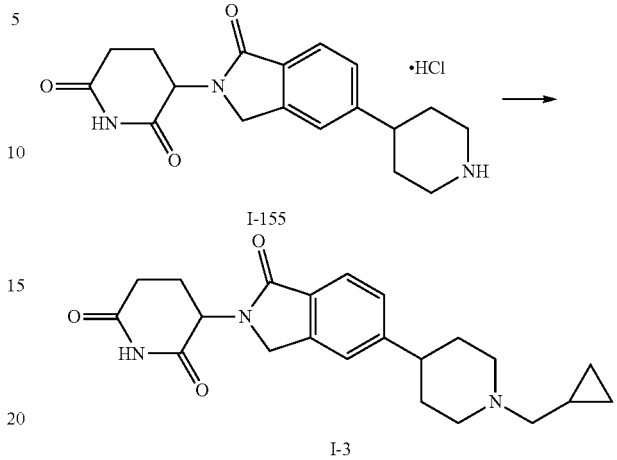

I-155

I-3

To a stirred solution of I-155 (100 mg, 0.30 mmol) and Et₃N (0.21 mL, 1.53 mmol) in DMF (2 mL) was added (bromomethyl)cyclopropane (0.06 mL, 0.61 mmol) and the resulting mixture was stirred at 80° C. for 16 h. The reaction mixture was then cooled to rt and quenched with ice-cold water. The resulting solid was filtered, washed with water, and dried under reduced pressure to afford I-3 as off-white solid (20 mg, 0.05 mmol, 17% yield). MS [M+H]⁺=382.2. ¹H NMR (400 MHz, DMSO-d₆): δ 10.97 (s, 1H), 7.65 (d, J=8.0 Hz, 1H), 7.49 (s, 1H), 7.39 (d, J=8.0 Hz, 1H), 5.83-5.79 (m, 1H), 5.12-5.09 (m, 2H), 5.01 (d, J=9.6 Hz, 1H), 4.43 (d, J=17.2 Hz, 1H), 4.29 (d, J=17.2 Hz, 1H), 3.18-3.02 (m, 2H), 2.91-2.88 (m, 2H), 2.67-2.51 (m, 2H), 2.41-2.40 (m, 1H), 2.38-2.36 m, 1H), 2.30-2.20 (m, 3H), 2.01-1.97 (m, 2H), 1.97-1.65 (m, 4H).

Example 33: 3-(1-oxo-5-(1-((tetrahydro-2H-pyran-4-yl)methyl)piperidin-4-yl)isoindolin-2-yl)piperidine-2,6-dione (I-13)

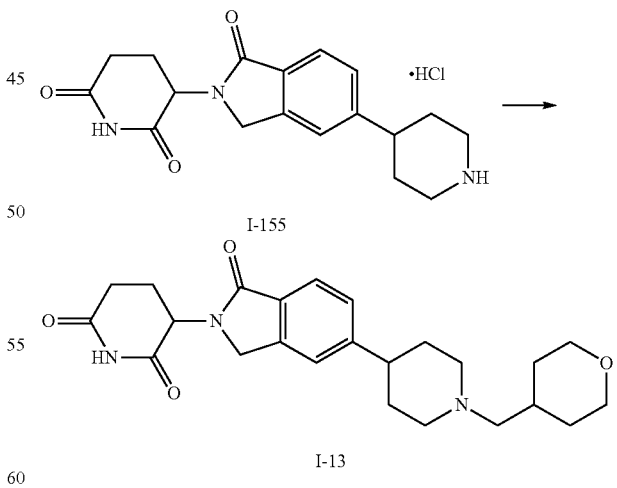

I-155

I-13

To a stirred solution of I-155 (100 mg, 0.23 mmol) and Et₃N (0.21 mL, 1.53 mmol) in DMF (2 mL) was added 4-(bromomethyl)tetrahydro-2H-pyran (0.08 mL, 0.61 mmol) and the resulting mixture was heated to 80° C. for 16 h. The reaction mixture was then cooled to rt and quenched with ice-cold water. The resulting solid was filtered, washed with water, and dried under reduced pressure to afford I-13 as an off-white solid (10 mg, 0.02 mmol, 8% yield). MS [M+H]⁺=426.2. ¹H NMR (400 MHz, DMSO-d₆): δ 10.97 (s, 1H), 7.66 (d, J=8.0 Hz, 1H), 7.48 (s, 1H), 7.39 (d, J=8.0 Hz, 1H), 5.10 (dd, J=13.2, 4.8 Hz, 1H), 4.43 (d, J=17.2 Hz, 1H), 4.30 (d, J=17.2 Hz, 1H), 3.84 (d, J=9.6 Hz, 2H), 3.31-3.27 (m, 1H), 2.95-2.86 (m, 3H), 2.67-2.57 (m, 3H), 2.43-2.3 (m, 2H), 2.17-2.13 (m, 2H), 2.00-1.97 (m, 3H), 1.90-1.62 (m, 6H), 1.18-1.58 (m, 2H).

Example 34: 3-(1-oxo-5-(1-phenethylpiperidin-4-yl) isoindolin-2-yl)piperidine-2,6-dione (I-14)

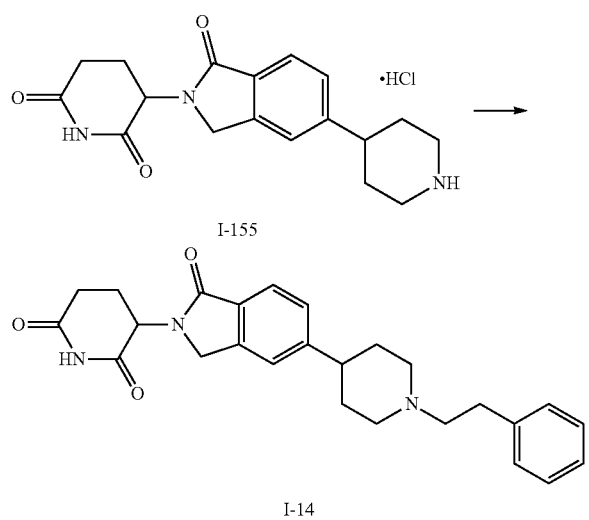

To a stirred solution of I-155 (100 mg, 0.30 mmol) and Et₃N (0.21 mL, 1.53 mmol) in DMF (2 mL) was added (2-bromoethyl)benzene (0.08 mL, 0.61 mmol) and the resulting mixture was stirred at rt for 16 h. The reaction mixture was then quenched with ice-cold water. The resulting solid was filtered, washed with water, and dried under reduced pressure to afford I-14 as an off-white solid (15 mg, 0.03 mmol, 11% yield). MS [M+H]+=432.1. H NMR (400 MHz, DMSO-d6): δ 10.97 (s, 1H), 7.64 (d, J=8.0 Hz, 1H), 7.49 (s, 1H), 7.40 (d, J=8.0 Hz, 1H), 7.30-7.23 (m, 4H), 7.20-7.16 (m, 1H), 5.09 (dd, J=13.2, 5.2 Hz, 1H), 4.42 (d, J=17.2 Hz, 1H), 4.29 (d, J=17.2 Hz, 1H), 3.08-3.05 (m, 2H), 2.88 (m, 1H), 2.88-2.67 (m, 2H), 2.63-2.50 (m, 4H), 2.41-2.38 (m, 1H), 2.11-2.09 (m, 2H), 2.00-1.98 (m, 1H), 1.97-1.68 (m, 4H).

Example 35: 3-(1-oxo-5-(1-(4-(trifluoromethoxy) benzyl)piperidin-4-yl)isoindolin-2-yl)piperidine-2,6-dione (I-51)

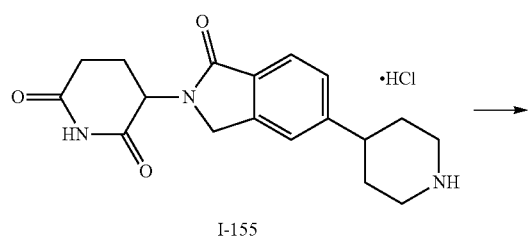

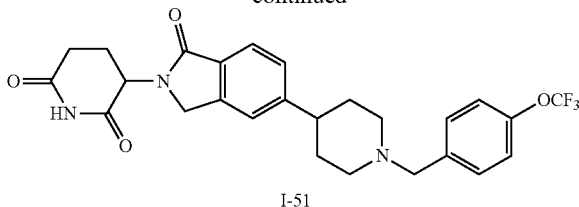

To a stirred solution of I-155 (100 mg, 0.30 mmol) and Et₃N (0.21 mL, 1.53 mmol) in DMF (2 mL) was added 2-(bromomethyl)-5-(trifluoromethoxy)benzene (0.09 mL, 0.61 mmol) and the resulting mixture was stirred at rt for 16 h. The reaction mixture was quenched with ice-cold water. The resulting solid was filtered, washed with water, and dried under reduced pressure to afford I-51 as an off-white solid (80 mg, 0.16 mmol, 52% yield). MS [M+H]⁺=502.1. ¹H NMR (400 MHz, DMSO-d6): δ 10.96 (s, 1H), 7.64 (d, J=8.0 Hz, 1H), 7.50 (s, 1H), 7.40 (d, J=8.0 Hz, 1H), 7.45 (d, J=8.4 Hz, 2H), 7.40 (d, J=8.0 Hz, 1H), 7.32 (d, J=8.4 Hz, 2H) 5.10 (dd, J=13.2, 5.2 Hz, 1H), 4.41 (d, J=17.2 Hz, 1H), 4.30 (d, J=17.2 Hz, 1H), 3.08 (s, 2H), 2.93-2.86 (m, 3H), 2.67-2.59 (m, 2H), 2.45-2.33 (m, 1H), 2.12-2.11 (m, 2H), 2.00-1.97 (m, 1H), 1.80-1.67 (m, 4H).

Example 36: 3-(1-oxo-5-(1-(3-(trifluoromethoxy) benzyl)piperidin-4-yl)isoindolin-2-yl)piperidine-2,6-dione (I-54)

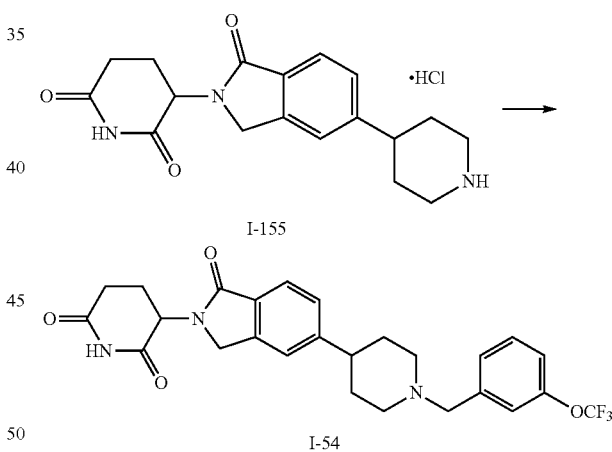

To a stirred solution of I-155 (100 mg, 0.30 mmol) and Et₃N (0.21 mL, 1.53 mmol) in DMF (2 mL) was added 1-(bromomethyl)-3-(trifluoromethoxy)benzene (0.09 mL, 0.61 mmol) and the resulting mixture was stirred at rt for 16 h. The reaction mixture was quenched with ice-cold water. The resulting solid was filtered, washed with water, and dried under reduced pressure to afford I-54 as an off-white solid (65 mg, 0.13 mmol, 42% yield). MS [M+H]⁺=502.1. ¹H NMR (400 MHz, DMSO-d6): δ 10.96 (d, J=8.0 Hz, 1H), 7.50-7.47 (m, 2H), 7.45-7.36 (m, 2H), 7.31 (brs, 1H), 7.25 (d, J=7.6 Hz, 1H), 5.11 (dd, J=13.2, 5.2 Hz, 1H), 4.41 (d, J=17.2 Hz, 1H), 4.29 (d, J=17.2 Hz, 1H), 3.58 (s, 2H), 2.94-2.90 (m, 3H), 2.67-2.62 (m, 2H), 2.41-2.33 (m, 1H), 2.13-2.08 (m, 2H), 2.00-1.98 (m, 1H), 1.79-1.70 (m, 4H).

Example 37: 3-(5-(1-(3,5-difluorobenzyl)piperidin-4-yl)-1-oxoisoindolin-2-yl)piperidine-2,6-dione (I-26)

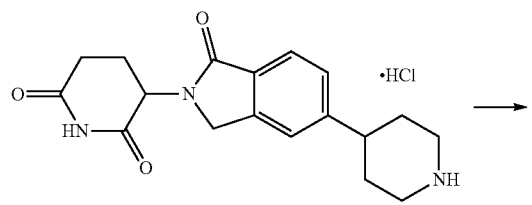

To a stirred solution of I-155 (100 mg, 0.30 mmol) and Et$_3$N (0.21 mL, 1.53 mmol) in DMF (2 mL) was added 1-(bromomethyl)-3,5-difluorobenzene (0.07 mL, 0.61 mmol)) and the resulting mixture was stirred at rt for 16 h. The reaction mixture was quenched with ice-cold water. The resulting solid was filtered, washed with water, and dried under reduced pressure to afford I-26 as an off-white solid (65 mg, 0.14 mmol, 47% yield). MS [M+H]$^+$=454.1. H NMR (400 MHz, DMSO-d$_6$): δ 10.95 (s, 1H), 7.62 (d, J=8.0 Hz, 1H), 7.50 (s, 1H), 7.40 (d, J=8.0 Hz, 1H), 7.10-7.04 (m, 3H), 5.09 (dd, J=13.2, 5.2 Hz, 1H), 4.41 (d, J=17.2 Hz, 1H), 4.28 (d, J=17.2 Hz, 1H), 3.53 (s, 2H), 2.92-2.66 (m, 3H), 2.65-2.49 (m, 2H), 2.44-2.31 (m, 1H), 2.12-2.07 (m, 2H), 2.00-1.96 (m, 1H), 1.76-1.71 (m, 4H).

Example 38: 3-(5-(1-ethylpiperidin-4-yl)-1-oxoisoindolin-2-yl)piperidine-2,6-dione (I-1)

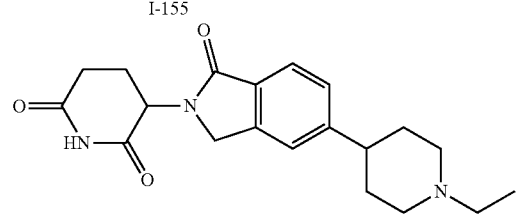

To a stirred solution of I-155 (100 mg, 0.30 mmol) and Et$_3$N (0.21 mL, 1.53 mmol) in DMF (2 mL) was added ethyl bromide (0.04 mL, 0.61 mmol) and the resulting mixture was stirred at rt for 16 h. The reaction mixture was quenched with ice-cold water. The resulting solid was filtered, washed with water, and dried under reduced pressure to afford I-1 as an off-white solid (21 mg, 0.06 mmol, 20% yield). MS [M+H]$^+$=356.1. $^1$H NMR (400 MHz, DMSO-d$_6$): δ 10.96 (s, 1H), 7.64 (d, J=8.0 Hz, 1H), 7.49 (s, 1H), 7.40 (d, J=8.0 Hz, 1H), 5.10 (dd, J=13.2, 5.2 Hz, 1H) 4.43 (d, J=17.2 Hz, 1H), 4.30 (d, J=17.2 Hz, 1H), 3.00-2.86 (m, 3H), 2.67-2.54 (m, 2H), 2.50-2.33 (m, 2H), 2.00-1.97 (m, 2H), 1.79-1.65 (m, 4H), 1.02 (t, J=7.2 Hz, 3H).

Example 39: cis-3-(1-oxo-5-(1-((4-(trifluoromethyl)cyclohexyl)methyl)piperidin-4-yl)isoindolin-2-yl)piperidine-2,6-dione (I-276)

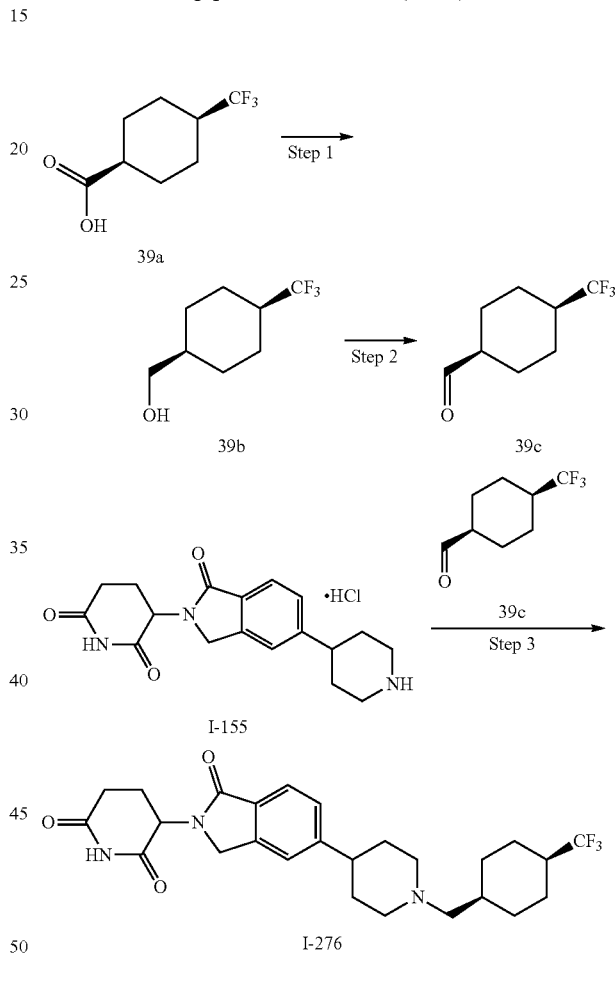

Step 1. cis-(4-(trifluoromethyl)cyclohexyl)methanol (39b)

To a stirred solution of 39a (1.0 g, 5.2 mmol) in THF (20 mL) was added LiAlH$_4$ (400 mg, 10.30 mmol) in small portions at 0° C. and stirred for 2 h. The reaction mixture was quenched with 10% aq. NaOH and then stirred at rt for 1 h. The reaction mixture was filtered through a pad of Celite® R filter aid and washed with EtOAc. The combined filtrate was dried over Na$_2$SO$_4$, filtered, and concentrated to dryness to afford 39b as a viscous oil (500 mg, 2.74 mmol, 54% yield). The product was used in the next step without further purification.

Step 2. cis-4-(trifluoromethyl)cyclohexane-1-carbaldehyde (39c)

To a stirred solution of 39b (500 mg, 2.74 mmol) in DCM (20 mL) was added DMP (2.33 g, 5.49 mmol) at 0° C. and the resulting mixture was stirred at rt for 3 h. The reaction mixture was diluted with DCM (20 mL), washed with 10% aq. NaHCO$_3$ (2×25 mL) and brine (25 mL), dried over Na$_2$SO$_4$, filtered, and concentrated to dryness. The crude material was purified by silica gel chromatography eluting with 15% EtOAc in hexane to afford 39c as a pale yellow viscous oil (180 mg, 1.00 mmol, 41% yield). $^1$H NMR (400 MHz, DMSO-d$_6$): δ 9.70 (s, 1H), 2.48-2.47 (m, 1H), 2.32-2.27 (m, 2H), 1.86-1.80 (m, 2H), 1.65-1.53 (m, 2H), 1.40-1.25 (m, 3H).

Step 3. cis-3-(1-oxo-5-(1-((4-(trifluoromethyl)cyclohexyl)methyl)piperidin-4-yl)isoindolin-2-yl)piperidine-2,6-dione (I-276)

To a stirred solution of I-155 (150 mg, 0.41 mmol) and 39c (165 mg, 0.91 mmol) in DMF (5 mL) was added NaBH(OAc)$_3$ (290 mg, 1.37 mmol) and the resulting mixture was stirred at 60° C. for 16 h. The reaction mixture quenched with ice-cold water and washed with EtOAc (2×25 mL). The aq. layer was basified with NaHCO$_3$ and extracted with 5% MeOH in DCM (2×25 mL). The combined organic extracts were dried over Na$_2$SO$_4$, filtered, and concentrated to dryness. The crude material was purified by silica gel chromatography eluting with 5% MeOH in DCM to afford I-276 as an off-white solid (24 mg, 0.05 mmol, 12% yield). MS [M+H]$^+$=492.2. $^1$H NMR (400 MHz, DMSO-d$_6$): δ 10.99 (s, 1H), 7.62 (d, J=8.0 Hz, 1H), 7.49 (s, 1H), 7.39 (d, J=8.0 Hz, 1H), 5.10 (dd, J=13.2, 5.2 Hz, 1H), 4.4 (d, J=17.2 Hz, 1H), 4.28 (d, J=17.2 Hz, 1H), 2.95-2.85 (m, 3H), 2.64-2.55 (m, 2H), 2.42-2.35 (m, 2H), 2.26-2.22 (m, 2H), 2.05-1.95 (m, 3H), 1.90-1.85 (m, 2H), 1.79-1.70 (m, 3H), 1.68-1.55 (m, 4H), 1.52-1.45 (m, 4H).

Example 40: ethyl 2-(4-(2-(2,6-dioxopiperidin-3-yl)-1-oxoisoindolin-5-yl)piperidin-1-yl)acetate (I-176)

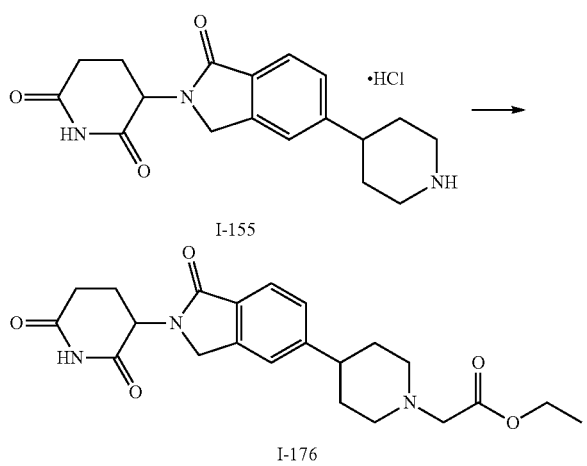

To a stirred solution of I-155 (100 mg, 0.30 mmol) and Et$_3$N (0.21 mL, 1.53 mmol) in DMF (2 mL) was added ethyl-2-bromoacetate (0.06 mL, 0.61 mmol) and the resulting mixture was stirred at rt for 16 h. The reaction mixture was quenched with ice-cold water and extracted with EtOAc (2×50 ml). The combined organic extracts were washed with brine (25 mL), dried over Na$_2$SO$_4$, and concentrated under reduced pressure. The crude material was purified by silica gel chromatography eluting with 5% MeOH in DCM. The pure fractions were evaporated and triturated with diethyl ether to afford I-176 as an off-white solid (20 mg, 0.05 mmol, 16% yield). MS [M+H]$^+$=414.2. $^1$H NMR (400 MHz, DMSO-d$_6$): δ 10.97 (s, 1H), 7.64 (d, J=8.0 Hz, 1H), 7.50 (s, 1H), 7.40 (d, J=8.0 Hz, 1H), 5.11 (dd, J=13.2, 5.2 Hz, 1H), 4.40 (d, J=17.2 Hz, 1H), 4.30 (d, J=17.2 Hz, 1H), 4.10 (q, J=6.8 Hz, 2H), 3.25 (s, 2H), 2.94-2.85 (m, 3H), 2.69-2.56 (m, 2H), 2.43-2.33 (m, 2H), 2.09-1.96 (m, 2H), 1.78-1.65 (m, 4H), 1.20 (t, J=6.8 Hz, 3H).

Example 41: 3-(5-(1-((1H-indazol-6-yl)methyl)piperidin-4-yl)-1-oxoisoindolin-2-yl)piperidine-2,6-dione (I-137)

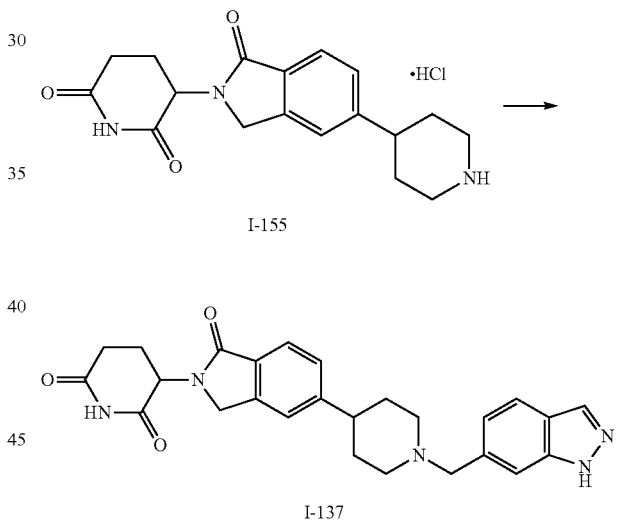

To a stirred solution of I-155 (450 mg, 1.24 mmol) and Et$_3$N (0.95 mL, 6.87 mmol) in DMF (5 mL) was added 6-(bromomethyl)-1H-indazole HBr salt (0.54 g, 1.86 mmol) [prepared following *Heterocyclic Communications*, 2015, 21, 5-8] and the resulting mixture was stirred at rt for 16 h. The reaction mixture was quenched with ice-cold water. The resulting solid was filtered, washed with water, and dried under reduced pressure to afford I-137 as an off-white solid (21 mg, 0.06 mmol, 20% yield). MS [M+H]+=458.3. $^1$H NMR (400 MHz, DMSO-d$_6$): δ 12.95 (s, 1H), 10.96 (s, 1H), 8.01 (s, 1H), 7.69 (d, J=8.0 Hz, 1H), 7.64 (d, J=8.0 Hz, 1H), 7.50 (s, 1H), 7.46 (s, 1H), 7.40 (d, J=8.0 Hz, 1H), 7.11 (d, J=8.4 Hz, 1H), 5.10 (dd, J=13.2, 5.2 Hz, 1H), 4.41 (d, J=17.2 Hz, 1H), 4.28 (d, J=17.2 Hz, 1H), 3.63 (s, 2H), 2.90-2.87 (m, 3H), 2.66-2.57 (m, 2H), 2.40-2.36 (m, 1H), 2.14-2.08 (m, 2H), 2.00-1.97 (m, 1H), 1.76-1.70 (m, 4H).

Example 42: tert-butyl 2-(4-(2-(2,6-dioxopiperidin-3-yl)-1-oxoisoindolin-5-yl)piperidin-1-yl)acetate (I-177)

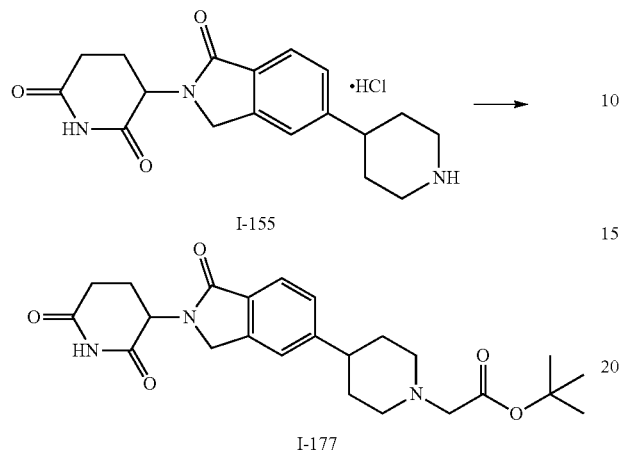

To a stirred solution of I-155 (200 mg, 0.61 mmol) and Et₃N (0.42 mL, 3.05 mmol) in DMF (2 mL) was added tert-butyl-2-bromo acetate (0.18 mL, 1.22 mmol) and the resulting mixture was stirred at rt for 16 h. The reaction mixture was quenched with ice-cold water. The solid was filtered, washed with water, and dried under reduced pressure to afford I-177 as an off-white solid (135 mg, 0.30 mmol, 50% yield). MS [M+H]$^+$=442.2. $^1$H NMR (400 MHz, DMSO-d$_6$): δ 10.96 (s, 1H), 7.64 (d, J=8.0 Hz, 1H), 7.49 (s, 1H), 7.39 (d, J=8.0 Hz, 1H), 5.10 (dd, J=13.2, 5.2 Hz, 1H), 4.43 (d, J=17.2 Hz, 1H), 4.30 (d, J=17.2 Hz, 1H), 3.13 (s, 2H), 2.95-2.87 (m, 3H), 2.67-2.57 (m, 2H), 2.33-2.28 (m, 3H), 2.00-1.98 (m, 1H), 1.74-1.68 (m, 4H), 1.43 (s, 9H).

Example 43: 2-(4-(2-(2,6-dioxopiperidin-3-yl)-1-oxoisoindolin-5-yl)piperidin-1-yl)acetic acid hydrochloride (I-178)

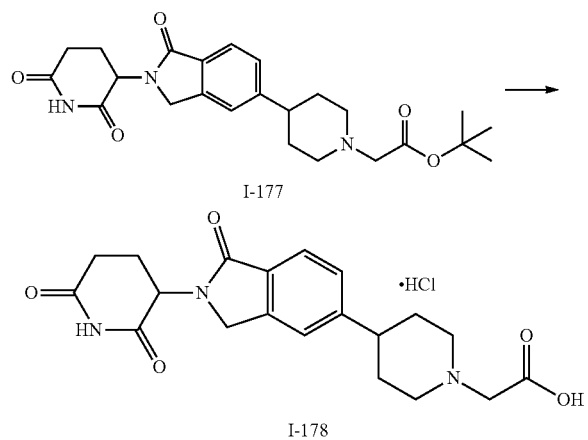

To a solution of I-177 (130 mg, 0.29 mmol) in DCM (2 mL) was added 2M HCl in diethyl ether (0.5 mL) dropwise at 0° C. and the resulting mixture was stirred at rt for 16 h. Upon complete consumption of the starting material, the solvent was evaporated and the crude material was dried under reduced pressure. The resulting solid was triturated with hexane followed by diethyl ether, collected by filtration, and dried under reduced pressure to afford I-178 as an off-white solid (60 mg, 0.15 mmol, 49% yield). MS [M+H]$^+$=386.2. $^1$H NMR (400 MHz, DMSO-d$_6$): δ 13.98 (brs, 1H), 10.98 (s, 1H), 7.71 (d, J=8.0 Hz, 1H), 7.50 (s, 1H), 7.42 (d, J=8.0 Hz, 1H), 5.12 (dd, J=13.2, 5.2 Hz, 1H), 4.45 (d, J=17.2 Hz, 1H), 4.33 (d, J=17.2 Hz, 1H), 4.16 (s, 2H), 3.62-3.59 (m, 2H), 3.33-3.18 (m, 3H), 2.96-2.92 (m, 2H), 2.62-2.51 (m, 1H), 2.50-2.38 (m, 1H), 2.10-1.98 (m, 4H).

Example 44: 3-(1-oxo-5-(1-(3,3,3-trifluoropropyl)piperidin-4-yl)isoindolin-2-yl)piperidine-2,6-dione (I-179)

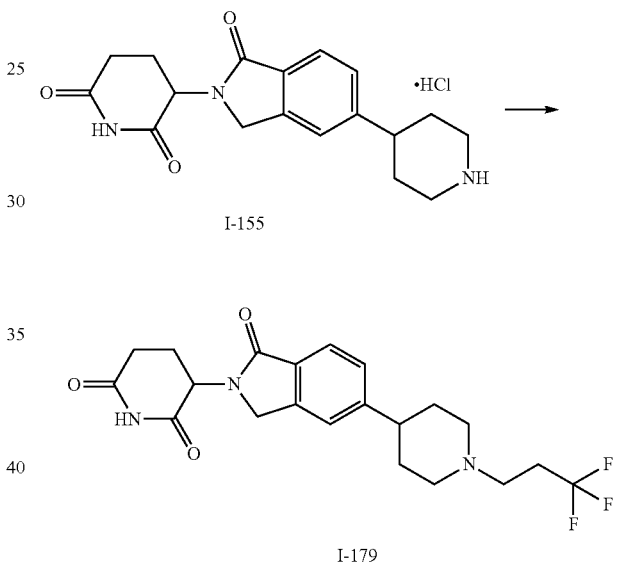

To a stirred solution of I-155 (200 mg, 0.61 mmol) and 3,3,3-trifluoropropanal (0.15 mL, 1.83 mmol) in DMF (2 mL) was added NaBH(OAc)₃ (390 mg, 1.82 mmol) in small portions at 0° C. and the resulting mixture was stirred for 48 h at rt. The reaction mixture was quenched with water and extracted with EtOAc (2×50 mL). The combined organic extracts were washed with brine (25 mL), dried over Na₂SO₄, and concentrated under reduced pressure. The crude material was purified by silica gel chromatography eluting with 10% MeOH in DCM. The pure fractions were evaporated and triturated with diethyl ether to afford I-179 as an off-white solid (115 mg, 0.27 mmol, 44% yield). MS [M+H]$^+$=424.2. $^1$H NMR (400 MHz, DMSO-d$_6$): δ 10.96 (s, 1H), 7.64 (d, J=8.0 Hz, 1H), 7.49 (s, 1H), 7.39 (d, J=8.0 Hz, 1H), 5.10 (dd, J=13.2, 5.2 Hz, 1H), 4.45 (d, J=17.2 Hz, 1H), 4.36 (d, J=17.2 Hz, 1H), 3.30-2.86 (m, 3H), 2.67-2.55 (m, 4H), 2.41-2.33 (m, 2H), 2.10-1.97 (m, 4H), 1.90-1.64 (m, 4H).

Example 45: 2-(4-(2-(2,6-dioxopiperidin-3-yl)-1-oxoisoindolin-5-yl)piperidin-1-yl)-N-phenylacetamide (I-180)

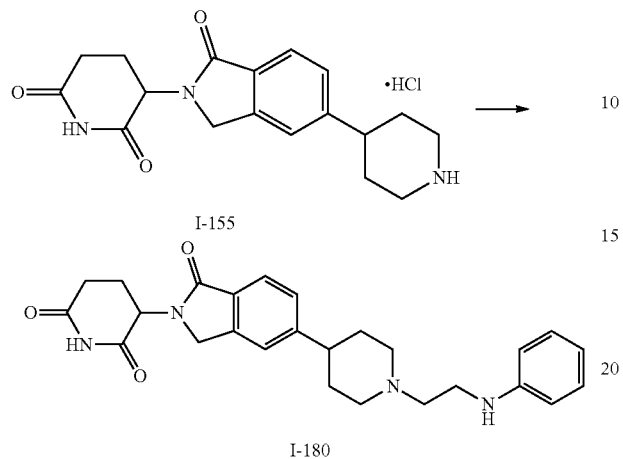

To a stirred solution of I-155 (200 mg, 0.61 mmol) and Et₃N (0.42 mL, 3.05 mmol) in DMF (2 mL) was added 2-bromo-N-phenylacetamide (0.19 g, 0.91 mmol) [prepared following *JMC,* 2016, 59, 6709-6728] and the resulting mixture was stirred at rt for 6 h. The reaction mixture was quenched with ice-cold water. The solid was filtered, washed with water, and dried under reduced pressure to afford I-180 as an off-white solid (60 mg, 0.13 mmol, 21% yield). MS [M+H]⁺=461.2. ¹H NMR (400 MHz, DMSO-d₆): δ 10.96 (s, 1H), 9.70 (s, 1H), 7.66 (d, J=8.0 Hz, 3H), 7.52 (s, 1H), 7.44 (d, J=8.0 Hz, 1H), 7.31 (t, J=7.4 Hz, 2H), 7.06 (t, J=7.4 Hz, 1H), 5.10 (dd, J=13.2, 5.2 Hz, 1H), 4.44 (d, J=17.2 Hz, 1H), 4.31 (d, J=17.2 Hz, 1H), 3.25 (s, 2H), 3.16-2.98 (m, 2H), 2.95-2.69 (m, 1H), 2.66-2.57 (m, 1H), 2.49-2.40 (m, 2H), 2.38-2.31 (m, 2H), 2.00-1.90 (m, 1H), 1.87-1.77 (m, 4H).

Example 46: 3-(5-(1-(3-fluoropropyl)piperidin-4-yl)-1-oxoisoindolin-2-yl)piperidine-2,6-dione (I-181)

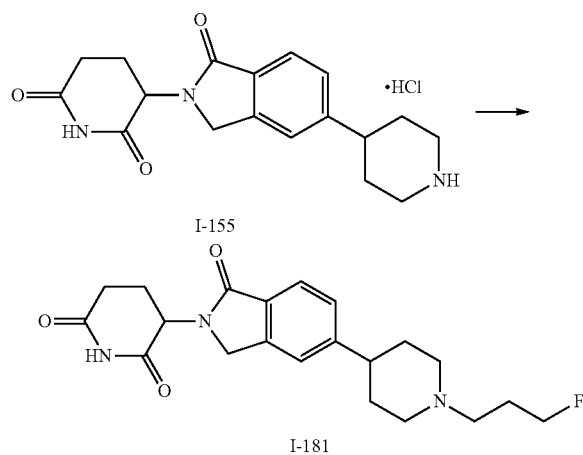

To a stirred solution of I-155 (50 mg, 0.14 mmol) and Et₃N (0.06 mL, 0.41 mmol) in DMF (2 mL) was added 1-fluoro-3-iodopropane (0.05 g, 0.27 mmol) and the resulting mixture was stirred at rt for 5 h. The reaction mixture was quenched with ice-cold water and extracted with EtOAc (2×50 mL). The combined organic extracts were washed with brine (25 mL) and concentrated under reduced pressure. The crude material was purified by silica gel chromatography eluting with 10% MeOH in DCM. The pure fractions were evaporated under reduced pressure to afford I-181 as an off-white solid (15 mg, 0.04 mmol, 28% yield). MS [M+H]⁺=388.0. H NMR (400 MHz, DMSO-d₆): δ 10.98 (s, 1H), 7.65 (d, J=8.0 Hz, 1H), 7.49 (s, 1H), 7.40 (d, J=8.0 Hz, 1H), 5.11 (dd, J=13.2, 5.2 Hz, 1H), 4.56 (t, J=5.8 Hz, 1H), 4.44 (t, J=5.6 Hz, 1H), 4.43 (d, J=17.2 Hz, 1H), 4.29 (d, J=17.2 Hz, 1H), 2.99-2.88 (m, 3H), 2.67-2.49 (m, 4H), 2.44-2.33 (m, 4H), 2.00-1.97 (m, 2H), 1.78-1.71 (m, 4H).

Example 47: 4-((4-(2-(2,6-dioxopiperidin-3-yl)-1-oxoisoindolin-5-yl)piperidin-1-yl)methyl)benzoic acid (I-72)

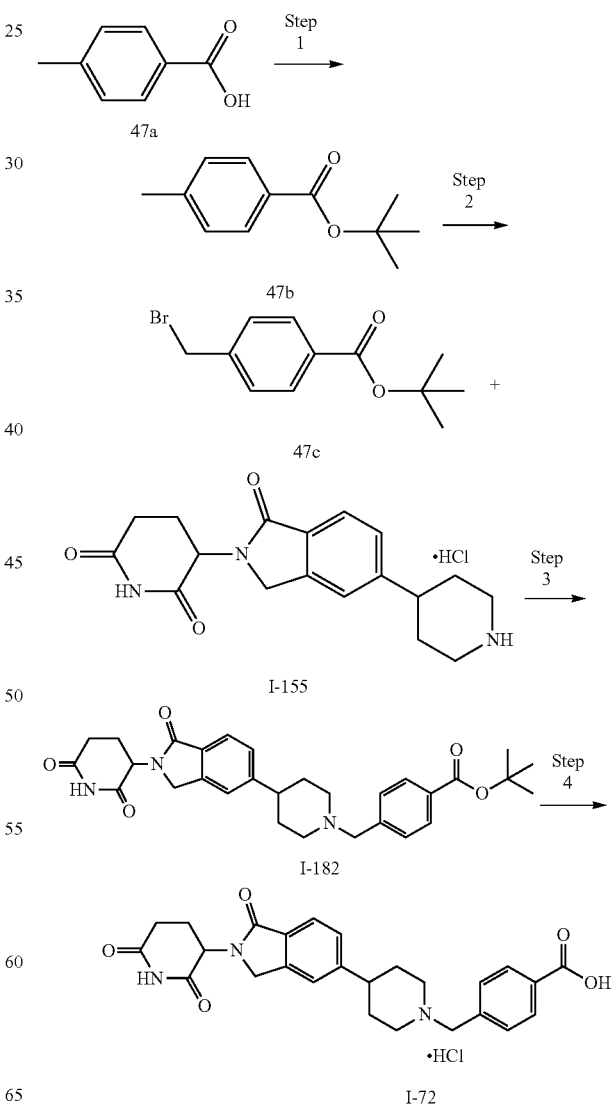

Step 1. tert-butyl 4-methylbenzoate (47b)

A solution of 4-methylbenzoic acid 47a (5 g, 36.76 mmol) in thionyl chloride (15 mL) was heated to 70° C. for 3 h. Upon complete consumption of the starting material, thionyl chloride was evaporated under reduced pressure. The obtained material (3 g, crude) was taken into t-butanol (15 mL) and pyridine (3.5 mL, 35.44 mmol) was added at 0° C. and the resulting mixture was stirred at rt for 16 h. Upon complete consumption of the starting material, the reaction mixture was quenched with water and extracted with DCM (2×100 mL). The combined organic extracts were washed with brine (50 mL), dried over $Na_2SO_4$, and concentrated under reduced pressure. The crude material was purified by silica gel chromatography eluting with 5% EtOAc in hexane. The pure fractions were collected and evaporated to afford compound 47b as pale brown liquid (3.3 g, 18.23 mmol, 50% yield). $^1$H NMR (400 MHz, $CDCl_3$): δ 7.87 (d, J=8.4 Hz, 2H), 7.20 (d, J=8.4 Hz, 2H), 2.39 (s, 3H), 1.58 (s, 9H).

Step 2. tert-butyl 4-(bromomethyl)benzoate (47c)

To a solution of 47b (3 g, 15.60 mmol) in carbon tetrachloride (30 mL) was added NBS (2.77 g, 15.60 mmol) followed by AIBN (260 mg, 1.56 mmol) and the resulting mixture was stirred at 60° C. for 8 h. Upon complete consumption of the starting material, the reaction mixture was cooled to rt, filtered through a small pad of Celite® filter aid, and washed with DCM. The combined organic extracts were dried over $Na_2SO_4$ and concentrated under reduced pressure. The crude material was purified by silica gel chromatography eluting with 2% EtOAc in hexane. The pure fractions were collected and evaporated under reduced pressure to afford 47c as a pale brown oil (2.2 g, 8.11 mmol, 52% yield). $^1$H NMR (400 MHz, $CDCl_3$): δ 7.95 (d, J=8.4 Hz, 2H), 7.43 (d, J=8.4 Hz, 2H), 4.94 (s, 2H), 1.59 (s, 9H).

Step 3. tert-butyl 4-((4-(2-(2,6-dioxopiperidin-3-yl)-1-oxoisoindolin-5-yl)piperidin-1-yl)methyl)benzoate (I-182)

To as stirred solution of I-155 (500 mg, 1.37 mmol) and potassium carbonate (380 mg, 2.74 mmol) in DMF (5 mL) was added dropwise 47c (410 mg, 1.51 mmol) in DMF (2 mL) and the resulting mixture was stirred at rt for 16 h. Upon complete consumption of the starting materials, the reaction mixture was quenched with water and extracted with EtOAc (3×50 mL). The combined organic extracts were washed with brine (50 mL) and evaporated under reduced pressure. The crude material was purified by silica gel chromatography eluting with 7% MeOH in DCM. The pure fractions were collected, evaporated, and dried to afford I-182 as pale brown solid (350 mg, 0.67 mmol, 49% yield). $^1$H NMR (400 MHz, DMSO-d6): δ 10.98 (s, 1H), 7.87 (d, J=10.4 Hz, 2H), 7.64 (d, J=10.8 Hz, 1H), 7.49 (s, 1H), 7.44 (d, J=10.4 Hz, 2H), 7.9 (d, J=10.4 Hz, 1H) 5.10 (dd, J=18.0, 6.4 Hz, 1H), 4.41 (d, J=17.6 Hz, 1H), 4.28 (d, J=17.6 Hz, 1H), 3.57 (s, 2H), 2.93-2.85 (m, 3H), 2.62-2.49 (m, 1H), 2.41-2.35 (m, 1H), 2.14-1.96 (m, 4H), 1.75-1.69 (m, 4H), 1.54 (s, 9H).

Step 4. 4-((4-(2-(2,6-dioxopiperidin-3-yl)-1-oxoisoindolin-5-yl)piperidin-1-yl)methyl)benzoic acid HCl salt (I-72)

To a solution of I-182 (300 mg, 0.57 mmol) in DCM (9 mL) was added 4M HCl in dioxane (5 mL) dropwise at 0° C. and the resulting mixture was stirred at rt for 30 h. Upon complete consumption of the starting material, the solvent was evaporated, triturated with diethyl ether, and the resulting solid was dried under reduced pressure to afford I-72 as an off-white solid (270 mg, 0.54 mmol, 94%, HCl salt). MS [M+H]$^+$=461.85. $^1$H NMR (400 MHz, DMSO-d6): δ 13.2 (brs, 1H), 10.99 (s, 1H), 10.28 (brs, 1H), 8.05-8.01 (m, 2H), 7.79-7.71 (m, 3H), 7.45 (s, 1H), 7.38 (d, J=8.4 Hz, 1H), 5.10 (dd, J=13.2, 5.2 Hz, 1H) 4.42-4.28 (m, 3H), 3.723.66 (m, 1H), 3.50-3.45 (m, 2H), 3.25-3.18 (m, 2H), 3.10-2.87 (m, 2H), 2.65-2.55 (m, 1H), 2.35-2.41 (m, 1H), 2.07-1.95 (m, 4H).

Example 48: 4-((4-(2-(2,6-dioxopiperidin-3-yl)-1-oxoisoindolin-5-yl)piperidin-1-yl)methyl)benzamide (I-71)

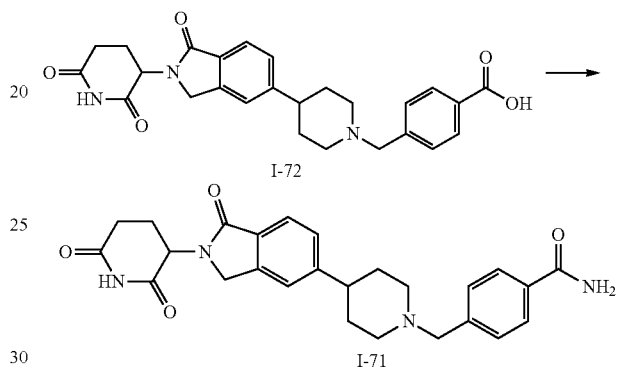

To a stirred solution of I-72 (250 mg, 0.50 mmol) and $NH_4Cl$ (40 mg, 0.75 mmol) in DMF (5 mL) was added DIPEA (0.27 mL, 1.5 mmol), followed by HATU (286 mg, 0.75 mmol) and the resulting mixture was stirred for 16 at rt. The reaction mixture was quenched with water and extracted with EtOAc (3×50 mL). The combined organic extracts were washed with brine (25 mL), dried over $Na_2SO_4$, and concentrated under reduced pressure. The crude material was purified by reverse phase HPLC to afford I-71 as an off-white solid (110 mg, 0.24 mmol, 47% yield). MS [M+H]$^+$=460.8. $^1$H NMR (400 MHz, DMSO-d$_6$): δ 10.99 (s, 1H), 7.95-7.85 (m, 3H), 7.65 (brs, 1H), 7.49-7.36 (m, 5H), 5.10 (dd, J=13.2, 5.2 Hz, 1H), 4.43 (d, J=17.2 Hz, 1H), 4.29 (d, J=17.2 Hz, 1H), 3.15 (s, 2H), 2.95-2.86 (m, 3H), 2.67-2.57 (m, 2H), 2.40-2.36 (m, 2H), 2.05-1.98 (m, 2H), 1.80-1.65 (m, 4H).

Example 49: 3-(5-(2-methylpiperidin-4-yl)-1-oxoisoindolin-2-yl)piperidine-2,6-dione hydrochloride (I-183)

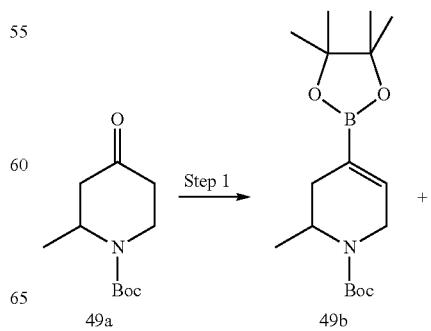

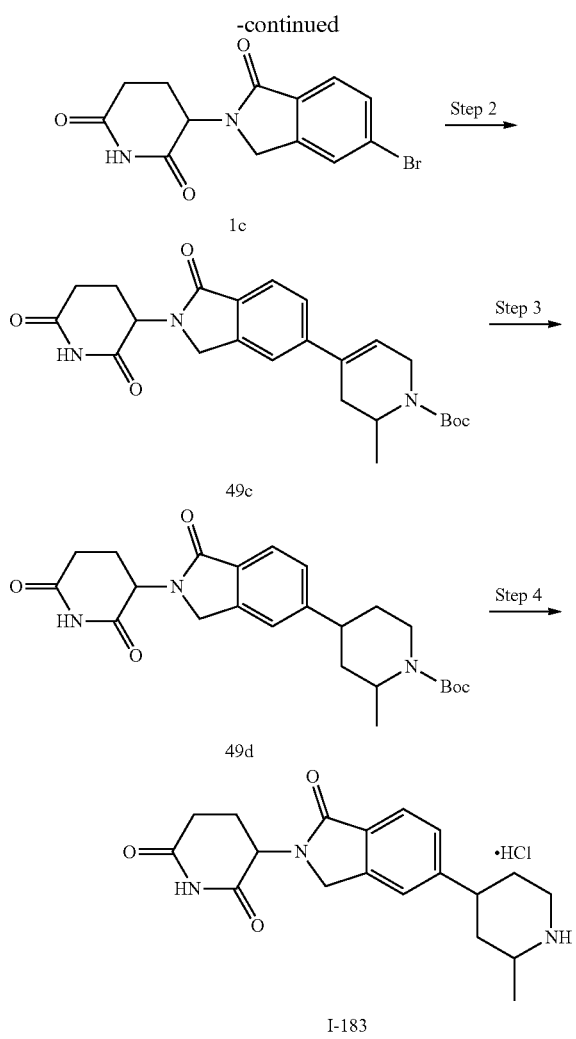

Step 1. tert-butyl 2-methyl-4-(4,4,5,5-tetramethyl-1,3,2-dioxaborolan-2-yl)-3,6-dihydropyridine-1(2H)-carboxylate (49b)

To a solution of 49a (2 g, 9.38 mmol) in THF (10 mL) was added 1M LiHMDS (11.3 mL, 5.63 mmol) dropwise at −78° C. After 1 h, 1,1,1-trifluoro-N-phenyl-N-(((trifluoromethyl) sulfonyl) methanesulfonamide (3.68 g, 10.32 mmol) in THF (10 mL) was added dropwise, the temperature was gradually increased to rt and the resulting mixture was stirred for 16 h. The solvent was evaporated (below 40° C.) and the resulting residue was taken in diethyl ether (100 mL). The organic extract was then washed with 0.5M NaOH (2×50 mL) and brine (50 mL), dried over Na$_2$SO$_4$, and concentrated under reduced pressure to afford tert-butyl 2-methyl-4-(((trifluoromethyl)sulfonyl)oxy)-3,6-dihydropyridine-1 (2H)-carboxylate as light yellow oil (2.4 g, crude). This crude material (2.4 g) was taken into dioxane (24 mL) and bis(pinacolato)diborane (970 mg, 3.82 mmol) was added followed by KOAc (625 mg, 6.37 mmol). The resulting mixture was degassed with argon for 10 min and PdCl$_2$ (dppf).DCM (130 mg, 0.16 mmol) was then added in one portion. The reaction mixture was stirred at 110° C. for 16 h, then quenched with water, and extracted with EtOAc (3×100 mL). The combined organic extracts were washed with brine (50 mL), dried over Na$_2$SO$_4$, and concentrated under reduced pressure. The crude material was purified by silica gel chromatography eluting with 10% EtOAc in hexane. The pure fractions were collected and evaporated under reduced pressure to afford 49b (1.85 g). This material was used in the next without further purification.

Step 2. tert-butyl 4-(2-(2,6-dioxopiperidin-3-yl)-1-oxoisoindolin-5-yl)-2-methyl-3,6-dihydropyridine-1 (2H)-carboxylate (49c)

To a solution of Ic (800 mg, 2.48 mmol) and 49b (1.2 g, 3.72 mmol) in DMF (10 mL) was added K$_2$CO$_3$ (685 mg, 4.96 mmol) followed by PdCl$_2$(dppf).DCM (101 mg, 0.12 mmol). The resulting mixture was degassed for 15 min and then stirred at 120° C. for 1 h in microwave. After complete consumption of the starting materials, the reaction mixture was quenched with water and extracted with EtOAc (2×50 mL). The combined organic extracts were washed with brine, dried over Na$_2$SO$_4$, and concentrated under reduced pressure. The crude material was purified by silica gel chromatography eluting with 80% EtOAc in hexane. The pure fractions were collected and evaporated under reduced pressure to afford 49c as a brown solid (620 mg, 1.41 mmol, 62% yield). MS [M+H]$^+$=440.2.

Step 3. tert-butyl 4-(2-(2,6-dioxopiperidin-3-yl)-1-oxoisoindolin-5-yl)-2-methylpiperidine-1-carboxylate (49d)

To a solution of 49c (500 mg, 1.14 mmol) in DMF (5 mL), was added 10% Pd/C (100 mg) under an inert atmosphere and the resulting mixture was stirred at rt for 4 h under hydrogen atmosphere (balloon). After complete consumption of the starting material, the reaction mixture was passed through a pad of Celite® filter aid and washed with EtOAc. The filtrate was concentrated under reduced pressure. The crude material was purified by silica gel chromatography eluting with 10% MeOH in DCM to afford 49d as an off-white solid (400 mg, 0.90 mmol, 80% yield). MS [(M-C$_4$Hs)+H]=386.1. $^1$H NMR (400 MHz, DMSO-d$_6$): δ 10.97 (s, 1H), 7.65 (d, J=8.0 Hz, 1H), 7.50 (s, 1H), 7.42 (d, J=8.0 Hz, 1H), 5.08 (dd, J=13.2, 5.2 Hz, 1H), 4.40 (d, J=17.2 Hz, 1H), 4.30 (d, J=17.2 Hz, 1H), 3.87-3.84 (m, 1H), 3.67-3.62 (m, 1H), 3.06-2.84 (m, 3H), 2.67-2.57 (m, 1H), 2.44-2.37 (m, 1H), 2.05-1.97 (m, 2H), 1.86-1.72 (m, 3H), 1.66-1.54 (m, 1H), 1.42 (s, 9H), 1.15 (d, J=6.0 Hz, 3H).

Step 4. 3-(5-(2-methylpiperidin-4-yl)-1-oxoisoindolin-2-yl)piperidine-2,6-dione hydrochloride (I-183)

To a solution of 49d (100 mg, 0.22 mmol) in DCM (2 mL) was added 4M HCl in dioxane (1 mL) at 0° C. and the resulting mixture was stirred at rt for 4 h. After complete consumption of the starting material, the solvent was evaporated and the obtained material was triturated with diethyl ether and dried under reduced pressure to afford the hydrochloride salt of I-183 as an off-white solid (60 mg, 0.16 mmol, 70% yield). MS [M+H]$^+$=342.0. $^1$H NMR (400 MHz, DMSO-d$_6$): δ 10.98 (s, 1H), 8.89 (brs, 1H), 7.70 (d, J=8.0 Hz, 1H), 7.50-7.37 (m, 2H), 5.11 (dd, J=13.2, 5.2 Hz, 1H), 4.45 (d, J=17.2 Hz, 1H), 4.31 (d, J=17.2 Hz, 1H), 3.41-3.38 (m, 1H), 3.23-3.11 (m, 3H), 2.96-2.87 (m, 1H), 2.67-2.58 (m, 1H), 2.41-2.32 (m, 1H), 2.12-1.95 (m, 4H), 1.84-1.65 (m, 2H), 1.27 (d, J=6.0 Hz, 3H).

Example 50: trans-3-(5-(1-((4-methoxycyclohexyl)methyl)piperidin-4-yl)-1-oxoisoindolin-2-yl)piperidine-2,6-dione (I-303)

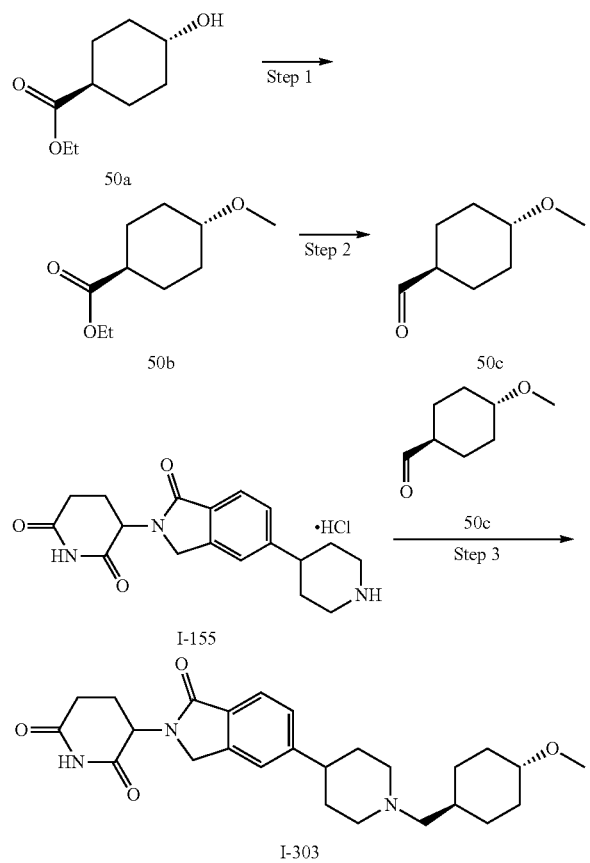

Step 1. trans-ethyl 4-methoxycyclohexane-1-carboxylate (50b)

To a stirred solution of 50a (2.0 g, 11.3 mmol) in THF (20 mL) was added NaH (700 mg, 17.4 mmol) in small portions at 0° C. After stirring for 30 min, methyl iodide (1.45 mL, 23.2 mmol) was added and the resulting mixture was stirred at rt for 3 h. The reaction mixture was quenched with ice-cold water and extracted with EtOAc (2×100 mL). The combined organic extracts were washed with brine, dried over $Na_2SO_4$, filtered, and concentrated under reduced pressure. The obtained crude material was purified by silica gel chromatography eluting with 20% EtOAc in hexane to afford 50b as a colorless oil (570 mg, 3.06 mmol, 26% yield). $^1$H NMR (400 MHz, DMSO-$d_6$): δ 4.10 (q, J=9.2 Hz, 2H), 3.34 (s, 3H), 3.16-3.08 (m, 1H), 2.26-2.11 (m, 1H), 2.07-1.99 (m, 4H), 1.61-1.39 (m, 2H), 1.28-1.19 (m, 2H), 1.24 (t, J=9.2 Hz, 3H).

Step 2. trans-4-methoxycyclohexane-1-carbaldehyde (50c)

To a solution of 50b (570 mg, 3.06 mmol) in DCM (10 mL) was added DIBAL-H (1 M, 3.67 mL, 3.67 mmol) dropwise at −78° C. and the resulting mixture was stirred for 4 h at −78° C. and then for 16 h at rt. The reaction mixture was diluted with DCM (20 mL) and quenched with saturated aq. Rochelle's salt. The organic layer was separated, washed with brine, dried over $Na_2SO_4$, filtered, and concentrated to dryness to afford the intermediate (4-methoxycyclohexyl)methanol (290 mg). This material was taken into DCM (10 mL), PCC (850 mg, 3.94 mmol) was added and the resulting mixture was stirred at rt for 2 h. The reaction mixture was then diluted with DCM (10 mL), filtered through a small pad of Celite® filter aid, and washed with DCM (10 mL). The combined filtrate was dried over $Na_2SO_4$, filtered, and concentrated under reduced pressure to afford crude 50c (150 mg) as a pale brown oil which was used in the next step without further purification.

Step 3. trans-3-(5-(1-((4-methoxycyclohexyl)methyl)piperidin-4-yl)-1-oxoisoindolin-2-yl)piperidine-2,6-dione (I-303)

To a stirred solution of I-155 (250 mg, 0.69 mmol) and 50c (195 mg, 1.37 mmol) in DMF (10 mL) was added NaBH(OAc)$_3$ (436 mg, 2.06 mmol) at 0° C. and the resulting mixture was stirred at rt for 1 h and then at 60° C. for 16 h. The reaction mixture was quenched with ice-cold water and extracted with EtOAc (2×50 mL). The combined organic extracts were washed with brine, dried over $Na_2SO_4$, filtered, and concentrated under reduced pressure. The crude material was purified by silica gel chromatography eluting with 10% MeOH in DCM to afford I-303 as an off-white solid (38 mg, 0.08 mmol, 12% yield). MS [M+H]$^+$=454.2. $^1$H NMR (400 MHz, DMSO-$d_6$): δ 10.99 (s, 1H), 7.63 (d, J=8.0 Hz, 1H), 7.49 (s, 1H), 7.39 (d, J=8.0 Hz, 1H), 5.10 (dd, J=13.2, 4.8 Hz, 1H), 4.41 (d, J=17.2 Hz, 1H), 4.28 (d, J=17.2 Hz, 1H), 3.22 (s, 3H), 3.04-3.01 (m, 1H), 2.94-2.91 (m, 3H), 2.67-2.33 (m, 4H), 2.10-2.08 (m, 2H), 1.99-1.97 (m, 5H), 1.80-1.66 (m, 5H), 1.50-1.48 (m, 1H), 1.11-1.03 (m, 2H), 0.89-0.81 (m, 2H).

Example 51: 3-(5-(1-benzyl-2-methylpiperidin-4-yl)-1-oxoisoindolin-2-yl)piperidine-2,6-dione (I-162)

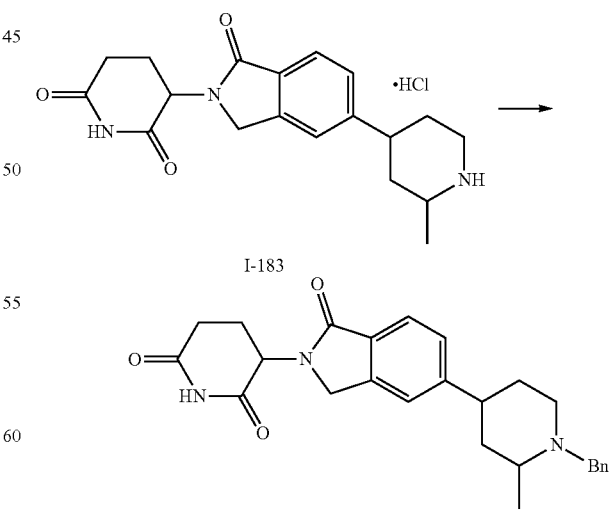

To a stirred solution of I-183 (120 mg, 0.32 mmol) and Et$_3$N (0.11 mL, 0.79 mmol) in DMF (2.5 mL) was added benzyl bromide (0.03 mL, 0.82 mmol) and the resulting mixture was stirred at rt for 4 h. After complete consumption of the starting material, the reaction mixture was quenched with water and extracted with EtOAc (2×50 mL). The combined organic extracts were washed with brine (25 mL), dried over $Na_2SO_4$, and concentrated under reduced pressure. The crude material was purified by silica gel chromatography eluting with 90% EtOAc in hexane. The pure fractions were collected and concentrated under reduced pressure to afford I-162 as an off-white solid (72 mg, 0.17 mmol, 48% yield). MS $[M+H]^+$=432.2. $^1$H NMR (400 MHz, DMSO-$d_6$): δ 10.98 (s, 1H), 7.65-7.62 (m, 1H), 7.51-7.48 (m, 1H), 7.42-7.30 (m, 5H), 7.25-7.23 (m, 1H), 5.10 (dd, J=13.2, 5.2 Hz, 1H), 4.42 (d, J=17.2 Hz, 1H), 4.29 (d, J=17.2 Hz, 1H), 3.63-3.57 (m, 2H), 3.15-3.09 (m, 1H), 3.01-2.86 (m, 2H), 2.67-2.52 (m, 2H), 2.41-2.36 (m, 2H), 2.00-1.94 (m, 2H), 1.70-1.62 (m, 3H), 1.10 (d, J=6.0 Hz, 3H).

Example 52: 3-(5-(3,3-dimethylpiperidin-4-yl)-1-oxoisoindolin-2-yl)piperidine-2,6-dione hydrochloride (I-184)

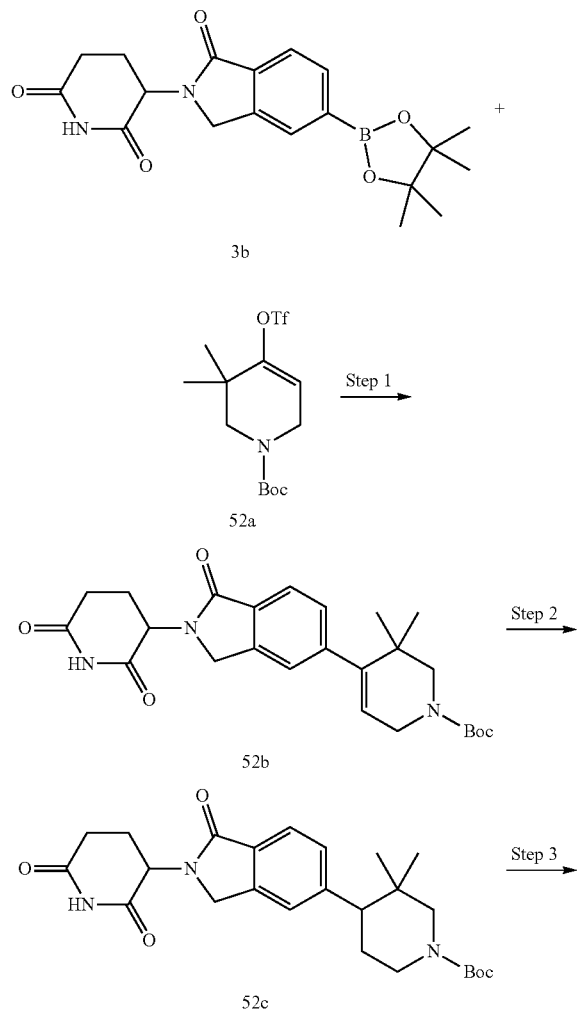

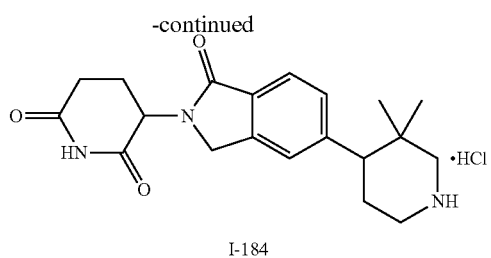

Step 1. tert-butyl 4-(2-(2,6-dioxopiperidin-3-yl)-1-oxoisoindolin-5-yl)-3,3-dimethylpiperidine-1-carboxylate (52b)

To a solution of 3b (200 mg, 0.54 mmol) and 52a (290 mg, 0.81 mmol, [prepared from tert-butyl 3,3-dimethyl-4-oxopiperidine-1-carboxylate following the procedure in Example 49]) in DMF (4 mL) was added $K_2CO_3$ (220 mg, 3.24 mmol) followed by $PdCl_2$(dppf).DCM (44 mg, 0.054 mmol) and the resulting mixture was degassed for 15 min and then stirred at 130° C. for 1 h in microwave. After complete consumption of the starting materials, the reaction mixture was cooled to rt, quenched with water, and extracted with EtOAc (2×50 mL). The combined organic extracts were washed with brine (25 mL), dried over $Na_2SO_4$, and concentrated under reduced pressure to afford compound 52b as red oil (120 mg, crude), which was used in the next step without further purification. MS $[M+H]^+$=454.1.

Step 2. tert-butyl 4-(2-(2,6-dioxopiperidin-3-yl)-1-oxoisoindolin-5-yl)-3,3-dimethylpiperidine-1-carboxylate (52c)

To a solution of 52b (120 mg, 0.26 mmol) in DMF (2.5 mL) was added 10% Pd/C (40 mg) and the resulting mixture was stirred at rt for 48 h under an atmosphere of hydrogen (balloon). After complete consumption of the starting materials, the reaction mixture was diluted with EtOAc (25 mL) and filtered through a pad of Celite® filter aid. The filtrate was concentrated under reduced pressure and passed through a short pad of silica gel eluting with 10% MeOH in DCM. The fractions containing desired product were combined and concentrated under reduced pressure to afford compound 52c as a pale brown gummy solid (70 mg, 0.15 mmol, 50% yield). MS $[M+H]^+$=456.1.

Step 3. 3-(5-(3,3-dimethylpiperidin-4-yl)-1-oxoisoindolin-2-yl)piperidine-2,6-dione hydrochloride (I-184)

To a solution of compound 52c (70 mg, 0.15 mmol) in DCM (2 mL) was added 4M dioxane (1 mL) at 0° C. and the resulting mixture was allowed to stir at rt 4 h. After complete consumption of the starting material, the solvent was evaporated under reduced pressure and then triturated with diethyl ether to afford the hydrochloride salt of I-184 as an off-white solid (35 mg, 0.09 mmol, 68% yield). MS $[M+H]^+$=356.1. $^1$H NMR (400 MHz, DMSO-$d_6$): δ 10.98 (s, 1H), 8.2 (brs, 1H), 7.68 (d, J=8.0 Hz, 1H), 7.40 (s, 1H), 7.30 (d, J=8.0 Hz, 1H), 5.10 (dd, J=13.2, 5.2 Hz, 1H), 4.42 (d, J=17.2 Hz, 1H), 4.34 (d, J=17.2 Hz, 1H), 3.26-3.11 (m, 1H), 2.96-2.83 (m, 3H), 2.67-2.58 (m, 1H), 2.45-2.38 (m, 2H), 2.33-2.30 (m, 2H), 2.08-1.99 (m, 1H), 1.73-1.69 (m, 1H), 0.87 (s, 3H), 0.80 (s, 3H).

Example 53: 3-(5-(1-benzyl-3,3-dimethylpiperidin-4-yl)-1-oxoisoindolin-2-yl)piperidine-2,6-dione (I-185)

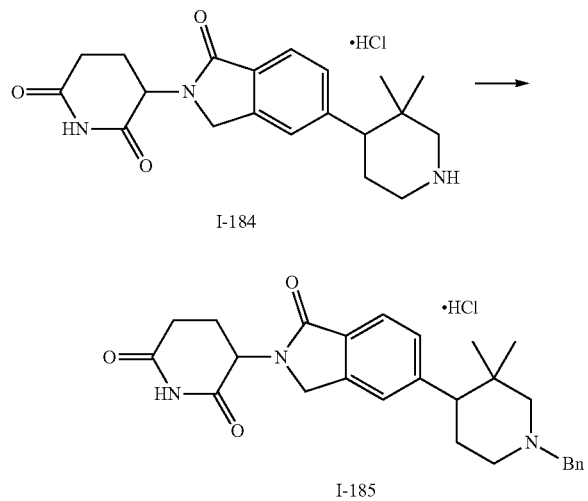

To a solution of I-184 (35 mg, 0.09 mmol) and Et₃N (0.11 mL, 0.78 mmol) in DMF (2 mL) was added benzyl bromide (0.03 mL, 0.38 mmol) and the resulting mixture was stirred at rt for 4 h. After complete consumption of the starting material, the reaction mixture was quenched with water and extracted with EtOAc (2×25 mL). The combined organic extracts were washed with brine (20 mL), dried over Na₂SO₄, and concentrated under reduced pressure. The crude material was purified by silica gel chromatography eluting with 80% EtOAc in hexane. The pure fractions were collected and concentrated under reduced pressure to afford I-185 as an off-white solid (8 mg, 0.017 mmol, 18%). MS [M+H]⁺=446.1. ¹H NMR (400 MHz, DMSO-d₆): δ 10.68 (s, 1H), 7.66-7.62 (m, 2H), 7.40-7.24 (m, 6H), 5.05 (dd, J=13.2, 5.2 Hz, 1H), 4.46-4.32 (m, 3H), 3.56-3.40 (m, 2H), 3.30-3.27 (m, 1H), 2.95-2.84 (m, 2H), 2.06-1.94 (m, 3H), 1.54-1.51 (m, 1H) 0.87 (s, 3H), 0.70 (s, 3H).

Example 54: 3-(5-(3-methylpiperidin-4-yl)-1-oxoisoindolin-2-yl)piperidine-2,6-dione hydrochloride (I-186)

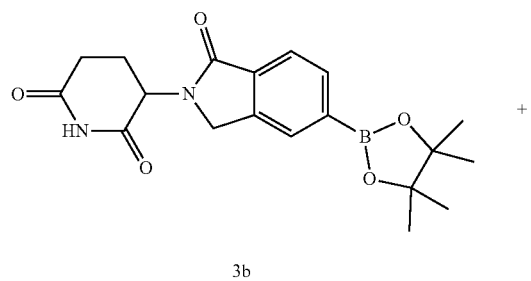

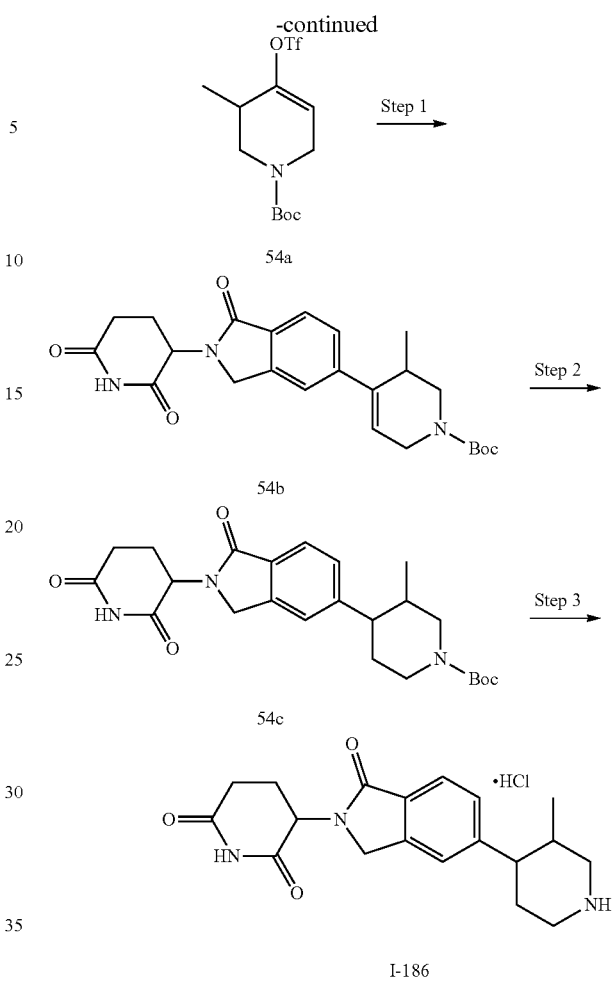

Step 1. tert-butyl 4-(2-(2,6-dioxopiperidin-3-yl)-1-oxoisoindolin-5-yl)-3-methyl-3,6-dihydropyridine-1(2H)-carboxylate (54b)

To a solution of 3b (900 mg, 2.4 mmol) and 54a (1.3 g, 3.6 mmol, [prepared from tert-butyl 3-methyl-4-oxopiperidine-1-carboxylate following the procedure in Example 49]) in DMF (10 mL) was added K₂CO₃ (990 mg, 14.58 mmol), followed by PdCl₂(dppf)*DCM (198 mg, 0.24 mmol), and the resulting mixture was degassed for 15 min and then heated to 130° C. for 1 h in microwave. After complete consumption of the starting material, the reaction mixture was cooled to rt, quenched with water and extracted with EtOAc (2×50 mL). The combined organic extracts were washed with brine (25 mL), dried over Na₂SO₄ and concentrated under reduced pressure to afford compound 54b as a red colored liquid (210 mg, crude), which was used in the next step without further purification.

Step 2: tert-butyl 4-(2-(2,6-dioxopiperidin-3-yl)-1-oxoisoindolin-5-yl)-3-methylpiperidine-1-carboxylate (54c)

To a solution of 54b (200 mg, 0.27 mmol) in DMF (4 mL) was added 10% Pd/C (40 mg) was transferred and the resulting mixture was stirred at rt for 48 h under an atmosphere of hydrogen (balloon). After complete consumption of the starting material, the reaction mixture was diluted with EtOAc (25 mL) and filtered through a pad of Celite® filter aid. The filtrate was evaporated under reduced pressure and passed through a short pad of silica gel eluting with 10% MeOH in DCM to afford 54c as an off-white solid (100 mg, 0.22 mmol, 50% yield). MS [(M-C$_4$H$_8$)+H]$^+$=386.0.

Step 3: 3-(5-(3-methylpiperidin-4-yl)-1-oxoisoindolin-2-yl)piperidine-2,6-dione hydrochloride (I-186)

To a solution of 54c (100 mg, 0.22 mmol) in DCM (2 mL) was added 4M HCl in dioxane (1 mL) and the resulting mixture was stirred at rt for 2 h. After complete consumption of the starting material, the solvent was evaporated and the resulting crude material was triturated with diethyl ether and dried under reduced pressure to afford the hydrochloride salt of I-186 as an off-white solid (55 mg, 0.14 mmol, 65% yield). MS [M+H]$^+$=342.1. $^1$H NMR (400 MHz, DMSO-d$_6$): δ 10.98 (s, 1H), 8.28 (brs, 1H), 7.70 (d, J=8.0 Hz, 1H), 7.44 (s, 1H), 7.36 (d, J=8.0 Hz, 1H), 5.10 (dd, J=13.2, 5.2 Hz, 1H), 4.47-4.28 (m, 2H), 3.32-3.25 (m, 2H), 3.04-2.87 (m, 3H), 2.67-2.58 (m, 2H), 2.41-2.33 (m, 2H), 2.19-2.16 (m, 1H), 2.00-1.98 (m, 1H), 1.86-1.82 (m, 1H), 0.75 (d, J=6.0 Hz, 3H).

Example 55: 3-(5-(1-benzyl-3-methylpiperidin-4-yl)-1-oxoisoindolin-2-yl)piperidine-2,6-dione (I-187)

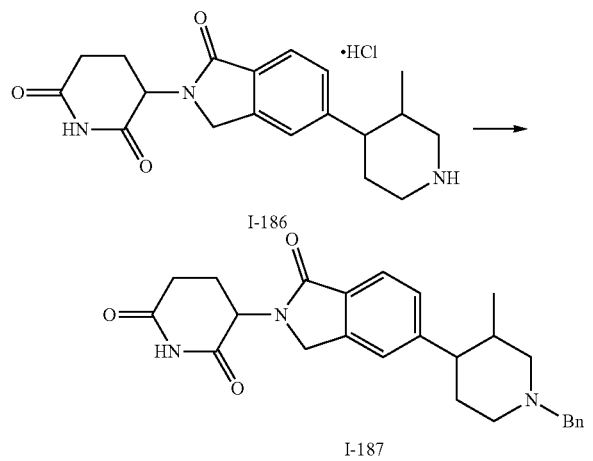

To a solution of I-186 (40 mg, 0.11 mmol) and Et$_3$N (0.05 mL, 0.35 mmol) in DMF (2 mL) was added benzyl bromide (0.016 mL, 0.14 mmol) and the resulting mixture was stirred at rt for 2 h. After complete consumption of the starting material, the reaction mixture was quenched with water and extracted with EtOAc (2×25 mL). The combined organic extracts were washed with brine (20 mL), dried over Na$_2$SO$_4$, and concentrated under reduced pressure. The crude material was purified by silica gel chromatography eluting with 80% EtOAc in hexane. The pure fractions were collected and evaporated under reduced pressure to afford I-187 as an off-white solid (18 mg, 0.04 mmol, 36% yield). MS [M+H]$^+$=432.1. $^1$H NMR (400 MHz, DMSO-d$_6$): δ 10.97 (s, 1H), 7.65 (d, J=8.0 HZ, 1H), 7.43 (s, 1H), 7.36-7.32 (m, 5H), 7.25-7.24 (m, 1H), 5.10 (dd, J=13.2, 5.2 Hz, 1H), 4.44 (d, J=17.2 Hz, 1H), 4.30 (d, J=17.2 Hz, 1H), 3.54 (d, J=13.6 Hz, 1H), 3.42 (d, J=13.6 Hz, 1H), 3.00-2.87 (m, 3H), 2.75-2.57 (m, 2H), 2.40-2.25 (m, 2H), 2.17-2.06 (m, 4H), 1.62-1.59 (m, 1H), 0.73 (d, J=6.0 Hz, 3H).

Example 56: 3-(5-(8-benzyl-8-azabicyclo[3.2.1]octan-3-yl)-1-oxoisoindolin-2-yl)piperidine-2,6-dione HC(O)OH salt (I-265)

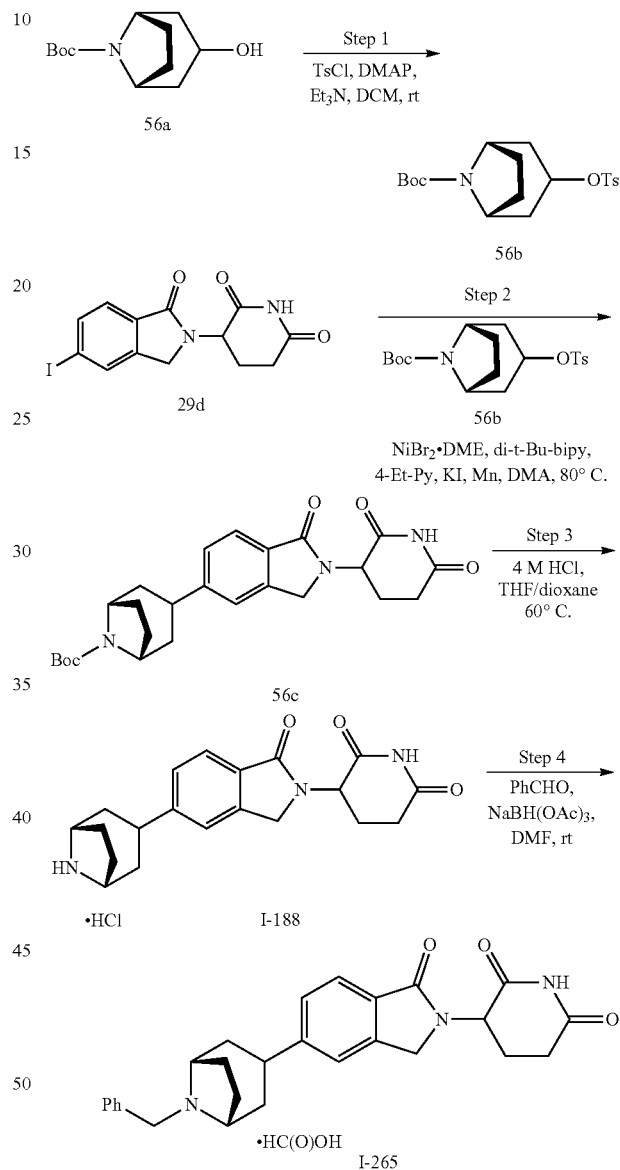

Step 1. tert-butyl 3-(tosyloxy)-8-azabicyclo[3.2.1]octane-8-carboxylate (56b)

To a stirred solution of 3-hydroxy-8-azabicyclo[3.2.1]octane-8-carboxylate (56a, 570 mg, 2.51 mmol), Et$_3$N (0.52 mL, 3.8 mmol), and DMAP (61 mg, 0.50 mmol) in DCM (5 mL) was added TsCl (574 mg, 3.01 mmol) and the resulting mixture was stirred overnight at rt. The reaction mixture was then quenched with sat. aq. NaHCO$_3$ and extracted with DCM (3×). The combined organic phases were dried over Na$_2$SO$_4$, filtered, and concentrated. The crude material was purified by silica gel chromatography eluting with 0% to 40% EtOAc in heptane to afford 56b (91 mg, 0.22 mmol, 9% yield) as a white solid. $^1$H NMR (400 MHz, Chloroform-d) δ 7.79 (d, J=8.3 Hz, 2H), 7.36 (d, J=8.5 Hz, 2H), 4.83 (t, J=5.0 Hz, 1H), 4.16 (s, 2H), 2.47 (s, 3H), 2.12-2.02 (m, 4H), 2.00-1.90 (m, 2H), 1.84 (d, J=15.3 Hz, 2H), 1.45 (s, 9H).

Step 2. tert-butyl 3-(2-(2,6-dioxopiperidin-3-yl)-1-oxoisoindolin-5-yl)-8-azabicyclo[3.2.1]octane-8-carboxylate (56c)

To a stirred suspension of 29d (56 mg, 0.15 mmol), 56b (69 mg, 0.18 mmol), NiBr$_2$(DME) (4.7 mg, 0.015 mmol), di-t-Bu-bipy (4.1 mg, 0.015 mmol), KI (25 mg, 0.15 mmol), and manganese powder (17 mg, 0.30 mmol) in DMA (0.7 mL) under an atmosphere of nitrogen was added 4-ethylpyridine (0.017 mL, 0.15 mmol) and the resulting mixture was stirred vigorously at 80° C. for 4 hours. The reaction mixture was then diluted with MeCN and filtered through a pad of Celite® filter aid eluting with MeCN. The filtrate was concentrated to dryness by azeotroping with heptane. The crude material was purified by silica gel chromatography eluting with 0% to 5% MeOH in DCM to afford 56c (38.4 mg, 0.085 mmol, 56% yield) as a white solid. MS [M+H]$^+$=454.5. $^1$H NMR (400 MHz, Chloroform-d) δ 8.58 (s, 1H), 7.80 (dd, J=7.9, 0.6 Hz, 1H), 7.32 (dd, J=7.9, 1.4 Hz, 1H), 7.29 (s, 1H), 5.23 (dd, J=13.3, 5.1 Hz, 1H), 4.46 (d, J=16.0 Hz, 1H), 4.39-4.24 (m, 3H), 3.20 (tt, J=11.8, 5.2 Hz, 1H), 2.94-2.74 (m, 2H), 2.34 (qd, J=12.8, 5.6 Hz, 1H), 2.23-2.13 (m, 1H), 2.09-2.02 (m, 2H), 1.90 (t, J=12.9 Hz, 2H), 1.80 (q, J=8.0, 6.6, 6.2 Hz, 2H), 1.76-1.69 (m, 2H), 1.51 (s, 9H).

Step 3. 3-(5-(8-azabicyclo[3.2.1]octan-3-yl)-1-oxoisoindolin-2-yl)piperidine-2,6-dione hydrochloride (I-188)

To a stirred solution of 56c (38 mg, 0.084 mmol) in THF (1 mL) was added 4 M HCl in dioxane (0.7 mL, 2.8 mmol) and the resulting mixture was stirred for 3 hours at 60° C. Formation of white precipitate was observed. The reaction mixture was then diluted with Et$_2$O and filtered. The precipitate was washed with Et$_2$O and then dried to afford the hydrochloride salt of I-188 (31.9 mg, 0.082 mmol, 98%) as a white solid. MS [M+H]$^+$=354.3. $^1$H NMR (400 MHz, DMSO-d$_6$) δ 10.98 (s, 1H), 9.18 (s, 1H), 7.69 (dd, J=7.8, 2.3 Hz, 1H), 7.56 (s, 1H), 7.50 (d, J=7.9 Hz, 1H), 5.10 (ddd, J=13.2, 5.2, 2.1 Hz, 1H), 4.45 (d, J=18.1 Hz, 1H), 4.30 (dd, J=17.3, 2.2 Hz, 1H), 4.03 (s, 2H), 3.26-3.21 (m, 1H), 2.92 (tt, J=14.0, 5.2 Hz, 1H), 2.67-2.54 (m, 1H), 2.45-2.31 (m, 1H), 2.17 (t, J=13.1 Hz, 2H), 2.09-1.92 (m, 5H), 1.89-1.73 (m, 2H).

Step 4. 3-(5-(8-benzyl-8-azabicyclo[3.2.1]octan-3-yl)-1-oxoisoindolin-2-yl)piperidine-2,6-dione HC(O)OH salt (I-265)

To a stirred solution of I-188 (20 mg, 0.051 mmol) and benzaldehyde (0.016 mL, 0.154 mmol) in DMF (1 mL) was added sodium triacetoxyborohydride (33 mg, 0.15 mmol) in one portion and the resulting mixture was stirred vigorously at rt overnight. One drop of HCOOH was then added and the reaction mixture was concentrated under reduced pressure. The crude material was purified by reverse phase HPLC (eluting with MeCN/H$_2$O with 0.1% formic acid). The fractions containing desired product were combined and lyophilized to afford the formate salt of I-265 (15.0 mg, 0.031 mmol, 60% yield) as a white solid. MS [M+H]$^+$=444.3. $^1$H NMR (400 MHz, DMSO-d$_6$) δ 10.98 (s, 1H), 8.25 (s, 1H), 7.64 (d, J=7.9 Hz, 1H), 7.52 (s, 1H), 7.42 (d, J=8.1 Hz, 3H), 7.35-7.31 (m, 2H), 7.24 (t, J=7.3 Hz, 1H), 5.10 (dd, J=13.0, 5.0 Hz, 1H), 4.42 (d, J=17.2 Hz, 1H), 4.29 (d, J=17.1 Hz, 1H), 3.61 (s, 2H), 3.25 (s, 2H), 3.13-3.01 (m, 1H), 2.91 (ddd, J=17.9, 13.2, 5.3 Hz, 1H), 2.59 (d, J=17.0 Hz, 1H), 2.46-2.31 (m, 1H), 2.14-1.94 (m, 3H), 1.85 (t, J=12.4 Hz, 2H), 1.76 (d, J=7.8 Hz, 2H), 1.63 (d, J=12.7 Hz, 2H).

Example 57: 3-(5-(1-benzylpyrrolidin-3-yl)-1-oxoisoindolin-2-yl)piperidine-2,6-dione HC(O)OH salt (I-260)

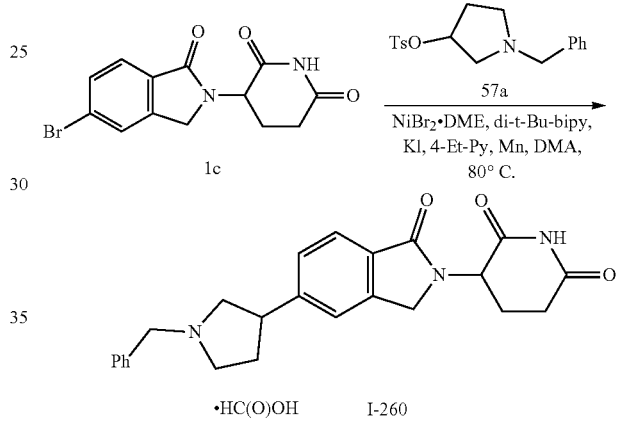

Tosylate 57a was prepared according to Tetrahedron Asymmetry, 2015, 26, 638.

To a stirred suspension of 1c (150 mg, 0.464 mmol), 57a (154 mg, 0.464 mmol), NiBr$_2$(DME) (14 mg, 0.046 mmol), di-t-Bu-bipy (13 mg, 0.046 mmol), KI (77 mg, 0.46 mmol), and manganese powder (51 mg, 0.93 mmol) in DMA (1.6 mL) under an atmosphere of nitrogen was added 4-ethylpyridine (0.053 mL, 0.46 mmol) and the resulting mixture was stirred vigorously at 80° C. for 4 hours. The reaction mixture was allowed to cool to rt, diluted with DCM (4 mL), filtered, and concentrated to dryness by azeotroping with heptane. The crude material was purified by silica gel chromatography eluting with 0% to 10% Et$_3$N in EtOAc. The obtained material was then repurified by reverse phase HPLC (eluting with MeCN/H$_2$O with 0.1% formic acid). The fractions containing desired product were combined and lyophilized to afford the formate salt of I-260 (35.2 mg, 0.078 mmol, 17% yield) as a white powder. MS [M+H]$^+$=404.2. $^1$H NMR (400 MHz, DMSO-d$_6$) δ 10.98 (s, 1H), 8.18 (s, 1H), 7.65 (d, J=7.8 Hz, 1H), 7.53 (s, 1H), 7.45 (dd, J=7.8, 1.4 Hz, 1H), 7.39-7.30 (m, 4H), 7.29-7.22 (m, 1H), 5.10 (dd, J=13.3, 5.1 Hz, 1H), 4.42 (d, J=17.2 Hz, 1H), 4.29 (d, J=17.1 Hz, 1H), 3.72-3.64 (m, 2H), 3.46 (dq, J=9.5, 7.1 Hz, 1H), 3.00-2.84 (m, 2H), 2.77 (td, J=8.8, 5.2 Hz, 1H), 2.72-2.65 (m, 1H), 2.64-2.52 (m, 2H), 2.45-2.35 (m, 1H), 2.35-2.26 (m, 1H), 2.04-1.93 (m, 1H), 1.88-1.76 (m, 1H).

Example 58: racemic 3-(1-oxo-5-(1-(1-phenylethyl)piperidin-4-yl)isoindolin-2-yl)piperidine-2,6-dione (I-62), 3-(1-oxo-5-(1-((R)-1-phenylethyl)piperidin-4-yl)isoindolin-2-yl)piperidine-2,6-dione (I-247) and 3-(1-oxo-5-(1-((S)-1-phenylethyl)piperidin-4-yl)isoindolin-2-yl)piperidine-2,6-dione (I-230)

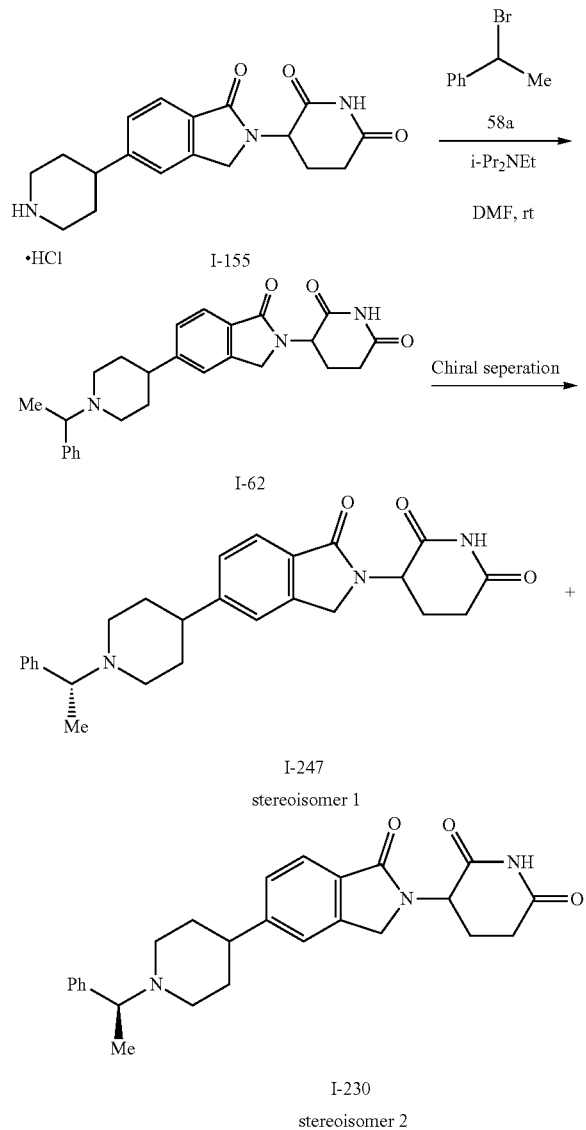

To a stirred solution of I-155 (100 mg, 0.275 mmol) and i-Pr₂NEt (0.096 mL, 0.55 mmol) in DMF (1 mL) was added (1-bromoethyl)benzene (58a, 0.053 mL, 0.39 mmol) in one portion and the resulting mixture was stirred vigorously overnight at rt. The reaction mixture was then concentrated to dryness. The crude material was purified by silica gel chromatography eluting with 0% to 10% Et₃N in EtOAc to afford I-62 (racemic, 44.3 mg, 0.10 mmol, 37% yield) as a white solid. MS [M+H]⁺=432.3. ¹H NMR (400 MHz, methylene chloride-d₂) δ 8.19 (s, 1H), 7.76 (dd, J=8.2, 1.6 Hz, 1H), 7.44-7.32 (m, 6H), 7.29-7.23 (m, 1H), 5.19 (dd, J=13.3, 5.1 Hz, 1H), 4.46-4.32 (m, 2H), 3.51 (q, J=6.8 Hz, 1H), 3.22 (d, J=11.3 Hz, 1H), 3.01-2.78 (m, 3H), 2.68-2.53 (m, 1H), 2.39 (qd, J=12.8, 5.9 Hz, 1H), 2.26-2.19 (m, 1H), 2.19-2.10 (m, 1H), 2.08-1.99 (m, 1H), 1.94-1.72 (m, 4H), 1.48-1.36 (m, 3H). The stereoisomers were separated using chiral SFC (Column: ChiralPak AS-H 21×250 mm; CO₂ co-solvent: 35% IPA with 10 mM NH₃; Flow Rate: 80 g per minute) to afford stereoisomer 1 (first peak, Rt=3.35 min, 7.4 mg, 0.015 mmol) and stereoisomer 2 (second peak, Rt=7.02 min, 10.2 mg, 0.024 mmol). The absolute stereochemistry of the two stereoisomers corresponding to the two product peaks is unknown and was assigned arbitrarily.

Example 59: 3-(5-(1-benzyl-2,5-dihydro-1H-pyrrol-3-yl)-1-oxoisoindolin-2-yl)piperidine-2,6-dione (I-191)

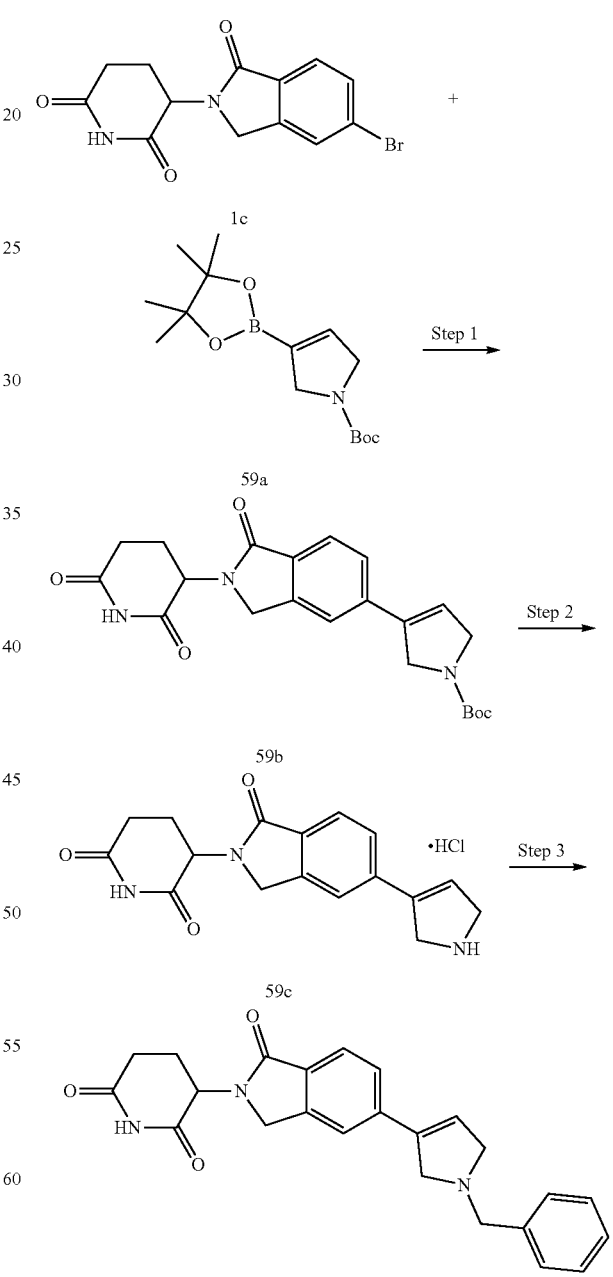

Step 1: tert-butyl 3-(2-(2,6-dioxopiperidin-3-yl)-1-oxoisoindolin-5-yl)-2,5-dihydro-1H-pyrrole-1-carboxylate (59b)

To a solution of compound 1c (150 mg, 0.46 mmol) and 59a (165 mg, 0.56 mmol, prepared from tert-butyl 3-oxopyrrolidine-1-carboxylate according to US2010/204265) and K$_2$CO$_3$ (128 mg, 0.93 mmol) in DMF (5 mL) was added PdCl$_2$(dppf)*DCM (19 mg, 0.02 mmol) and the resulting mixture was degassed and then stirred at 120° C. in a microwave. After 1 h, the reaction mixture was cooled to rt, quenched with ice-cold water, and extracted with EtOAc (2×50 mL). The combined organic extracts were washed with brine (20 mL), dried over Na$_2$SO$_4$, and concentrated under reduced pressure. The crude material was purified by silica gel chromatography eluting with 2% MeOH in DCM. The fractions containing desired product were collected and concentrated under reduced pressure to afford 59b as brown colored oil (80 mg, 0.31 mmol, 42% yield). MS [M+H]$^+$=412.0.

Step 2. 3-(5-(2,5-dihydro-1H-pyrrol-3-yl)-1-oxoisoindolin-2-yl)piperidine-2,6-dione hydrochloride (59c)

To a solution of compound 59b (80 mg, 0.31 mmol) in dioxane (1 mL) was added 4M HCl in dioxane (1 mL) and the resulting reaction mixture was stirred at rt for 5 h. After complete consumption of the starting material, the solvent was evaporated under reduced pressure to afford the hydrochloride salt 59c as an off-white solid (60 mg, 0.17 mmol, 90% yield) which was carried onto the next step without further purification. MS [M+H]$^+$=312.0.

Step 3: 3-(5-(1-benzyl-2,5-dihydro-1H-pyrrol-3-yl)-1-oxoisoindolin-2-yl)piperidine-2,6-dione (I-191)

To a solution of 59c (60 mg, 0.17 mmol) and benzaldehyde (0.02 mL, 0.21 mmol) in DMF:DCM (4 mL, v/v=1:1) was added NaBH(OAc)$_3$ (109 mg, 0.52 mmol) and the resulting mixture was stirred at rt for 4 h. After complete consumption of the starting material, DCM was evaporated. The resulting residue was taken into EtOAc (50 mL), washed with brine, dried over Na$_2$SO$_4$, and concentrated under reduced pressure. The crude material was purified by silica gel chromatography eluting with 80% EtOAc in hexane. The pure fractions were collected and concentrated under reduced pressure to afford I-191 as an off-white solid (32 mg, 0.08 mmol, 46% yield). MS [M+H]$^+$=402.1. $^1$H NMR (400 MHz, DMSO-d$_6$): δ 10.97 (s, 1H), 7.67 (d, J=8.4 Hz, 1H), 7.66 (s, 1H), 7.57 (d, J=7.8 Hz, 1H), 7.39-7.24 (m, 5H), 6.52 (brs, 1H), 5.10 (dd, J=13.2, 4.8 Hz, 1H), 4.42 (d, J=17.2 Hz, 1H), 4.31 (d, J=17.2 Hz, 1H), 3.86 (s, 2H), 3.83 (brs, 2H), 3.65 (brs, 2H), 2.90-2.87 (m, 1H), 2.62-2.55 (m, 1H), 2.45-2.40 (m, 1H), 2.01-1.98 (m, 1H).

Example 60: 3-(5-(1-benzyl-2-oxo-1,2-dihydropyridin-4-yl)-1-oxoisoindolin-2-yl)piperidine-2,6-dione (I-192)

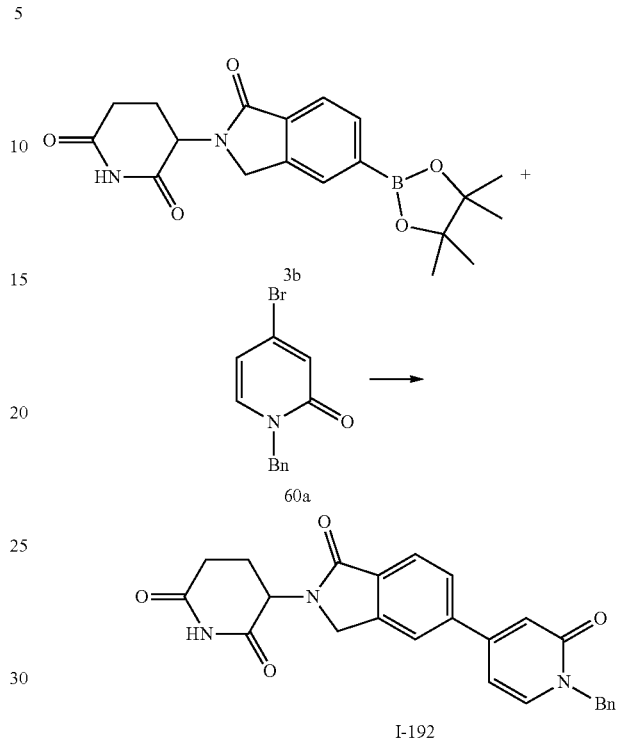

To a stirred suspension of 3b (500 mg, 1.35 mmol), 60a (428 mg, 1.62 mmol), and K$_2$CO$_3$ in DMF (5 mL) was added PdCl$_2$(dppf)*DCM (55 mg, 0.07 mmol) and the resulting mixture was sparged with argon for 10 min and then stirred at 130° C. for 90 min. After complete consumption of the starting material, the reaction mixture was quenched with ice-cold water and extracted with EtOAc (3×50 mL). The combined organic extracts were washed with brine, dried over Na$_2$SO$_4$, and concentrated under reduced pressure. The crude material was purified by silica gel chromatography eluting with 5% MeOH in DCM to afford I-192 as an off-white solid (20 mg, 0.46 mmol, 35% yield). MS [M+H]$^+$=427.8. $^1$H NMR (400 MHz, DMSO-d$_6$): δ 10.98 (s, 1H), 7.94 (s, 1H), 7.90 (d, J=7.6 Hz, 1H), 7.80-7.76 (m, 2H), 7.33-7.25 (m, 5H), 6.76 (d, J=2.0 Hz, 1H), 6.64 (dd, J=7.2, 2.0 Hz, 1H), 5.12 (s, 2H), 5.12-5.08 (m, 1H), 4.48 (d, J=17.2 Hz, 1H), 4.36 (d, J=17.2 Hz, 1H), 2.80-2.75 (m, 1H), 2.60-2.53 (m, 1H), 2.45-2.38 (m, 1H), 2.02-1.97 (m, 1H).

Example 61: 3-(5-(1-benzyl-2-oxopiperidin-4-yl)-1-oxoisoindolin-2-yl)piperidine-2,6-dione (I-193)

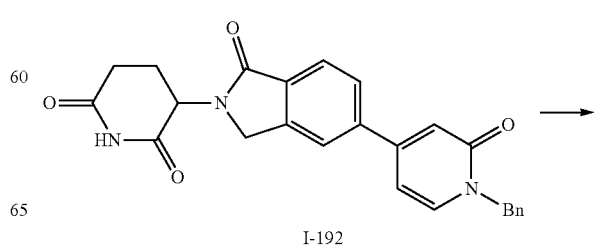

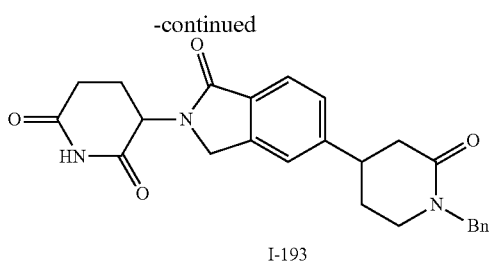

I-193

To a de-oxygenated solution of I-192 (70 mg, 0.16 mmol) in DMF (10 mL) was added 10% Pd/C (70 mg) and the resulting mixture was stirred at rt under an atmosphere of hydrogen (70 psi, in parr-apparatus) for 16 h. After complete consumption of the starting material, the reaction mixture was passed through a short pad of Celite® filter aid and washed with EtOAc (50 mL). The filtrate was evaporated under reduced pressure and the crude material was purified by silica gel chromatography eluting with 10% MeOH in DCM. The pure fractions were collected and evaporated under reduced pressure to afford I-193 as an off-white solid (30 mg, 0.07 mmol, 42% yield). MS [M+H]$^+$=431.9. $^1$H NMR (400 MHz, DMSO-d6): δ 10.96 (s, 1H), 7.64 (d, J=7.6 Hz, 1H), 7.50 (s, 1H), 7.43 (d, J=7.6 Hz, 1H), 7.35-7.31 (m, 2H), 7.26-7.23 (m, 3H), 5.09 (dd, J=13.2, 5.4 Hz, 1H), 4.62 (dd, J=15.2, 4.4 Hz, 1H), 4.48-4.37 (m, 2H), 4.29 (dd, J=15.2, 4.4 Hz, 1H), 3.30-3.18 (m, 3H), 2.93-2.84 (m, 1H), 2.64-2.39 (m, 4H), 2.01-1.94 (m, 3H).

Example 62: 3-(1-oxo-5-(2-oxopiperidin-4-yl)isoindolin-2-yl)piperidine-2,6-dione (I-194) and 3-(1-oxo-5-(2-oxo-1,2-dihydropyridin-4-yl)isoindolin-2-yl)piperidine-2,6-dione (I-195)

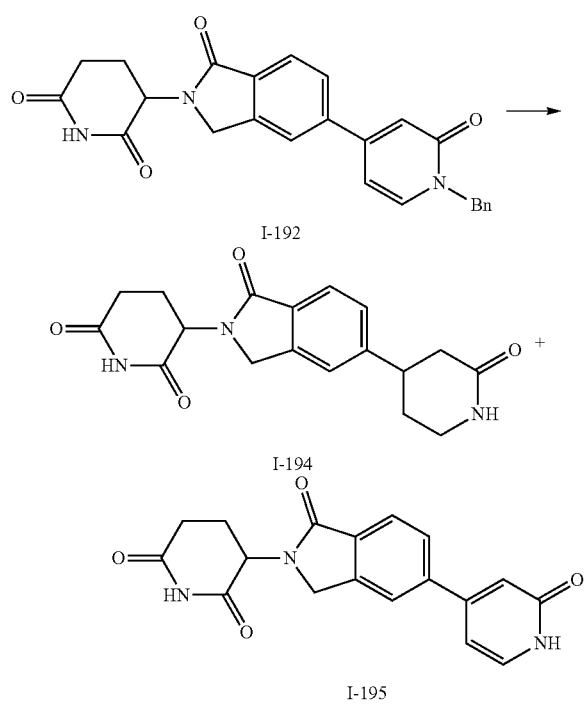

I-192

I-194

I-195

To a de-oxygenated solution of I-192 (130 mg, 0.18 mmol) in TFA:AcOH (6 mL, v/v=5:1) was added 10% Pd/C (50 mg) and the resulting mixture was stirred at rt under an atmosphere of hydrogen (balloon) for 16 h. After complete consumption of the starting material, the reaction mixture was diluted with EtOAc (20 mL), passed through a short pad of Celite® filter aid and washed with EtOAc (10 mL). The filtrate was evaporated under reduced pressure and the obtained crude material was purified by silica gel chromatography eluting with 5% to 10% MeOH in DCM. The pure fractions were combined and concentrated to afford I-194 (eluted first from the column) as an off-white solid (10 mg, 0.03 mmol, 10% yield) and I-195 (eluted second) as an off-white solid (70 mg, 0.21 mmol, 68% yield).

I-194: MS [M+H]$^+$=341.8. $^1$H NMR (400 MHz, DMSO-d6): δ 10.99 (s, 1H) 7.68 (d, J=10.4 Hz, 1H), 7.60 (s, 1H), 7.53 (s, 1H), 7.44 (d, J=10.4 Hz, 1H), 5.10 (dd, J=17.6, 6.0 Hz, 1H), 4.45 (d, J=22.8 Hz, 1H), 4.30 (d, J=22.8 Hz, 1H), 3.37-3.22 (m, 3H), 2.92-2.88 (m, 1H), 2.65-2.60 (m, 1H), 2.44-2.27 (m, 3H), 2.00-1.89 (m, 3H). I-195: MS [M+H]$^+$=338.1. $^1$H NMR (400 MHz, DMSO-d$_6$): δ 11.72 (brs, 1H), 11.02 (s, 1H), 7.94 (s, 1H), 7.81 (d, J=8.0 Hz, 2H), 7.50 (d, J=6.4 Hz, 1H), 6.66 (d, J=1.6 Hz, 1H), 6.55 (dd, J=6.4, 1.6 Hz, 1H), 5.14 (dd, J=13.2, 4.8 Hz, 1H), 4.52 (d, J=17.6 Hz, 1H), 4.39 (d, J=17.6 Hz, 1H), 2.97-2.87 (m, 1H), 2.67-2.58 (m, 1H), 2.45-2.37 (m, 1H), 2.08-2.00 (m, 1H).

Example 63: 3-(1-oxo-5-(1,2,3,4-tetrahydroquinolin-4-yl)isoindolin-2-yl)piperidine-2,6-dione (I-196)

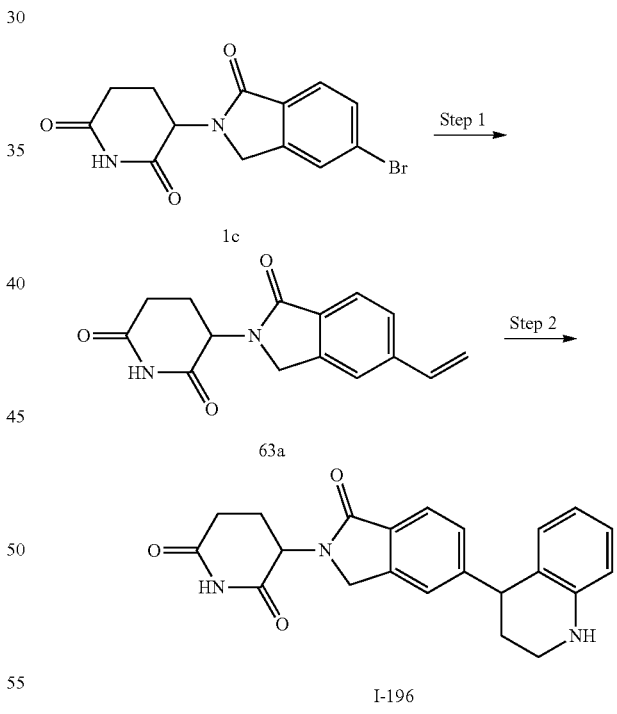

1c

63a

I-196

Step 1: 3-(1-oxo-5-vinylisoindolin-2-yl)piperidine-2,6-dione (63a)

To a solution of 1c (1.5 g, 4.66 mmol) and tributyl(vinyl)stannane (2.04 mL, 6.95 mmol) in dioxane (15 mL) was added PdCl$_2$(PPh$_3$)$_2$(162 mg, 0.23 mmol) and the resulting mixture was purged with argon for 10 min and then stirred at 110° C. for 1 h in the microwave. After complete consumption of the starting material, the reaction mixture was quenched with water and extracted with EtOAc (2×50 mL). The combined organic extracts were washed with brine, dried over Na$_2$SO$_4$, and concentrated under reduced pressure. The obtained crude material was purified by silica gel chromatography eluting with 90% EtOAc in hexane. The pure fractions were collected and evaporated under reduced pressure to afford 63a as a pale brown solid (500 mg, 1.85 mmol, 40% yield). MS [M+H]$^+$=271.2.

Step 2: 3-(1-oxo-5-(1,2,3,4-tetrahydroquinolin-4-yl)isoindolin-2-yl)piperidine-2,6-dione (I-196)

To a solution of 63a (200 g, 0.74 mmol) and (azidomethyl)benzene (118 mg, 0.89 mmol) in DCM (4 mL) was added triflic acid (0.08 mL, 0.89 mmol) and the resulting mixture was stirred at rt for 2 h. After complete consumption of the starting material, the reaction mixture was quenched with water and extracted with EtOAc (2×50 mL). The combined organic extracts were washed with brine, dried over Na$_2$SO$_4$ and concentrated under reduced pressure. The obtained crude material was purified by reverse phase HPLC (eluting with 0.01% NH$_4$OAc in MeCN) to afford I-196 as an off-white solid (15 mg, 0.04 mmol, 6% yield). MS [M+H]$^+$=376.2. $^1$H NMR (400 MHz, DMSO-d$_6$): δ 10.96 (s, 1H), 7.66 (d, J=8.0 Hz, 1H), 7.32-7.23 (m, 2H), 6.92 (t, J=7.6 Hz, 1H), 6.59-6.55 (m, 2H), 6.41 (t, J=7.2 Hz, 1H), 5.08 (dd, J=13.2, 5.2 Hz, 1H), 4.44-4.23 (m, 3H), 3.24-3.18 (m, 1H), 3.10-3.05 (m, 1H), 2.95-2.86 (m, 1H), 2.66-2.50 (m, 2H), 2.42-2.31 (m, 1H), 2.10-1.98 (m, 3H).

Example 64: 3-(5-(1-benzyl-1,2,3,4-tetrahydroquinolin-4-yl)-1-oxoisoindolin-2-yl)piperidine-2,6-dione (I-197)

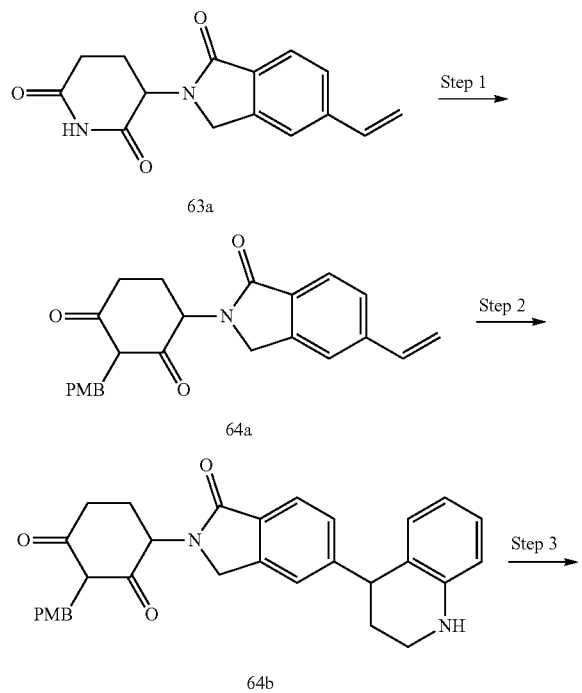

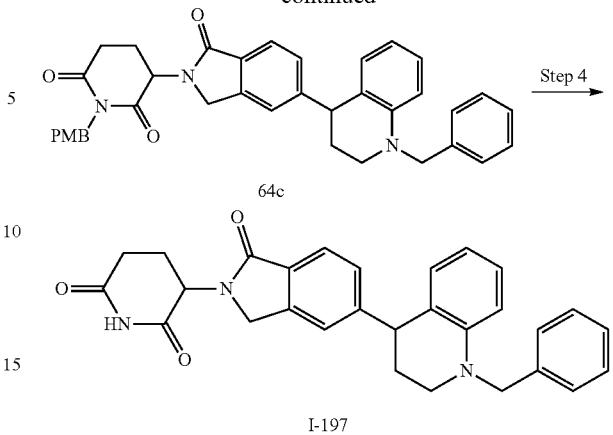

Step 1. 1-(4-methoxybenzyl)-3-(1-oxo-5-vinylisoindolin-2-yl)piperidine-2,6-dione (64a)

To a stirred suspension of 63a (1 g, 3.70 mmol) and K$_2$CO$_3$ (255 mg, 7.4 mmol) in DMF (10 mL) was added PMB-Cl (640 mg, 4.07 mmol), followed by Bu$_4$NI (683 mg, 0.74 mmol) and the resulting mixture was stirred at rt for 16 h. After complete consumption of the starting material, the reaction mixture was quenched with water and extracted with DCM (2×100 mL). The combined organic extracts were washed with brine, dried over Na$_2$SO$_4$, and concentrated under reduced pressure. The obtained crude material was purified by silica gel chromatography eluting with 80% EtOAc in hexane. The pure fractions were collected and evaporated under reduced pressure to afford 64a as a pale brown solid (700 mg, 1.79 mmol, 52% yield). MS [M+H]$^+$=391.1.

Step 2. 1-(4-methoxybenzyl)-3-(1-oxo-5-(1,2,3,4-tetrahydroquinolin-4-yl)isoindolin-2-yl)piperidine-2,6-dione (64b)

To a solution of 64a (700 mg, 1.79 mmol) and (azidomethyl)benzene (102 mg, 2.15 mmol) in DCM (10 mL) was added triflic acid (0.19 mL, 2.15 mmol) and the resulting mixture was stirred at rt for 24 h. After complete consumption of the starting material, the reaction mixture was quenched with water and extracted with EtOAc (2×50 mL). The combined organic extracts were washed with brine, dried over Na$_2$SO$_4$, and concentrated under reduced pressure. The obtained material was triturated with diethyl ether and the resulting solid was dried under reduced pressure to afford 64b as pale brown solid (500 mg, 1.01 mmol, 56% yield). MS [M+H]$^+$=496.2.

Step 3: 3-(5-(1-benzyl-1,2,3,4-tetrahydroquinolin-4-yl)-1-oxoisoindolin-2-yl)-1-(4-methoxybenzyl)piperidine-2,6-dione (64c)

To a stirred suspension of 64b (300 mg, 0.60 mmol) and K$_2$CO$_3$ (168 mg, 1.22 mmol) in DMF (6 mL) was added benzyl bromide (120 mg, 0.72 mmol), followed by CuI, (11 mg, 0.058 mmol) and the resulting mixture was stirred at rt for 4 h. After complete consumption of the starting material, the reaction mixture was quenched with water and extracted with EtOAc (2×50 mL). The combined organic extracts were washed with brine, dried over Na$_2$SO$_4$, and concentrated under reduced pressure. The obtained crude material was purified by silica gel chromatography eluting with 70% EtOAc in hexane. The pure fractions were collected and evaporated under reduced pressure to afford 64c as a pale brown solid (300 mg, 0.51 mmol, 85% yield). MS [M+H]$^+$=586.4.

Step 4: 3-(5-(1-benzyl-1,2,3,4-tetrahydroquinolin-4-yl)-1-oxoisoindolin-2-yl)piperidine-2,6-dione (I-197)

A solution of 64c (150 mg, 0.05 mmol) in TFA-TfOH (6 mL, 1:1) was stirred at 60° C. for 16 h. After complete consumption of the starting material, the reaction mixture was quenched with water, neutralized with sat. aq. NaHCO$_3$ solution, and extracted with EtOAc (2×50 mL). The combined organic extracts were washed with brine, dried over Na$_2$SO$_4$, and concentrated under reduced pressure. The obtained crude material was purified by silica gel chromatography eluting with 90% EtOAc in hexane. The pure fractions were collected and evaporated under reduced pressure to afford I-197 as a pale brown solid (25 mg, 0.05 mmol, 21%). MS [M+H]$^+$=466.2. $^1$H NMR (400 MHz, DMSO-d$_6$): δ 11.99 (s, 1H), 7.67 (d, J=8.0 Hz, 1H), 7.34-7.24 (m, 7H), 7.01-6.95 (m, 1H), 6.65-6.60 (m, 2H), 6.47-6.44 (m, 1H), 5.10 (dd, J=13.2, 5.2 Hz, 1H), 4.59-4.24 (m, 5H), 3.38-3.32 (m, 1H), 3.22-3.19 (m, 1H), 2.92-2.88 (m, 1H), 2.61-2.55 (m, 1H), 2.46-2.39 (m, 1H), 2.25-2.21 (m, 1H), 2.15-2.08 (m, 1H), 2.02-1.95 (m, 1H).

Example 65: 3-(5-(1-(2-fluoro-1-phenylethyl)piperidin-4-yl)-1-oxoisoindolin-2-yl)piperidine-2,6-dione (I-212)

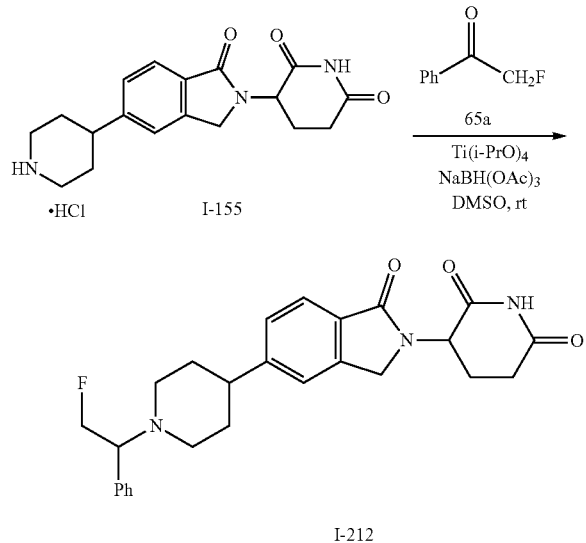

To a stirred solution of I-155 (100 mg, 0.275 mmol) and 2-fluoro-1-phenylethanone (65a, 228 mg, 1.65 mmol) in DMSO (1 mL) was added Ti(Oi-Pr)$_4$ (0.17 mL, 0.55 mmol) and the resulting mixture was stirred for 30 min. NaBH(OAc)$_3$ (233 mg, 1.10 mmol) was then added in one portion and the reaction mixture was stirred for 44 hours at rt. The reaction mixture was diluted with 0.1 M aq. HCOOH (0.2 mL), filtered, and purified by reverse phase HPLC (eluting with MeCN/H$_2$O with 0.1% formic acid). The fractions containing the desired product were combined and lyophilized. The obtained product was repurified by silica gel chromatography eluting with 0% to 10% Et$_3$N in EtOAc. Fractions containing desired product were combined and concentrated to afford I-212 (20.6 mg, 0.045 mmol, 16.5% yield) as a white solid. MS [M+H]$^+$=450.2. $^1$H NMR (400 MHz, methylene chloride-d$_2$) δ 8.38 (s, 1H), 7.76-7.69 (m, 1H), 7.43-7.27 (m, 7H), 5.16 (dd, J=13.3, 5.1 Hz, 1H), 4.90-4.53 (m, 2H), 4.39 (d, J=16.1 Hz, 1H), 4.32 (d, J=16.0 Hz, 1H), 3.78-3.62 (m, 1H), 3.26 (d, J=11.1 Hz, 1H), 2.97-2.75 (m, 3H), 2.67-2.53 (m, 1H), 2.41-2.27 (m, 2H), 2.22-2.14 (m, 1H), 2.08 (t, J=10.7 Hz, 1H), 1.94-1.81 (m, 2H), 1.80-1.69 (m, 2H).

Example 66: 3-(5-(1-(2,2-difluoro-1-phenylethyl)piperidin-4-yl)-1-oxoisoindolin-2-yl)piperidine-2,6-dione (I-209)

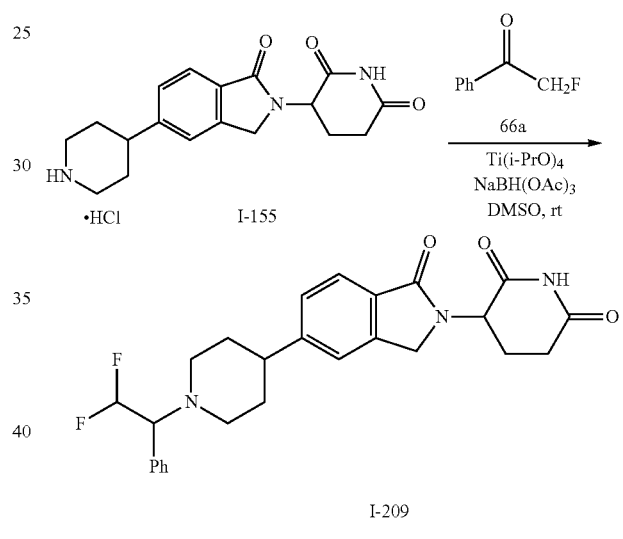

To a stirred solution of I-155 (50 mg, 0.14 mmol) and 2,2-difluoro-1-phenylethanone (66a, 0.11 mL, 0.83 mmol) in DMSO (1 mL) was added Ti(Oi-Pr)$_4$ (0.083 mL, 0.28 mmol) and the resulting mixture was stirred for 30 min. NaBH(OAc)$_3$ (117 mg, 0.550 mmol) was then added in one portion and the reaction mixture was stirred for 44 hours at rt. The reaction mixture was diluted with 0.1 M aq. HCOOH (0.2 mL), filtered, and purified by reverse phase HPLC (eluting with MeCN/H$_2$O with 0.1% formic acid). The fractions containing desired product were combined and lyophilized. The obtained product was repurified by silica gel chromatography eluting with 0% to 10% Et$_3$N in EtOAc. Fractions containing desired product were combined and concentrated to afford I-209 (9.6 mg, 0.021 mmol, 15% yield) as a white solid. MS [M+H]$^+$=468.4. $^1$H NMR (400 MHz, methylene chloride-d$_2$) δ 8.26 (s, 1H), 7.82-7.65 (m, 1H), 7.50-7.29 (m, 7H), 6.21 (t, J=55.5 Hz, 1H), 5.15 (dd, J=13.3, 5.1 Hz, 1H), 4.42-4.27 (m, 2H), 3.78 (t, J=13.8 Hz, 1H), 3.18 (d, J=11.0 Hz, 1H), 2.98 (d, J=11.3 Hz, 1H), 2.92-2.76 (m, 2H), 2.56 (quint, J=8.1 Hz, 1H), 2.47-2.29 (m, 2H), 2.22-2.08 (m, 2H), 1.92-1.72 (m, 4H).

Example 67: 3-(1-oxo-5-(1-(2,2,2-trifluoro-1-phenylethyl)piperidin-4-yl)isoindolin-2-yl)piperidine-2,6-dione HC(O)OH salt (I-224)

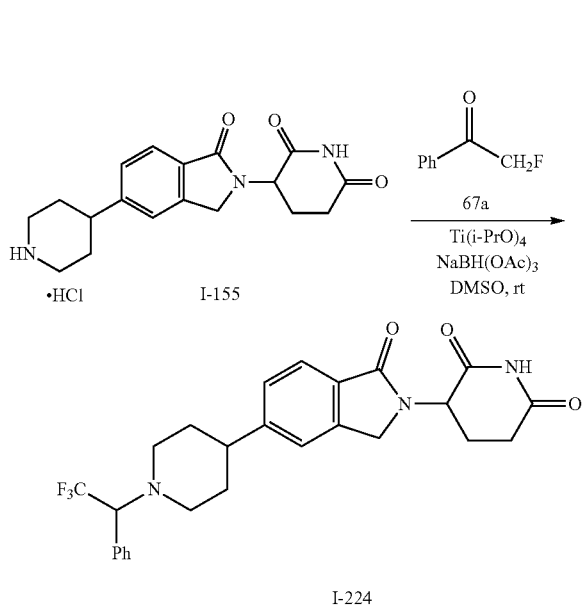

To a stirred solution of I-155 (20 mg, 0.055 mmol) and 2,2,2-trifluoro-1-phenylethanone (67a, 0.023 mL, 0.17 mmol) in DMSO (1 mL) was added Ti(Oi-Pr)$_4$ (0.017 mL, 0.055 mmol) and the resulting mixture was stirred for 30 min. NaBH(OAc)$_3$ (35 mg, 0.17 mmol) was then added in one portion and the reaction mixture was stirred for 48 hours at rt. The reaction mixture was diluted with 0.1 M aq. HCOOH (0.2 mL), filtered, and purified by reverse phase HPLC (eluting with MeCN/H$_2$O with 0.1% formic acid). The fractions containing desired product were combined and lyophilized to afford the formate salt of I-224 (3.5 mg, 6.58 μmol, 12% yield) as a white solid. MS [M+H]$^+$=486.2. $^1$H NMR (400 MHz, acetonitrile-d$_3$) δ 9.03 (s, 1H), 7.68 (d, J=7.9 Hz, 1H), 7.54-7.42 (m, 6H), 7.38 (dd, J=8.0, 1.4 Hz, 1H), 5.08 (dd, J=13.4, 5.2 Hz, 1H), 4.50-4.22 (m, 3H), 3.22-3.04 (m, 2H), 2.95-2.67 (m, 2H), 2.62-2.52 (m, 2H), 2.49-2.45 (m, 1H), 2.21-2.08 (m, 2H), 1.90-1.69 (m, 4H).

Example 68: 3-(5-(1-((R)-2-hydroxy-1-phenylethyl)piperidin-4-yl)-1-oxoisoindolin-2-yl)piperidine-2,6-dione (I-202) and 3-(5-(1-((S)-2-hydroxy-1-phenylethyl)piperidin-4-yl)-1-oxoisoindolin-2-yl)piperidine-2,6-dione (I-249)

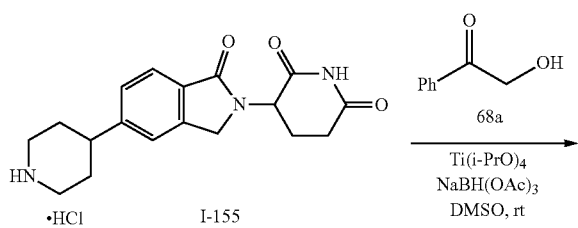

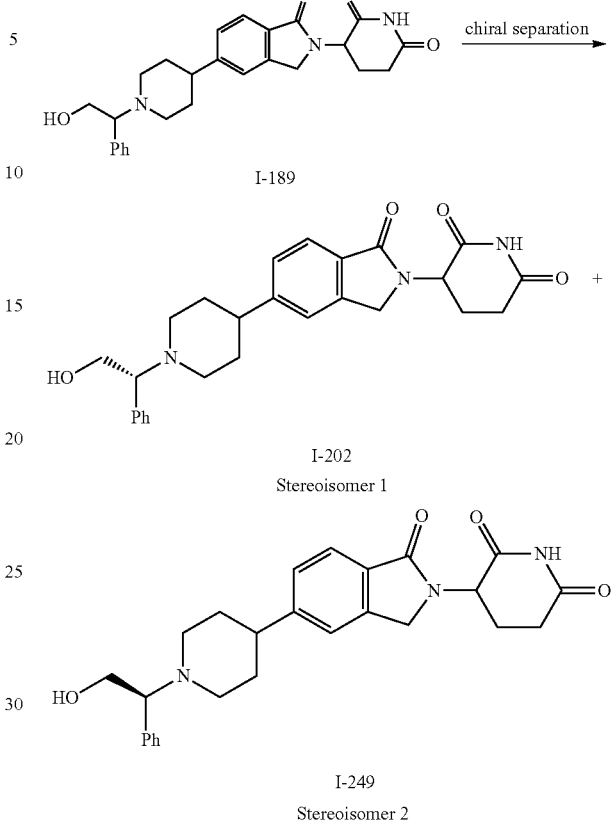

I-189

I-202
Stereoisomer 1

I-249
Stereoisomer 2

To a stirred solution of I-155 (100 mg, 0.275 mmol) and 2-hydroxy-1-phenylethanone (68a, 112 mg, 0.825 mmol) in DMSO (1 mL) was added Ti(Oi-Pr)$_4$ (0.17 mL, 0.55 mmol) and the resulting mixture was stirred for 30 min. NaBH(OAc)$_3$ (175 mg, 0.825 mmol) was then added in one portion and the reaction mixture was stirred for 48 hours at rt. The reaction mixture was diluted with 0.1 M aq. HCOOH (0.2 mL), filtered, and purified by reverse phase HPLC (eluting with MeCN/H$_2$O with 0.1% formic acid). The fractions containing desired product were combined and lyophilized to afford the formate salt of I-189 (27 mg, 0.055 mmol, 20% yield) as a white solid. MS [M+H]$^+$=448.4. $^1$H NMR (400 MHz, methylene chloride-d$_2$) δ 8.07-7.98 (m, 2H), 7.72 (d, J=8.4 Hz, 1H), 7.63-7.52 (m, 1H), 7.49-7.41 (m, 2H), 7.39-7.32 (m, 2H), 5.13 (dd, J=13.3, 5.2 Hz, 1H), 4.57-4.23 (m, 2H), 3.81 (s, 2H), 3.09 (d, J=11.0 Hz, 2H), 2.91-2.72 (m, 2H), 2.71-2.58 (m, 1H), 2.41-2.24 (m, 2H), 2.22-2.11 (m, 1H), 1.84 (d, J=8.5 Hz, 3H), 1.25 (s, 4H). The stereoisomers were separated using chiral SFC (Column: Chiralcel OJ-H 21×250 mm; CO$_2$ co-solvent: 30% IPA with 10 mM NH$_3$; Flow Rate: 80 g per minute) to afford Stereoisomer 1 (first peak, Rt=5.29 min, 1.7 mg, 3.2 μmol) and Stereoisomer 2 (second peak, Rt=6.68 min, 2.1 mg, 4.0 μmol). The absolute stereochemistry of the two stereoisomers corresponding to the two product peaks is unknown and was assigned arbitrarily.

Example 69: 3-(5-(1-((3-fluorobicyclo[1.1.1]pentan-1-yl)methyl)piperidin-4-yl)-1-oxoisoindolin-2-yl)piperidine-2,6-dione HC(O)OH salt (I-210)

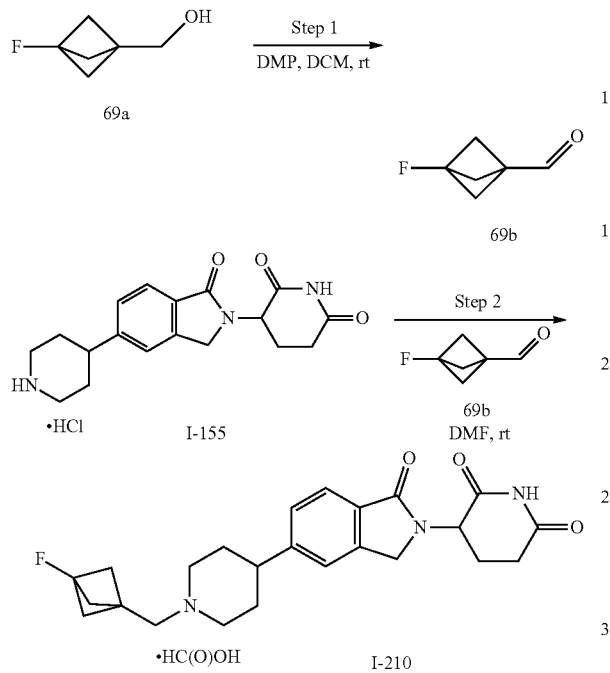

Step 1. 3-fluorobicyclo[1.1.1]pentane-1-carbaldehyde (69b)

To a stirred solution of (3-fluorobicyclo[1.1.1]pentan-1-yl)methanol (69a, 0.890 g, 7.66 mmol) in DCM (10 mL) was added DMP (4.87 g, 11.49 mmol) and the reaction mixture was stirred for 6 hours. The reaction mixture was diluted with Et$_2$O (30 mL), filtered, and concentrated to dryness to afford crude product as a pale yellow oil. The crude product 69b was used in the next step without further purification. $^1$H NMR (400 MHz, DMSO-d$_6$) δ 9.29 (d, J=6.4 Hz, 1H), 1.91 (d, J=2.7 Hz, 6H).

Step 2. 3-(5-(1-((3-fluorobicyclo[1.1.1]pentan-1-yl)methyl)piperidin-4-yl)-1-oxoisoindolin-2-yl)piperidine-2,6-dione HC(O)OH salt (I-210)

To a stirred solution of I-155 (80 mg, 0.22 mmol) and crude 3-fluorobicyclo[1.1.1]pentane-1-carbaldehyde 69b (167 mg, 0.44 mmol) in DMF (1 mL) was added NaBH(OAc)$_3$ (93 mg, 0.44 mmol) in one portion and the resulting mixture was stirred for 48 hours at rt. The reaction mixture was concentrated to dryness and the obtained crude material was purified by reverse phase HPLC (eluting with MeCN/H$_2$O with 0.1% formic acid). The fractions containing desired product were combined and lyophilized to afford the formate salt of I-210 (29.3 mg, 0.062 mmol, 28% yield)) as a white solid. MS [M+H]$^+$=426.3. $^1$H NMR (400 MHz, methylene chloride-d$_2$) δ 8.32 (s, 1H), 7.75 (d, J=7.9 Hz, 1H), 7.45-7.33 (m, 2H), 5.15 (dd, J=13.3, 5.2 Hz, 1H), 4.43-4.31 (m, 2H), 3.42 (br s, 1H), 3.32-3.25 (m, 2H), 2.96 (s, 2H), 2.92-2.77 (m, 2H), 2.77-2.66 (m, 1H), 2.47-2.30 (m, 3H), 2.23-2.15 (m, 1H), 2.12 (d, J=2.6 Hz, 6H), 2.10-2.00 (m, 2H), 1.92-1.86 (m, 2H).

Example 70: 3-(1-oxo-5-(1-(2,2,2-trifluoroethyl)piperidin-4-yl)isoindolin-2-yl)piperidine-2,6-dione (I-253)

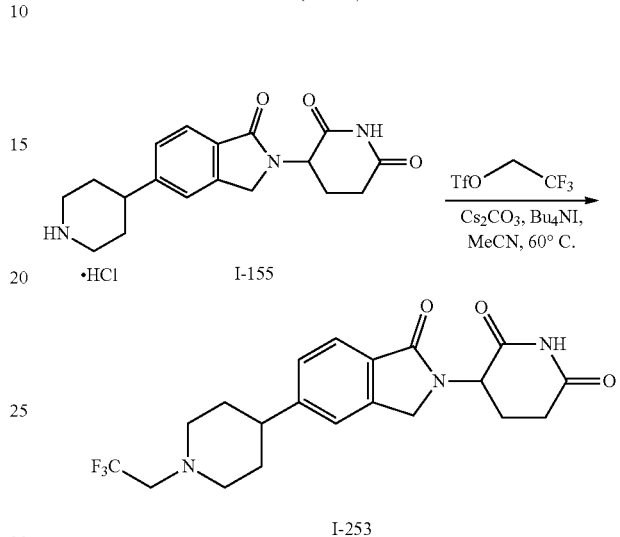

To a stirred suspension of I-155 (21 mg, 0.07 mmol), Cs$_2$CO$_3$ (38 mg, 0.12 mmol), Bu$_4$NI (2 mg, 6 µmol) in MeCN (1.0 mL) was added 2,2,2-trifluoroethyl trifluoromethanesulfonate (0.01 mL, 0.08 mmol) and the resulting mixture was stirred vigorously for 4 hours at 60° C. The reaction was diluted with EtOAc (4 mL), filtered through a short pad of Celite® filter aid, and concentrated to dryness. The crude material was purified by silica gel chromatography eluting with 0% to 5% MeOH in DCM to afford I-253 (4 mg, 9 µmol 16% yield) as a white film. MS [M+H]$^+$=410.0. $^1$H NMR (400 MHz, Chloroform-d) δ 7.92 (s, 1H), 7.82 (d, J=8.1 Hz, 1H), 7.37-7.34 (m, 2H), 5.22 (dd, J=13.2, 5.1 Hz, 1H), 4.47 (d, J=16.0 Hz, 1H), 4.32 (d, J=15.9 Hz, 1H), 3.42-2.97 (m, 4H), 2.99-2.78 (m, 3H), 2.75-2.47 (m, 3H), 2.45-2.28 (m, 1H), 2.24-2.19 (m, 1H), 2.10-1.80 (m, 3H).

Example 71: 3-(5-(octahydroindolizin-7-yl)-1-oxoisoindolin-2-yl)piperidine-2,6-dione (I-271)

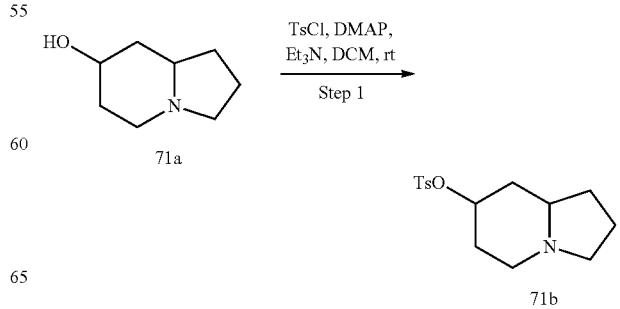

303

-continued

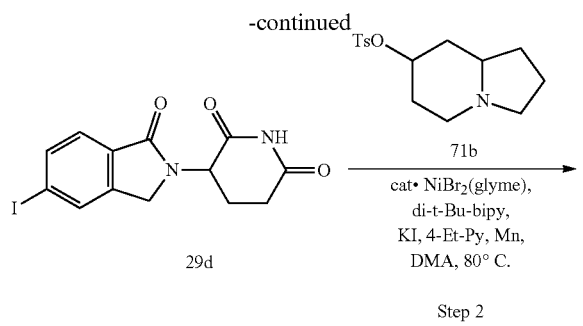

Step 1. octahydroindolizin-7-yl 4-methylbenzenesulfonate 71b

To a stirred solution of 71a (653 mg, 4.62 mmol), TEA (1.6 mL, 12 mmol), and DMAP (113 mg, 0.925 mmol) in DCM (5 mL) was added TsCl (1060 mg, 5.55 mmol) in one portion and the resulting mixture was stirred overnight at rt. The reaction mixture was quenched with sat. aq. NaHCO$_3$ and extracted with DCM (3×). The combined organic phases were dried over Na$_2$SO$_4$, filtered, and concentrated to dryness. The crude material was purified by silica gel chromatography eluting with 0% to 100% EtOAc in heptane to afford 71b (308 mg, 1.01 mmol, 22% yield) as a brown oil. MS [M+H]$^+$=296.2. $^1$H NMR (400 MHz, Chloroform-d) δ 7.84-7.79 (m, 2H), 7.38-7.34 (m, 2H), 4.48 (tt, J=11.0, 4.9 Hz, 1H), 3.13-2.98 (m, 2H), 2.47 (s, 3H), 2.21-2.02 (m, 3H), 1.99-1.67 (m, 6H), 1.59-1.41 (m, 2H).

Step 2. 3-(5-(octahydroindolizin-7-yl)-1-oxoisoindolin-2-yl)piperidine-2,6-dione HC(O)OH salt (I-271)

To a stirred suspension of 29d (50 mg, 0.14 mmol), 71b (55.9 mg, 0.189 mmol), NiBr$_2$(DME) (4.2 mg, 0.014 mmol), di-t-Bu-bipy (3.6 mg, 0.014 mmol), KI (22 mg, 0.35 mmol) and manganese powder (15 mg, 0.30 mmol) in DMA (0.68 mL) under an atmosphere of nitrogen was added 4-ethyl-pyridine (0.015 mL, 0.14 mmol) and the resulting mixture was stirred vigorously at 80° C. overnight. The reaction mixture was then diluted with DCM (4 mL), filtered, and concentrated to dryness by azeotroping with heptane. The crude material was purified by reverse phase HPLC (eluting with MeCN/H$_2$O with 0.1% formic acid). The fractions containing the desired product were combined and lyophilized to afford the formate salt of I-271 (2.0 mg, 4.6 µmol, 3% yield) as a white solid. The title compound was isolated as a 4:1 mixture of diastereoisomers. MS [M+H]$^+$=368.2.

304

Example 72: trans-3-(1-oxo-5-(1-((4-(trifluoromethyl)cyclohexyl)methyl)piperidin-4-yl)isoindolin-2-yl)piperidine-2,6-dione (I-266)

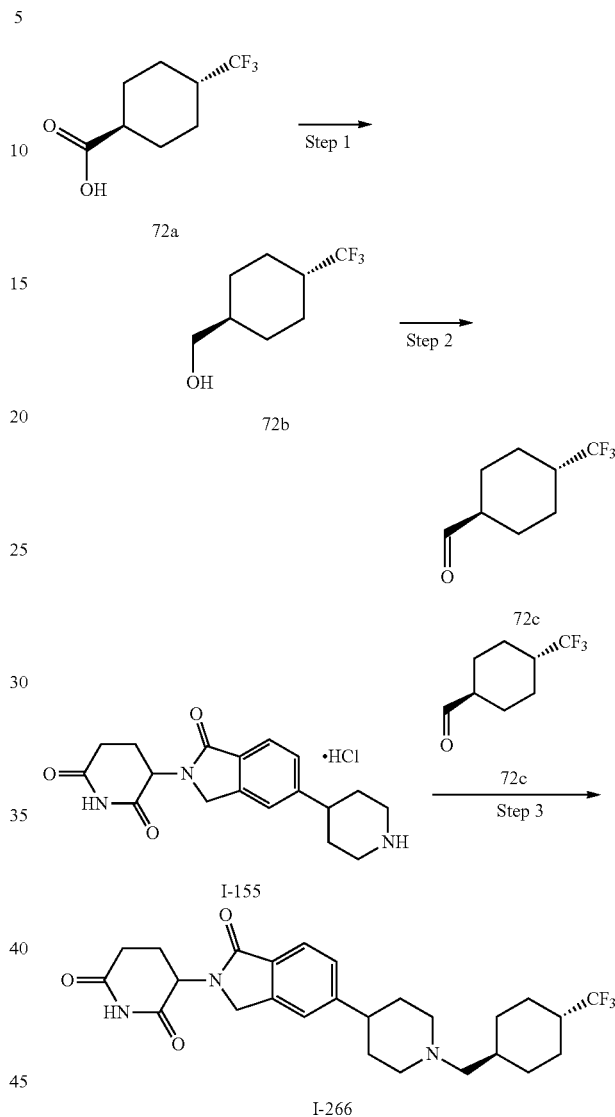

Step 1. trans-(4-(trifluoromethyl)cyclohexyl)methanol (72b)

To a stirred solution of compound 72a (500 mg, 2.55 mmol) in THF (10 mL), was added LiAlH$_4$ (200 mg, 5.10 mmol) in small portions at 0° C. and the resulting mixture was stirred for 2 hours. The reaction mixture was quenched with 10% NaOH and then stirred at rt for 1 h. The solids were filtered through a small pad of Celite® filter aid and washed with EtOAc. The combined filtrate was dried over Na$_2$SO$_4$, filtered, and concentrated under reduced pressure to afford compound 72b as a viscous oil (270 mg, 1.48 mmol, 58% yield). The material was used in the next step without further purification.

Step 2. trans-4-(trifluoromethyl)cyclohexane-1-carbaldehyde (72c)

To a stirred solution of 72b (270 mg, 1.48 mmol) in DCM (10 mL) was added DMP (1.26 g, 2.96 mmol) at 0° C. and the resulting mixture was stirred at rt for 3 h. The reaction mixture was then diluted with DCM (20 mL), washed with 10% aq. NaHCO$_3$ (2×25 mL) and brine (25 mL), dried over Na$_2$SO$_4$, filtered, and concentrated under reduced pressure. The obtained material was purified by silica gel chromatography eluting with 15% EtOAc in hexane to afford 72c as a pale yellow oil (120 mg, 0.66 mmol, 45% yield). $^1$H NMR (400 MHz, DMSO-d6): δ 9.64 (s, 1H), 2.27-2.00 (m, 6H), 1.43-1.22 (m, 4H).

Step 3. trans-3-(1-oxo-5-(1-((4-(trifluoromethyl)cyclohexyl)methyl)piperidin-4-yl)isoindolin-2-yl)piperidine-2,6-dione (I-266)

To a stirred solution of I-155 (150 mg, 0.41 mmol), 72c (111 mg, 0.62 mmol) in DMF (5 mL) was added NaBH(OAc)$_3$ (262 mg, 1.23 mmol) and the resulting mixture was stirred at 60° C. for 16 h. The reaction mixture was quenched with ice-cold water and washed with EtOAc (2×25 mL). The aq. layer was basified with NaHCO$_3$ and extracted with 5% MeOH in DCM (2×25 mL). The combined extracts were dried over Na$_2$SO$_4$, filtered, and concentrated to dryness. The crude material was purified by reverse phase HPLC (eluting with MeCN/H$_2$O with 0.1% TFA) to afford the trifluoroacetate salt of I-266 as an off-white solid (55 mg, 0.11 mmol, 28% yield). MS [M+H]$^+$=492.1. $^1$H NMR (400 MHz, DMSO-d$_6$): δ 10.98 (s, 1H), 7.62 (d, J=8.0 Hz, 1H), 7.49 (s, 1H), 7.39 (d, J=8.0 Hz, 1H), 5.10 (dd, J=13.2, 5.2 Hz, 1H), 4.4 (d, J=17.2 Hz, 1H), 4.28 (d, J=17.2 Hz, 1H), 2.95-2.89 (m, 3H), 2.62-2.55 (m, 2H), 2.42-2.35 (m, 1H), 2.21-2.15 (m, 1H), 2.12-2.08 (m, 2H), 1.99-1.96 (m, 3H), 1.85-1.82 (m, 4H), 1.75-1.65 (m, 4H), 1.52-1.48 (m, 1H), 1.28-1.20 (m, 2H), 0.95-0.88 (m, 2H).

Biological Assays and Data

The activity of a compound according to the present disclosure can be assessed by the following in vitro methods.

Example 73: Prolabel Quantification of IKZF1, IKZF2 or GSPT1 Protein Levels in 293GT Cells The Prolabel system from DiscoverX was used to develop high-throughput and quantitative assays to measure changes in IKZF1, IKZF2 and GSPT1 protein levels in response to compounds. The prolabel tag was derived from the alpha fragment of beta galactosidase and has the following protein sequence: mssnslavvlqrrdwenpgvtqlnrlaahppfaswrnseeartdrpsqqlrslnge. The complementary fragment of beta-galactosidase (from DiscoverX), is added to the prolabel tag to form an active beta galactosidase enzyme whose activity can be precisely measured. In this way, the levels of a fusion protein with the prolabel tag can be quantified in cell lysates.

Lentiviral vectors, based on the Invitrogen pLenti6.2/V5 DEST backbone, were constructed that placed the prolabel tag upstream of IKZF1, IKZF2 or GSPT1 and expressed the fusion protein from a CMV promoter.

To ensure moderate and consistent expression of the prolabel fusion proteins across all cells in the population, stable cell lines were constructed from cells expressing a single copy of the construct. Lentivirus packaged with the constructs was made using the Virapower kit from Invitrogen. Strongly adherent 293GT cell, GripTite 293 MSR cells from Thermo Fisher Scientific (Catalog number: R79507), were infected with the virus at low multiplicity of infection and selected by 5 μg/mL blasticidin for 2 weeks.

The levels of prolabel tagged fusion proteins in compound treated cell lines were measured as follows:

Day 1, Cells were diluted to 1.0×10$^6$ cells/ml in normal growth medium. 17.5 μL of cells were plated in each well of a solid white 384 well plate. Plates were incubated overnight in a 37° C. tissue culture incubator.

Day 2, Serial dilutions of compounds were made in 384 well plates from 10 mM stocks. 15 μL of DMSO was added to each well of a 384 well plate. In the first column 15 μL of stock compound was added. The solution was mixed and 15 μL was transferred to the next column. This was repeated until 20 two-fold dilutions were prepared. 2.5 μL of diluted compounds were transferred into 60 μL of cell culture medium in another 384 well plate, and mixed well. 2.5 μL of this mixture was added to the plated cells. The final DMSO concentration was 0.5% and the highest concentration of compound was 50 μM. Plates were incubated overnight (e.g., about 14 h, 18 h, or 24 h) in a 37° C. tissue culture incubator.

Day 3, Plates were removed from the incubator and allowed to equilibrate at rt for 30 minutes. Prolabel substrate (DiscoverX PathHunter Prolabel Detection Kit, User manual: 93-0180) was added as described by the manufacturers protocols. Plates were incubated at rt for three hours and luminescence was read using an Envision reader (Perkin Elmer) Data was analyzed and visualized using the Spotfire software package.

As shown in FIGS. 4-11, the compounds of the present disclosure decreased IKZF2 levels compared to control in the Prolabel assay in HEK293GT cells. Reduction of IKZF2 levels ranging from 50% to 80% compared to control were observed for compounds I-43, I-57, I-68, I-69, I-136, I-147, I-219, and I-236 in FIGS. 4-11.

Table 3 shows Helios (IKZF2), Ikaros (IKZF1) and G1 to S phase transition 1 protein (GSPT1) degradation activity of compounds of the disclosure in Pro-label assays in 293GT cells, (% degradation is at 10 μM). Pomalidomide was tested as the control.

TABLE 3

| IKZF2, IKFZ1, and GSPT1 Activity | | | | | | | | | |
|---|---|---|---|---|---|---|---|---|---|
| | IKZF2 | | | | | IKZF2 | | | |
| Cmpd No. | EC$_{50}$ (μM) | % protein reduction at 10 μM, 24 h | IKZF1 EC$_{50}$ (μM) | GSPT1 EC$_{50}$ (μM) | Cmpd No. | EC$_{50}$ (μM) | % protein reduction at 10 μM, 24 h | IKZF1 EC$_{50}$ (μM) | GSPT1 EC$_{50}$ (μM) |
| I-155 | — | 40 | >50 | >50 | I-97 | 0.027 | 55 | >50 | >50 |
| I-171 | — | 5 | >50 | >50 | I-158 | 0.016 | 55 | >50 | >50 |
| I-166 | — | 25 | >50 | >50 | I-157 | 0.056 | 55 | >50 | >50 |
| I-167 | — | 25 | >50 | >50 | I-159 | 0.019 | 55 | >50 | >50 |
| I-163 | — | 35 | >50 | >50 | I-39 | 0.006 | 45 | >50 | >50 |
| I-169 | — | 20 | >50 | >50 | I-31 | 0.004 | 60 | >50 | >50 |
| I-170 | — | 5 | >50 | >50 | I-90 | 0.007 | 65 | >50 | >50 |

TABLE 3-continued

IKZF2, IKFZ1, and GSPT1 Activity

| Cmpd No. | IKZF2 $EC_{50}$ (μM) | IKZF2 % protein reduction at 10 μM, 24 h | IKZF1 $EC_{50}$ (μM) | GSPT1 $EC_{50}$ (μM) | Cmpd No. | IKZF2 $EC_{50}$ (μM) | IKZF2 % protein reduction at 10 μM, 24 h | IKZF1 $EC_{50}$ (μM) | GSPT1 $EC_{50}$ (μM) |
|---|---|---|---|---|---|---|---|---|---|
| I-11 | 0.013 | 65 | >50 | >50 | I-156 | 0.022 | 70 | >50 | >50 |
| I-57 | 0.009 | 70 | >50 | >50 | I-118 | 0.065 | 55 | >50 | >50 |
| I-112 | 0.007 | 63 | >50 | >50 | I-164 | 0.018 | 50 | >50 | >50 |
| I-168 | 0.014 | 55 | >50 | >50 | I-87 | 0.013 | 80 | >30 | — |
| I-160 | 0.018 | 50 | >50 | >50 | I-67 | 0.058 | 70 | >30 | — |
| I-173 | 0.074 | 65 | >30 | — | I-83 | 0.052 | 80 | >30 | — |
| I-175 | 0.005 | 50 | >50 | — | I-69 | 0.015 | 80 | >30 | — |
| I-265 | 0.005 | 70 | >50 | — | I-252 | 0.030 | 75 | >30 | — |
| I-88 | 0.005 | 70 | >30 | >30 | I-89 | 0.033 | 70 | >30 | >30 |
| I-91 | 0.018 | 75 | >30 | >30 | I-108 | 0.023 | 65 | >30 | >30 |
| I-70 | 0.012 | 75 | >30 | >30 | I-78 | 0.21 | 40 | >30 | — |
| I-64 | 0.025 | 75 | >30 | >30 | I-68 | 0.003 | 50 | >50 | >30 |
| I-75 | 0.020 | 80 | >30 | — | I-82 | 0.004 | 60 | >30 | — |
| I-38 | 0.041 | 55 | >30 | — | I-206 | 0.009 | 80 | >30 | >30 |
| I-77 | 0.007 | 80 | >30 | >30 | I-113 | 0.015 | 50 | >30 | >30 |
| I-110 | 0.074 | 75 | >30 | >30 | I-106 | 0.014 | 50 | >30 | — |
| I-225 | 0.12 | 65 | >30 | >30 | I-218 | 0.004 | 60 | >30 | — |
| I-32 | 0.046 | 80 | >30 | — | I-84 | 0.015 | 60 | >30 | — |
| I-76 | 0.017 | 75 | >30 | — | I-104 | 0.005 | 60 | >30 | — |
| I-36 | 0.017 | 75 | >30 | >30 | I-101 | 0.017 | 60 | >30 | — |
| I-79 | 0.003 | 75 | >30 | — | I-42 | 0.009 | 60 | >30 | — |
| I-74 | 2.1 | 55 | >30 | — | I-227 | 0.004 | 60 | >30 | — |
| I-236 | 0.003 | 80 | >25 | — | I-228 | 0.010 | 70 | >30 | — |
| I-244 | 0.091 | 75 | >30 | — | I-24 | 0.039 | 60 | >30 | — |
| I-248 | 0.016 | 70 | >30 | — | I-231 | 0.25 | 60 | >30 | — |
| I-29 | 0.036 | 70 | >30 | — | I-73 | 0.011 | 70 | >30 | — |
| I-90 | 0.007 | 65 | >50 | >50 | I-237 | 0.020 | 70 | >30 | — |
| I-255 | 0.049 | 60 | >30 | — | I-66 | 0.009 | 70 | >30 | — |
| I-63 | 0.011 | 75 | >30 | — | I-232 | 0.018 | 70 | >30 | >30 |
| I-114 | 0.029 | 40 | >50 | — | I-226 | 0.010 | 50 | >25 | — |
| I-80 | 0.012 | 60 | >30 | — | I-251 | 0.021 | 60 | >30 | >30 |
| I-215 | 0.019 | 50 | >30 | — | I-208 | 1.5 | 60 | >30 | — |
| I-47 | 0.008 | 80 | >30 | — | I-212 | 0.049 | 60 | >30 | — |
| I-16 | 0.008 | 70 | >30 | — | I-209 | 0.14 | 40 | >30 | — |
| I-49 | 0.004 | 60 | >30 | — | I-129 | 0.19 | 40 | >30 | — |
| I-242 | >30 | 5 | >30 | — | I-132 | 1.08 | 60 | >30 | — |
| I-18 | 0.019 | 65 | >30 | — | I-121 | 0.062 | 60 | >30 | — |
| I-45 | 0.008 | 80 | >30 | — | I-127 | 0.19 | 45 | >30 | — |
| I-200 | 0.067 | 35 | >30 | — | I-141 | 0.009 | 80 | >30 | — |
| I-10 | 0.085 | 60 | >30 | — | I-136 | 0.012 | 80 | >30 | >30 |
| I-203 | 0.016 | 50 | >30 | >30 | I-126 | 0.39 | 60 | >30 | — |
| I-213 | 0.045 | 70 | >30 | >30 | I-139 | 0.081 | 70 | >30 | >30 |
| I-214 | 0.019 | 70 | >50 | >30 | I-115 | 0.072 | 60 | >30 | — |
| I-217 | 0.008 | 40 | >30 | — | I-119 | 0.14 | 65 | >30 | — |
| I-219 | 0.011 | 80 | >25 | — | I-259 | 1.3 | 60 | >30 | — |
| I-221 | 0.036 | 30 | >50 | — | I-146 | 0.17 | 60 | >30 | — |
| I-235 | 2.44 | 40% | >30 | — | I-147 | 0.025 | 75 | >30 | >30 |
| I-238 | 0.11 | 60 | >25 | — | I-148 | 0.039 | 70 | >30 | — |
| I-239 | 0.007 | 70 | >30 | >30 | I-122 | 0.076 | 70 | >30 | — |
| I-245 | 0.037 | 40 | >50 | — | I-135 | 0.057 | 60 | >30 | >30 |
| I-246 | 0.012 | 40 | >50 | — | I-149 | 0.016 | 80 | >30 | >30 |
| I-254 | 0.68 | 40 | >30 | — | I-124 | 9.8 | 40 | >30 | — |
| I-43 | 0.012 | 80 | >30 | >30 | I-143 | 0.026 | 60 | >30 | >30 |
| I-120 | 0.83 | 50 | >30 | — | I-51 | 0.015 | 60 | >30 | — |
| I-140 | 0.019 | 80 | >30 | — | I-1 | 0.067 | 60 | >30 | — |
| I-86 | 0.029 | 75 | >30 | >30 | I-26 | 0.007 | 65 | >30 | — |
| I-125 | 0.24 | 60 | >30 | >30 | I-54 | 0.020 | 60 | >30 | — |
| I-130 | 0.008 | 80 | >30 | >30 | I-179 | 0.067 | 40 | >30 | — |
| I-151 | 0.095 | 60 | >30 | — | I-72 | 4.5 | 55 | >30 | — |
| I-123 | 0.069 | 75 | >30 | — | I-71 | 0.027 | 80 | >30 | >30 |
| I-201 | 0.033 | 75 | >30 | — | I-142 | 0.016 | 75 | >30 | >30 |
| I-205 | 0.050 | 70 | >30 | >30 | I-285 | 0.012 | 70 | >30 | — |
| I-117 | 0.050 | 50 | >30 | — | I-286 | 0.72 | 40 | >30 | — |
| I-134 | 0.034 | 80 | >30 | >30 | I-287 | 0.018 | 70 | >30 | — |
| I-128 | 0.012 | 75 | >30 | >30 | I-288 | 0.012 | 80 | >30 | — |
| I-58 | 0.053 | 60 | >30 | — | I-289 | 0.076 | 60 | >30 | — |
| I-59 | 0.031 | 80 | >30 | >30 | I-290 | 0.49 | 60 | >30 | — |
| I-234 | 0.12 | 50 | >30 | — | I-116 | 0.16 | 60 | >30 | — |
| I-5 | 0.027 | 60 | >30 | — | I-62 | 0.007 | 75 | >50 | >30 |
| I-4 | 0.031 | 60 | >30 | — | I-185 | >30 | 20 | >30 | — |
| I-187 | 0.067 | 50 | >30 | — | I-137 | 0.009 | 80 | >30 | >30 |
| I-3 | 0.023 | 60 | >30 | — | I-95 | 0.13 | 20 | >30 | — |

TABLE 3-continued

IKZF2, IKFZ1, and GSPT1 Activity

| Cmpd No. | IKZF2 EC$_{50}$ (µM) | IKZF2 % protein reduction at 10 µM, 24 h | IKZF1 EC$_{50}$ (µM) | GSPT1 EC$_{50}$ (µM) | Cmpd No. | IKZF2 EC$_{50}$ (µM) | IKZF2 % protein reduction at 10 µM, 24 h | IKZF1 EC$_{50}$ (µM) | GSPT1 EC$_{50}$ (µM) |
|---|---|---|---|---|---|---|---|---|---|
| I-13 | 0.029 | 60 | >30 | | I-260 | >30 | 20 | >30 | — |
| I-14 | 0.014 | 65 | >30 | | I-216 | 0.010 | 80 | 0.22 | >30 |
| I-230 | 0.009 | 65 | >30 | | I-224 | >50 | 0 | >50 | — |
| I-247 | 0.017 | 70 | >30 | | I-204 | >50 | 0 | >50 | — |
| I-202 | 0.59 | 40 | >30 | | I-172 | 0.103 | 60 | 0.25 | — |
| I-249 | 0.85 | 40 | >30 | | I-253 | >50 | 0 | >50 | >50 |
| I-190 | 0.17 | 30 | >30 | — | I-154 | 0.008 | 85 | 0.043 | >30 |
| I-273 | 0.21 | 20 | >30 | — | I-301 | 0.14 | 60 | 0.32 | — |
| I-191 | 4.2 | 10 | >30 | — | Control | >50 | | 0.05 | >50 |
| I-282 | >30 | 0 | >30 | — | | | | (80% degradation @ 10 µM) | |
| I-107 | 0.023 | 80 | 0.14 | >30 | | | | | |
| I-211 | 0.024 | 80 | 0.039 | >30 | | | | | |

Example 74: Quantification of In Vitro Suppressive Potency of Primary Human Regulatory T Cells Expanded in the Presence of Compounds Materials and Methods Treg Cell Sorting:

Human buffy coats were obtained from Bioreclamation-IVT, in the USA. CD4+ T cells were isolated from said buffy coats using the RosetteSep Human CD4+ T cell enrichment Cocktail (Stemcell technologies, USA) and gradient centrifugation over Ficoll Paque Plus (GE HealthCare Life-Sciences, USA) as per manufacturer's recommendations. Cells were resuspended in RPMI medium supplemented with 1% penicillin-Streptomycin solution, 10% Fetal Bovine Serum, HEPES (10 mM), MEM NEAA (100 nM), sodium pyruvate (1 mM) (all supplements from Thermo Fisher Scientific, USA), thereafter referred to as complete RPMI (cRPMI), and rested overnight at 37° C., 5% $CO_2$ in the presence of 2 U/mL rhIL-2 (Proleukin, Novartis). Cells were collected and resuspended in autoMACS Running Buffer supplemented with BSA (Miltenyi Biotec, USA) and labelled using CD4-FITC antibody (clone RPA-T4), CD25-APC antibody (clone M-A251) (Biolegend) and CD25 Microbeads (Miltenyi Biotec, USA). CD25-enriched cells were then isolated using the autoMACS Pro Separator. A highly purified population of Treg cells was then obtained by further sorting CD4+CD25Hi cells using a Sony SH800 cell sorter. The resulting Treg cell population was routinely above 90% pure according to FOXP3 expression.

Treg Cell Expansion:

Purified Treg cells were plated in cRPMI in 96-well, round-bottom plates at a density of 25000-50000 cells per well and activated in the presence of 500 U/mL rhIL2, and Treg expander Dynabeads (Thermo Fisher Scientific, USA) according to manufacturer's recommendations, in the presence or absence of 100 µM rapamycin (Thermo Fisher Scientific, USA). The compounds of the present disclosure were then added at a final concentration of 10 µM and DMSO was added as a vehicle control. Cells were incubated at 37° C., 5% $CO_2$ for a total of 12-14 days. The compound and rhIL2 were replenished every 48 h during the entirety of the culture.

Phenotypic Analysis of Expanded Treg Cells:

Cell were collected and counted and the fold expansion was calculated as (number of cells recovered)/(number of cells plated). A fraction of the cells was fixed and permeabilized using the eBioscience Foxp3 staining Buffer kit (eBioscience, Thermo Fisher Scientific, USA) and stained with Helios-PECyanine7 antibody (Clone 22F6). To determine IL2-expression, expanded Treg cells were further incubated in the presence of the eBioscience Cell Stimulation Cocktail with Protein inhibitors (Thermo Fisher Scientific) for 4 hours, followed by fixation and staining with IL2-BV711 antibody (clone MQ1-17H12) (Biolegend, USA). Cells were acquired on an LSRFortessa (Becton Dickinson, USA) and analysis was performed using the FlowJo software (TreeStar, USA).

Functional Analysis of Expanded Treg Cells:

Primary human PBMCs were obtained from freshly prepared buffy coats (BioReclamationIVT) using gradient centrifugation over Ficoll Paque Plus as per manufacturer's recommendations. Cells were then labelled with CFSE (5(6)-Carboxyfluorescein diacetate N-succinimidyl ester, Sigma-Aldrich, USA) and plated in triplicates cRPMI in round bottom 96-well plates, alone or with expanded Treg cells at a 1:2 PBMC:Treg ratio. The compounds of the present disclosure were then added at a final concentration of 10 µM and DMSO was added as a vehicle control. Cells were activated using soluble anti-CD3 antibody (clone OKT3) (eBioscience, ThermoFisher Scientific, USA) at a final concentration of 100 ng/ml. Cells were incubated at 37° C., 5% $CO_2$ for a total of 4-5 days. At the end of the culture, cells were stained using the Live/dead Blue viability stain (Thermo Fisher Scientific, USA) as per manufacturer's instructions, followed by staining with CD4-BUV737 (Clone SK3) (BDBiosciences, USA) and CD8-BV711 (clone RPA-T8) (Biolegend, USA). Cells were acquired on an LSRFortessa (Becton Dickinson, USA) and analysis was performed using the FlowJo software (TreeStar, USA). Proliferation was assessed in each population as the proportion of cells having diluted CFSE. Suppression was assessed for each condition in comparison to the responders plated alone.

Figure 2:
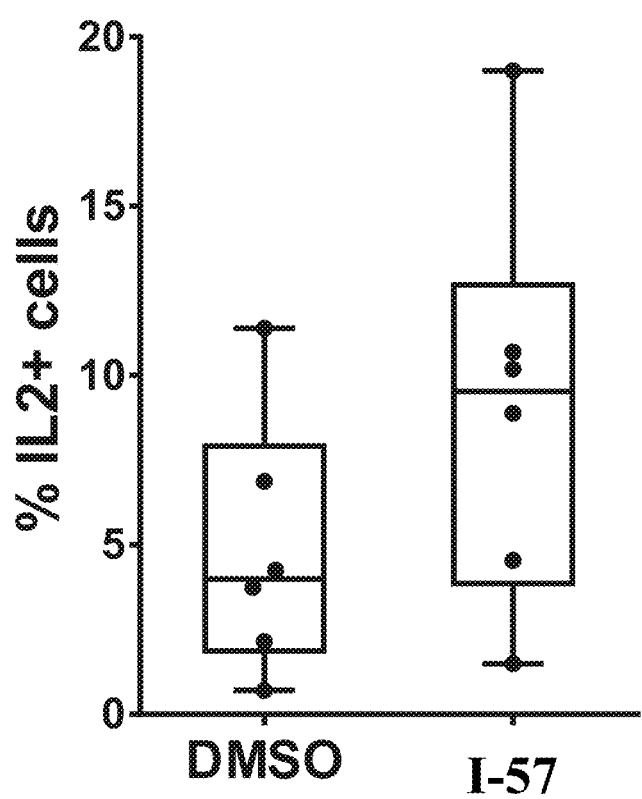
FIG. 2. is a box-and-whiskers graph showing the effects on IL2 levels in purified primary human Treg cells when treated with DMSO (Control) or Compound I-57. For each treatment, each dot represents one of five donors. The results in FIG. 2 show that production of IL2 is enhanced in Treg cells treated with Compound I-57 as compared to the control.
Figure 3:
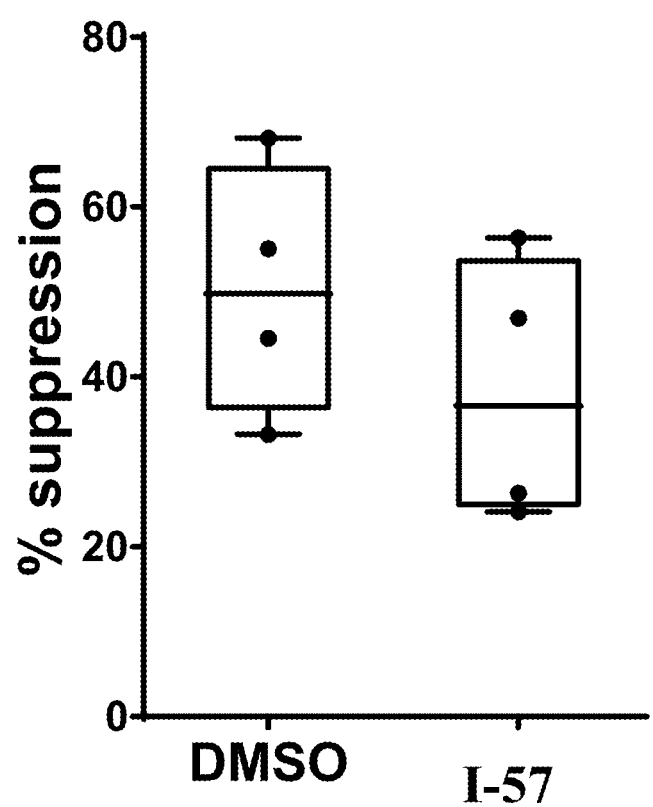
FIG. 3. is a box-and-whiskers graph showing the effects on in vitro suppression of the proliferation of CD4+ T cells in purified primary human Treg cells when expanded in the presence of DMSO (Control) or Compound I-57. For each treatment, each dot represents one of five donors. The results in FIG. 3 show that in vitro suppression of the proliferation of CD4+ T Cells is impaired in human Treg cells when treated with Compound I-57 as compared to the control.
Figure 4:
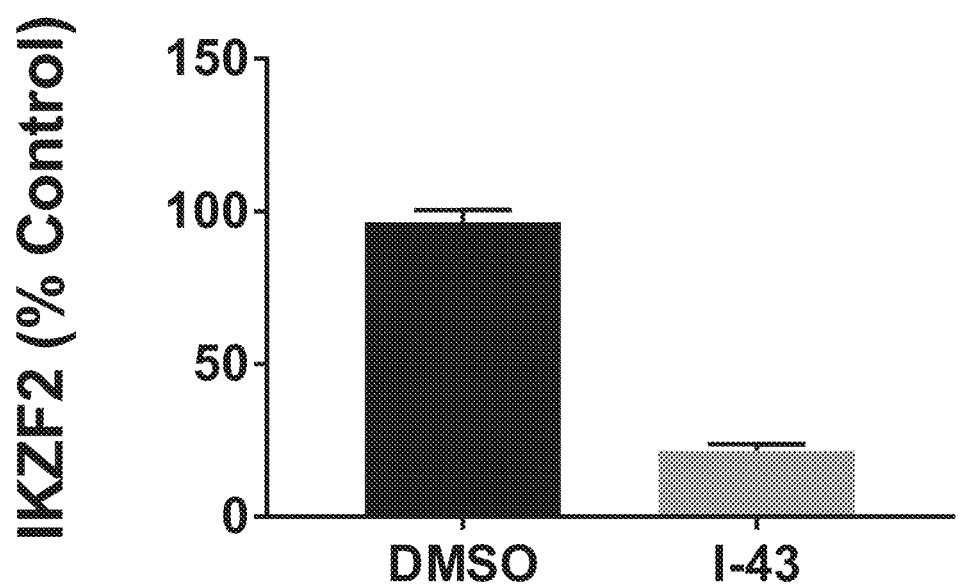
FIG. 4. is a bar graph showing the percentage change of IKZF2 protein levels in HEK293GT cells when treated with DMSO (Control) or Compound I-43 using the Prolabel assay. The results in FIG. 4 show that the levels of IKZF2 are decreased when treated with Compound I-43 as compared to the control.
Figure 5:
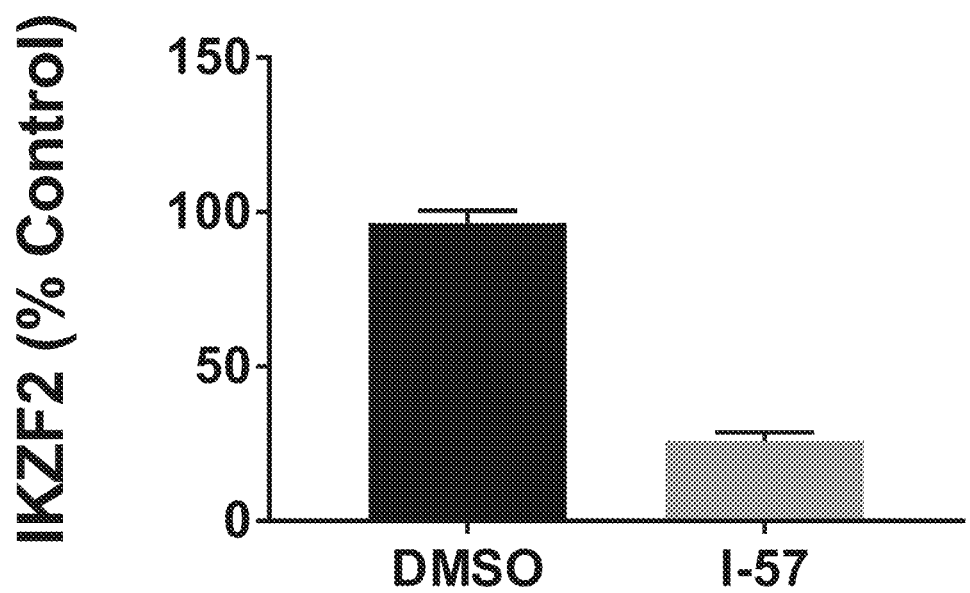
FIG. 5. is a bar graph showing the percentage change of IKZF2 protein levels in HEK293GT cells when treated with DMSO (Control) or Compound I-57 using the Prolabel assay. The results in FIG. 5 show that the levels of IKZF2 are decreased when treated with Compound I-57 as compared to the control.
Figure 6:
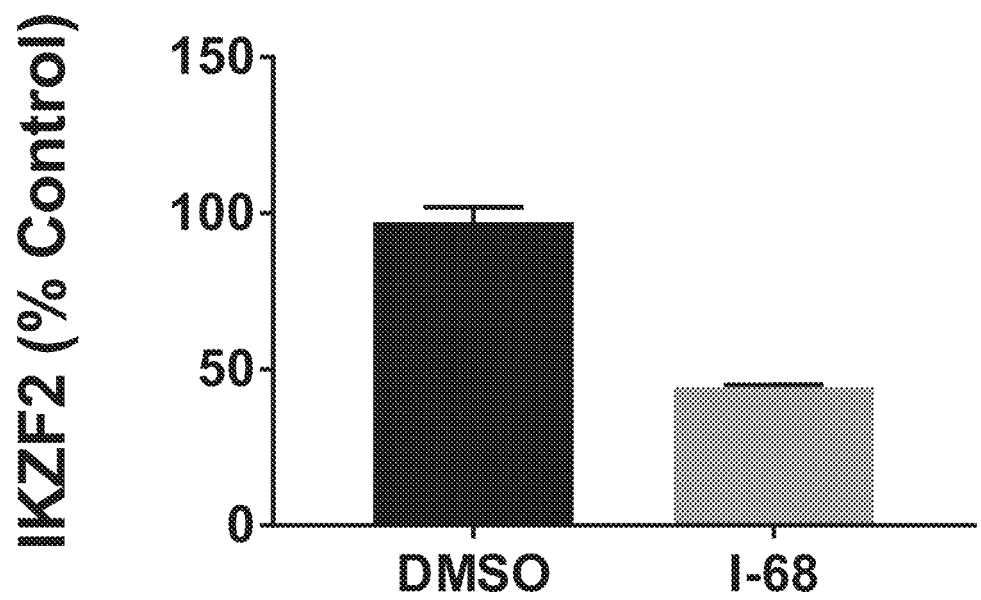
FIG. 6. is a bar graph showing the percentage change of IKZF2 protein levels in HEK293GT cells when treated with DMSO (Control) or Compound I-68 using the Prolabel assay. The results in FIG. 6 show that the levels of IKZF2 are decreased when treated with Compound I-68 as compared to the control.
Figure 7:
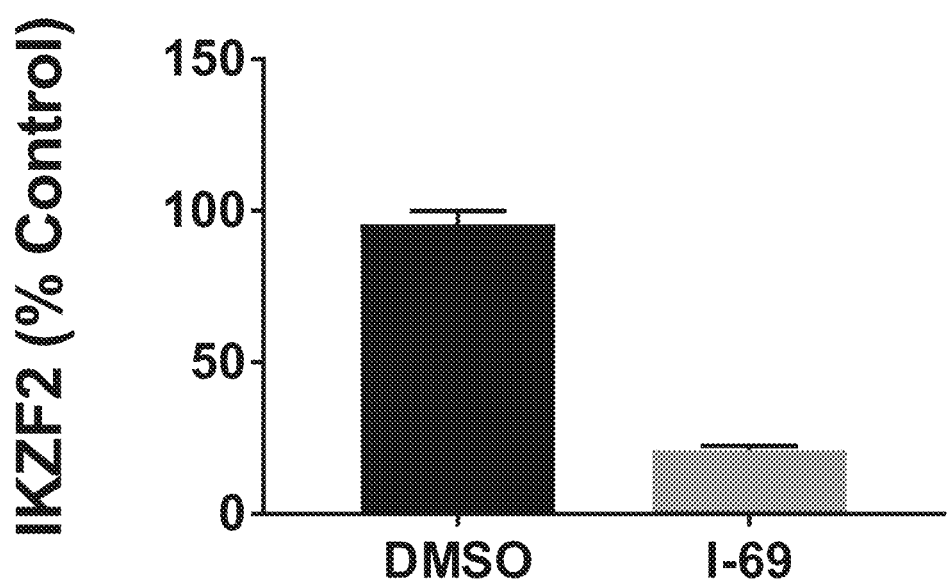
FIG. 7. is a bar graph showing the percentage change of IKZF2 protein levels in HEK293GT cells when treated with DMSO (Control) or Compound I-69 using the Prolabel assay. The results in FIG. 7 show that the levels of IKZF2 are decreased when treated with Compound I-69 as compared to the control.
Figure 8:
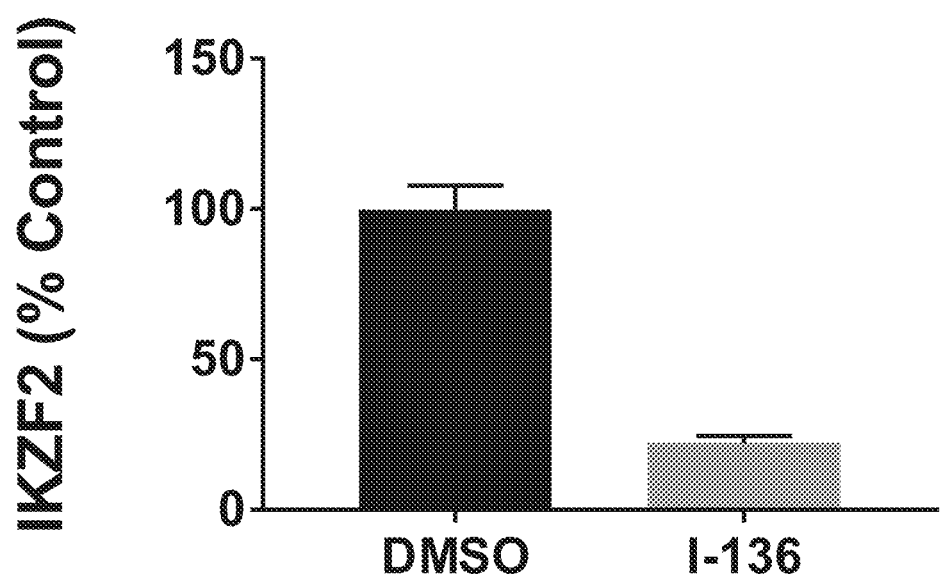
FIG. 8. is a bar graph showing the percentage change of IKZF2 protein levels in HEK293GT cells when treated with DMSO (Control) or Compound I-136 using the Prolabel assay. The results in FIG. 8 show that the levels of IKZF2 are decreased when treated with Compound I-136 as compared to the control.
Figure 9:
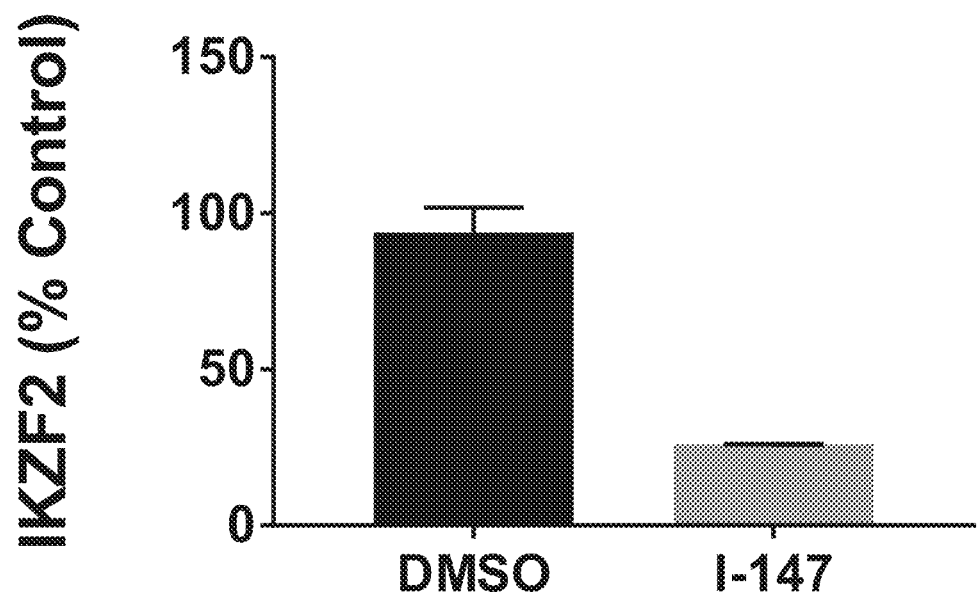
FIG. 9. is a bar graph showing the percentage change of IKZF2 protein levels in HEK293GT cells when treated with DMSO (Control) or Compound I-147 using the Prolabel assay. The results in FIG. 9 show that the levels of IKZF2 are decreased when treated with Compound I-147 as compared to the control.
Figure 10:
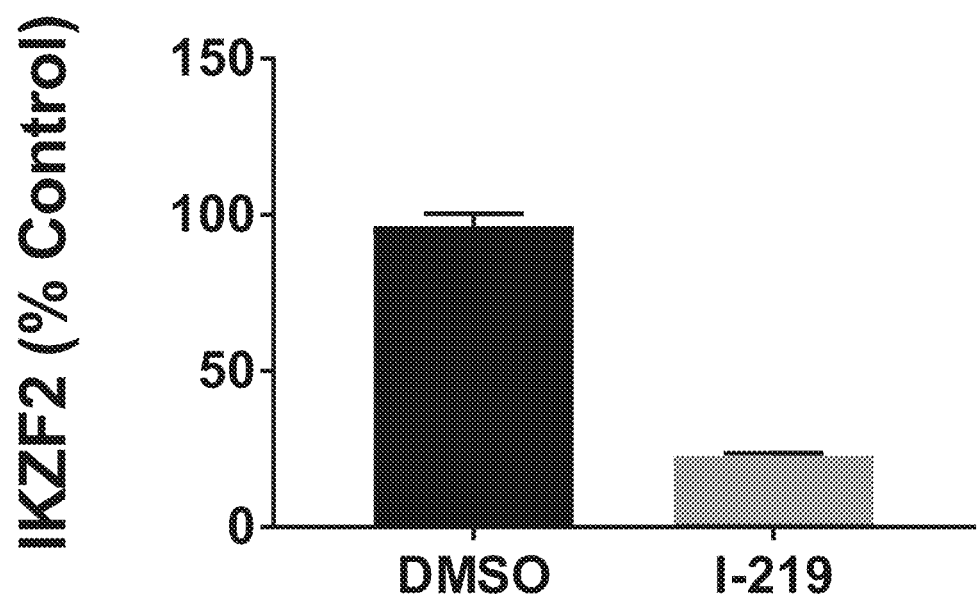
FIG. 10. is a bar graph showing the percentage change of IKZF2 protein levels in HEK293GT cells when treated with DMSO (Control) or Compound I-219 using the Prolabel assay. The results in FIG. 10 show that the levels of IKZF2 are decreased when treated with Compound I-219 as compared to the control.
Figure 11:
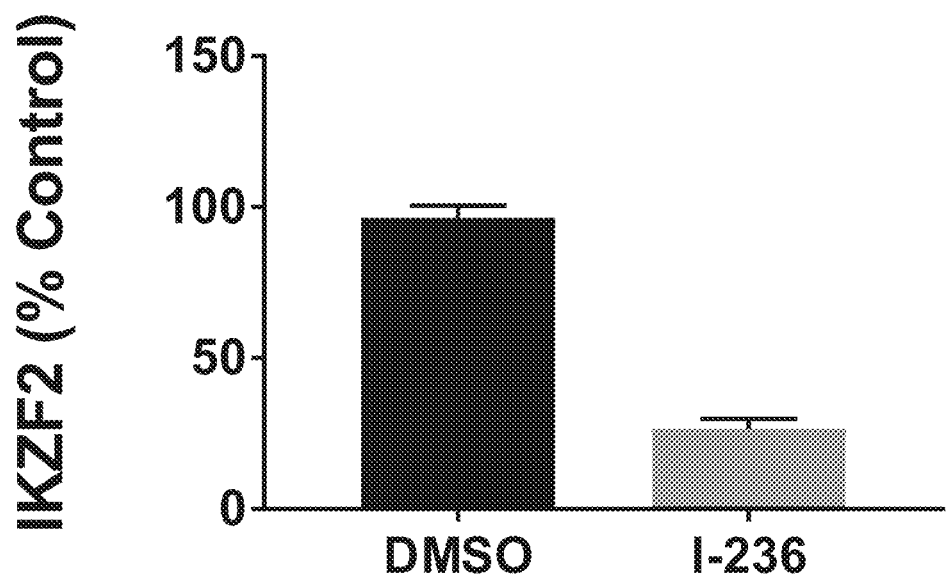
FIG. 11. is a bar graph showing the percentage change of IKZF2 protein levels in HEK293GT cells when treated with DMSO (Control) or Compound I-236 using the Prolabel assay. The results in FIG. 11 show that the levels of IKZF2 are decreased when treated with Compound I-236 as compared to the control.

Human primary regulatory T cells were expanded in vitro in the presence of Compound I-57 and equivalent volume of DMSO (control) for a period of 12 days. The expanded Treg cells were counted (FIG. 1) and analyzed for production of IL-2 (FIG. 2) and in vitro suppression of the proliferation of CD4+ T cells (FIG. 3). Repressed IL-2 production is a hallmark of Treg cell lineage stability and function. Treg cells were found to expand 30% less in the presence of compound I-57 (FIG. 1) and the proportion of cells producing IL-2 was increased in these cells by a median of 2.16 fold over five independent donors (FIG. 2). In addition, the expanded Treg cells were less able to repress the proliferation of CD4+ T cells in vitro in five independent donors (FIG. 3). These findings show that Compound I-57 induces a loss of Treg cell proliferation, stability and suppressive function.

Those skilled in the art will recognize, or be able to ascertain, using no more than routine experimentation, numerous equivalents to the specific embodiments described specifically herein. Such equivalents are intended to be encompassed in the scope of the following claims.

What is claimed is:
1. A compound of Formula (Ic):

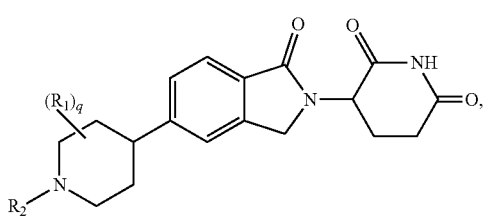

(Ic)

or a pharmaceutically acceptable salt, hydrate, solvate, prodrug, stereoisomer, or tautomer thereof,
wherein:
each $R_1$ is independently $(C_1-C_6)$alkyl;
$R_2$ is $(C_1-C_6)$alkyl substituted with one to three $R_4$;
each $R_4$ is independently selected from phenyl or 5- or 6-membered heteroaryl comprising 1 to 4 heteroatoms selected from O, N, and S, wherein the phenyl and heteroaryl groups are optionally substituted with one to three $R_7$;
each $R_7$ is independently selected from $(C_1-C_6)$alkyl, $(C_2-C_6)$alkenyl, $(C_2-C_6)$alkynyl, $(C_1-C_6)$alkoxy, $(C_1-C_6)$haloalkyl, $(C_1-C_6)$haloalkoxy, —C(O)R$_8$, —C(O)OR$_8$, —C(O)NR$_8$R$_9$, —NR$_8$C(O)R$_9$, $(C_1-C_6)$hydroxyalkyl, halogen, —OH, —NH$_2$, CN, $(C_6-C_{10})$aryl, 5- or 6-membered heteroaryl comprising 1 to 3 heteroatoms selected from O, N, and S, $(C_3-C_7)$cycloalkyl, and 5- to 7-membered heterocycloalkyl comprising 1 to 3 heteroatoms selected from O, N, and S, or
two $R_7$, when on adjacent atoms, together with the atoms to which they are attached form a $(C_6-C_{10})$aryl ring or a 5- or 6-membered heteroaryl ring comprising 1 to 3 heteroatoms selected from O, N, and S, optionally substituted with one or more $R_{10}$, or
two $R_7$, when on adjacent atoms, together with the atoms to which they are attached form a $(C_5-C_7)$cycloalkyl ring or a 5- to 7-membered heterocycloalkyl ring comprising 1 to 3 heteroatoms selected from O, N, and S, optionally substituted with one or more $R_{10}$;
$R_8$ and $R_9$ are each independently H or $(C_1-C_6)$alkyl;
each $R_{10}$ is independently selected from $(C_1-C_6)$alkyl, $(C_1-C_6)$alkoxy, $(C_1-C_6)$haloalkyl, $(C_1-C_6)$haloalkoxy, $(C_1-C_6)$hydroxyalkyl, halogen, —OH, —NH$_2$, and CN; and
q is 0.

2. The compound according to claim 1, wherein $R_4$ is phenyl substituted with one to three $R_7$.

3. The compound according to claim 1, wherein $R_4$ is 5-membered heteroaryl comprising 1 to 3 heteroatoms selected from O, N, and S, are optionally substituted with one to three $R_7$.

4. The compound according to claim 1, wherein $R_4$ is 6-membered heteroaryl comprising 1 to 3 heteroatoms selected from O, N, and S, optionally substituted with one to three $R_7$.

5. The compound according to claim 1, wherein the compound is selected from:

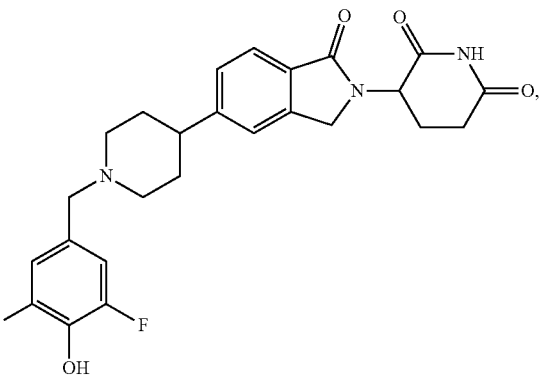

(I-156)

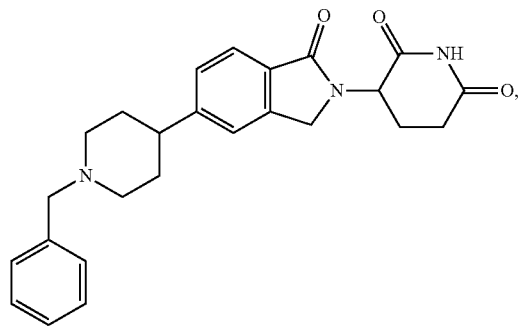

(I-57)

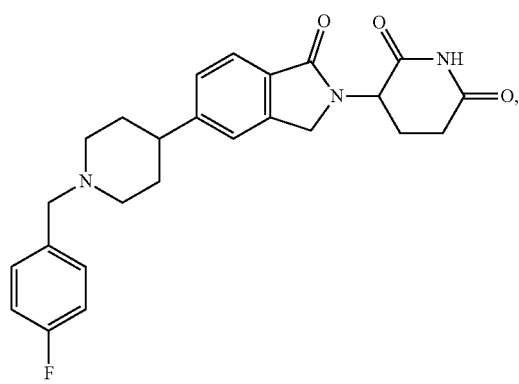

(I-112)

(I-118)

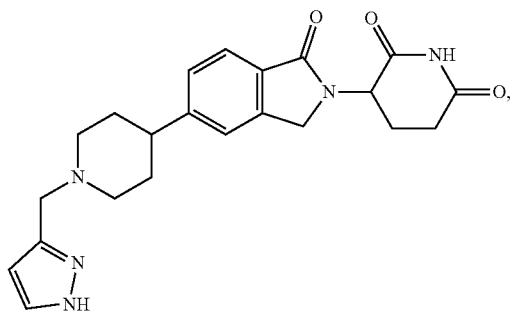

(I-78)

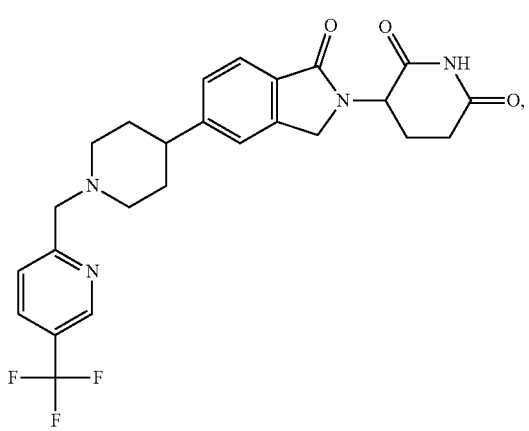

(I-68)

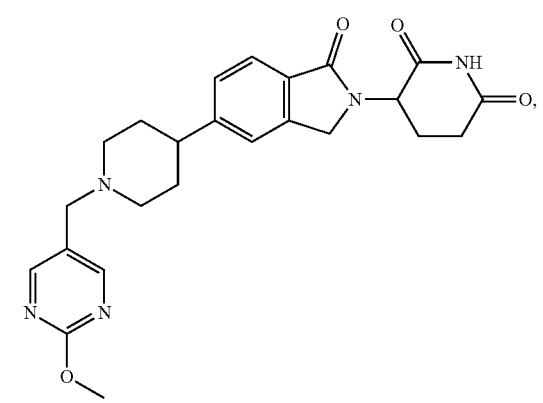

(I-289)

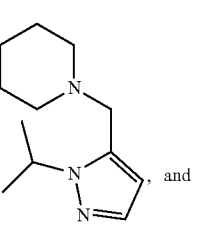, and (I-285)

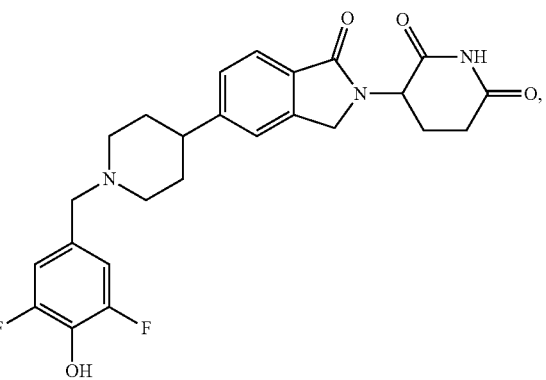

or a pharmaceutically acceptable salt, hydrate, solvate, prodrug, stereoisomer, or tautomer thereof.

6. A pharmaceutical composition comprising a therapeutically effective amount of a compound according to claim 1, or a pharmaceutically acceptable salt, hydrate, solvate, prodrug, stereoisomer, or tautomer thereof, and a pharmaceutically acceptable carrier or excipient.

7. The pharmaceutical composition of claim 6 further comprising at least one additional pharmaceutical agent.

8. A method of degrading IKZF2 comprising administering to the patient in need thereof a compound according to claim 1, or a pharmaceutically acceptable salt, hydrate, solvate, prodrug, stereoisomer, or tautomer thereof.

9. A method of treating a disease or disorder that is affected by the modulation of IKZF2 protein levels comprising administering to the patient in need thereof a compound according to claim 1, or a pharmaceutically acceptable salt, hydrate, solvate, prodrug, stereoisomer, or tautomer thereof.

10. A method of modulating IKZF2 protein levels comprising administering to the patient in need thereof a compound according to claim 1, or a pharmaceutically acceptable salt, hydrate, solvate, prodrug, stereoisomer, or tautomer thereof.

11. A method of reducing the proliferation of a cell the method comprising, contacting the cell with a compound according to claim 1, or a pharmaceutically acceptable salt, hydrate, solvate, prodrug, stereoisomer, or tautomer thereof, and reducing IKZF2 protein levels.

12. A pharmaceutical composition comprising a therapeutically effective amount of a compound selected from:

(I-57)

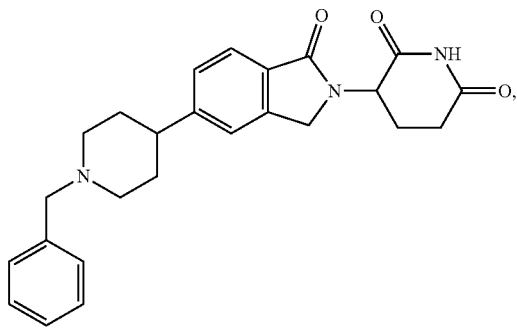

(I-112)

(I-118)

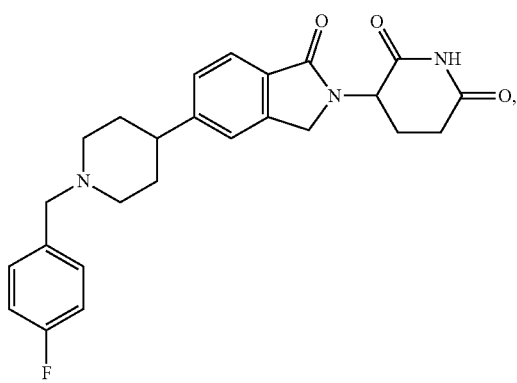

(I-78)

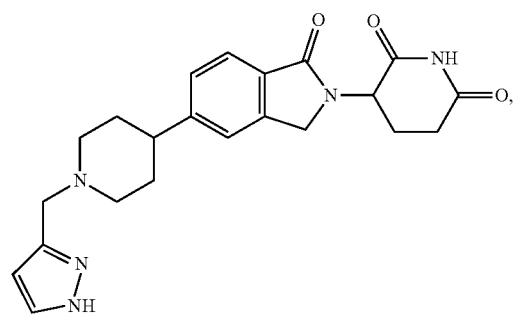

(I-68)

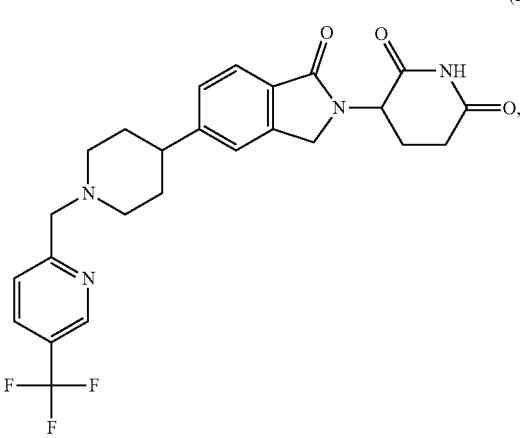

(I-289)

(I-285)

or a pharmaceutically acceptable salt, hydrate, solvate, prodrug, stereoisomer, or tautomer thereof, and a pharmaceutically acceptable carrier or excipient.

13. The pharmaceutical composition of claim 12 further comprising at least one additional pharmaceutical agent.

14. A method of treating an IKZF2-dependent cancer comprising administering to the patient in need thereof a compound selected from:

(I-156)
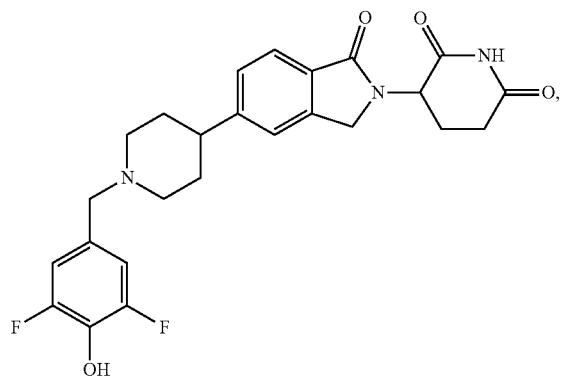
(I-57)
(I-112)
(I-118)
(I-78)
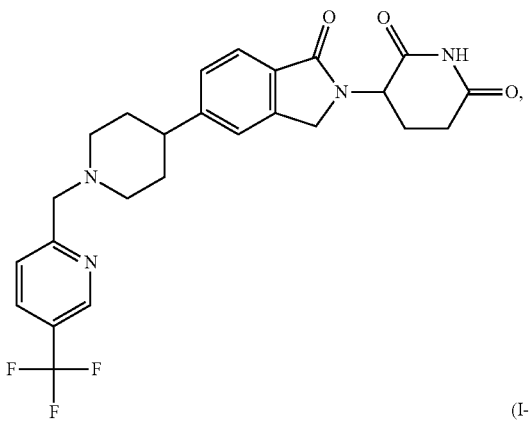
(I-68)
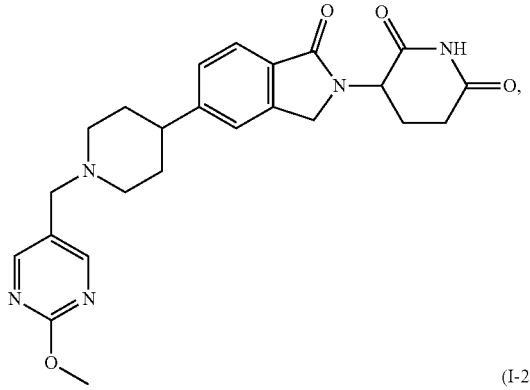
(I-289)
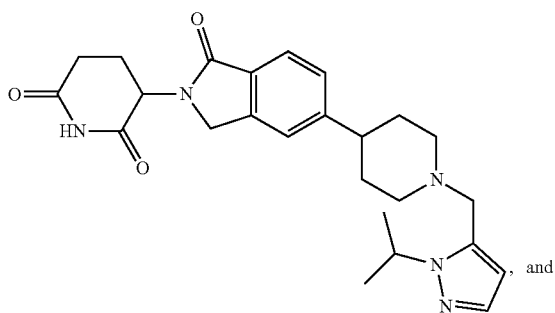
, and
(I-285)
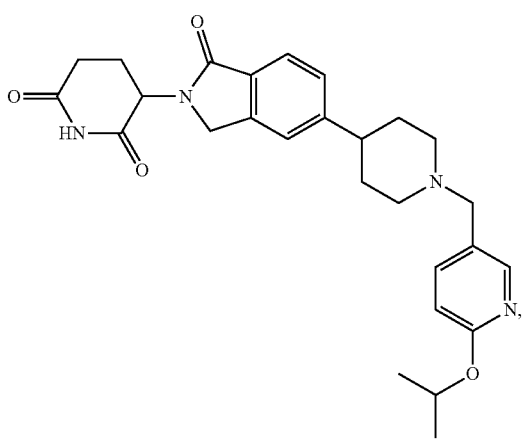
or a pharmaceutically acceptable salt, hydrate, solvate, prodrug, stereoisomer, or tautomer thereof.

15. The method of claim 14, wherein the cancer is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, and gastrointestinal stromal tumor (GIST).

16. The method of claim 14, wherein the cancer is a cancer for which the immune response is deficient or an immunogenic cancer.

* * * * *